(12) United States Patent
Schraub et al.

(10) Patent No.: US 11,014,901 B2
(45) Date of Patent: *May 25, 2021

(54) HYDROPHOBIC COMPOUNDS FOR OPTICALLY ACTIVE DEVICES

(71) Applicant: Merck Patent GmbH, Darmstadt (DE)

(72) Inventors: Martin Schraub, Alsbach-Haehnlein (DE); Lars Dobelmann-Mara, Darmstadt (DE); Stefan Riedmueller, Frankfurt Am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/485,844

(22) PCT Filed: Feb. 14, 2018

(86) PCT No.: PCT/EP2018/053625
§ 371 (c)(1),
(2) Date: Aug. 14, 2019

(87) PCT Pub. No.: WO2018/149852
PCT Pub. Date: Aug. 23, 2018

(65) Prior Publication Data
US 2020/0055833 A1  Feb. 20, 2020

(30) Foreign Application Priority Data

Feb. 15, 2017 (EP) .................................... 17156329

(51) Int. Cl.
| | | |
|---|---|---|
| *C07D 307/83* | (2006.01) | |
| *A61F 2/16* | (2006.01) | |
| *C07D 209/32* | (2006.01) | |
| *C07D 333/64* | (2006.01) | |
| *C07D 405/04* | (2006.01) | |
| *C07D 409/04* | (2006.01) | |
| *C08L 33/14* | (2006.01) | |
| *G02B 1/04* | (2006.01) | |

(52) U.S. Cl.
CPC .............. *C07D 307/83* (2013.01); *A61F 2/16* (2013.01); *C07D 209/32* (2013.01); *C07D 333/64* (2013.01); *C07D 405/04* (2013.01); *C07D 409/04* (2013.01); *C08L 33/14* (2013.01); *G02B 1/041* (2013.01)

(58) Field of Classification Search
CPC ................................................... C07D 307/83

USPC ......................................................... 549/462
See application file for complete search history.

(56) References Cited

U.S. PATENT DOCUMENTS

| | | | |
|---|---|---|---|
| 5,290,892 A | 3/1994 | Namdaran et al. | |
| 5,331,073 A | 7/1994 | Weinschenk et al. | |
| 5,693,095 A | 12/1997 | Freeman et al. | |
| 8,109,999 B2 | 2/2012 | Hampp | |
| 2010/0324165 A1 | 12/2010 | Ritter et al. | |
| 2018/0086725 A1 | 3/2018 | Kumar | |
| 2019/0389827 A1* | 12/2019 | Dobelmann-Mara | ...................... C07D 333/56 |
| 2020/0231559 A1* | 7/2020 | Dobelmann-Mara | ...................... C07D 409/06 |

FOREIGN PATENT DOCUMENTS

| | | | |
|---|---|---|---|
| WO | 07033831 A1 | 3/2007 | |
| WO | 09074520 A2 | 6/2009 | |
| WO | 16200401 A1 | 12/2016 | |

OTHER PUBLICATIONS

M. Schraub et al., European Polymer Journal, vol. 51, 2014, pp. 21-27.
C.H. Krauch et al., Chemische Berichte Jahrg, vol. 99, 1966, pp. 1723.
A. Bouquet et al., Tetrahedron, vol. 37, 1981, pp. 75-81.
David L. Oldroyd et al., Tetrahedron Letters, vol. 34, No. 7, 1993, pp. 1087-1090.
T. Truong et al., Journal of the American Chemical Society, 2014, vol. 136, No. 24, pp. 8568-8576, XP055356858.
International search report PCT/EP2018/053625 dated Mar. 26, 2018 (pp. 1-3).
Jean-Marc Legeais, J. Cataract. Refract. Surg. 1998, 24, 371-379.
P. L. Beaulieu et al., Journal of Medicinal Chemistry, 2012, vol. 55, No. 17, pp. 7650-7666, XP055356857.
Sohn: "Tuning Surface Properties . . . " Langmuir 2016, 32, pp. 9748-9756.

* cited by examiner

*Primary Examiner* — Nizal S Chandrakumar
(74) *Attorney, Agent, or Firm* — Millen White Zelano & Branigan, PC; Brion P. Heaney

(57) ABSTRACT

The present invention relates to novel compounds, particularly to compounds comprising a photoactive unit, said novel compounds being particularly suitable for compositions and ophthalmic devices as well as to compositions and ophthalmic devices comprising such compounds.

38 Claims, No Drawings

# HYDROPHOBIC COMPOUNDS FOR OPTICALLY ACTIVE DEVICES

FIELD OF THE INVENTION

The present invention relates to novel compounds, particularly to compounds comprising a photoactive unit, said novel compounds being particularly suitable for compositions and ophthalmic devices as well as to compositions and ophthalmic devices comprising such compounds.

BACKGROUND OF THE INVENTION

Cataract is a general term for an affection of the eye that leads to a loss of vision and in the extreme to blindness by clouding of the normally clear lens of the eye. It is the major cause of blindness in the world, affecting more than 100 million people. Due to the fact that its major cause is age and the population's average age is increasing, it is expected that the number of cataracts will continue to increase substantially in the future.

Effective treatment of cataract is only possible by surgical intervention, whereby the natural lens of the eye is removed through an incision in the cornea and replaced with an artificial lens, often also referred to as "intraocular lens". In preparation of surgery current state-of-the-art surgical methods employ eye mapping so as to approximate the refractive power best suited to the respective patient.

Even though cataract surgery is one of the most widely used and safest surgical procedures it is not without specific post-surgery problems. It frequently happens that the refractive power of the implanted intraocular lens (IOL) is insufficient for restoring good vision. Such problems may, for example, be caused by changes in eye geometry as consequence of the surgery as well as irregular wound healing and positioning errors that result in the artificial lens not having the optimal optical properties. As a result the patient will still require corrective vision aids, e.g. glasses, to be able to see correctly. In some cases the resulting refractive power of the implanted artificial lens is so far removed from the required refractive power that further surgery will be required. Particularly for aged persons this is not desirable because the body's capability for healing is reduced with increasing age. Furthermore, there is the risk of attracting endophthalmitis, an inflammation of the eye, which can even lead to a complete loss of vision or worse, loss of the eye.

There is therefore a need in the health sector for optically active devices, and particularly for artificial intraocular lenses, that would allow for non-invasive adjustment of refractive power after implantation of the lens, thereby preferably further reducing the need for post-surgery vision aids.

Some developments in this sense have already been made, as for example evidenced by WO 2007/033831 A1, WO 2009/074520 A2 or US 20100324165 A1.

WO 2016/200401 A1 describes liquid crystal materials having photoalignment properties.

M. Schraub et al, European Polymer Journal 51 (2014) 21-27 describes the photochemistry of 3-phenyl-coumarin containing polymethacrylates.

C. H. Krauch et al, Chemische Berichte Jahrg. 99, 1966, 1723 describe photochemical reactions on coumaron.

A. Bouquet et al, Tetrahedron, 1981, vol. 37, 75 to 81 describe the photochemical behavior of several benzo[b]thiophenes in neutral solutions or in the presence of primary and tertiary amines.

David L. Oldroyd et al, Tetrahedron Letters, 1993, vol. 34, no. 7, 1087-1090 describe photochemical dimerization reactions of N-acylindoles.

Poly(methyl methacrylate) (PMMA) intraocular lenses (IOLs) that were coated with Teflon AF®, an amorphous, transparent, and highly hydrophobic fluorocarbon polymer is known from Jean-Marc Legeais, J Cataract Refract Surg. 1998, 24, 371-379. Teflon AF® (Dupont de Nemours) is a poly(tetra-fluoroethylene co-hexafluoro-propyl-2 cyclodethoxydifluoroethylene). Constituted entirely of high-energy bonds, it is stable at temperatures up to 260° C. and chemically very resistant. The refractive index is 1.32. It transmits light from 200 to 2000 nm with a constant light absorption below 5%. The contact angle with water is 129 degrees. The surface modification is described using a PMMA IOL (model 808A, Kabi Pharmacia Production B.V.) having an overall diameter of 12.0 mm and optic diameter of 6.5 mm which is coated by immersing the lense in a 5% solution of Teflon AF in a fluorocarbon solvent (C8F18) for 3 seconds and then placing it at a temperature of 37° C. to evaporate the solvent. As a result, the surface of the PMMA IOL was completely coated with Teflon AF.

Eun-Ho Sohn et al describe surface properties of poly (methyl methacrylate) (PMMA) films using poly(perfluoromethyl methacrylate)s (PFMMAs) with short perfluorinated side chains. 2,2,2-Trifluoroethyl methacrylate, 1,1,1,3,3,3-hexafluoroisopropyl methacrylate, 2,2,3,3,3-pentafluoropropyl methacrylate, 2,2,3,3,4,4,4-heptafluorobutyl methacrylate were prepared by radical polymerization of the corresponding monomers. Film preparation is reported with PMMA, PFMMA and their blends.

P. L. Beaulieu et al, Journal of Medicinal Chemistry, 2012, 55, 17, 7650-7666 describes indole derivatives as inhibitors satisfying potency criteria and displaying improved in vitro ADME profiles.

However, the compounds disclosed therein suffer from being too stiff and too brittle so that they can't be rolled or folded and are thus not fit to be implanted by state of the art cataract surgical methods, particularly by state of the art micro-incision cataract surgical methods.

Consequently, it is an objective of the present application to provide for novel compounds suitable for ophthalmic devices.

It is also an objective of the present application to provide for compounds, the optical properties of which may be changed, preferably by non-invasive techniques.

It is a further objective of the present application to provide for novel compounds having advantages over currently known compounds, preferably in combination with being suitable for ophthalmic devices.

Advantages such as better flexibility and objectives of the compounds of the present application will be evident to the skilled person from the following detailed description as well as from the examples.

SUMMARY OF THE INVENTION

The present inventors have now found that the above objects may be attained either individually or in any combination by the compounds and ophthalmic devices of the present application.

The invention relates to compounds of formula (I)

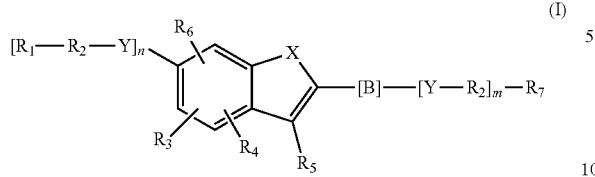
(I)

wherein
X is O, S or NR$_0$,
Y is independently of each other O, S or a bond,
n is 0 or 1,
m is 0 or 1,
n+m is 1 or 2,
—[B]— is selected from the group consisting of formula (1) to formula (4),

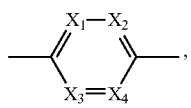
(1)

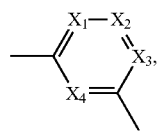
(2)

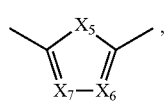
(3)

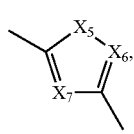
(4)

$X_1$, $X_2$, $X_3$, $X_4$ are each independently of each other CR' or N,
$X_5$ is each independently O, S, C=O or NR$_0$,
$X_6$, $X_7$ are each independently CR' or N,
R is at each occurrence independently selected from the group consisting of H, F, a linear or branched alkyl group having 1 to 8 C atoms or a linear or branched partially or fully fluorinated alkyl group having 1 to 4 C atoms,
R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms,
R$_0$ is at each occurrence independently selected from the group consisting of a linear or branched alkyl group having 1 to 10 C atoms or a cycloalkyl group having 3 to 6 C atoms,
R$_1$ is a polymerizable group selected from the group consisting of an alkenyl group of formula (5),

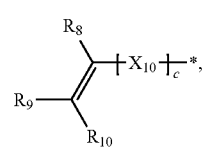
(5)

wherein
$X_{10}$ is selected from the group consisting of O, S, C(=O), C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1; and
trialkoxysilyl groups or dialkoxyalkylsilyl groups where the alkyl and/or alkoxy groups are each independently linear or branched having 1 to 6 C atoms; and silyl groups of formula (6), (7) or (8),

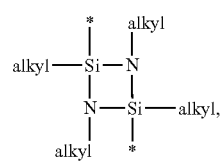
(6)

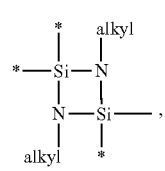
(7)

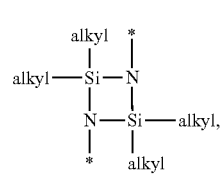
(8)

where alkyl means at each occurrence independently of each other a linear or branched alkyl group having 1 to 6 C atoms and the asterisk "*" denotes at each occurrence independently of each other a linkage to the linker [—R$_2$—Y]$_n$ and/or [Y—R$_2$]$_m$,
R$_2$— is —(C(R)$_2$)$_o$—, wherein at least one R is F or a linear or branched partially or fully fluorinated alkyl group having 1 to 4 C atoms or —(C(R)$_2$)$_p$—X$_8$—(C(R)$_2$)$_q$—(X$_9$)$_s$—(C(R)$_2$)$_r$—(X$_{10}$)$_t$—(C(R)$_2$)$_u$—, wherein at least one R is F or a linear or branched partially or fully fluorinated alkyl group having 1 to 4 C atoms,
or
a cycloalkylene group having 5 or 6 C atoms which is substituted with at least one R which is F or a linear or branched partially or fully fluorinated alkyl group having 1 to 4 C atoms,
o is selected from the group consisting of 1 to 20,
$X_8$, $X_9$, $X_{10}$ are at each occurrence independently O, S or NR$_0$,
s, t are at each occurrence independently 0 or 1,
p, q are at each occurrence independently selected from the group consisting of 1 to 10, r, u are at each occurrence independently selected from the group consisting of 0 to 10, wherein the overall number of atoms for —$(C(R)_2)_p$—$X_8$—$(C(R)_2)_q$—$(X_9)_s$—$(C(R)_2)_r$($X_{10})_t$—$(C(R)_2)_u$—, is up to 20 atoms, $R_3$, $R_4$, $R_5$, $R_6$ are at each occurrence independently R', $R_7$ is R' in case m is 0 and $R_7$ is $R_1$ in case m is 1.

The invention relates further to compositions comprising at least one of said compounds of formula (I) and/or their polymerized forms as well as to articles comprising at least one polymerized compound of formula (I).

In addition, the invention relates to a process for forming such article, said process comprising the steps of
 providing a composition comprising at least one compound of formula (I) and/or an oligomer or polymer as described before;
 subsequently forming the article of said composition.

Furthermore, the invention relates to a process for changing the optical properties of an article according to the invention, said process comprising the steps of
 providing an article comprising at least one polymerized compound of formula (I), and
 subsequently exposing said article to irradiation having a wavelength of at least 200 nm and at most 1500 nm.

DETAILED DESCRIPTION OF THE INVENTION

The compounds of formula (I) and all preferred embodiments of compounds of formula (I) according to the present invention include all stereoisomers or racemic mixtures.

The compounds of formula (I) provide several advantages over prior art materials
 by adding a linker —[B]— to the benzo[b]furan, benzo[b]thiophene or benzo[b]pyrrol ring system their melting point or glass transition temperature will decrease and π stacking will be disturbed, thus becoming better foldable or bendable,
 by incorporating at least one F atom or at least one partially or fully fluorinated alkyl group they develop a non-sticky behavior with characteristic surfactant properties; through their non-stickiness the compounds show a smoother behavior in a physiological environment.

In comparison to known coumarin-type photoactive chromophores, compounds according to the invention are more stable toward UV-irradiation due to lower absorption range. Furthermore the chemical and hydrolytical stability is higher and given due to their intrinsic chemical nature e.g. due to lack of positions prone to nucleophilic attacks, like $sp^2$ centers and the absence of cyclic lactone structure motifs, compared to coumarin-type photoactive chromophores.

Polymers that are foldable at room temperature generally exhibit glass transition temperatures ($T_g$) lower than room temperature (ca. 21° C.). They are easily deformable at this temperature without causing physical damage to the polymer, for example by inducing creep, stress or fissures. For polymers in intraocular lenses, $T_g$s of less than or equal to 15° C. are preferred.

Polymers used in intraocular lens manufacturing have preferably relative high refractive indices, which enable the fabrication of thinner intraocular lenses. Preferably, the polymer used in an intraocular lens will have a refractive index greater than about 1.5 and presently most preferably greater than about 1.55.

In case an asterisk ("*") is used within the description of the present invention, it denotes a linkage to an adjacent unit or group or, in case of a polymer, to an adjacent repeating unit or any other group.

A linear or branched alkyl group having 1 to 10 C atoms denotes an alkyl group having 1, 2, 3, 4, 5, 6, 7, 8, 9 or 10 C atoms, for example methyl, ethyl, iso-propyl, n-propyl, iso-butyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl or n-decyl. A linear or branched alkyl group having 1 to 20 C atoms include all examples for a linear or branched alkyl group having 1 to 10 C atoms including any alkyl group having 11, 12, 13, 14, 15, 16, 17, 18, 19 and 20 C atoms such as n-undecyl, n-dodecyl, n-tridecyl, n-tetradecyl, n-pentadecyl, n-hexadecyl, n-heptadecyl, n-octadecyl, n-nonadecyl and n-eicosyl.

The term partially halogenated alkyl group denotes that at least one H atom of the alkyl group is replaced by F, Cl, Br or I. Preferably, the alkyl group is partially fluorinated meaning that at least one H atom of the alkyl group is replaced by F.

The term completely halogenated alkyl group denotes that all H atoms of the alkyl group are replaced by F, Cl, Br and/or I. Preferably, the alkyl group is completely fluorinated meaning that all H atoms of the alkyl group are replaced by F. A preferred completely fluorinated alkyl group is trifluoromethyl.

The term halogenated or preferably fluorinated corresponds additionally to other groups such as a halogenated cycloalkyl group, a halogenated alkoxy group or a halogenated thioalkyl group.

A cycloalkyl group having 3 to 6 C atoms includes cyclopropyl, cyclobutyl, cyclopentyl and cyclohexyl which may be partially or completely halogenated or fluorinated as explained before.

A linear or branched alkoxy group having 1 to 20 C atoms denotes an O-alkyl group having 1, 2, 3, 4, 5, 6, 7, 8, 9, 10, 11, 12, 13, 14, 15, 16, 17, 18, 19 or 20 C atoms, for example methoxy, ethoxy, iso-propoxy, n-propoxy, iso-butoxy, n-butoxy, tert-butoxy, n-pentyloxy, 1-, 2- or 3-methylbutyloxy, 1,1-, 1,2- or 2,2-dimethylpropoxy, 1-ethylpropoxy, n-hexyloxy, n-heptyloxy, n-octyloxy, ethylhexyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-nonadecyloxy and n-eicosyloxy which may be partially or completely halogenated or preferably may be partially or completely fluorinated. A preferred completely fluorinated alkoxy group is trifluoromethoxy.

A linear or branched thioalkyl group having 1 to 20 C atoms denotes a S-alkyl group having 1, 2, 3, 4, 5, 6, 7, 8, 9, 10, 11, 12, 13, 14, 15, 16, 17, 18, 19 or 20 C atoms, for example thiomethyl, 1-thioethyl, 1-thio-iso-propyl, 1-thio-n-propoyl, 1-thio-iso-butyl, 1-thio-n-butyl, 1-thio-tert-butyl, 1-thio-n-pentyl, 1-thio-1-, -2- or -3-methylbutyl, 1-thio-1,1-, -1,2- or -2,2-dimethylpropyl, 1-thio-1-ethylpropyl, 1-thio-n-hexyl, 1-thio-n-heptyl, 1-thio-n-octyl, 1-thio-ethylhexyl, 1-thio-n-nonyl, 1-thio-n-decyl, 1-thio-n-undecyl, 1-thio-n-dodecyl, 1-thio-n-tridecyl, 1-thio-n-tetradecyl, 1-thio-n-pentadecyl, 1-thio-n-hexadecyl, 1-thio-n-heptadecyl, 1-thio-n-octadecyl, 1-thio-n-nonadecyl and 1-thio-n-eicosyl which may be partially or completely halogenated or preferably may be partially or completely fluorinated. A preferred completely fluorinated thioether group is trifluoromethyl thioether.

Preferred alkyl and alkoxy radicals have 1, 2, 3, 4, 5, 6, 7, 8, 9 or 10 C atoms.

A polymerizable group is a group which can be subject to or can undergo polymerization thus forming an oligomer or a polymer.

Polymerization is the process of taking individual monomers and chaining them together to make longer units. These longer units are called polymers. The compounds of formula (I) as described before and preferably described below are suitable monomers.

Within the gist of the invention, the polymerizable group $R_1$ once oligomerized or polymerized thus forms or is part of the backbone of the oligomer or polymer comprising polymerized compounds of formula (I). Suitable polymerizable groups contain at least one double bond or at least one triple bond thus forming polymers where the linking is formed via carbon-carbon bonds. Alternatively, a suitable polymerizable group may contain silicon thus forming polysiloxanes or polysilazanes.

The suitable polymerizable groups are selected from the group consisting of an alkenyl group of formula (5),

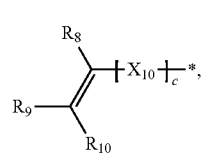
(5)

wherein
$X_{10}$ is selected from the group consisting of O, S, C(=O), C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1;
trialkoxysilyl groups or dialkoxyalkylsilyl groups where the alkyl and/or alkoxy groups are each independently linear or branched having 1 to 6 C atoms; and
silyl groups of formula (6), (7) or (8),

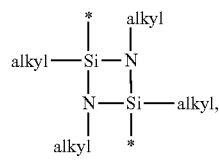
(6)

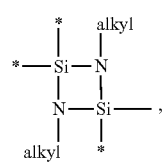
(7)

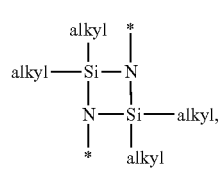
(8)

where alkyl means at each occurrence independently of each other a linear or branched alkyl group having 1 to 6 C atoms and the asterisk "*" denotes at each occurrence independently of each other a linkage to the linker [—$R_2$—Y]$_n$ and/or [Y—$R_2$-]$_m$ as described before or preferably described before.

A preferred polymerizable group is selected from the group consisting of trimethoxysilyl, triethoxysilyl, diethoxymethylsilyl and the alkenyl group of formula (5) as described before and preferably described below.

Aryl with 6 to 14 C atoms is an aryl group preferably selected from the group consisting of phenyl, naphthyl or anthryl, particularly preferably phenyl.

The linker —[B]— is selected from the group of formulae (1) to (4), wherein $X_1$, $X_2$, $X_3$, $X_4$ are each independently of each other CR' or N, $X_5$ is each independently O, S, C=O or NR$_0$ and $X_6$ and $X_7$ are each independently CR' or N, wherein R' and $R_0$ have a meaning as described before or preferably described below.

Preferred examples for the linker —[B]— are therefore selected from the group of formulae (B-1) to (B-34),

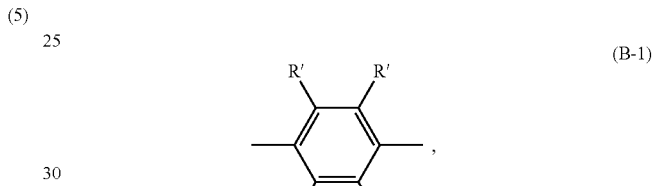
(B-1)

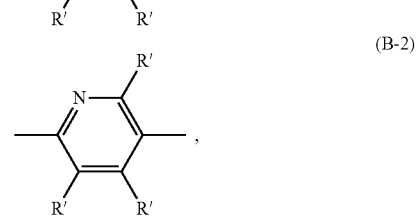
(B-2)

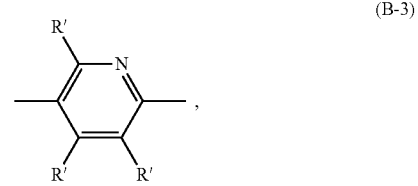
(B-3)

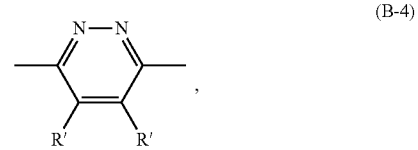
(B-4)

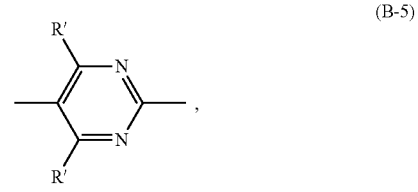
(B-5)

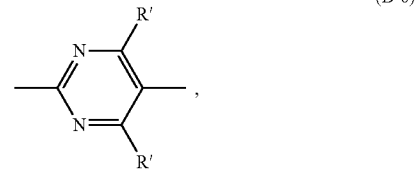
(B-6)

(B-7) 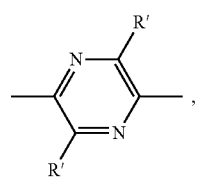
(B-8) 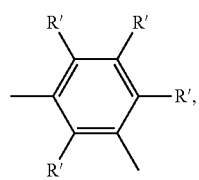
(B-9) 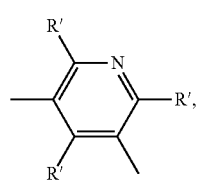
(B-10) 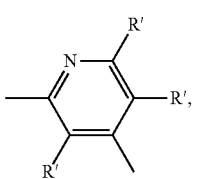
(B-11) 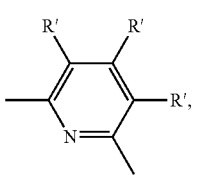
(B-12) 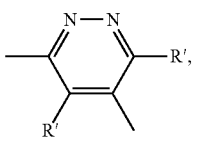
(B-13) 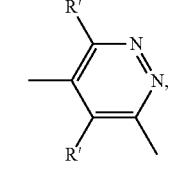
(B-14) 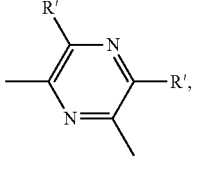
(B-15) 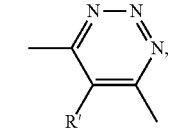
(B-16) 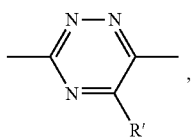
(B-17) 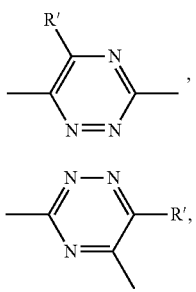
(B-18) 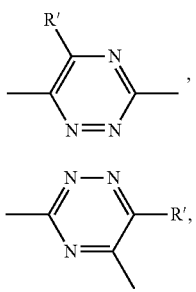
(B-19) 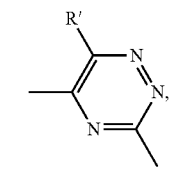
(B-20) 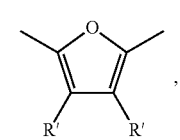
(B-21) 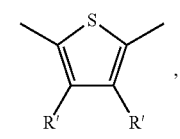
(B-22) 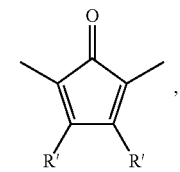
(B-23) 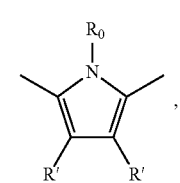
(B-24) 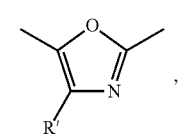
(B-25) 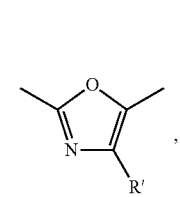

-continued

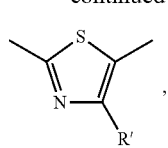 (B-26)

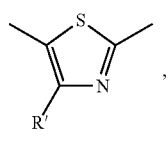 (B-27)

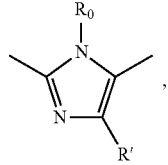 (B-28)

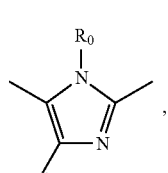 (B-29)

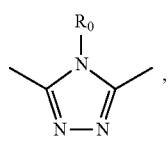 (B-30)

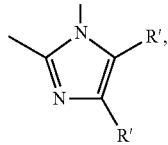 (B-31)

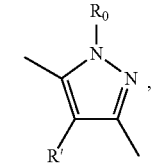 (B-32)

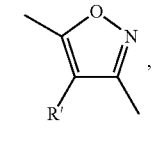 (B-33)

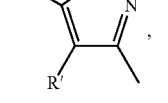 (B-34)

wherein R' and $R_0$ have a meaning as described before or preferably described below.

Compounds of formula (I) as described before are preferred where the linker —[B]— corresponds to formula (1) or (2) and $X_1$, $X_2$, $X_3$ and $X_4$ have a meaning as described before. Therefore, compounds of formula (I) are preferred where the linker —[B]— corresponds to formulae (B-1) to (B-19).

The invention therefore relates additionally to compounds of formula (I) as described before wherein —[B]— corresponds to formula (1) and (2) and $X_1$, $X_2$, $X_3$ and $X_4$ have a meaning as described before.

Compounds of formula (I) as described before are particularly preferred where the linker —[B]— corresponds to formula (1) or (2) and $X_1$, $X_3$ and $X_4$ are CR' and R' has at each occurrence independently a meaning as described before or preferably described below. Therefore, compounds of formula (I) are particularly preferred where the linker —[B]— corresponds to formulae (B-1), (B-3), (B-8) or (B-9).

The invention therefore relates additionally to compounds of formula (I) as described before wherein —[B]— corresponds to formula (1) and (2) and $X_1$, $X_3$ and $X_4$ are CR' and R' has at each occurrence independently a meaning as described before or preferably described below.

Compounds of formula (I) as described or preferably described before are especially preferred where the linker —[B]— corresponds to formula (1) or (2) and $X_2$ is CR' and R' has at each occurrence independently a meaning as described before or preferably described below. Therefore, compounds of formula (I) are especially preferred where the linker —[B]— corresponds to formulae (B-1), (B-2), (B-6), (B-7), (B-8), (B-10) or (B-11). Additionally, compounds of formula (I) having a linker —[B]— which corresponds to formula (B-1) or (B-8) are very particularly preferred and R' has at each occurrence independently a meaning as described before or preferably described below. Within this very particular preferred compounds of formula (I), it is preferred to select the linker of formula (B-1) and R' has at each occurrence independently a meaning as described before or preferably described below.

The invention therefore relates additionally to compounds of formula (I) as described or preferably described before wherein —[B]— corresponds to formula (1) and (2) and $X_2$ is CR' and R' has at each occurrence independently a meaning as described before or preferably described below.

R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms. It is preferred that at least one R' in —[B]— as described before or preferably described before is different from H and is selected from the group consisting of F, a linear or branched, non-halogenated, partially or completely halogenated alkyl group having 1 to 20 C atoms, a non-halogenated, a linear or branched hydroxyalkyl group having 1 to 20 C atoms, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms. It is particularly preferred that at least two R' are different from H and are independently selected from the group consisting of F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thio-alkyl group having 1 to 20 C atoms.

With regard to said substituent R', R' is at each occurrence independently preferably selected from the group consisting of H, F, a linear or branched, non-halogenated, partially or completely halogenated alkyl group having 1 to 10 C atoms, a linear or branched, non-halogenated and a partially or completely halogenated alkoxy group having 1 to 10 C atoms.

It is preferred that at least one R' in —[B]— as described before or preferably described before is different from H and is selected from the group consisting of F, a linear or branched, non-halogenated, partially or completely halogenated alkyl group having 1 to 10 C atoms, a linear or branched, non-halogenated and a partially or completely halogenated alkoxy group having 1 to 10 C atoms.

It is particularly preferred that at least two R' are different from H and are independently selected from the group consisting of F, a linear or branched, non-halogenated, partially or completely halogenated alkyl group having 1 to 10 C atoms, a linear or branched, non-halogenated and a partially or completely halogenated alkoxy group having 1 to 10 C atoms.

R' is at each occurrence independently particularly preferably selected from the group consisting of H, F, methyl, ethyl, n-propyl, n-butyl, n-pentyl, n-hexyl, n-heptyl, n-octyl, trifluoromethyl, pentafluoroethyl, heptafluoropropyl, methoxy, ethoxy, propoxy, trifluoromethoxy and pentafluoroethoxy.

R' is at each occurrence independently very particularly preferably selected from the group consisting of H, F, ethyl, n-pentyl, trifluoromethyl, methoxy, and trifluoromethoxy.

Therefore, the invention is further directed to compounds of formula (I) as described before where —[B]— corresponds to formulae (1) to (4) and wherein at least one R' within $X_1$, $X_2$, $X_3$, $X_4$, $X_6$ or $X_7$ is not H.

Therefore, the invention is further directed to compounds of formula (I) as described before where —[B]— corresponds to formulae (B-1) to (B-29) or (B-31) to (B-34) or to preferred linkers as described before, wherein at least one R' is not H and $R_0$ has a meaning as described before or preferably described below.

The substituent R' within $X_1$ or $X_3$ in formula (1) is particularly preferred not H.

The substituent R' within $X_7$ in formula (3) is particularly preferred not H.

As described before, the substituents $R_3$, $R_4$, $R_5$ and $R_6$ are at each occurrence independently R' where R' has a meaning or a preferred or particularly preferred meaning as described before.

$R_5$ is preferably H or F. $R_5$ is particularly preferably H.

As described before, the substituent $R_7$ corresponds to R' in case m is 0 wherein R' has a meaning or a preferred or particularly preferred meaning as described before. Preferably, $R_7$ corresponds to R' which is not H in case m is 0.

In all cases when R' is preferably not H, it is selected from the preferred group consisting of F, methyl, ethyl, n-propyl, n-butyl, n-pentyl, n-hexyl, n-heptyl, n-octyl, trifluoromethyl, pentafluoroethyl, heptafluoropropyl, methoxy, ethoxy, propoxy, trifluoromethoxy and pentafluoroethoxy or from the particular preferred group consisting of F, ethyl, n-pentyl, trifluoromethyl, methoxy and trifluoromethoxy.

Therefore, the invention is further directed to compounds of formula (I) as described before where —[B]— corresponds to formulae (1) to (4) and wherein at least one R' within $X_1$, $X_2$, $X_3$. $X_4$, $X_6$ or $X_7$ is not H and $R_7$ is not H in case m is 0.

Therefore, the invention is further directed to compounds of formula (I) as described before where —[B]— corresponds to formulae (B-1) to (B-29) or (B-31) to (B-34) or to preferred linkers as described before, wherein at least one R' is not H and $R_7$ is not H in case m is 0 and $R_0$ has a meaning as described before or as preferably described below.

As described before, the substituent $R_7$ corresponds to $R_1$ in case m is 1 wherein $R_1$ has a meaning or a preferred meaning as described before or further below. Compounds of formula (I) in which m is 1 are preferred having a linker —[B]— selected from the group consisting of formula (1) to (4) wherein at least one substituent R' within $X_1$, $X_2$, $X_3$, $X_4$, $X_6$ or $X_7$ is not H and in which at least one substituent $R_3$, $R_4$ or $R_6$ is not H.

Therefore, the invention is further directed to compounds of formula (I) as described before where —[B]— corresponds to formulae (1) to (4) and wherein at least one R' within $X_1$, $X_2$, $X_3$. $X_4$, $X_6$ or $X_7$ is not H, in which at least one substituent $R_3$, $R_4$ or $R_6$ is not H and $R_7$ corresponds to $R_1$ in case m is 1.

Therefore, the invention is further directed to compounds of formula (I) as described before where —[B]— corresponds to formulae (B-1) to (B-29) or (B-31) to (B-34) or to preferred linkers as described before, wherein at least one R' is not H, in which at least one substituent $R_3$, $R_4$ or $R_6$ is not H and $R_7$ corresponds to $R_1$ in case m is 1 wherein $R_0$ and $R_1$ has a meaning as described before or further below.

Compounds of formula (I) with linkers —[B]— as defined before or preferably defined before with the described or preferred substitution pattern on the linker —[B]— and its substituents $R_3$, $R_4$, $R_5$ and $R_6$ as described before or preferably described before are based on a benzo[b]furan ring system in case X is O.

Compounds of formula (I) with linkers —[B]— as defined before or preferably defined before with the described or preferred substitution pattern on the linker —[B]— and its substituents $R_3$, $R_4$, $R_5$ and $R_6$ as described before or preferably described before are based on a benzo[b]thiophene ring system in case X is S.

Compounds of formula (I) with linkers —[B]— as defined before or preferably defined before with the described or preferred substitution pattern on the linker —[B]— and its substituents $R_3$, $R_4$, $R_5$ and $R_6$ as described before or preferably described before are based on a benzo[b]pyrrol ring system in case X is $NR_0$ and $R_0$ is independently selected from the group consisting of a linear or branched alkyl group having 1 to 10 C atoms or a cycloalkyl group having 3 to 6 C atoms.

$R_0$ is at each occurrence independently preferably methyl, ethyl, iso-propyl, 2-methyl-propyl, n-butyl, n-pentyl, 4-methyl-pentyl or cyclopropyl.

In case X is $NR_0$, $R_0$ is particularly preferably ethyl, iso-propyl, 2-methyl-propyl, n-pentyl or 4-methyl-pentyl.

In case $X_5$ is $NR_0$, $R_0$ is particularly preferably methyl or n-butyl. In case $X_8$, $X_9$ or $X_{10}$ is $NR_0$, $R_0$ is particularly preferably methyl.

Compounds of formula (I) with linkers and substituents as described before or preferably described before or below are preferred when X is O or S.

Compounds of formula (I) with linkers and substituents as described before or preferably described before or below are particularly preferred when X is O.

In one preferred embodiment of the invention, the compounds of formula (I) as described before or preferably described before contain one polymerizable group $R_1$. This is the case for compounds of formula (I) in which n is 1 or m is 1 and the sum of n and m is 1. Such compounds can be preferably used as monomers for the preparation of a blank which may be transformed to an ophthalmic device such as an eye-implant or specifically an intraocular lens or to the ophthalmic device as such as described before.

The invention is therefore additionally directed to compounds of formula (I) wherein n is 1 and m is 0 which can preferably be described according to formula (I')

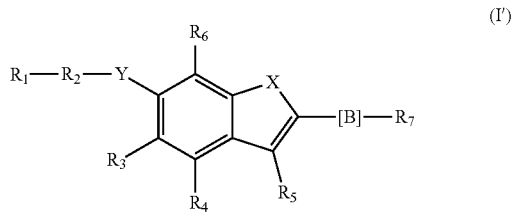

wherein $R_1$, —$R_2$—, Y, $R_3$, $R_4$, $R_5$, $R_6$, X, —[B]— and $R_7$ have a meaning as described before or preferably described before or below.

The invention is therefore additionally directed to compounds of formula (I) wherein n is 0 and m is 1 which can preferably be described according to formula (I")

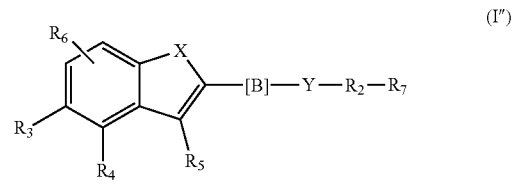

wherein $R_1$, —$R_2$—, Y, $R_3$, $R_4$, $R_5$, $R_6$, X, —[B]— and $R_7$ have a meaning as described before or preferably described before or below.

In another preferred embodiment of the invention, the compounds of formula (I) as described before or preferably described before contain two polymerizable groups $R_1$. This is the case for compounds of formula (I) in which n is 1 and m is 1 and the sum of n and m is 2. Such compounds can be preferably used as cross-linking agent for the preparation of a blank which may be transformed to an ophthalmic device such as an eye-implant or specifically an intraocular lens or to the ophthalmic device as such as described before.

The invention is therefore additionally directed to compounds of formula (I) wherein n is 1 and m is 1 which can preferably be described according to formula (I''')

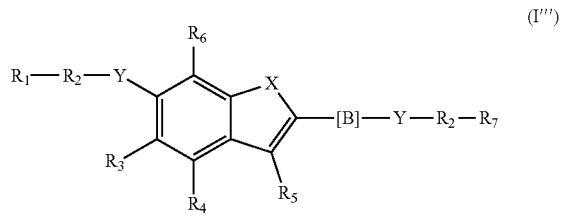

wherein $R_1$, —$R_2$—, Y, $R_3$, $R_4$, $R_5$, $R_6$, X, —[B]— and $R_7$ have a meaning as described before or preferably described before or below.

Compounds of formula (I), (I'), (I") and (I''') with linkers —[B]— and substituents as described before or preferably described before have a polymerizable group as described before or preferably described before or below and have at least one linking element Y—$R_2$—.

Y is at each occurrence independently O, S or a bond.

The linking element —$R_2$— is selected from the group consisting of —$(C(R)_2)_o$— wherein at least one R is F or a linear or branched partially or fully fluorinated alkyl group having 1 to 4 C atoms, —$(C(R)_2)_p$—$X_8$—$(C(R)_2)_q$—$(X_9)_s$—$(C(R)_2)_r$—$(X_{10})_t$—$(C(R)_2)_u$—, wherein at least one R is F or a linear or branched partially or fully fluorinated alkyl group having 1 to 4 C atoms and a cycloalkylene group having 5 or 6 C atoms which is substituted with at least one R which is F or a linear or branched partially or fully fluorinated alkyl group having 1 to 4 C atoms and o is selected from the group consisting of 1 to 20, $X_8$, $X_9$ and $X_{10}$ are at each occurrence O, S or $NR_0$, s and t are at each occurrence independently 0 or 1, p and q are at each occurrence independently selected from the group consisting of 1 to 10, r and u are at each occurrence independently selected from the group consisting of 0 to 10, wherein the overall number of atoms for —$(C(R)_2)_p$—$X_8$—$(C(R)_2)_q$—$(X_9)_s$—$(C(R)_2)_r$—$(X_{10})_t$—$(C(R)_2)_u$—, is up to 20 C atoms.

Preferably, the linking element —$R_2$— is selected from the group consisting of —$(C(R)_2)_o$— wherein at least two R are F, —$(C(R)_2)_p$—$X_8$—$(C(R)_2)_q$—$(X_9)_s$—$(C(R)_2)_r$—$(X_{10})_t$—$(C(R)_2)_u$—, wherein at least two R are F and a cycloalkylene group having 5 or 6 C atoms which is substituted with at least one R which is F or a linear or branched partially or fully fluorinated alkyl group having 1 to 4 C atoms and o, $X_8$, $X_9$, $X_{10}$, s, t, p, q, r and u have a meaning as described or preferably described before or below.

R is at each occurrence independently selected from the group consisting of H, F, a linear or branched alkyl group having 1 to 8 C atoms or a linear or branched partially or fully fluorinated alkyl group having 1 to 4 C atoms.

R is preferably at each occurrence independently selected from the group consisting of H, F, methyl, ethyl, n-propyl, isopropyl, n-butyl, n-pentyl, isobutyl, ethylhexyl, 2,2,2-trifluoroethyl, 3,3,3-trifluoropropyl, 2,2,3,3,3-pentafluoropropyl, trifluoromethyl, pentafluoroethyl, heptafluoropropyl and nonafluorobutyl. R is particularly preferably at each occurrence independently H, F, methyl, 2,2,2-trifluoroethyl or trifluoromethyl.

Preferably, o is selected from the group consisting of 3 to 12, particularly preferably 8 to 12.

Preferably, s is 1.

Preferably t is 0 or 1.

Preferably, $X_8$, $X_9$ and $X_{10}$ are O.

Preferably, p and u are each independently 1, 3, 3, 4, 5 or 6, particularly preferably 1 or 2.

Preferably, q and r are each independently 1, 2 or 3, particularly preferably 1.

Suitable examples for —$R_2$— are
—$(CF_2)$—$(CH_2)$—, —$(CH_2)$—$(CF_2)$—, —$(CH_2)$—$(CF_2)$—$(CH_2)$—, —$(CH_2)$—$(CF_2)$—$(CH_2)_2$—, —$(CH_2)$—$(CF_2)$—$(CH_2)_3$—, —$(CH_2)$—$(CF_2)$—$(CH_2)_4$—, —$(CH_2)$—$(CF_2)$—$(CH_2)_5$—, —$(CH_2)$—$(CF_2)$—$(CH_2)_6$—, —$(CH_2)$—$(CF_2)$—$(CH_2)_7$—, —$(CH_2)$—$(CF_2)$—$(CH_2)_8$—, —$(CH_2)$—$(CF_2)$—$(CH_2)_9$—, —$(CH_2)$—$(CF_2)$—$(CH_2)_{10}$—, —$(CH_2)_2$—$(CF_2)$—$(CH_2)$—, —$(CH_2)_3$—$(CF_2)$—$(CH_2)$—, —$(CH_2)_4$—$(CF_2)$—$(CH_2)$—, —$(CH_2)_5$—$(CF_2)$—$(CH_2)$—, —$(CH_2)_6$—$(CF_2)$—$(CH_2)$—, —$(CH_2)_7$—$(CF_2)$—$(CH_2)$—, —$(CH_2)_8$—$(CF_2)$—$(CH_2)$—, —$(CH_2)_9$—$(CF_2)$—$(CH_2)$—, —$(CH_2)_{10}$—

—(CF$_2$)—(CH$_2$)—, —(CH$_2$)$_2$—(CF$_2$)—(CH$_2$)$_2$—, —(CH$_2$)$_3$—(CF$_2$)—(CH$_2$)$_3$—, —(CH$_2$)$_4$—(CF$_2$)—(CH$_2$)$_4$—, —(CH$_2$)$_5$—(CF$_2$)—(CH$_2$)$_5$—, —(CH$_2$)$_2$—(CF$_2$)—(CH$_2$)—, —(CH$_2$)$_2$—(CF$_2$)—(CH$_2$)$_3$—, —(CH$_2$)$_2$—(CF$_2$)—(CH$_2$)$_4$—, —(CH$_2$)$_2$—(CF$_2$)—(CH$_2$)$_5$—, —(CH$_2$)$_2$—(CF$_2$)—(CH$_2$)$_6$—, —(CH$_2$)$_2$—(CF$_2$)—(CH$_2$)$_7$—, —(CH$_2$)$_2$—(CF$_2$)—(CH$_2$)$_8$—, —(CH$_2$)$_2$—(CF$_2$)—(CH$_2$)$_9$—, —(CH$_2$)$_3$—(CF$_2$)—(CH$_2$)—, —(CH$_2$)$_3$—(CF$_2$)—(CH$_2$)$_2$—, —(CH$_2$)$_3$—(CF$_2$)—(CH$_2$)$_4$—, —(CH$_2$)$_3$—(CF$_2$)—(CH$_2$)$_5$—, —(CH$_2$)$_3$—(CF$_2$)—(CH$_2$)$_6$—, —(CH$_2$)$_3$—(CF$_2$)—(CH$_2$)$_7$—, —(CH$_2$)$_3$—(CF$_2$)—(CH$_2$)$_8$—, —(CH$_2$)$_4$—(CF$_2$)—(CH$_2$)—, —(CH$_2$)$_4$—(CF$_2$)—(CH$_2$)$_2$—, —(CH$_2$)$_4$—(CF$_2$)—(CH$_2$)$_3$—, —(CH$_2$)$_4$—(CF$_2$)—(CH$_2$)$_5$—, —(CH$_2$)$_4$—(CF$_2$)—(CH$_2$)$_6$—, —(CH$_2$)$_4$—(CF$_2$)—(CH$_2$)$_7$—, —(CH$_2$)$_5$—(CF$_2$)—(CH$_2$)—, —(CH$_2$)$_5$—(CF$_2$)—(CH$_2$)$_2$—, —(CH$_2$)$_5$—(CF$_2$)—(CH$_2$)$_3$—, —(CH$_2$)$_5$—(CF$_2$)—(CH$_2$)$_4$—, —(CH$_2$)$_5$—(CF$_2$)—(CH$_2$)$_6$—, —(CH$_2$)$_6$—(CF$_2$)—(CH$_2$)—, —(CH$_2$)$_6$—(CF$_2$)—(CH$_2$)$_2$—, —(CH$_2$)$_6$—(CF$_2$)—(CH$_2$)$_3$—, —(CH$_2$)$_6$—(CF$_2$)—(CH$_2$)$_4$—, —(CH$_2$)$_6$—(CF$_2$)—(CH$_2$)$_5$—,

—(CFH)—(CH$_2$)—, —(CH$_2$)—(CFH)—, —(CH$_2$)—(CFH)—(CH$_2$)—, —(CH$_2$)—(CFH)—(CH$_2$)$_2$—, —(CH$_2$)—(CFH)—(CH$_2$)$_3$—, —(CH$_2$)—(CFH)—(CH$_2$)$_4$—, —(CH$_2$)—(CFH)—(CH$_2$)$_5$—, —(CH$_2$)—(CFH)—(CH$_2$)$_6$—, —(CH$_2$)—(CFH)—(CH$_2$)$_7$—, —(CH$_2$)—(CFH)—(CH$_2$)$_8$—, —(CH$_2$)—(CFH)—(CH$_2$)$_9$—, —(CH$_2$)—(CFH)—(CH$_2$)$_{10}$—, —(CH$_2$)$_2$—(CFH)—(CH$_2$)—, —(CH$_2$)$_3$—(CFH)—(CH$_2$)—, —(CH$_2$)$_4$—(CFH)—(CH$_2$)—, —(CH$_2$)$_5$—(CFH)—(CH$_2$)—, —(CH$_2$)$_6$—(CFH)—(CH$_2$)—, —(CH$_2$)$_7$—(CFH)—(CH$_2$)—, —(CH$_2$)$_8$—(CFH)—(CH$_2$)—, —(CH$_2$)$_9$—(CFH)—(CH$_2$)—, —(CH$_2$)$_{10}$—(CFH)—(CH$_2$)—, —(CH$_2$)$_2$—(CFH)—(CH$_2$)$_2$—, —(CH$_2$)$_3$—(CFH)—(CH$_2$)$_3$—, —(CH$_2$)$_4$—(CFH)—(CH$_2$)$_4$—, —(CH$_2$)$_5$—(CFH)—(CH$_2$)$_5$—, —(CH$_2$)$_2$—(CFH)—(CH$_2$)—, —(CH$_2$)$_2$—(CFH)—(CH$_2$)$_3$—, —(CH$_2$)$_2$—(CFH)—(CH$_2$)$_4$—, —(CH$_2$)$_2$—(CFH)—(CH$_2$)$_5$—, —(CH$_2$)$_2$—(CFH)—(CH$_2$)$_6$—, —(CH$_2$)$_2$—(CFH)—(CH$_2$)$_7$—, —(CH$_2$)$_2$—(CFH)—(CH$_2$)$_8$—, —(CH$_2$)$_2$—(CFH)—(CH$_2$)$_9$—, —(CH$_2$)$_3$—(CFH)—(CH$_2$)—, —(CH$_2$)$_3$—(CFH)—(CH$_2$)$_2$—, —(CH$_2$)$_3$—(CFH)—(CH$_2$)$_4$—, —(CH$_2$)$_3$—(CFH)—(CH$_2$)$_5$—, —(CH$_2$)$_3$—(CFH)—(CH$_2$)$_6$—, —(CH$_2$)$_3$—(CFH)—(CH$_2$)$_7$—, —(CH$_2$)$_3$—(CFH)—(CH$_2$)$_8$—, —(CH$_2$)$_4$—(CFH)—(CH$_2$)—, —(CH$_2$)$_4$—(CFH)—(CH$_2$)$_2$—, —(CH$_2$)$_4$—(CFH)—(CH$_2$)$_3$—, —(CH$_2$)$_4$—(CFH)—(CH$_2$)$_5$—, —(CH$_2$)$_4$—(CFH)—(CH$_2$)$_6$—, —(CH$_2$)$_4$—(CFH)—(CH$_2$)$_7$—, —(CH$_2$)$_5$—(CFH)—(CH$_2$)—, —(CH$_2$)$_5$—(CFH)—(CH$_2$)$_2$—, —(CH$_2$)$_5$—(CFH)—(CH$_2$)$_3$—, —(CH$_2$)$_5$—(CFH)—(CH$_2$)$_4$—, —(CH$_2$)$_5$—(CFH)—(CH$_2$)$_6$—, —(CH$_2$)$_6$—(CFH)—(CH$_2$)—, —(CH$_2$)$_6$—(CFH)—(CH$_2$)$_2$—, —(CH$_2$)$_6$—(CFH)—(CH$_2$)$_3$—, —(CH$_2$)$_6$—(CFH)—(CH$_2$)$_4$—, —(CH$_2$)$_6$—(CFH)—(CH$_2$)$_5$—,

—(CF$_2$)$_2$—(CH$_2$)—, —(CH$_2$)—(CF$_2$)$_2$—, —(CH$_2$)—(CF$_2$)$_2$—(CH$_2$)—, —(CH$_2$)—(CF$_2$)$_2$—(CH$_2$)$_2$—, —(CH$_2$)—(CF$_2$)$_2$—(CH$_2$)$_3$—, —(CH$_2$)—(CF$_2$)$_2$—(CH$_2$)$_4$—, —(CH$_2$)—(CF$_2$)$_2$—(CH$_2$)$_5$—, —(CH$_2$)—(CF$_2$)$_2$—(CH$_2$)$_6$—, —(CH$_2$)—(CF$_2$)$_2$—(CH$_2$)$_7$—, —(CH$_2$)—(CF$_2$)$_2$—(CH$_2$)$_8$—, —(CH$_2$)—(CF$_2$)$_2$—(CH$_2$)$_9$—, —(CH$_2$)$_2$—(CF$_2$)$_2$—(CH$_2$)—, —(CH$_2$)$_3$—(CF$_2$)$_2$—(CH$_2$)—, —(CH$_2$)$_4$—(CF$_2$)$_2$—(CH$_2$)—, —(CH$_2$)$_5$—(CF$_2$)$_2$—(CH$_2$)—, —(CH$_2$)$_6$—(CF$_2$)$_2$—(CH$_2$)—, —(CH$_2$)$_7$—(CF$_2$)$_2$—(CH$_2$)—, —(CH$_2$)$_8$—(CF$_2$)$_2$—(CH$_2$)—, —(CH$_2$)$_2$—(CF$_2$)$_2$—(CH$_2$)$_2$—, —(CH$_2$)$_3$—(CF$_2$)$_2$—(CH$_2$)$_3$—, —(CH$_2$)$_4$—(CF$_2$)$_2$—(CH$_2$)$_4$—, —(CH$_2$)$_5$—(CF$_2$)$_2$—(CH$_2$)$_5$—, —(CH$_2$)$_2$—(CF$_2$)$_2$—(CH$_2$)—, —(CH$_2$)$_2$—(CF$_2$)$_2$—(CH$_2$)$_3$—, —(CH$_2$)$_2$—(CF$_2$)$_2$—(CH$_2$)$_4$—, —(CH$_2$)$_2$—(CF$_2$)$_2$—(CH$_2$)$_5$—, —(CH$_2$)$_2$—(CF$_2$)$_2$—(CH$_2$)$_6$—, —(CH$_2$)$_2$—(CF$_2$)$_2$—(CH$_2$)$_7$—, —(CH$_2$)$_2$—(CF$_2$)$_2$—(CH$_2$)$_8$—, —(CH$_2$)$_3$—(CF$_2$)$_2$—(CH$_2$)—, —(CH$_2$)$_3$—(CF$_2$)$_2$—(CH$_2$)$_2$—, —(CH$_2$)$_3$—(CF$_2$)$_2$—(CH$_2$)$_4$—, —(CH$_2$)$_3$—(CF$_2$)$_2$—(CH$_2$)$_5$—, —(CH$_2$)$_3$—(CF$_2$)$_2$—(CH$_2$)$_6$—, —(CH$_2$)$_3$—(CF$_2$)$_2$—(CH$_2$)$_7$—, —(CH$_2$)$_4$—(CF$_2$)$_2$—(CH$_2$)—, —(CH$_2$)$_4$—(CF$_2$)$_2$—(CH$_2$)$_2$—, —(CH$_2$)$_4$—(CF$_2$)$_2$—(CH$_2$)$_3$—, —(CH$_2$)$_4$—(CF$_2$)$_2$—(CH$_2$)$_5$—, —(CH$_2$)$_4$—(CF$_2$)$_2$—(CH$_2$)$_6$—, —(CH$_2$)$_5$—(CF$_2$)$_2$—(CH$_2$)—, —(CH$_2$)$_5$—(CF$_2$)$_2$—(CH$_2$)$_2$—, —(CH$_2$)$_5$—(CF$_2$)$_2$—(CH$_2$)$_3$—, —(CH$_2$)$_5$—(CF$_2$)$_2$—(CH$_2$)$_4$—, —(CH$_2$)$_6$—(CF$_2$)$_2$—(CH$_2$)—, —(CH$_2$)$_6$—(CF$_2$)$_2$—(CH$_2$)$_2$—, —(CH$_2$)$_6$—(CF$_2$)$_2$—(CH$_2$)$_3$—, —(CH$_2$)$_6$—(CF$_2$)$_2$—(CH$_2$)$_4$—,

—(CFH)$_2$—(CH$_2$)—, —(CH$_2$)—(CFH)$_2$—, —(CH$_2$)—(CFH)$_2$—(CH$_2$)—, —(CH$_2$)—(CFH)$_2$—(CH$_2$)$_2$—, —(CH$_2$)—(CFH)$_2$—(CH$_2$)$_3$—, —(CH$_2$)—(CFH)$_2$—(CH$_2$)$_4$—, —(CH$_2$)—(CFH)$_2$—(CH$_2$)$_5$—, —(CH$_2$)—(CFH)$_2$—(CH$_2$)$_6$—, —(CH$_2$)—(CFH)$_2$—(CH$_2$)$_7$—, —(CH$_2$)—(CFH)$_2$—(CH$_2$)$_8$—, —(CH$_2$)—(CFH)$_2$—(CH$_2$)$_9$—, —(CH$_2$)$_2$—(CFH)$_2$—(CH$_2$)—, —(CH$_2$)$_3$—(CFH)$_2$—(CH$_2$)—, —(CH$_2$)$_4$—(CFH)$_2$—(CH$_2$)—, —(CH$_2$)$_5$—(CFH)$_2$—(CH$_2$)—, —(CH$_2$)$_6$—(CFH)$_2$—(CH$_2$)—, —(CH$_2$)$_7$—(CFH)$_2$—(CH$_2$)—, —(CH$_2$)$_8$—(CFH)$_2$—(CH$_2$)—, —(CH$_2$)$_9$—(CFH)$_2$—(CH$_2$)—, —(CH$_2$)$_2$—(CFH)$_2$—(CH$_2$)$_2$—, —(CH$_2$)$_3$—(CFH)$_2$—(CH$_2$)$_3$—, —(CH$_2$)$_4$—(CFH)$_2$—(CH$_2$)$_4$—, —(CH$_2$)$_5$—(CFH)$_2$—(CH$_2$)$_5$—, —(CH$_2$)$_2$—(CFH)$_2$—(CH$_2$)—, —(CH$_2$)$_2$—(CFH)$_2$—(CH$_2$)$_3$—, —(CH$_2$)$_2$—(CFH)$_2$—(CH$_2$)$_4$—, —(CH$_2$)$_2$—(CFH)$_2$—(CH$_2$)$_5$—, —(CH$_2$)$_2$—(CFH)$_2$—(CH$_2$)$_6$—, —(CH$_2$)$_2$—(CFH)$_2$—(CH$_2$)$_7$—, —(CH$_2$)$_2$—(CFH)$_2$—(CH$_2$)$_8$—, —(CH$_2$)$_3$—(CFH)$_2$—(CH$_2$)—, —(CH$_2$)$_3$—(CFH)$_2$—(CH$_2$)$_2$—, —(CH$_2$)$_3$—(CFH)$_2$—(CH$_2$)$_4$—, —(CH$_2$)$_3$—(CFH)$_2$—(CH$_2$)$_5$—, —(CH$_2$)$_3$—(CFH)$_2$—(CH$_2$)$_6$—, —(CH$_2$)$_3$—(CFH)$_2$—(CH$_2$)$_7$—, —(CH$_2$)$_4$—(CFH)$_2$—(CH$_2$)—, —(CH$_2$)$_4$—(CFH)$_2$—(CH$_2$)$_2$—, —(CH$_2$)$_4$—(CFH)$_2$—(CH$_2$)$_3$—, —(CH$_2$)$_4$—(CFH)$_2$—(CH$_2$)$_5$—, —(CH$_2$)$_4$—(CFH)$_2$—(CH$_2$)$_6$—, —(CH$_2$)$_5$—(CFH)$_2$—(CH$_2$)—, —(CH$_2$)$_5$—(CFH)$_2$—(CH$_2$)$_2$—, —(CH$_2$)$_5$—(CFH)$_2$—(CH$_2$)$_3$—, —(CH$_2$)$_5$—(CFH)$_2$—(CH$_2$)$_4$—, —(CH$_2$)$_6$—(CFH)$_2$—(CH$_2$)—, —(CH$_2$)$_6$—(CFH)$_2$—(CH$_2$)$_2$—, —(CH$_2$)$_6$—(CFH)$_2$—(CH$_2$)$_3$—, —(CH$_2$)$_6$—(CFH)$_2$—(CH$_2$)$_4$—,

—(CF$_2$)$_3$—(CH$_2$)—, —(CH$_2$)—(CF$_2$)$_3$—(CH$_2$)—, —(CH$_2$)—(CF$_2$)$_3$—(CH$_2$)$_2$—, —(CH$_2$)—(CF$_2$)$_3$—(CH$_2$)$_3$—, —(CH$_2$)—(CF$_2$)$_3$—(CH$_2$)$_4$—, —(CH$_2$)—(CF$_2$)$_3$—(CH$_2$)$_5$—, —(CH$_2$)—(CF$_2$)$_3$—(CH$_2$)$_6$—, —(CH$_2$)—(CF$_2$)$_3$—(CH$_2$)$_7$—, —(CH$_2$)—(CF$_2$)$_3$—(CH$_2$)$_8$—, —(CH$_2$)$_2$—(CF$_2$)$_3$—(CH$_2$)—, —(CH$_2$)$_3$—(CF$_2$)$_3$—(CH$_2$)—, —(CH$_2$)$_4$—(CF$_2$)$_3$—(CH$_2$)—, —(CH$_2$)$_5$—(CF$_2$)$_3$—(CH$_2$)—, —(CH$_2$)$_6$—(CF$_2$)$_3$—(CH$_2$)—, —(CH$_2$)$_7$—(CF$_2$)$_3$—(CH$_2$)—, —(CH$_2$)$_8$—(CF$_2$)$_3$—(CH$_2$)—, —(CH$_2$)$_2$—(CF$_2$)$_3$—(CH$_2$)$_2$—, —(CH$_2$)$_3$—(CF$_2$)$_3$—(CH$_2$)$_3$—, —(CH$_2$)$_4$—(CF$_2$)$_3$—(CH$_2$)$_4$—, —(CH$_2$)$_2$—(CF$_2$)$_3$—(CH$_2$)—, —(CH$_2$)$_2$—(CF$_2$)$_3$—(CH$_2$)$_3$—, —(CH$_2$)$_2$—(CF$_2$)$_3$—(CH$_2$)$_4$—, —(CH$_2$)$_2$—(CF$_2$)$_3$—(CH$_2$)$_5$—, —(CH$_2$)$_2$—(CF$_2$)$_3$—(CH$_2$)$_6$—, —(CH$_2$)$_2$—(CF$_2$)$_3$—(CH$_2$)$_7$—, —(CH$_2$)$_3$—(CF$_2$)$_3$—(CH$_2$)—, —(CH$_2$)$_3$—(CF$_2$)$_3$—(CH$_2$)$_2$—, —(CH$_2$)$_3$—(CF$_2$)$_3$—(CH$_2$)$_4$—, —(CH$_2$)$_3$—(CF$_2$)$_3$—(CH$_2$)$_5$—, —(CH$_2$)$_3$—(CF$_2$)$_3$—(CH$_2$)$_6$—, —(CH$_2$)$_4$—(CF$_2$)$_3$—(CH$_2$)—, —(CH$_2$)$_4$—(CF$_2$)$_3$—(CH$_2$)$_2$—, —(CH$_2$)$_4$—(CF$_2$)$_3$—(CH$_2$)$_3$—, —(CH$_2$)$_4$—(CF$_2$)$_3$—(CH$_2$)$_5$—, —(CH$_2$)$_5$—(CF$_2$)$_3$—

—(CH$_2$)—, —(CH$_2$)$_5$—(CF$_2$)$_3$—(CH$_2$)$_2$—, —(CH$_2$)$_5$—(CF$_2$)$_3$—(CH$_2$)$_3$—, —(CH$_2$)$_5$—(CF$_2$)$_3$—(CH$_2$)$_4$—, —(CH$_2$)$_6$—(CF$_2$)$_3$—(CH$_2$)—, —(CH$_2$)$_6$—(CF$_2$)$_3$—(CH$_2$)$_2$—, —(CH$_2$)$_6$—(CF$_2$)$_3$—(CH$_2$)$_3$—, —(CF$_2$)$_4$—(CH$_2$)—, —(CH$_2$)—(CF$_2$)$_4$—, —(CH$_2$)—(CF$_2$)$_4$—(CH$_2$)—, —(CH$_2$)—(CF$_2$)$_4$—(CH$_2$)$_2$—, —(CH$_2$)—(CF$_2$)$_4$—(CH$_2$)$_3$—, —(CH$_2$)—(CF$_2$)$_4$—(CH$_2$)$_4$—, —(CH$_2$)—(CF$_2$)$_4$—(CH$_2$)$_5$—, —(CH$_2$)—(CF$_2$)$_4$—(CH$_2$)$_6$—, —(CH$_2$)—(CF$_2$)$_4$—(CH$_2$)$_7$—, —(CH$_2$)—(CF$_2$)$_4$—(CH$_2$)$_8$—, —(CH$_2$)—(CF$_2$)$_4$—(CH$_2$)$_9$—, —(CH$_2$)—(CF$_2$)$_4$—(CH$_2$)$_{10}$—, —(CH$_2$)$_2$—(CF$_2$)$_4$—(CH$_2$)—, —(CH$_2$)$_3$—(CF$_2$)$_4$—(CH$_2$)—, —(CH$_2$)$_4$—(CF$_2$)$_4$—(CH$_2$)—, —(CH$_2$)$_5$—(CF$_2$)$_4$—(CH$_2$)—, —(CH$_2$)$_6$—(CF$_2$)$_4$—(CH$_2$)—, —(CH$_2$)$_7$—(CF$_2$)$_4$—(CH$_2$)—, —(CH$_2$)$_2$—(CF$_2$)$_4$—(CH$_2$)$_2$—, —(CH$_2$)$_3$—(CF$_2$)$_4$—(CH$_2$)$_3$—, —(CH$_2$)$_4$—(CF$_2$)$_4$—(CH$_2$)$_4$—, —(CH$_2$)$_5$—(CF$_2$)$_4$—(CH$_2$)$_5$—, —(CH$_2$)$_2$—(CF$_2$)$_4$—(CH$_2$)$_3$—, —(CH$_2$)$_2$—(CF$_2$)$_4$—(CH$_2$)$_4$—, —(CH$_2$)$_2$—(CF$_2$)$_4$—(CH$_2$)$_5$—, —(CH$_2$)$_2$—(CF$_2$)$_4$—(CH$_2$)$_6$—, —(CH$_2$)$_3$—(CF$_2$)$_4$—(CH$_2$)$_2$—, —(CH$_2$)$_3$—(CF$_2$)$_4$—(CH$_2$)$_4$—, —(CH$_2$)$_4$—(CF$_2$)$_4$—(CH$_2$)$_2$—, —(CH$_2$)$_4$—(CF$_2$)$_4$—(CH$_2$)$_3$—, —(CH$_2$)$_5$—(CF$_2$)$_4$—(CH$_2$)$_2$—, —(CH$_2$)$_5$—(CF$_2$)$_4$—(CH$_2$)$_3$—, —(CH$_2$)$_6$—(CF$_2$)$_4$—(CH$_2$)$_2$—, —(CF$_2$)$_5$—(CH$_2$)—, —(CH$_2$)—(CF$_2$)$_5$—, —(CH$_2$)—(CF$_2$)$_5$—(CH$_2$)—, —(CH$_2$)—(CF$_2$)$_5$—(CH$_2$)$_2$—, —(CH$_2$)—(CF$_2$)$_5$—(CH$_2$)$_3$—, —(CH$_2$)—(CF$_2$)$_5$—(CH$_2$)$_4$—, —(CH$_2$)—(CF$_2$)$_5$—(CH$_2$)$_5$—, —(CH$_2$)—(CF$_2$)$_5$—(CH$_2$)$_6$—, —(CH$_2$)$_2$—(CF$_2$)$_5$—(CH$_2$)—, —(CH$_2$)$_3$—(CF$_2$)$_5$—(CH$_2$)—, —(CH$_2$)$_4$—(CF$_2$)$_5$—(CH$_2$)—, —(CH$_2$)$_5$—(CF$_2$)$_5$—(CH$_2$)—, —(CH$_2$)$_6$—(CF$_2$)$_5$—(CH$_2$)—, —(CH$_2$)$_2$—(CF$_2$)$_5$—(CH$_2$)$_2$—, —(CH$_2$)$_3$—(CF$_2$)$_5$—(CH$_2$)$_3$—, —(CH$_2$)$_4$—(CF$_2$)$_5$—(CH$_2$)$_4$—, —(CH$_2$)$_2$—(CF$_2$)$_5$—(CH$_2$)$_3$—, —(CH$_2$)$_2$—(CF$_2$)$_5$—(CH$_2$)$_4$—, —(CH$_2$)$_2$—(CF$_2$)$_5$—(CH$_2$)$_5$—, —(CH$_2$)$_2$—(CF$_2$)$_5$—(CH$_2$)$_6$—, —(CH$_2$)$_3$—(CF$_2$)$_5$—(CH$_2$)$_2$—, —(CH$_2$)$_3$—(CF$_2$)$_5$—(CH$_2$)$_4$—, —(CH$_2$)$_4$—(CF$_2$)$_5$—(CH$_2$)$_2$—, —(CH$_2$)$_4$—(CF$_2$)$_5$—(CH$_2$)$_3$—, —(CH$_2$)$_5$—(CF$_2$)$_5$—(CH$_2$)$_2$—,

—(CHCF$_3$)—(CH$_2$)—, —(CH$_2$)—(CHCF$_3$)—, —(CH$_2$)—(CHCF$_3$)—(CH$_2$)—, —(CH$_2$)—(CHCF$_3$)—(CH$_2$)$_2$—, —(CH$_2$)—(CHCF$_3$)—(CH$_2$)$_3$—, —(CH$_2$)—(CHCF$_3$)—(CH$_2$)$_4$—, —(CH$_2$)—(CHCF$_3$)—(CH$_2$)$_5$—, —(CH$_2$)—(CHCF$_3$)—(CH$_2$)$_6$—, —(CH$_2$)—(CHCF$_3$)—(CH$_2$)$_7$—, —(CH$_2$)—(CHCF$_3$)—(CH$_2$)$_8$—, —(CH$_2$)—(CHCF$_3$)—(CH$_2$)$_9$—, —(CH$_2$)—(CHCF$_3$)—(CH$_2$)$_{10}$—, —(CH$_2$)$_2$—(CHCF$_3$)—(CH$_2$)—, —(CH$_2$)$_3$—(CHCF$_3$)—(CH$_2$)—, —(CH$_2$)$_4$—(CHCF$_3$)—(CH$_2$)—, —(CH$_2$)$_5$—(CHCF$_3$)—(CH$_2$)—, —(CH$_2$)$_6$—(CHCF$_3$)—(CH$_2$)—, —(CH$_2$)$_7$—(CHCF$_3$)—(CH$_2$)—, —(CH$_2$)$_8$—(CHCF$_3$)—(CH$_2$)—, —(CH$_2$)$_9$—(CHCF$_3$)—(CH$_2$)—, —(CH$_2$)$_{10}$—(CHCF$_3$)—(CH$_2$)—, —(CH$_2$)$_2$—(CHCF$_3$)—(CH$_2$)$_2$—, —(CH$_2$)$_3$—(CHCF$_3$)—(CH$_2$)$_3$—, —(CH$_2$)$_4$—(CHCF$_3$)—(CH$_2$)$_4$—, —(CH$_2$)$_5$—(CHCF$_3$)—(CH$_2$)$_5$—, —(CH$_2$)$_2$—(CHCF$_3$)—(CH$_2$)$_3$—, —(CH$_2$)$_2$—(CHCF$_3$)—(CH$_2$)$_4$—, —(CH$_2$)$_2$—(CHCF$_3$)—(CH$_2$)$_5$—, —(CH$_2$)$_2$—(CHCF$_3$)—(CH$_2$)$_6$—, —(CH$_2$)$_2$—(CHCF$_3$)—(CH$_2$)$_7$—, —(CH$_2$)$_2$—(CHCF$_3$)—(CH$_2$)$_8$—, —(CH$_2$)$_2$—(CHCF$_3$)—(CH$_2$)$_9$—, —(CH$_2$)$_2$—(CHCF$_3$)$_2$—(CH$_2$)—, —(CH$_2$)$_3$—(CHCF$_3$)$_2$—(CH$_2$)—, —(CH$_2$)$_4$—(CHCF$_3$)$_2$—(CH$_2$)—, —(CH$_2$)$_5$—(CHCF$_3$)$_2$—(CH$_2$)—, —(CH$_2$)$_6$—(CHCF$_3$)$_2$—(CH$_2$)—, —(CH$_2$)$_7$—(CHCF$_3$)$_2$—(CH$_2$)—, —(CH$_2$)$_8$—(CHCF$_3$)$_2$—(CH$_2$)—, —(CH$_2$)$_9$—(CHCF$_3$)$_2$—(CH$_2$)—, —(CH$_2$)$_2$—(CHCF$_3$)$_2$—(CH$_2$)$_2$—, —(CH$_2$)$_3$—(CHCF$_3$)$_2$—(CH$_2$)$_3$—, —(CH$_2$)$_4$—(CHCF$_3$)$_2$—(CH$_2$)$_4$—, —(CH$_2$)$_5$—(CHCF$_3$)$_2$—(CH$_2$)$_5$—, —(CH$_2$)$_2$—(CHCF$_3$)$_2$—(CH$_2$)$_3$—, —(CH$_2$)$_2$—(CHCF$_3$)$_2$—(CH$_2$)$_4$—, —(CH$_2$)$_2$—(CHCF$_3$)$_2$—(CH$_2$)$_5$—, —(CH$_2$)$_2$—(CHCF$_3$)$_2$—(CH$_2$)$_6$—, —(CH$_2$)$_2$—(CHCF$_3$)$_2$—(CH$_2$)$_7$—, —(CH$_2$)$_2$—(CHCF$_3$)$_2$—(CH$_2$)$_8$—, —(CH$_2$)$_3$—(CHCF$_3$)$_2$—(CH$_2$)$_2$—, —(CH$_2$)$_3$—(CHCF$_3$)$_2$—(CH$_2$)$_4$—, —(CH$_2$)$_3$—(CHCF$_3$)$_2$—(CH$_2$)$_5$—, —(CH$_2$)$_3$—(CHCF$_3$)$_2$—(CH$_2$)$_6$—, —(CH$_2$)$_3$—(CHCF$_3$)$_2$—(CH$_2$)$_7$—, —(CH$_2$)$_4$—(CHCF$_3$)$_2$—(CH$_2$)$_2$—, —(CH$_2$)$_4$—(CHCF$_3$)$_2$—(CH$_2$)$_3$—, —(CH$_2$)$_4$—(CHCF$_3$)$_2$—(CH$_2$)$_5$—, —(CH$_2$)$_4$—(CHCF$_3$)$_2$—(CH$_2$)$_6$—, —(CH$_2$)$_5$—(CHCF$_3$)$_2$—(CH$_2$)$_3$—, —(CH$_2$)$_5$—(CHCF$_3$)$_2$—(CH$_2$)$_4$—, —(CH$_2$)$_6$—(CHCF$_3$)$_2$—(CH$_2$)$_2$—, —(CH$_2$)$_6$—(CHCF$_3$)$_2$—(CH$_2$)$_3$—, —(CH$_2$)$_6$—(CHCF$_3$)$_2$—(CH$_2$)$_4$—, —(CHCF$_3$)$_3$—(CH$_2$)—, —(CH$_2$)—(CHCF$_3$)$_3$—, —(CH$_2$)—(CHCF$_3$)$_3$—(CH$_2$)—, —(CH$_2$)—(CHCF$_3$)$_3$—(CH$_2$)$_2$—, —(CH$_2$)—(CHCF$_3$)$_3$—(CH$_2$)$_3$—, —(CH$_2$)—(CHCF$_3$)$_3$—(CH$_2$)$_4$—, —(CH$_2$)—(CHCF$_3$)$_3$—(CH$_2$)$_5$—, —(CH$_2$)—(CHCF$_3$)$_3$—(CH$_2$)$_6$—, —(CH$_2$)—(CHCF$_3$)$_3$—(CH$_2$)$_7$—, —(CH$_2$)—(CHCF$_3$)$_3$—(CH$_2$)$_8$—, —(CH$_2$)$_2$—(CHCF$_3$)$_3$—(CH$_2$)—, —(CH$_2$)$_3$—(CHCF$_3$)$_3$—(CH$_2$)—, —(CH$_2$)$_4$—(CHCF$_3$)$_3$—(CH$_2$)—, —(CH$_2$)$_5$—(CHCF$_3$)$_3$—(CH$_2$)—, —(CH$_2$)$_6$—(CHCF$_3$)$_3$—(CH$_2$)—, —(CH$_2$)$_7$—(CHCF$_3$)$_3$—(CH$_2$)—, —(CH$_2$)$_8$—(CHCF$_3$)$_3$—(CH$_2$)—, —(CH$_2$)$_2$—(CHCF$_3$)$_3$—(CH$_2$)$_2$—, —(CH$_2$)$_3$—(CHCF$_3$)$_3$—(CH$_2$)$_3$—, —(CH$_2$)$_4$—(CHCF$_3$)$_3$—(CH$_2$)$_4$—, —(CH$_2$)$_2$—(CHCF$_3$)$_3$—(CH$_2$)$_3$—, —(CH$_2$)$_2$—(CHCF$_3$)$_3$—(CH$_2$)$_4$—, —(CH$_2$)$_2$—(CHCF$_3$)$_3$—(CH$_2$)$_5$—, —(CH$_2$)$_2$—(CHCF$_3$)$_3$—(CH$_2$)$_6$—, —(CH$_2$)$_2$—(CHCF$_3$)$_3$—(CH$_2$)$_7$—, —(CH$_2$)$_3$—(CHCF$_3$)$_3$—(CH$_2$)$_2$—, —(CH$_2$)$_3$—(CHCF$_3$)$_3$—(CH$_2$)$_4$—, —(CH$_2$)$_3$—(CHCF$_3$)$_3$—(CH$_2$)$_5$—, —(CH$_2$)$_3$—(CHCF$_3$)$_3$—(CH$_2$)$_6$—, —(CH$_2$)$_4$—(CHCF$_3$)$_3$—(CH$_2$)$_2$—, —(CH$_2$)$_4$—(CHCF$_3$)$_3$—(CH$_2$)$_3$—, —(CH$_2$)$_4$—(CHCF$_3$)$_3$—(CH$_2$)$_5$—, —(CH$_2$)$_5$—(CHCF$_3$)$_3$—(CH$_2$)$_2$—, —(CH$_2$)$_5$—(CHCF$_3$)$_3$—(CH$_2$)$_3$—, —(CH$_2$)$_5$—(CHCF$_3$)$_3$—(CH$_2$)$_4$—, —(CH$_2$)$_6$—(CHCF$_3$)$_3$—(CH$_2$)$_2$—, —(CH$_2$)$_6$—(CHCF$_3$)$_3$—(CH$_2$)$_3$—, —(CHCF$_3$)$_4$—(CH$_2$)—, —(CH$_2$)—(CHCF$_3$)$_4$—, —(CH$_2$)—(CHCF$_3$)$_4$—(CH$_2$)—, —(CH$_2$)—(CHCF$_3$)$_4$—(CH$_2$)$_2$—, —(CH$_2$)—(CHCF$_3$)$_4$—(CH$_2$)$_3$—, —(CH$_2$)—(CHCF$_3$)$_4$—(CH$_2$)$_4$—, —(CH$_2$)—(CHCF$_3$)$_4$—(CH$_2$)$_5$—, —(CH$_2$)—(CHCF$_3$)$_4$—(CH$_2$)$_6$—, —(CH$_2$)—(CHCF$_3$)$_4$—(CH$_2$)$_7$—, —(CH$_2$)—(CHCF$_3$)$_4$—(CH$_2$)$_8$—, —(CH$_2$)—(CHCF$_3$)$_4$—(CH$_2$)$_9$—, —(CH$_2$)—(CHCF$_3$)$_4$—(CH$_2$)$_{10}$—, —(CH$_2$)$_2$—(CHCF$_3$)$_4$—(CH$_2$)—, —(CH$_2$)$_3$—(CHCF$_3$)$_4$—(CH$_2$)—, —(CH$_2$)$_4$—(CHCF$_3$)$_4$—(CH$_2$)—, —(CH$_2$)$_5$—(CHCF$_3$)$_4$—(CH$_2$)—, —(CH$_2$)$_6$—(CHCF$_3$)$_4$—(CH$_2$)—,

—(CH₂)₇—(CHCF₃)₄—(CH₂)—, —(CH₂)₂—(CHCF₃)₄—(CH₂)₂—, —(CH₂)₃—(CHCF₃)₄—(CH₂)₃—, —(CH₂)₄—(CHCF₃)₄—(CH₂)₄—, —(CH₂)₅—(CHCF₃)₄—(CH₂)₅—, —(CH₂)₂—(CHCF₃)₄—(CH₂)₃—, —(CH₂)₂—(CHCF₃)₄—(CH₂)₄—, —(CH₂)₂—(CHCF₃)₄—(CH₂)₅—, —(CH₂)₂—(CHCF₃)₄—(CH₂)₆—, —(CH₂)₃—(CHCF₃)₄—(CH₂)₂—, —(CH₂)₄—(CHCF₃)₄—(CH₂)₂—, —(CH₂)₄—(CHCF₃)₄—(CH₂)₃—, —(CH₂)₅—(CHCF₃)₄—(CH₂)₂—, —(CH₂)₅—(CHCF₃)₄—(CH₂)₃—, —(CH₂)₆—(CHCF₃)₄—(CH₂)₂—, —(CHCF₃)₅—(CH₂)—, —(CH₂)—(CHCF₃)₅—, —(CH₂)—(CHCF₃)₅—(CH₂)—, —(CH₂)—(CHCF₃)₅—(CH₂)₂—, —(CH₂)—(CHCF₃)₅—(CH₂)₃—, —(CH₂)—(CHCF₃)₅—(CH₂)₄—, —(CH₂)—(CHCF₃)₅—(CH₂)₅—, —(CH₂)—(CHCF₃)₅—(CH₂)₆—, —(CH₂)₂—(CHCF₃)₅—(CH₂)—, —(CH₂)₃—(CHCF₃)₅—(CH₂)—, —(CH₂)₄—(CHCF₃)₅—(CH₂)—, —(CH₂)₅—(CHCF₃)₅—(CH₂)—, —(CH₂)₆—(CHCF₃)₅—(CH₂)—, —(CH₂)₂—(CHCF₃)₅—(CH₂)₂—, —(CH₂)₃—(CHCF₃)₅—(CH₂)₃—, —(CH₂)₄—(CHCF₃)₅—(CH₂)₄—, —(CH₂)₂—(CHCF₃)₅—(CH₂)₃—, —(CH₂)₂—(CHCF₃)₅—(CH₂)₄—, —(CH₂)₂—(CHCF₃)₅—(CH₂)₅—, —(CH₂)₂—(CHCF₃)₅—(CH₂)₆—, —(CH₂)₃—(CHCF₃)₅—(CH₂)₂—, —(CH₂)₃—(CHCF₃)₅—(CH₂)₄—, —(CH₂)₄—(CHCF₃)₅—(CH₂)₃—, —(CH₂)₅—(CHCF₃)₅—(CH₂)₂—, —[C(CH₃)CF₃]—(CH₂)—, —(CH₂)—[C(CH₃)CF₃]—, —(CH₂)—[C(CH₃)CF₃]—(CH₂)—, —(CH₂)—[C(CH₃)CF₃]—(CH₂)₂—, —(CH₂)—[C(CH₃)CF₃]—(CH₂)₃—, —(CH₂)—[C(CH₃)CF₃]—(CH₂)₄—, —(CH₂)—[C(CH₃)CF₃]—(CH₂)₅—, —(CH₂)—[C(CH₃)CF₃]—(CH₂)₆—, —(CH₂)—[C(CH₃)CF₃]—(CH₂)₇—, —(CH₂)—[C(CH₃)CF₃]—(CH₂)₈—, —(CH₂)—[C(CH₃)CF₃]—(CH₂)₉—, —(CH₂)—[C(CH₃)CF₃]—(CH₂)₁₀—, —(CH₂)₂—[C(CH₃)CF₃]—(CH₂)—, —(CH₂)₃—[C(CH₃)CF₃]—(CH₂)—, —(CH₂)₄—[C(CH₃)CF₃]—(CH₂)—, —(CH₂)₅—[C(CH₃)CF₃]—(CH₂)—, —(CH₂)₆—[C(CH₃)CF₃]—(CH₂)—, —(CH₂)₇—[C(CH₃)CF₃]—(CH₂)—, —(CH₂)₈—[C(CH₃)CF₃]—(CH₂)—, —(CH₂)₉—[C(CH₃)CF₃]—(CH₂)—, —(CH₂)₁₀—[C(CH₃)CF₃]—(CH₂)—, —(CH₂)₂—[C(CH₃)CF₃]—(CH₂)₂—, —(CH₂)₃—[C(CH₃)CF₃]—(CH₂)₃—, —(CH₂)₄—[C(CH₃)CF₃]—(CH₂)₄—, —(CH₂)₅—[C(CH₃)CF₃]—(CH₂)₅—, —(CH₂)₂—[C(CH₃)CF₃]—(CH₂)₃—, —(CH₂)₂—[C(CH₃)CF₃]—(CH₂)₄—, —(CH₂)₂—[C(CH₃)CF₃]—(CH₂)₅—, —(CH₂)₂—[C(CH₃)CF₃]—(CH₂)₆—, —(CH₂)₂—[C(CH₃)CF₃]—(CH₂)₇—, —(CH₂)₂—[C(CH₃)CF₃]—(CH₂)₈—, —(CH₂)₂—[C(CH₃)CF₃]—(CH₂)₉—, —(CH₂)₃—[C(CH₃)CF₃]—(CH₂)₂—, —(CH₂)₃—[C(CH₃)CF₃]—(CH₂)₄—, —(CH₂)₃—[C(CH₃)CF₃]—(CH₂)₅—, —(CH₂)₃—[C(CH₃)CF₃]—(CH₂)₆—, —(CH₂)₃—[C(CH₃)CF₃]—(CH₂)₇—, —(CH₂)₃—[C(CH₃)CF₃]—(CH₂)₈—, —(CH₂)₄—[C(CH₃)CF₃]—(CH₂)₂—, —(CH₂)₄—[C(CH₃)CF₃]—(CH₂)₃—, —(CH₂)₄—[C(CH₃)CF₃]—(CH₂)₅—, —(CH₂)₄—[C(CH₃)CF₃]—(CH₂)₆—, —(CH₂)₄—[C(CH₃)CF₃]—(CH₂)₇—, —(CH₂)₅—[C(CH₃)CF₃]—(CH₂)₂—, —(CH₂)₅—[C(CH₃)CF₃]—(CH₂)₃—, —(CH₂)₅—[C(CH₃)CF₃]—(CH₂)₄—, —(CH₂)₅—[C(CH₃)CF₃]—(CH₂)₆—, —(CH₂)₆—[C(CH₃)CF₃]—(CH₂)₂—, —(CH₂)₆—[C(CH₃)CF₃]—(CH₂)₃—, —(CH₂)₆—[C(CH₃)CF₃]—(CH₂)₄—, —(CH₂)₆—[C(CH₃)CF₃]—(CH₂)₅—, —[C(CH₃)CF₃]₂—(CH₂)—, —(CH₂)—[C(CH₃)CF₃]₂—, —(CH₂)—[C(CH₃)CF₃]₂—(CH₂)—, —(CH₂)—[C(CH₃)CF₃]₂—(CH₂)₂—, —(CH₂)—[C(CH₃)CF₃]₂—(CH₂)₃—, —(CH₂)—[C(CH₃)CF₃]₂—(CH₂)₄—, —(CH₂)—[C(CH₃)CF₃]₂—(CH₂)₅—, —(CH₂)—[C(CH₃)CF₃]₂—(CH₂)₆—, —(CH₂)—[C(CH₃)CF₃]₂—(CH₂)₇—, —(CH₂)—[C(CH₃)CF₃]₂—(CH₂)₈—, —(CH₂)—[C(CH₃)CF₃]₂—(CH₂)₉—, —(CH₂)₂—[C(CH₃)CF₃]₂—(CH₂)—, —(CH₂)₃—[C(CH₃)CF₃]₂—(CH₂)—, —(CH₂)₄—[C(CH₃)CF₃]₂—(CH₂)—, —(CH₂)₅—[C(CH₃)CF₃]₂—(CH₂)—, —(CH₂)₆—[C(CH₃)CF₃]₂—(CH₂)—, —(CH₂)₇—[C(CH₃)CF₃]₂—(CH₂)—, —(CH₂)₈—[C(CH₃)CF₃]₂—(CH₂)—, —(CH₂)₉—[C(CH₃)CF₃]₂—(CH₂)—, —(CH₂)₂—[C(CH₃)CF₃]₂—(CH₂)₂—, —(CH₂)₃—[C(CH₃)CF₃]₂—(CH₂)₃—, —(CH₂)₄—[C(CH₃)CF₃]₂—(CH₂)₄—, —(CH₂)₅—[C(CH₃)CF₃]₂—(CH₂)₅—, —(CH₂)₂—[C(CH₃)CF₃]₂—(CH₂)₃—, —(CH₂)₂—[C(CH₃)CF₃]₂—(CH₂)₄—, —(CH₂)₂—[C(CH₃)CF₃]₂—(CH₂)₅—, —(CH₂)₂—[C(CH₃)CF₃]₂—(CH₂)₆—, —(CH₂)₂—[C(CH₃)CF₃]₂—(CH₂)₇—, —(CH₂)₂—[C(CH₃)CF₃]₂—(CH₂)₈—, —(CH₂)₃—[C(CH₃)CF₃]₂—(CH₂)₂—, —(CH₂)₃—[C(CH₃)CF₃]₂—(CH₂)₄—, —(CH₂)₃—[C(CH₃)CF₃]₂—(CH₂)₅—, —(CH₂)₃—[C(CH₃)CF₃]₂—(CH₂)₆—, —(CH₂)₃—[C(CH₃)CF₃]₂—(CH₂)₇—, —(CH₂)₄—[C(CH₃)CF₃]₂—(CH₂)₂—, —(CH₂)₄—[C(CH₃)CF₃]₂—(CH₂)₃—, —(CH₂)₄—[C(CH₃)CF₃]₂—(CH₂)₅—, —(CH₂)₄—[C(CH₃)CF₃]₂—(CH₂)₆—, —(CH₂)₅—[C(CH₃)CF₃]₂—(CH₂)₂—, —(CH₂)₅—[C(CH₃)CF₃]₂—(CH₂)₃—, —(CH₂)₅—[C(CH₃)CF₃]₂—(CH₂)₄—, —(CH₂)₆—[C(CH₃)CF₃]₂—(CH₂)₂—, —(CH₂)₆—[C(CH₃)CF₃]₂—(CH₂)₃—, —(CH₂)₆—[C(CH₃)CF₃]₂—(CH₂)₄—,

—[C(CH₃)CF₃]₃—(CH₂)—, —(CH₂)—[C(CH₃)CF₃]₃—, —(CH₂)—[C(CH₃)CF₃]₃—(CH₂)—, —(CH₂)—[C(CH₃)CF₃]₃—(CH₂)₂—, —(CH₂)—[C(CH₃)CF₃]₃—(CH₂)₃—, —(CH₂)—[C(CH₃)CF₃]₃—(CH₂)₄—, —(CH₂)—[C(CH₃)CF₃]₃—(CH₂)₅—, —(CH₂)—[C(CH₃)CF₃]₃—(CH₂)₆—, —(CH₂)—[C(CH₃)CF₃]₃—(CH₂)₇—, —(CH₂)—[C(CH₃)CF₃]₃—(CH₂)₈—, —(CH₂)₂—[C(CH₃)CF₃]₃—(CH₂)—, —(CH₂)₃—[C(CH₃)CF₃]₃—(CH₂)—, —(CH₂)₄—[C(CH₃)CF₃]₃—(CH₂)—, —(CH₂)₅—[C(CH₃)CF₃]₃—(CH₂)—, —(CH₂)₆—[C(CH₃)CF₃]₃—(CH₂)—, —(CH₂)₇—[C(CH₃)CF₃]₃—(CH₂)—, —(CH₂)₈—[C(CH₃)CF₃]₃—(CH₂)—, —(CH₂)₂—[C(CH₃)CF₃]₃—(CH₂)₂—, —(CH₂)₃—[C(CH₃)CF₃]₃—(CH₂)₃—, —(CH₂)₄—[C(CH₃)CF₃]₃—(CH₂)₄—, —(CH₂)₂—[C(CH₃)CF₃]₃—(CH₂)₃—, —(CH₂)₂—[C(CH₃)CF₃]₃—(CH₂)₄—, —(CH₂)₂—[C(CH₃)CF₃]₃—(CH₂)₅—, —(CH₂)₂—[C(CH₃)CF₃]₃—(CH₂)₆—, —(CH₂)₂—[C(CH₃)CF₃]₃—(CH₂)₇—, —(CH₂)₃—[C(CH₃)CF₃]₃—(CH₂)₂—, —(CH₂)₃—[C(CH₃)CF₃]₃—(CH₂)₄—, —(CH₂)₃—[C(CH₃)CF₃]₃—(CH₂)₅—, —(CH₂)₃—[C(CH₃)CF₃]₃—(CH₂)₆—, —(CH₂)₄—[C(CH₃)CF₃]₃—(CH₂)₂—, —(CH₂)₄—[C(CH₃)CF₃]₃—(CH₂)₃—, —(CH₂)₄—[C(CH₃)CF₃]₃—(CH₂)₅—, —(CH₂)₅—[C(CH₃)CF₃]₃—(CH₂)₂—, —(CH₂)₅—[C(CH₃)CF₃]₃—(CH₂)₃—, —(CH₂)₅—[C(CH₃)CF₃]₃—(CH₂)₄—, —(CH₂)₆—[C(CH₃)CF₃]₃—(CH₂)₂—, —(CH₂)₆—[C(CH₃)CF₃]₃—(CH₂)₃—,

—[C(CH₃)CF₃]₄—(CH₂)—, —(CH₂)—[C(CH₃)CF₃]₄—, —(CH₂)—[C(CH₃)CF₃]₄—(CH₂)—, —(CH₂)—[C(CH₃)CF₃]₄—(CH₂)₂—, —(CH₂)—[C(CH₃)CF₃]₄—(CH₂)₃—, —(CH₂)—[C(CH₃)CF₃]₄—(CH₂)₄—, —(CH₂)—[C(CH₃)CF₃]₄—(CH₂)₅—, —(CH₂)—[C(CH₃)CF₃]₄—(CH₂)₆—, —(CH₂)—[C(CH₃)CF₃]₄—(CH₂)₇—, —(CH₂)—[C(CH₃)CF₃]₄—(CH₂)₈—, —(CH₂)—[C(CH₃)CF₃]₄—(CH₂)₉—, —(CH₂)—[C(CH₃)CF₃]₄—(CH₂)₁₀—, —(CH₂)₂—[C(CH₃)CF₃]₄—(CH₂)—, —(CH₂)₃—[C(CH₃)CF₃]₄—(CH₂)—, —(CH₂)₄—[C(CH₃)CF₃]₄—(CH₂)—, —(CH₂)₅—[C(CH₃)CF₃]₄—(CH₂)—, —(CH₂)₆—[C(CH₃)CF₃]₄—(CH₂)—, —(CH₂)₇—[C(CH₃)CF₃]₄—(CH₂)—, —(CH₂)₂—[C(CH₃)CF₃]₄—(CH₂)₂—, —(CH₂)₃—[C (CH₃)CF₃]₄—(CH₂)₃—, —(CH₂)₄—[C(CH₃)CF₃]₄—(CH₂)₄—, —(CH₂)₅—[C(CH₃)CF₃]₄—(CH₂)₅—, —(CH₂)₂—[C(CH₃)CF₃]₄—(CH₂)₃—, —(CH₂)₂—[C(CH₃)CF₃]₄—(CH₂)₄—, —(CH₂)₂—[C(CH₃)CF₃]₄—(CH₂)₅—, —(CH₂)₂—[C(CH₃)CF₃]₄—(CH₂)₆—, —(CH₂)₃—[C(CH₃)CF₃]₄—(CH₂)₂—, —(CH₂)₄—[C(CH₃)CF₃]₄—(CH₂)₂—, —(CH₂)₄—[C(CH₃)CF₃]₄—(CH₂)₃—, —(CH₂)₅—[C(CH₃)CF₃]₄—(CH₂)₂—, —(CH₂)₅—[C(CH₃)CF₃]₄—(CH₂)₃—, —(CH₂)₆—[C(CH₃)CF₃]₄—(CH₂)₂—,

—[C(CH₃)CF₃]₅—(CH₂)—, —(CH₂)—[C(CH₃)CF₃]₅—, —(CH₂)—[C(CH₃)CF₃]₅—(CH₂)—, —(CH₂)—[C(CH₃)CF₃]₅—(CH₂)₂—, —(CH₂)—[C(CH₃)CF₃]₅—(CH₂)₃—, —(CH₂)—[C(CH₃)CF₃]₅—(CH₂)₄—, —(CH₂)—[C(CH₃)CF₃]₅—(CH₂)₅—, —(CH₂)—[C(CH₃)CF₃]₅—(CH₂)₆—, —(CH₂)₂—[C(CH₃)CF₃]₅—(CH₂)—, —(CH₂)₃—[C(CH₃)CF₃]₅—(CH₂)—, —(CH₂)₄—[C(CH₃)CF₃]₅—(CH₂)—, —(CH₂)₅—[C(CH₃)CF₃]₅—(CH₂)—, —(CH₂)₆—[C(CH₃)CF₃]₅—(CH₂)—, —(CH₂)₂—[C(CH₃)CF₃]₅—(CH₂)₂—, —(CH₂)₃—[C(CH₃)CF₃]₅—(CH₂)₃—, —(CH₂)₄—[C(CH₃)CF₃]₅—(CH₂)₄—, —(CH₂)₂—[C(CH₃)CF₃]₅—(CH₂)₃—, —(CH₂)₂—[C(CH₃)CF₃]₅—(CH₂)₄—, —(CH₂)₂—[C(CH₃)CF₃]₅—(CH₂)₅—, —(CH₂)₂—[C(CH₃)CF₃]₅—(CH₂)₆—, —(CH₂)₃—[C(CH₃)CF₃]₅—(CH₂)₂—, —(CH₂)₄—[C(CH₃)CF₃]₅—(CH₂)₂—, —(CH₂)₄—[C(CH₃)CF₃]₅—(CH₂)₃—, —(CH₂)₅—[C(CH₃)CF₃]₅—(CH₂)₂—,

—[CH(CH₂CF₃)]—(CH₂)—, —(CH₂)—[CH(CH₂CF₃)]—, —(CH₂)—[CH(CH₂CF₃)]—(CH₂)—, —(CH₂)—[CH(CH₂CF₃)]—(CH₂)₂—, —(CH₂)—[CH(CH₂CF₃)]—(CH₂)₃—, —(CH₂)—[CH(CH₂CF₃)]—(CH₂)₄—, —(CH₂)—[CH(CH₂CF₃)]—(CH₂)₅—, —(CH₂)—[CH(CH₂CF₃)]—(CH₂)₆—, —(CH₂)—[CH(CH₂CF₃)]—(CH₂)₇—, —(CH₂)—[CH(CH₂CF₃)]—(CH₂)₈—, —(CH₂)—[CH(CH₂CF₃)]—(CH₂)₉—, —(CH₂)—[CH(CH₂CF₃)]—(CH₂)₁₀—, —(CH₂)₂—[CH(CH₂CF₃)]—(CH₂)—, —(CH₂)₃—[CH(CH₂CF₃)]—(CH₂)—, —(CH₂)₄—[CH(CH₂CF₃)]—(CH₂)—, —(CH₂)₅—[CH(CH₂CF₃)]—(CH₂)—, —(CH₂)₆—[CH(CH₂CF₃)]—(CH₂)—, —(CH₂)₇—[CH(CH₂CF₃)]—(CH₂)—, —(CH₂)₈—[CH(CH₂CF₃)]—(CH₂)—, —(CH₂)₉—[CH(CH₂CF₃)]—(CH₂)—, —(CH₂)₁₀—[CH(CH₂CF₃)]—(CH₂)—, —(CH₂)₂—[CH(CH₂CF₃)]—(CH₂)₂—, —(CH₂)₃—[CH(CH₂CF₃)]—(CH₂)₃—, —(CH₂)₄—[CH(CH₂CF₃)]—(CH₂)₄—, —(CH₂)₅—[CH(CH₂CF₃)]—(CH₂)₅—, —(CH₂)₂—[CH(CH₂CF₃)]—(CH₂)₃—, —(CH₂)₂—[CH(CH₂CF₃)]—(CH₂)₄—, —(CH₂)₂—[CH(CH₂CF₃)]—(CH₂)₅—, —(CH₂)₂—[CH(CH₂CF₃)]—(CH₂)₆—, —(CH₂)₂—[CH(CH₂CF₃)]—(CH₂)₇—, —(CH₂)₂—[CH(CH₂CF₃)]—(CH₂)₈—, —(CH₂)₂—[CH(CH₂CF₃)]—(CH₂)₉—, —(CH₂)₃—[CH(CH₂CF₃)]—(CH₂)₂—, —(CH₂)₃—[CH(CH₂CF₃)]—(CH₂)₄—, —(CH₂)₃—[CH(CH₂CF₃)]—(CH₂)₅—, —(CH₂)₃—[CH(CH₂CF₃)]—(CH₂)₆—, —(CH₂)₃—[CH(CH₂CF₃)]—(CH₂)₇—, —(CH₂)₃—[CH(CH₂CF₃)]—(CH₂)₈—, —(CH₂)₄—[CH(CH₂CF₃)]—(CH₂)₂—, —(CH₂)₄—[CH(CH₂CF₃)]—(CH₂)₃—, —(CH₂)₄—[CH(CH₂CF₃)]—(CH₂)₅—, —(CH₂)₄—[CH(CH₂CF₃)]—(CH₂)₆—, —(CH₂)₄—[CH(CH₂CF₃)]—(CH₂)₇—, —(CH₂)₅—[CH(CH₂CF₃)]—(CH₂)₂—, —(CH₂)₅—[CH(CH₂CF₃)]—(CH₂)₃—, —(CH₂)₅—[CH(CH₂CF₃)]—(CH₂)₄—, —(CH₂)₅—[CH(CH₂CF₃)]—(CH₂)₆—, —(CH₂)₆—[CH(CH₂CF₃)]—(CH₂)₂—, —(CH₂)₆—[CH(CH₂CF₃)]—(CH₂)₃—, —(CH₂)₆—[CH(CH₂CF₃)]—(CH₂)₄—, —(CH₂)₆—[CH(CH₂CF₃)]—(CH₂)₅—,

—[CH(CH₂CF₃)]₂—(CH₂)—, —(CH₂)—[CH(CH₂CF₃)]₂—, —(CH₂)—[CH(CH₂CF₃)]₂—(CH₂)—, —(CH₂)—[CH(CH₂CF₃)]₂—(CH₂)₂—, —(CH₂)—[CH(CH₂CF₃)]₂—(H₂)₃—, —(CH₂)—[CH(CH₂CF₃)]₂—(CH₂)—, —(CH₂)—[CH(CH₂CF₃)]₂—(CH₂)₅—, —(CH₂)—[CH(CH₂CF₃)]₂—(CH₂)₆—, —(CH₂)—[CH(CH₂CF₃)]₂—(CH₂)₇—, —(CH₂)—[CH(CH₂CF₃)]₂—(CH₂)₈—, —(CH₂)—[CH(CH₂CF₃)]₂—(CH₂)₉—, —(CH₂)₂—[CH(CH₂CF₃)]₂—(CH₂)—, —(CH₂)₃—[CH(CH₂CF₃)]₂—(CH₂)—, —(CH₂)₄—[CH(CH₂CF₃)]₂—(CH₂)—, —(CH₂)₅—[CH(CH₂CF₃)]₂—(CH₂)—, —(CH₂)₆—[CH(CH₂CF₃)]₂—(CH₂)—, —(CH₂)₇—[CH(CH₂CF₃)]₂—(CH₂)—, —(CH₂)₈—[CH(CH₂CF₃)]₂—(CH₂)—, —(CH₂)₉—[CH(CH₂CF₃)]₂—(CH₂)—, —(CH₂)₂—[CH(CH₂CF₃)]₂—(CH₂)₂—, —(CH₂)₃—[CH(CH₂CF₃)]₂—(CH₂)₃—, —(CH₂)₄—[CH(CH₂CF₃)]₂—(CH₂)₄—, —(CH₂)₅—[CH(CH₂CF₃)]₂—(CH₂)₅—, —(CH₂)₂—[CH(CH₂CF₃)]₂—(CH₂)₃—, —(CH₂)₂—[CH(CH₂CF₃)]₂—(CH₂)₄—, —(CH₂)₂—[CH(CH₂CF₃)]₂—(CH₂)₅—, —(CH₂)₂—[CH(CH₂CF₃)]₂—(CH₂)₆—, —(CH₂)₂—[CH(CH₂CF₃)]₂—(CH₂)₇—, —(CH₂)₂—[CH(CH₂CF₃)]₂—(CH₂)₈—, —(CH₂)₃—[CH(CH₂CF₃)]₂—(CH₂)₂—, —(CH₂)₃—[CH(CH₂CF₃)]₂—(CH₂)₄—, —(CH₂)₃—[CH(CH₂CF₃)]₂—(CH₂)₅—, —(CH₂)₃—[CH(CH₂CF₃)]₂—(CH₂)₆—, —(CH₂)₃—[CH(CH₂CF₃)]₂—(CH₂)₇—, —(CH₂)₄—[CH(CH₂CF₃)]₂—(CH₂)₂—, —(CH₂)₄—[CH(CH₂CF₃)]₂—(CH₂)₃—, —(CH₂)₄—[CH(CH₂CF₃)]₂—(CH₂)₅—, —(CH₂)₄—[CH(CH₂CF₃)]₂—(CH₂)₆—, —(CH₂)₅—[CH(CH₂CF₃)]₂—(CH₂)₂—, —(CH₂)₅—[CH(CH₂CF₃)]₂—(CH₂)₃—, —(CH₂)₅—[CH(CH₂CF₃)]₂—(CH₂)₄—, —(CH₂)₆—[CH(CH₂CF₃)]₂—(CH₂)₂—, —(CH₂)₆—[CH(CH₂CF₃)]₂—(CH₂)₃—, —(CH₂)₆—[CH(CH₂CF₃)]₂—(CH₂)₄—,

—[CH(CH₂CF₃)]₃—(CH₂)—, —(CH₂)—[CH(CH₂CF₃)]₃—, —(CH₂)—[CH(CH₂CF₃)]₃—(CH₂)—, —(CH₂)—[CH(CH₂CF₃)]₃—(CH₂)₂—, —(CH₂)—[CH(CH₂CF₃)]₃—(CH₂)₃—, —(CH₂)—[CH(CH₂CF₃)]₃—(CH₂)₄—, —(CH₂)—[CH(CH₂CF₃)]₃—(CH₂)₅—, —(CH₂)—[CH(CH₂CF₃)]₃—(CH₂)₆—, —(CH₂)—[CH(CH₂CF₃)]₃—(CH₂)₇—, —(CH₂)—[CH(CH₂CF₃)]₃—(CH₂)₈—, —(CH₂)₂—[CH(CH₂CF₃)]₃—(CH₂)—, —(CH₂)₃—[CH(CH₂CF₃)]₃—(CH₂)—, —(CH₂)₄—[CH(CH₂CF₃)]₃—(CH₂)—, —(CH₂)₅—[CH(CH₂CF₃)]₃—(CH₂)—, —(CH₂)₆—[CH(CH₂CF₃)]₃—(CH₂)—, —(CH₂)₇—[CH(CH₂CF₃)]₃—(CH₂)—, —(CH₂)₈—[CH(CH₂CF₃)]₃—(CH₂)—, —(CH₂)₂—[CH(CH₂CF₃)]₃—(CH₂)₂—, —(CH₂)₃—[CH(CH₂CF₃)]₃—(CH₂)₃—, —(CH₂)₄—[CH(CH₂CF₃)]₃—(CH₂)₄—, —(CH₂)₂—[CH(CH₂CF₃)]₃—(CH₂)₃—, —(CH₂)₂—[CH(CH₂CF₃)]₃—(CH₂)₄—, —(CH₂)₂—[CH(CH₂CF₃)]₃—(CH₂)₅—, —(CH₂)₂—[CH(CH₂CF₃)]₃—(CH₂)₆—, —(CH₂)₂—[CH(CH₂CF₃)]₃—(CH₂)₇—, —(CH₂)₃—[CH(CH₂CF₃)]₃—(CH₂)₂—, —(CH₂)₃—[CH(CH₂CF₃)]₃—(CH₂)₄—, —(CH₂)₃—[CH(CH₂CF₃)]₃—(CH₂)₅—, —(CH₂)₃—[CH(CH₂CF₃)]₃—(CH₂)₆—, —(CH₂)₄—[CH(CH₂CF₃)]₃—(CH₂)₂—, —(CH₂)₄—[CH(CH₂CF₃)]₃—(CH₂)₃—, —(CH₂)₄—[CH(CH₂CF₃)]₃—(CH₂)₅—, —(CH₂)₅—[CH(CH₂CF₃)]₃—(CH₂)₂—, —(CH₂)₅—[CH(CH₂CF₃)]₃—(CH₂)₃—, —(CH₂)₅—[CH(CH₂CF₃)]₃—(CH₂)₄—, —(CH₂)₆—[CH(CH₂CF₃)]₃—(CH₂)₂—, —(CH₂)₆—[CH(CH₂CF₃)]₃—(CH₂)₃—,

—[CH(CH₂CF₃)]₄—(CH₂)—, —(CH₂)—[CH(CH₂CF₃)]₄—, —(CH₂)—[CH(CH₂CF₃)]₄—(CH₂)—, —(CH₂)—[CH(CH₂CF₃)]₄—(CH₂)₂—, —(CH₂)—[CH(CH₂CF₃)]₄—(H₂)₃—, —(CH₂)—[CH(CH₂CF₃)]₄—(CH₂)₄—, —(CH₂)—[CH(CH₂CF₃)]₄—(CH₂)₅—, —(CH₂)—[CH(CH₂CF₃)]₄—(CH₂)₆—, —(CH₂)—[CH(CH₂CF₃)]₄—(CH₂)₇—, —(CH₂)—[CH (CH₂CF₃)]₄—(CH₂)₈—, —(CH₂)—[CH(CH₂CF₃)]₄—(CH₂)₉—, —(CH₂)—[CH(CH₂CF₃)]₄—(CH₂)₁₀, —(CH₂)₂—[CH(CH₂CF₃)]₄—(CH₂)—, —(CH₂)₃—[CH(CH₂CF₃)]₄—(CH₂)—, —(CH₂)₄—[CH(CH₂CF₃)]₄—(CH₂)—, —(CH₂)₅—[CH(CH₂CF₃)]₄—(CH₂)—, —(CH₂)₆—[CH(CH₂CF₃)]₄—(CH₂)—, —(CH₂)₇—[CH(CH₂CF₃)]₄—(CH₂)₂—, —(CH₂)₃—[CH(CH₂CF₃)]₄—(CH₂)₃—, —(CH₂)₄—[CH(CH₂CF₃)]₄—(CH₂)₄—, —(CH₂)₅—[CH(CH₂CF₃)]₄—(CH₂)₅—, —(CH₂)₂—[CH(CH₂CF₃)]₄—(CH₂)₃—, —(CH₂)₂—[CH(CH₂CF₃)]₄—(CH₂)₄—, —(CH₂)₂—[CH(CH₂CF₃)]₄—(CH₂)₅—, —(CH₂)₂—[CH(CH₂CF₃)]₄—(CH₂)₆—, —(CH₂)₃—[CH(CH₂CF₃)]₄—(CH₂)₂—, —(CH₂)₃—[CH(CH₂CF₃)]₄—(CH₂)₄—, —(CH₂)₄—[CH(CH₂CF₃)]₄—(CH₂)₂—, —(CH₂)₄—[CH(CH₂CF₃)]₄—(CH₂)₃—, —(CH₂)₅—[CH(CH₂CF₃)]₄—(CH₂)₂—, —(CH₂)₅—[CH(CH₂CF₃)]₄—(CH₂)₃—, —(CH₂)₆—[CH(CH₂CF₃)]₄—(CH₂)₂—, —[CH(CH₂CF₃)]₅—(CH₂)—, —(CH₂)—[CH(CH₂CF₃)]₅—(CH₂)—, —(CH₂)—[CH(CH₂CF₃)]₅—(CH₂)₂—, —(CH₂)—[CH(CH₂CF₃)]₅—(CH₂)₃—, —(CH₂)—[CH(CH₂CF₃)]₅—(CH₂)₄—, —(CH₂)—[CH(CH₂CF₃)]₅—(CH₂)₅—, —(CH₂)—[CH(CH₂CF₃)]₅—(CH₂)₆—, —(CH₂)₂—[CH(CH₂CF₃)]₅—(CH₂)—, —(CH₂)₃—[CH(CH₂CF₃)]₅—(CH₂)—, —(CH₂)₄—[CH(CH₂CF₃)]₅—(CH₂)—, —(CH₂)₅—[CH(CH₂CF₃)]₅—(CH₂)—, —(CH₂)₆—[CH(CH₂CF₃)]₅—(CH₂)—, —(CH₂)—[CH(CH₂CF₃)]₅—(CH₂)₂—, —(CH₂)₃—[CH(CH₂CF₃)]₅—(CH₂)₃—, —(CH₂)₄—[CH(CH₂CF₃)]₅—(CH₂)₄—, —(CH₂)₂—[CH(CH₂CF₃)]₅—(CH₂)₃—, —(CH₂)₂—[CH(CH₂CF₃)]₅—(CH₂)₄—, —(CH₂)₂—[CH(CH₂CF₃)]₅—(CH₂)₅—, —(CH₂)₂—[CH(CH₂CF₃)]₅—(CH₂)₆—, —(CH₂)₃—[CH(CH₂CF₃)]₅—(CH₂)₂—, —(CH₂)₃—[CH(CH₂CF₃)]₅—(CH₂)₄—, —(CH₂)₄—[CH(CH₂CF₃)]₅—(CH₂)₂—, —(CH₂)₄—[CH(CH₂CF₃)]₅—(CH₂)₃—, —(CH₂)₅—[CH(CH₂CF₃)]₅—(CH₂)₂—, —[C(CH₃)(CH₂CF₃)]—(CH₂)—, —(CH₂)—[C(CH₃)(CH₂CF₃)]—, —(CH₂)—[C(CH₃)(CH₂CF₃)]—(CH₂)—, —(CH₂)—[C(CH₃)(CH₂CF₃)]—(CH₂)₂—, —(CH₂)—[C(CH₃)(CH₂CF₃)]—(CH₂)₃—, —(CH₂)—[C(CH₃)(CH₂CF₃)]—(CH₂)₄—, —(CH₂)—[C(CH₃)(CH₂CF₃)]—(CH₂)₅—, —(CH₂)—[C(CH₃)(CH₂CF₃)]—(CH₂)₆—, —(CH₂)—[C(CH₃)(CH₂CF₃)]—(CH₂)₇—, —(CH₂)—[C(CH₃)(CH₂CF₃)]—(CH₂)₈—, —(CH₂)—[C(CH₃)(CH₂CF₃)]—(CH₂)₉, —(CH₂)—[C(CH₃)(CH₂CF₃)]—(CH₂)₁₀, —(CH₂)₂—[C(CH₃)(CH₂CF₃)]—(CH₂)—, —(CH₂)₃—[C(CH₃)(CH₂CF₃)]—(CH₂)—, —(CH₂)₄—[C(CH₃)(CH₂CF₃)]—(CH₂)—, —(CH₂)₅—[C(CH₃)(CH₂CF₃)]—(CH₂)—, —(CH₂)₆—[C(CH₃)(CH₂CF₃)]—(CH₂)—, —(CH₂)₇—[C(CH₃)(CH₂CF₃)]—(CH₂)—, —(CH₂)₈—[C(CH₃)(CH₂CF₃)]—(CH₂)—, —(CH₂)₉—[C(CH₃)(CH₂CF₃)]—(CH₂)—, —(CH₂)₁₀—[C(CH₃)(CH₂CF₃)]—(CH₂)—, —(CH₂)₂—[C(CH₃)(CH₂CF₃)]—(CH₂)₂—, —(CH₂)₃—[C(CH₃)(CH₂CF₃)]—(CH₂)₃—, —(CH₂)₄—[C(CH₃)(CH₂CF₃)]—(CH₂)₄—, —(CH₂)₅—[C(CH₃)(CH₂CF₃)]—(CH₂)₅—, —(CH₂)₂—[C(CH₃)(CH₂CF₃)]—(CH₂)₃—, —(CH₂)₂—[C(CH₃)(CH₂CF₃)]—(CH₂)₄—, —(CH₂)₂—[C(CH₃)(CH₂CF₃)]—(CH₂)₅—, —(CH₂)₂—[C(CH₃)(CH₂CF₃)]—(CH₂)₆—, —(CH₂)₂—[C(CH₃)(CH₂CF₃)]—(CH₂)₇—, —(CH₂)₂—[C(CH₃)(CH₂CF₃)]—(CH₂)₈—, —(CH₂)₂—[C(CH₃)(CH₂CF₃)]—(CH₂)₉—, —(CH₂)₃—[C(CH₃)(CH₂CF₃)]—(CH₂)₂—, —(CH₂)₃—[C(CH₃)(CH₂CF₃)]—(CH₂)₄—, —(CH₂)₃—[C(CH₃)(CH₂CF₃)]—(CH₂)₅—, —(CH₂)₃—[C(CH₃)(CH₂CF₃)]—(CH₂)₆—, —(CH₂)₃—[C(CH₃)(CH₂CF₃)]—(CH₂)₇—, —(CH₂)₃—[C(CH₃)(CH₂CF₃)]—(CH₂)₈—, —(CH₂)₄—[C(CH₃)(CH₂CF₃)]—(CH₂)₂—, —(CH₂)₄—[C(CH₃)(CH₂CF₃)]—(CH₂)₃—, —(CH₂)₄—[C(CH₃)(CH₂CF₃)]—(CH₂)₅—, —(CH₂)₄—[C(CH₃)(CH₂CF₃)]—(CH₂)₆—, —(CH₂)₄—[C(CH₃)(CH₂CF₃)]—(CH₂)₇—, —(CH₂)₅—[C(CH₃)(CH₂CF₃)]—(CH₂)₂—, —(CH₂)₅—[C(CH₃)(CH₂CF₃)]—(CH₂)₃—, —(CH₂)₅—[C(CH₃)(CH₂CF₃)]—(CH₂)₄—, —(CH₂)₅—[C(CH₃)(CH₂CF₃)]—(CH₂)₆—, —(CH₂)₆—[C(CH₃)(CH₂CF₃)]—(CH₂)₂—, —(CH₂)₆—[C(CH₃)(CH₂CF₃)]—(CH₂)₃—, —(CH₂)₆—[C(CH₃)(CH₂CF₃)]—(CH₂)₄—, —(CH₂)₆—[C(CH₃)(CH₂CF₃)]—(CH₂)₅—, —[C(CH₃)(CH₂CF₃)]₂—(CH₂)—, —(CH₂)—[C(CH₃)(CH₂CF₃)]₂—, —(CH₂)—[C(CH₃)(CH₂CF₃)]₂—(CH₂)—, —(CH₂)—[C(CH₃)(CH₂CF₃)]₂—(CH₂)₂—, —(CH₂)—[C(CH₃)(CH₂CF₃)]₂—(CH₂)₃—, —(CH₂)—[C(CH₃)(CH₂CF₃)]₂—(CH₂)₄—, —(CH₂)—[C(CH₃)(CH₂CF₃)]₂—(CH₂)₅—, —(CH₂)—[C(CH₃)(CH₂CF₃)]₂—(CH₂)₆—, —(CH₂)—[C(CH₃)(CH₂CF₃)]₂—(CH₂)₇—, —(CH₂)—[C(CH₃)(CH₂CF₃)]₂—(CH₂)₈—, —(CH₂)—[C(CH₃)(CH₂CF₃)]₂—(CH₂)₉—, —(CH₂)₂—[C(CH₃)(CH₂CF₃)]₂—(CH₂)—, —(CH₂)₃—[C(CH₃)(CH₂CF₃)]₂—(CH₂)—, —(CH₂)₄—[C(CH₃)(CH₂CF₃)]₂—(CH₂)—, —(CH₂)₅—[C(CH₃)(CH₂CF₃)]₂—(CH₂)—, —(CH₂)₆—[C(CH₃)(CH₂CF₃)]₂—(CH₂)—, —(CH₂)₇—[C(CH₃)(CH₂CF₃)]₂—(CH₂)—, —(CH₂)₈—[C(CH₃)(CH₂CF₃)]₂—(CH₂)—, —(CH₂)₉—[C(CH₃)(CH₂CF₃)]₂—(CH₂)—, —(CH₂)₂—[C(CH₃)(CH₂CF₃)]₂—(CH₂)₂—, —(CH₂)₃—[C(CH₃)(CH₂CF₃)]₂—(CH₂)₃—, —(CH₂)₄—[C(CH₃)(CH₂CF₃)]₂—(CH₂)₄—, —(CH₂)₅—[C(CH₃)(CH₂CF₃)]₂—(CH₂)₅—, —(CH₂)₂—[C(CH₃)(CH₂CF₃)]₂—(CH₂)₃—, —(CH₂)₂—[C(CH₃)(CH₂CF₃)]₂—(CH₂)₄—, —(CH₂)₂—[C(CH₃)(CH₂CF₃)]₂—(CH₂)₅—, —(CH₂)₂—[C(CH₃)(CH₂CF₃)]₂—(CH₂)₆—, —(CH₂)₂—[C(CH₃)(CH₂CF₃)]₂—(CH₂)₇—, —(CH₂)₂—[C(CH₃)(CH₂CF₃)]₂—(CH₂)₈—, —(CH₂)₃—[C(CH₃)(CH₂CF₃)]₂—(CH₂)₂—, —(CH₂)₃—[C(CH₃)(CH₂CF₃)]₂—(CH₂)₄—, —(CH₂)₃—[C(CH₃)(CH₂CF₃)]₂—(CH₂)₅—, —(CH₂)₃—[C(CH₃)(CH₂CF₃)]₂—(CH₂)₆—, —(CH₂)₃—[C(CH₃)(CH₂CF₃)]₂—(CH₂)₇—, —(CH₂)₄—[C(CH₃)(CH₂CF₃)]₂—(CH₂)₂—, —(CH₂)₄—[C(CH₃)(CH₂CF₃)]₂—(CH₂)₃—, —(CH₂)₄—[C(CH₃)(CH₂CF₃)]₂—(CH₂)₅—, —(CH₂)₄—[C(CH₃)(CH₂CF₃)]₂—(CH₂)₆—, —(CH₂)₅—[C(CH₃)(CH₂CF₃)]₂—(CH₂)₂—, —(CH₂)₅—[C(CH₃)(CH₂CF₃)]₂—(CH₂)₃—, —(CH₂)₅—[C(CH₃)(CH₂CF₃)]₂—(CH₂)₄—, —(CH₂)₆—[C(CH₃)(CH₂CF₃)]₂—(CH₂)₂—, —(CH₂)₆—[C(CH₃)(CH₂CF₃)]₂—(CH₂)₃—, —(CH₂)₆—[C(CH₃)(CH₂CF₃)]₂—(CH₂)₄—, —[C(CH₃)(CH₂CF₃)]₃—(CH₂)—, —(CH₂)—[C(CH₃)(CH₂CF₃)]₃—(CH₂)—, —(CH₂)—[C(CH₃)(CH₂CF₃)]₃—(CH₂)₂—, —(CH₂)—[C(CH₃)(CH₂CF₃)]₃—(CH₂)₃—, —(CH₂)—[C(CH₃)(CH₂CF₃)]₃—(CH₂)₄—, —(CH₂)—[C(CH₃)(CH₂CF₃)]₃—(CH₂)₅—, —(CH₂)—[C(CH₃)(CH₂CF₃)]₃—(CH₂)₆—, —(CH₂)—[C(CH₃)(CH₂CF₃)]₃—(CH₂)₇—, —(CH₂)—[C(CH₃)(CH₂CF₃)]₃—(CH₂)₈—, —(CH₂)₂—[C(CH₃)(CH₂CF₃)]₃—(CH₂)—, —(CH₂)₃—[C(CH₃)(CH₂CF₃)]₃—(CH₂)—, —(CH₂)₄—[C(CH₃)(CH₂CF₃)]₃—(CH₂)—, —(CH₂)₅—[C(CH₃)(CH₂CF₃)]₃—(CH₂)—, —(CH₂)₆—[C(CH₃)(CH₂CF₃)]₃—(CH₂)—, —(CH₂)₇—[C(CH₃)(CH₂CF₃)]₃—(CH₂)—, —(CH₂)₈—[C(CH₃)(CH₂CF₃)]₃—(CH₂)—, —(CH₂)₂—[C(CH₃)(CH₂CF₃)]₃—(CH₂)₂—, —(CH₂)₃—[C(CH₃)(CH₂CF₃)]₃—(CH₂)₃—, —(CH₂)₄—[C(CH₃)(CH₂CF₃)]₃—(CH₂)₄—, —(CH₂)₂—[C(CH₃)(CH₂CF₃)]₃—(CH₂)₃—, —(CH₂)₂—[C(CH₃)(CH₂CF₃)]₃—(CH₂)₄—, —(CH₂)₂—[C(CH₃)(CH₂CF₃)]₃—(CH₂)₅—, —(CH₂)₂—[C(CH₃)(CH₂CF₃)]₃—(CH₂)₆—, —(CH₂)₂—[C(CH₃)(CH₂CF₃)]₃—(CH₂)₇—, —(CH₂)₃—[C(CH₃)(CH₂CF₃)]₃—(CH₂)₂—, —(CH₂)₃—[C(CH₃

—(CH$_2$CF$_3$)]$_3$—(CH$_2$)$_4$—, —(CH$_2$)$_3$—[C(CH$_3$)(CH$_2$CF$_3$)]$_3$—(CH$_2$)$_5$—, —(CH$_2$)$_3$—[C(CH$_3$)(CH$_2$CF$_3$)]$_3$—(CH$_2$)$_6$—, —(CH$_2$)$_4$—[C(CH$_3$)(CH$_2$CF$_3$)]$_3$—(CH$_2$)$_2$—, —(CH$_2$)$_4$—[C(CH$_3$)(CH$_2$CF$_3$)]$_3$—(CH$_2$)$_3$—, —(CH$_2$)$_4$—[C(CH$_3$)(CH$_2$CF$_3$)]$_3$—(CH$_2$)$_4$—, —(CH$_2$)$_5$—[C(CH$_3$)(CH$_2$CF$_3$)]$_3$—(CH$_2$)$_2$—, —(CH$_2$)$_5$—[C(CH$_3$)(CH$_2$CF$_3$)]$_3$—(CH$_2$)$_3$—, —(CH$_2$)$_5$—[C(CH$_3$)(CH$_2$CF$_3$)]$_3$—(CH$_2$)$_4$—, —(CH$_2$)$_6$—[C(CH$_3$)(CH$_2$CF$_3$)]$_3$—(CH$_2$)$_2$—, —(CH$_2$)$_6$—[C(CH$_3$)(CH$_2$CF$_3$)]$_3$—(CH$_2$)$_3$—,
—[C(CH$_3$)(CH$_2$CF$_3$)]$_4$—(CH$_2$)—, —(CH$_2$)—[C(CH$_3$)(CH$_2$CF$_3$)]$_4$—, —(CH$_2$)—[C(CH$_3$)(CH$_2$CF$_3$)]$_4$—(CH$_2$)—, —(CH$_2$)—[C(CH$_3$)(CH$_2$CF$_3$)]$_4$—(CH$_2$)$_2$—, —(CH$_2$)—[C(CH$_3$)(CH$_2$CF$_3$)]$_4$—(CH$_2$)$_3$—, —(CH$_2$)—[C(CH$_3$)(CH$_2$CF$_3$)]$_4$—(CH$_2$)$_4$—, —(CH$_2$)—[C(CH$_3$)(CH$_2$CF$_3$)]$_4$—(CH$_2$)$_5$—, —(CH$_2$)—[C(CH$_3$)(CH$_2$CF$_3$)]$_4$—(CH$_2$)$_6$—, —(CH$_2$)—[C(CH$_3$)(CH$_2$CF$_3$)]$_4$—(CH$_2$)$_7$—, —(CH$_2$)—[C(CH$_3$)(CH$_2$CF$_3$)]$_4$—(CH$_2$)$_8$—, —(CH$_2$)—[C(CH$_3$)(CH$_2$CF$_3$)]$_4$—(CH$_2$)$_9$—, —(CH$_2$)—[C(CH$_3$)(CH$_2$CF$_3$)]$_4$—(CH$_2$)$_{10}$—, —(CH$_2$)$_2$—[C(CH$_3$)(CH$_2$CF$_3$)]$_4$—(CH$_2$)—, —(CH$_2$)$_3$—[C(CH$_3$)(CH$_2$CF$_3$)]$_4$—(CH$_2$)—, —(CH$_2$)$_4$—[C(CH$_3$)(CH$_2$CF$_3$)]$_4$—(CH$_2$)—, —(CH$_2$)$_5$—[C(CH$_3$)(CH$_2$CF$_3$)]$_4$—(CH$_2$)—, —(CH$_2$)$_6$—[C(CH$_3$)(CH$_2$CF$_3$)]$_4$—(CH$_2$)—, —(CH$_2$)$_7$—[C(CH$_3$)(CH$_2$CF$_3$)]$_4$—(CH$_2$)—, —(CH$_2$)$_2$—[C(CH$_3$)(CH$_2$CF$_3$)]$_4$—(CH$_2$)$_2$—, —(CH$_2$)$_3$—[C(CH$_3$)(CH$_2$CF$_3$)]$_4$—(CH$_2$)$_3$—, —(CH$_2$)$_4$—[C(CH$_3$)(CH$_2$CF$_3$)]$_4$—(CH$_2$)$_4$—, —(CH$_2$)$_5$—[C(CH$_3$)(CH$_2$CF$_3$)]$_4$—(CH$_2$)$_5$—, —(CH$_2$)$_2$—[C(CH$_3$)(CH$_2$CF$_3$)]$_4$—(CH$_2$)$_3$—, —(CH$_2$)$_2$—[C(CH$_3$)(CH$_2$CF$_3$)]$_4$—(CH$_2$)$_4$—, —(CH$_2$)$_2$—[C(CH$_3$)(CH$_2$CF$_3$)]$_4$—(CH$_2$)$_5$—, —(CH$_2$)$_2$—[C(CH$_3$)(CH$_2$CF$_3$)]$_4$—(CH$_2$)$_6$—, —(CH$_2$)$_3$—[C(CH$_3$)(CH$_2$CF$_3$)]$_4$—(CH$_2$)$_2$—, —(CH$_2$)$_3$—[C(CH$_3$)(CH$_2$CF$_3$)]$_4$—(CH$_2$)$_4$—, —(CH$_2$)$_4$—[C(CH$_3$)(CH$_2$CF$_3$)]$_4$—(CH$_2$)$_2$—, —(CH$_2$)$_4$—[C(CH$_3$)(CH$_2$CF$_3$)]$_4$—(CH$_2$)$_3$—, —(CH$_2$)$_5$—[C(CH$_3$)(CH$_2$CF$_3$)]$_4$—(CH$_2$)$_2$—, —(CH$_2$)$_5$—[C(CH$_3$)(CH$_2$CF$_3$)]$_4$—(CH$_2$)$_3$—, —(CH$_2$)$_6$—[C(CH$_3$)(CH$_2$CF$_3$)]$_4$—(CH$_2$)$_2$—,
—[C(CH$_3$)(CH$_2$CF$_3$)]$_5$—(CH$_2$)—, —(CH$_2$)—[C(CH$_3$)(CH$_2$CF$_3$)]$_5$—, —(CH$_2$)—[C(CH$_3$)(CH$_2$CF$_3$)]$_5$—(CH$_2$)—, —(CH$_2$)—[C(CH$_3$)(CH$_2$CF$_3$)]$_5$—(CH$_2$)$_2$—, —(CH$_2$)—[C(CH$_3$)(CH$_2$CF$_3$)]$_5$—(CH$_2$)$_3$—, —(CH$_2$)—[C(CH$_3$)(CH$_2$CF$_3$)]$_5$—(CH$_2$)$_4$—, —(CH$_2$)—[C(CH$_3$)(CH$_2$CF$_3$)]$_5$—(CH$_2$)$_5$—, —(CH$_2$)—[C(CH$_3$)(CH$_2$CF$_3$)]$_5$—(CH$_2$)$_6$—, —(CH$_2$)$_2$—[C(CH$_3$)(CH$_2$CF$_3$)]$_5$—(CH$_2$)—, —(CH$_2$)$_3$—[C(CH$_3$)(CH$_2$CF$_3$)]$_5$—(CH$_2$)—, —(CH$_2$)$_4$—[C(CH$_3$)(CH$_2$CF$_3$)]$_5$—(CH$_2$)—, —(CH$_2$)$_5$—[C(CH$_3$)(CH$_2$CF$_3$)]$_5$—(CH$_2$)—, —(CH$_2$)$_6$—[C(CH$_3$)(CH$_2$CF$_3$)]$_5$—(CH$_2$)—, —(CH$_2$)$_2$—[C(CH$_3$)(CH$_2$CF$_3$)]$_5$—(CH$_2$)$_2$—, —(CH$_2$)$_3$—[C(CH$_3$)(CH$_2$CF$_3$)]$_5$—(CH$_2$)$_3$—, —(CH$_2$)$_4$—[C(CH$_3$)(CH$_2$CF$_3$)]$_5$—(CH$_2$)$_4$—, —(CH$_2$)$_2$—[C(CH$_3$)(CH$_2$CF$_3$)]$_5$—(CH$_2$)$_3$—, —(CH$_2$)$_2$—[C(CH$_3$)(CH$_2$CF$_3$)]$_5$—(CH$_2$)$_4$—, —(CH$_2$)$_2$—[C(CH$_3$)(CH$_2$CF$_3$)]$_5$—(CH$_2$)$_5$—, —(CH$_2$)$_2$—[C(CH$_3$)(CH$_2$CF$_3$)]$_5$—(CH$_2$)$_6$—, —(CH$_2$)$_3$—[C(CH$_3$)(CH$_2$CF$_3$)]$_5$—(CH$_2$)$_2$—, —(CH$_2$)$_3$—[C(CH$_3$)(CH$_2$CF$_3$)]$_5$—(CH$_2$)$_4$—, —(CH$_2$)$_4$—[C(CH$_3$)(CH$_2$CF$_3$)]$_5$—(CH$_2$)$_2$—, —(CH$_2$)$_4$—[C(CH$_3$)(CH$_2$CF$_3$)]$_5$—(CH$_2$)$_3$—, —(CH$_2$)$_5$—[C(CH$_3$)(CH$_2$CF$_3$)]$_5$—(CH$_2$)$_2$—,
—(CH$_2$)—(CF$_2$)—O—(CF$_2$)—O—(CF$_2$)—(CH$_2$)—, —(CH$_2$)$_2$—(CF$_2$)—O—(CF$_2$)—O—(CF$_2$)—(CH$_2$)$_2$—, —(CH$_2$)$_3$—(CF$_2$)—O—(CF$_2$)—O—(CF$_2$)—(CH$_2$)$_3$—, —(CH$_2$)$_4$—(CF$_2$)—O—(CF$_2$)—O—(CF$_2$)—(CH$_2$)$_4$—, —(CH$_2$)—(CF$_2$)—O—(CF$_2$)—O—(CF$_2$)—(CH$_2$)$_2$—, —(CH$_2$)—(CF$_2$)—O—(CF$_2$)—O—(CF$_2$)—(CH$_2$)$_3$—, —(CH$_2$)—(CF$_2$)—O—(CF$_2$)—O—(CF$_2$)—(CH$_2$)$_4$—, —(CH$_2$)—(CF$_2$)—O—(CF$_2$)—O—(CF$_2$)—(CH$_2$)$_5$—, —(CH$_2$)—(CF$_2$)—O—(CF$_2$)—O—(CF$_2$)—(CH$_2$)$_6$—, —(CH$_2$)—(CF$_2$)—O—(CF$_2$)—O—(CF$_2$)—(CH$_2$)$_7$—, —(CH$_2$)$_2$—(CF$_2$)—O—(CF$_2$)—O—(CF$_2$)—(CH$_2$)—, —(CH$_2$)$_3$—(CF$_2$)—O—(CF$_2$)—O—(CF$_2$)—(CH$_2$)—, —(CH$_2$)$_4$—(CF$_2$)—O—(CF$_2$)—O—(CF$_2$)—(CH$_2$)—, —(CH$_2$)$_5$—(CF$_2$)—O—(CF$_2$)—O—(CF$_2$)—(CH$_2$)—, —(CH$_2$)$_6$—(CF$_2$)—O—(CF$_2$)—O—(CF$_2$)—(CH$_2$)—, —(CH$_2$)$_7$—(CF$_2$)—O—(CF$_2$)—O—(CF$_2$)—(CH$_2$)—, —(CH$_2$)$_2$—(CF$_2$)—O—(CF$_2$)—O—(CF$_2$)—(CH$_2$)$_3$—, —(CH$_2$)$_2$—(CF$_2$)—O—(CF$_2$)—O—(CF$_2$)—(CH$_2$)$_4$—, —(CH$_2$)$_2$—(CF$_2$)—O—(CF$_2$)—O—(CF$_2$)—(CH$_2$)$_5$—, —(CH$_2$)$_2$—(CF$_2$)—O—(CF$_2$)—O—(CF$_2$)—(CH$_2$)$_6$—, —(CH$_2$)$_3$—(CF$_2$)—O—(CF$_2$)—O—(CF$_2$)—(CH$_2$)$_2$—, —(CH$_2$)$_4$—(CF$_2$)—O—(CF$_2$)—O—(CF$_2$)—(CH$_2$)$_2$—, —(CH$_2$)$_5$—(CF$_2$)—O—(CF$_2$)—O—(CF$_2$)—(CH$_2$)$_2$—, —(CH$_2$)$_6$—(CF$_2$)—O—(CF$_2$)—O—(CF$_2$)—(CH$_2$)$_2$—, —(CH$_2$)$_3$—(CF$_2$)—O—(CF$_2$)—O—(CF$_2$)—(CH$_2$)$_4$—, —(CH$_2$)$_4$—(CF$_2$)—O—(CF$_2$)—O—(CF$_2$)—(CH$_2$)$_3$—, —(CH$_2$)$_3$—(CF$_2$)—O—(CF$_2$)—O—(CF$_2$)—(CH$_2$)$_5$—, —(CH$_2$)$_5$—(CF$_2$)—O—(CF$_2$)—O—(CF$_2$)—(CH$_2$)$_3$—,
—(CH$_2$)—(CF$_2$)—O—(CF$_2$)$_2$—O—(CF$_2$)—(CH$_2$)—, —(CH$_2$)$_2$—(CF$_2$)—O—(CF$_2$)$_2$—O—(CF$_2$)—(CH$_2$)$_2$—, —(CH$_2$)$_3$—(CF$_2$)—O—(CF$_2$)$_2$—O—(CF$_2$)—(CH$_2$)$_3$—, —(CH$_2$)$_4$—(CF$_2$)—O—(CF$_2$)$_2$—O—(CF$_2$)—(CH$_2$)$_4$—, —(CH$_2$)—(CF$_2$)—O—(CF$_2$)$_2$—O—(CF$_2$)—(CH$_2$)$_2$—, —(CH$_2$)—(CF$_2$)—O—(CF$_2$)$_2$—O—(CF$_2$)—(CH$_2$)$_3$—, —(CH$_2$)—(CF$_2$)—O—(CF$_2$)$_2$—O—(CF$_2$)—(CH$_2$)$_4$—, —(CH$_2$)—(CF$_2$)—O—(CF$_2$)$_2$—O—(CF$_2$)—(CH$_2$)$_5$—, —(CH$_2$)—(CF$_2$)—O—(CF$_2$)$_2$—O—(CF$_2$)—(CH$_2$)$_6$—, —(CH$_2$)—(CF$_2$)—O—(CF$_2$)$_2$—O—(CF$_2$)—(CH$_2$)$_7$—, —(CH$_2$)$_2$—(CF$_2$)—O—(CF$_2$)$_2$—O—(CF$_2$)—(CH$_2$)—, —(CH$_2$)$_3$—(CF$_2$)—O—(CF$_2$)$_2$—O—(CF$_2$)—(CH$_2$)—, —(CH$_2$)$_4$—(CF$_2$)—O—(CF$_2$)$_2$—O—(CF$_2$)—(CH$_2$)—, —(CH$_2$)$_5$—(CF$_2$)—O—(CF$_2$)$_2$—O—(CF$_2$)—(CH$_2$)—, —(CH$_2$)$_6$—(CF$_2$)—O—(CF$_2$)$_2$—O—(CF$_2$)—(CH$_2$)—, —(CH$_2$)$_7$—(CF$_2$)—O—(CF$_2$)$_2$—O—(CF$_2$)—(CH$_2$)—, —(CH$_2$)$_2$—(CF$_2$)—O—(CF$_2$)$_2$—O—(CF$_2$)—(CH$_2$)$_3$—, —(CH$_2$)$_2$—(CF$_2$)—O—(CF$_2$)$_2$—O—(CF$_2$)—(CH$_2$)$_4$—, —(CH$_2$)$_2$—(CF$_2$)—O—(CF$_2$)$_2$—O—(CF$_2$)—(CH$_2$)$_5$—, —(CH$_2$)$_2$—(CF$_2$)—O—(CF$_2$)$_2$—O—(CF$_2$)—(CH$_2$)$_6$—, —(CH$_2$)$_3$—(CF$_2$)—O—(CF$_2$)$_2$—O—(CF$_2$)—(CH$_2$)$_2$—, —(CH$_2$)$_4$—(CF$_2$)—O—(CF$_2$)$_2$—O—(CF$_2$)—(CH$_2$)$_2$—, —(CH$_2$)$_5$—(CF$_2$)—O—(CF$_2$)$_2$—O—(CF$_2$)—(CH$_2$)$_2$—, —(CH$_2$)$_6$—(CF$_2$)—O—(CF$_2$)$_2$—O—(CF$_2$)—(CH$_2$)$_2$—, —(CH$_2$)$_3$—(CF$_2$)—O—(CF$_2$)$_2$—O—(CF$_2$)—(CH$_2$)$_4$—, —(CH$_2$)$_4$—(CF$_2$)—O—(CF$_2$)$_2$—O—(CF$_2$)—(CH$_2$)$_3$—, —(CH$_2$)$_3$—(CF$_2$)—O—(CF$_2$)$_2$—O—(CF$_2$)—(CH$_2$)$_5$—, —(CH$_2$)$_5$—(CF$_2$)—O—(CF$_2$)$_2$—O—(CF$_2$)—(CH$_2$)$_3$—,
—(CH$_2$)—(CF$_2$)$_2$—O—(CF$_2$)$_2$—O—(CF$_2$)$_2$—(CH$_2$)—, —(CH$_2$)$_2$—(CF$_2$)$_2$—O—(CF$_2$)$_2$—O—(CF$_2$)$_2$—(CH$_2$)$_2$—, —(CH$_2$)$_3$—(CF$_2$)$_2$—O—(CF$_2$)$_2$—O—(CF$_2$)$_2$—(CH$_2$)$_3$—, —(CH$_2$)$_4$—(CF$_2$)$_2$—O—(CF$_2$)$_2$—O—(CF$_2$)$_2$—(CH$_2$)$_4$—, —(CH$_2$)—(CF$_2$)$_2$—O—(CF$_2$)$_2$—O—(CF$_2$)$_2$—(CH$_2$)$_2$—, —(CH$_2$)—(CF$_2$)$_2$—O—(CF$_2$)$_2$—O—(CF$_2$)$_2$—(CH$_2$)$_3$—, —(CH$_2$)—(CF$_2$)$_2$—O—(CF$_2$)$_2$—O—(CF$_2$)$_2$—(CH$_2$)$_3$—, —(CH$_2$)—(CF$_2$)$_2$—O—(CF$_2$)$_2$—O—(CF$_2$)$_2$—(CH$_2$)$_4$—, —(CH$_2$)—(CF$_2$)$_2$—O—(CF$_2$)$_2$—O—(CF$_2$)$_2$—(CH$_2$)$_5$—, —(CH$_2$)—(CF$_2$)$_2$—O—(CF$_2$)$_2$—O—(CF$_2$)$_2$—(CH$_2$)$_6$—, —(CH$_2$)—(CF$_2$)$_2$—O—(CF$_2$)$_2$—O—(CF$_2$)$_2$—(CH$_2$)$_7$—, —(CH$_2$)$_2$—(CF$_2$)$_2$—O—(CF$_2$)$_2$—O—(CF$_2$)$_2$—(CH$_2$)—, —(CH$_2$)$_3$—(CF$_2$)$_2$—O—(CF$_2$)$_2$—O—(CF$_2$)$_2$—(CH$_2$)—, —(CH$_2$)$_4$—(CF$_2$)$_2$—O—(CF$_2$)$_2$—O—(CF$_2$)$_2$—(CH$_2$)—, —(CH$_2$)$_5$—(CF$_2$)$_2$—O—(CF$_2$)$_2$—O—(CF$_2$)$_2$—(CH$_2$)—, —(CH$_2$)$_6$—(CF$_2$)$_2$—O—(CF$_2$)$_2$—O—(CF$_2$)$_2$—(CH$_2$)—, —(CH$_2$)$_7$—(CF$_2$)$_2$—O—(CF$_2$)$_2$—O—(CF$_2$)$_2$—(CH$_2$)—, —(CH$_2$)$_2$—(CF$_2$)$_2$—O—(CF$_2$)$_2$—O—(CF$_2$)$_2$—(CH$_2$)$_3$—, —(CH$_2$)$_2$—(CF$_2$)$_2$—O—(CF$_2$)$_2$—O—(CF$_2$)$_2$—(CH$_2$)$_4$—, —(CH$_2$)$_2$—(CF$_2$)$_2$—O—(CF$_2$)$_2$—O—(CF$_2$)$_2$—(CH$_2$)$_5$—, —(CH$_2$)$_2$—(CF$_2$)$_2$—O—(CF$_2$)$_2$—O—(CF$_2$)$_2$—(CH$_2$)$_6$—, —(CH$_2$)$_3$—(CF$_2$)$_2$—O—(CF$_2$)$_2$—O—(CF$_2$)$_2$—(CH$_2$)$_2$—, —(CH$_2$)$_4$—(CF$_2$)$_2$—O—(CF$_2$)$_2$—O—(CF$_2$)$_2$—(CH$_2$)$_2$—,

—(CH$_2$)$_5$—(CF$_2$)$_2$—O—(CF$_2$)$_2$—O—(CF$_2$)$_2$—(CH$_2$)$_2$—,
—(CH$_2$)$_6$—(CF$_2$)$_2$—O—(CF$_2$)$_2$—O—(CF$_2$)$_2$—(CH$_2$)$_2$—,
—(CH$_2$)$_3$—(CF$_2$)$_2$—O—(CF$_2$)$_2$—O—(CF$_2$)$_2$—(CH$_2$)$_4$—,
—(CH$_2$)$_4$—(CF$_2$)$_2$—O—(CF$_2$)$_2$—O—(CF$_2$)$_2$—(CH$_2$)$_3$—,
—(CH$_2$)$_3$—(CF$_2$)$_2$—O—(CF$_2$)$_2$—O—(CF$_2$)$_2$—(CH$_2$)$_5$—,
(CH$_2$)$_5$—(CF$_2$)$_2$—O—(CF$_2$)$_2$—O—(CF$_2$)$_2$—(CH$_2$)$_3$—,
—(CH$_2$)—(CF$_2$)—O—(CF$_2$)—O—(CF$_2$)—O—(CF$_2$)—(CH$_2$)—, —(CH$_2$)$_2$—(CF$_2$)—O—(CF$_2$)—O—(CF$_2$)—O—(CF$_2$)—(CH$_2$)$_2$—, —(CH$_2$)$_3$—(CF$_2$)—O—(CF$_2$)—O—(CF$_2$)—O—(CF$_2$)—(CH$_2$)$_3$—, —(CH$_2$)$_4$—(CF$_2$)—O—(CF$_2$)—O—(CF$_2$)—O—(CF$_2$)—(CH$_2$)$_4$—, —(CH$_2$)—(CF$_2$)—O—(CF$_2$)—O—(CF$_2$)—O—(CF$_2$)—(CH$_2$)$_2$—, —(CH$_2$)—(CF$_2$)—O—(CF$_2$)—O—(CF$_2$)—O—(CF$_2$)—(CH$_2$)$_3$—, (CH$_2$)—(CF$_2$)—O—(CF$_2$)—O—(CF$_2$)—O—(CF$_2$)—(CH$_2$)$_4$—, —(CH$_2$)—(CF$_2$)—O—(CF$_2$)—O—(CF$_2$)—O—(CF$_2$)—(CH$_2$)$_5$—, —(CH$_2$)—(CF$_2$)—O—(CF$_2$)—O—(CF$_2$)—O—(CF$_2$)—(CH$_2$)$_6$—, (CH$_2$)—(CF$_2$)—O—(CF$_2$)—O—(CF$_2$)—O—(CF$_2$)—(CH$_2$)$_7$—, —(CH$_2$)$_2$—(CF$_2$)—O—(CF$_2$)—O—(CF$_2$)—O—(CF$_2$)—(CH$_2$)—, —(CH$_2$)$_3$—(CF$_2$)—O—(CF$_2$)—O—(CF$_2$)—O—(CF$_2$)—(CH$_2$)—, (CH$_2$)$_4$—(CF$_2$)—O—(CF$_2$)—O—(CF$_2$)—O—(CF$_2$)—(CH$_2$)—, —(CH$_2$)$_5$—(CF$_2$)—O—(CF$_2$)—O—(CF$_2$)—O—(CF$_2$)—(CH$_2$)—, —(CH$_2$)$_6$—(CF$_2$)—O—(CF$_2$)—O—(CF$_2$)—O—(CF$_2$)—(CH$_2$)—, (CH$_2$)$_7$—(CF$_2$)—O—(CF$_2$)—O—(CF$_2$)—O—(CF$_2$)—(CH$_2$)—, —(CH$_2$)$_2$—(CF$_2$)—O—(CF$_2$)—O—(CF$_2$)—O—(CF$_2$)—(CH$_2$)$_3$—, —(CH$_2$)$_3$—(CF$_2$)—O—(CF$_2$)—O—(CF$_2$)—O—(CF$_2$)—(CH$_2$)$_2$—, —(CH$_2$)$_2$—(CF$_2$)—O—(CF$_2$)—O—(CF$_2$)—O—(CF$_2$)—(CH$_2$)$_4$—, —(CH$_2$)$_4$—(CF$_2$)—O—(CF$_2$)—O—(CF$_2$)—O—(CF$_2$)—(CH$_2$)$_2$—, —(CH$_2$)$_2$—(CF$_2$)—O—(CF$_2$)—O—(CF$_2$)—O—(CF$_2$)—(CH$_2$)$_5$—, —(CH$_2$)$_2$—(CF$_2$)—O—(CF$_2$)—O—(CF$_2$)—O—(CF$_2$)—(CH$_2$)$_6$—, —(CH$_2$)$_3$—(CF$_2$)—O—(CF$_2$)—O—(CF$_2$)—O—(CF$_2$)—(CH$_2$)$_2$—, —(CH$_2$)$_4$—(CF$_2$)—O—(CF$_2$)—O—(CF$_2$)—O—(CF$_2$)—(CH$_2$)$_2$—, —(CH$_2$)$_5$—(CF$_2$)—O—(CF$_2$)—O—(CF$_2$)—O—(CF$_2$)—(CH$_2$)$_2$—, —(CH$_2$)$_6$—(CF$_2$)—O—(CF$_2$)—O—(CF$_2$)—O—(CF$_2$)—(CH$_2$)$_2$—, (CH$_2$)$_3$—(CF$_2$)—O—(CF$_2$)—O—(CF$_2$)—O—(CF$_2$)—(CH$_2$)$_4$—, —(CH$_2$)$_4$—(CF$_2$)—O—(CF$_2$)—O—(CF$_2$)—O—(CF$_2$)—(CH$_2$)$_3$—, —(CH$_2$)$_3$—(CF$_2$)—O—(CF$_2$)—O—(CF$_2$)—O—(CF$_2$)—(CH$_2$)$_5$—, (CH$_2$)$_5$—(CF$_2$)—O—(CF$_2$)—O—(CF$_2$)—O—(CF$_2$)—(CH$_2$)$_3$—,
—(CH$_2$)—(CF$_2$)$_2$—O—(CF$_2$)$_2$—O—(CF$_2$)$_2$—O—(CF$_2$)$_2$—(CH$_2$)—, —(CH$_2$)$_2$—(CF$_2$)$_2$—O—(CF$_2$)$_2$—O—(CF$_2$)$_2$—O—(CF$_2$)$_2$—(CH$_2$)$_2$—, —(CH$_2$)$_3$—(CF$_2$)$_2$—O—(CF$_2$)$_2$—O—(CF$_2$)$_2$—O—(CF$_2$)$_2$—(CH$_2$)$_3$—, —(CH$_2$)$_4$—(CF$_2$)$_2$—O—(CF$_2$)$_2$—O—(CF$_2$)$_2$—O—(CF$_2$)$_2$—(CH$_2$)$_4$—,
—(CH$_2$)—(CF$_2$)$_2$—O—(CF$_2$)$_2$—O—(CF$_2$)$_2$—O—(CF$_2$)$_2$—(CH$_2$)$_2$—, —(CH$_2$)—(CF$_2$)$_2$—O—(CF$_2$)$_2$—O—(CF$_2$)$_2$—O—(CF$_2$)$_2$—(CH$_2$)$_3$—, —(CH$_2$)$_2$—(CF$_2$)$_2$—O—(CF$_2$)$_2$—O—(CF$_2$)$_2$—O—(CF$_2$)$_2$—(CH$_2$)$_3$—, —(CH$_2$)$_2$—(CF$_2$)$_2$—O—(CF$_2$)$_2$—O—(CF$_2$)$_2$—O—(CF$_2$)$_2$—(CH$_2$)$_4$—, —(CH$_2$)—(CF$_2$)$_2$—O—(CF$_2$)$_2$—O—(CF$_2$)$_2$—O—(CF$_2$)$_2$—(CH$_2$)$_5$—, —(CH$_2$)—(CF$_2$)$_2$—O—(CF$_2$)$_2$—O—(CF$_2$)$_2$—O—(CF$_2$)$_2$—(CH$_2$)$_6$—, —(CH$_2$)$_2$—(CF$_2$)$_2$—O—(CF$_2$)$_2$—O—(CF$_2$)$_2$—O—(CF$_2$)$_2$—(CH$_2$)$_5$—, —(CH$_2$)$_2$—(CF$_2$)$_2$—O—(CF$_2$)$_2$—O—(CF$_2$)$_2$—O—(CF$_2$)$_2$—(CH$_2$)$_6$—, —(CH$_2$)$_3$—(CF$_2$)$_2$—O—(CF$_2$)$_2$—O—(CF$_2$)$_2$—O—(CF$_2$)$_2$—(CH$_2$)$_2$—, —(CH$_2$)$_4$—(CF$_2$)$_2$—O—(CF$_2$)$_2$—O—(CF$_2$)$_2$—O—, (CF$_2$)$_2$—(CH$_2$)—, —(CH$_2$)$_5$—(CF$_2$)$_2$—O—(CF$_2$)$_2$—O—(CF$_2$)$_2$—(CH$_2$)—, —(CH$_2$)$_6$—(CF$_2$)$_2$—O—(CF$_2$)$_2$—O—(CF$_2$)$_2$—(CH$_2$)—, —(CH$_2$)$_7$—(CF$_2$)$_2$—O—(CF$_2$)$_2$—O—(CF$_2$)$_2$—(CH$_2$)—, —(CH$_2$)$_2$—(CF$_2$)$_2$—O—(CF$_2$)$_2$—O—(CF$_2$)$_2$—O—(CF$_2$)$_2$—(CH$_2$)$_3$—, (CH$_2$)$_2$—(CF$_2$)$_2$—O—(CF$_2$)$_2$—O—(CF$_2$)$_2$—O—(CF$_2$)$_2$—(CH$_2$)$_4$—, —(CH$_2$)$_2$—(CF$_2$)$_2$—O—(CF$_2$)$_2$—O—(CF$_2$)$_2$—O—(CF$_2$)$_2$—(CH$_2$)$_5$—, —(CH$_2$)$_2$—(CF$_2$)$_2$—O—(CF$_2$)$_2$—O—(CF$_2$)$_2$—O—(CF$_2$)$_2$—(CH$_2$)$_6$—, —(CH$_2$)$_3$—(CF$_2$)$_2$—O—(CF$_2$)$_2$—O—(CF$_2$)$_2$—O—(CF$_2$)$_2$—(CH$_2$)$_2$—, —(CH$_2$)$_4$—(CF$_2$)$_2$—O—(CF$_2$)$_2$—O—

(CF$_2$)$_2$—O—(CF$_2$)$_2$—(CH$_2$)$_2$—, —(CH$_2$)$_5$—(CF$_2$)$_2$—O—(CF$_2$)$_2$—O—(CF$_2$)$_2$—(CH$_2$)$_2$—, —(CH$_2$)$_6$—(CF$_2$)$_2$—O—(CF$_2$)$_2$—O—(CF$_2$)$_2$—O—(CF$_2$)$_2$—(CH$_2$)$_2$—, (CH$_2$)$_3$—(CF$_2$)$_2$—O—(CF$_2$)$_2$—O—(CF$_2$)$_2$—O—(CF$_2$)$_2$—(CH$_2$)$_4$—, —(CH$_2$)$_4$—(CF$_2$)$_2$—O—(CF$_2$)$_2$—O—(CF$_2$)$_2$—O—(CF$_2$)$_2$—(CH$_2$)$_3$—, —(CH$_2$)$_3$—(CF$_2$)$_2$—O—(CF$_2$)$_2$—O—(CF$_2$)$_2$—O—(CF$_2$)$_2$—(CH$_2$)$_5$—, —(CH$_2$)$_5$—(CF$_2$)$_2$—O—(CF$_2$)$_2$—O—(CF$_2$)$_2$—O—(CF$_2$)$_2$—(CH$_2$)$_3$—,

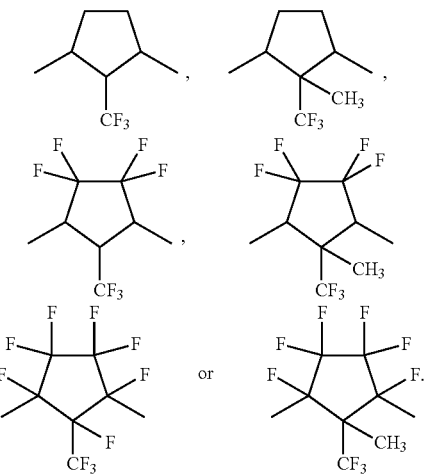

Preferred examples for —R$_2$— are —(CH$_2$)$_3$—(CF$_2$)—(CH$_2$)$_3$—, —(CH$_2$)—(CF$_2$)$_3$—(CH$_2$)—, —(CH$_2$)$_2$—(CF$_2$)$_4$—(CH$_2$)$_2$—, —(CH$_2$)—[CH(CF$_3$)]—(CH$_2$)—, —(CH$_2$)—[C(CH$_3$)CF$_3$]—(CH$_2$)—(CH$_2$)—[CH(CH$_2$CF$_3$)]—(CH$_2$)—, —(CH$_2$)—[C(CH$_3$)(CH$_2$CF$_3$)]—(CH$_2$)—, —(CH$_2$)$_2$—(CF$_2$)—O—(CF$_2$)—O—(CF$_2$)—(CH$_2$)$_2$—, —(CH$_2$)—(CF$_2$)—O—(CF$_2$)—O—(CF$_2$)—O—(CF$_2$)—(CH$_2$)—,

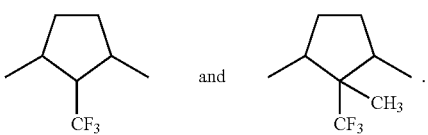

Compounds of formula (I), (I'), (I") and (I''') with linkers —[B]— and substituents as described before or preferably described before having a polymerizable group as described before or preferably described before or below are preferred in case the substituent —R$_2$— within the at least one linking element Y—R$_2$— corresponds to —(C(R)$_2$)$_o$—, wherein at least one R is F or a linear or branched partially or fully fluorinated alkyl group having 1 to 4 C atoms or —(C(R)$_2$)$_p$—X$_8$—(C(R)$_2$)$_q$—(X$_9$)$_s$—(C(R)$_2$)$_r$—(X$_{10}$)$_t$—(C(R)$_2$)$_u$—, wherein at least one R is F or a linear or branched partially or fully fluorinated alkyl group having 1 to 4 C atoms and all other R, o, X$_8$, X$_9$, X$_{10}$, s, t, p, q, r and u have a meaning as described before.

The invention therefore relates to compounds of formula (I), (I'), (I") and (I''') as described before or preferably described before wherein —R$_2$— is at each occurrence independently —(C(R)$_2$)$_o$—, wherein at least one R is F or a linear or branched partially or fully fluorinated alkyl group having 1 to 4 C atoms or —(C(R)$_2$)$_p$—X$_8$—(C(R)$_2$)$_q$—(X$_9$)$_s$—(C(R)$_2$)$_r$—(X$_{10}$)$_t$—(C(R)$_2$)$_u$—, wherein at least one R is F or a linear or branched partially or fully fluorinated alkyl group having 1 to 4 C atoms and all other R, o, $X_8$, $X_9$, $X_{10}$, s, t, p, q, r and u have a meaning as described before.

The linking element —$(C(R)_2)_o$— or —$(C(R)_2)_p$—$X_8$—$(C(R)_2)_q$—$(X_9)_s$—$(C(R)_2)_r$—$(X_{10})_t$—$(C(R)_2)_u$— as —$R_2$— is particularly preferably selected from the group consisting of —$(CH_2)_3$—$(CF_2)$—$(CH_2)_3$—, —$(CH_2)$—$(CF_2)_3$—$(CH_2)$—, —$(CH_2)_2$—$(CF_2)_4$—$(CH_2)_2$—, —$(CH_2)$—$[CH(CF_3)]$—$(CH_2)$—, —$(CH_2)$—$[C(CH_3)CF_3]$—$(CH_2)$—, —$(CH_2)$—$[CH(CH_2CF_3)]$—$(CH_2)$—, —$(CH_2)$—$[C(CH_3)(CH_2CF_3)]$—$(CH_2)$—, —$(CH_2)_2$—$(CF_2)$—O—$(CF_2)$—O—$(CF_2)$—$(CH_2)_2$—, —$(CH_2)$—$(CF_2)$—O—$(CF_2)$—O—$(CF_2)$—O—$(CF_2)$—$(CH_2)$—.

The substituent Y—$R_2$—$R_1$ is particularly preferably selected from the group consisting of O—$R_2$—$R_1$, —$R_2$—$R_1$, and S—$R_2$—$R_1$ wherein —$R_2$— has a meaning as described before or preferably or particularly preferably described before and wherein $R_1$ is a polymerizable group selected from the group consisting of a trialkoxysilyl group, a dialkoxyalkylsilyl group, a silyl group of formula (6), (7) or (8) as described before where the alkyl and/or alkoxy groups are each independently linear or branched having 1 to 6 C atoms, or an alkenyl group of formula (5),

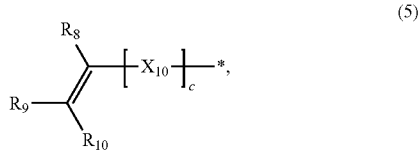
(5)

wherein
$X_{10}$ is selected from the group consisting of O, S, C(=O), C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1.

The substituent Y—$R_2$—$R_1$ is preferably selected from the group consisting of O—$R_2$—$R_1$, —$R_2$—$R_1$ and S—$R_2$—$R_1$, wherein —$R_2$— is selected from the group consisting of —$(CH_2)_3$—$(CF_2)$—$(CH_2)_3$—, —$(CH_2)$—$(CF_2)_3$—$(CH_2)$—, —$(CH_2)_2$—$(CF_2)_4$—$(CH_2)_2$—, —$(CH_2)$—$[CH(CF_3)]$—$(CH_2)$—, —$(CH_2)$—$[C(CH_3)CF_3]$—$(CH_2)$—, —$(CH_2)$—$[CH(CH_2CF_3)]$—$(CH_2)$—, —$(CH_2)$—$[C(CH_3)(CH_2CF_3)]$—$(CH_2)$—, —$(CH_2)_2$—$(CF_2)$—O—$(CF_2)$—O—$(CF_2)$—$(CH_2)_2$—, —$(CH_2)$—$(CF_2)$—O—$(CF_2)$—O—$(CF_2)$—O—$(CF_2)$—$(CH_2)$—,

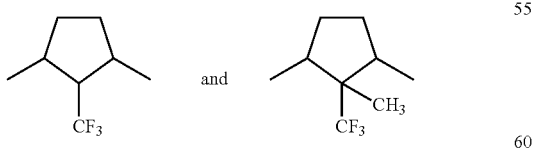

and wherein $R_1$ is a polymerizable group selected from the group consisting of a trialkoxysilyl group, a dialkoxyalkylsilyl group, a silyl group of formula (6), (7) or (8) as described before where the alkyl and/or alkoxy groups are each independently linear or branched having 1 to 6 C atoms, or an alkenyl group of formula (5),

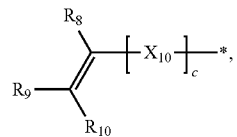
(5)

wherein
$X_{10}$ is selected from the group consisting of O, S, C(=O), C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1.

Preferably, $R_9$ and $R_{10}$ are H.

Preferably, $R_8$ is H, methyl, ethyl or phenyl.

Preferably, $X_{11}$ is C(=O) or C(=O)O.

Preferred alkenyl groups of formula (5) are therefore represented by any one selected from the group consisting of formulae (5-1), (5-2), (5-3), (5-4), (5-5), (5-6), (5-7), (5-8), and (5-9):

(5-1)

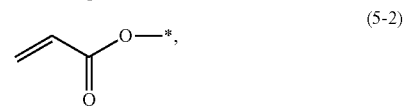
(5-2)

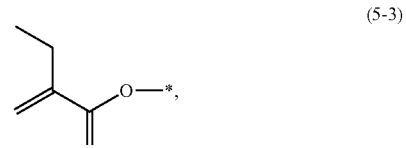
(5-3)

(5-4)

(5-5)

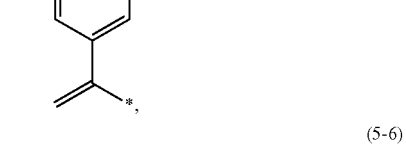
(5-6)

(5-7)

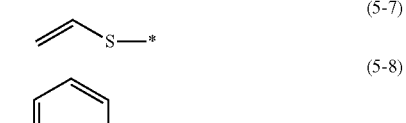
(5-8)

(5-9)

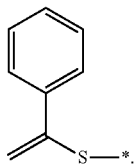

The alkenyl group represented by formula (5-1) is called methacrylate. The alkenyl group represented by formula (5-2) is called acrylate.

The preferred groups $R_1$ are preferably combined with preferred groups of the linking element —$R_2$— and/or the linking element Y—$R_2$—. Combinations are excluded where two O atoms or one O atom and one S atom are directly bonded to each other as known for a skilled artisan in the field of organic chemistry.

The substituent Y—$R_2$—$R_1$ is therefore particularly preferably selected from the group consisting of O—(CH$_2$)$_3$—(CF$_2$)—(CH$_2$)$_3$—R$_1$, O—(CH$_2$)—(CF$_2$)$_3$—(CH$_2$)—R$_1$, O—(CH$_2$)$_2$—(CF$_2$)$_4$—(CH$_2$)$_2$—R$_1$, O—(CH$_2$)—[CH(CF$_3$)]—(CH$_2$)—R$_1$, O—(CH$_2$)—[C(CH$_3$)CF$_3$]—(CH$_2$)—R$_1$, O—(CH$_2$)—[CH(CH$_2$CF$_3$)]—(CH$_2$)—R$_1$, O—(CH$_2$)—[C(CH$_3$)(CH$_2$CF$_3$)]—(CH$_2$)—R$_1$, O—(CH$_2$)$_2$—(CF$_2$)—O—(CF$_2$)—O—(F$_2$)—)—(CH$_2$)$_2$—R$_1$, O—(CH$_2$)—(CF$_2$)—O—(CF$_2$)—O—(CF$_2$)—O—(CF$_2$)—(CH$_2$)—R$_1$,

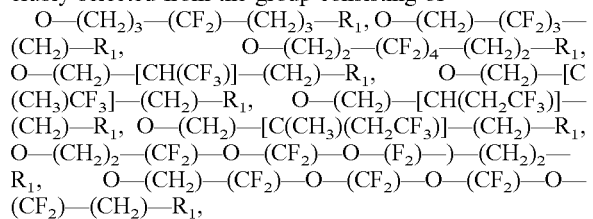

wherein $R_1$ is selected from the group consisting of an alkenyl of formula (5-1), (5-2), (5-3), (5-4), (5-5), (5-6), (5-7), (5-8), or (5-9);
—(CH$_2$)$_3$—(CF$_2$)—(CH$_2$)$_3$—R$_1$, —(CH$_2$)—(CF$_2$)$_3$—(CH$_2$)—R$_1$, —(CH$_2$)$_2$—(CF$_2$)$_4$—(CH$_2$)$_2$—R$_1$, —(CH$_2$)—[CH(CF$_3$)]—(CH$_2$)—R$_1$, —(CH$_2$)—[C(CH$_3$)CF$_3$]—(CH$_2$)—R$_1$, —(CH$_2$)—[CH(CH$_2$CF$_3$)]—(CH$_2$)—R$_1$, —(CH$_2$)—[C(CH$_3$)(CH$_2$CF$_3$)]—(CH$_2$)—R$_1$, —(CH$_2$)$_2$—(CF$_2$)—O—(CF$_2$)—O—(CF$_2$)—(CH$_2$)$_2$—R$_1$, —(CH$_2$)—(CF$_2$)—O—(CF$_2$)—O—(CF$_2$)—O—(CF$_2$)—(CH$_2$)—R$_1$,

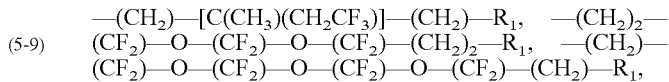

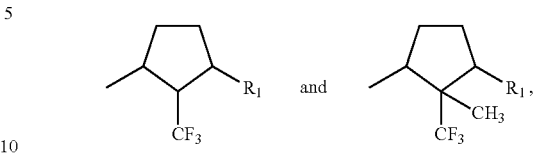

wherein $R_1$ is selected from the group consisting of an alkenyl of formula (5-1), (5-2), (5-3), (5-4), (5-5), (5-6), (5-7), (5-8), or (5-9);
S—(CH$_2$)$_3$—(CF$_2$)—(CH$_2$)$_3$—R$_1$, S—(CH$_2$)—(CF$_2$)$_3$—(CH$_2$)—R$_1$, S—(CH$_2$)$_2$—(CF$_2$)$_4$—(CH$_2$)$_2$—R$_1$, S—(CH$_2$)—[CH(CF$_3$)]—(CH$_2$)—R$_1$, S—(CH$_2$)—[C(CH$_3$)CF$_3$]—(CH$_2$)—R$_1$, S—(CH$_2$)—[CH(CH$_2$CF$_3$)]—(CH$_2$)—R$_1$, S—(CH$_2$)—[C(CH$_3$)(CH$_2$CF$_3$)]—(CH$_2$)—R$_1$, S—(CH$_2$)$_2$—(CF$_2$)—O—(CF$_2$)—O—(CF$_2$)—(CH$_2$)$_2$—R$_1$, S—(CH$_2$)—(CF$_2$)—O—(CF$_2$)—O—(CF$_2$)—O—(CF$_2$)—(CH$_2$)—R$_1$,

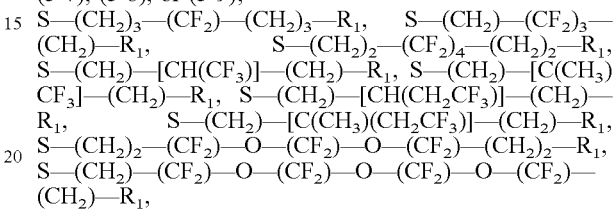

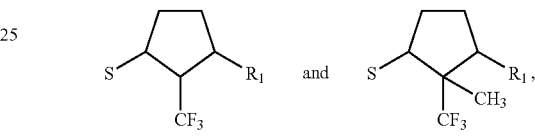

wherein $R_1$ is selected from the group consisting of an alkenyl of formula (5-1), (5-2), (5-3), (5-4), (5-5), (5-6), (5-7), (5-8), or (5-9).

Very particularly preferably, the compounds of formula (I), (I'), (I'') and (I''') comprise a polymerizable group $R_1$ which is a methacryl or an acryl group represented by formula (5-1) and (5-2).

The invention therefore relates further to compounds of formula (I), (I'), (I'') and/or (I''') as described before or preferably described before wherein $R_1$ is at each occurrence independently an acryl or methacryl group.

Examples for compounds of formula (I), (I'), (I'') and/or (I''') are the following compounds O-001 to O-289, S-001 to S-169 and N-001 to N-172:

O-001

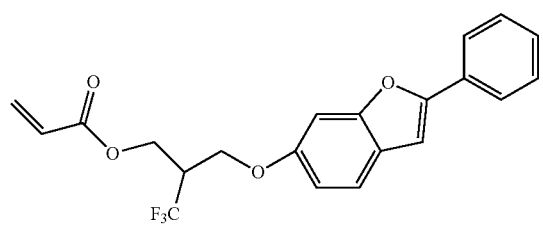

O-002

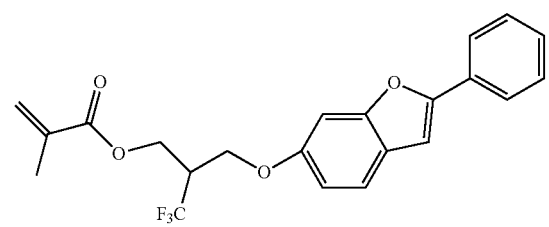

O-003

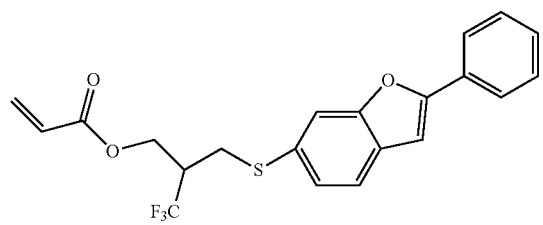

O-004

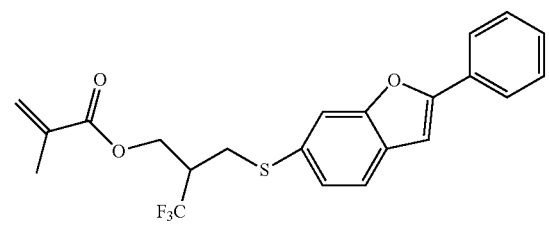

-continued
O-005
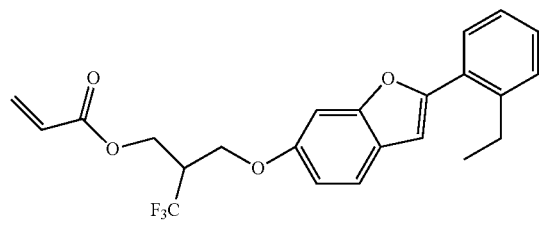
O-006
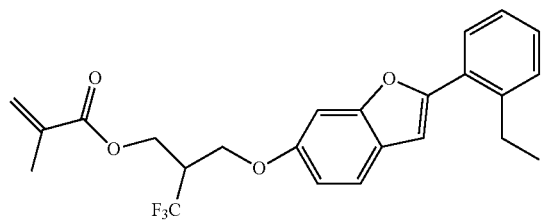
O-007
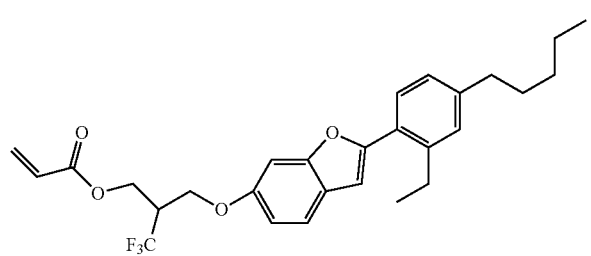
O-008
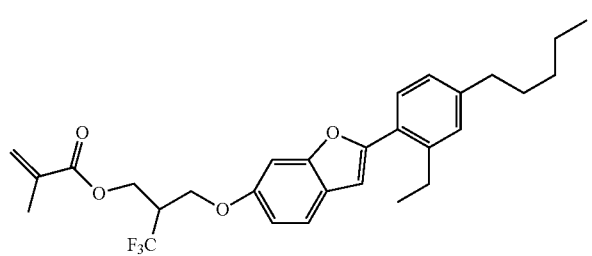
O-009
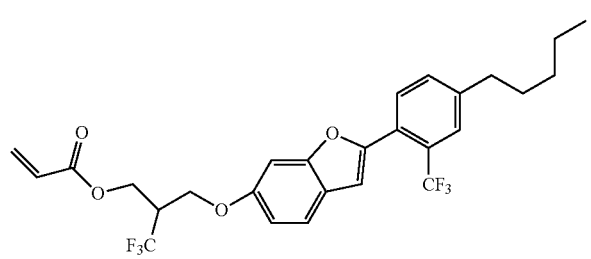
O-010
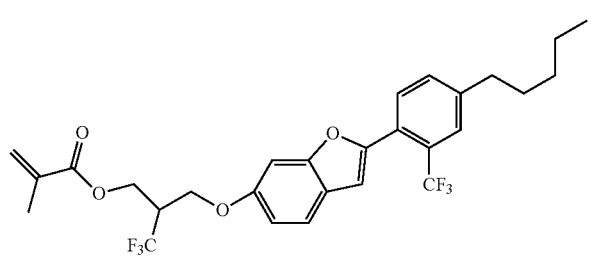
O-011
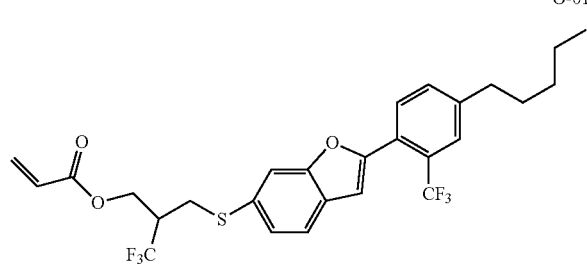
O-012
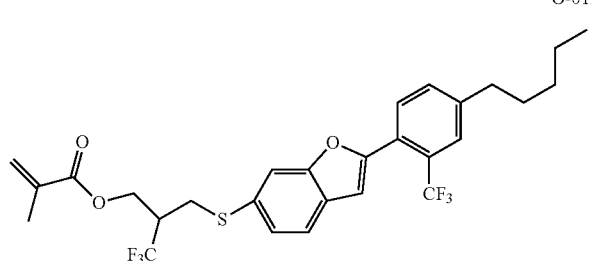
O-013
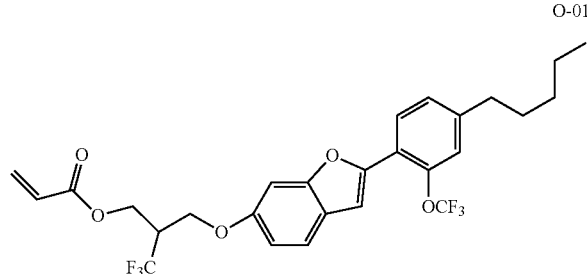
O-014
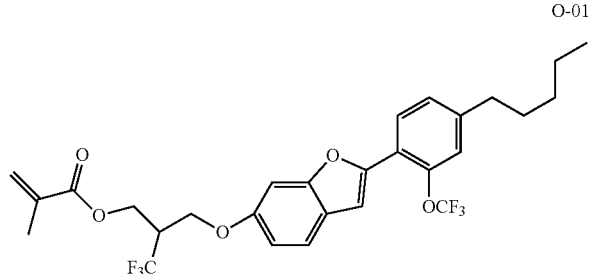
O-015
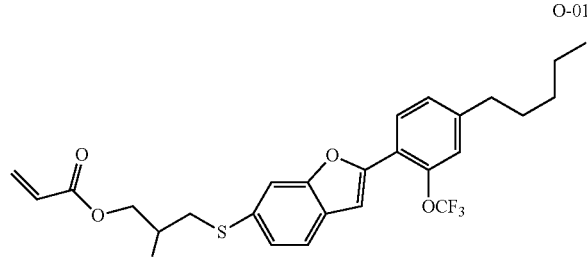
O-016
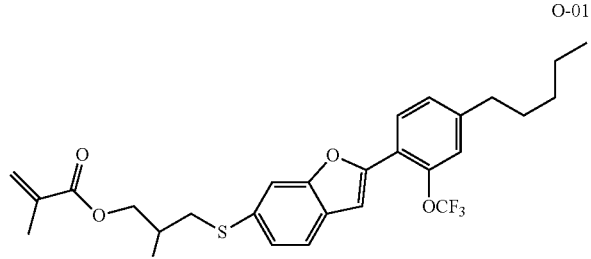

-continued
O-017
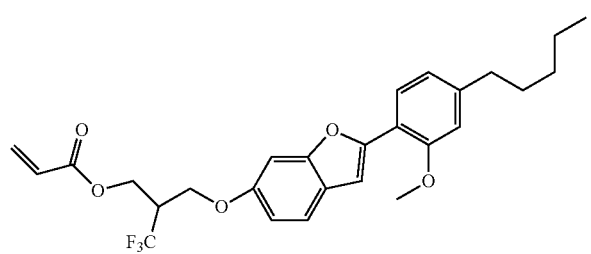
O-018
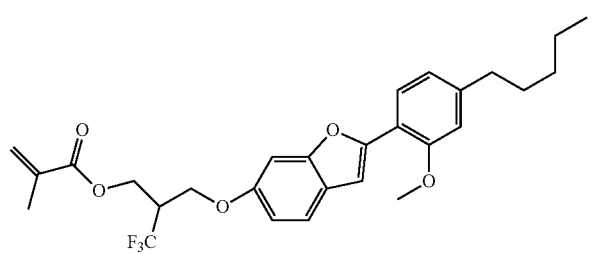
O-019
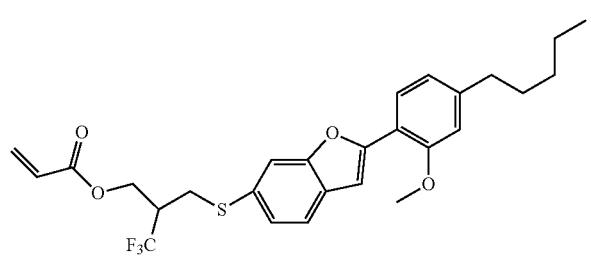
O-020
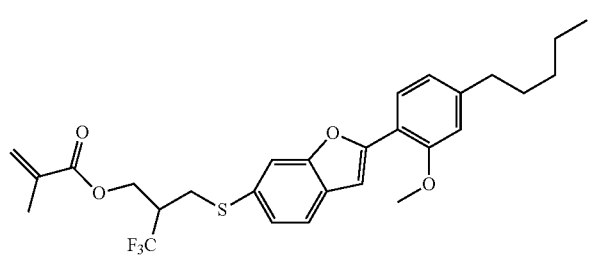
O-021
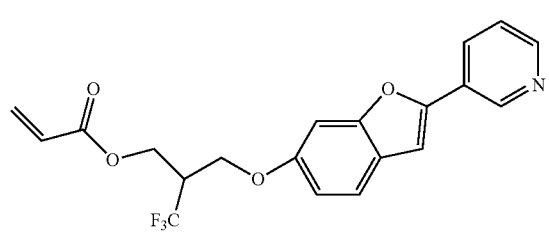
O-022
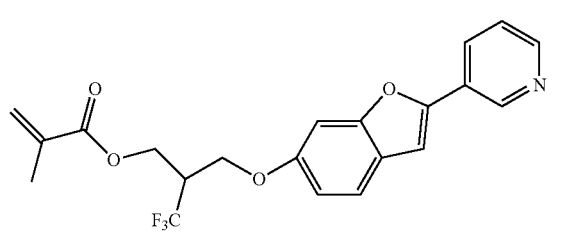
O-023
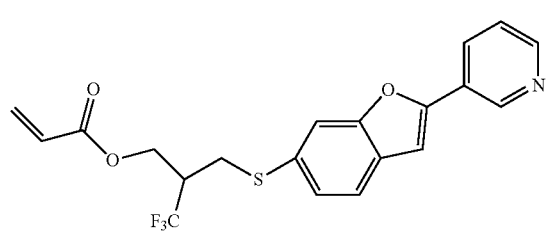
O-024
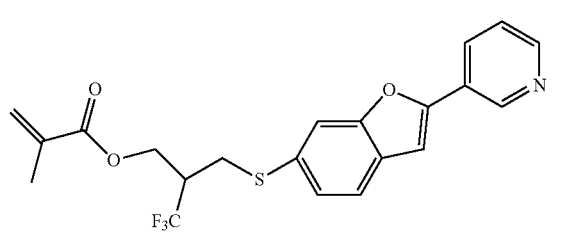
O-025
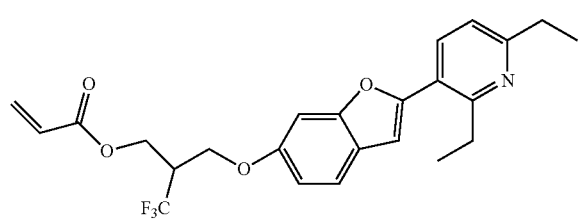
O-026
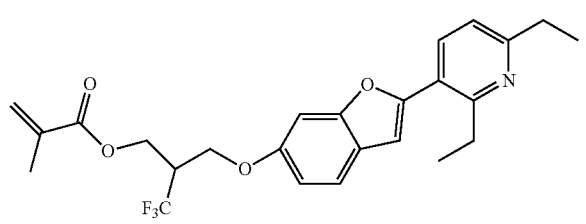
O-027
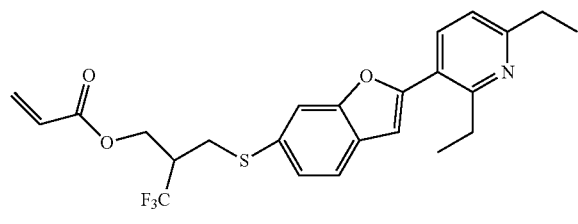
O-028
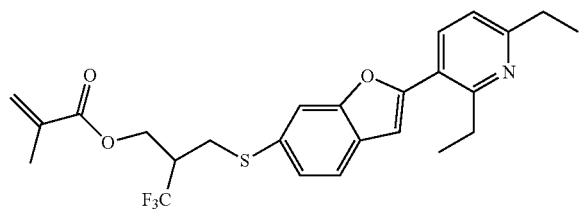

-continued
O-029
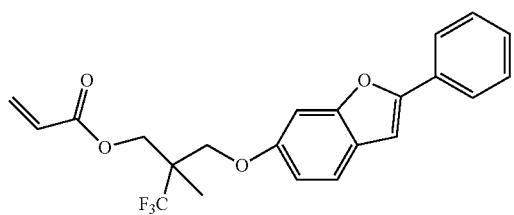
O-030
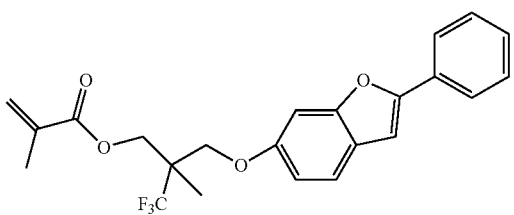
O-031
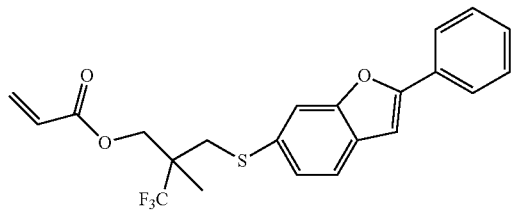
O-032
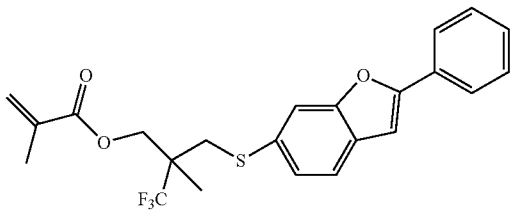
O-033
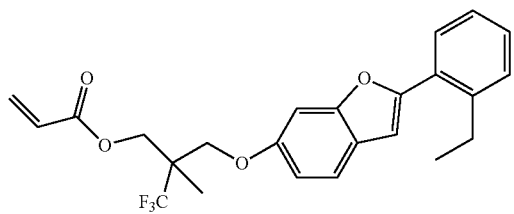
O-034
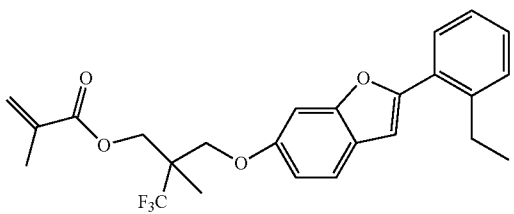
O-035
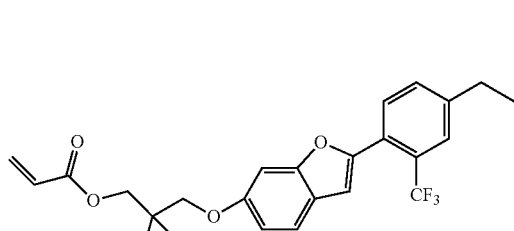
O-036
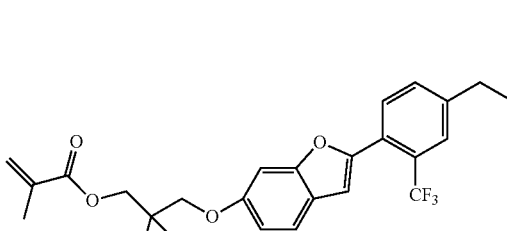
O-037
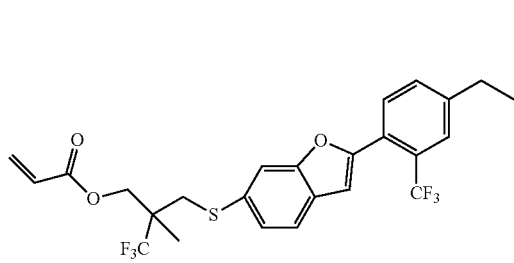
O-038
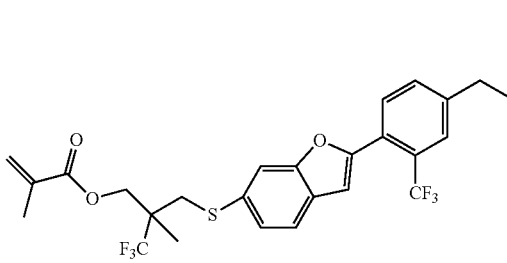
O-039
O-040

-continued
O-041
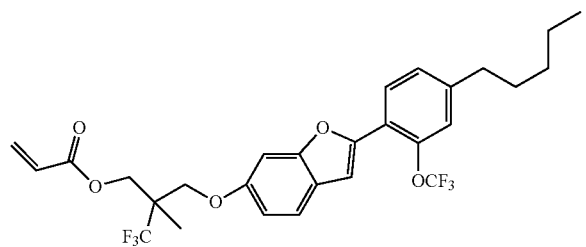
O-042
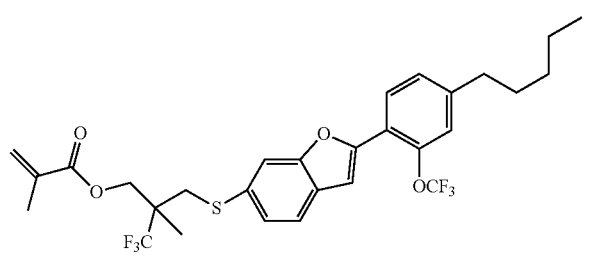
O-043
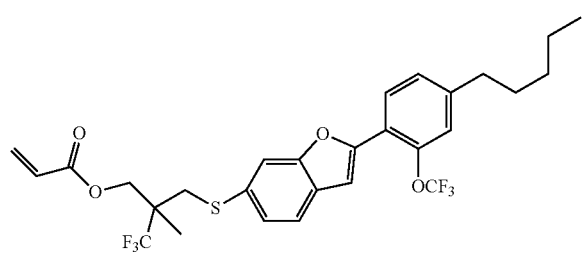
O-044
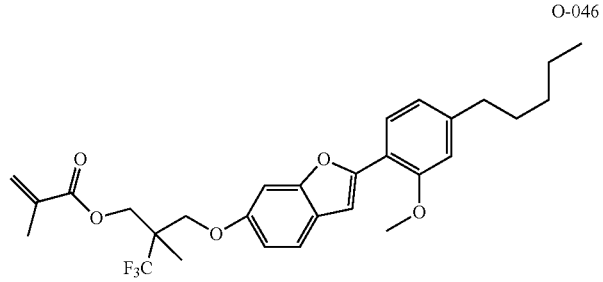
O-045
O-046
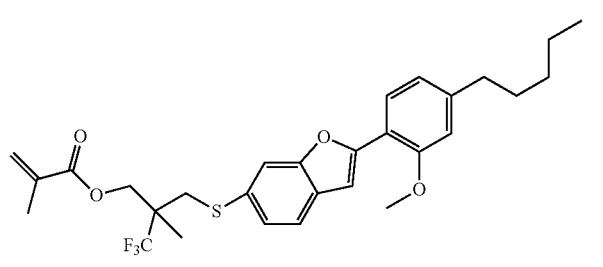
O-047
O-048
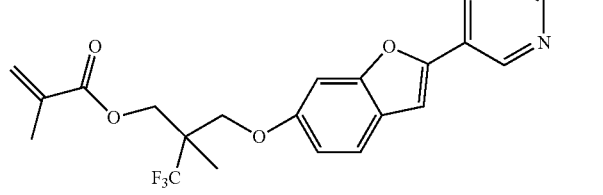
O-049
O-050
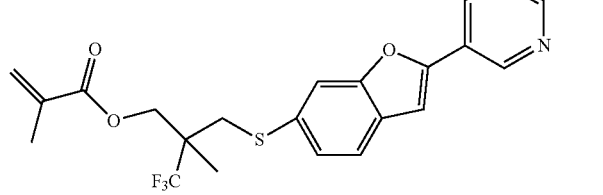
O-051
O-052

-continued
O-053
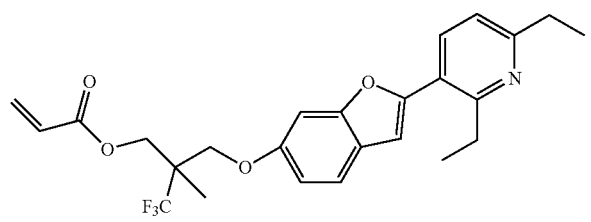
O-054
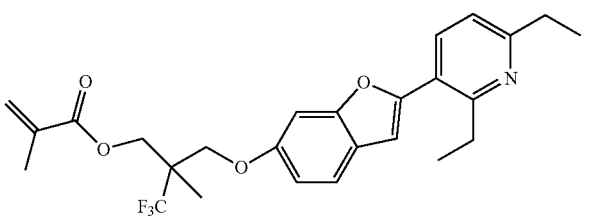
O-055
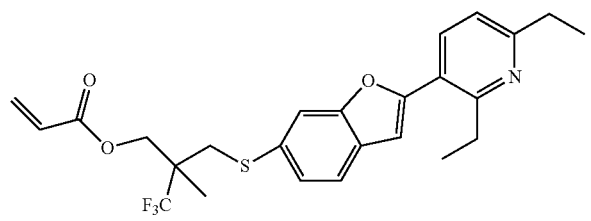
O-056
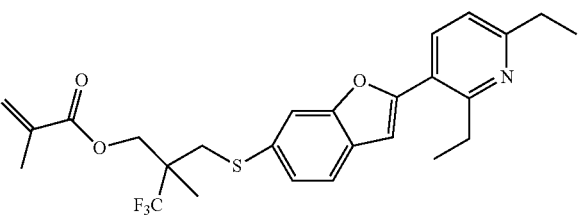
O-057
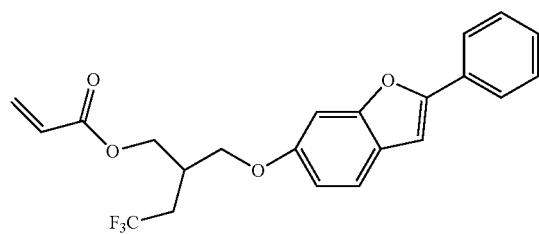
O-058
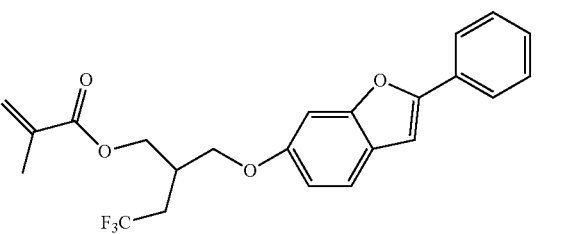
O-059
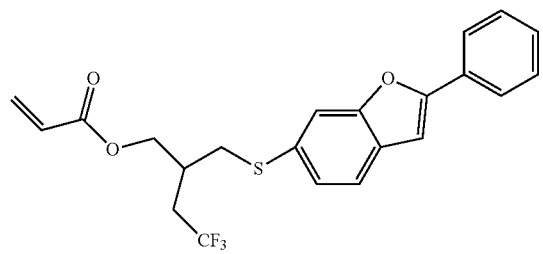
O-060
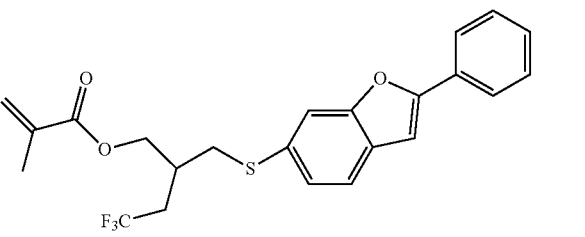
O-061
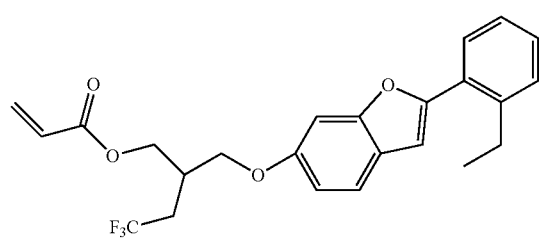
O-062
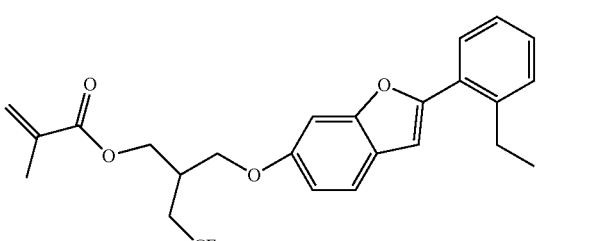
O-063
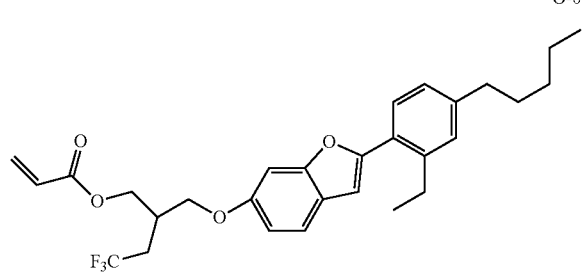
O-064
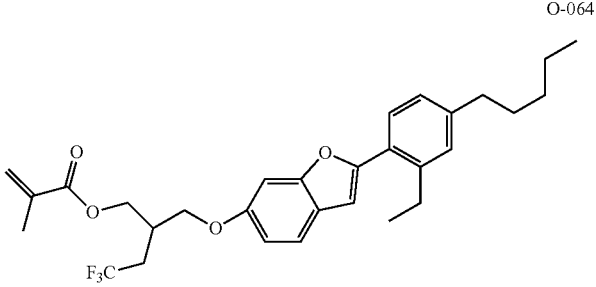

O-065
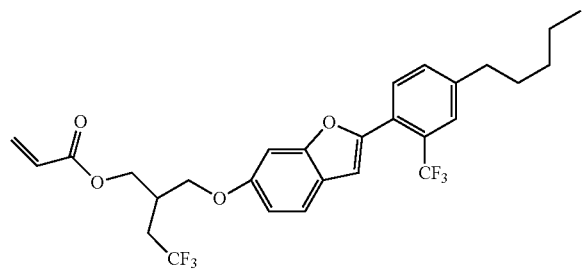
O-066
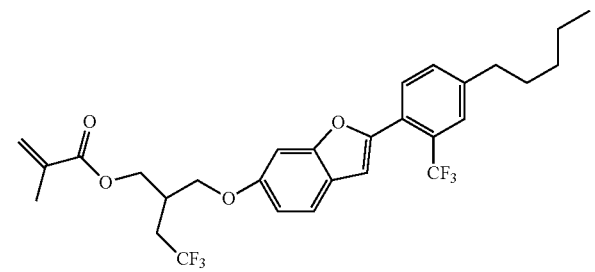
O-067
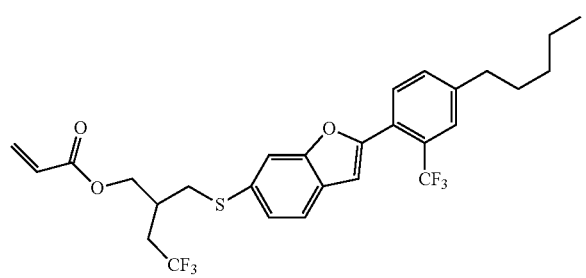
O-068
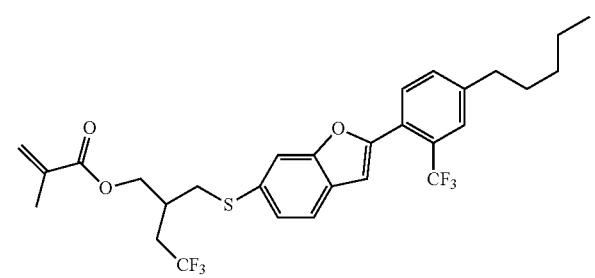
O-069
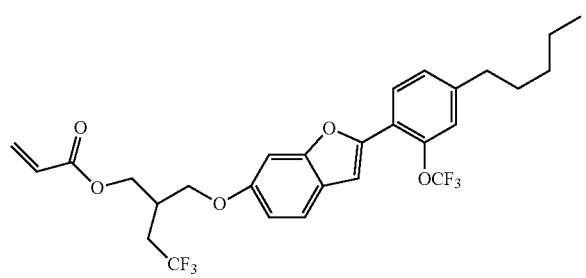
O-070
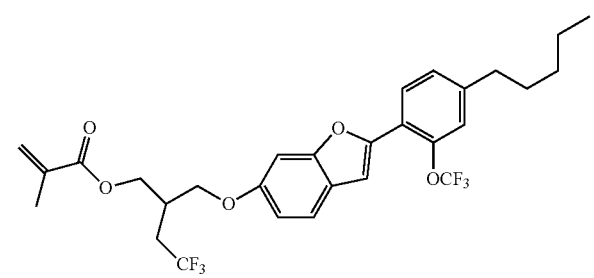
O-071
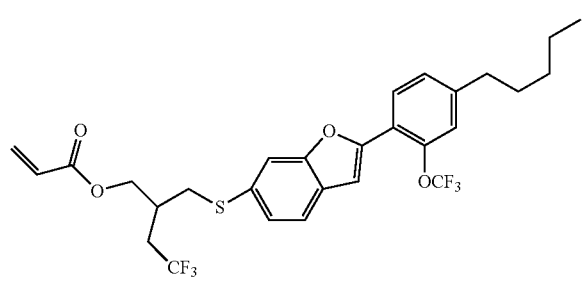
O-072
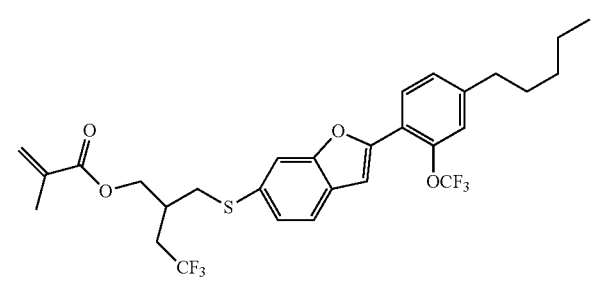
O-073
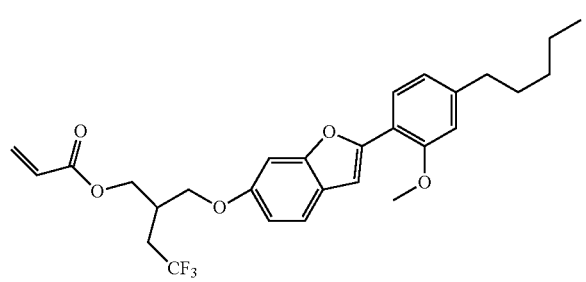
O-074
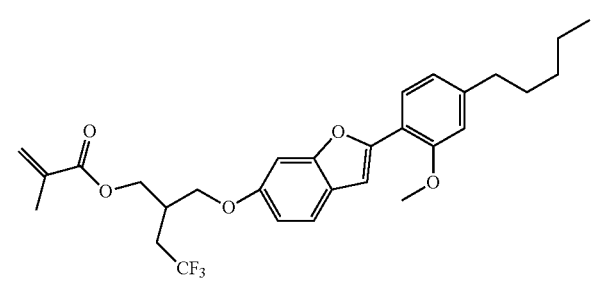

-continued
O-075
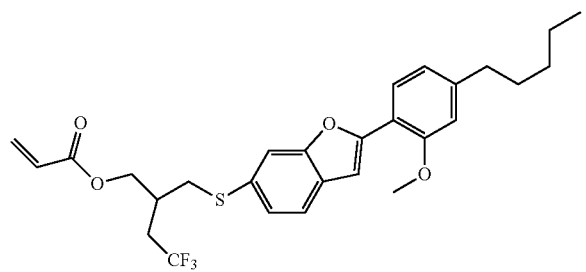
O-076
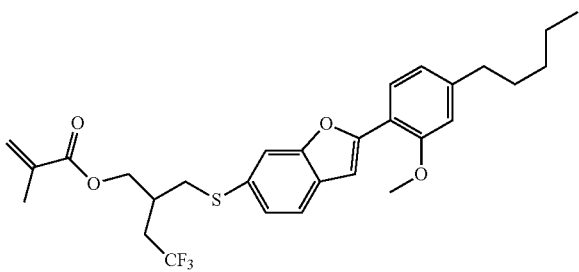
O-077
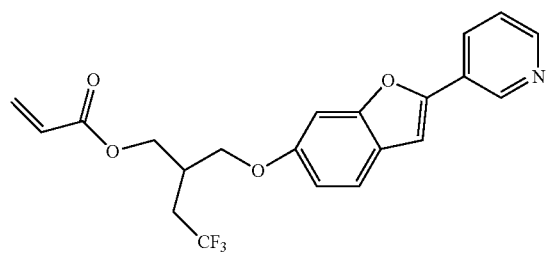
O-078
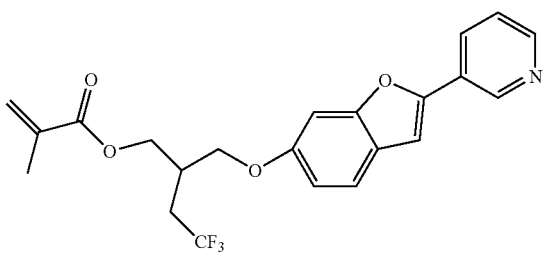
O-079
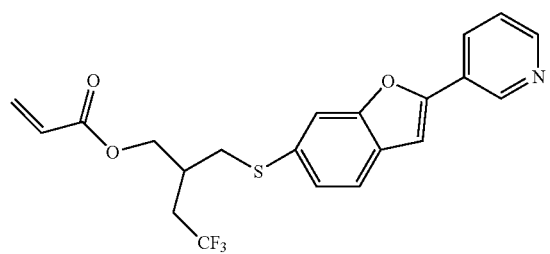
O-080
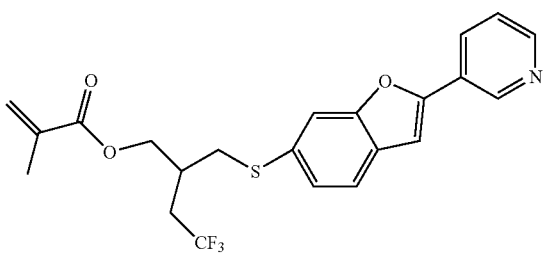
O-081
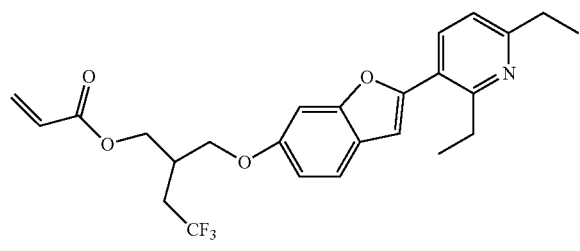
O-082
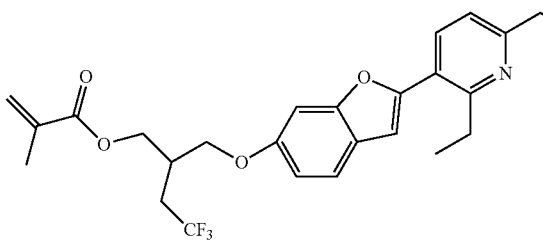
O-083
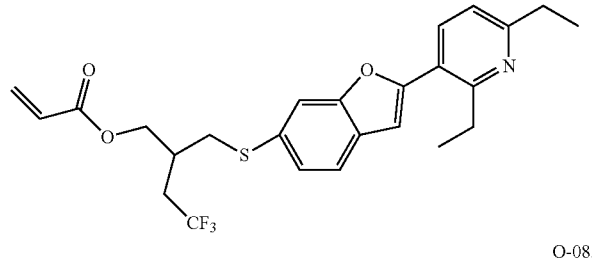
O-084
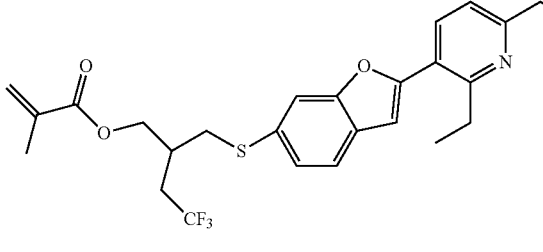
O-085
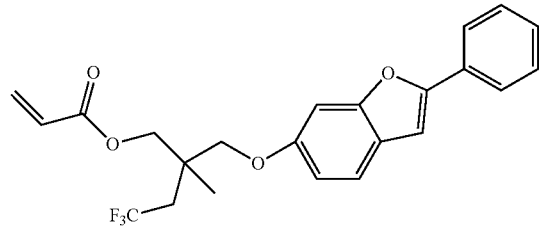
O-086
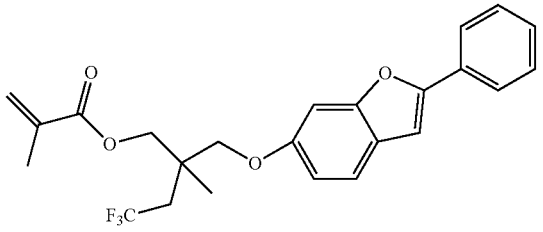

-continued
O-087
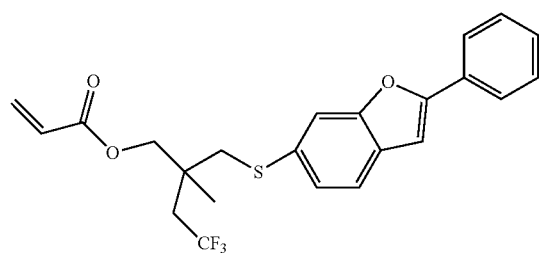
O-088
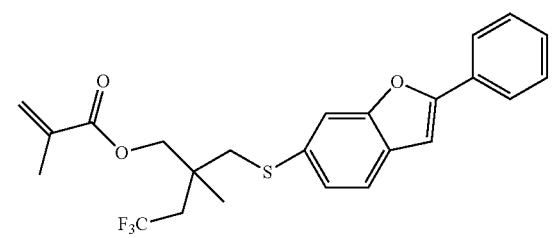
O-089
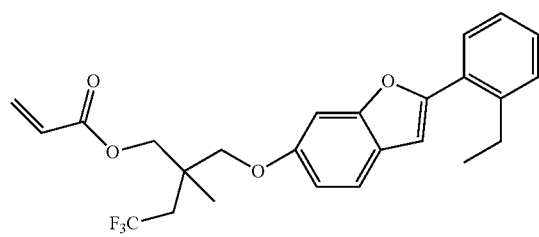
O-090
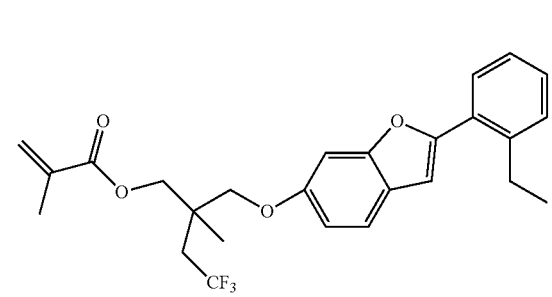
O-091
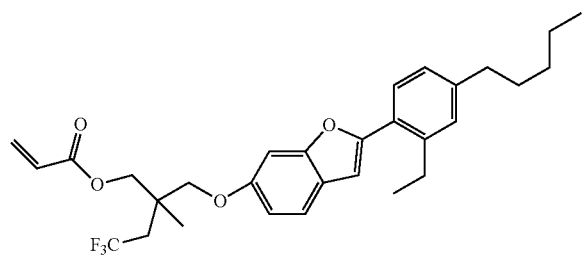
O-092
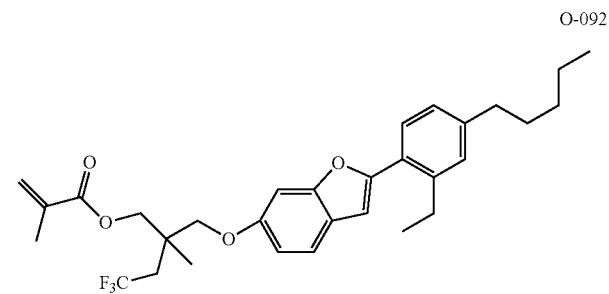
O-093
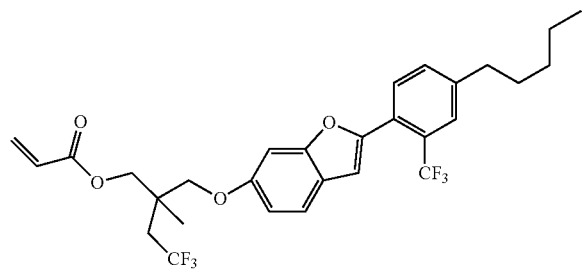
O-094
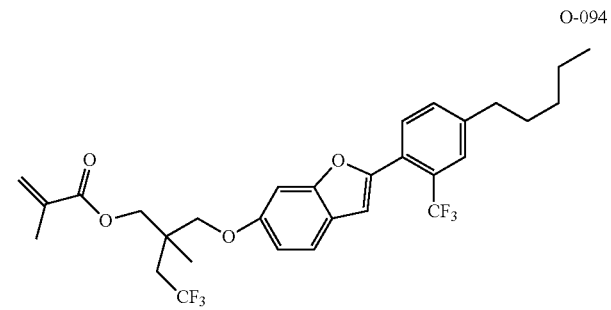
O-095
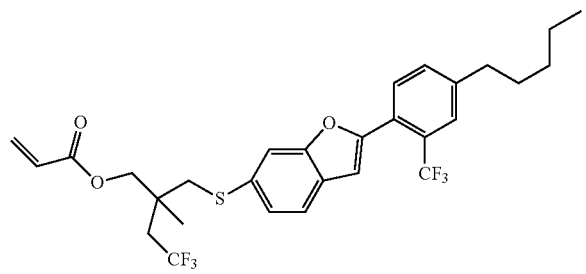
O-096
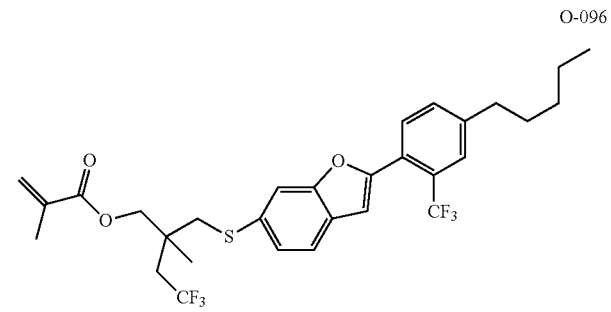

-continued
O-097
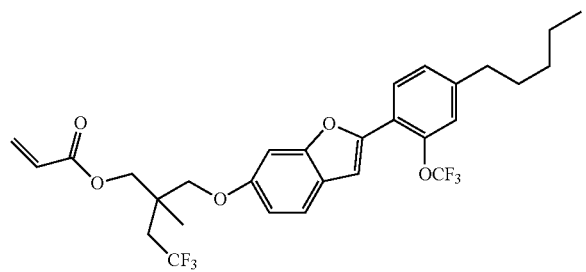
O-098
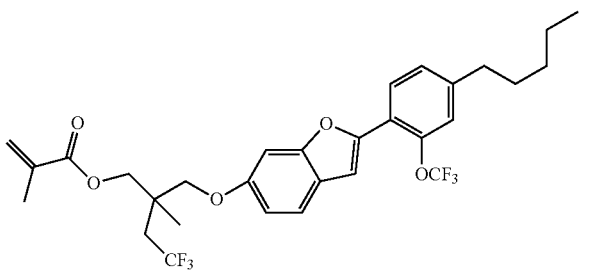
O-099
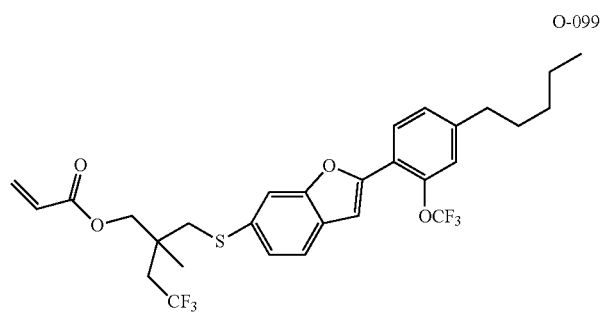
O-100
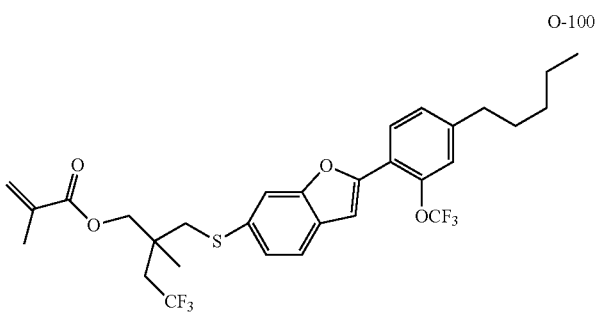
O-101
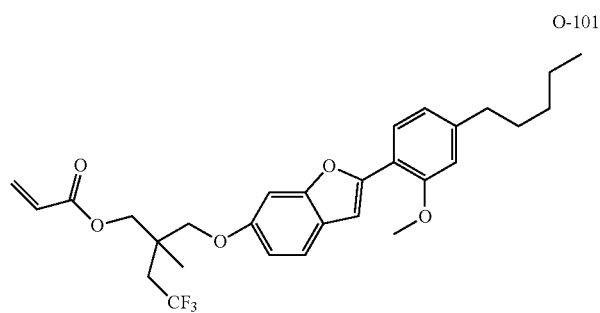
O-102
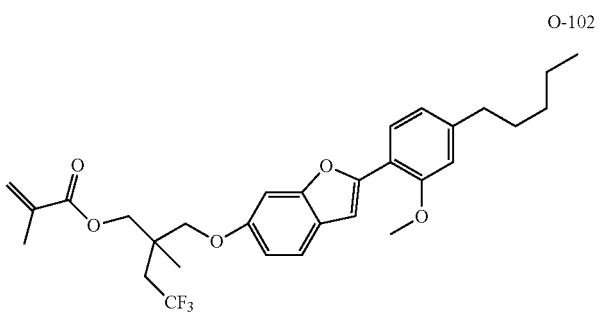
O-103
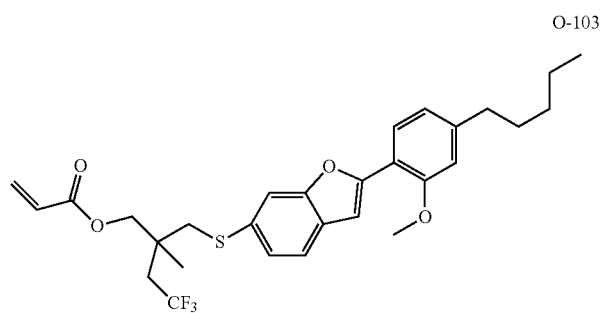
O-104
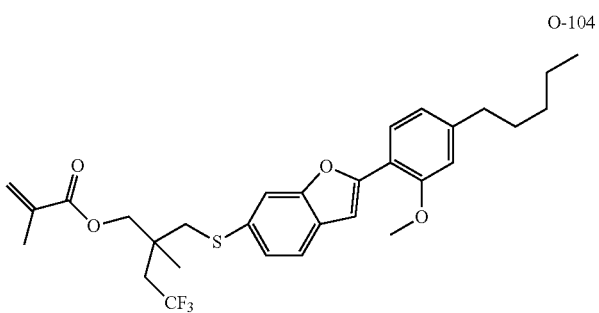
O-105
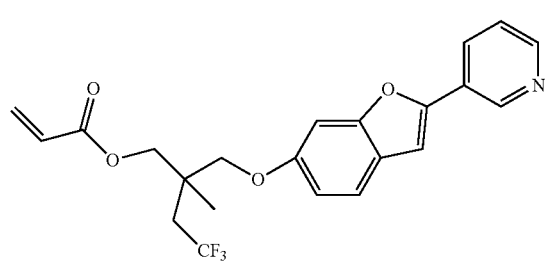
O-106
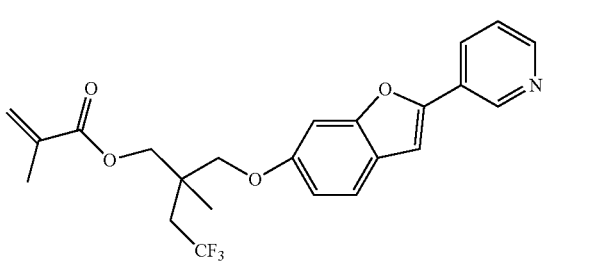

-continued
O-107
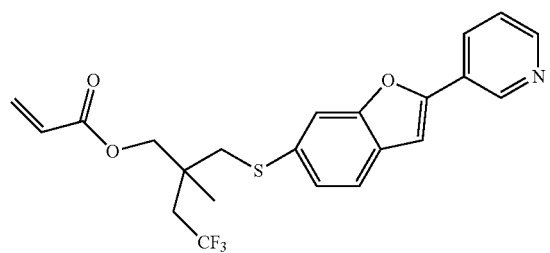
O-108
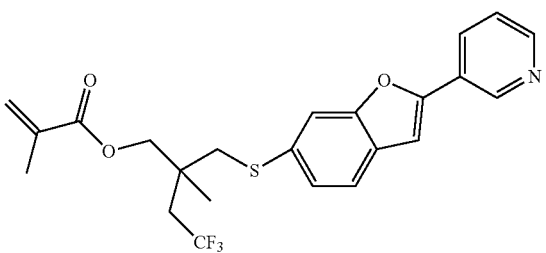
O-109
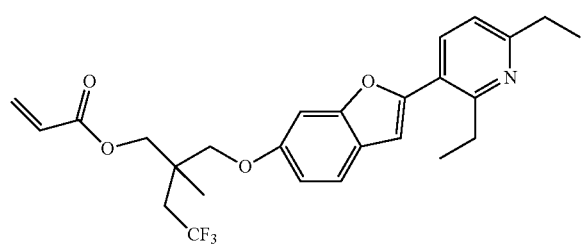
O-110
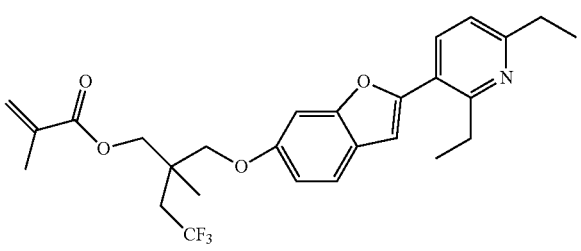
O-111
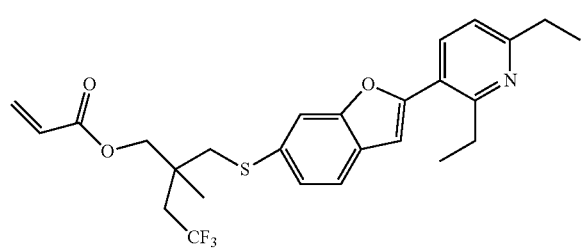
O-112
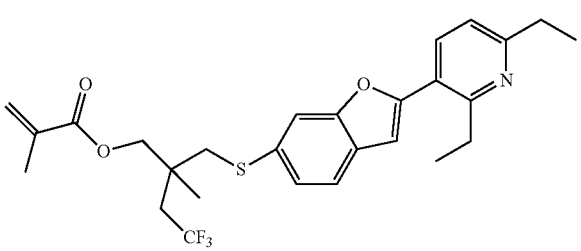
O-113
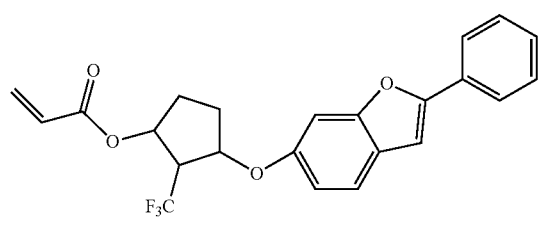
O-114
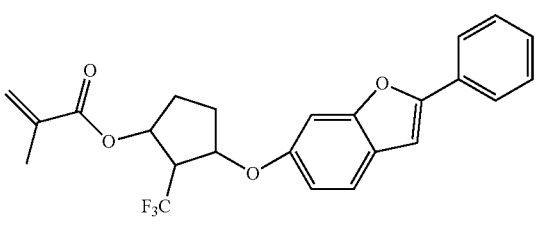
O-115
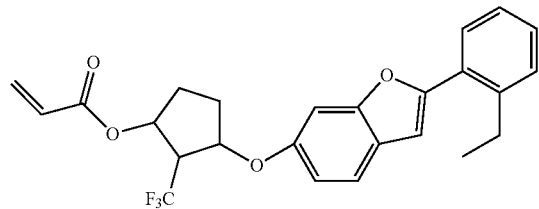
O-116
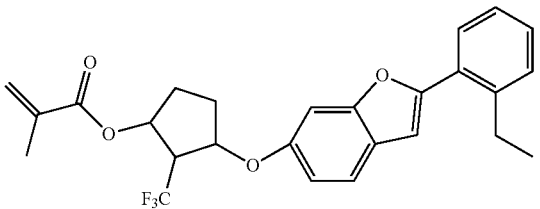
O-117
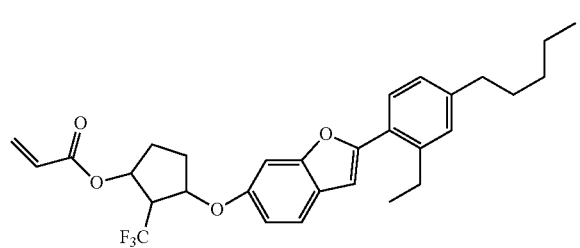
O-118
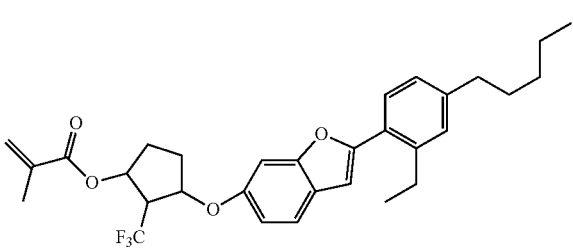

-continued
O-119
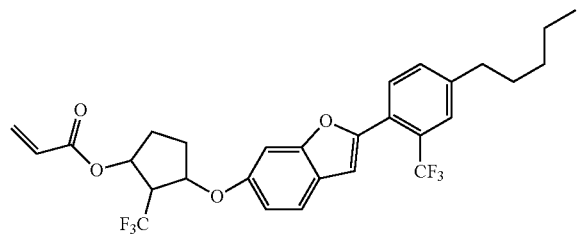
O-120
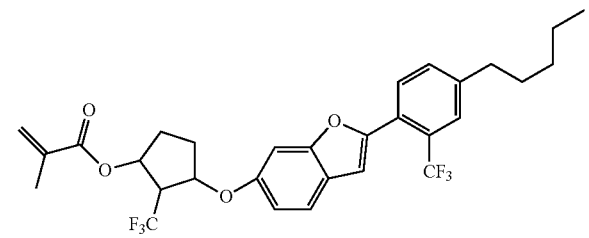
O-121
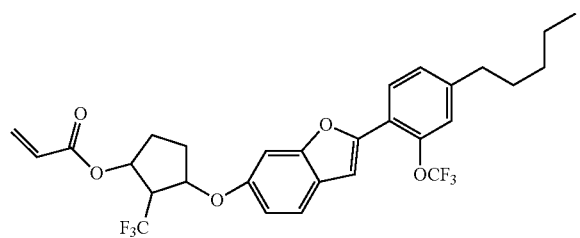
O-122
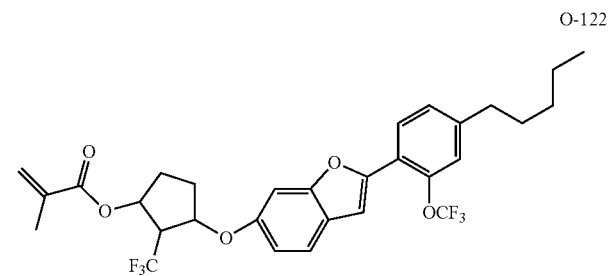
O-123
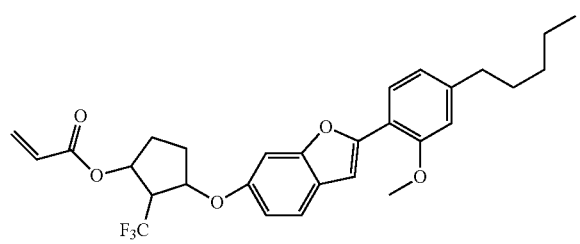
O-124
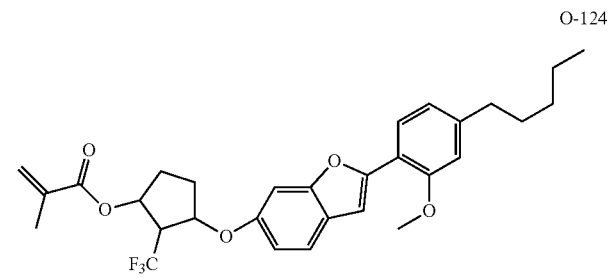
O-125
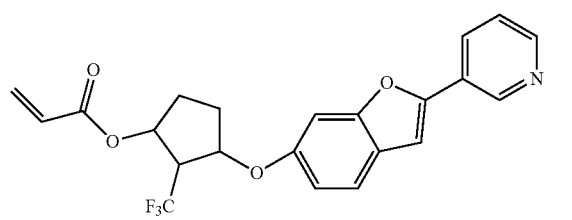
O-126
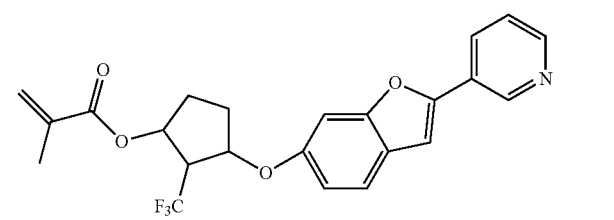
O-127
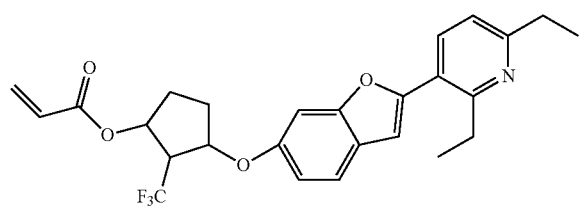
O-128
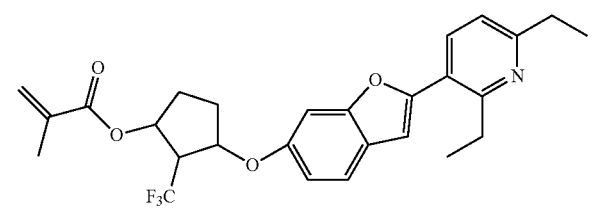
O-129
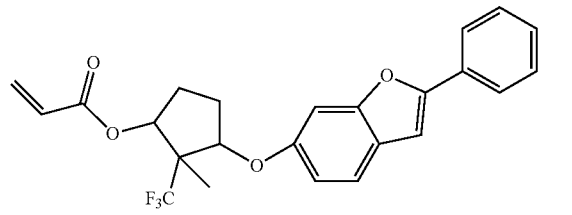
O-130
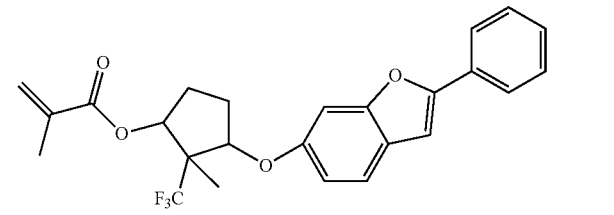

-continued
O-131
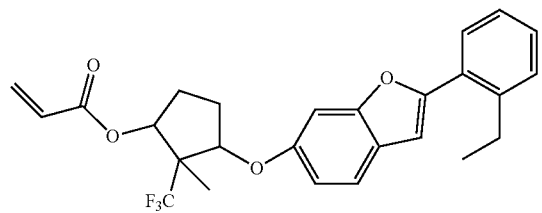
O-132
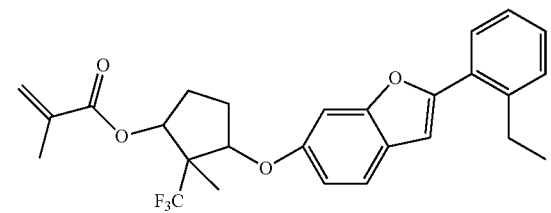
O-133
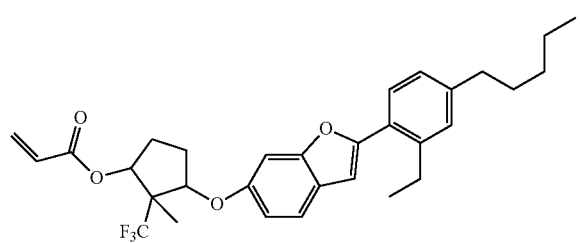
O-134
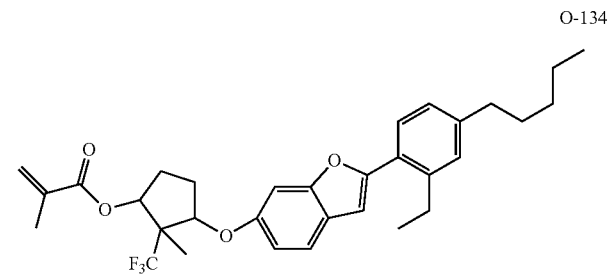
O-135
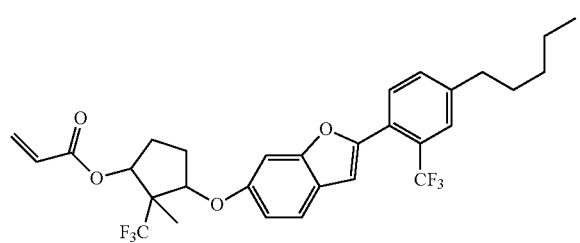
O-136
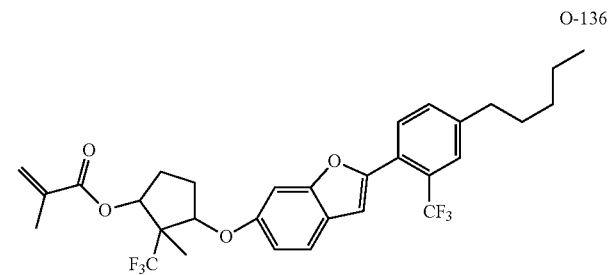
O-137
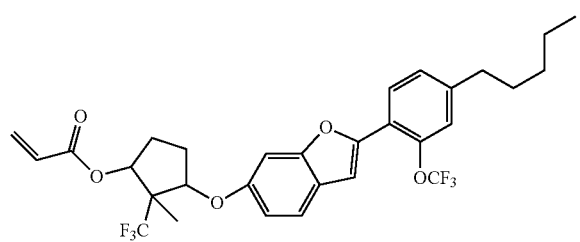
O-138
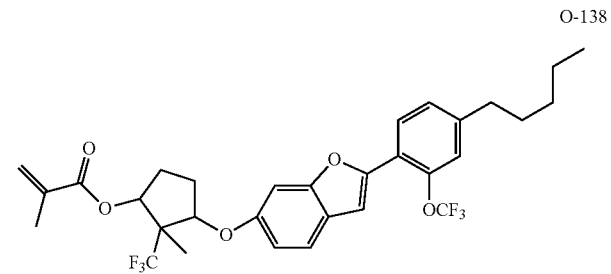
O-139
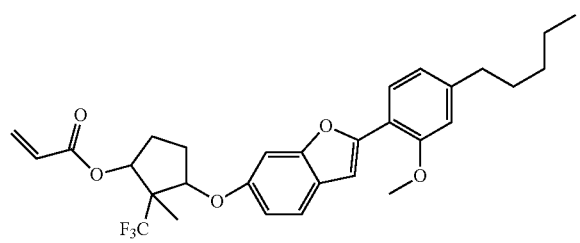
O-140
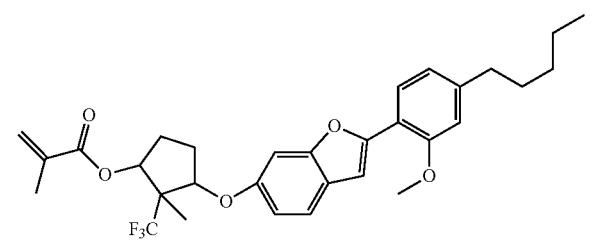
O-141
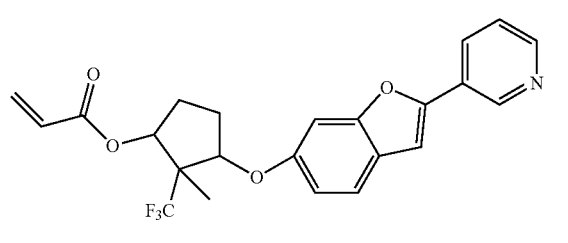
O-142
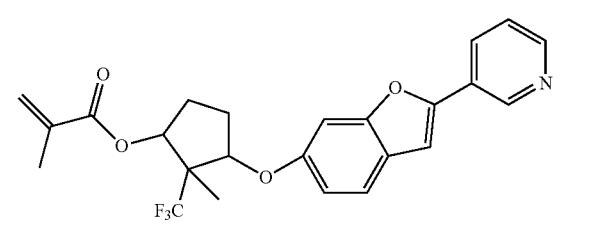

-continued
O-143
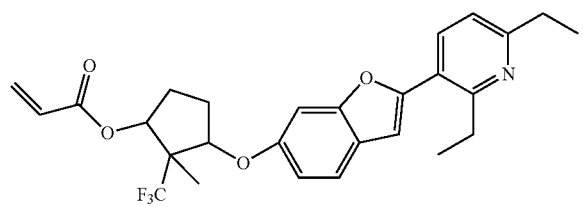
O-144
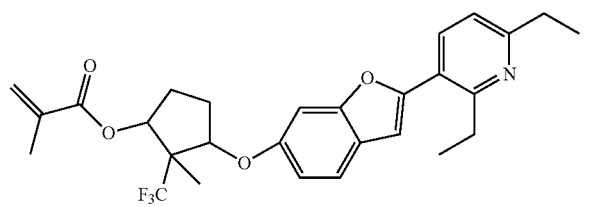
O-145
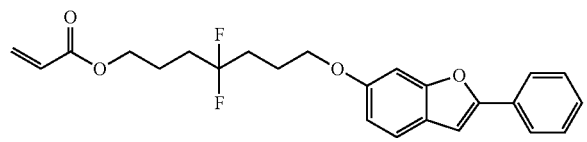
O-146
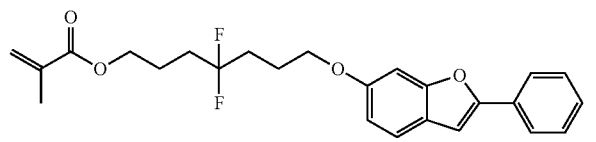
O-147
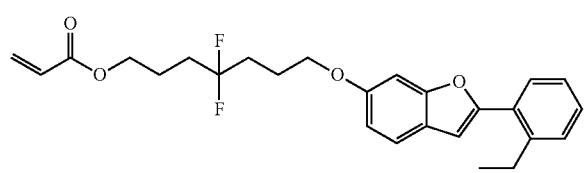
O-148
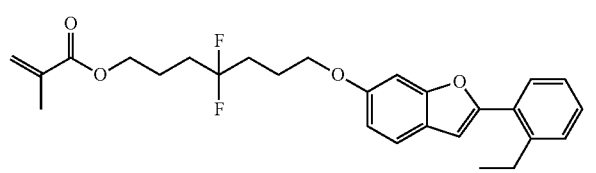
O-149

O-150
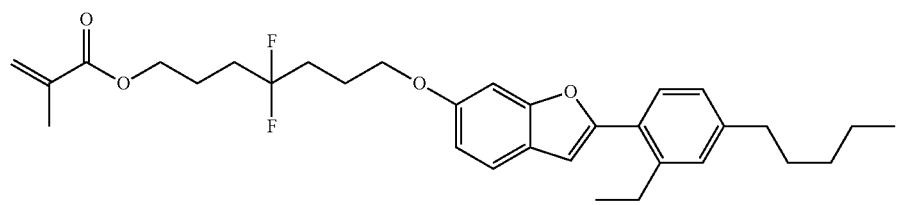
O-151
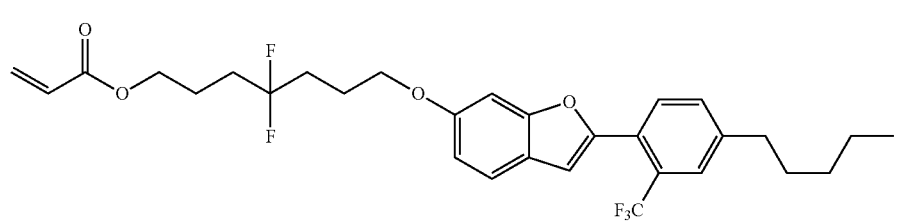
O-152
O-153
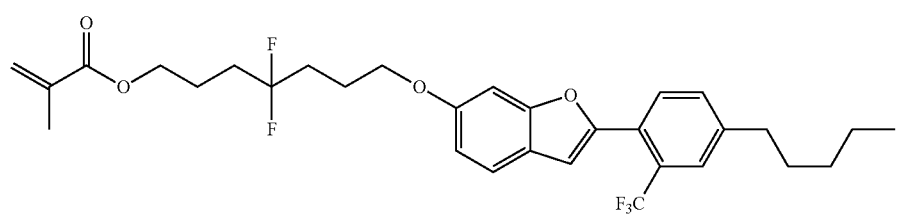

-continued
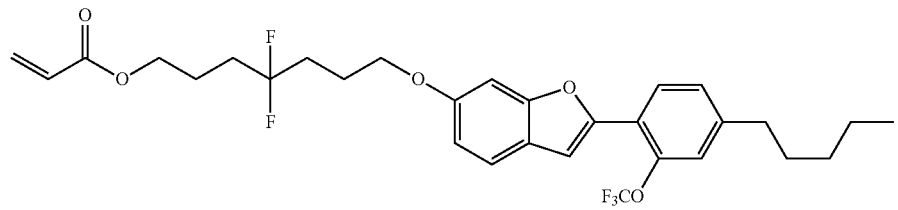
O-154
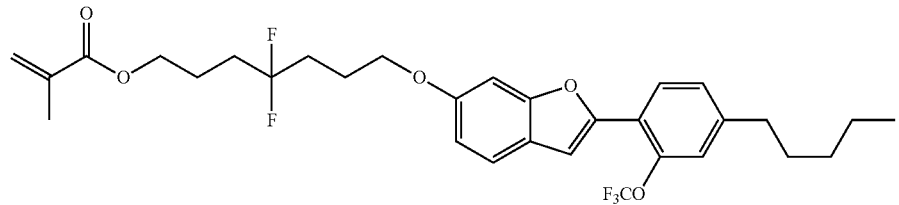
O-155
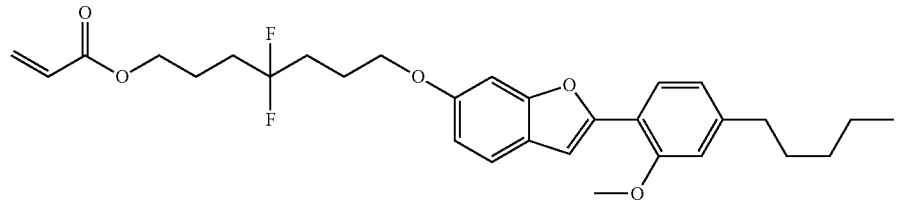
O-156
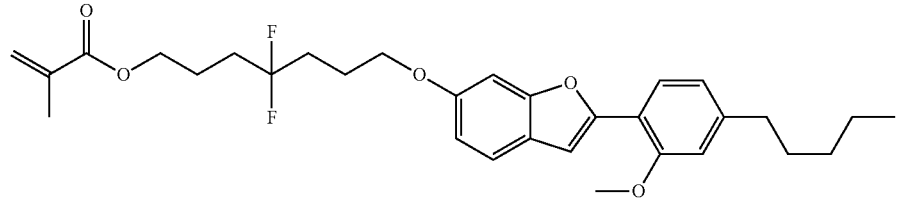
O-157
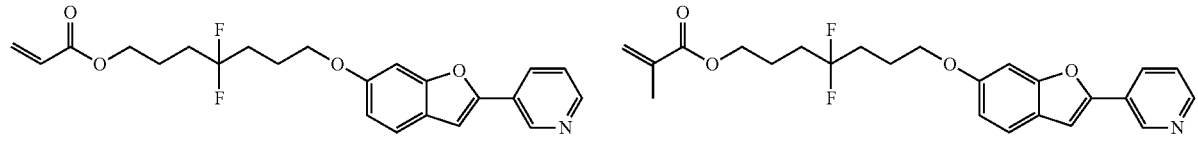
O-158    O-159

O-160

O-161
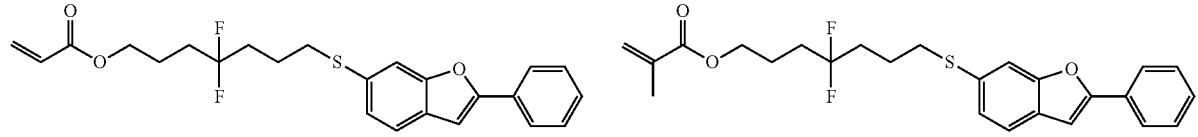
O-162    O-163

O-164
O-165
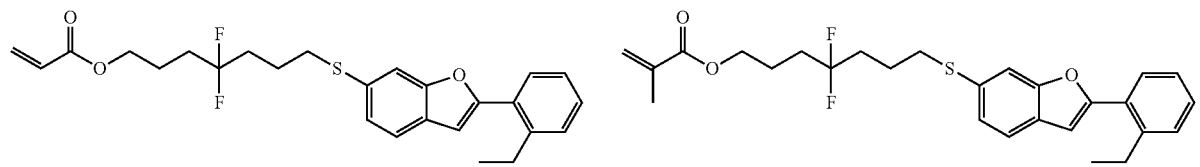
O-166
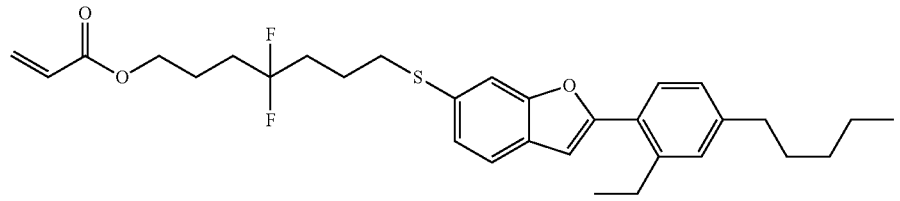
O-167
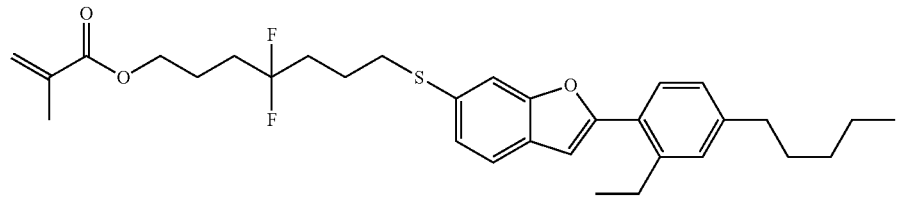
O-168
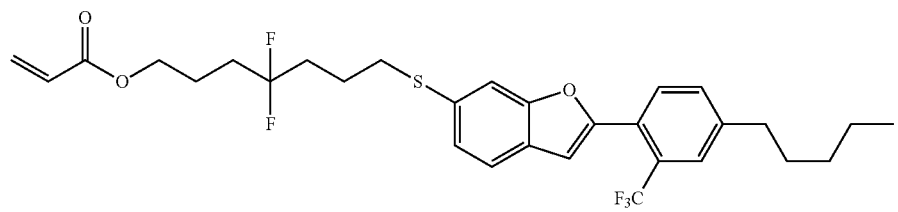
O-169
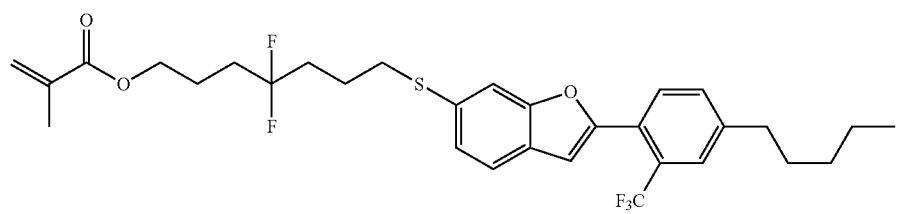
O-170
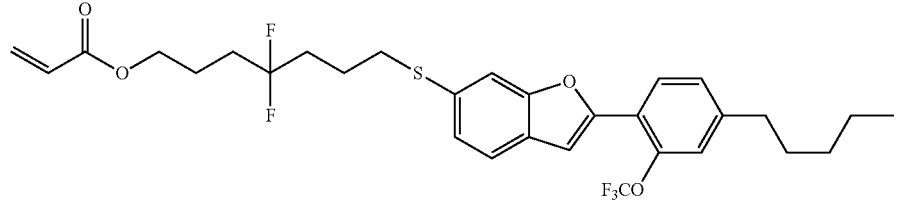
O-171
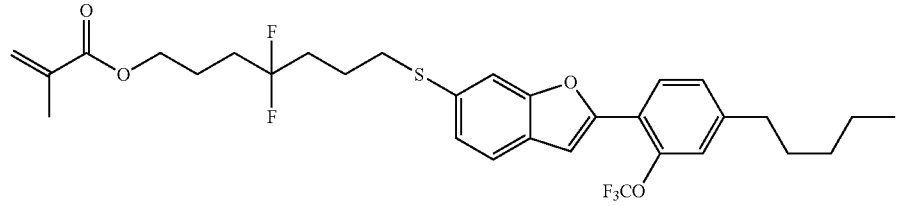

-continued
O-172
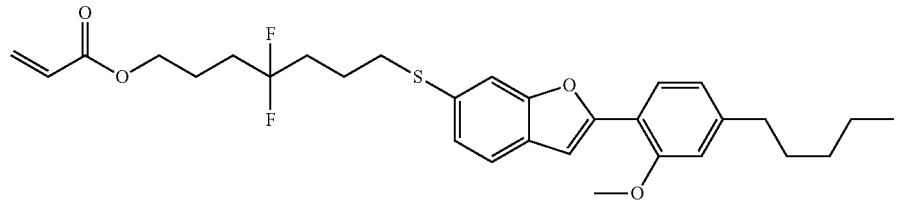
O-173
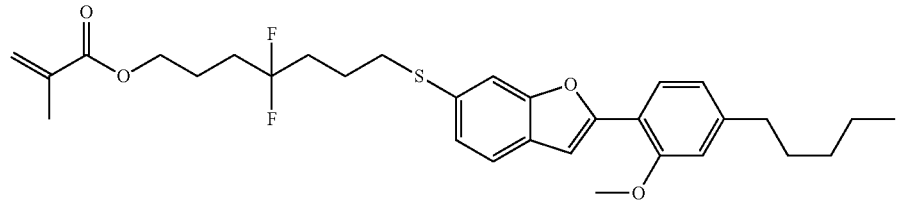
O-174     O-175
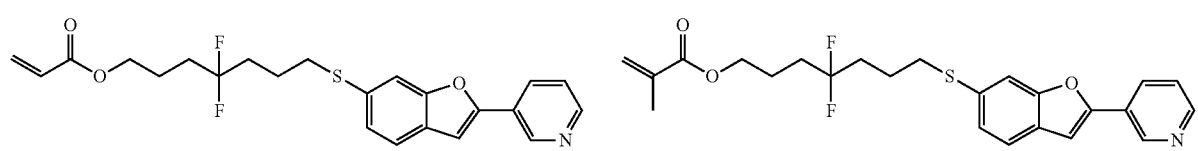
O-176
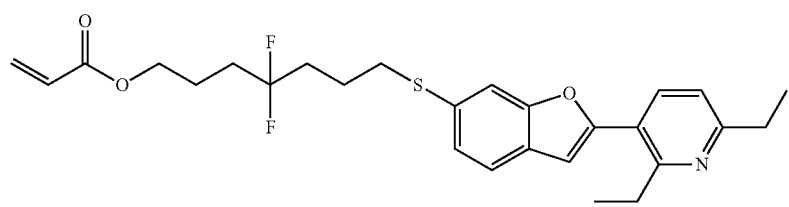
O-177
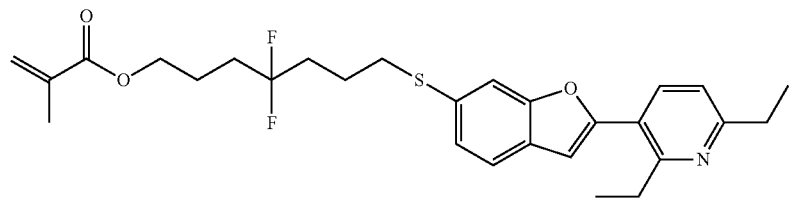
O-178     O-179
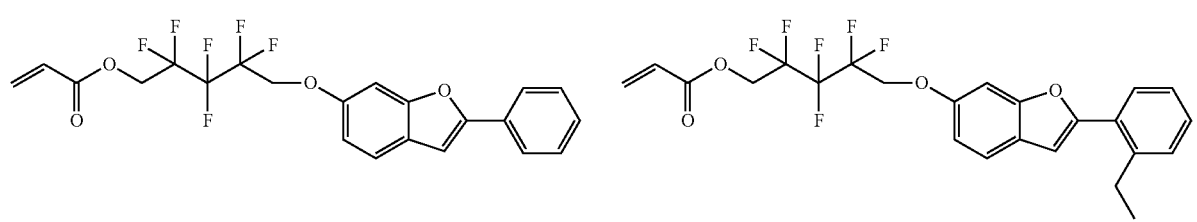
O-180
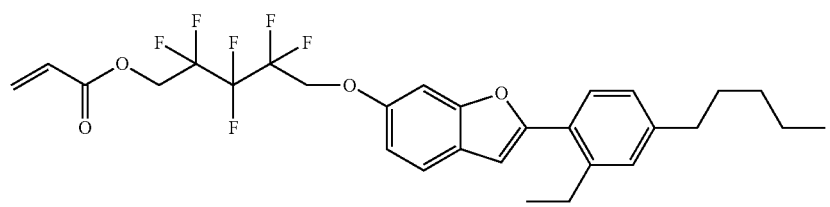

O-181
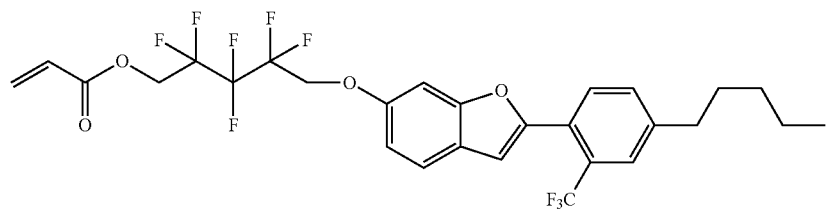
O-182
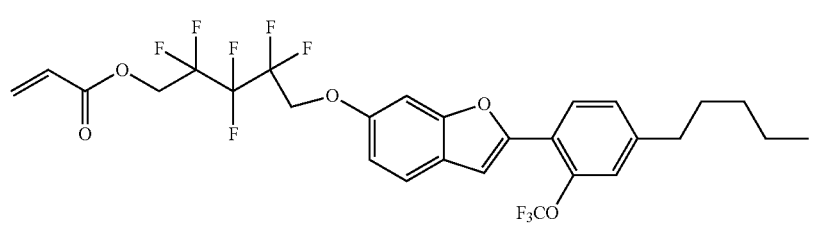
O-183
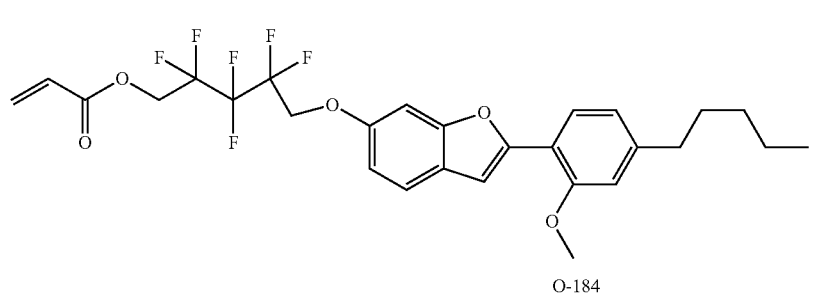
O-184
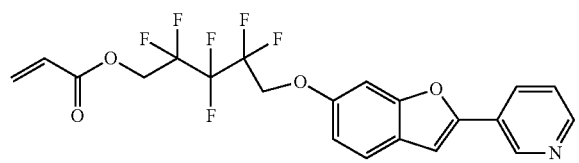
O-185
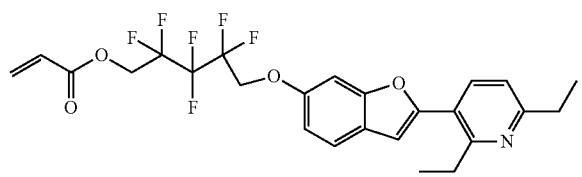
O-186
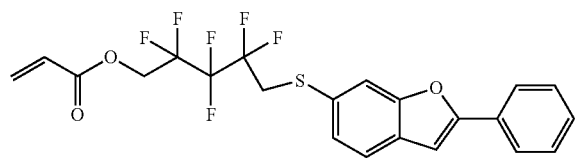
O-187
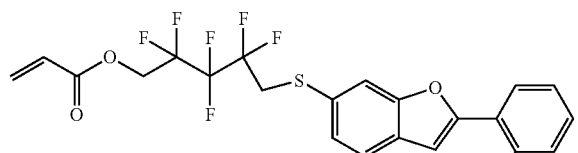
O-188
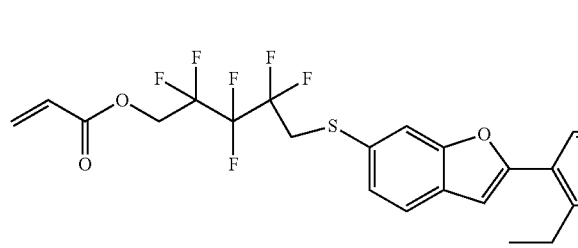
O-189
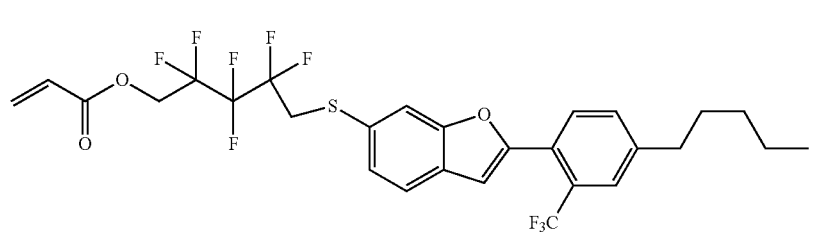

-continued
O-190
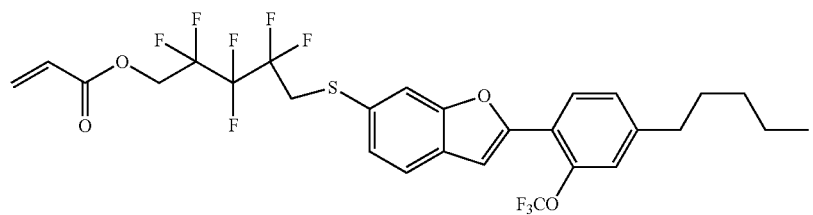
O-191
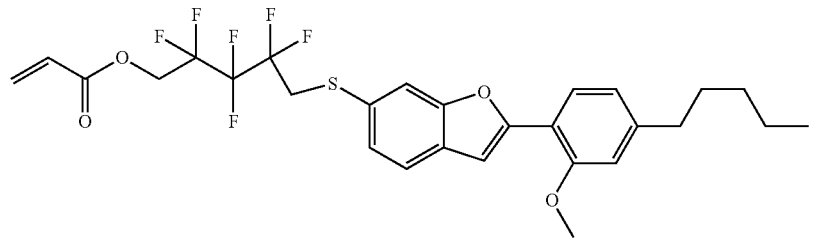
O-192 O-193
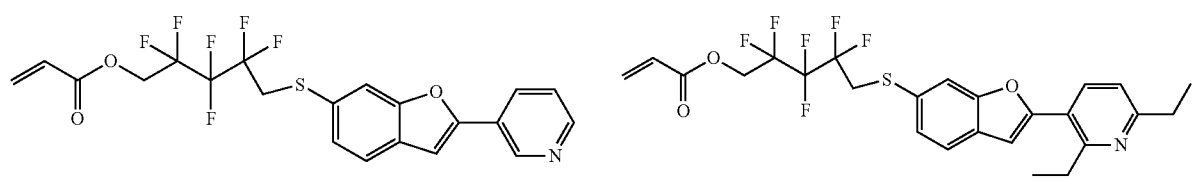
O-194 O-195
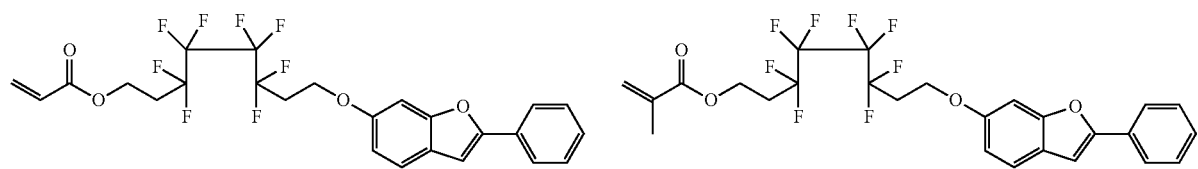
O-196 O-197
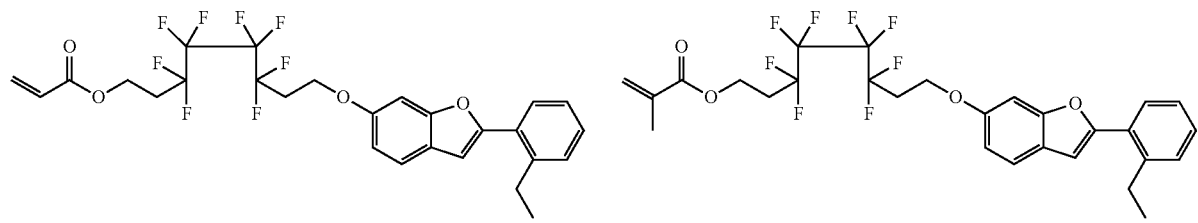
O-198
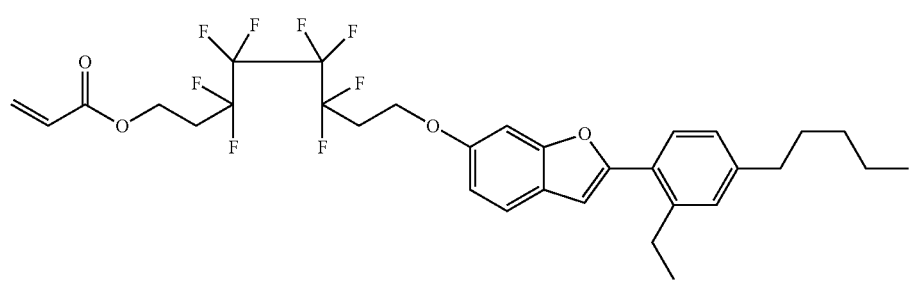

-continued
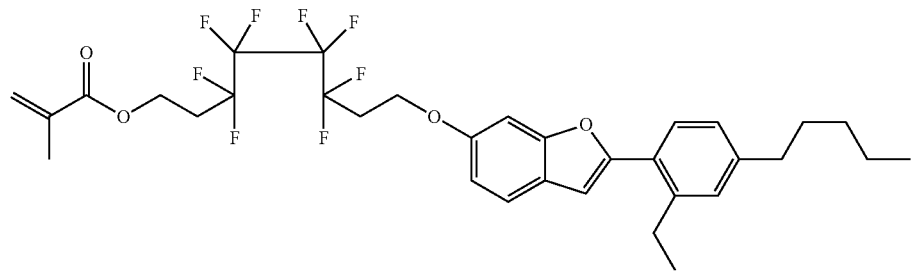
O-199
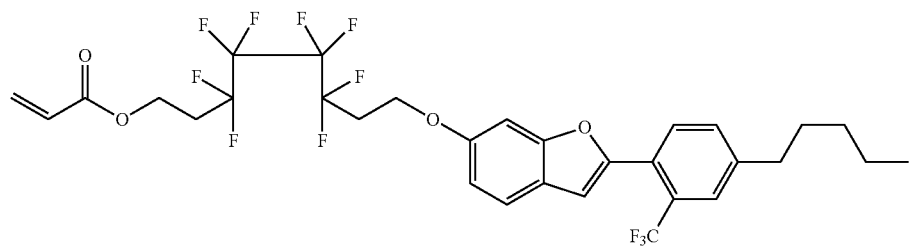
O-200
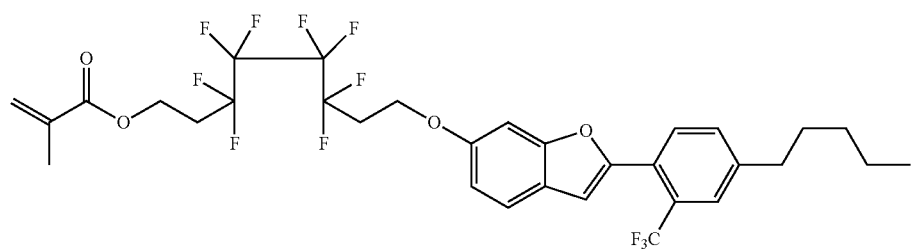
O-201
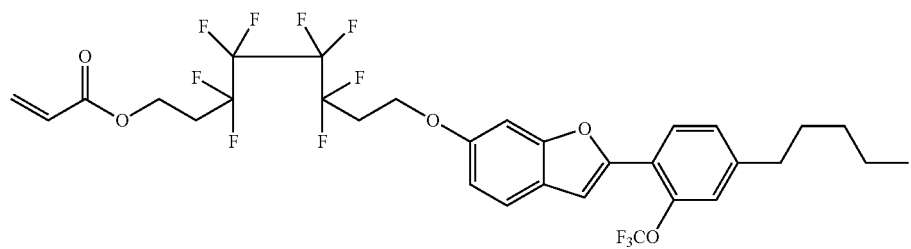
O-202
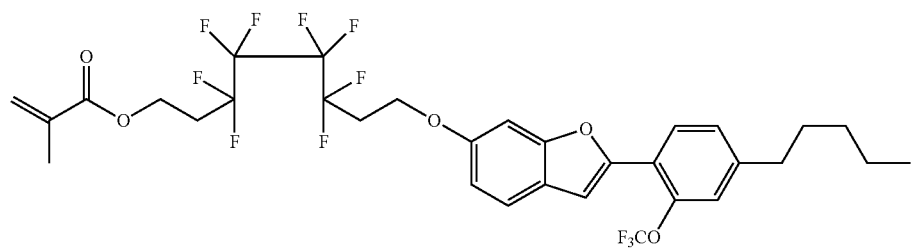
O-203
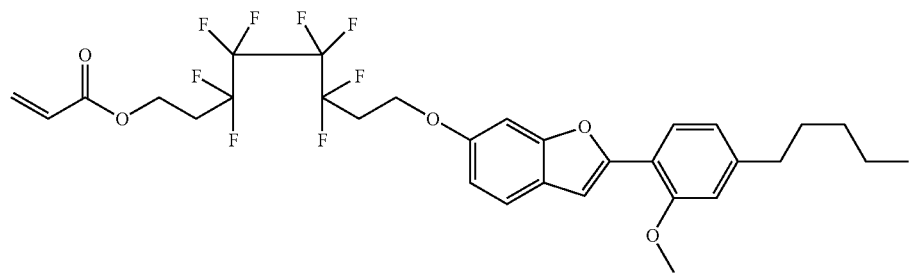
O-204

O-205
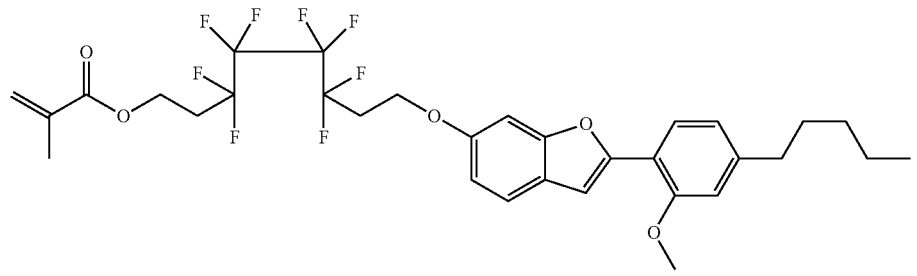
O-206
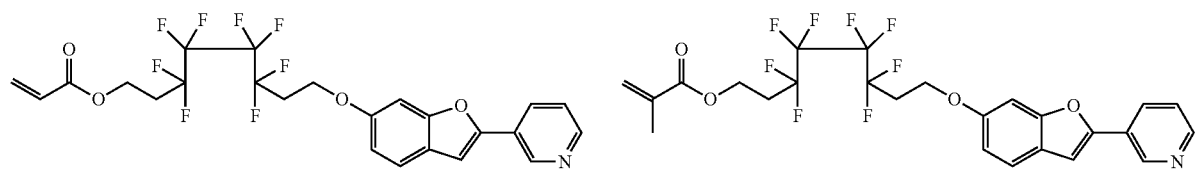
O-207
O-208
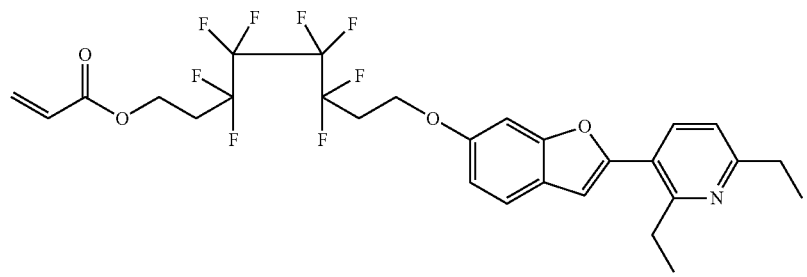
O-209
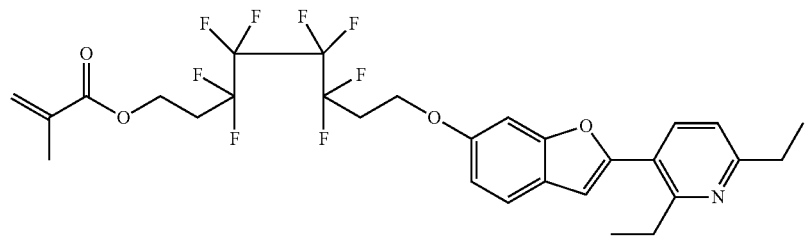
O-210 O-211
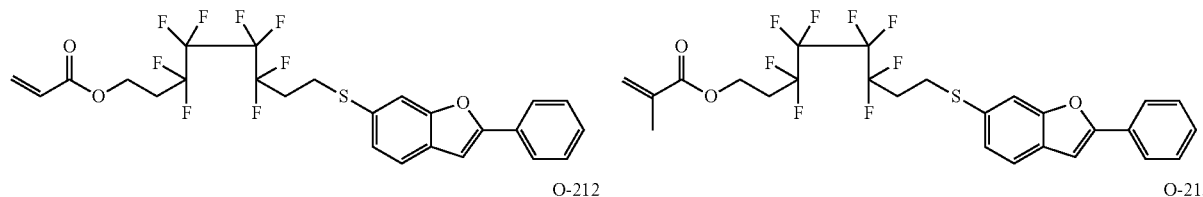
O-212 O-213
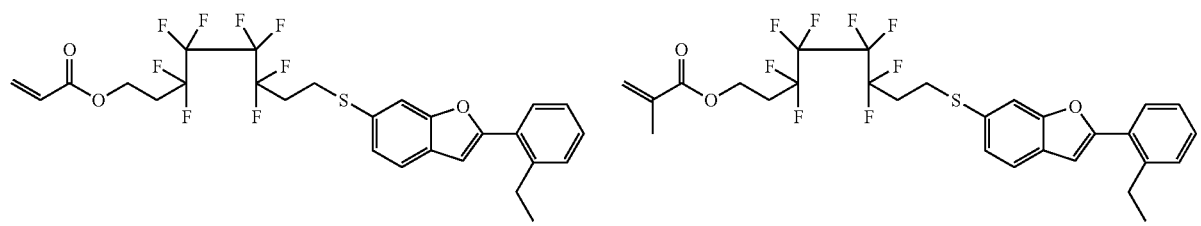

-continued
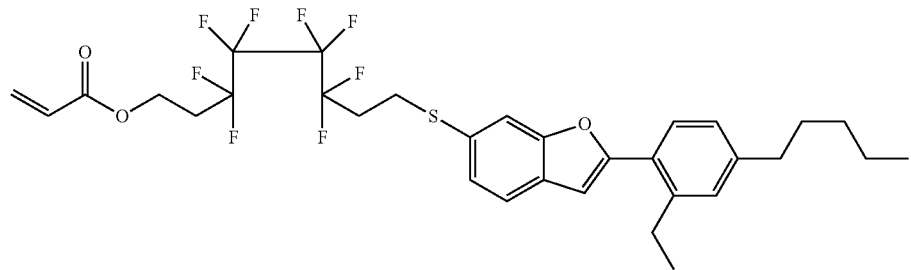
O-214
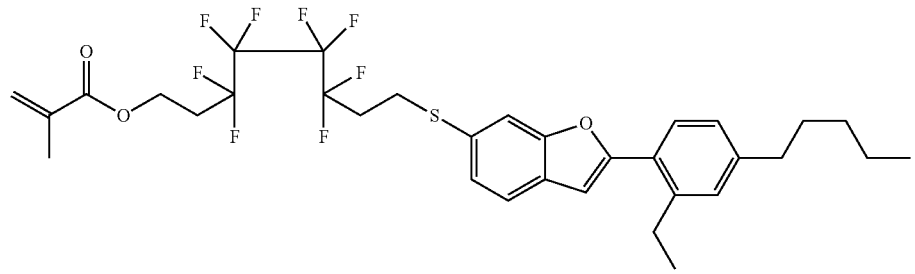
O-215
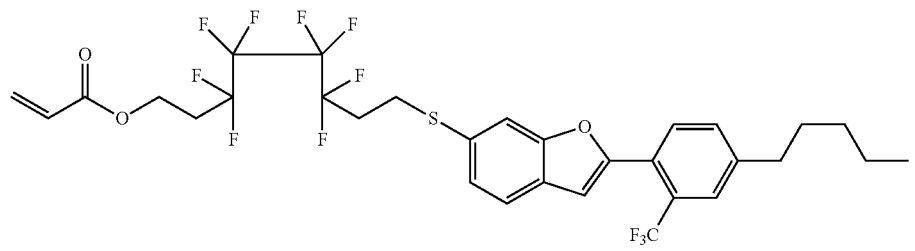
O-216
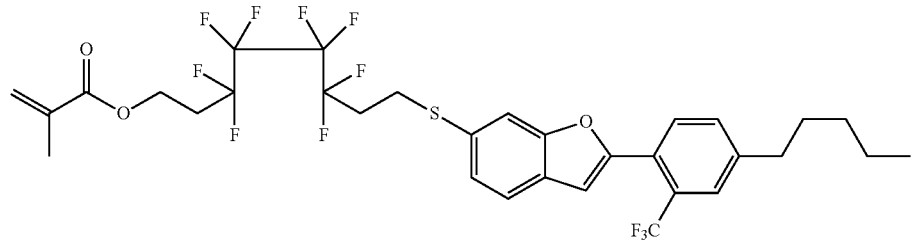
O-217
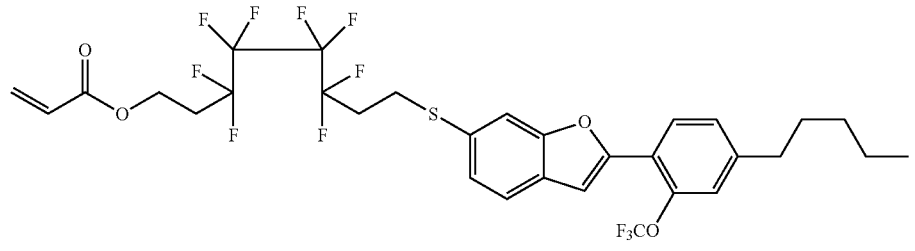
O-218
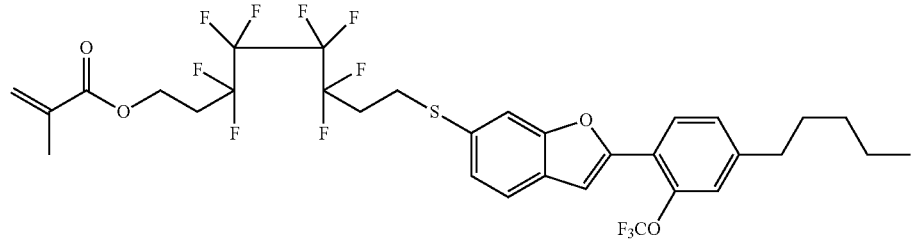
O-219

-continued
O-220
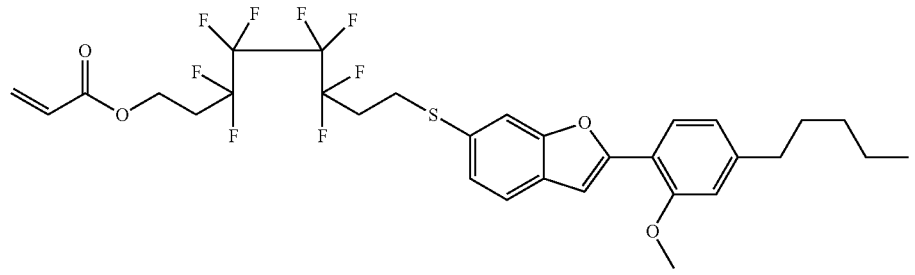
O-221
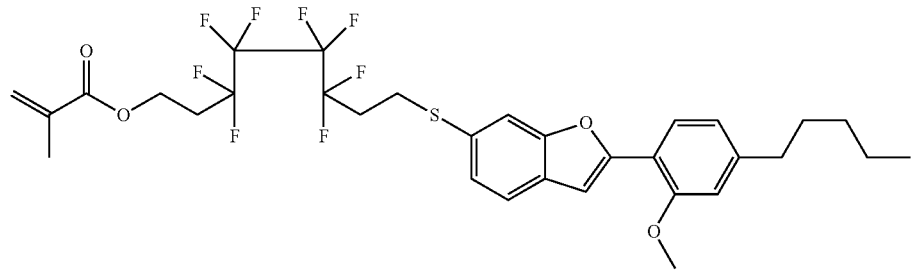
O-222     O-223
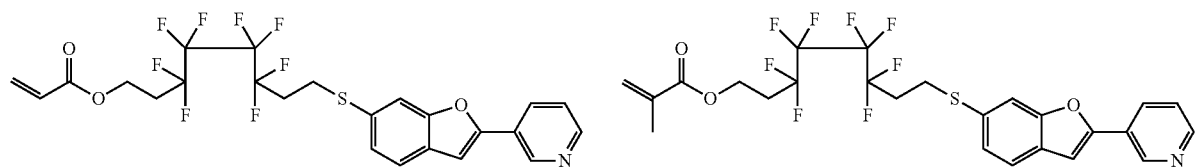
O-224
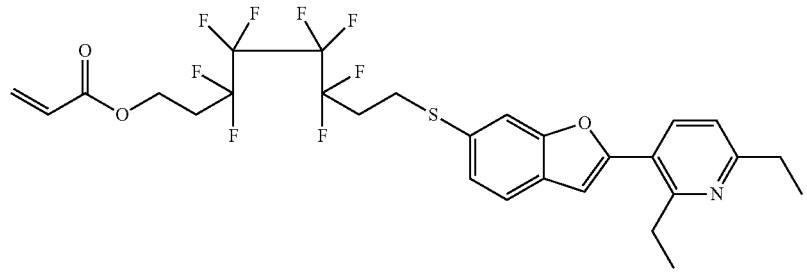
O-225
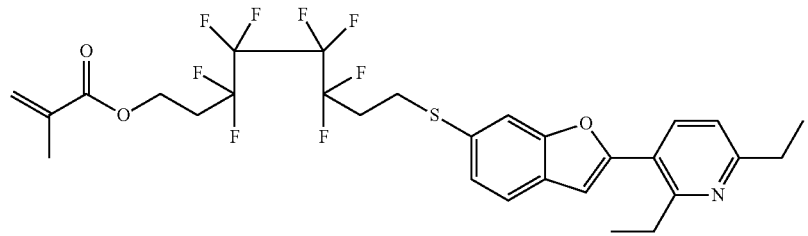
O-226     O-227
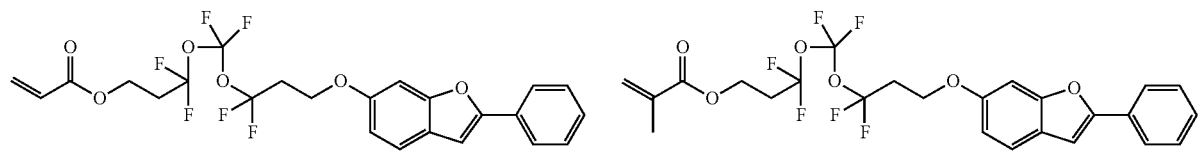

O-228
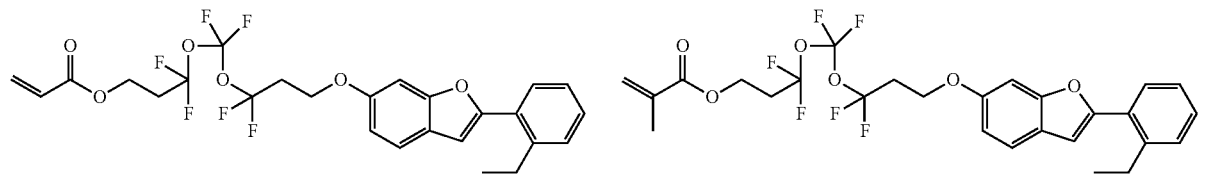
O-229
O-230
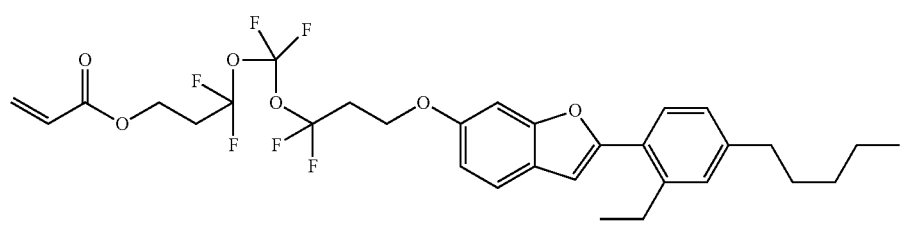
O-231
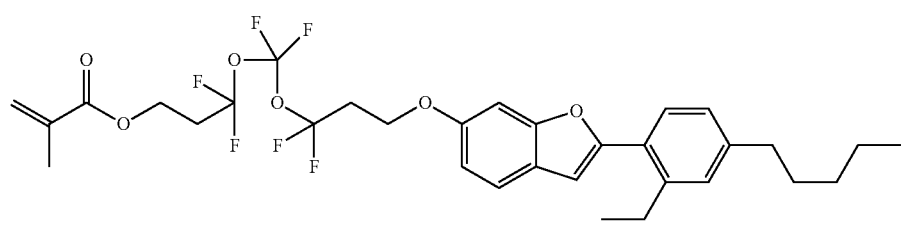
O-232
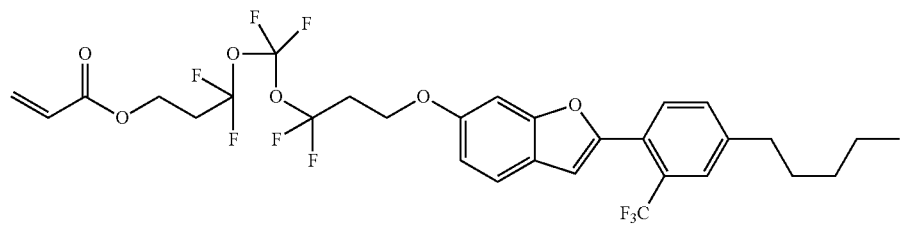
O-233
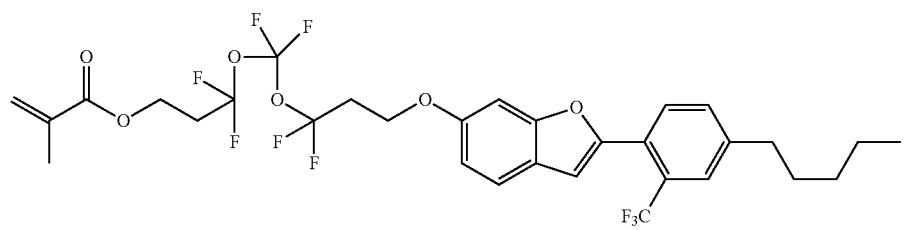
O-234
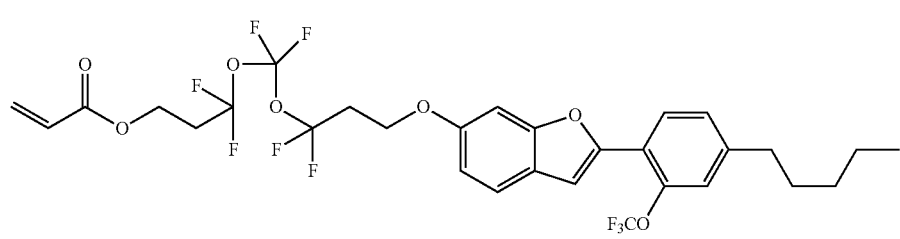
O-235
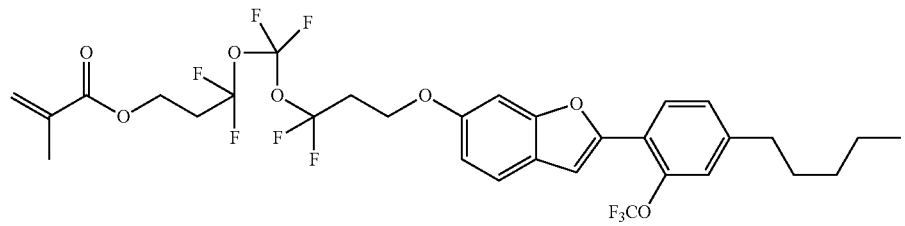

O-236
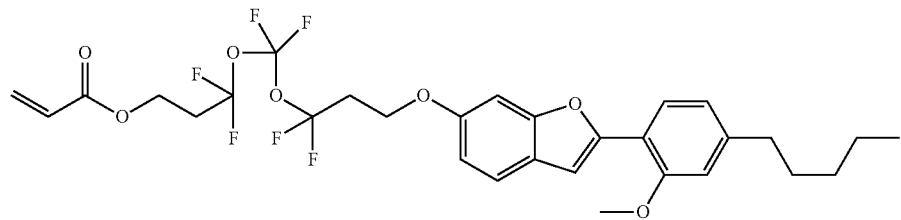
O-237
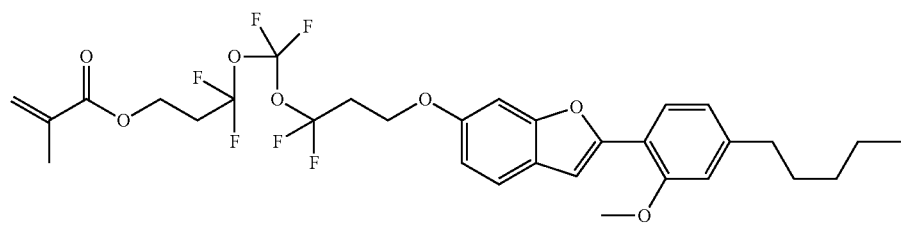
O-238 O-239
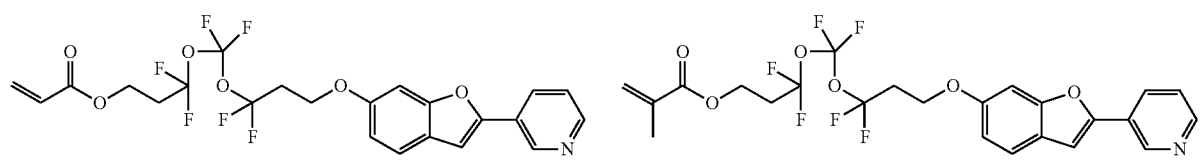
O-240
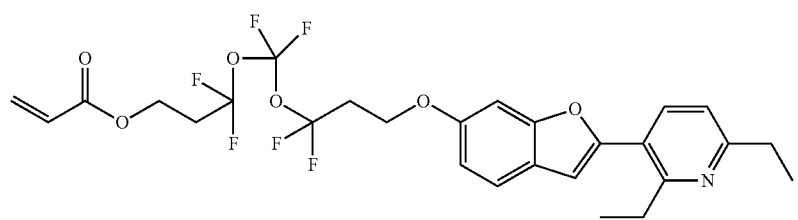
O-241
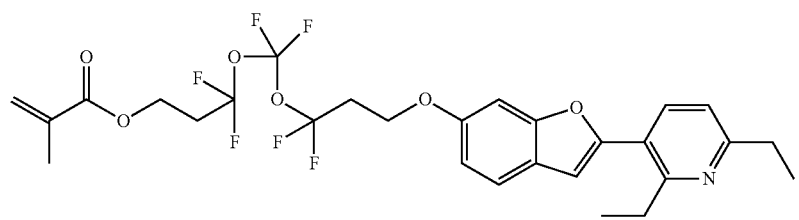
O-242 O-243
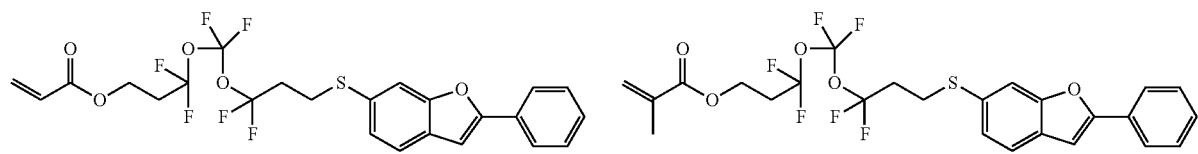

-continued
O-244
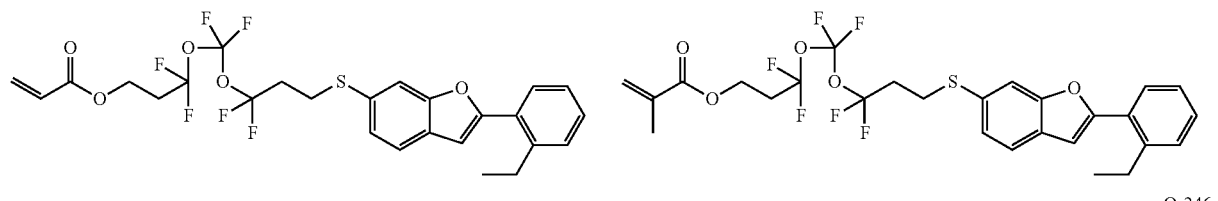
O-245
O-246
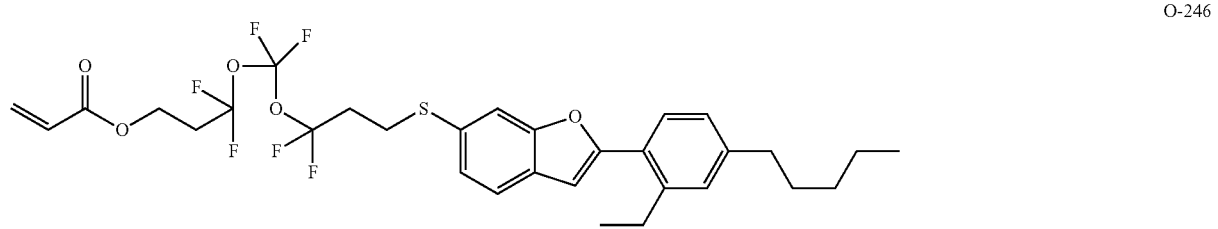
O-247
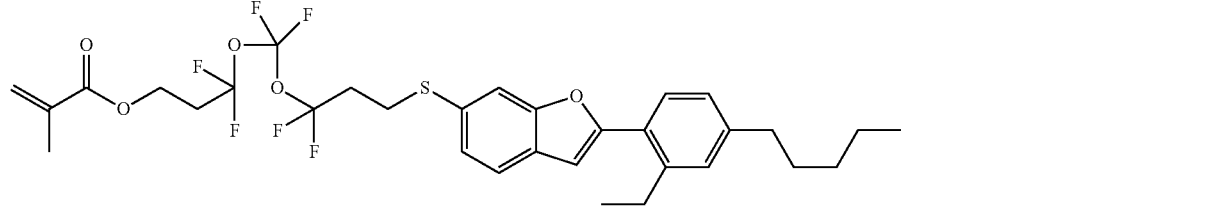
O-248
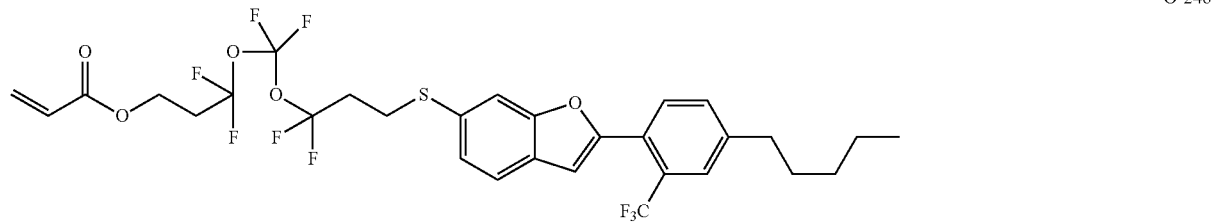
O-249
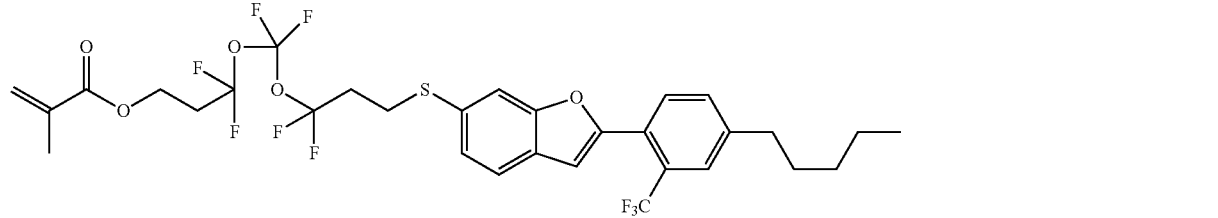
O-250
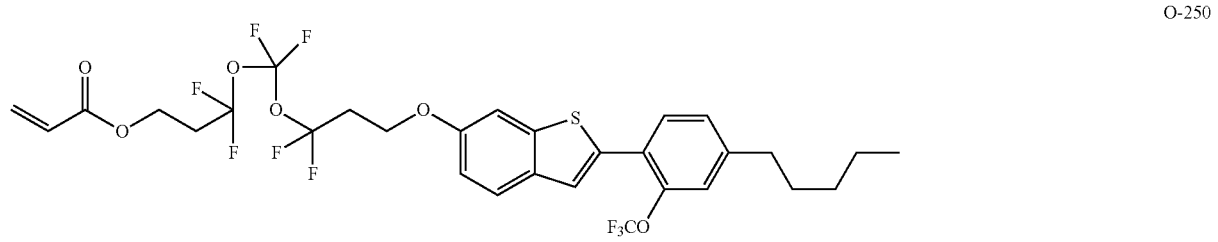
O-251
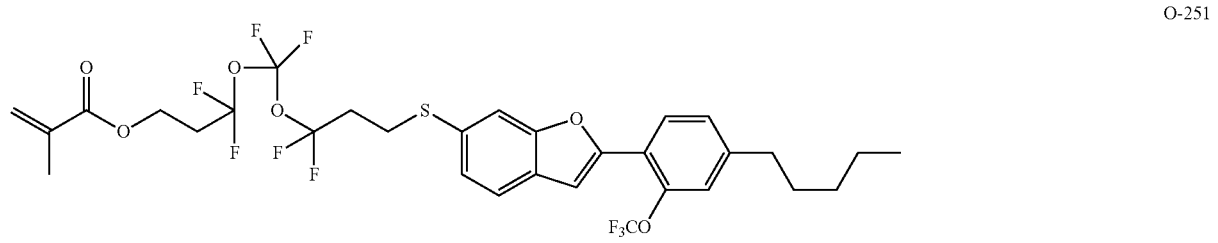

O-252
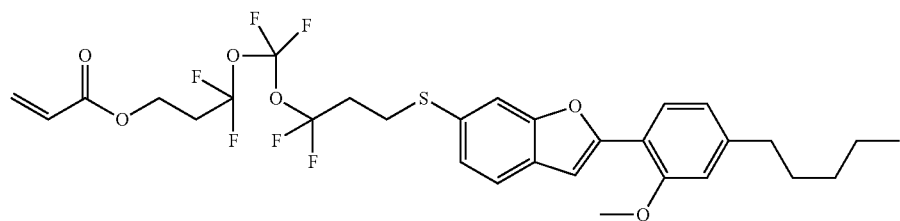
O-253
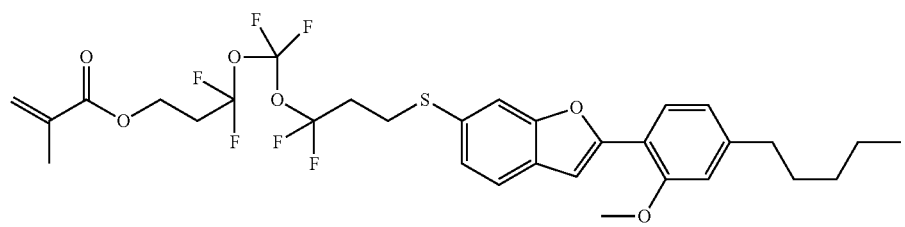
O-254
O-255
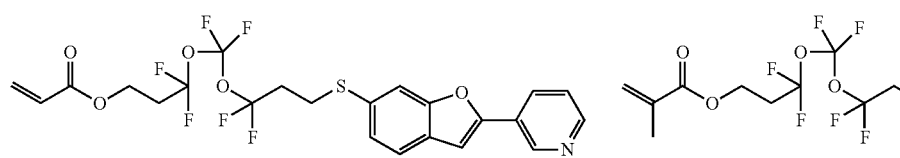
O-256
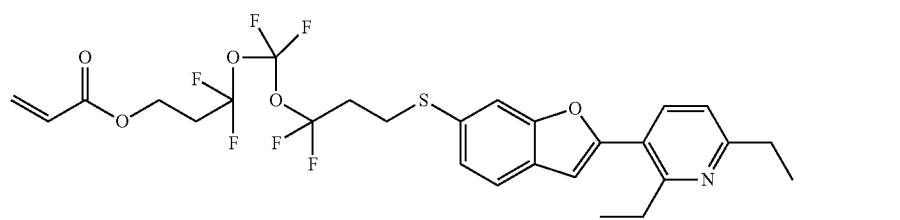
O-257
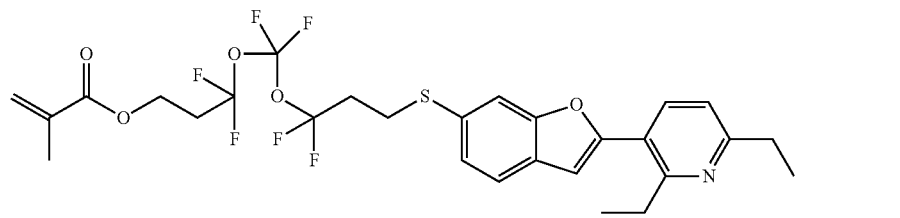
O-258
O-259
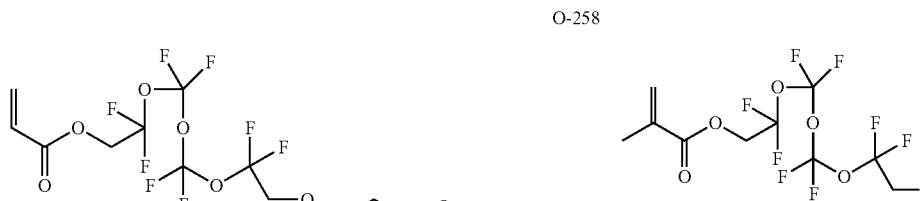
O-260
O-261
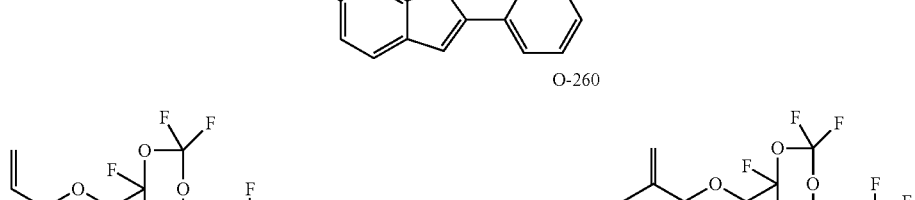
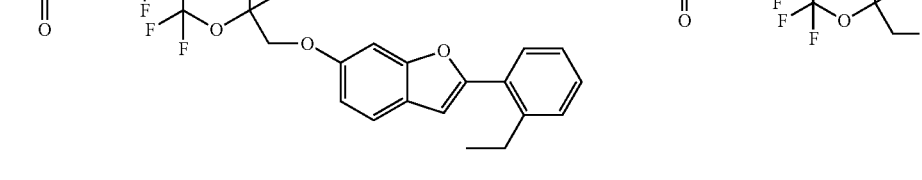

-continued
O-262
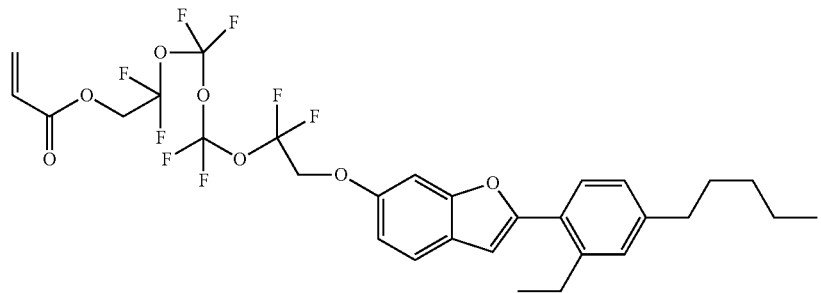
O-263
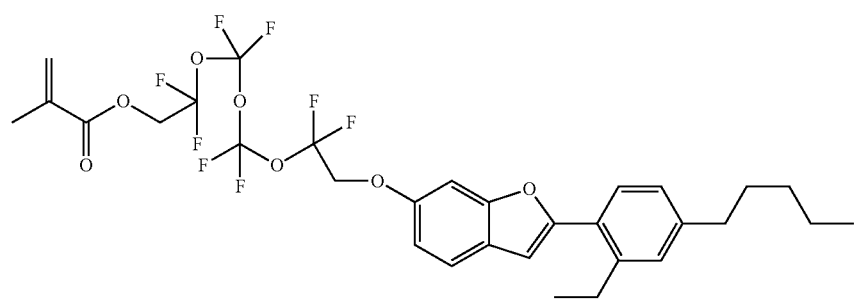
O-264
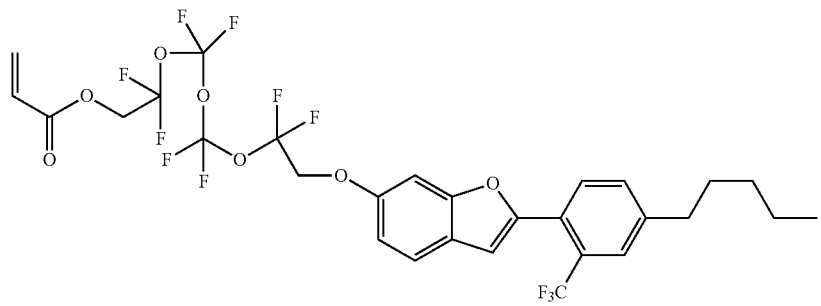
O-265
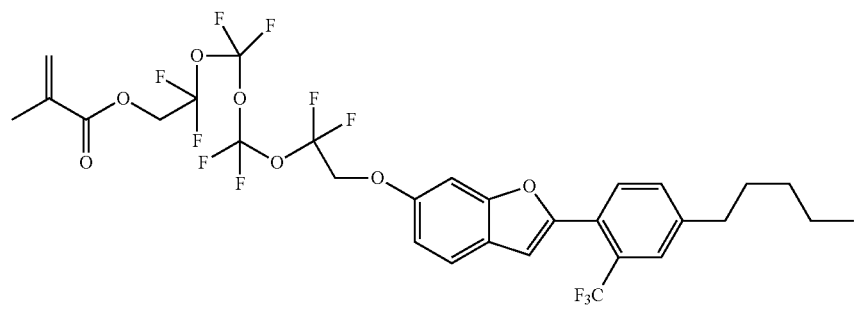
O-266
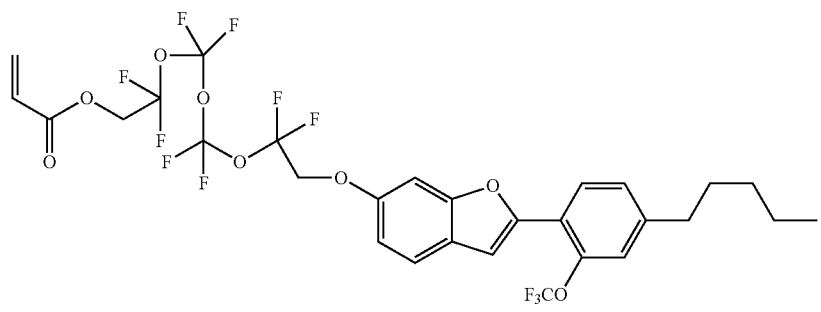

-continued
O-267
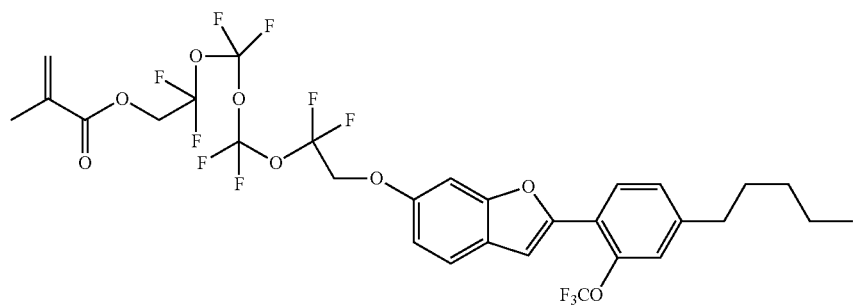
O-268
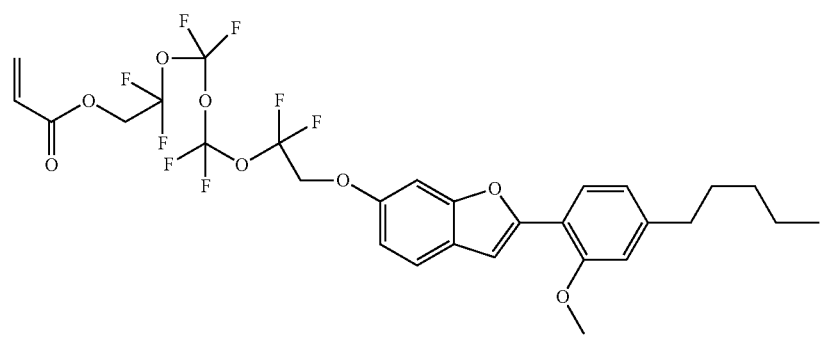
O-269
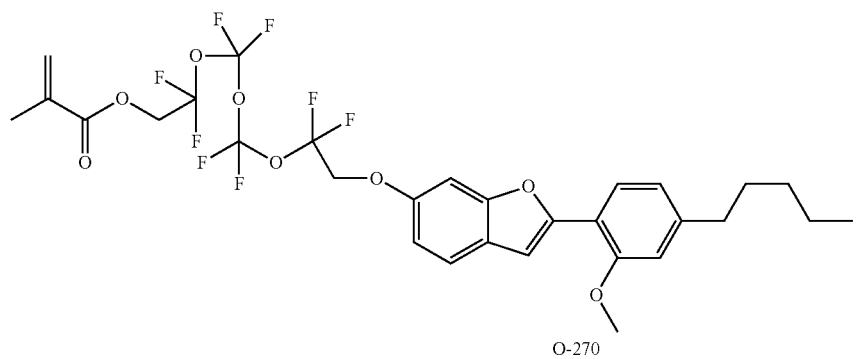
O-270    O-271
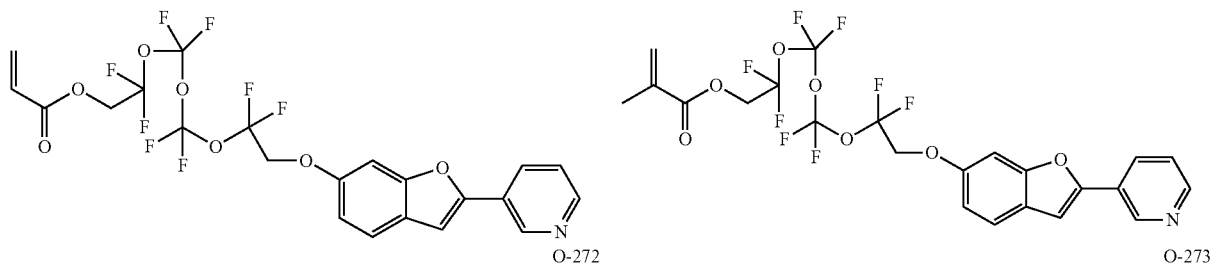
O-272    O-273
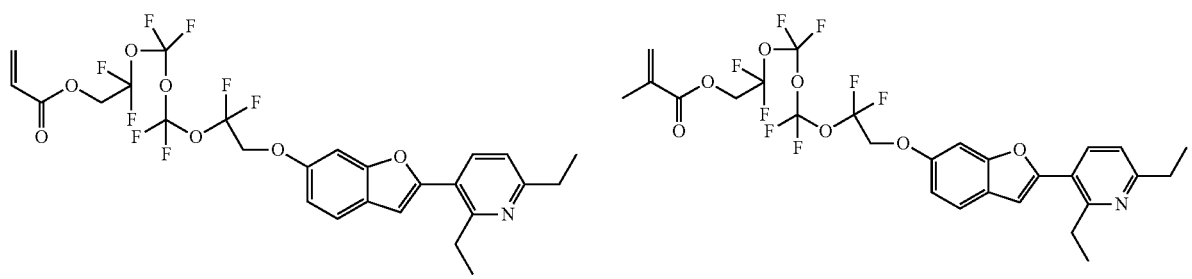

O-274
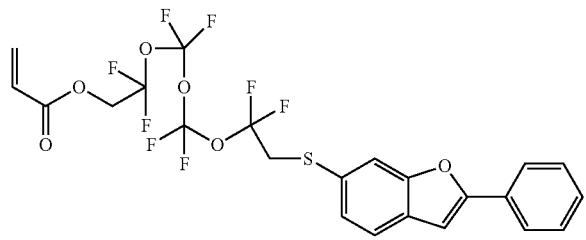
O-275
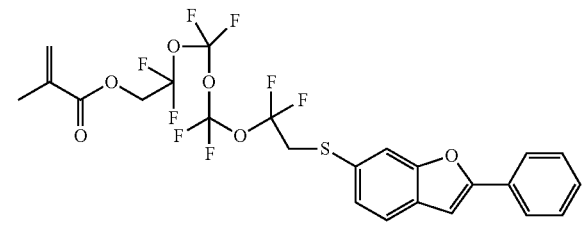
O-276
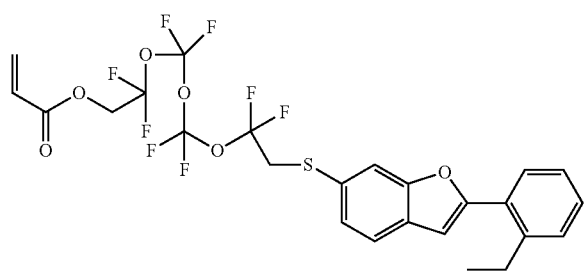
O-277
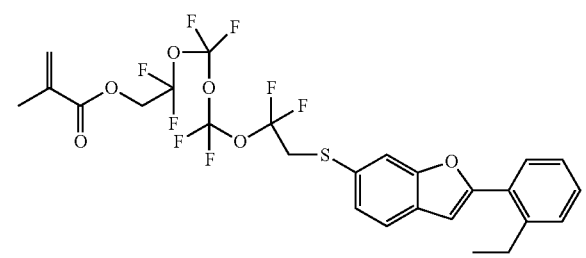
O-278
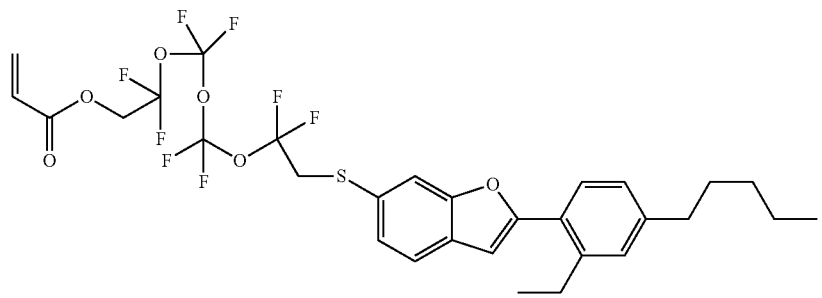
O-279
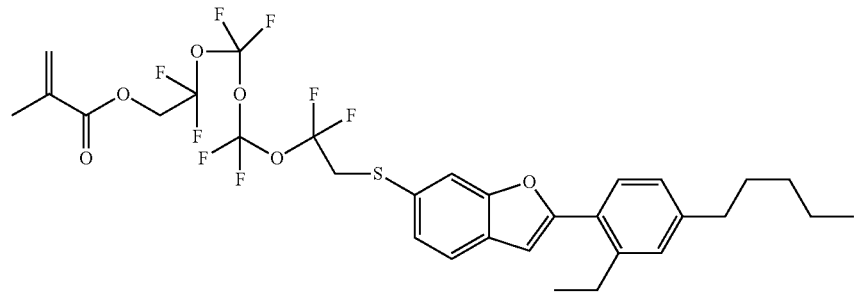
O-280
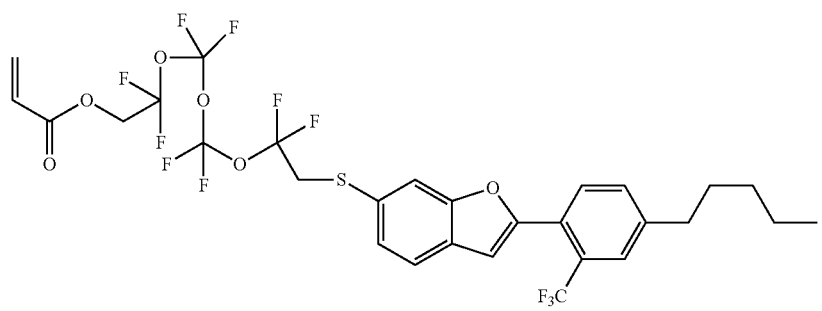

-continued
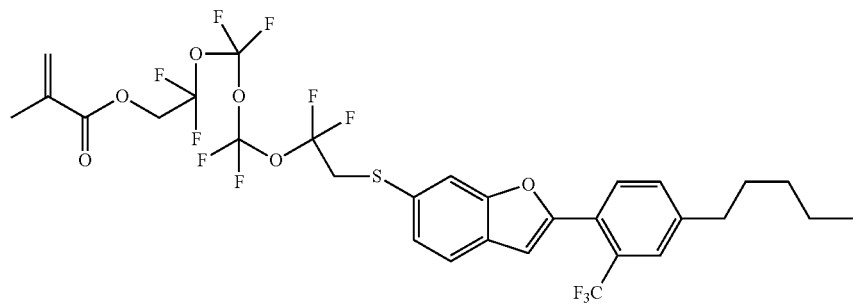
O-281
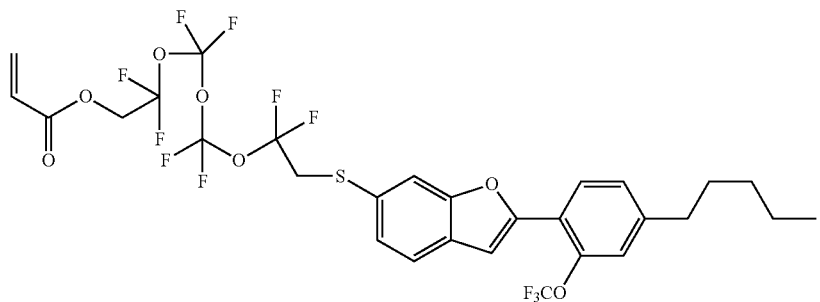
O-282
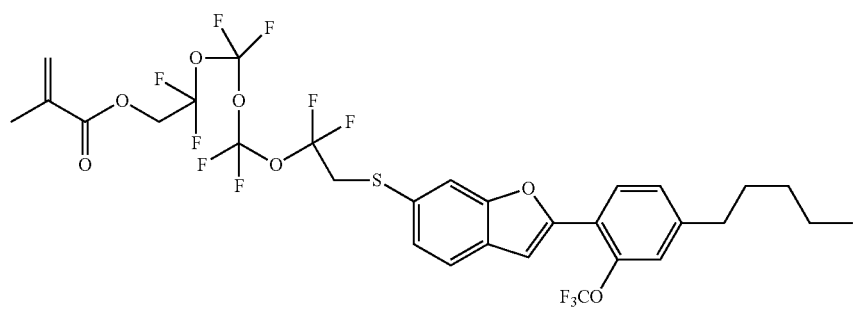
O-283
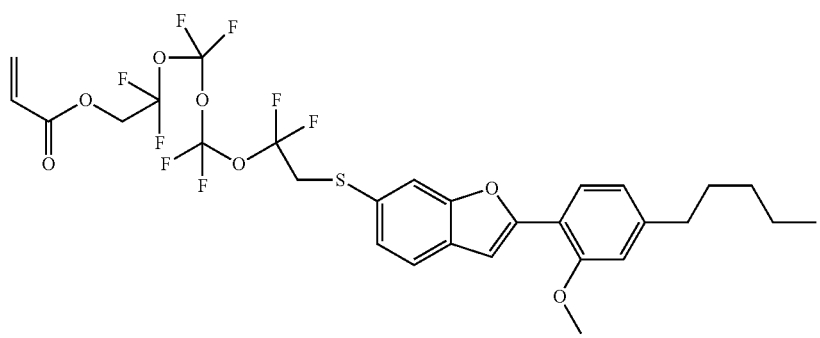
O-284
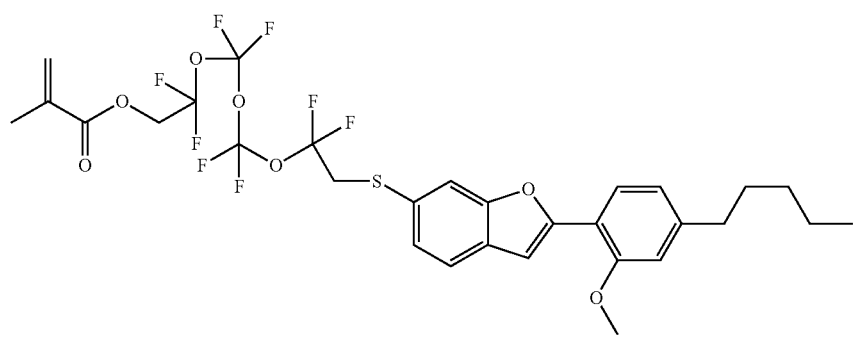
O-285

-continued
O-286
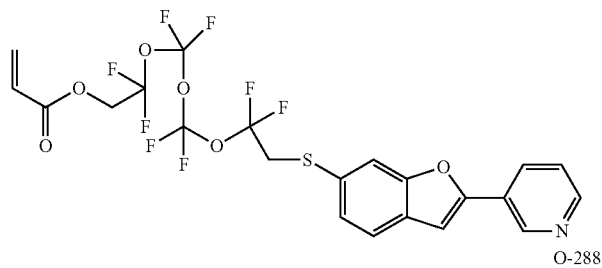
O-287
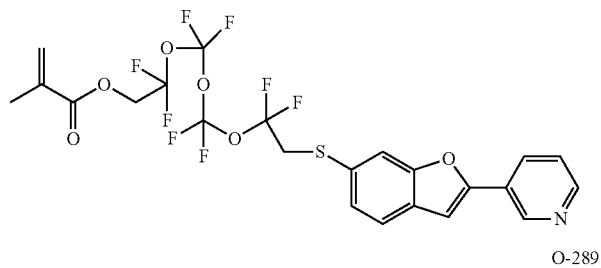
O-288
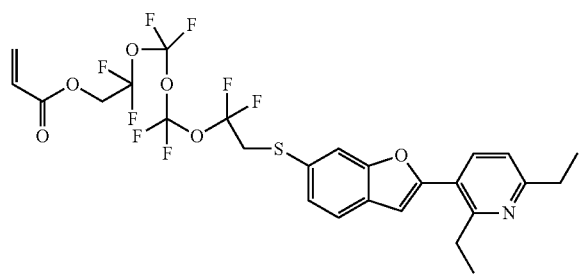
O-289
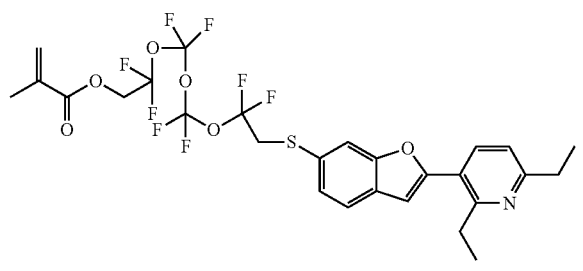
S-001
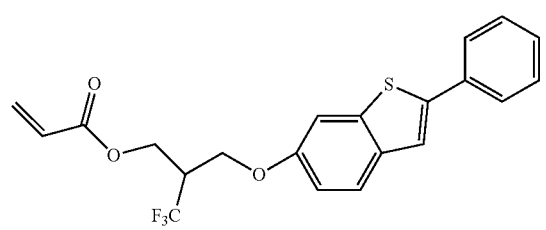
S-002
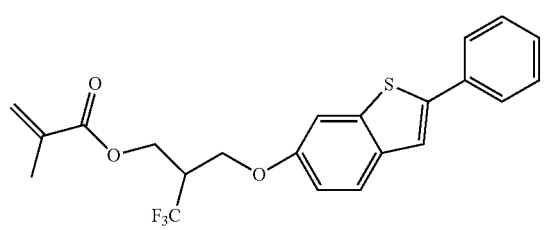
S-003
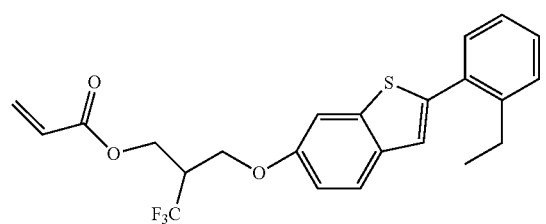
S-004
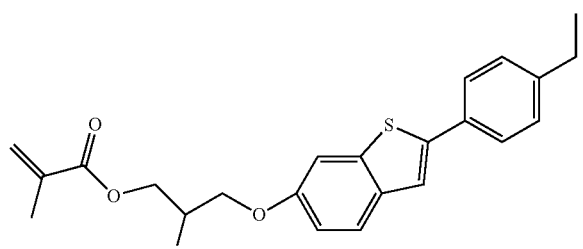
S-005
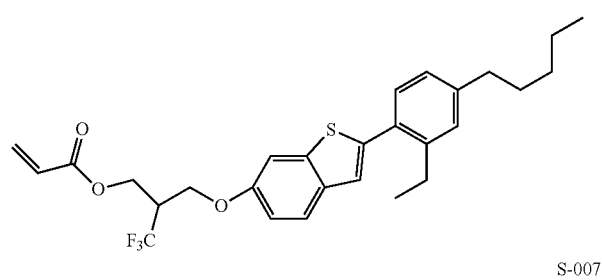
S-006
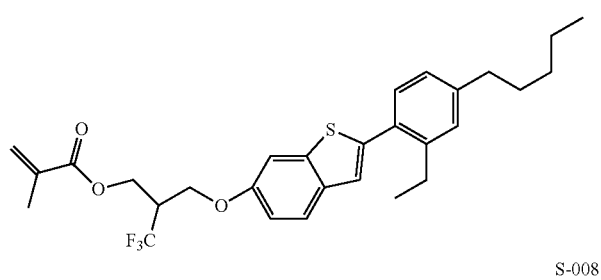
S-007
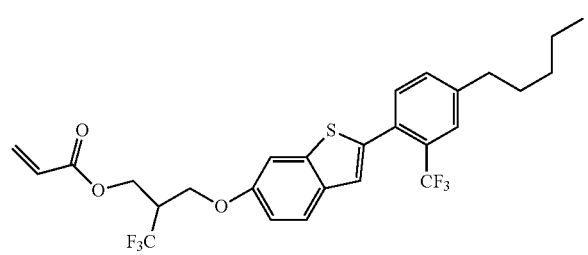
S-008
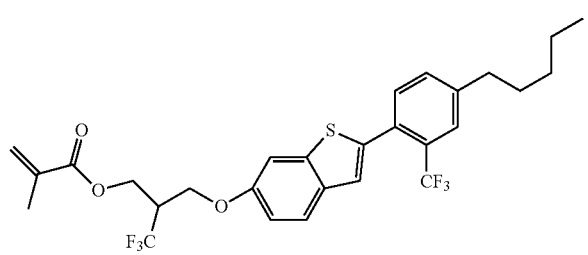

-continued
S-009
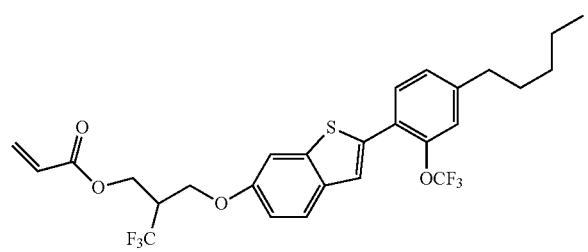
S-010
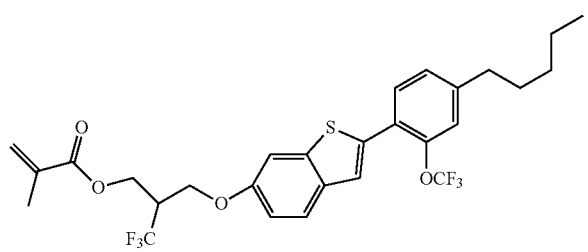
S-011
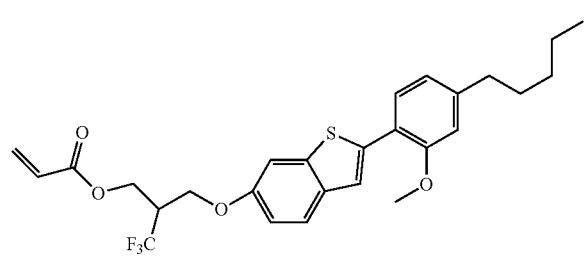
S-012
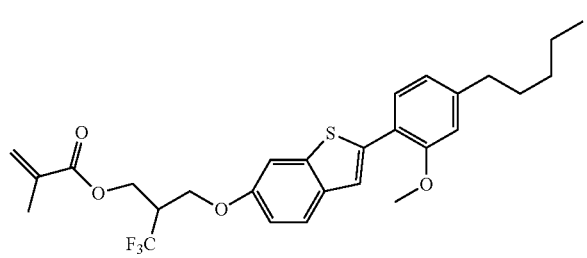
S-013
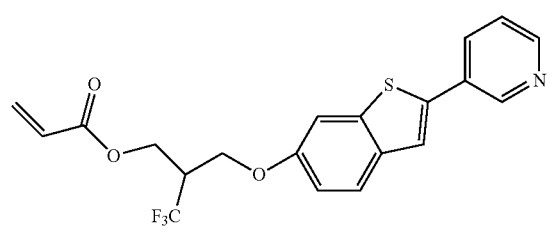
S-014
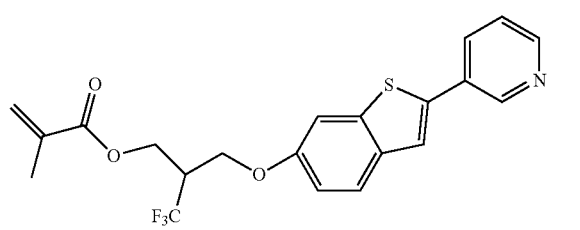
S-015
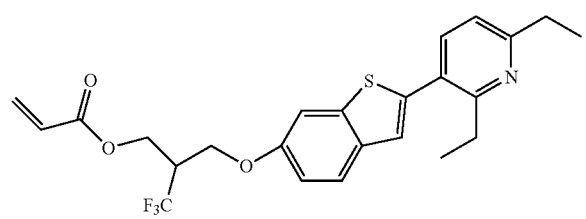
S-016
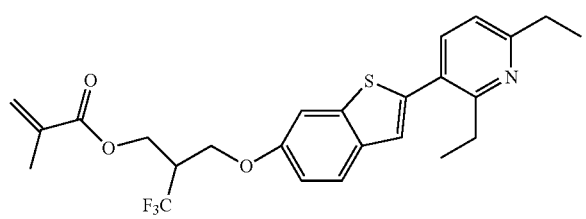
S-017
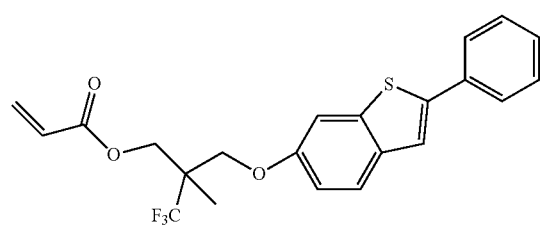
S-018
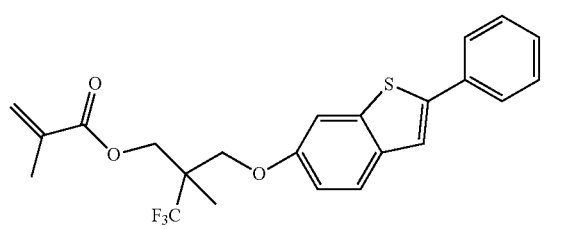
S-019
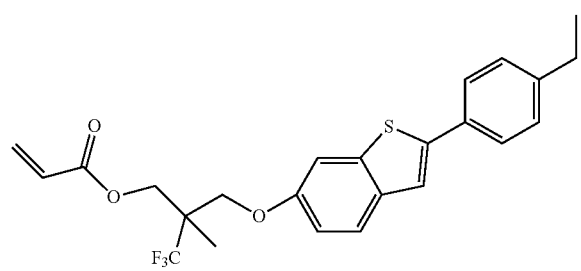
S-020
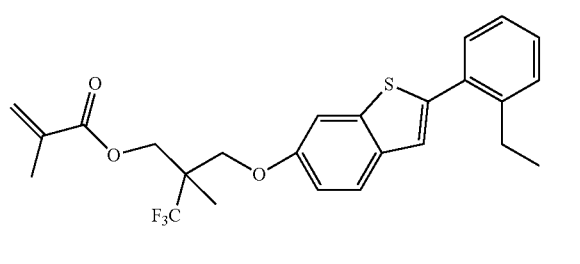

-continued
S-021
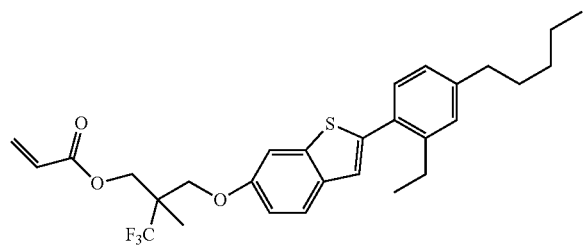
S-022
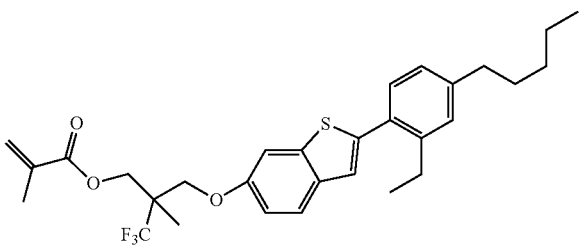
S-023
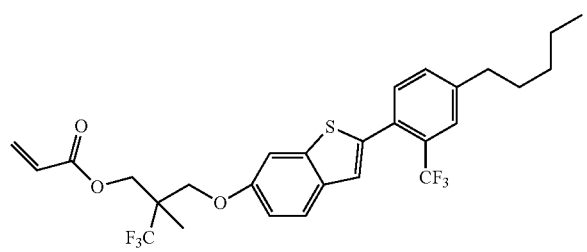
S-024
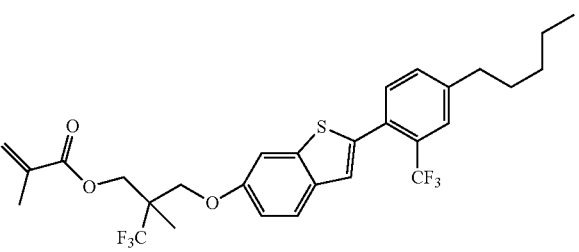
S-025
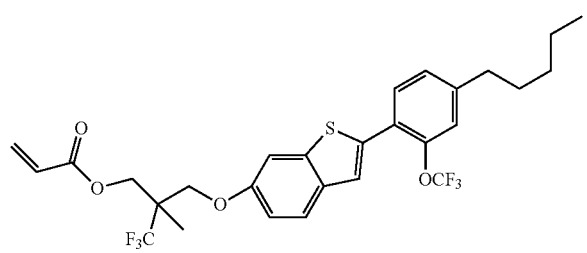
S-026
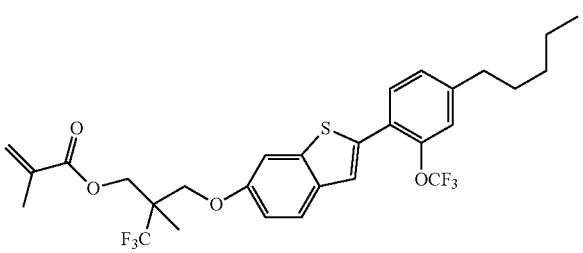
S-027
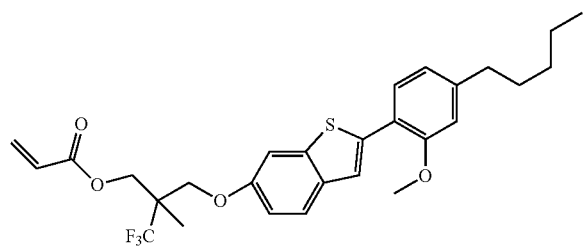
S-028
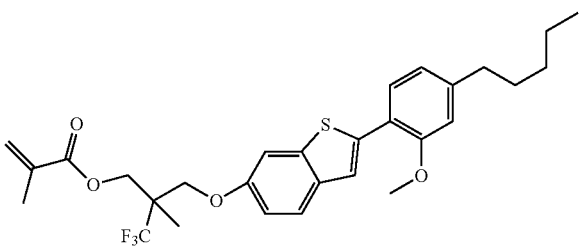
S-029
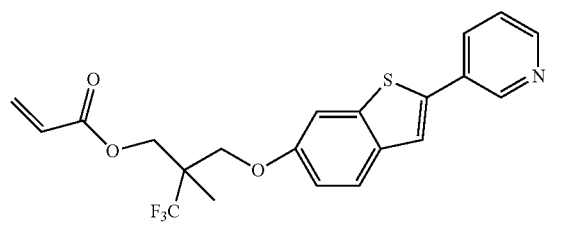
S-030
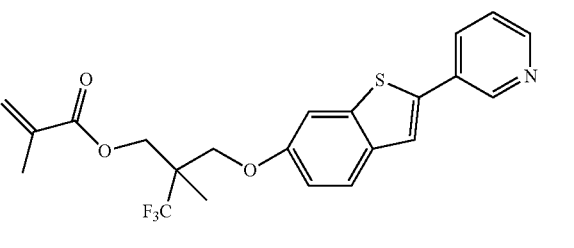
S-031
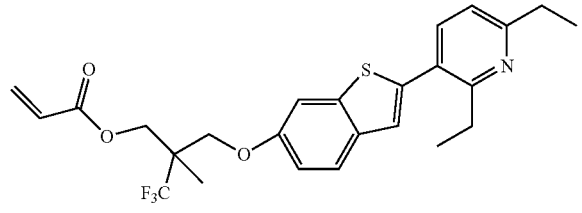
S-032
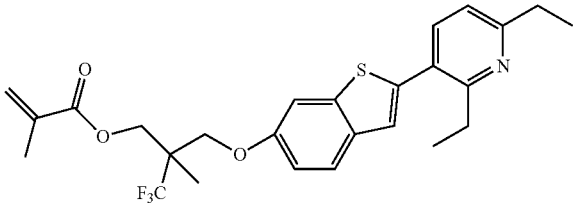

-continued
S-033
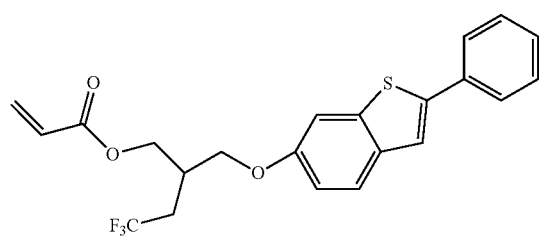
S-034
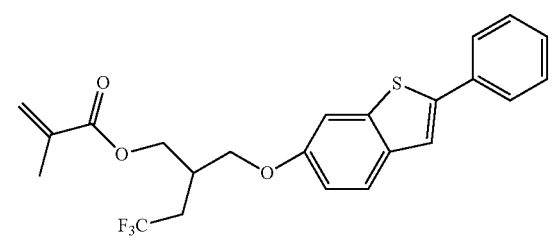
S-035
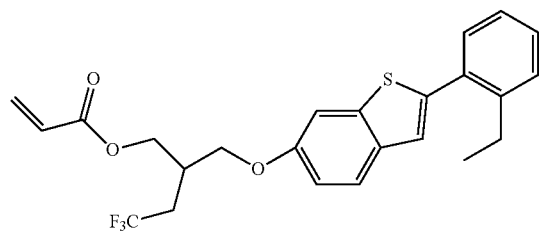
S-036
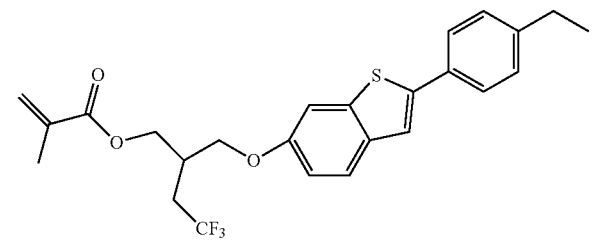
S-037
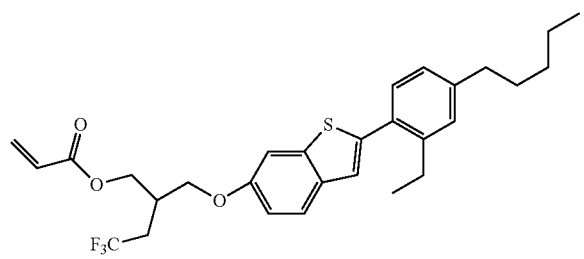
S-038
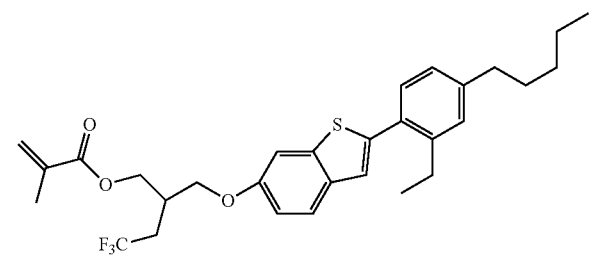
S-039
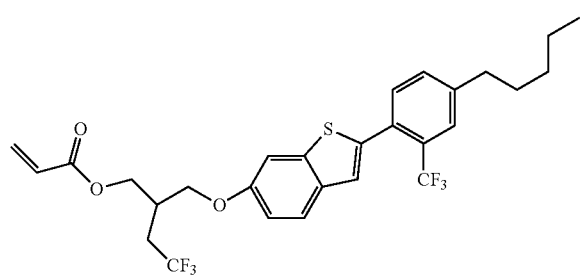
S-040
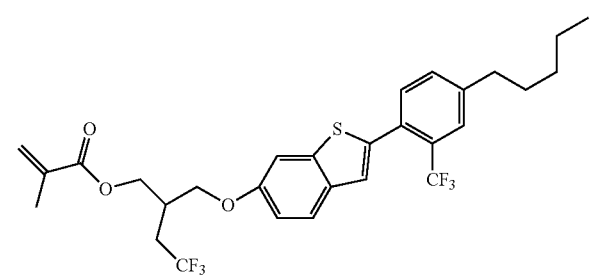
S-041
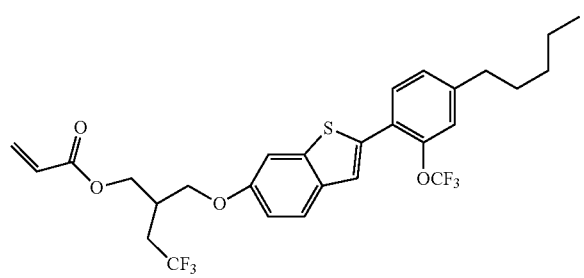
S-042
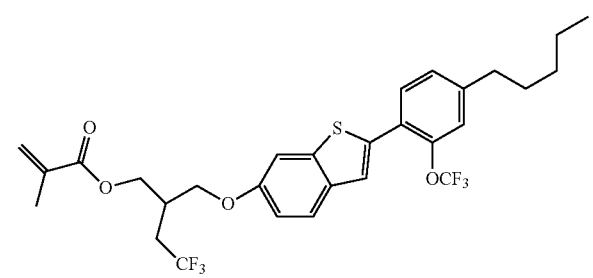

-continued
S-043
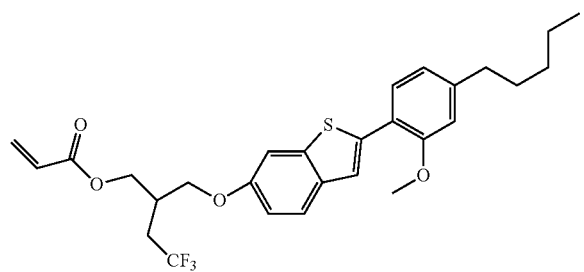
S-044
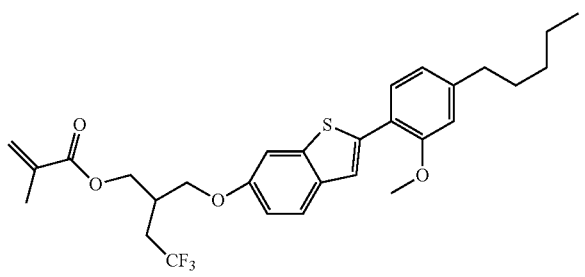
S-045
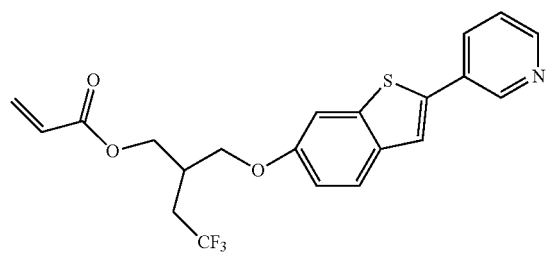
S-046
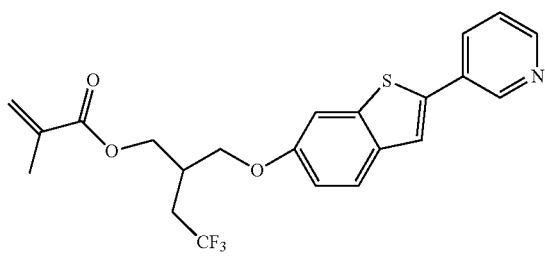
S-047
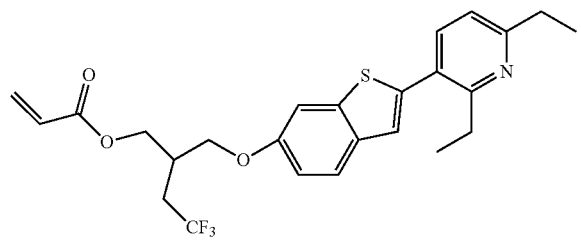
S-048
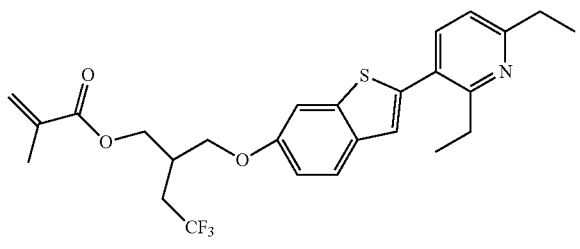
S-049
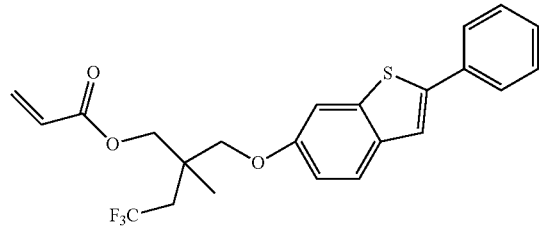
S-050
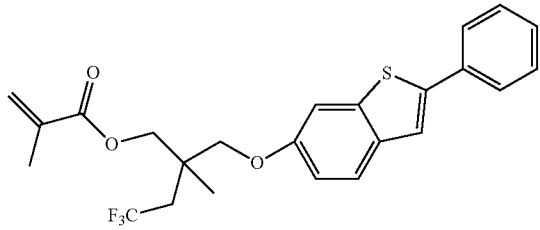
S-051
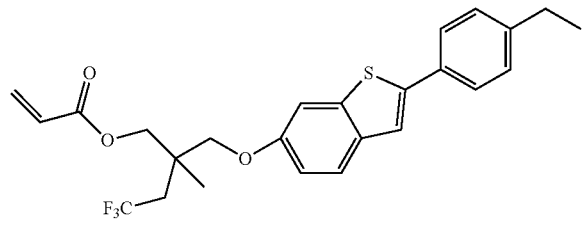
S-052
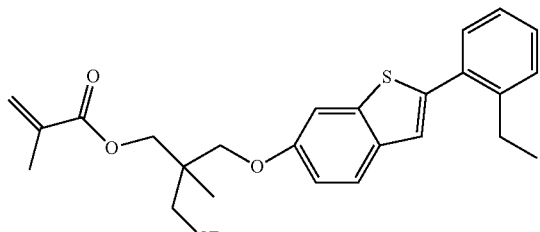

-continued
S-053
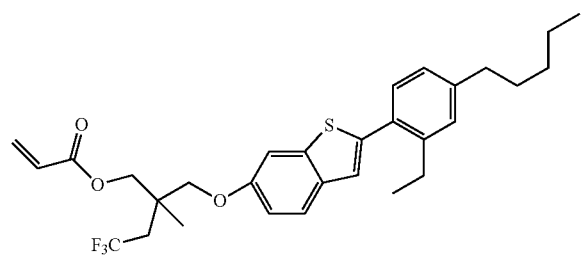
S-054
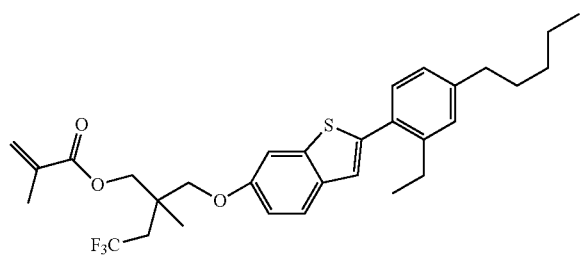
S-055
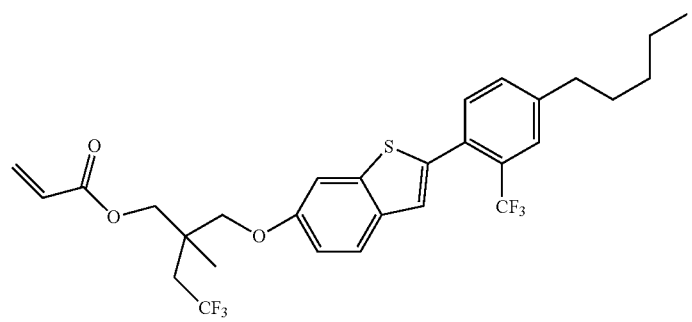
S-056
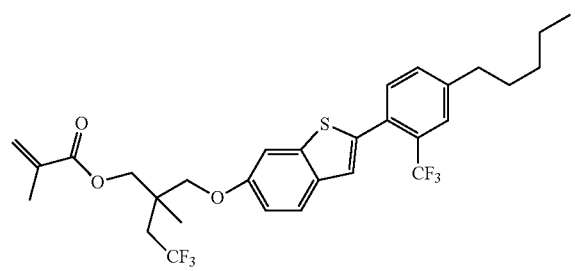
S-057
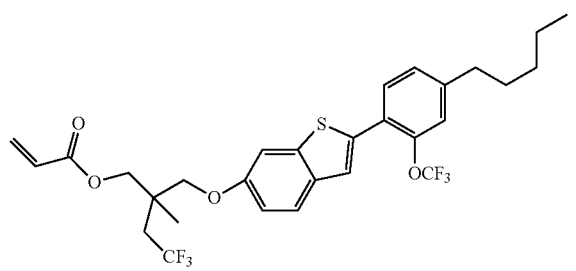
S-058
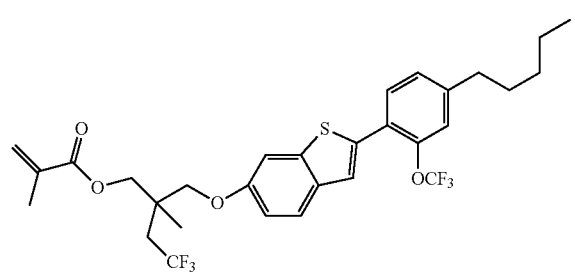
S-059
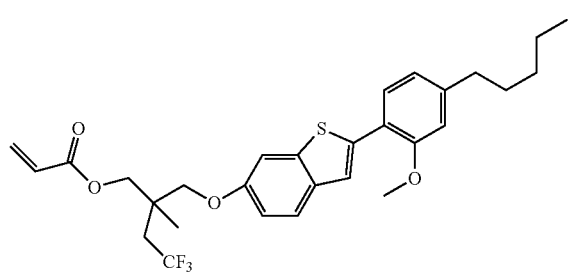
S-060
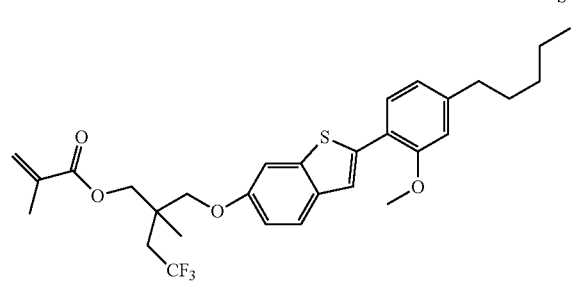
S-061
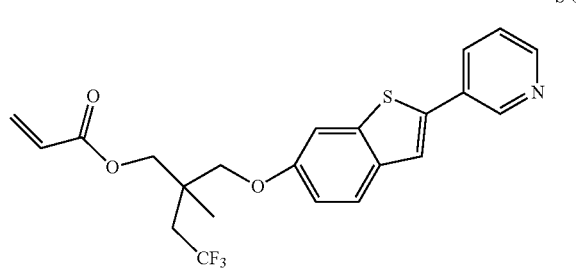

-continued
S-062
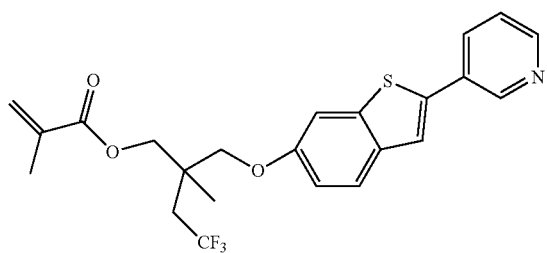
S-063
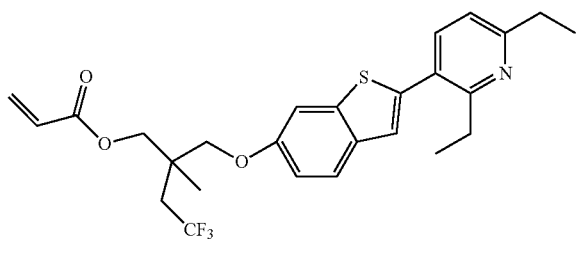
S-064
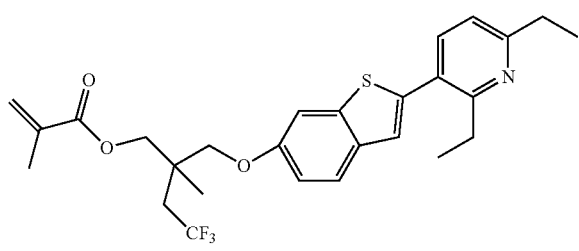
S-065
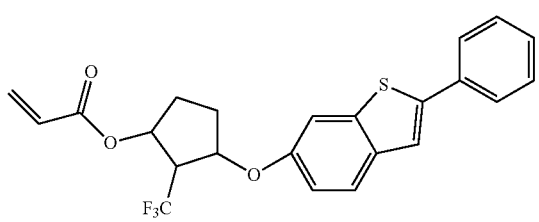
S-066
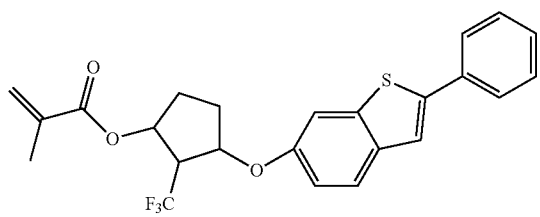
S-067
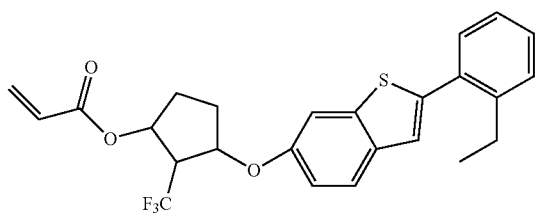
S-068
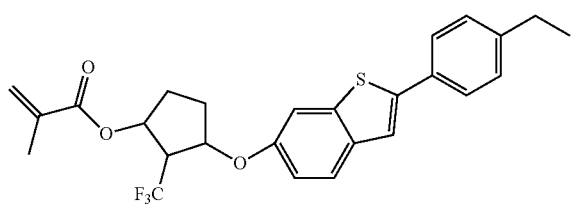
S-069
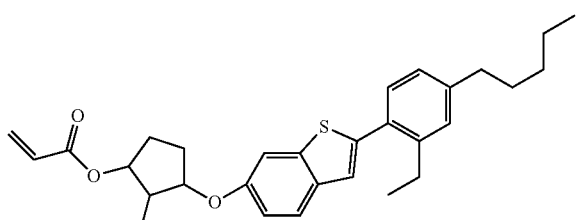
S-070
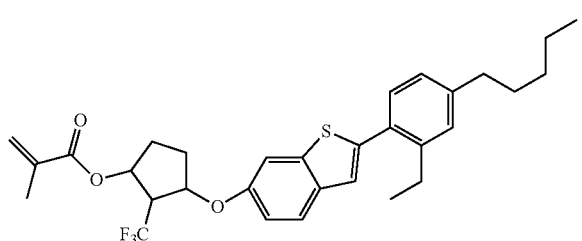
S-071
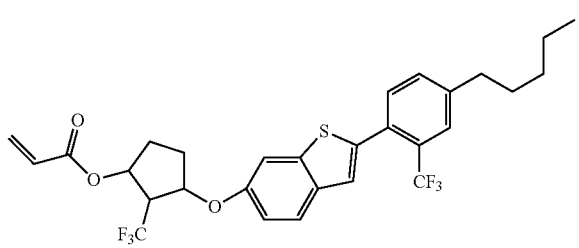
S-072
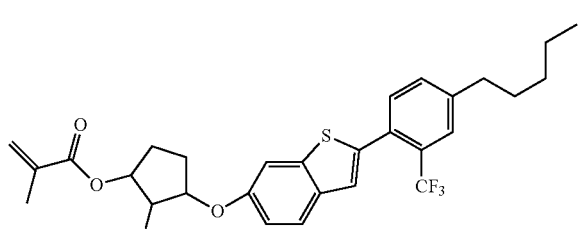
S-073
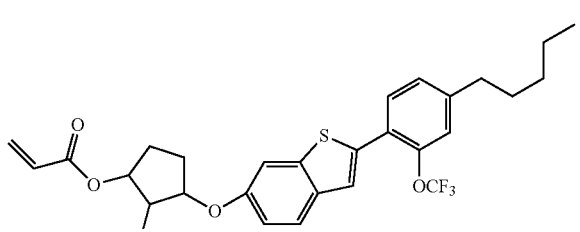

-continued
S-074
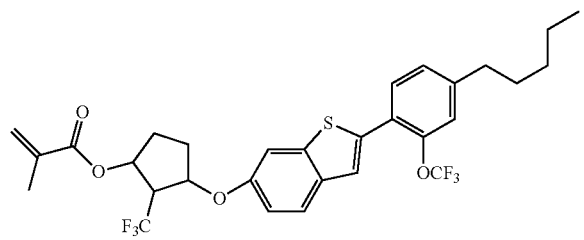
S-075
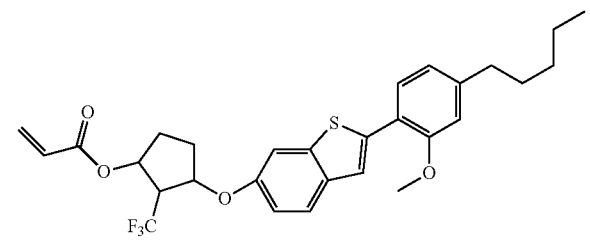
S-076
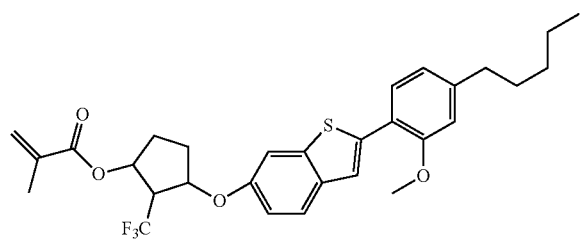
S-077
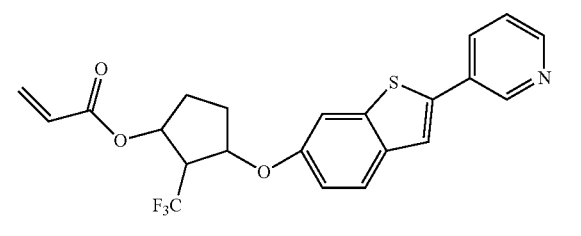
S-078
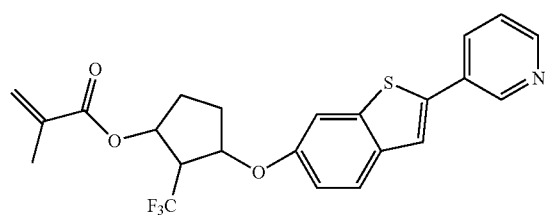
S-079
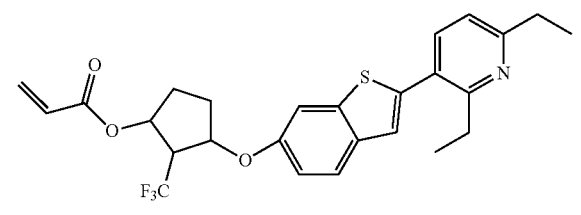
S-080
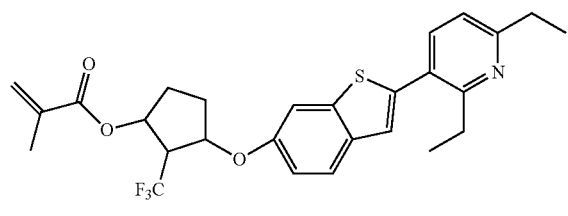
S-081
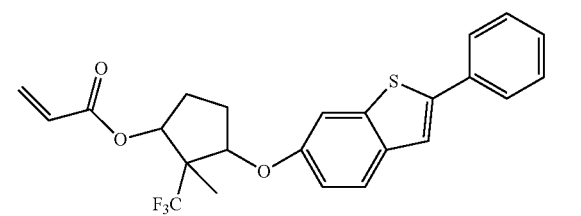
S-082
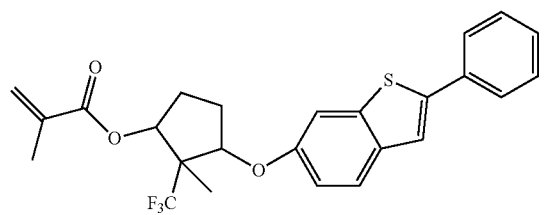
S-083
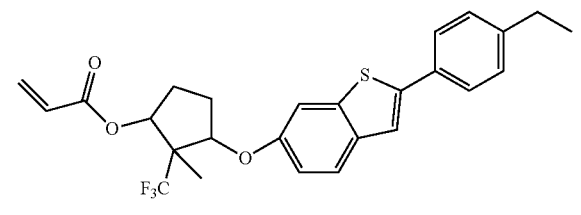
S-084
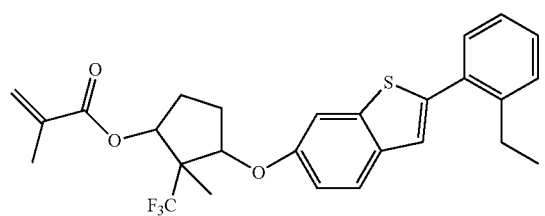
S-085
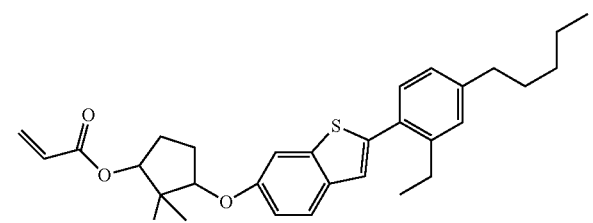

-continued
S-086
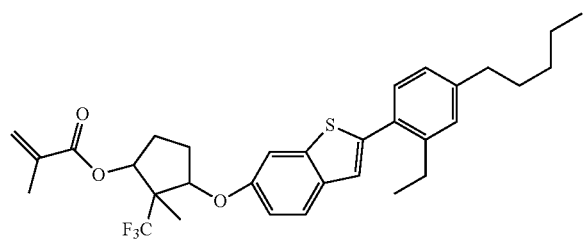
S-087
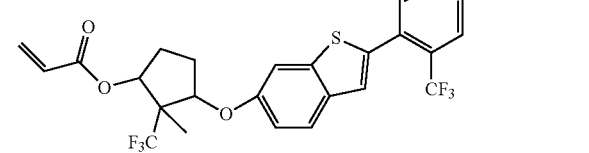
S-088
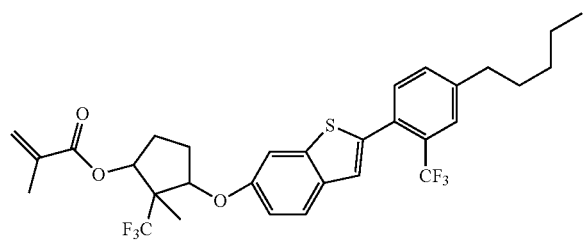
S-089
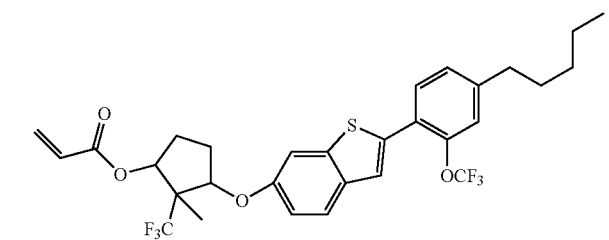
S-090
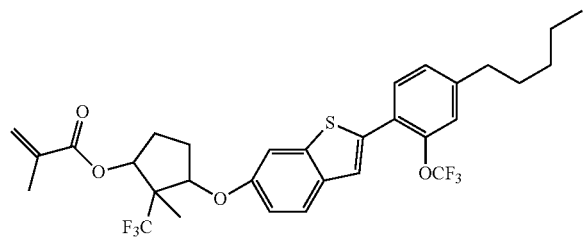
S-091
S-092
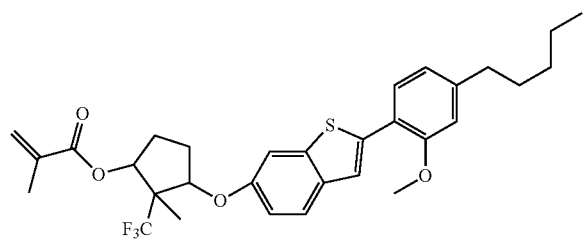
S-093
S-094
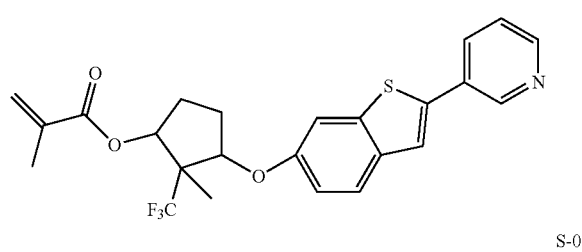
S-095
S-096
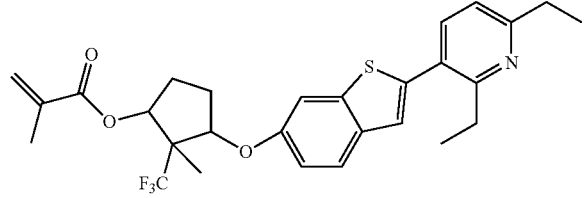
S-097
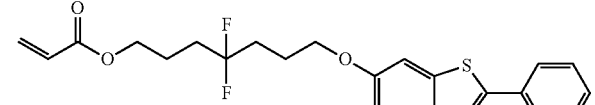

-continued
S-098
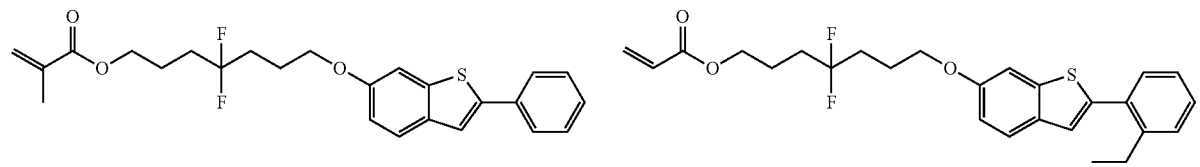
S-099
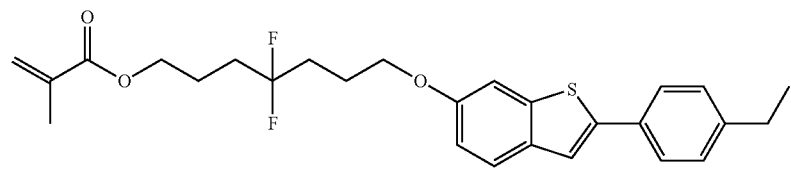
S-100
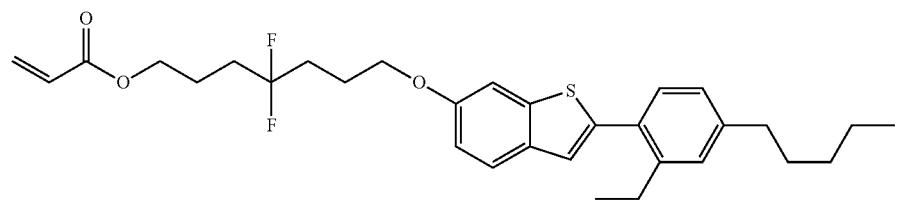
S-101
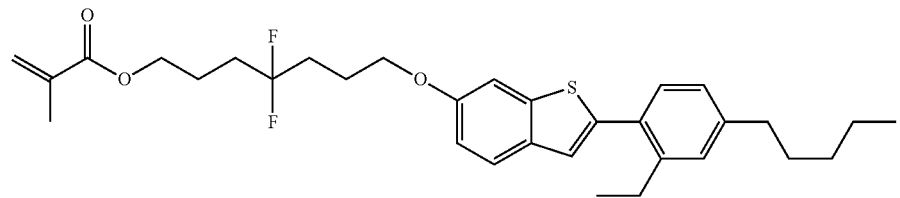
S-102
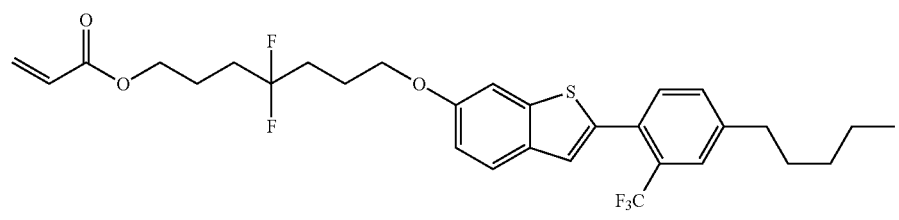
S-103
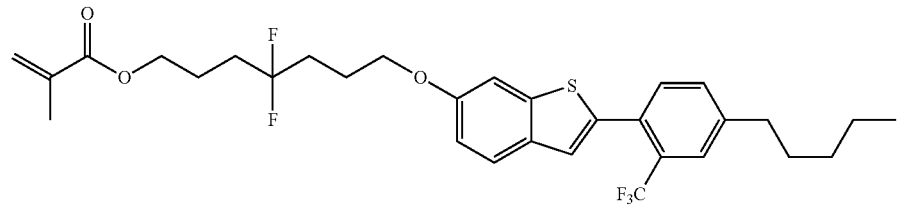
S-104
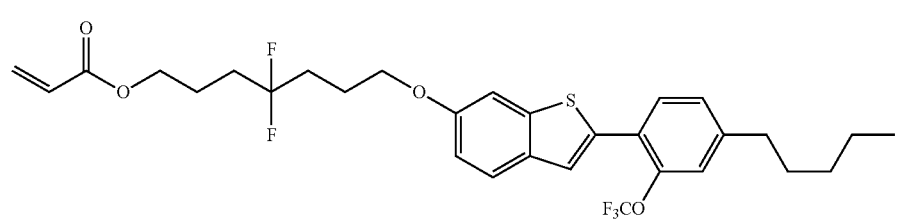
S-105

-continued
S-106
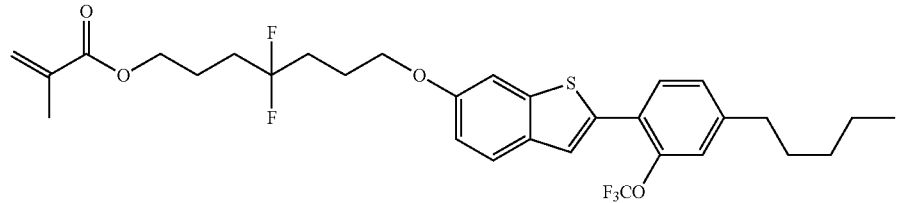
S-107
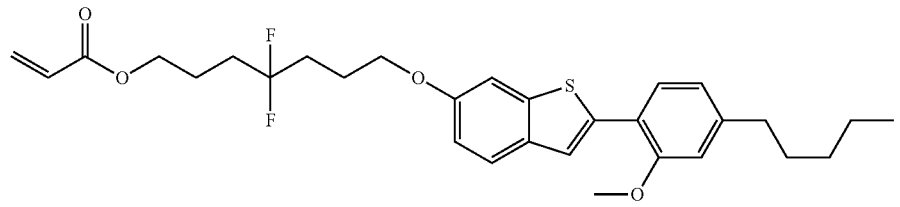
S-108
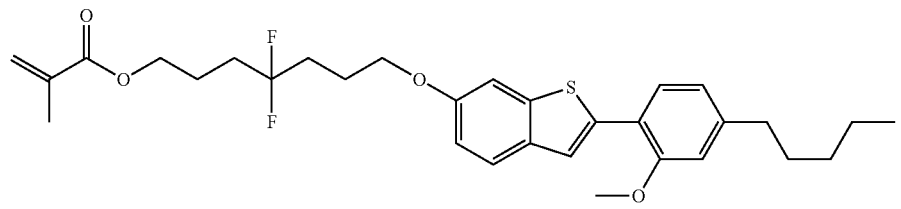
S-109
S-110
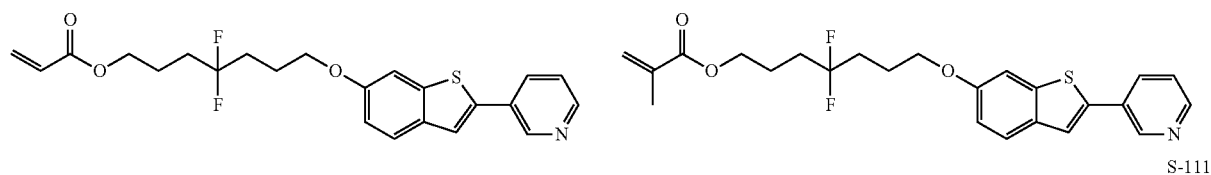
S-111
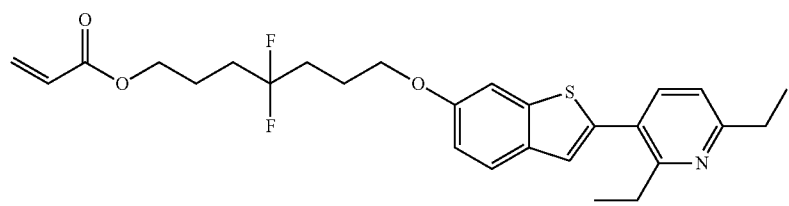
S-112
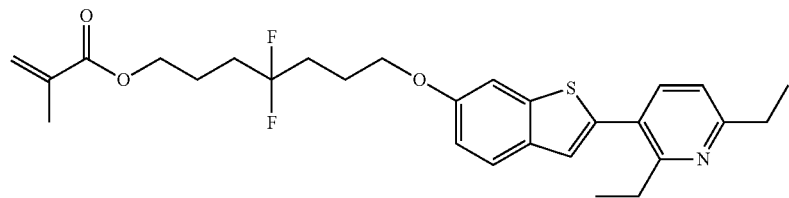
S-113
S-114
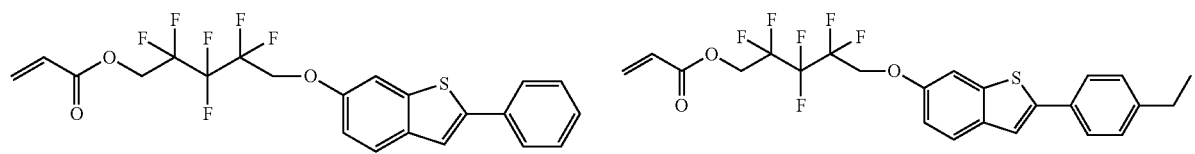
S-115
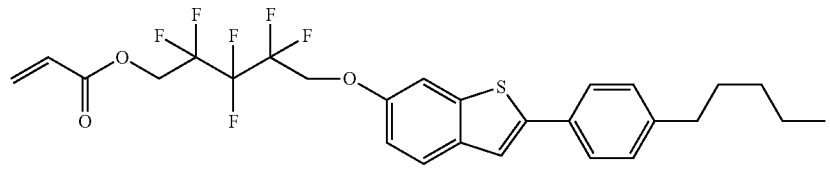

-continued
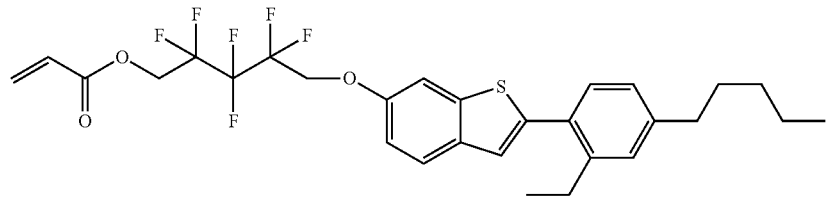
S-116
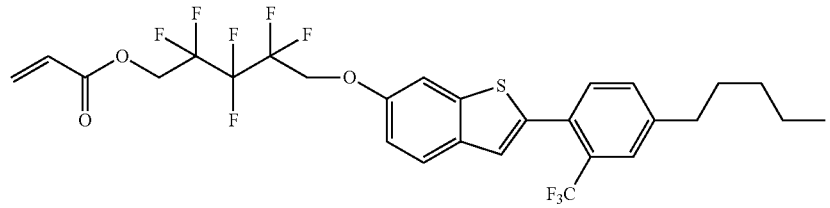
S-117
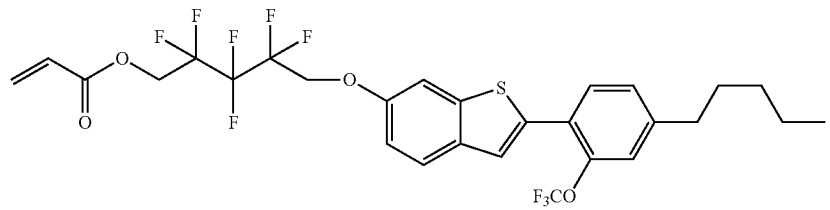
S-118
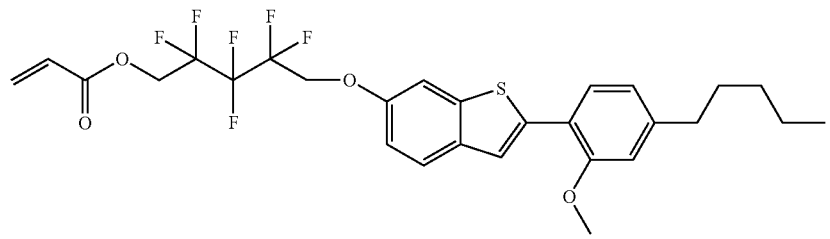
S-119
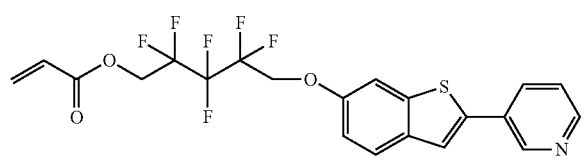
S-120
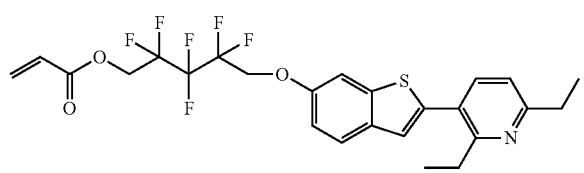
S-121
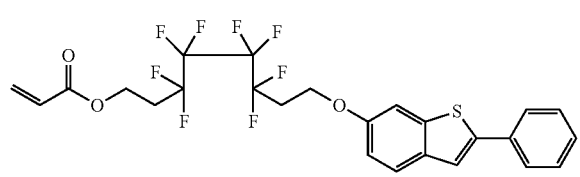
S-122
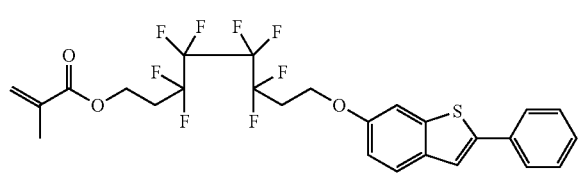
S-123
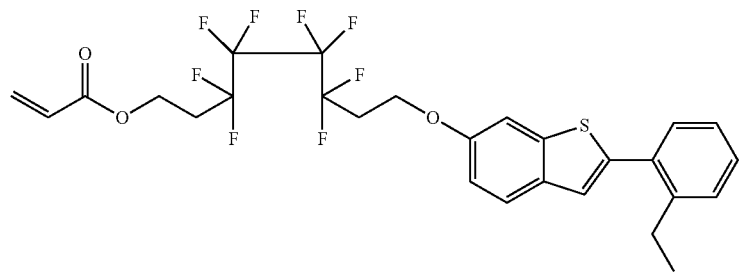
S-124

-continued
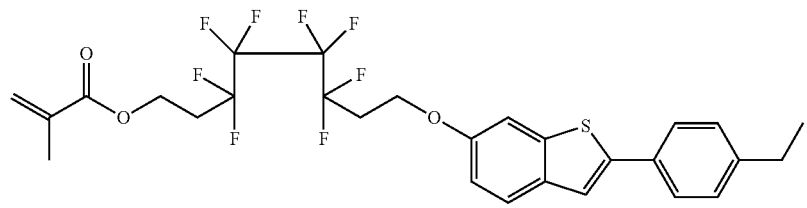
S-125
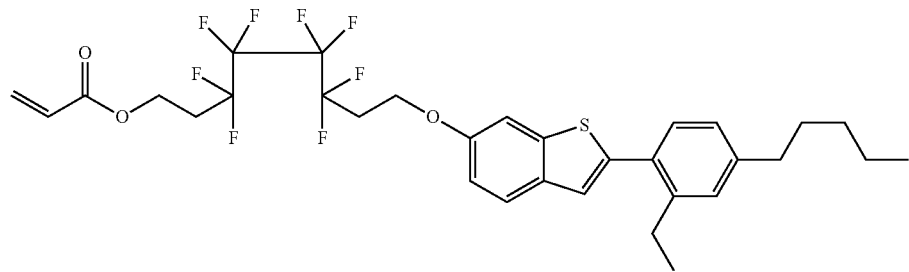
S-126
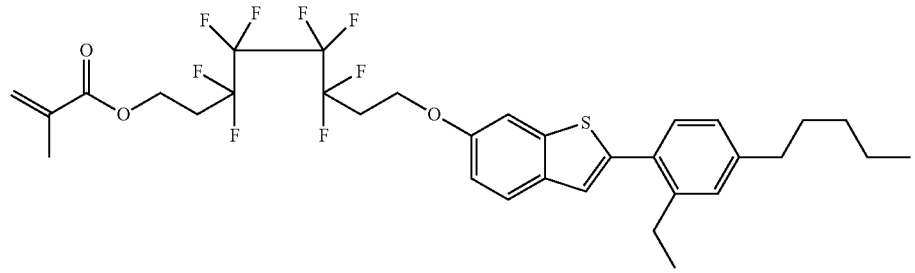
S-127
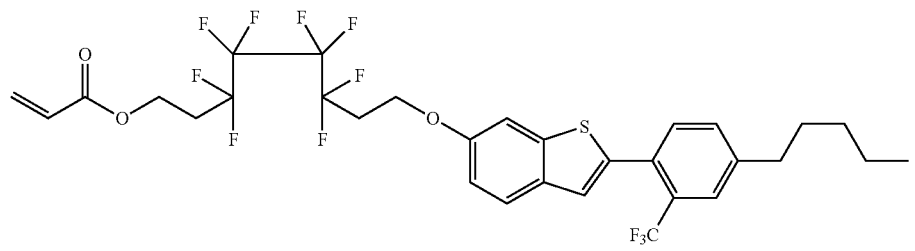
S-128
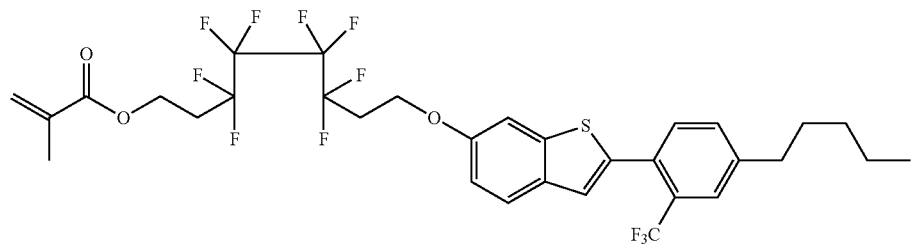
S-129
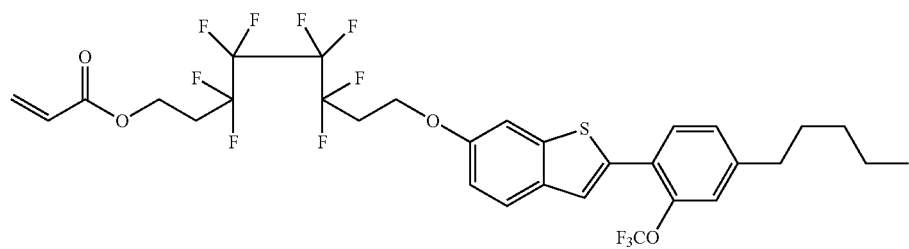
S-130

-continued
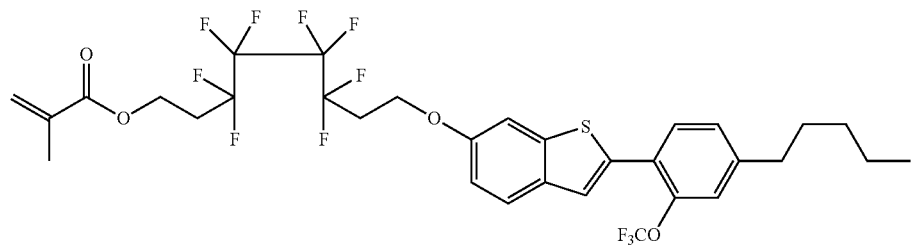
S-131
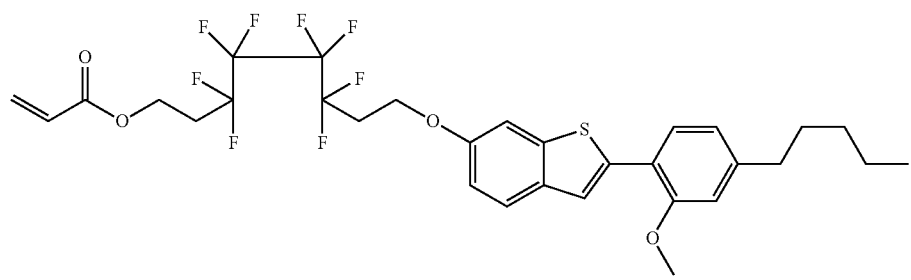
S-132
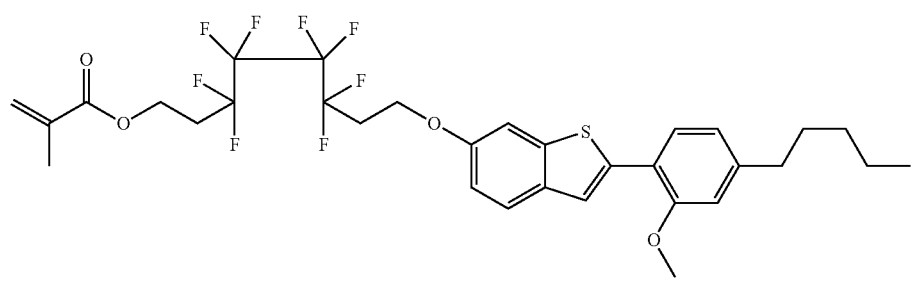
S-133
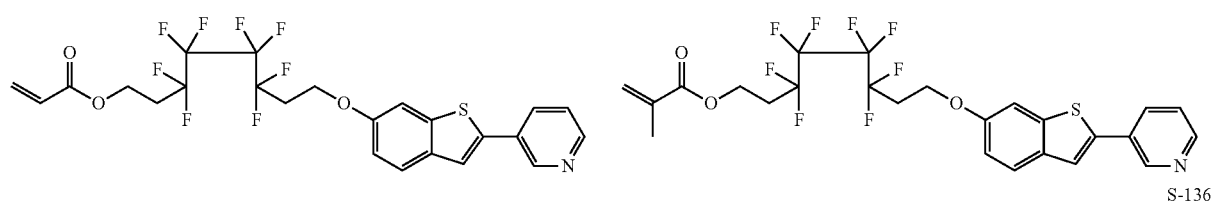
S-134   S-135
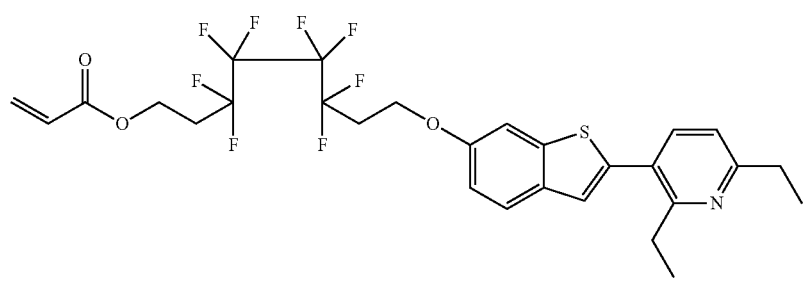
S-136
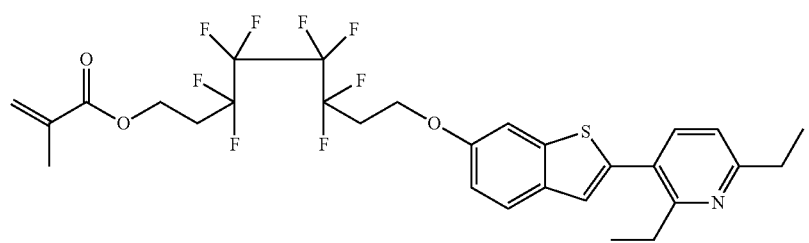
S-137

-continued
S-138
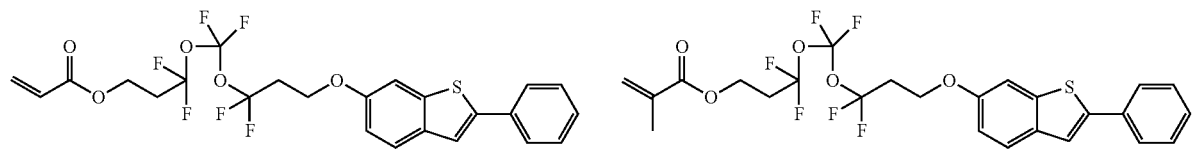
S-139
S-140
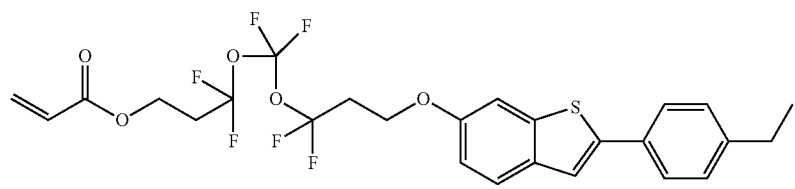
S-141
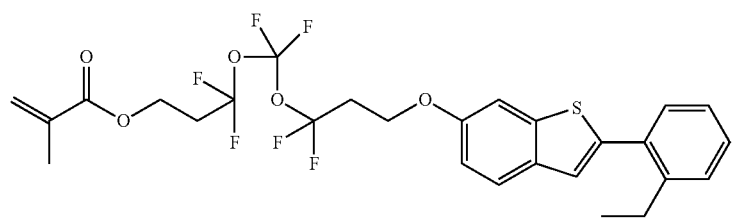
S-142
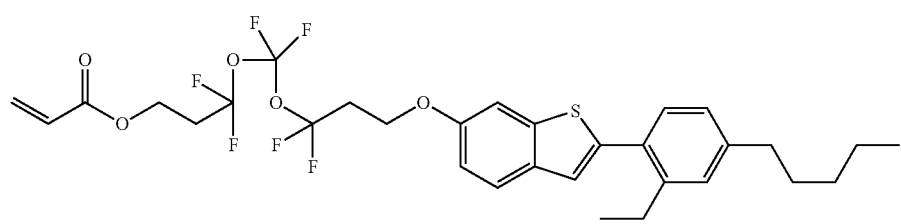
S-143
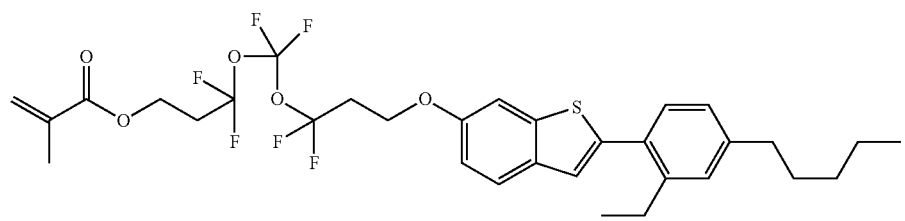
S-144
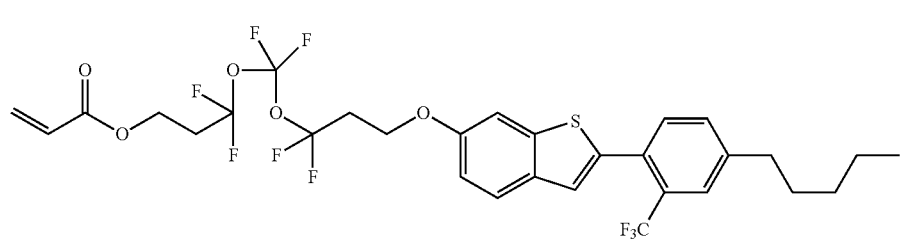
S-145
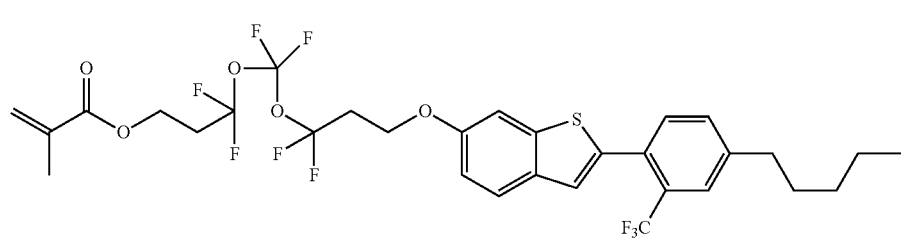

-continued
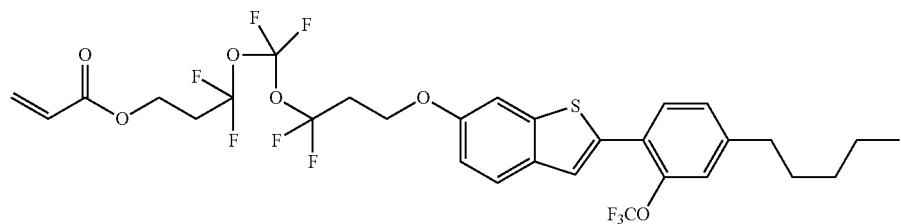
S-146
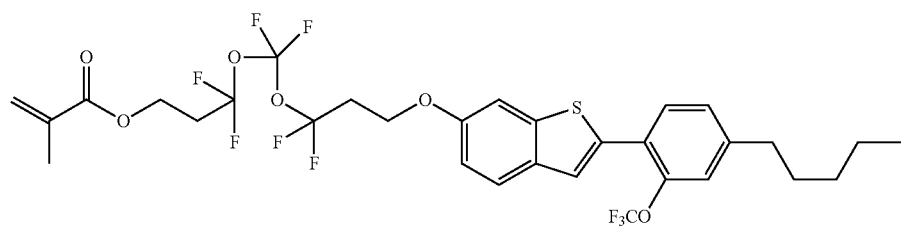
S-147
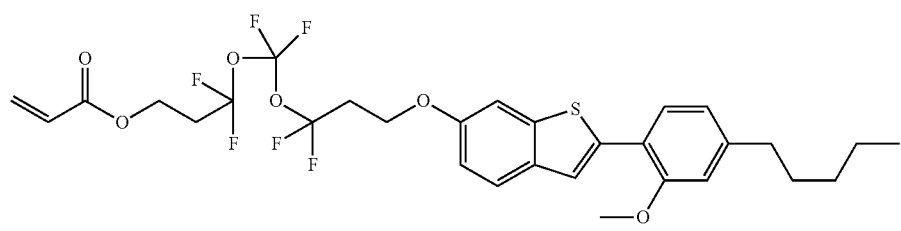
S-148
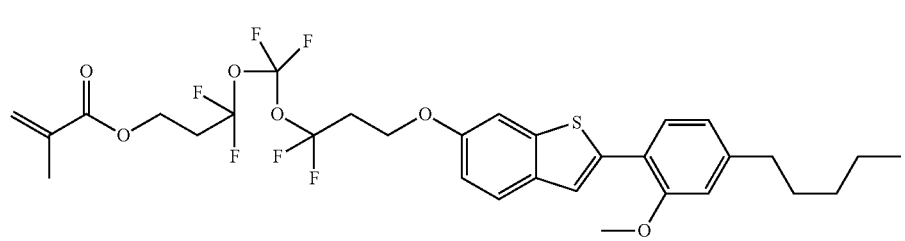
S-149
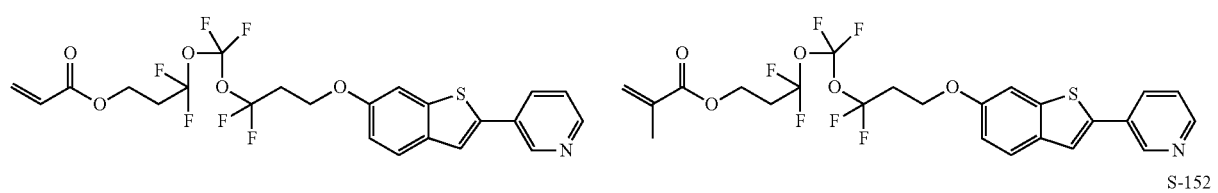
S-150     S-151
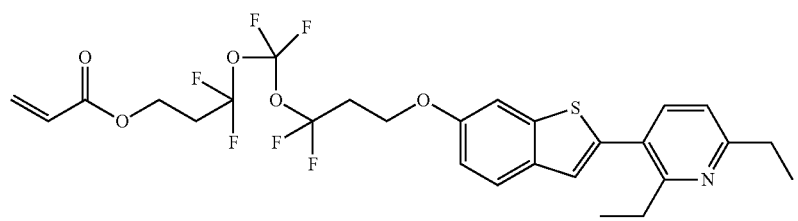
S-152
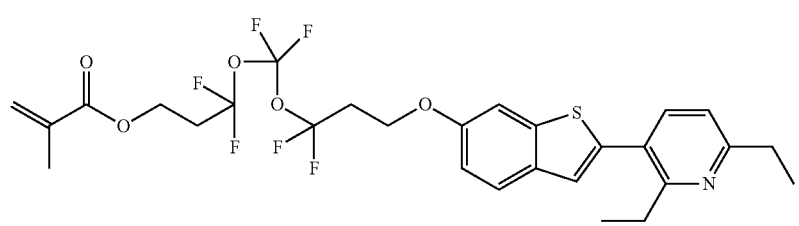
S-153

-continued
S-154
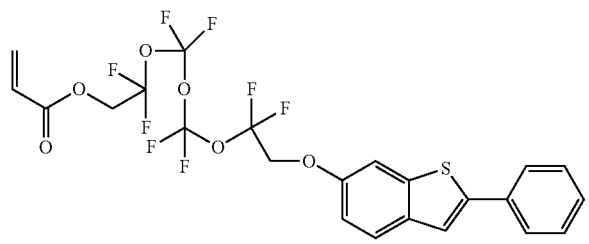
S-155
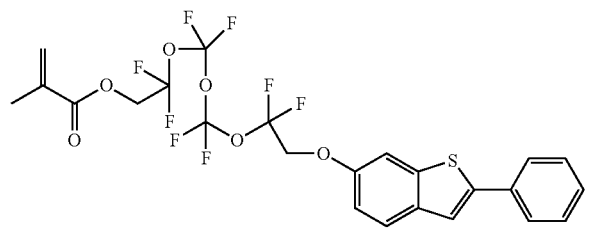
S-156
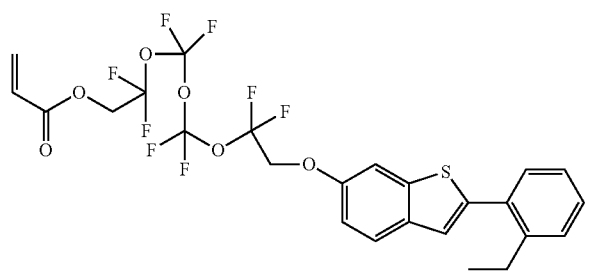
S-157
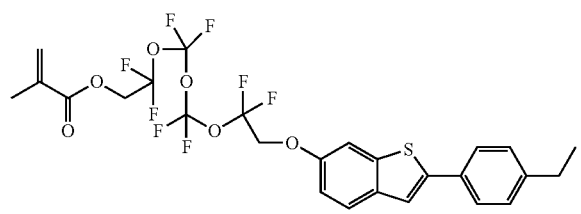
S-158
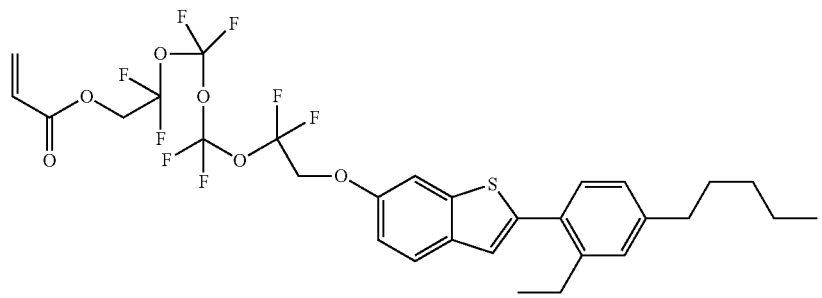
S-159
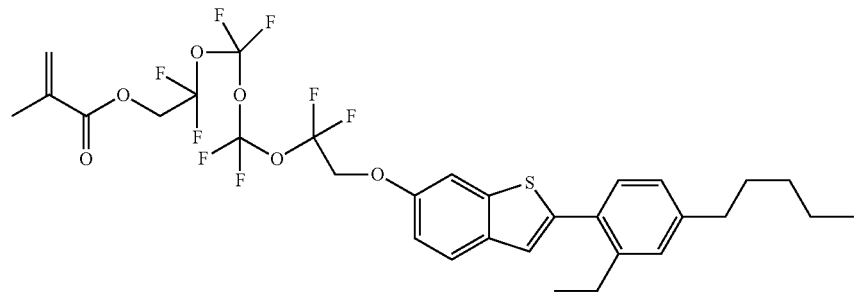
S-160
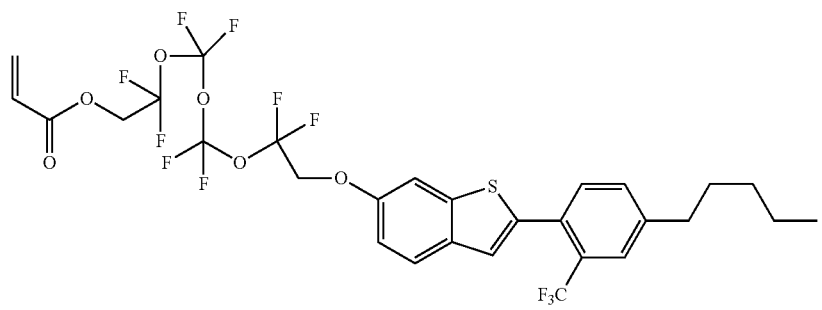

-continued
S-161
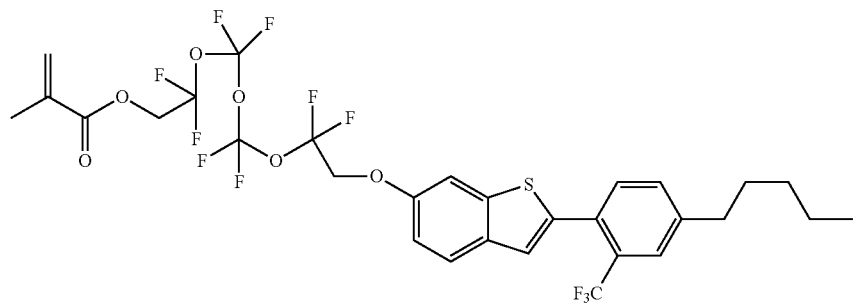
S-162
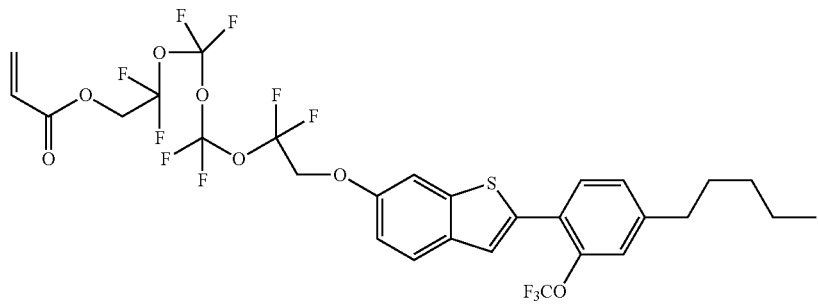
S-163
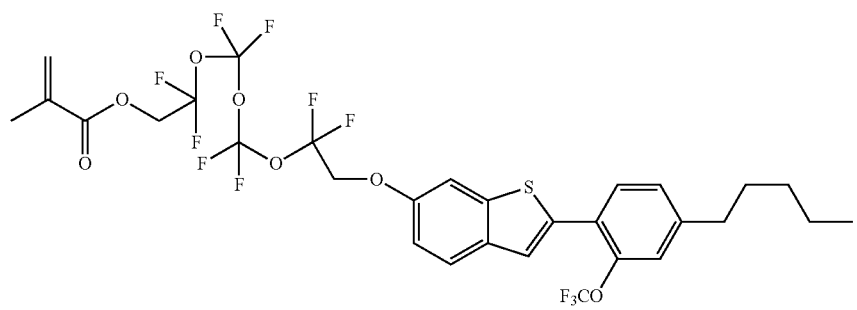
S-164
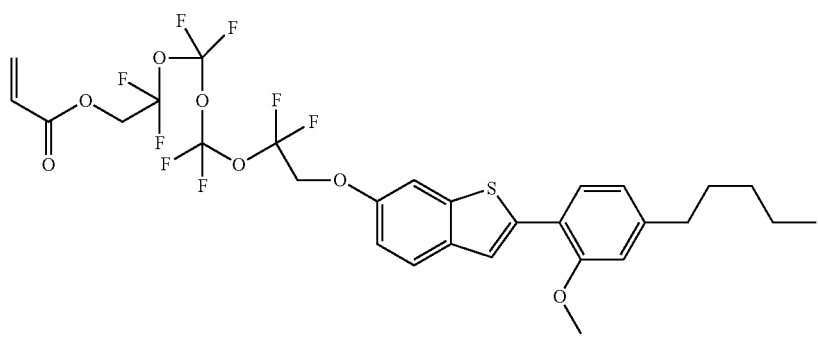
S-165
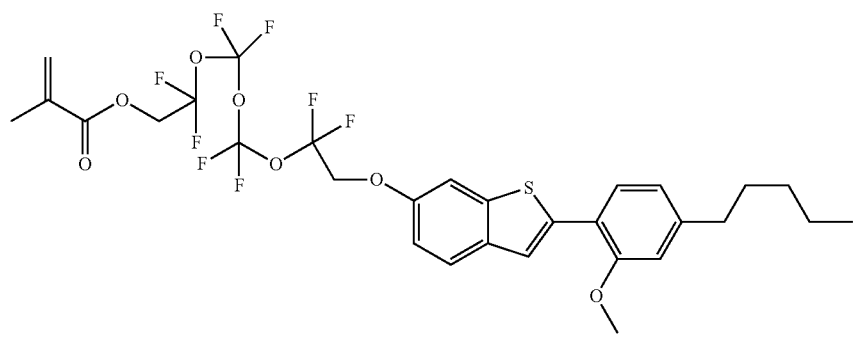

-continued
S-166
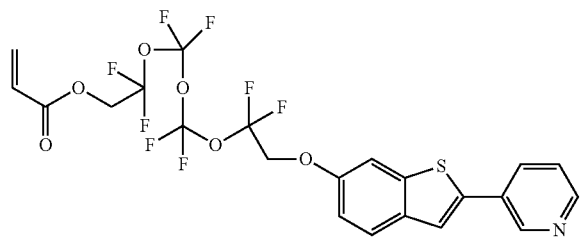
S-167
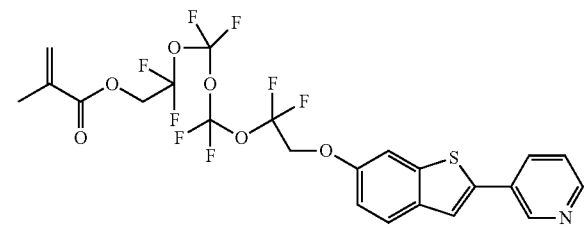
S-168
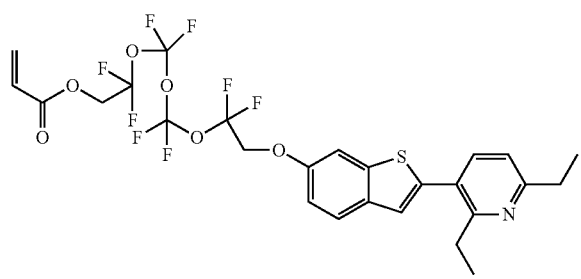
S-169
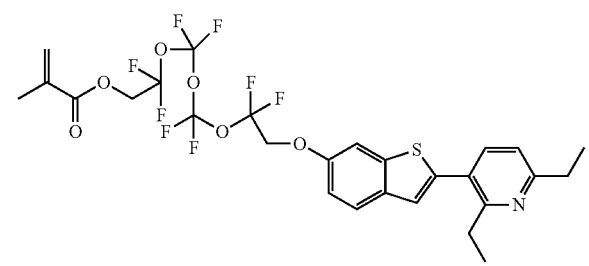
N-001
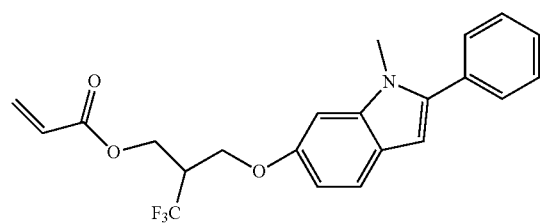
N-002
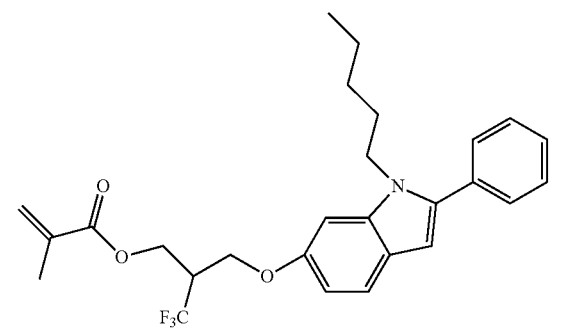
N-003
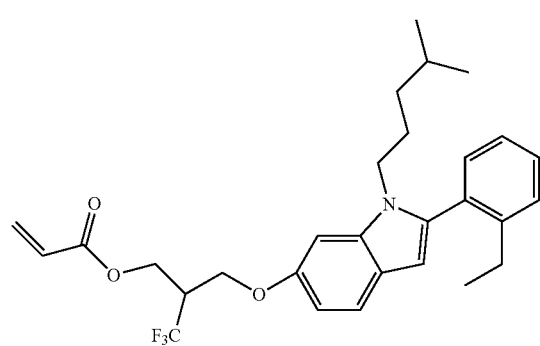
N-004
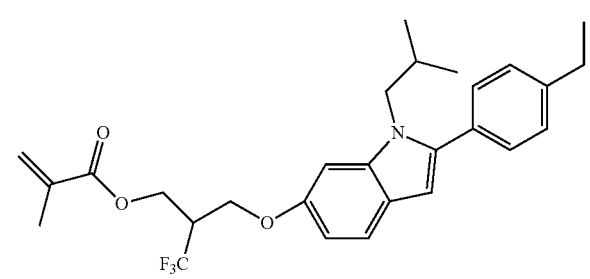
N-005
N-006
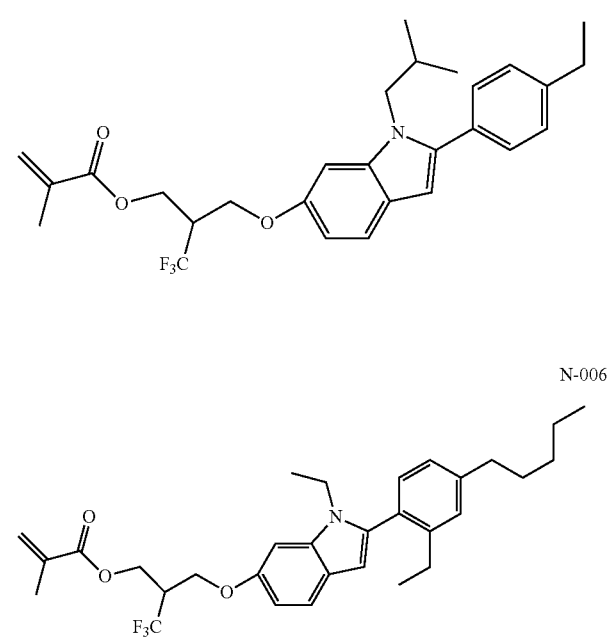

-continued
N-007
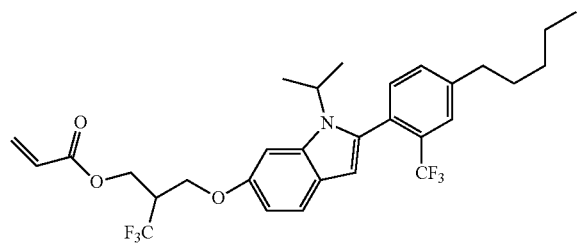
N-008
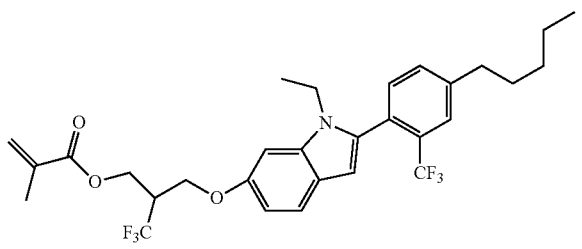
N-009
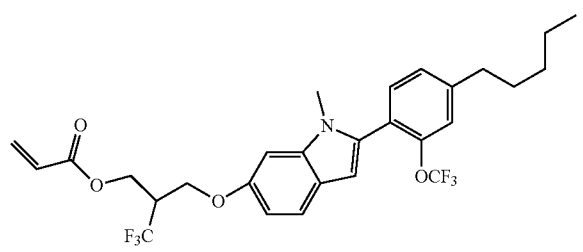
N-010
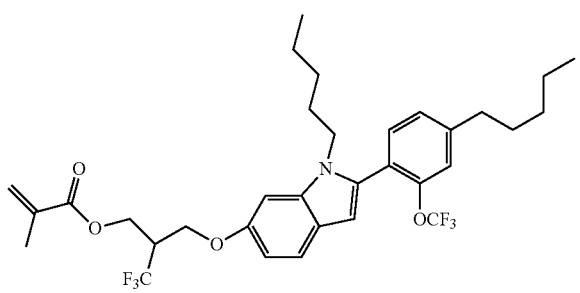
N-011
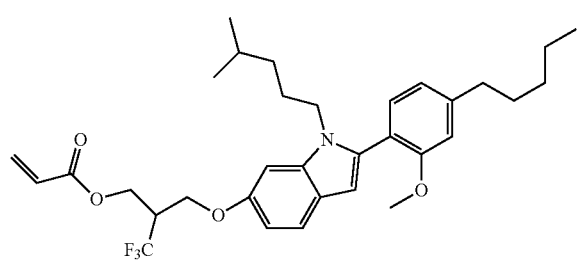
N-012
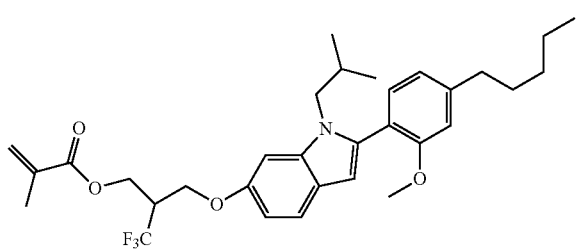
N-013
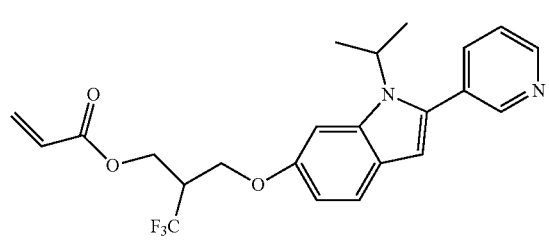
N-014
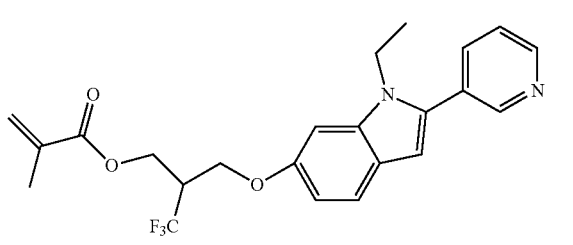
N-015
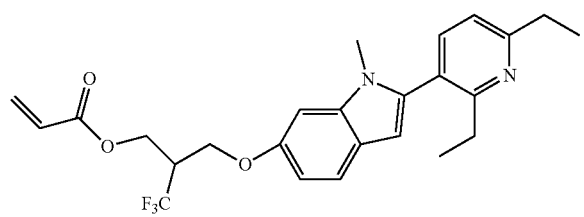
N-016
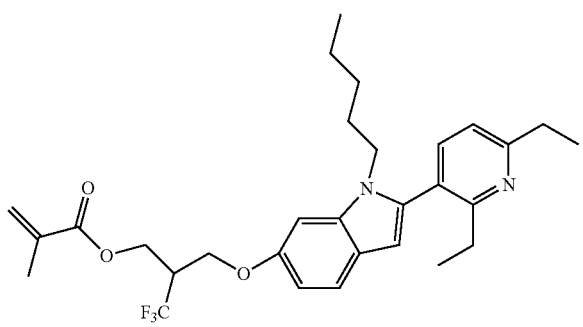

-continued
N-017
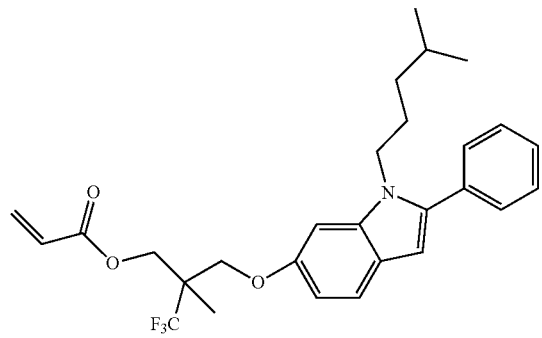
N-018
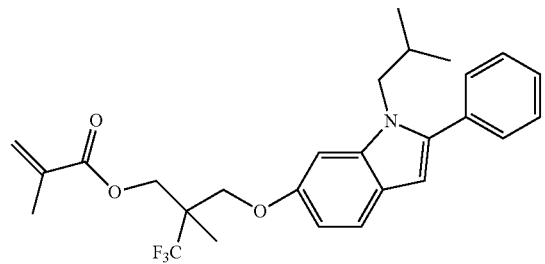
N-019
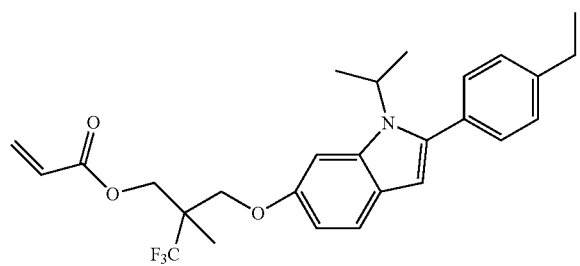
N-020
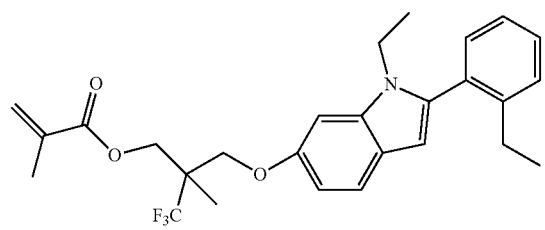
N-021
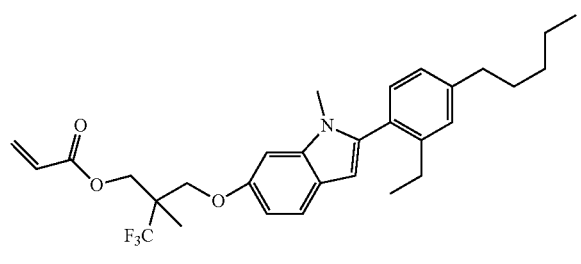
N-022
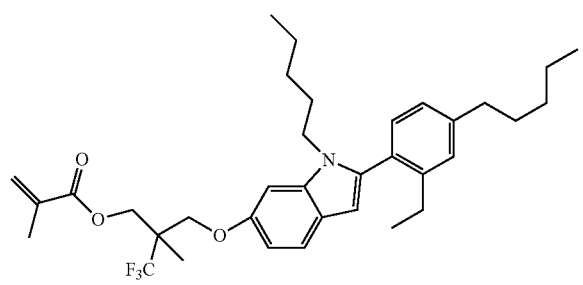
N-023
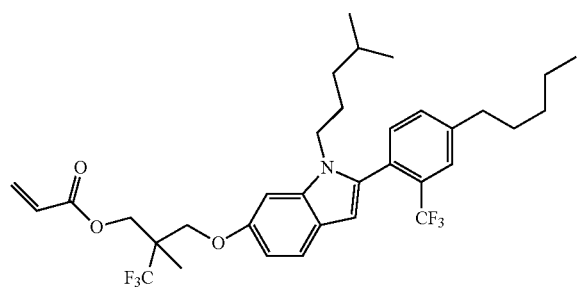
N-024
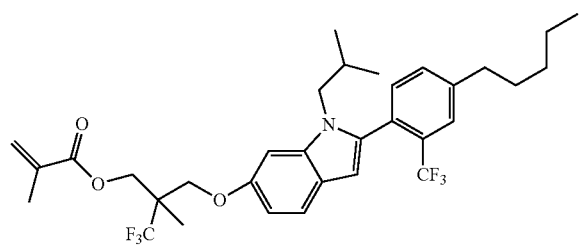
N-025
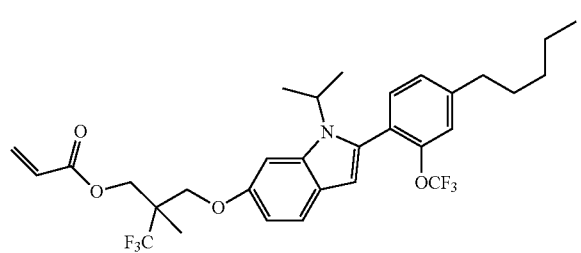
N-026

-continued
N-027
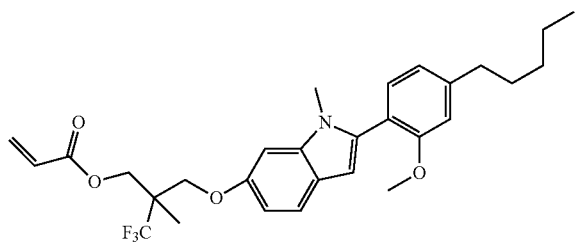
N-028
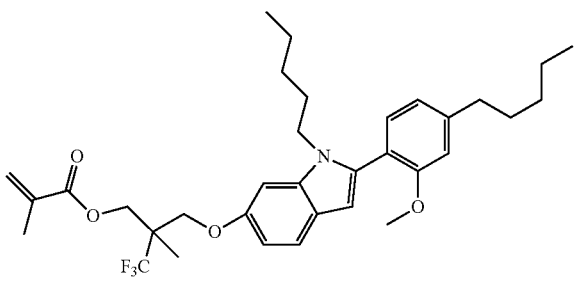
N-029
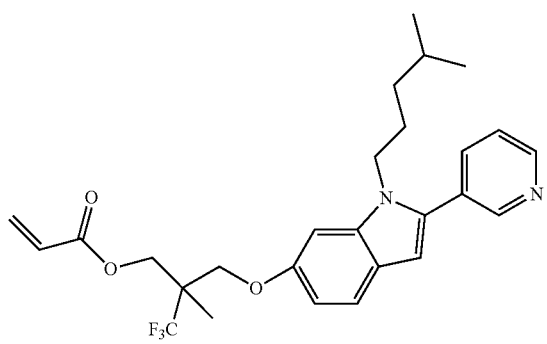
N-030
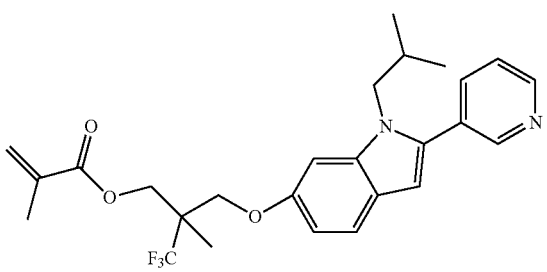
N-031
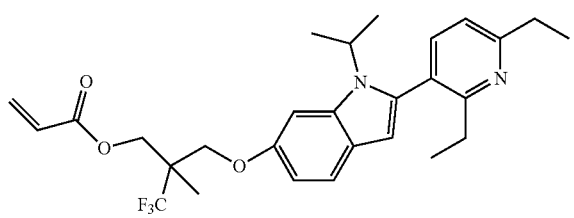
N-032
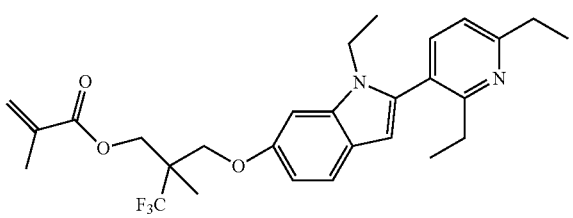
N-033
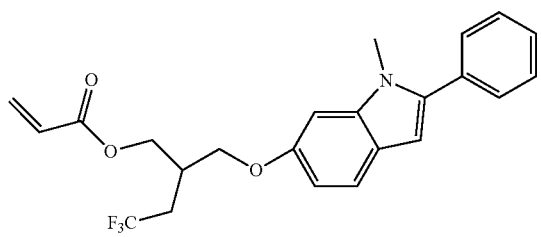
N-034
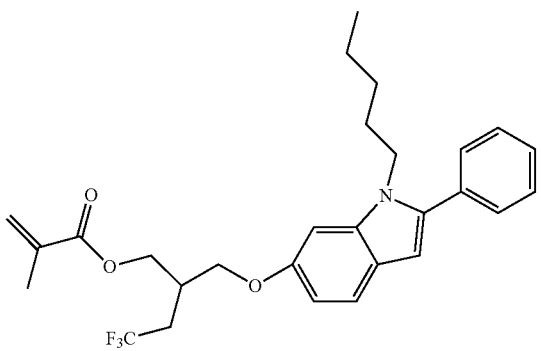
N-035
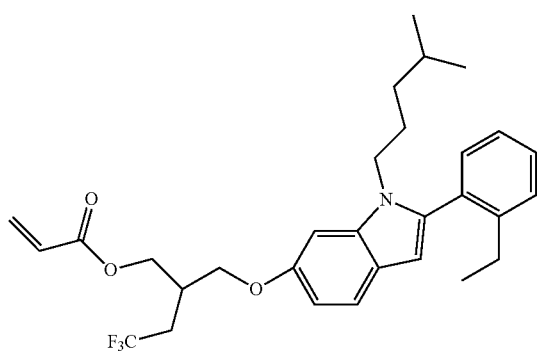
N-036
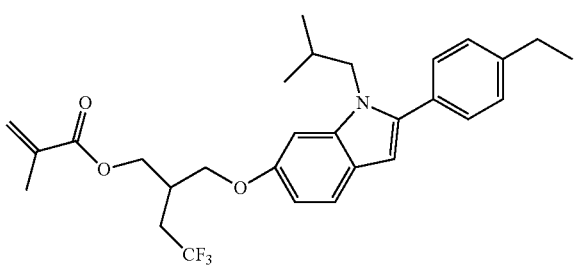

-continued
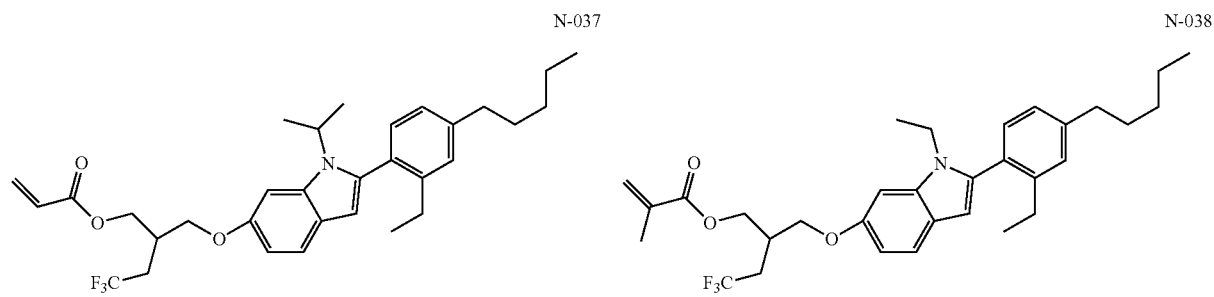
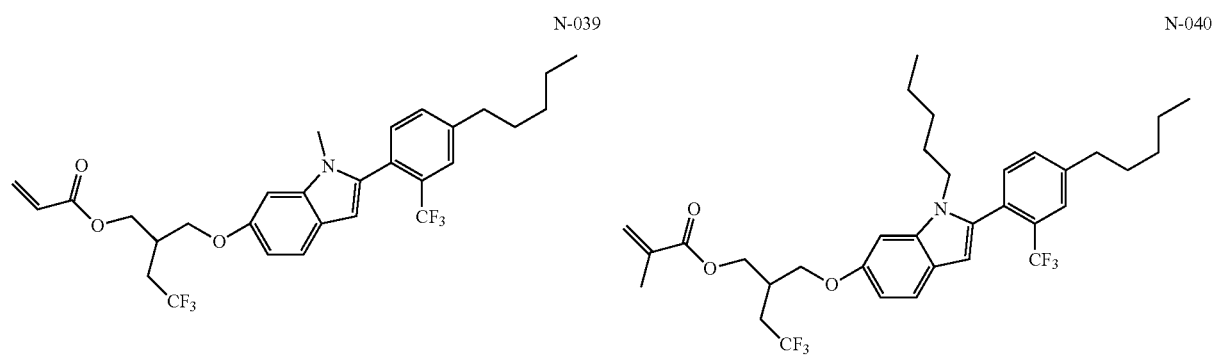
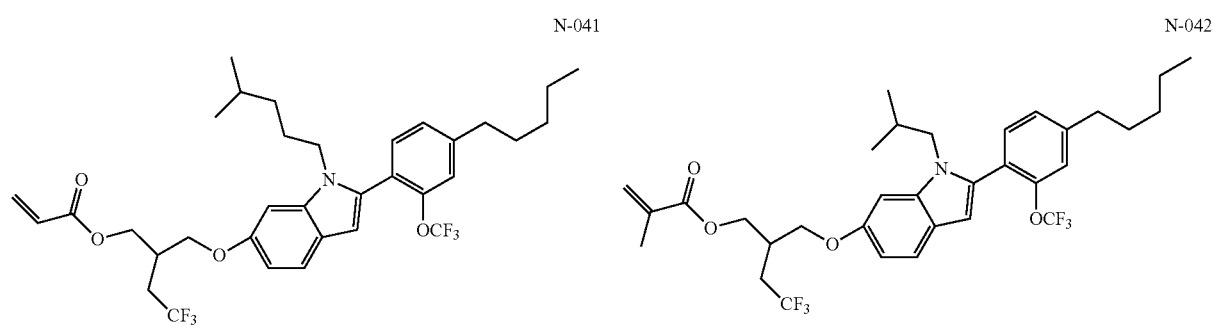 [SMILES: C=CC(=O)OCC(COc1ccc2cc(-c3ccc(CCCCC)cc3OC(F)(F)F)n(CCCC(C)C)c2c1)CC(F)(F)F ; C=C(C)C(=O)OCC(COc1ccc2cc(-c3ccc(CCCCC)cc3OC(F)(F)F)n(CC(C)C)c2c1)CC(F)(F)F]
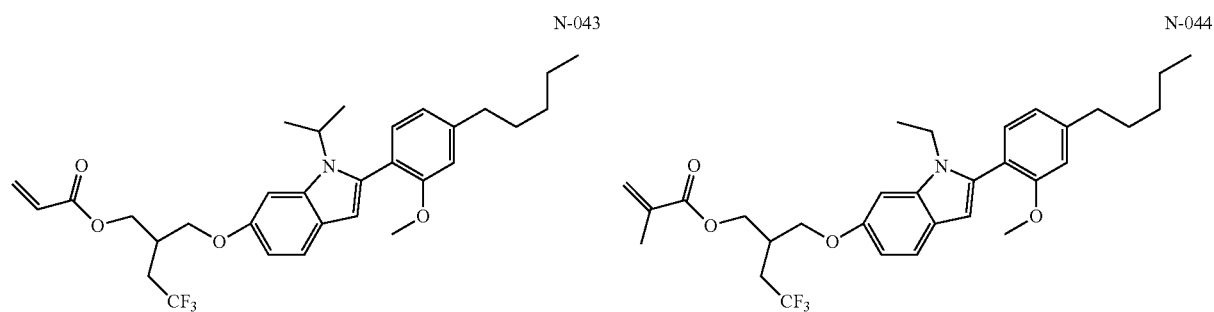

-continued
N-045
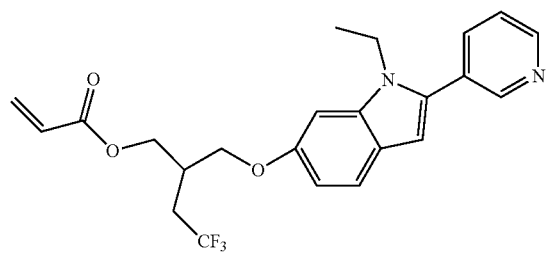
N-046
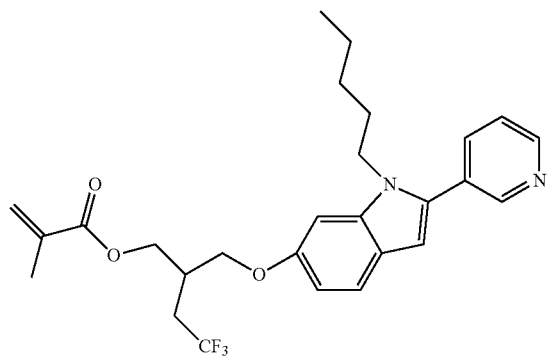
N-047
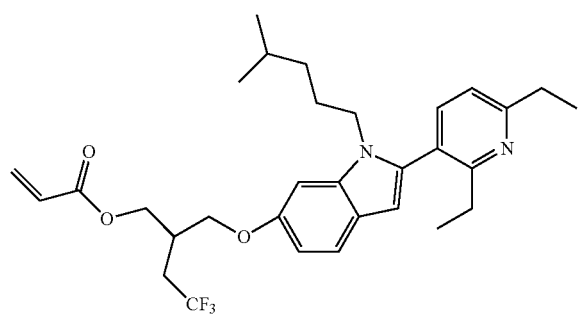
N-048
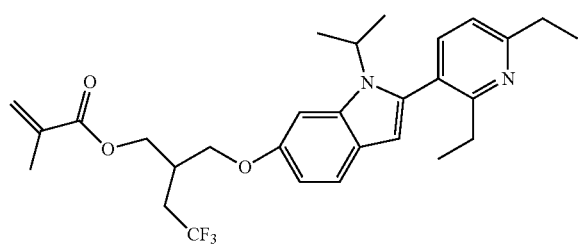
N-049
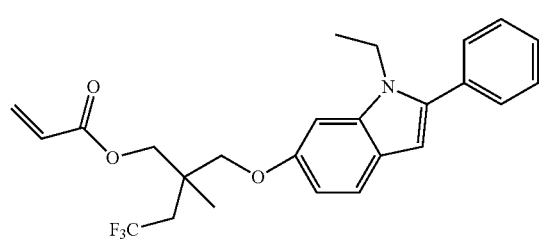
N-050
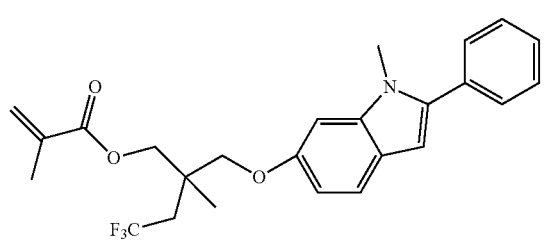
N-051
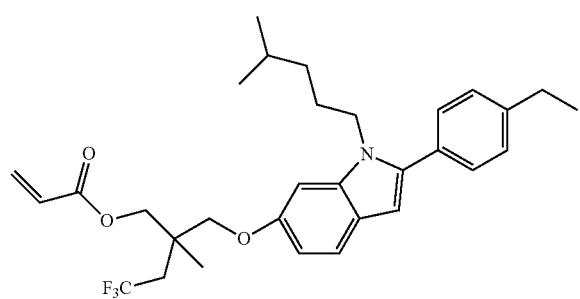
N-052
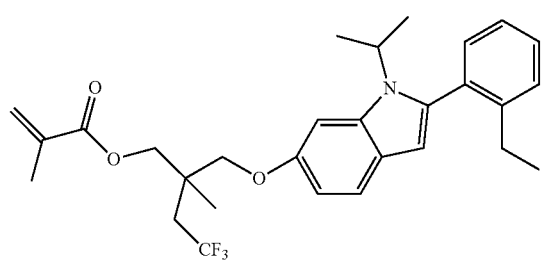
N-053
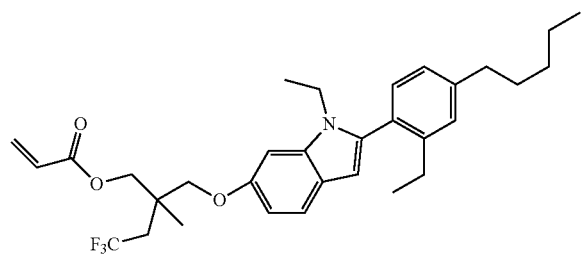
N-054
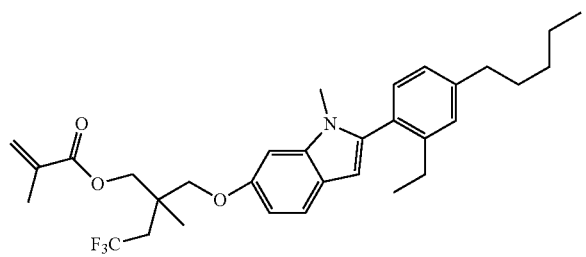

-continued
N-055
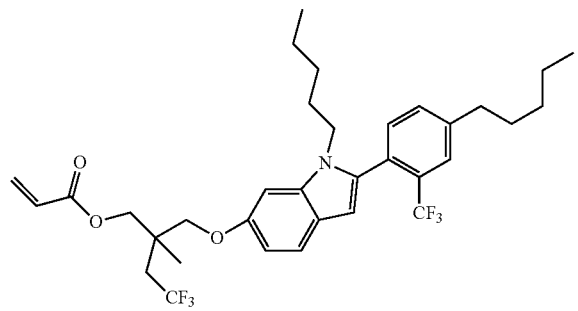
N-056
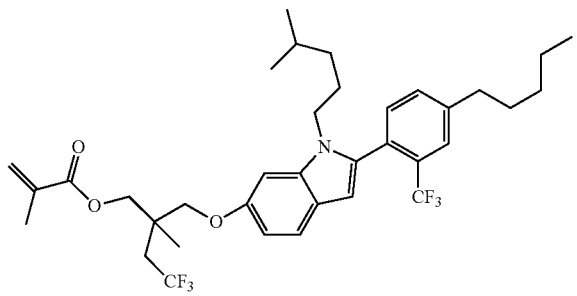
N-057
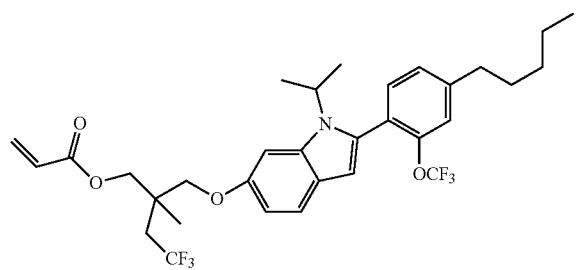
N-058
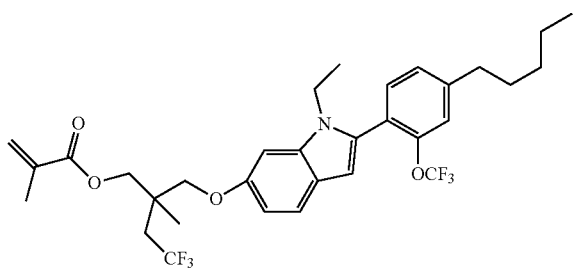
N-059
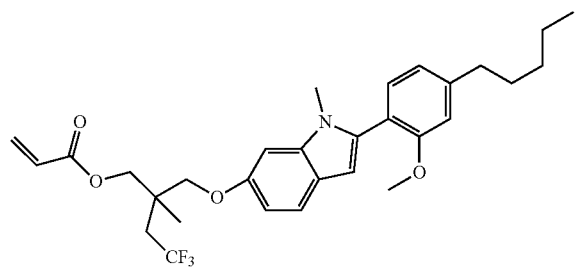
N-060
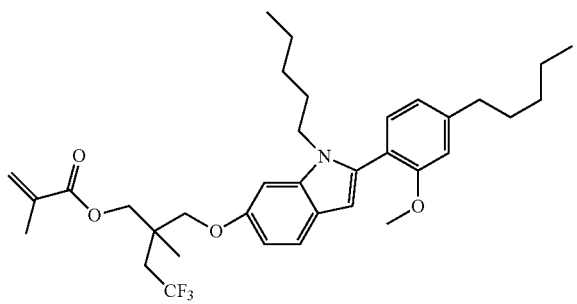
N-061
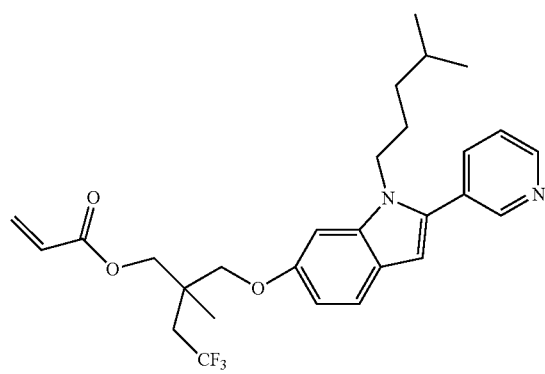
N-062
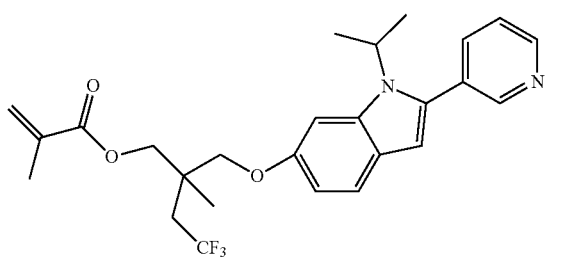
N-063
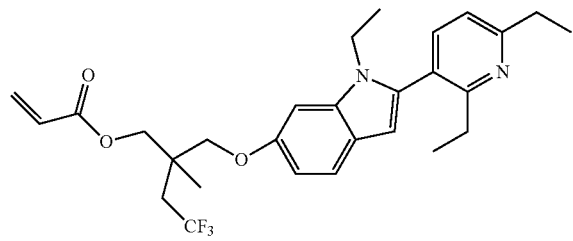
N-064
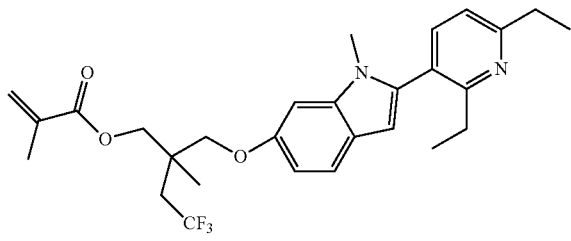

-continued
N-065
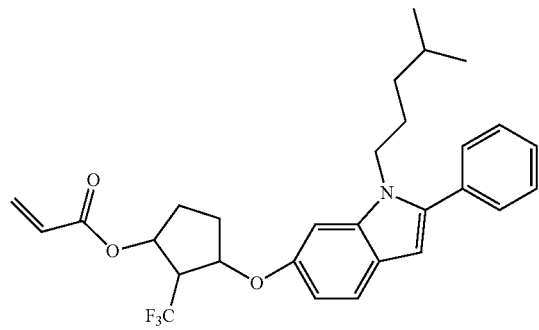
N-066
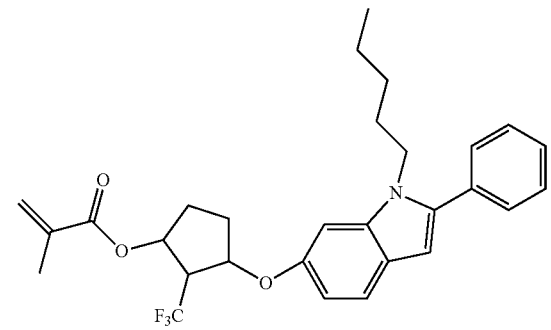
N-067
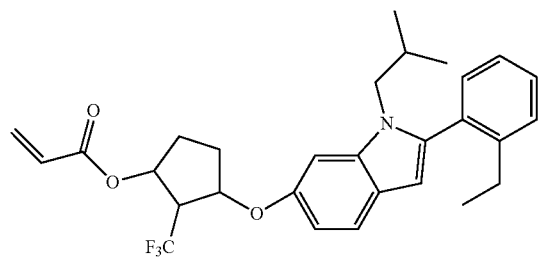
N-068
N-069
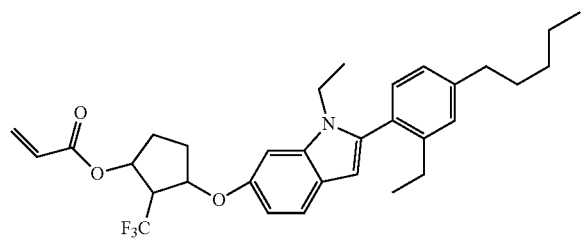
N-070
N-071
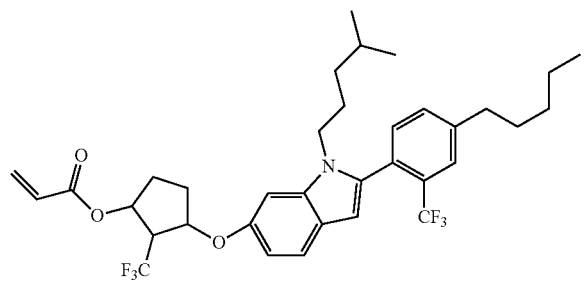
N-072
N-073
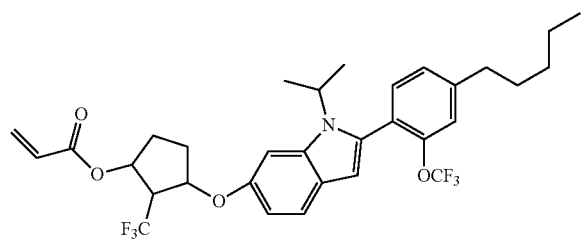
N-074
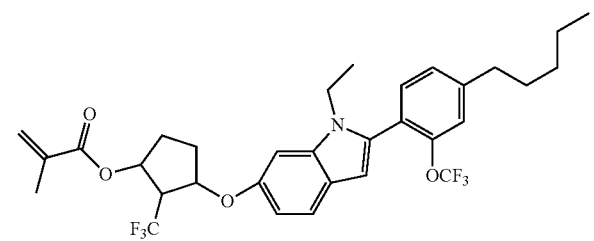

-continued
N-075
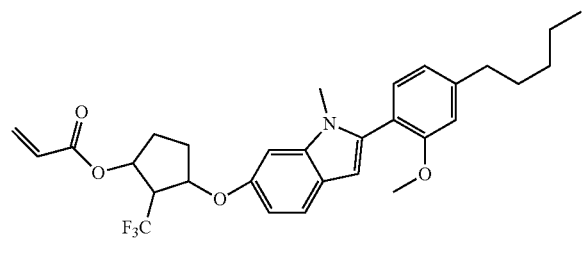
N-076
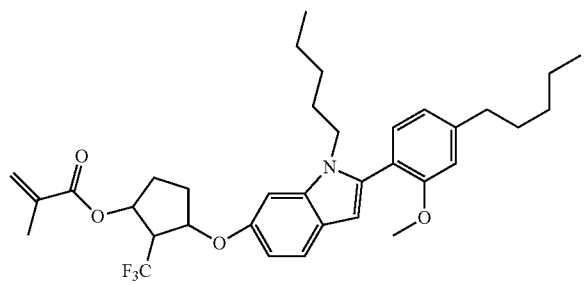
N-077
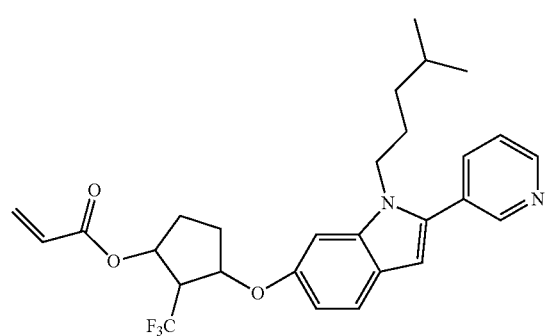
N-078
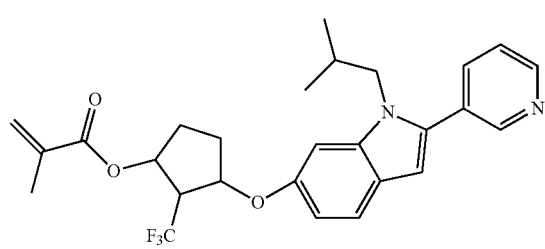
N-079
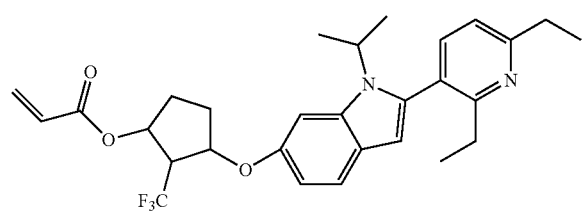
N-080
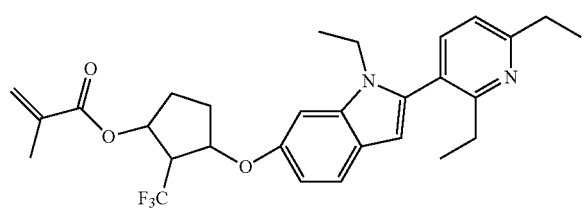
N-081
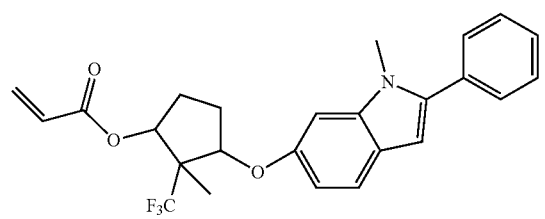
N-082
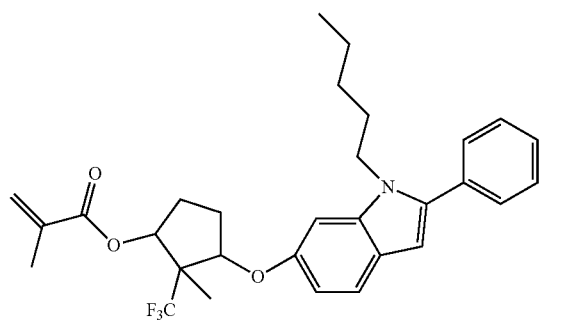
N-083
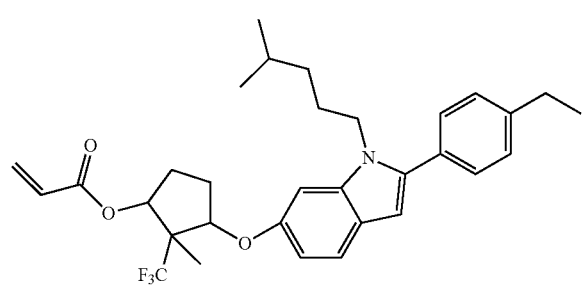
N-084
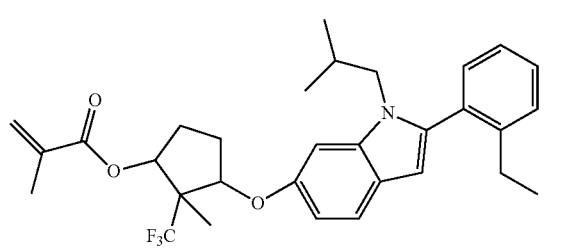

-continued
N-085
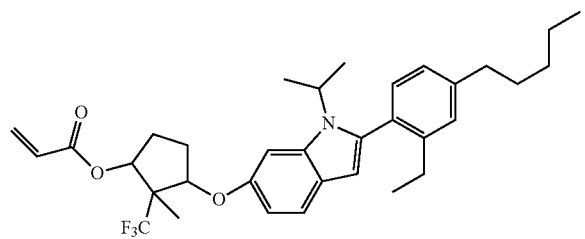
N-086
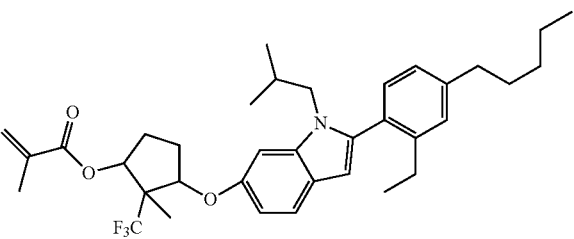
N-087
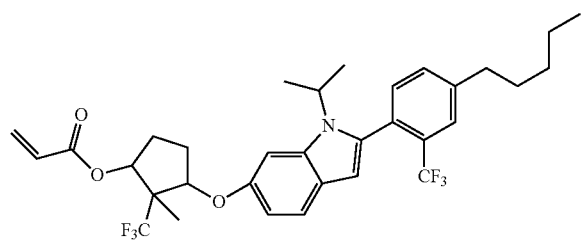
N-088
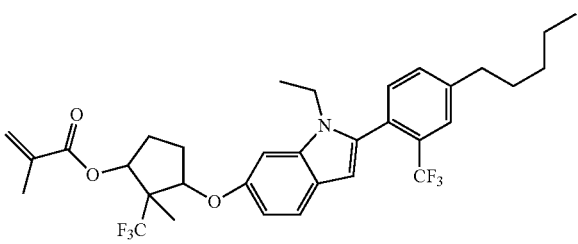
N-089
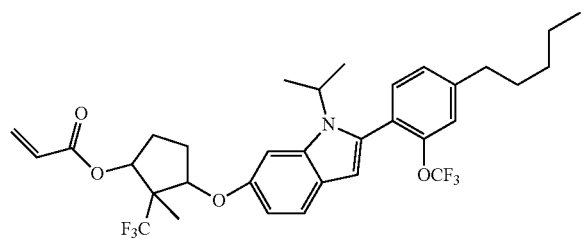
N-090
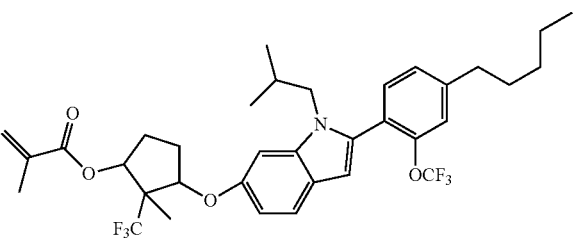
N-091
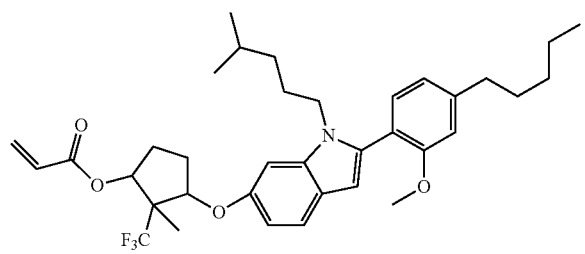
N-092
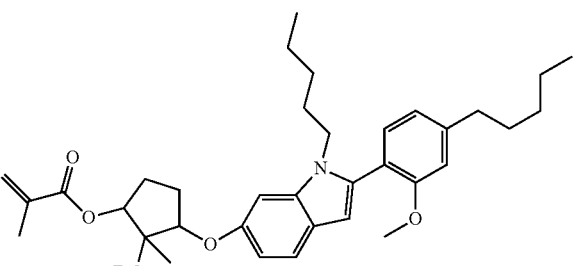
N-093
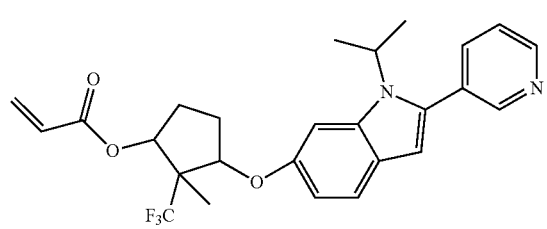
N-094

-continued
N-095
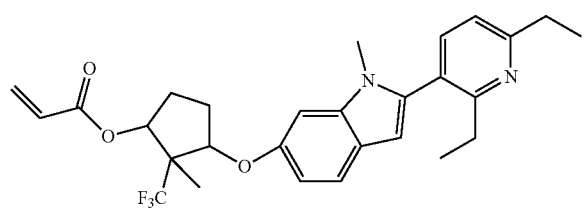
N-096
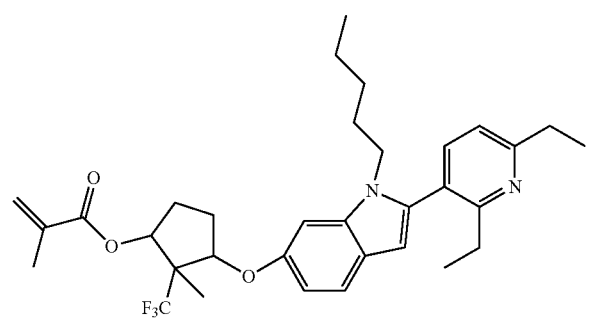
N-097
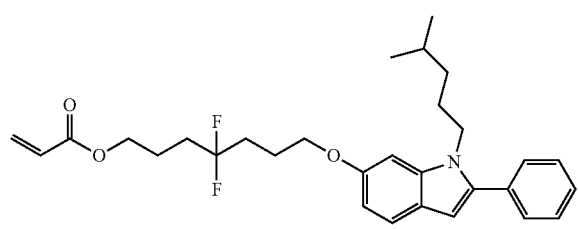
N-098
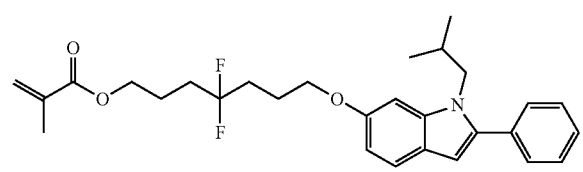
N-099
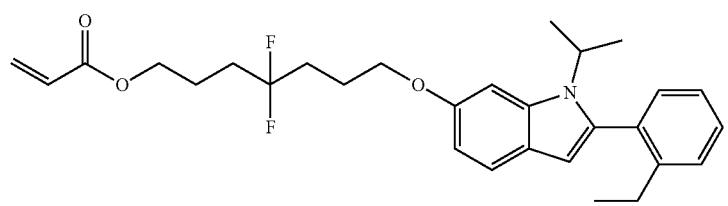
N-100
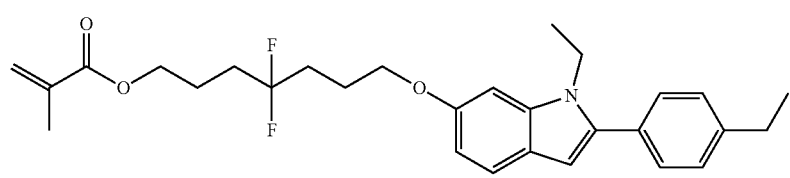
N-101
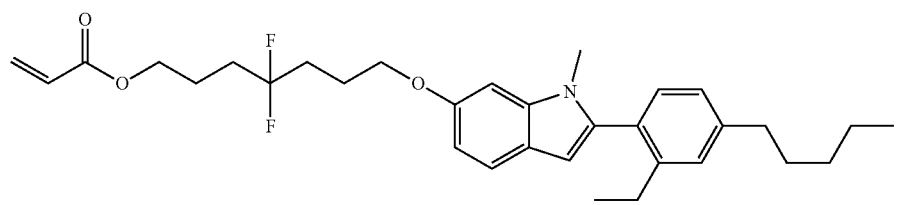
N-102
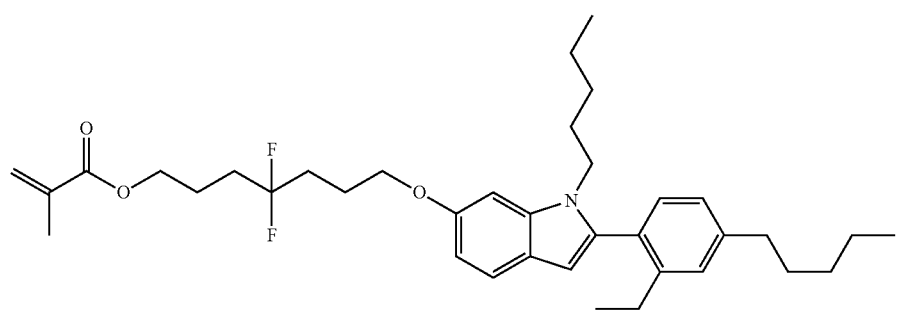

-continued
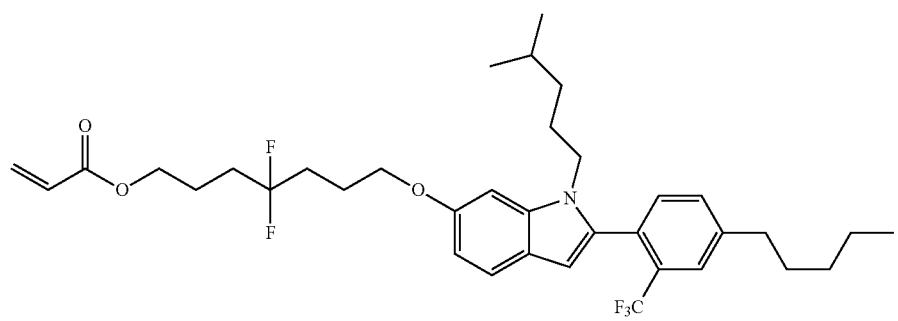
N-103
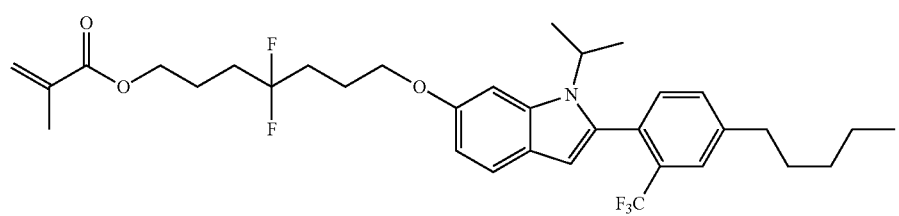
N-104
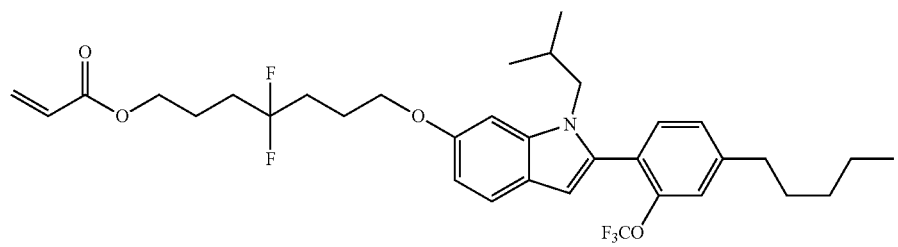
N-105
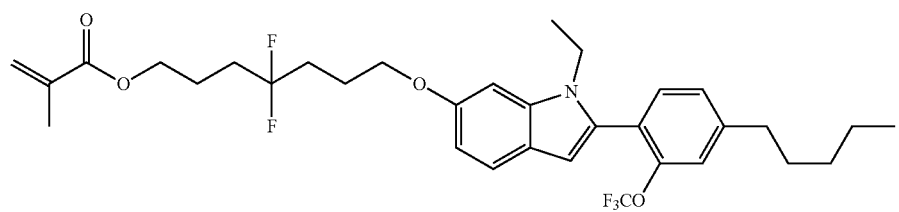
N-106
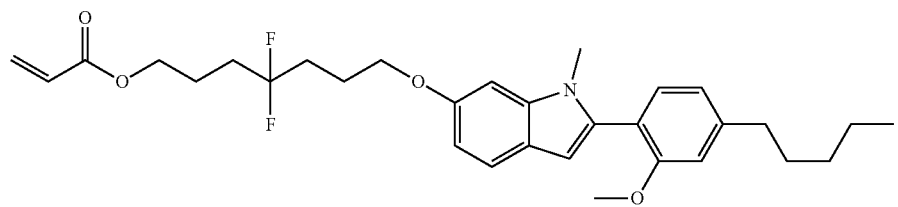
N-107
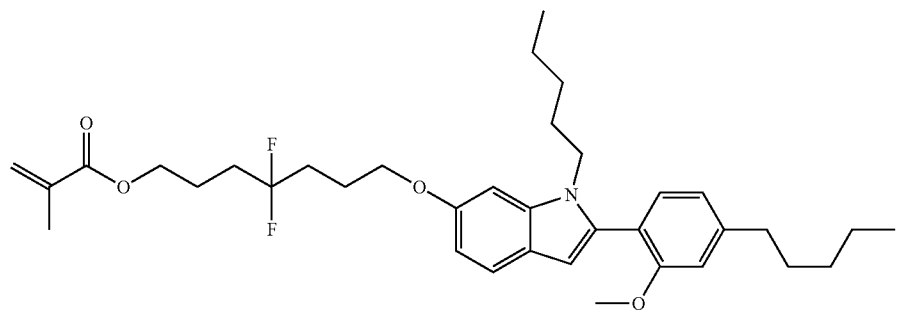
N-108

-continued
N-109
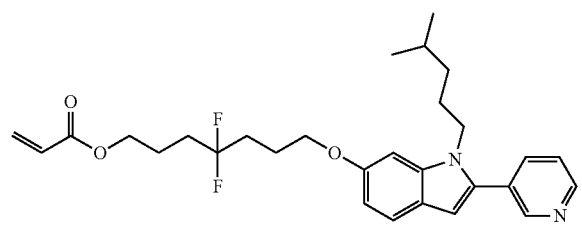
N-110
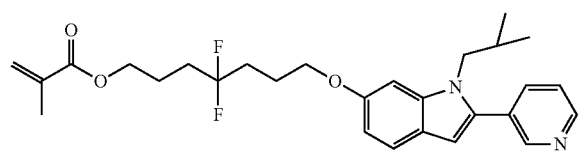
N-111
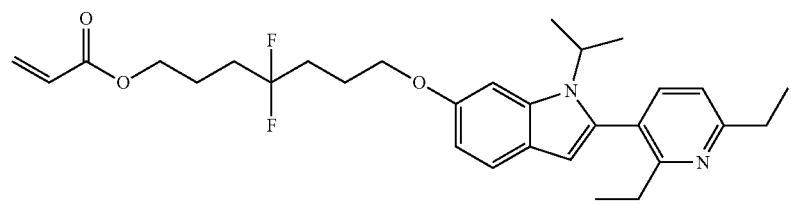
N-112
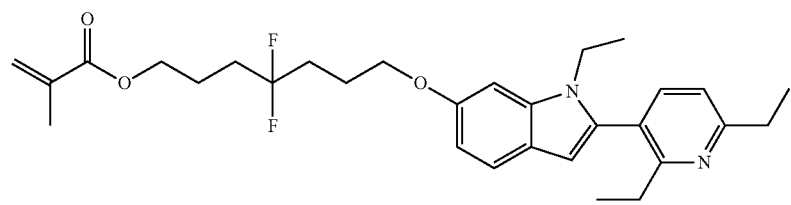
N-113
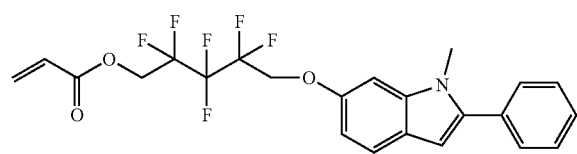
N-114
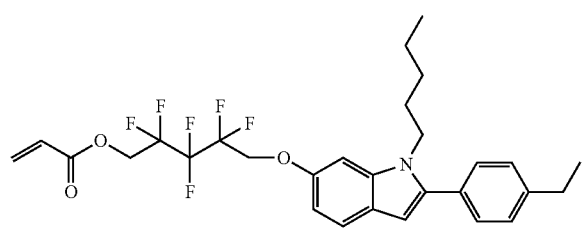
N-115
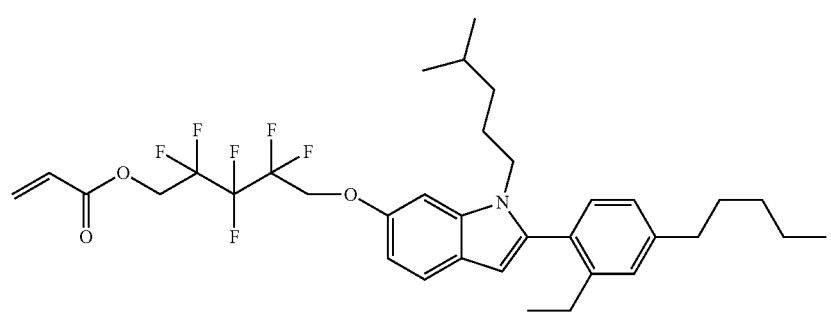
N-116
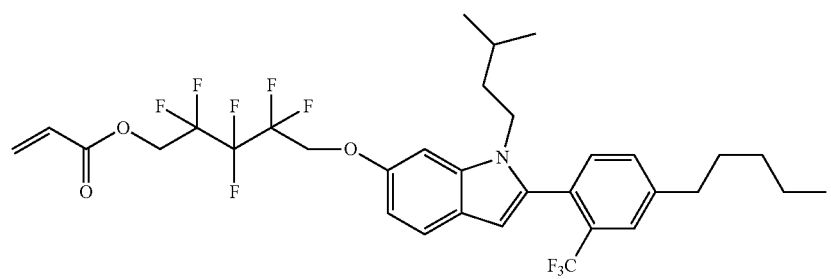

-continued
N-117
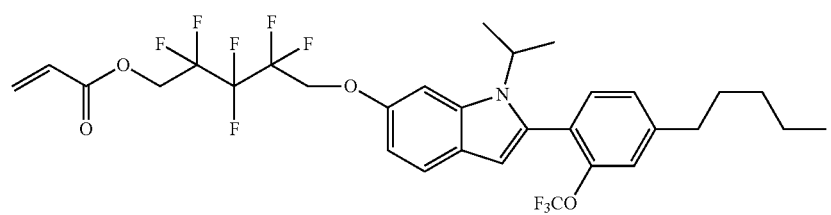
N-118
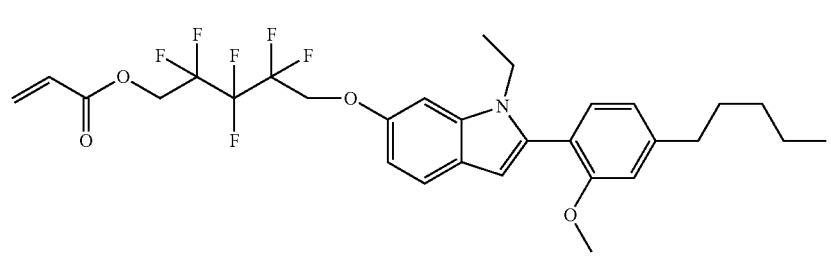
N-119
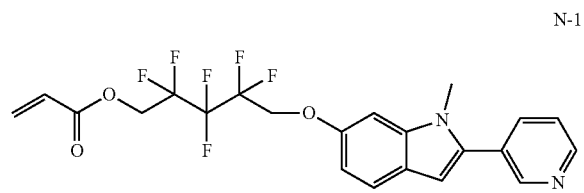
N-120
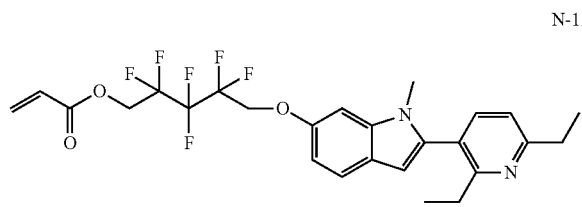
N-121
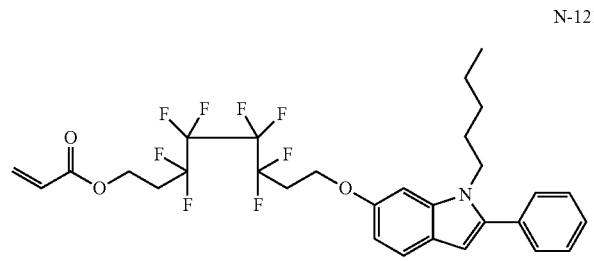
N-122
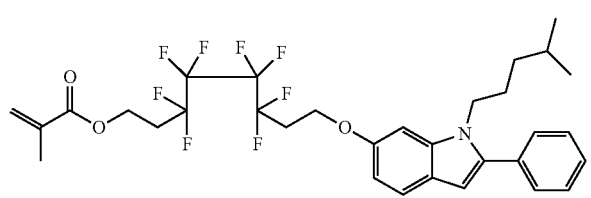
N-123
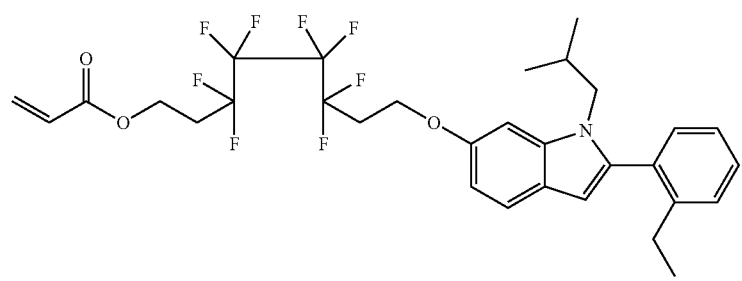
N-124
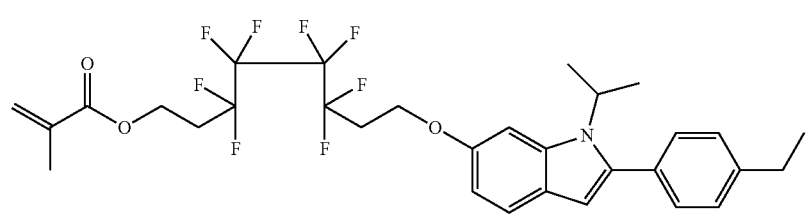

-continued
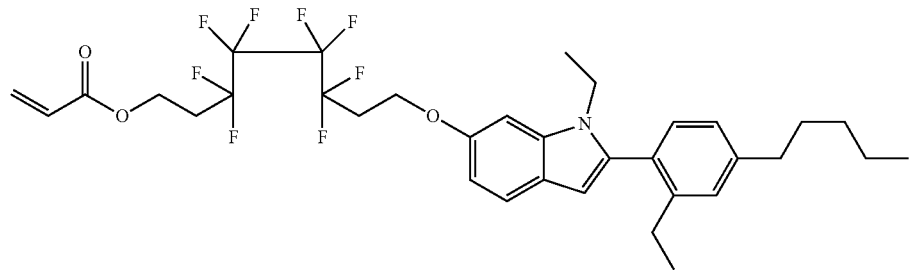
N-125
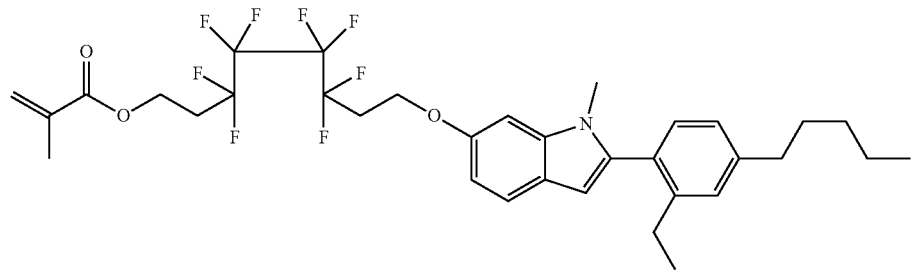
N-126
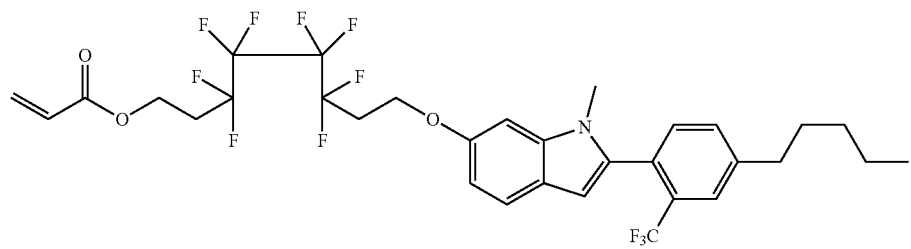
N-127
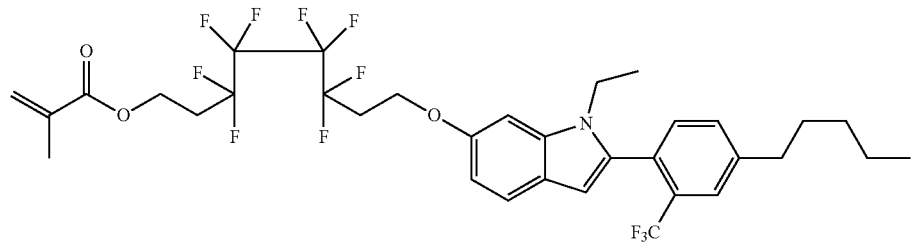
N-128
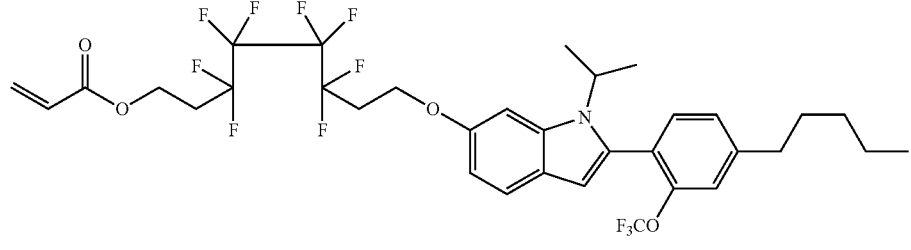
N-129
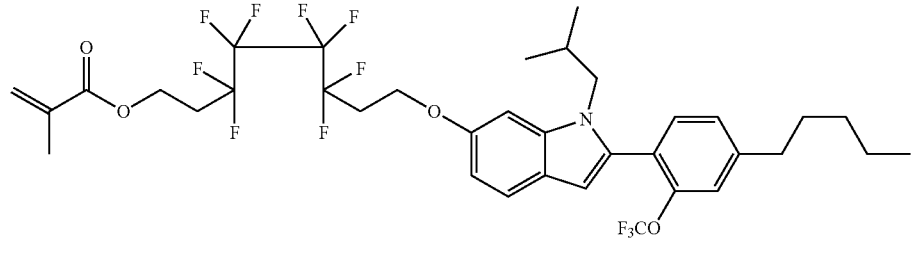
N-130

-continued
N-131
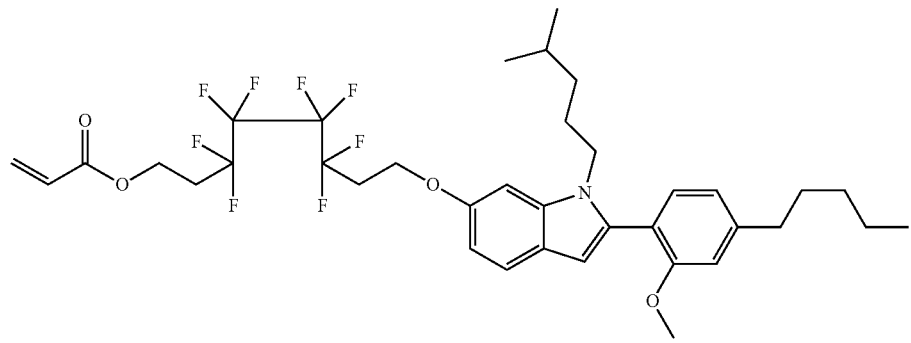
N-132
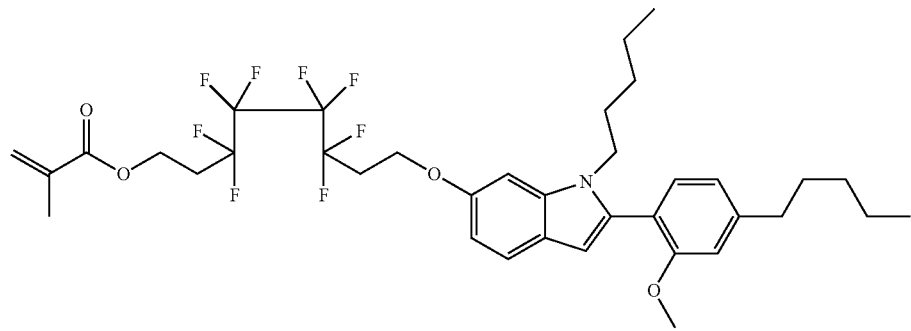
N-133 N-134
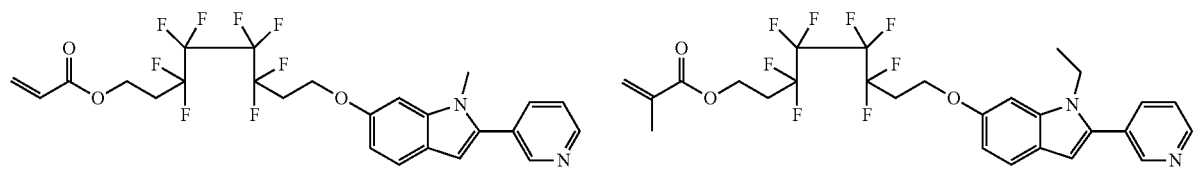
N-135
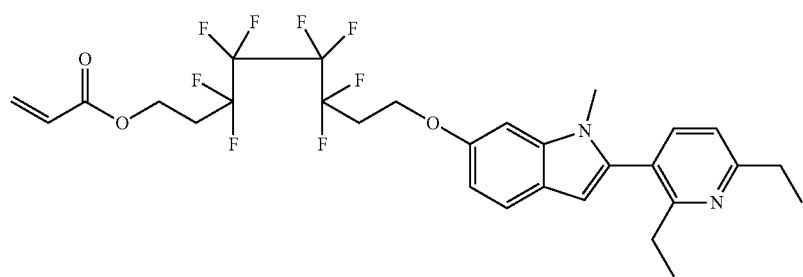
N-136
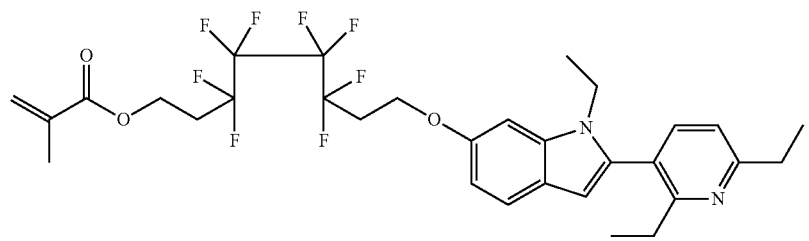
N-137 N-138
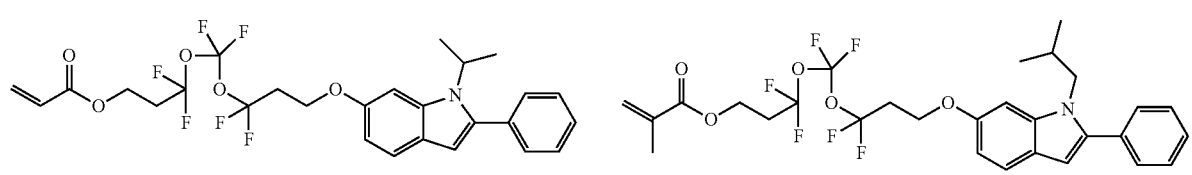

-continued
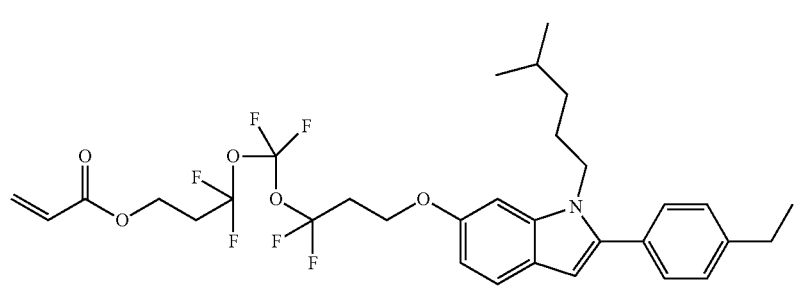
N-139
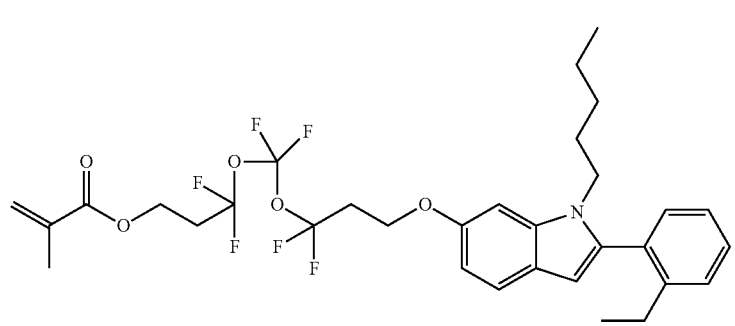
N-140
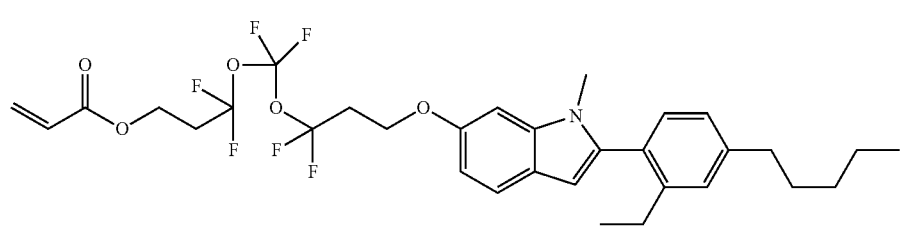
N-141
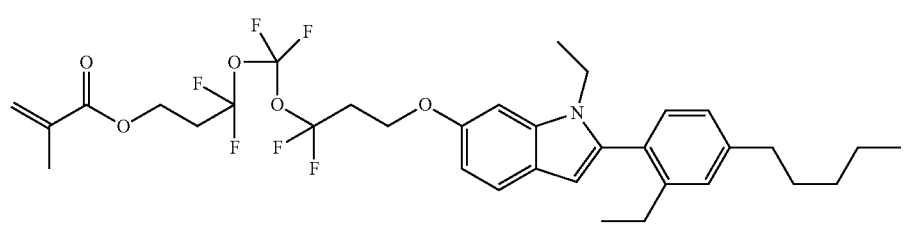
N-142
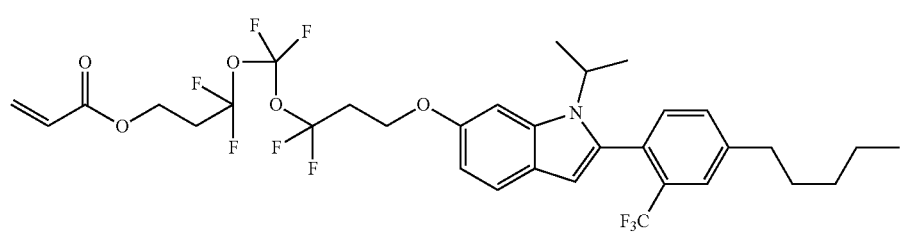
N-143
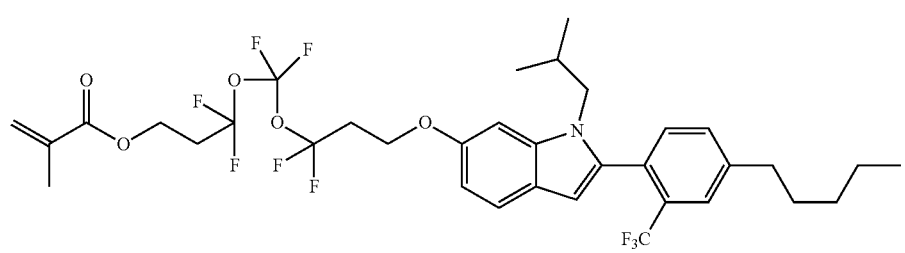
N-144

-continued
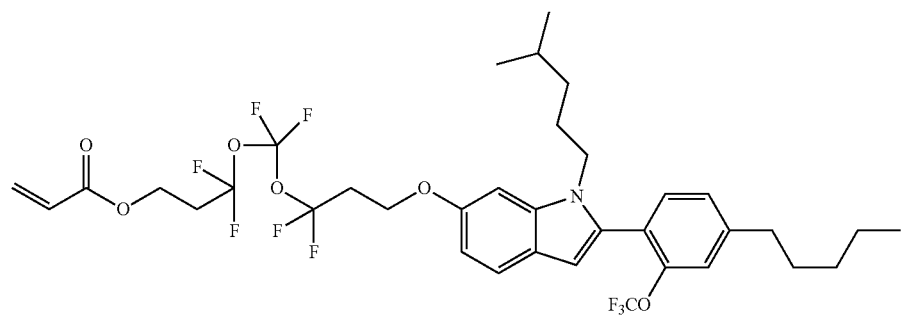
N-145
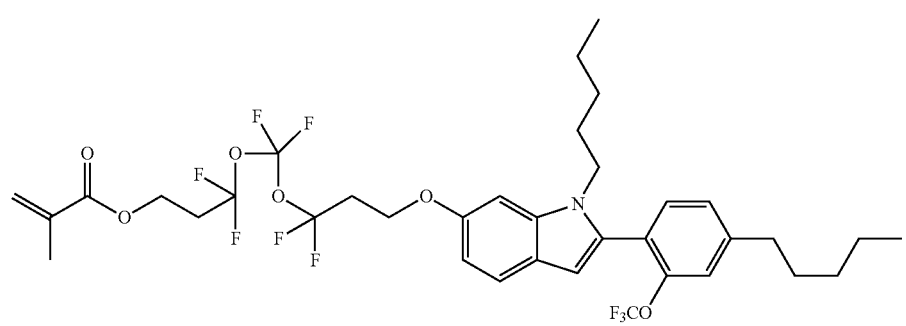
N-146
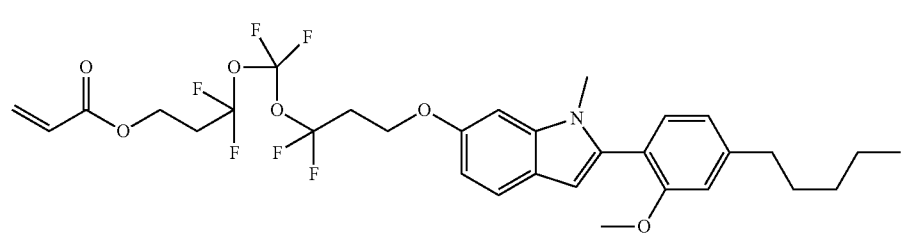
N-147
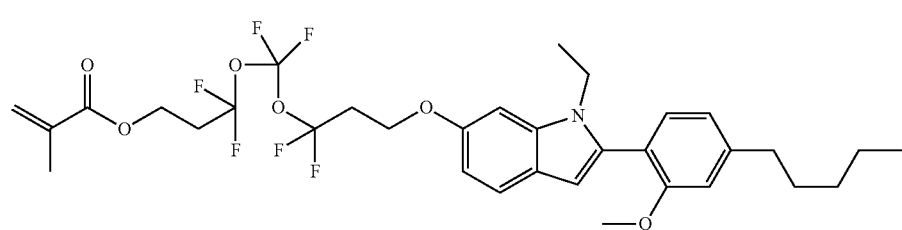
N-148
N-149
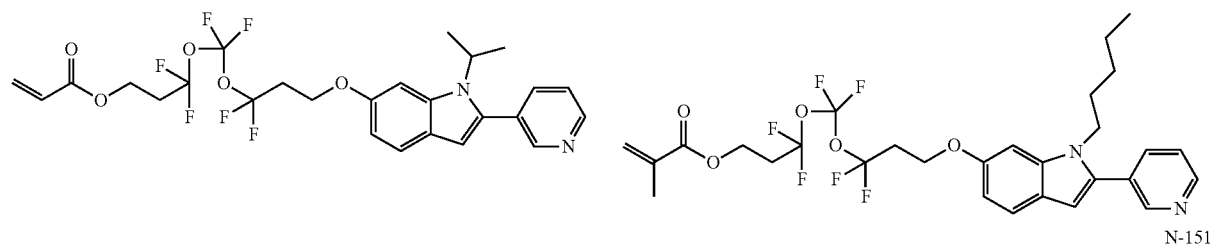
N-150
N-151
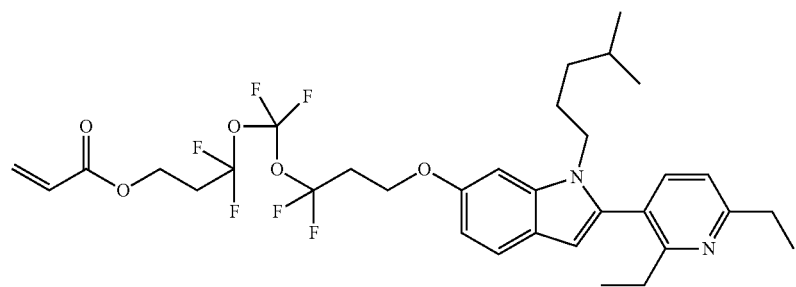

-continued
N-152
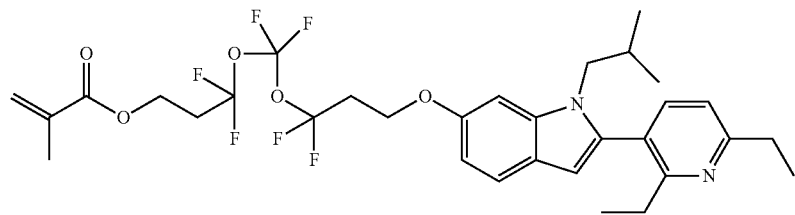
N-153
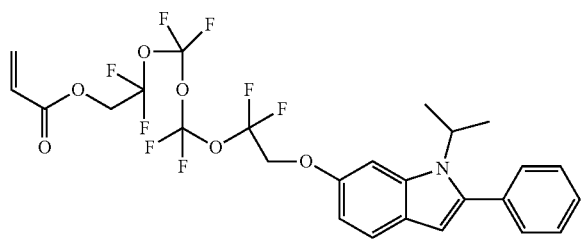
N-154
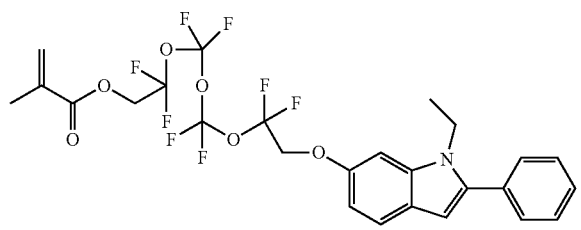
N-155
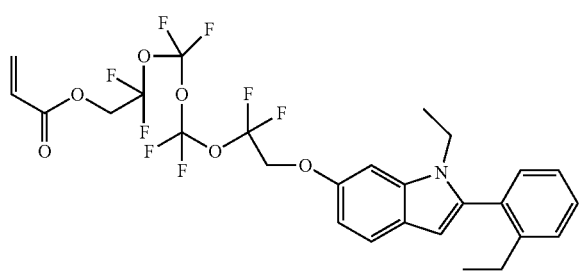
N-156
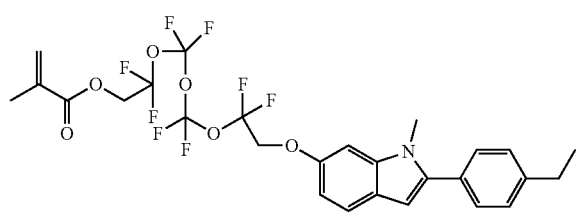
N-157
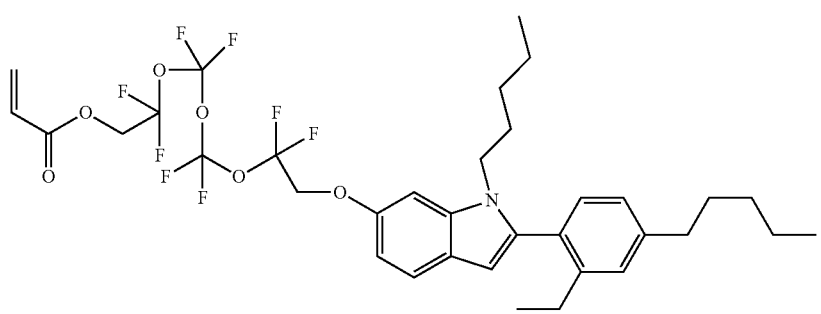
N-158
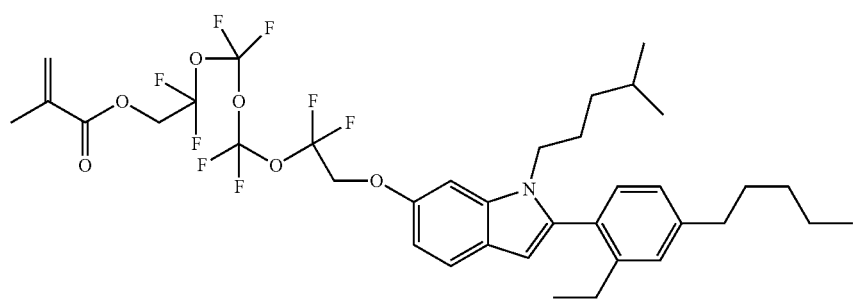

-continued
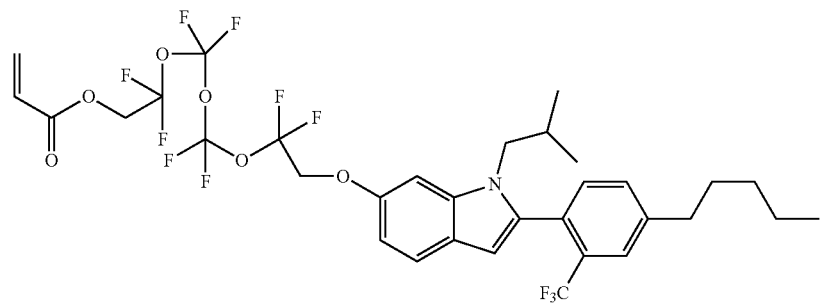
N-159
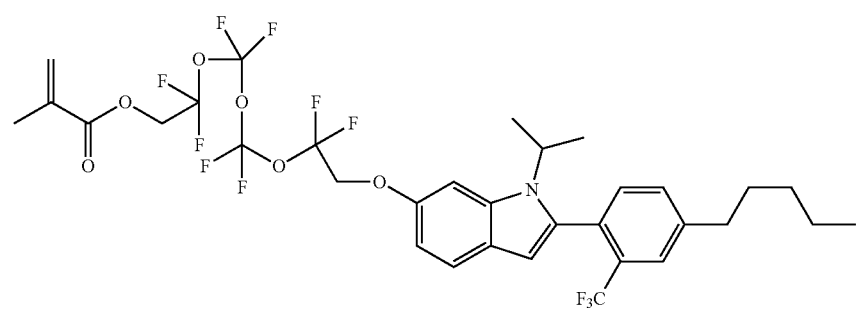
N-160
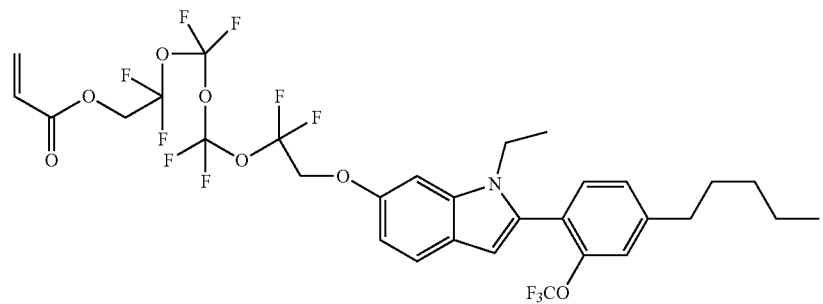
N-161
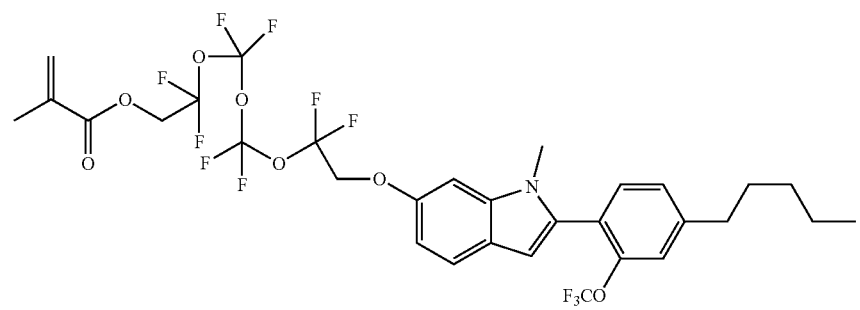
N-162
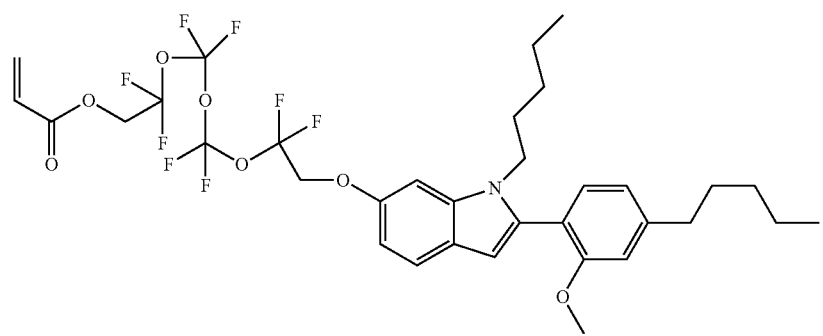
N-163

N-164
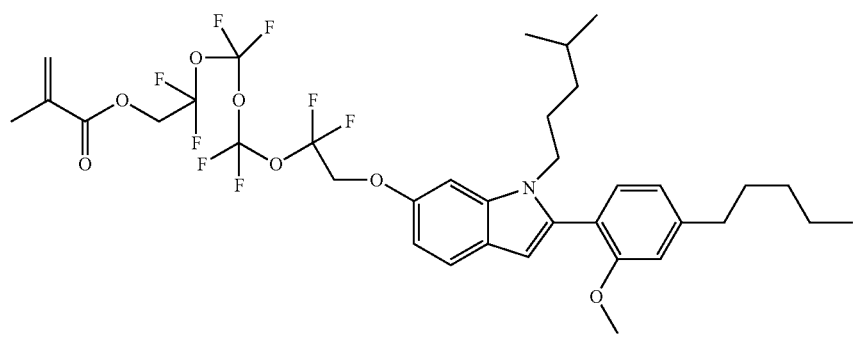
N-165
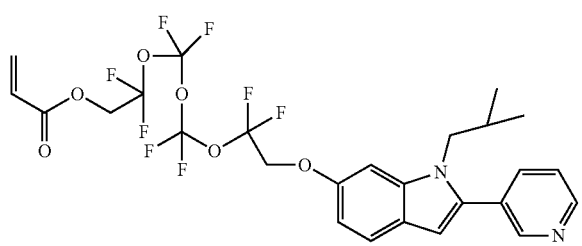
N-166
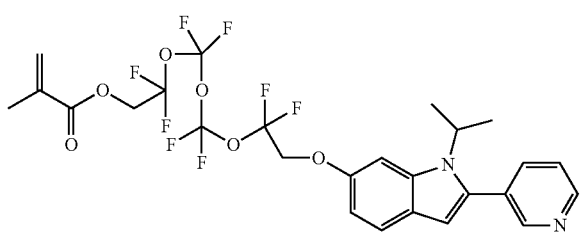
N-167
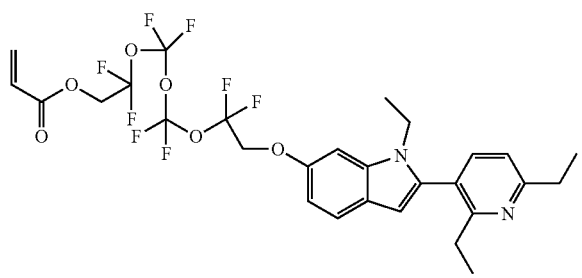
N-168
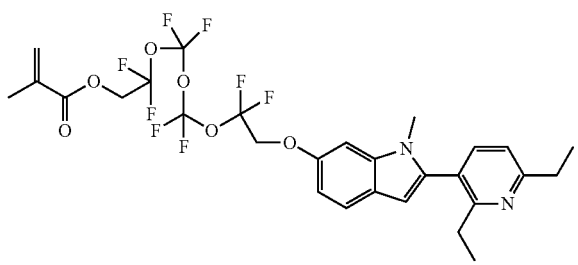
N-169
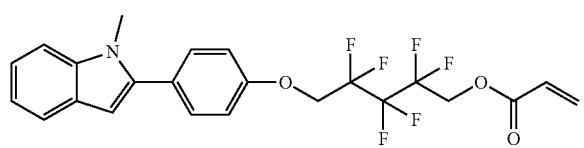
N-170
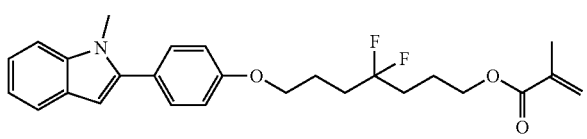
N-171
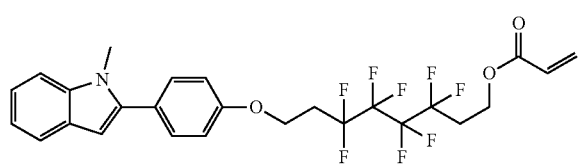
N-172
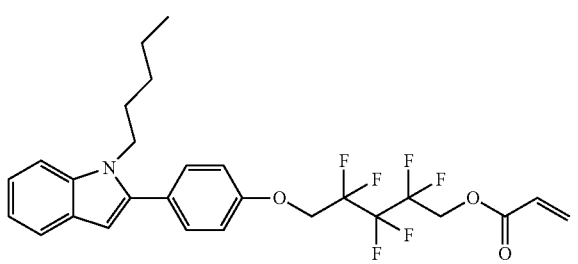
The compounds of the present application may be synthesized by methods well known to the skilled person. Preferably, all syntheses are carried out under an inert atmosphere using dried solvents.
An exemplary reaction sequence is shown in Scheme 1 for the compound O-149.
Scheme 1:
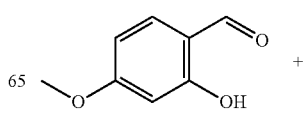

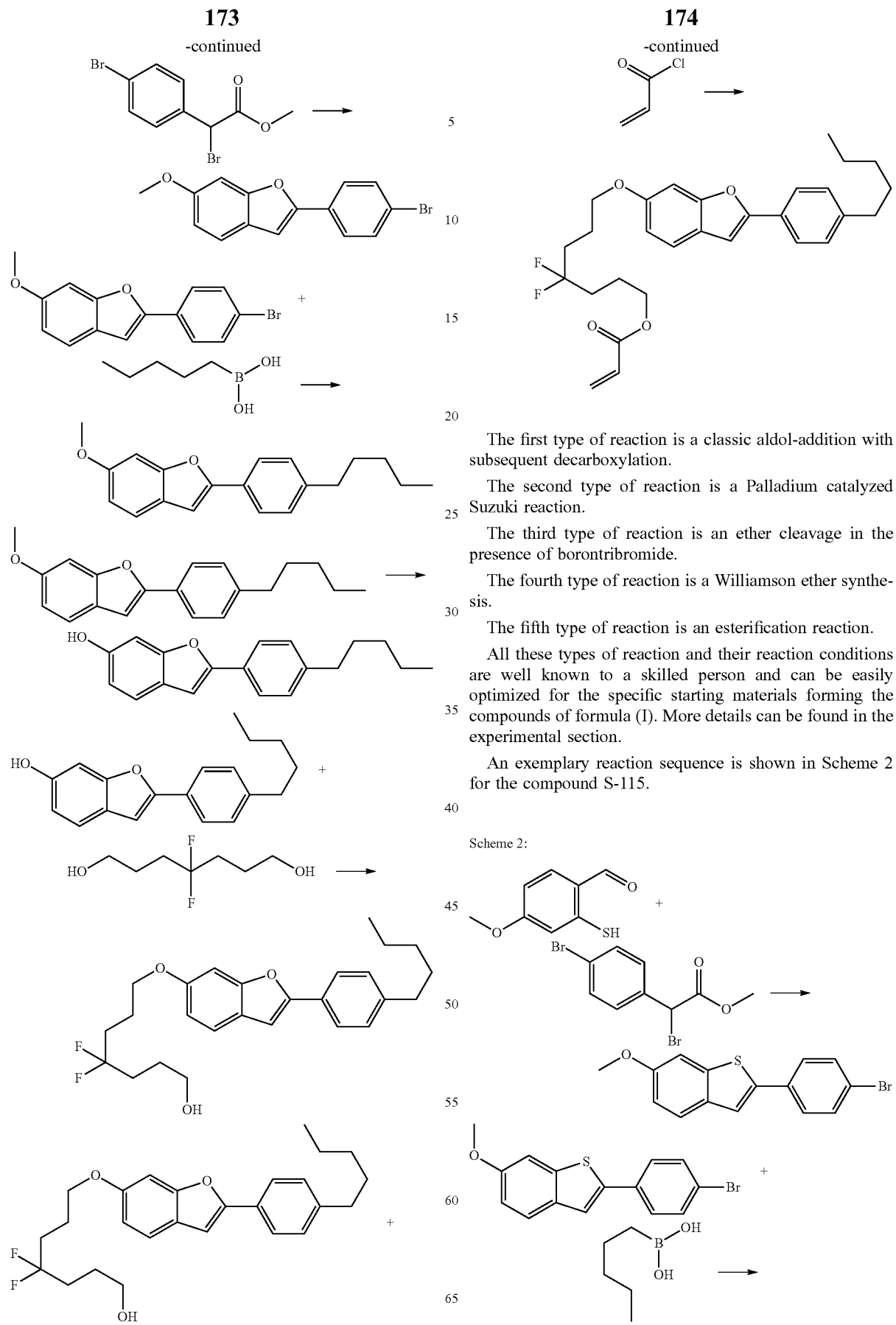

The first type of reaction is a classic aldol-addition with subsequent decarboxylation.

The second type of reaction is a Palladium catalyzed Suzuki reaction.

The third type of reaction is an ether cleavage in the presence of borontribromide.

The fourth type of reaction is a Williamson ether synthesis.

The fifth type of reaction is an esterification reaction.

All these types of reaction and their reaction conditions are well known to a skilled person and can be easily optimized for the specific starting materials forming the compounds of formula (I). More details can be found in the experimental section.

An exemplary reaction sequence is shown in Scheme 2 for the compound S-115.

Scheme 2:

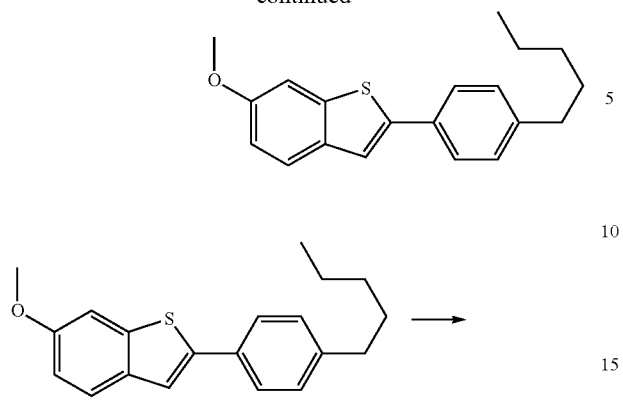

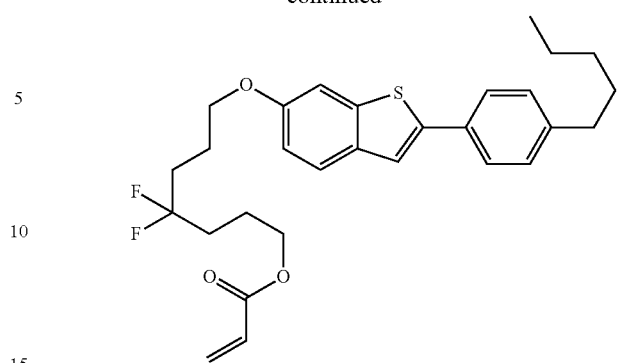

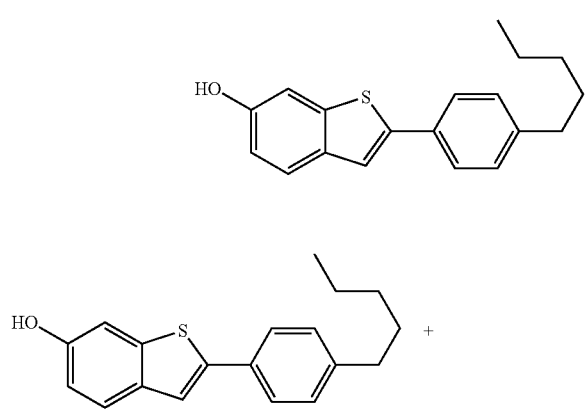

The first type of reaction is a classical ring closure via nucleophilic substitution, aldol-addition followed by decarboxylation. In the second step, a pentyl substituent is introduced via palladium-catalyzed Suzuki reaction. The third type of reaction is an ether cleavage in the presence of borontribromide. The fourth type of reaction is a Williamson ether synthesis followed by an esterification reaction.

All these types of reaction and their reaction conditions are well known to a skilled person and can be easily optimized for the specific starting materials forming the compounds of formula (I). More details can be found in the experimental section.

An exemplary reaction sequence is shown in Scheme 3 for the compound N-098 in case "Alkyl" in Scheme 3 is isobutyl and "R" in Scheme 3 is Methyl.

Scheme 3:

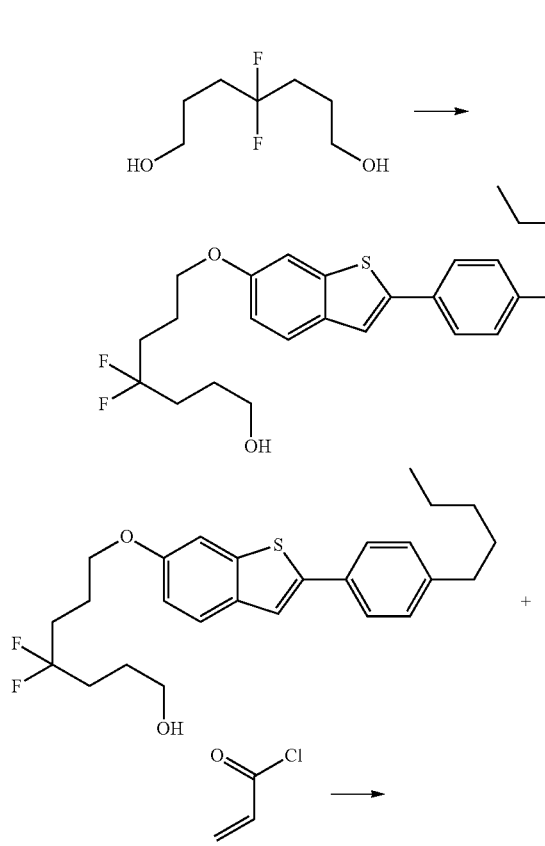

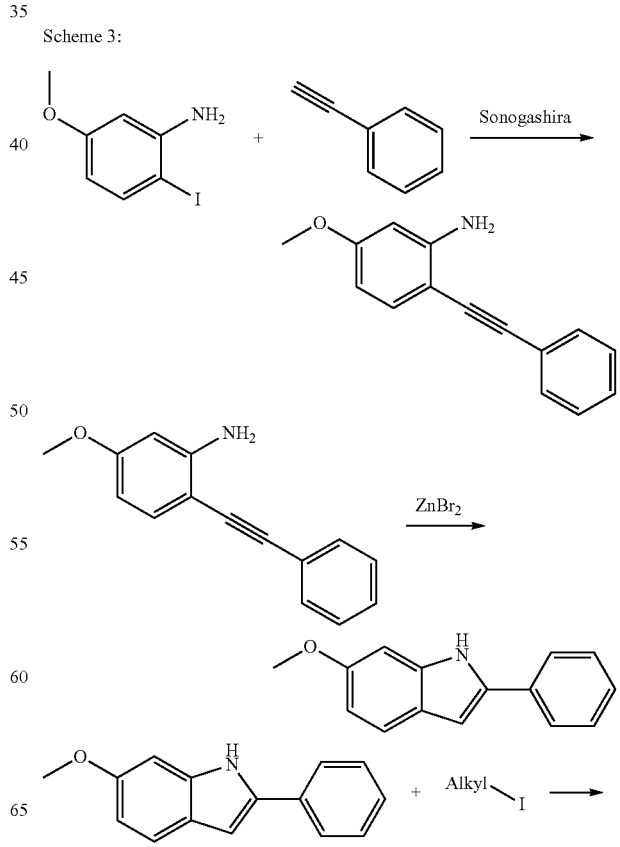

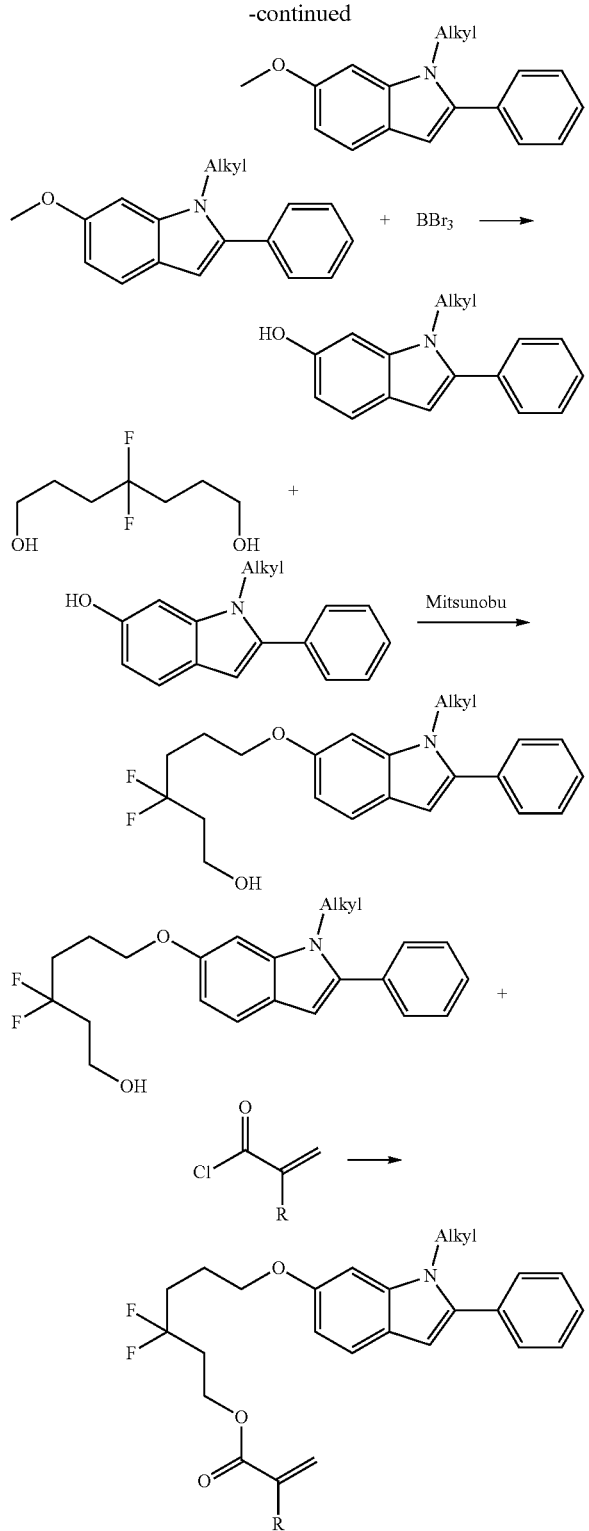

The first type of reaction is a Sonogashira reaction followed by a ring closure in the presence of Zinc bromide. In the third step, an alkyl group on the N atom is introduced via alkyl iodide. The third type of reaction is an ether cleavage in the presence of borontribromide. The fourth type of reaction is a Williamson ether synthesis followed by an esterification reaction.

All these types of reaction and their reaction conditions are well known to a skilled person and can be easily optimized for the specific starting materials forming the compounds of formula (I). More details can be found in the experimental section.

As described before, the compounds of formula (I), (I'), (I") and/or (I''') as described before or preferably described before contain a polymerizable group and are predestinated as monomers for an oligomerization or a polymerization.

The invention is therefore further directed to an oligomer or polymer comprising polymerized compounds of formula (I), (I'), (I") and/or (I''') as described before or preferably described before.

The term "polymer" generally means a molecule of high relative molecular mass, the structure of which essentially comprises the multiple repetition of units derived, actually or conceptually, from molecules of low relative molecular mass (PAC, 1996, 68, 2291). The term "polymer" includes homopolymers and co-polymers. The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense a polymer means a compound having ≥30 repeating units, and an oligomer means a compound with >1 and <30 repeating units.

Above and below, in formulae showing a polymer, an oligomer, a compound of formula (I) or a monomeric unit formed from a compound of formula (I), an asterisk ("*") denotes a linkage to the adjacent repeating unit in the polymer chain or oligomer chain or to a terminal end group.

Suitable terminal end groups are known to the skilled artisan and depend on the polymerization method used.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

Unless stated otherwise, the molecular weight is given as the number average molecular weight $M_n$ or weight average molecular weight Mw, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, tetrahydrofuran is used as solvent. The degree of polymerization (n) means the number average degree of polymerization given as $n=M_n/Mu$, wherein Mu is the molecular weight of the single repeating unit as described in J. M. G. Cowie, Polymers: Chemistry & Physics of Modern Materials, Blackie, Glasgow, 1991.

In the polymers according to the present invention, the total number of repeating units n is seen preferably ≥30, very preferably ≥100, most preferably ≥200, and preferably up to 5000, very preferably up to 3000, most preferably up to 2000, including any combination of the aforementioned lower and upper limits of n.

The polymers of the present invention include homopolymers, statistical co-polymers, random co-polymers, alternating co-polymers and block co-polymers, and combinations of the aforementioned.

Throughout the description and claims of this specification, the words "comprise" and "contain" and variations of the words, for example "comprising" and "comprises", mean "including but not limited to", and are not intended to (and do not) exclude other components Preferably the polymerizable group $R_1$ forms the regioregular, alternated, regiorandom, statistical, block or random homopolymer or co-polymer backbone or is part of the polymer backbone where $R_1$ has a meaning as described or preferably described before. Particularly preferably, such oligomer or polymer comprises a constitutional unit $M^o$ of formulae (5-p-1), (5-p-2), (5-p-3)

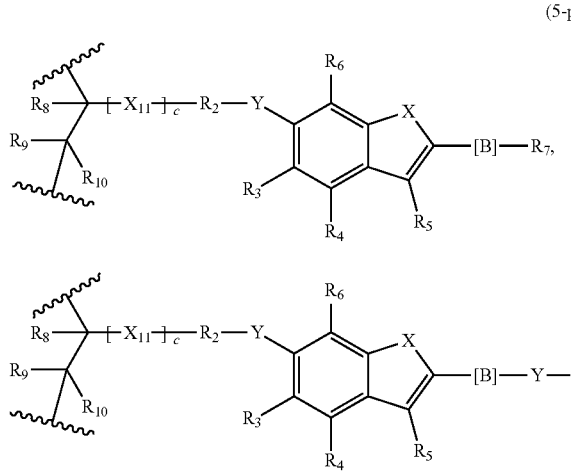

(5-p-1)

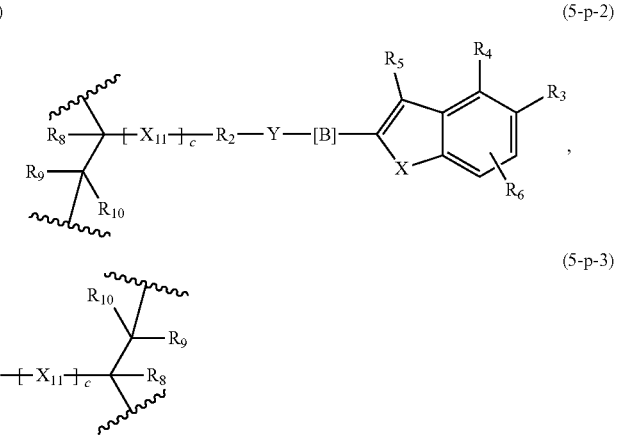

(5-p-2)

(5-p-3)

wherein
—R$_2$—, Y, R$_3$, R$_4$, R$_5$, R$_6$, X, —[B]—, R$_7$, X$_{11}$, R$_8$, R$_9$, R$_{10}$ and c have a meaning or a preferred meaning as described or preferably described before. Combinations are excluded where two O atoms or an O atom and a S atom are directly linked to each other as known for a skilled artisan in the field of organic chemistry.

The co-polymer may be an oligomer or polymer comprising one or more polymerized compounds of formula (I), (I'), (I'') or (I''') or a constitutional unit M$^0$ of formulae (5-p-1), (5-p-2), (5-p-3), which may be the same or different from one another, and one or more constitutional units M$^2$, which may be the same or different from one another.

Said one or more constitutional units M$^2$ are chemically different from the units M$^0$. Preferably, said one or more constitutional units M$^2$ are derived by polymerization of one or more monomers selected from the group consisting of styrene, ethoxyethyl methacrylate (EOEMA), methyl methacrylate (MMA), n-alkyl methacrylates (the n-alkyl groups comprising 2-20 C-atoms), n-alkyl methacrylates (the n-alkyl groups comprising 2-20 C-atoms), ethoxyethoxy ethylacrylate (EEEA), 2-hydroxyethyl methacrylate (HEMA), tetrahydrofuryl methacrylate (THFMA), glycidylmethacrylate (GMA), 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate (EGPEA), Bisphenol A diacrylate-1 EO/Phenol (BPADA), 2-[3'-2'H-benzotriazol-2'-yl)-4'-hydroxyphenyl]ethyl methacrylate (BTPEM), trialkoxyalkenylsilane, dialkoxyalkylalkenylsilane or a silane of formula (9) and (10), where the alkyl and/or alkoxy groups are at each occurrence independently of each other linear or branched having 1 to 6 C atoms and where the alkenyl group is at each occurrence independently linear having 2 to 4 C atoms.

Particularly preferably, said one or more constitutional units M$^2$ are derived by polymerization of one or more monomers selected from the group consisting of styrene, ethoxyethyl methacrylate (EOEMA), methyl methacrylate (MMA), n-alkyl methacrylates (the n-alkyl groups comprising 2-20 C-atoms), n-alkyl methacrylates (the n-alkyl groups comprising 2-20 C-atoms), ethoxyethyl methacrylate (EOEMA), methyl methacrylate (MMA), ethoxyethoxy ethylacrylate (EEEA), 2-hydroxyethyl methacrylate (HEMA), tetrahydrofuryl methacrylate (THFMA), glycidylmethacrylate (GMA), 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate (EGPEA), Bisphenol A diacrylate-1 EO/Phenol (BPADA) and 2-[3'-2'H-benzotriazol-2'-yl)-4'-hydroxyphenyl]ethyl methacrylate (BTPEM) in combination with inventive monomers containing an alkenyl group of formula (5) as described or preferably described before.

Particularly preferably, said one or more constitutional units M$^2$ are derived by polymerization of one or more monomers selected from the group consisting of trialkoxyalkenylsilane, dialkoxyalkylalkenylsilane or a silane of formula (9) and (10), $$\begin{array}{c} \phantom{a} \text{H} \phantom{aa} \text{alkyl} \\ \phantom{a} | \phantom{aaa} | \\ \text{alkyl}-\text{Si}-\text{N} \\ \phantom{aaaa} | \phantom{aa} | \\ \phantom{aaaa} \text{N}-\text{Si}-\text{alkyl}, \\ \phantom{aaaaa} | \phantom{aa} | \\ \phantom{aaaaa} \text{alkyl} \phantom{a} \text{H} \end{array} \quad (9)$$

$$\begin{array}{c} \phantom{a} \text{alkyl} \phantom{a} \text{alkyl} \\ \phantom{a} | \phantom{aaaa} | \\ \text{alkenyl}-\text{Si}-\text{N} \\ \phantom{aaaaaa} | \phantom{aa} | \\ \phantom{aaaaaa} \text{N}-\text{Si}-\text{alkenyl}, \\ \phantom{aaaaaaa} | \phantom{aa} | \\ \phantom{aaaaaaa} \text{alkyl} \phantom{a} \text{alkyl} \end{array} \quad (10)$$

$$\begin{array}{c} \phantom{a} \text{H} \phantom{aa} \text{alkyl} \\ \phantom{a} | \phantom{aaa} | \\ \text{alkyl}-\text{Si}-\text{N} \\ \phantom{aaaa} | \phantom{aa} | \\ \phantom{aaaa} \text{N}-\text{Si}-\text{alkyl}, \\ \phantom{aaaaa} | \phantom{aa} | \\ \phantom{aaaaa} \text{alkyl} \phantom{a} \text{H} \end{array} \quad (9)$$

$$\begin{array}{c} \phantom{a} \text{alkyl} \phantom{a} \text{alkyl} \\ \phantom{a} | \phantom{aaaa} | \\ \text{alkenyl}-\text{Si}-\text{N} \\ \phantom{aaaaaa} | \phantom{aa} | \\ \phantom{aaaaaa} \text{N}-\text{Si}-\text{alkenyl}, \\ \phantom{aaaaaaa} | \phantom{aa} | \\ \phantom{aaaaaaa} \text{alkyl} \phantom{a} \text{alkyl} \end{array} \quad (10)$$

where the alkyl and/or alkoxy groups are at each occurrence independently of each other linear or branched having 1 to 6 C atoms and where the alkenyl group is at each occurrence independently linear having 2 to 4 C atoms in combination with inventive monomers containing a polymerizable group containing at least one Si atom.

Alternatively the oligomer or polymer according to the invention is a homopolymer, i.e. an oligomer or polymer comprising one or more constitutional unit $M^o$ of formulae (5-p-1), (5-p-2), (5-p-3), wherein all constitutional units $M^o$ are the same.

Exemplary polymeric compounds may be selected from the following formulae (P-001) to (P-628):

P-001
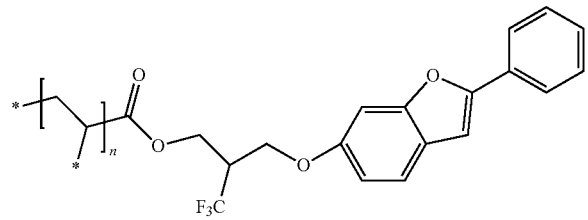

P-002
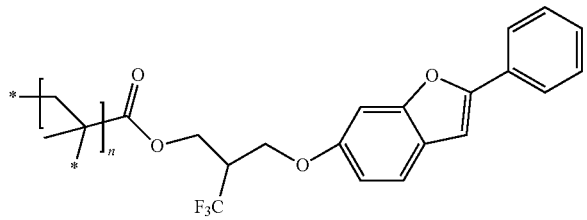

P-003
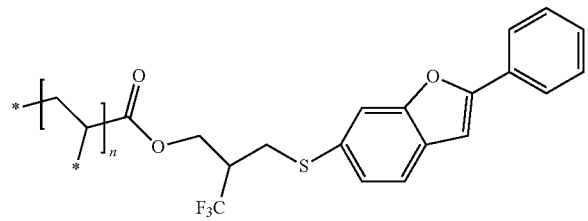

P-004
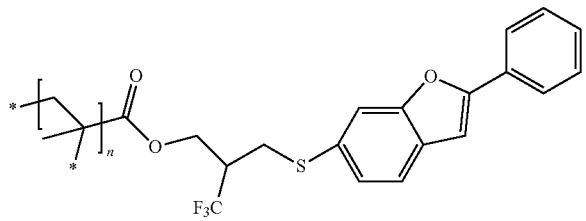

P-005
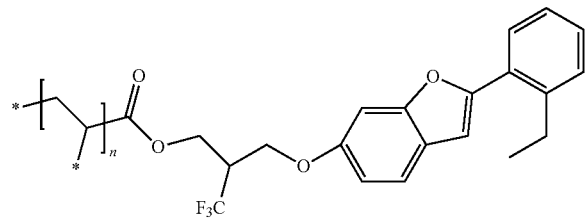

P-006
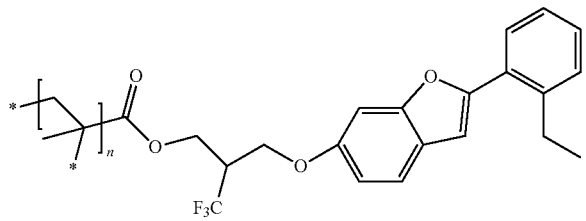

P-007
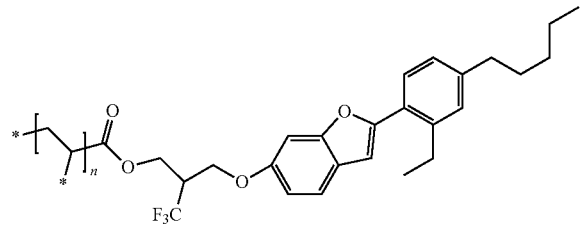

P-008
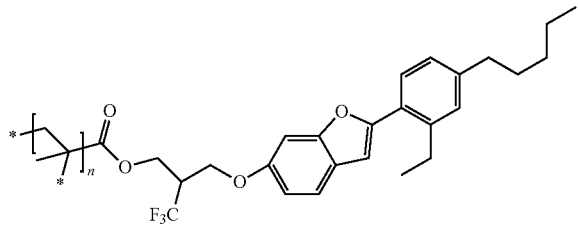

P-009
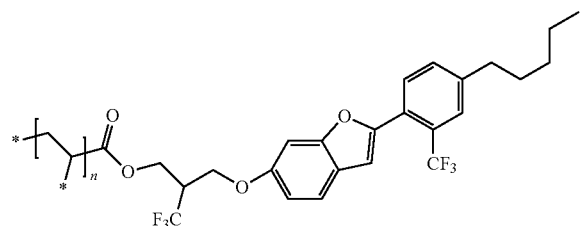

P-010
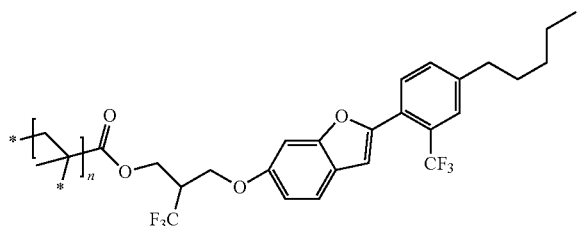

-continued
P-011
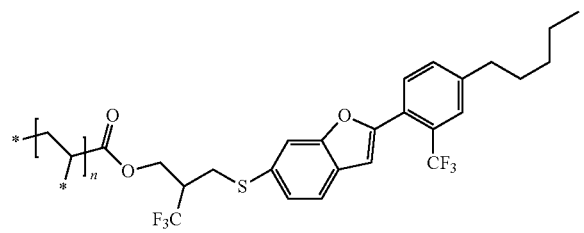
P-012
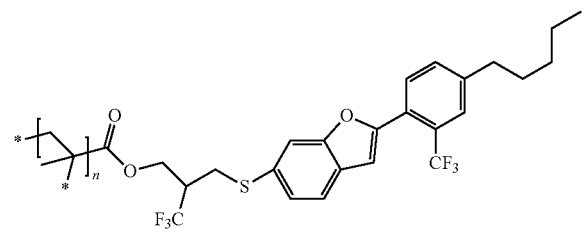
P-013
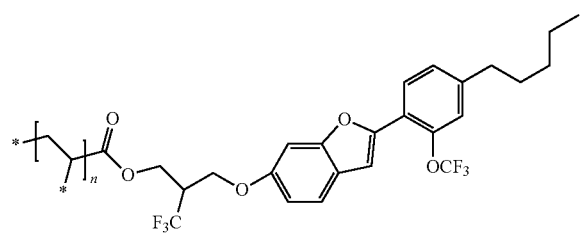
P-014
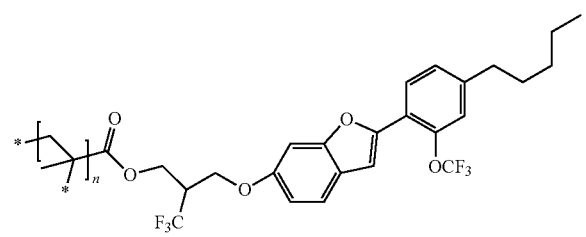
P-015
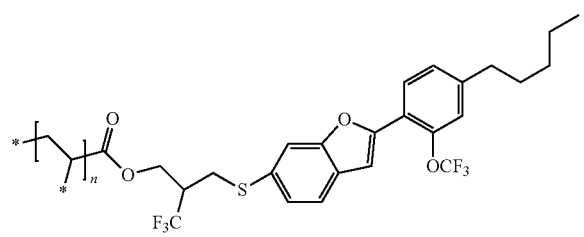
P-016
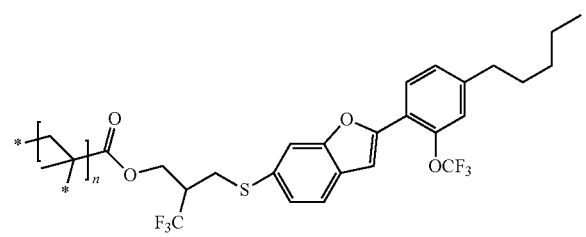
P-017
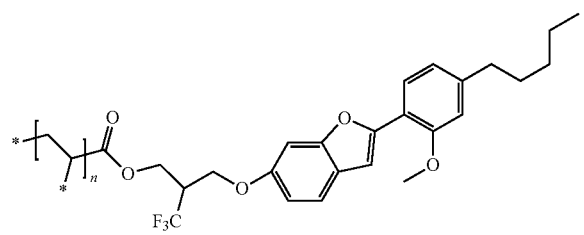
P-018
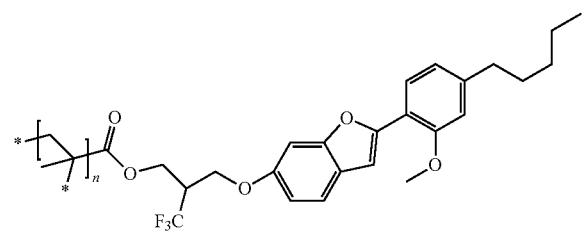
P-019
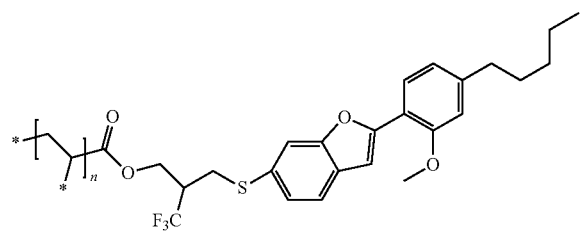
P-020
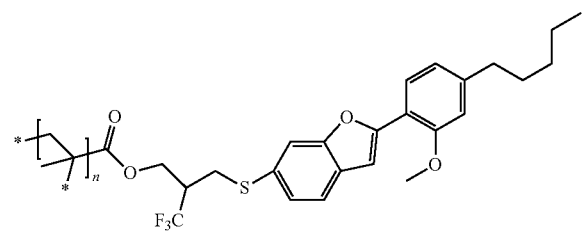
P-021
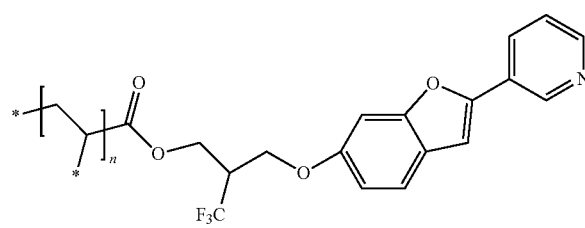
P-022
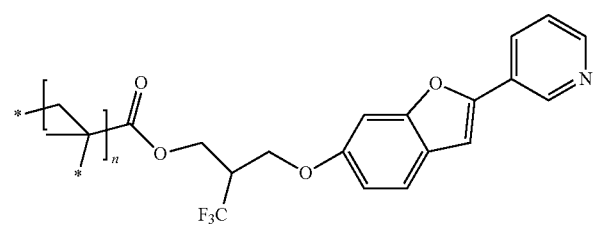

-continued
P-023
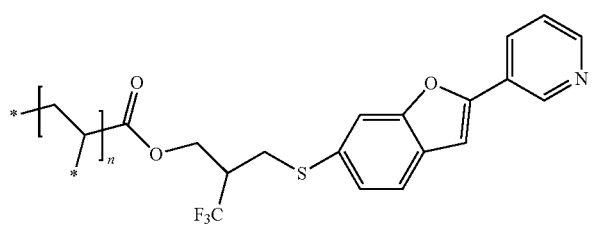
P-024
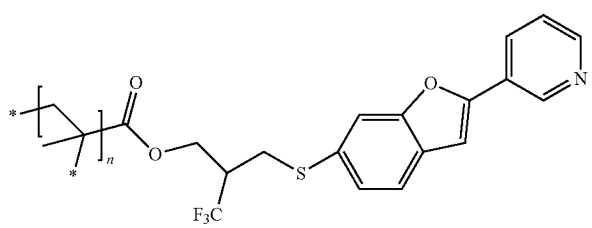
P-025
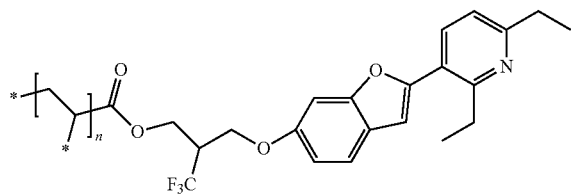
P-026
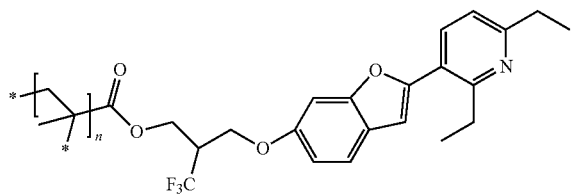
P-027
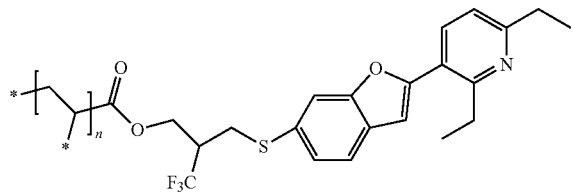
P-028
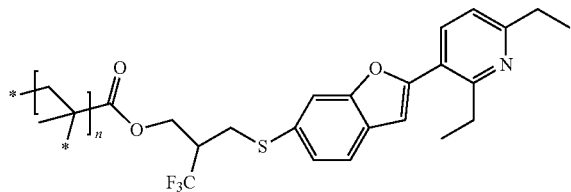
P-029
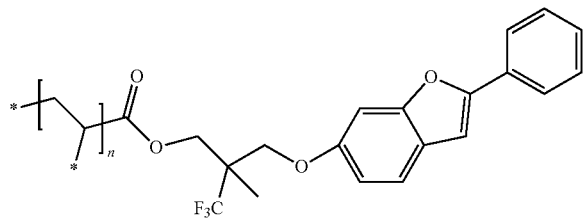
P-030
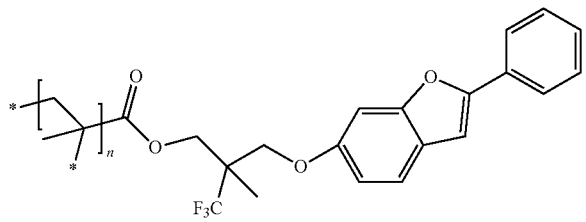
P-031
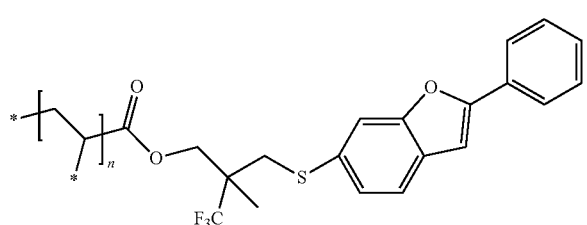
P-032
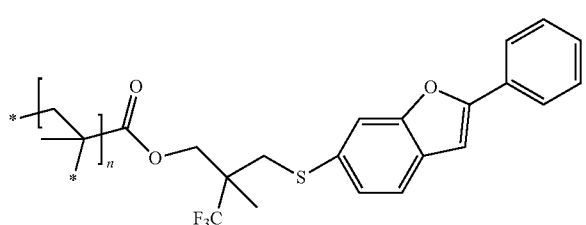
P-033
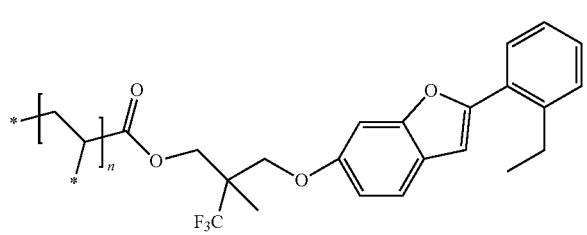
P-034
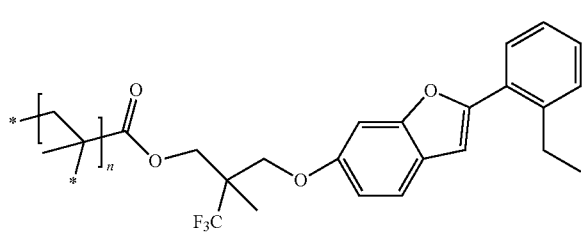

-continued
P-035
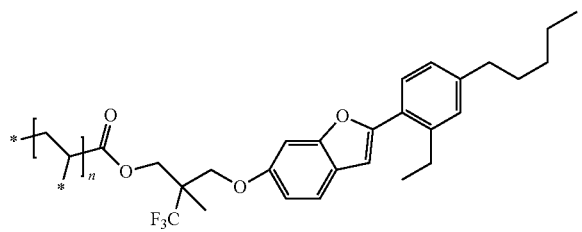
P-036
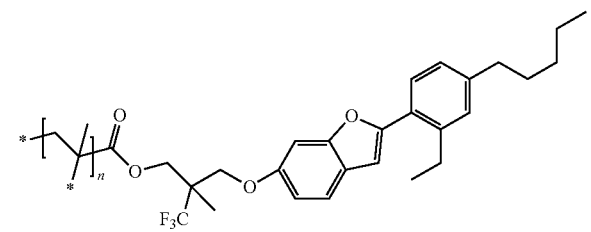
P-037
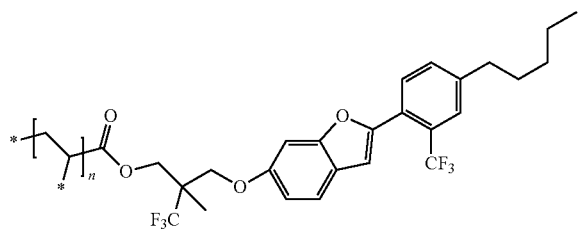
P-038
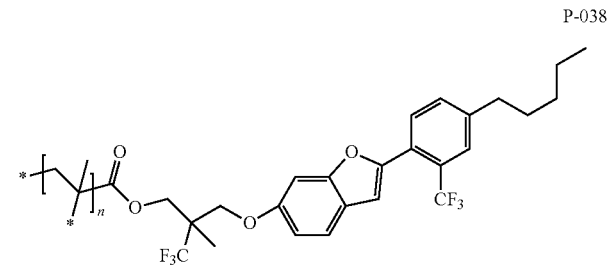
P-039
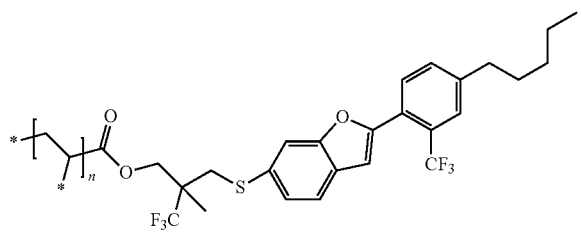
P-040
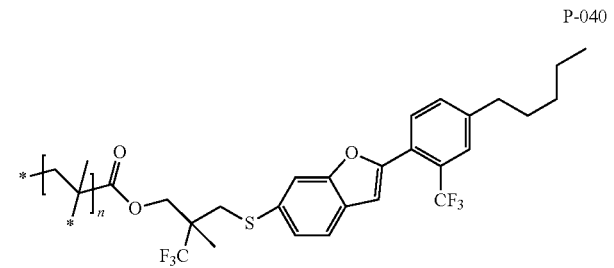
P-041
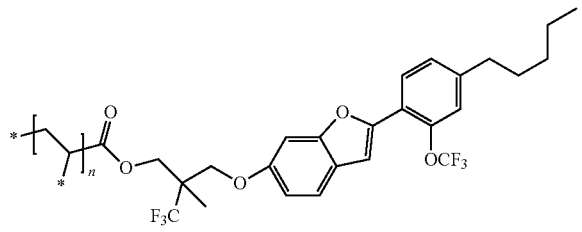
P-042
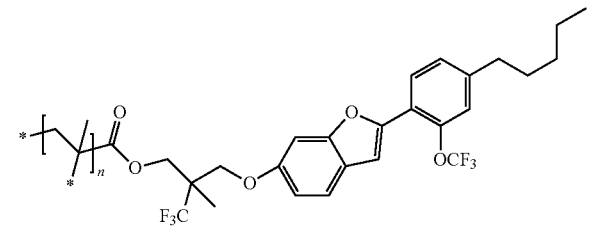
P-043
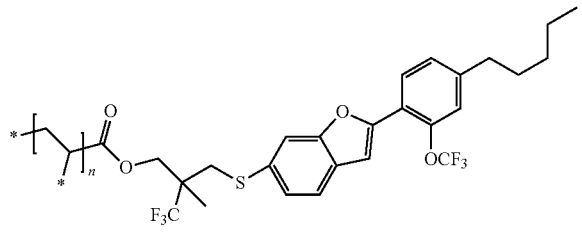
P-044
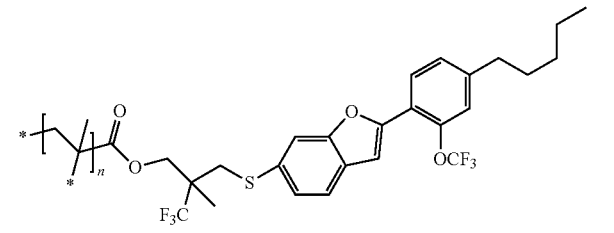
P-045
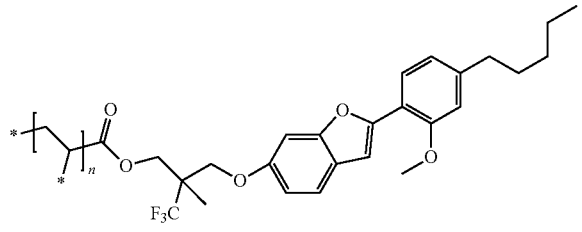
P-046
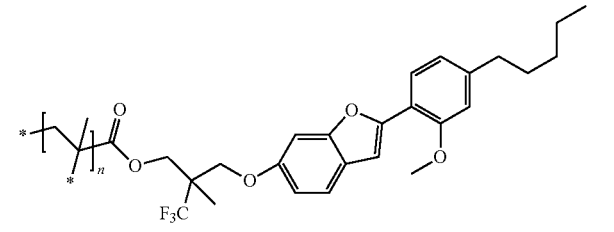

-continued
P-047
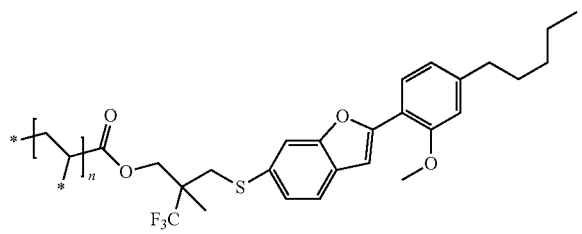
P-048
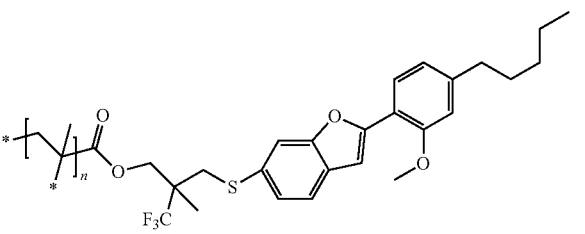
P-049
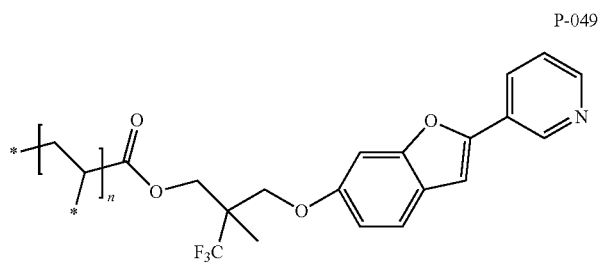
P-050
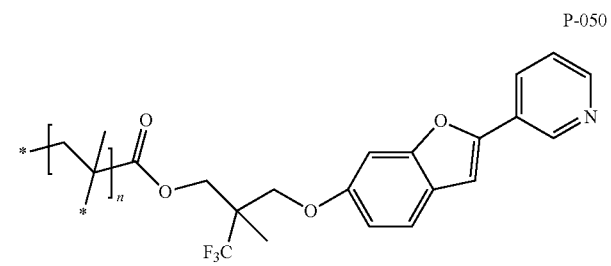
P-051
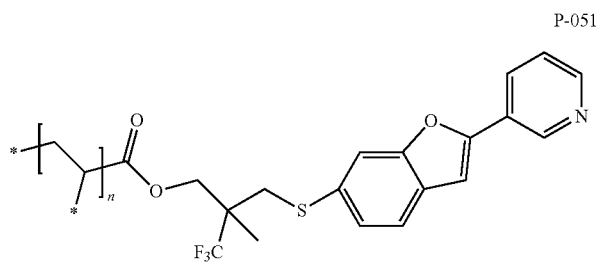
P-052
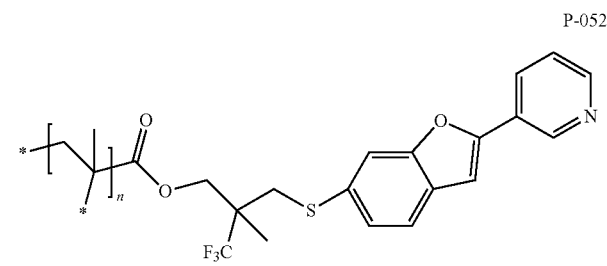
P-053
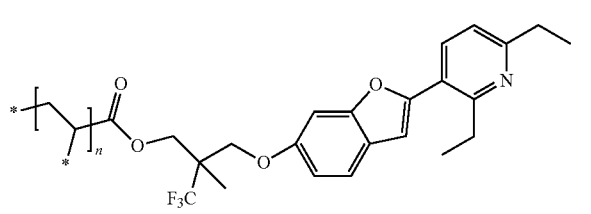
P-054
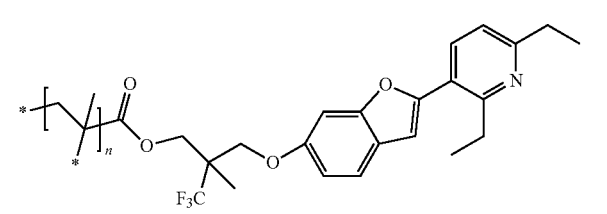
P-055
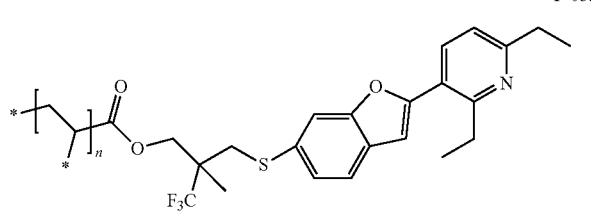
P-056
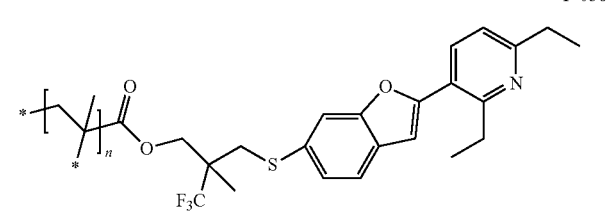
P-057
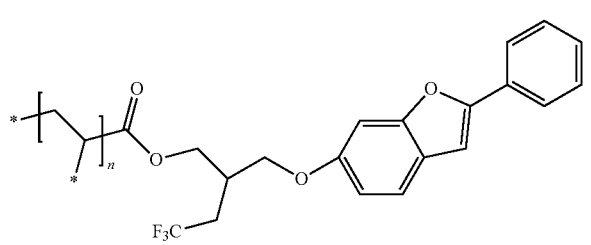
P-058
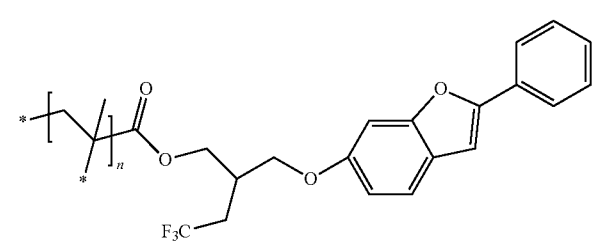

-continued
P-059
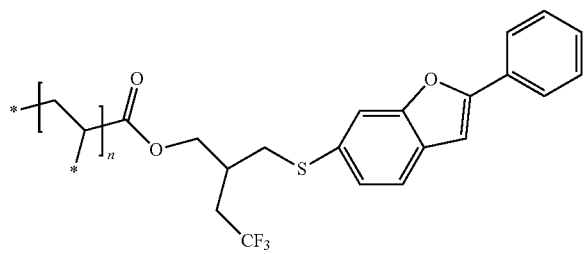
P-060
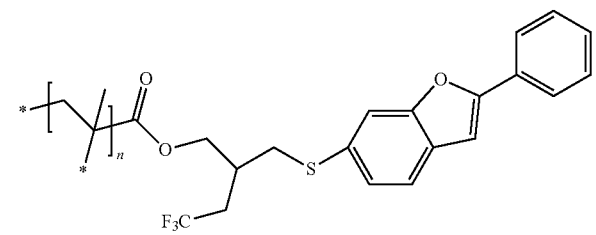
P-061
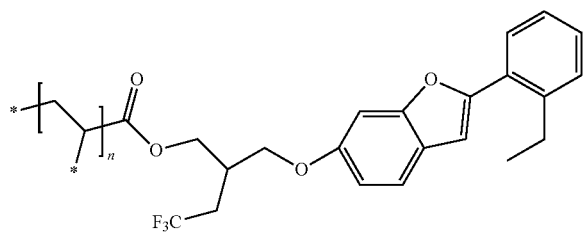
P-062
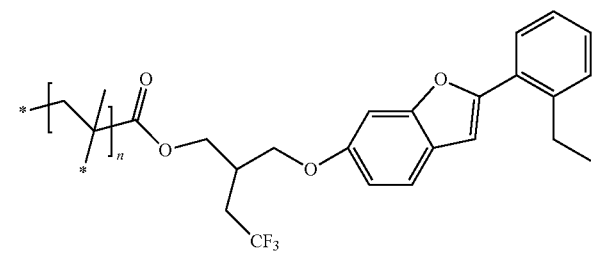
P-063
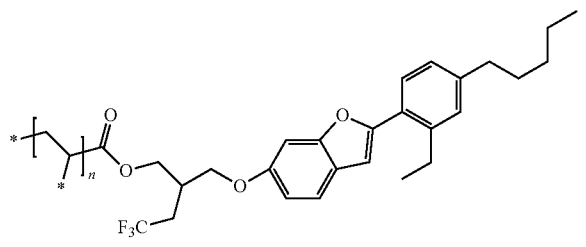
P-064
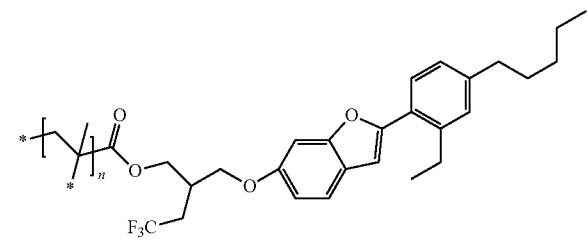
P-065
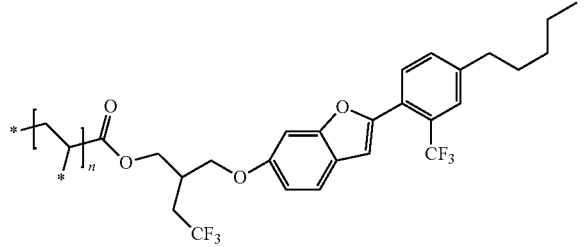
P-066
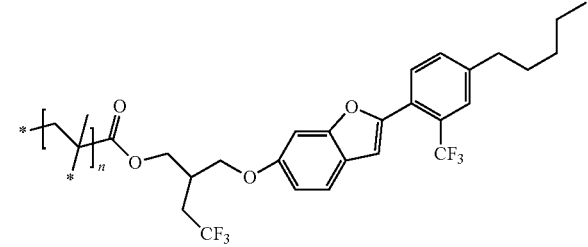
P-067
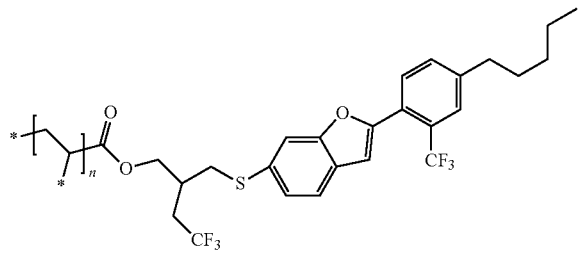
P-068
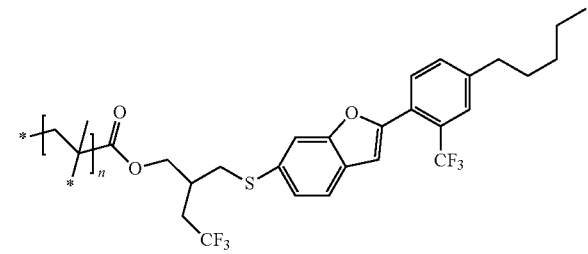

-continued
P-069
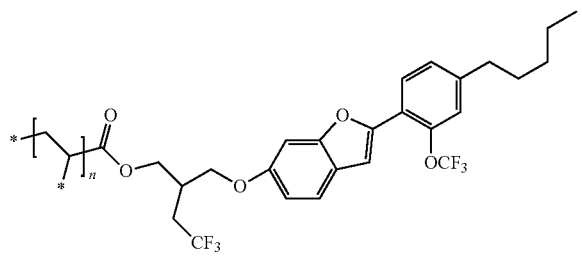
P-070
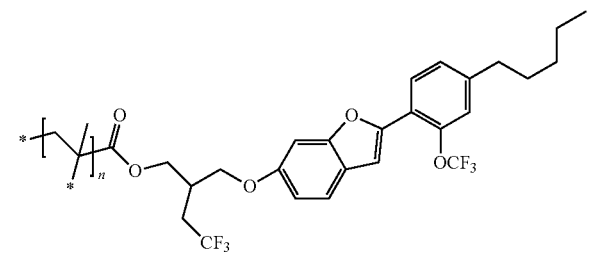
P-071
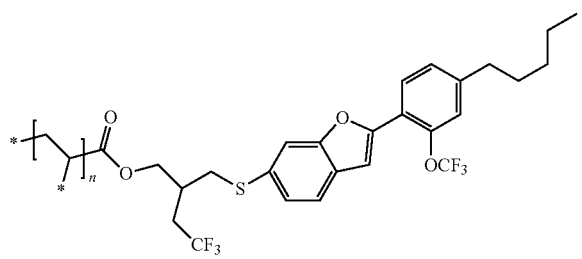
P-072
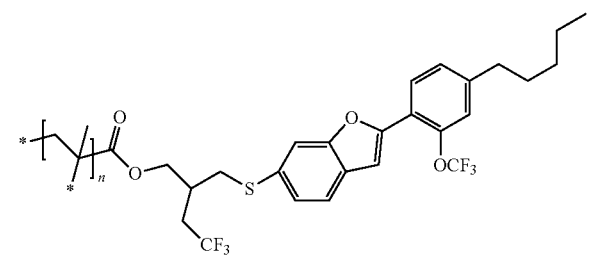
P-073
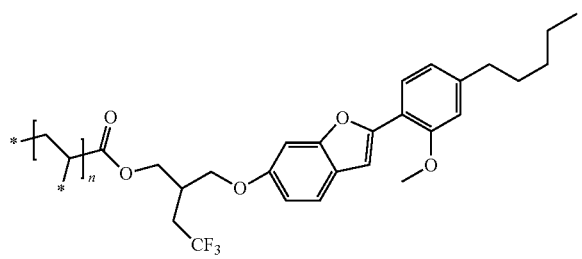
P-074
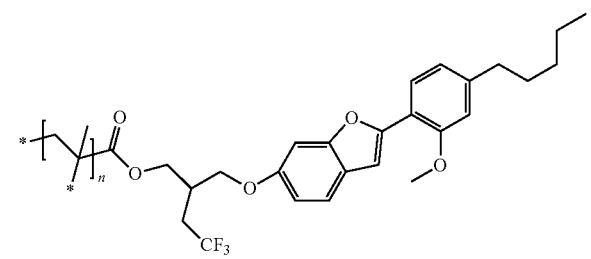
P-075
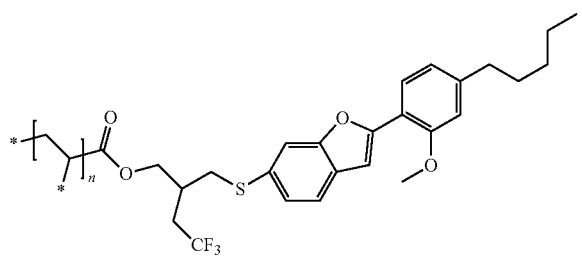
P-076
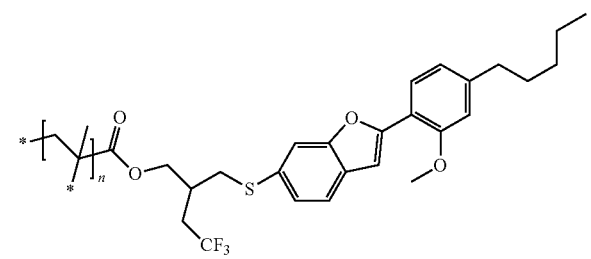
P-077
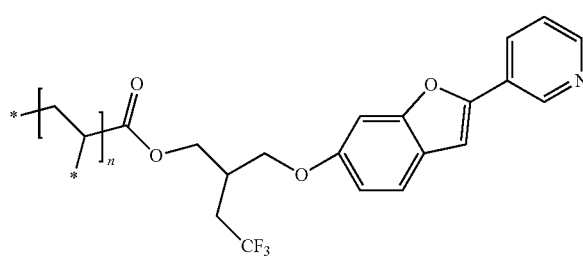
P-078
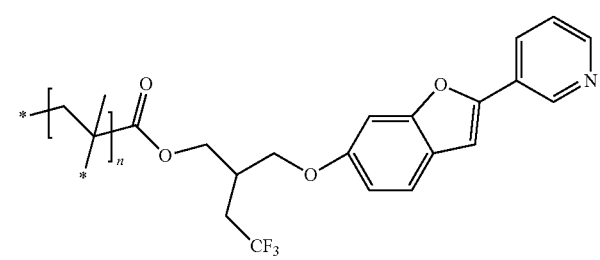

-continued
P-079
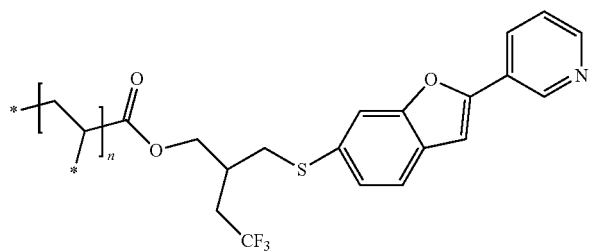
P-080
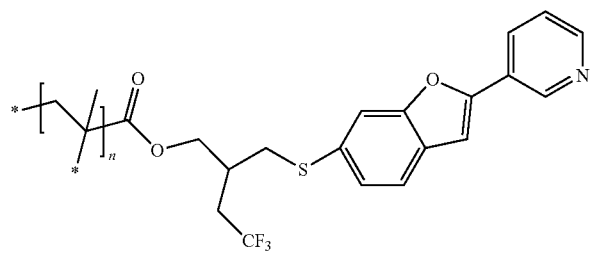
P-081
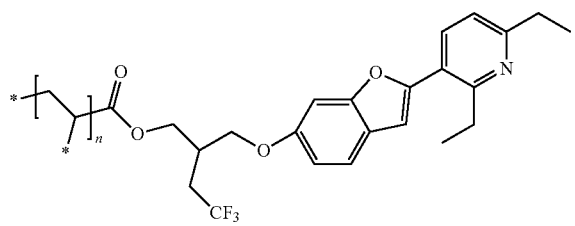
P-082
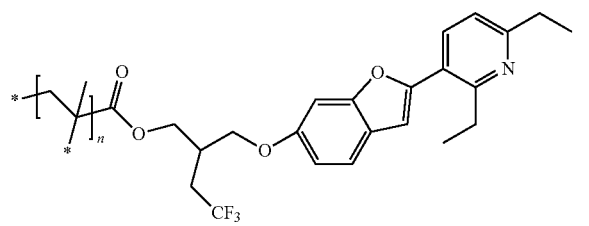
P-083
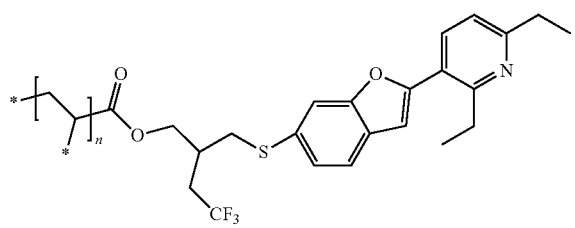
P-084
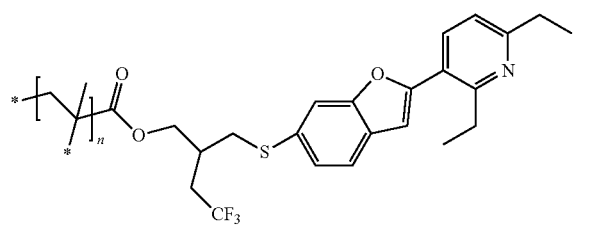
P-085
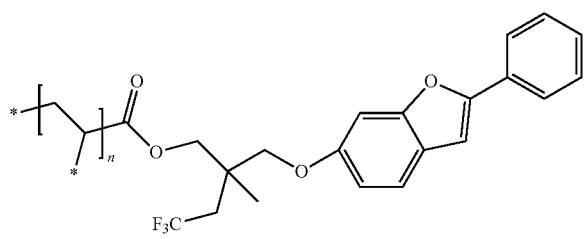
P-086
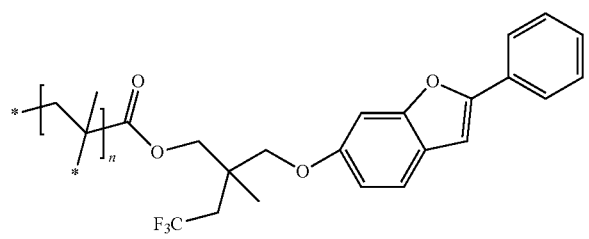
P-087
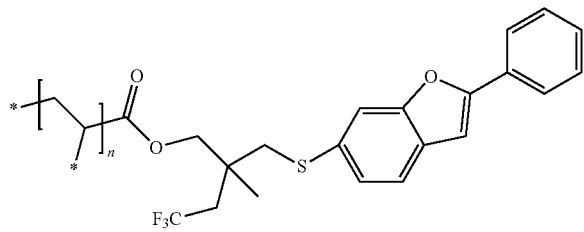
P-088
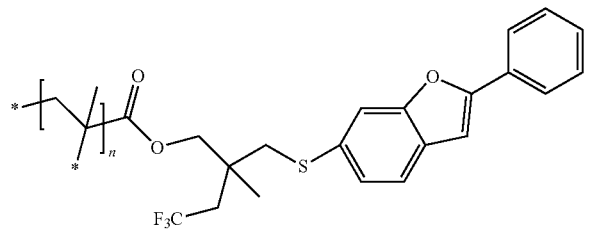
P-089
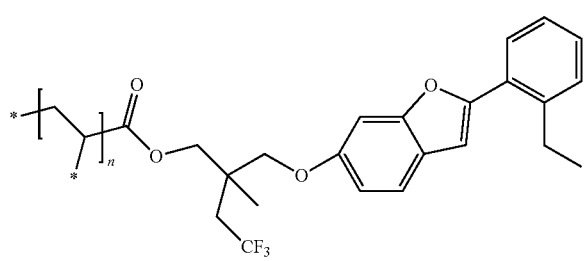
P-090
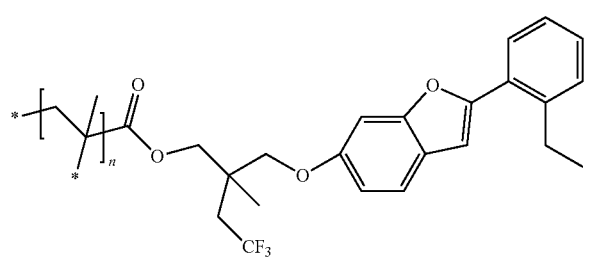

-continued
P-091
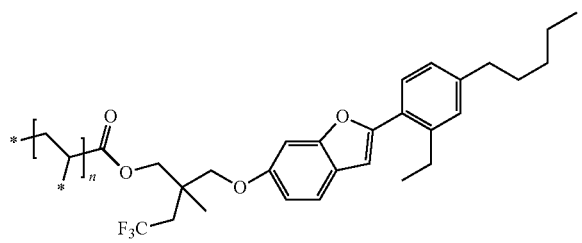
P-092
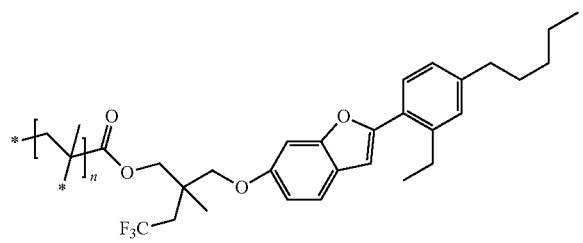
P-093
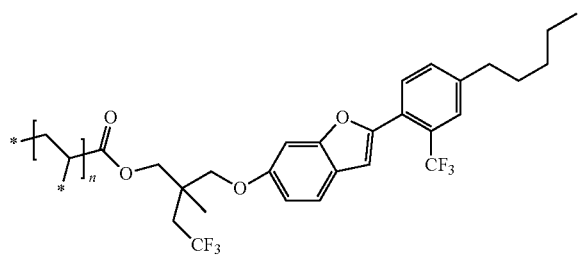
P-094
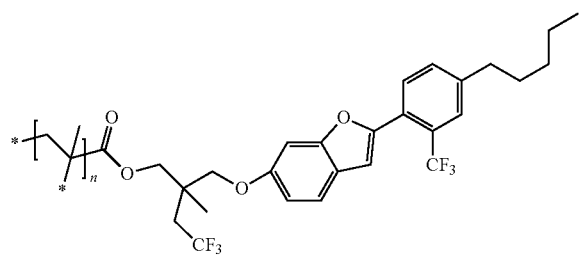
P-095
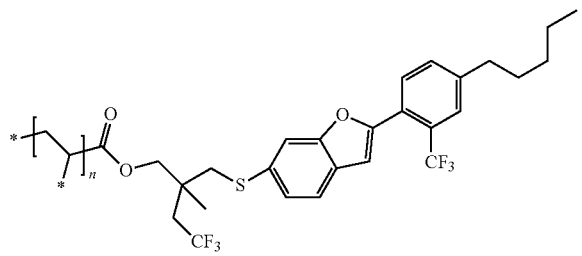
P-096
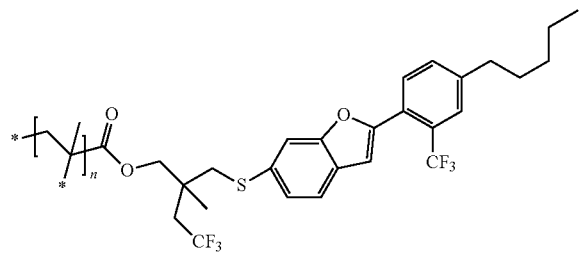
P-097
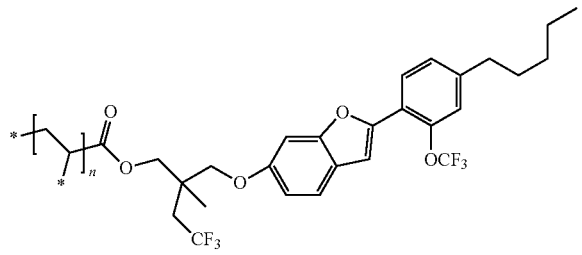
P-098
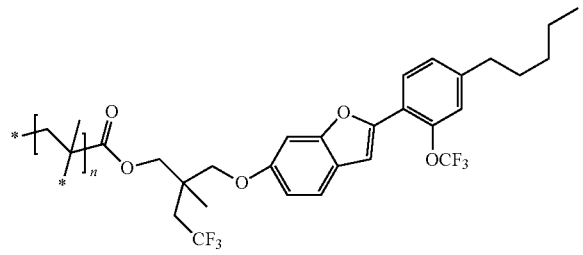
P-099
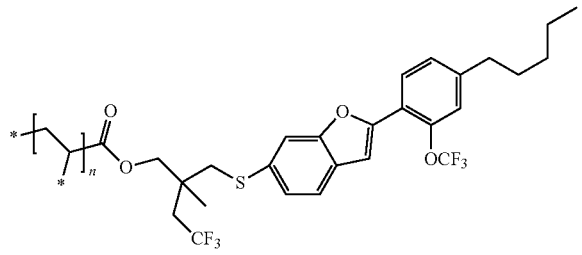
P-100
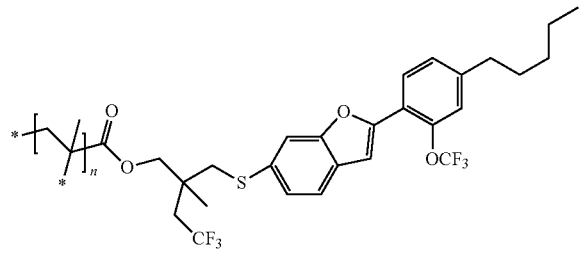

-continued
P-101
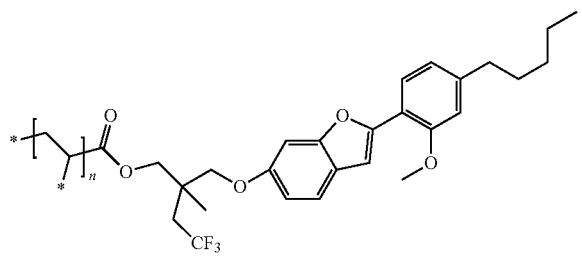
P-102
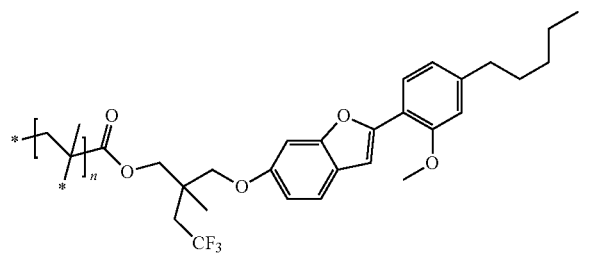
P-103
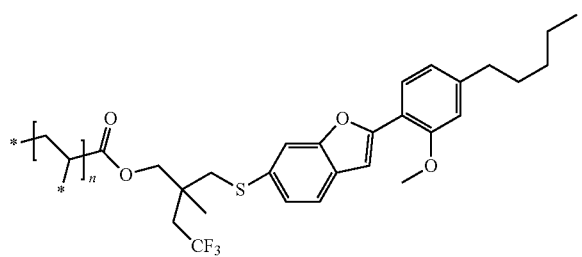
P-104
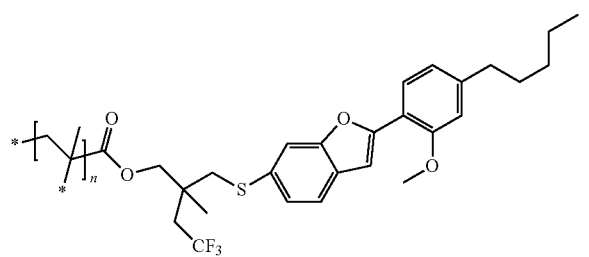
P-105
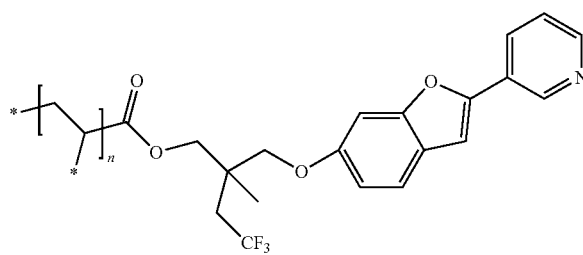
P-106
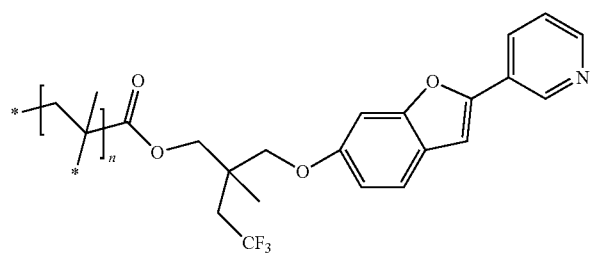
P-107
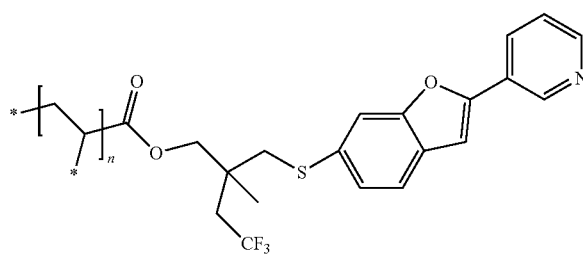
P-108
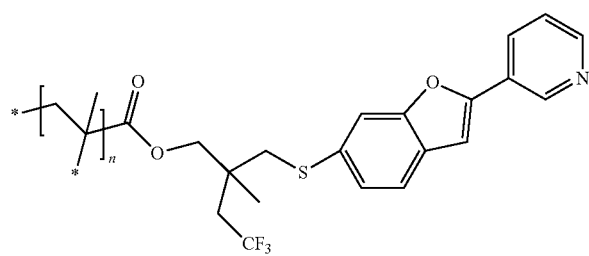
P-109
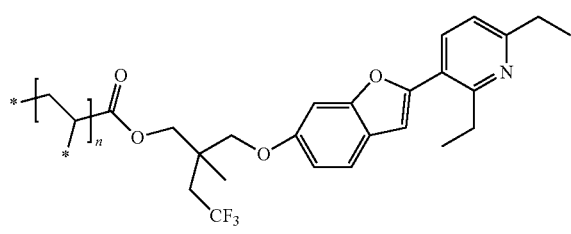
P-110
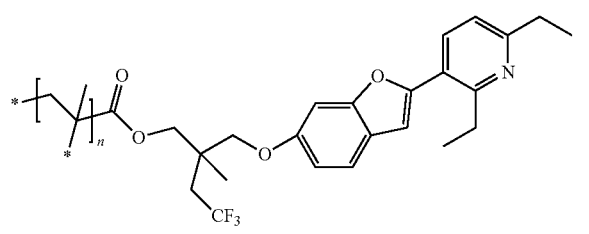
P-111
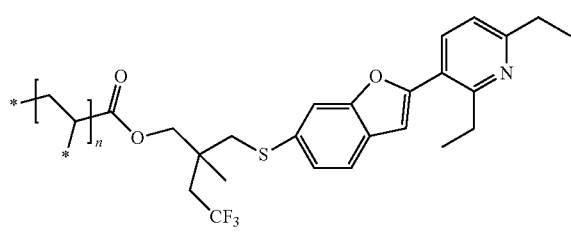
P-112
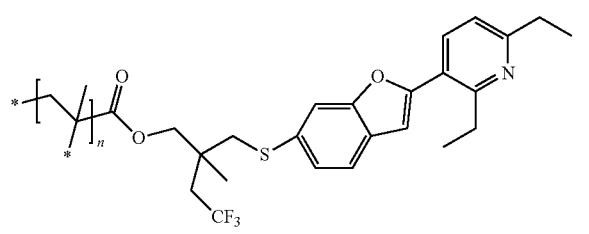

-continued
P-113
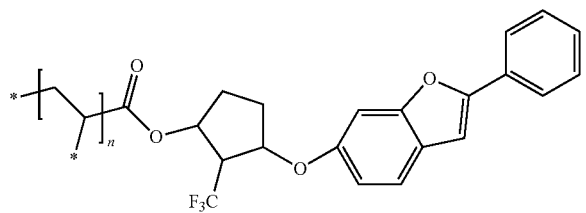
P-114
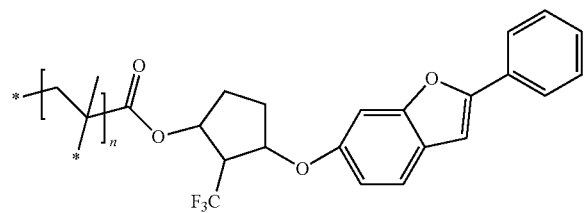
P-115
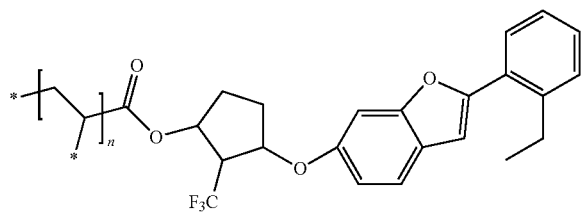
P-116
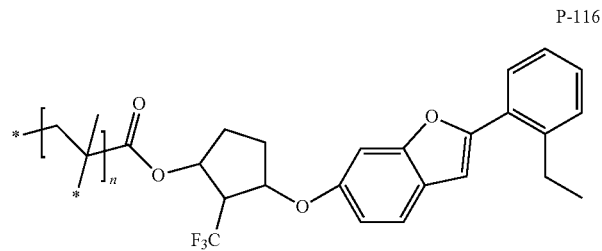
P-117
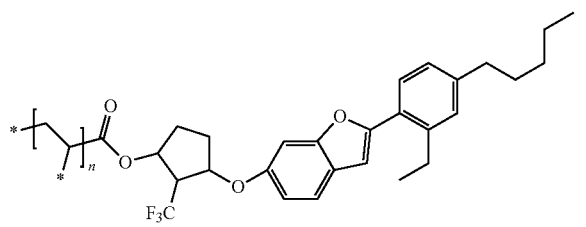
P-118
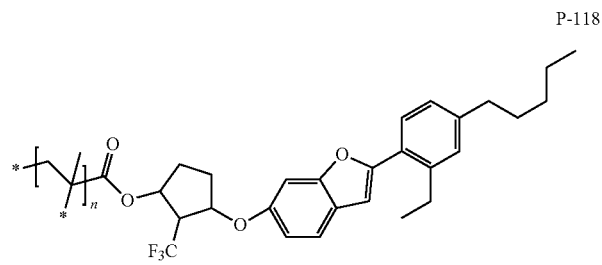
P-119
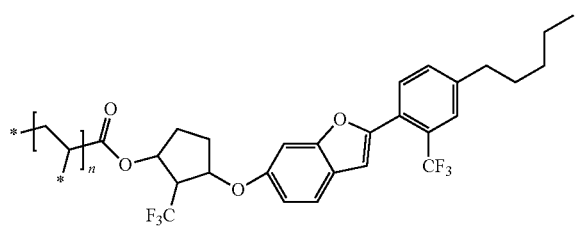
P-120
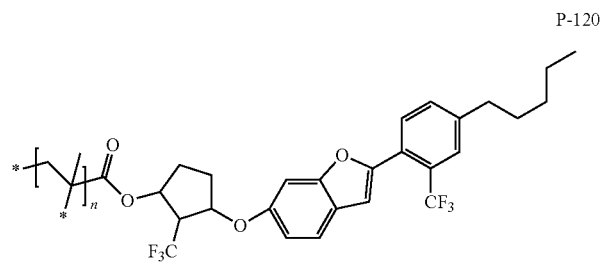
P-121
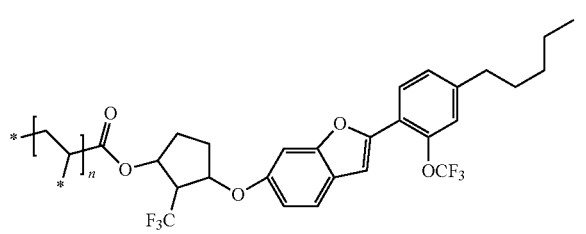
P-122
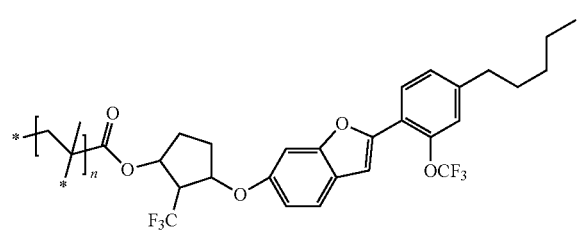
P-123
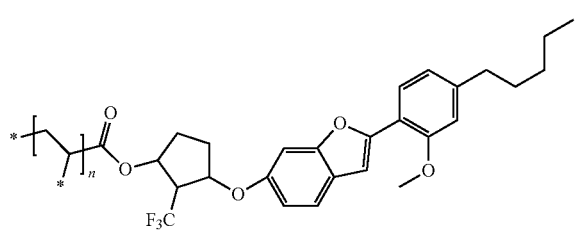
P-124
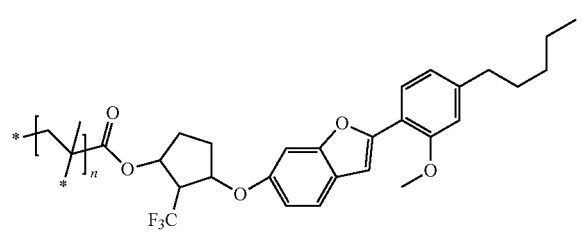

-continued
P-125 P-126
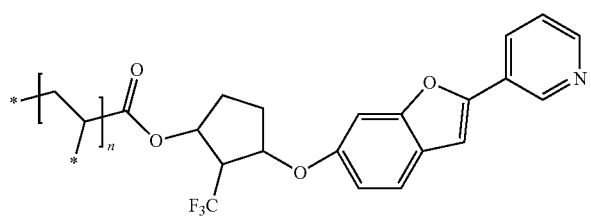
P-127 P-128
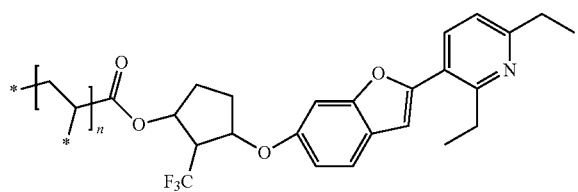
P-129 P-130
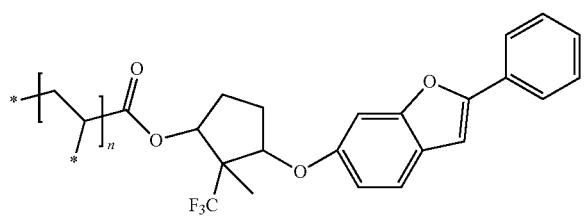
P-131 P-132
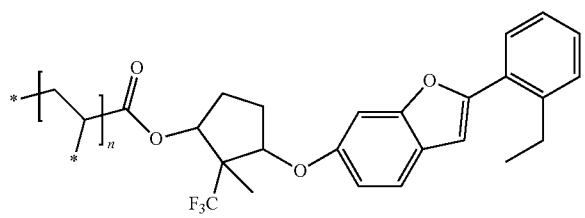
P-133 P-134
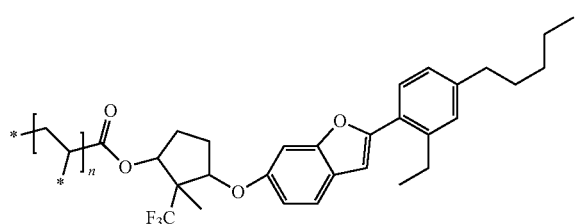
P-135 P-136
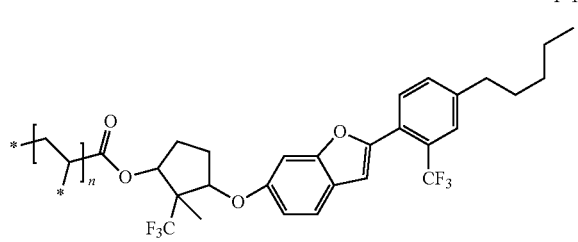

-continued
P-137
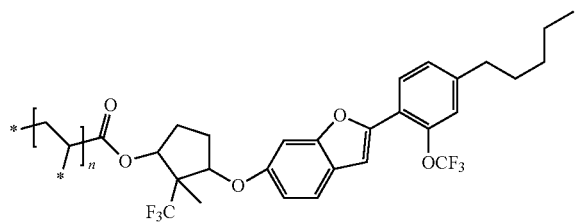
P-138
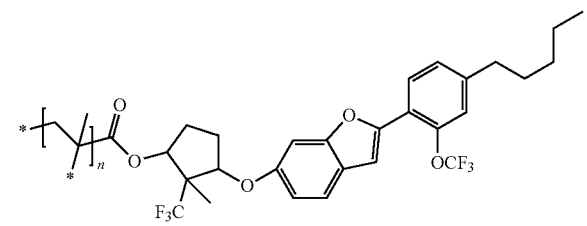
P-139
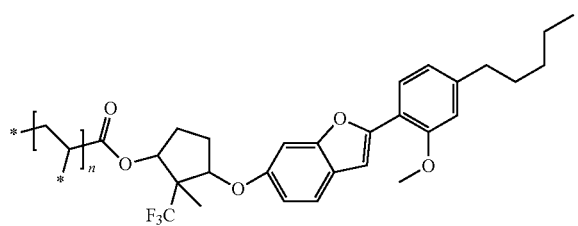
P-140
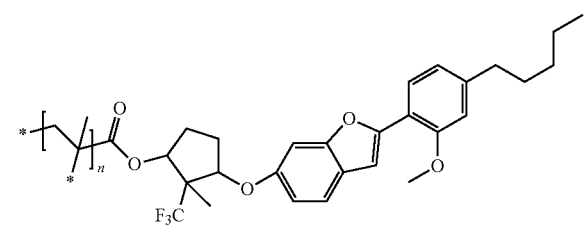
P-141
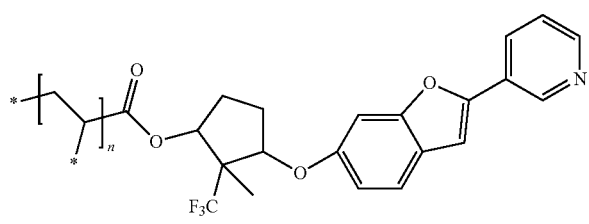
P-142
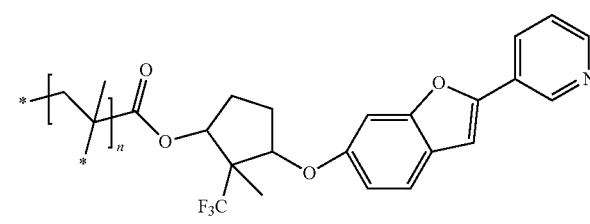
P-143
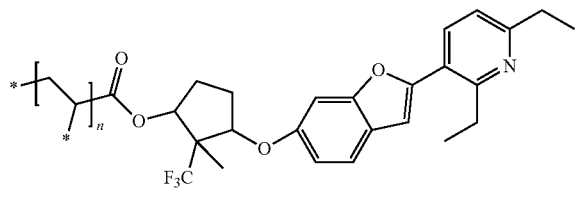
P-144
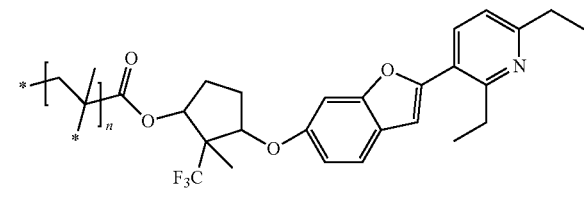
P-145
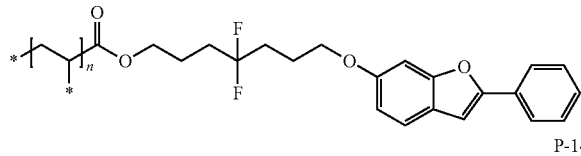
P-146
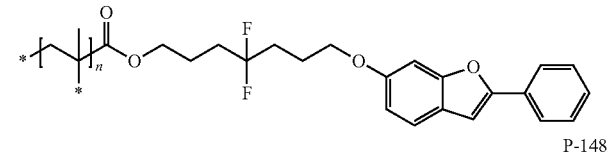
P-147
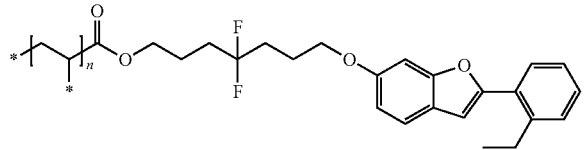
P-148
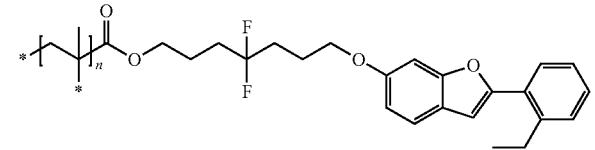
P-150
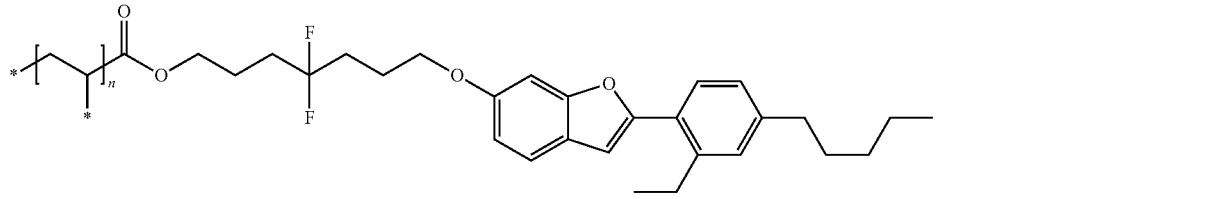

-continued
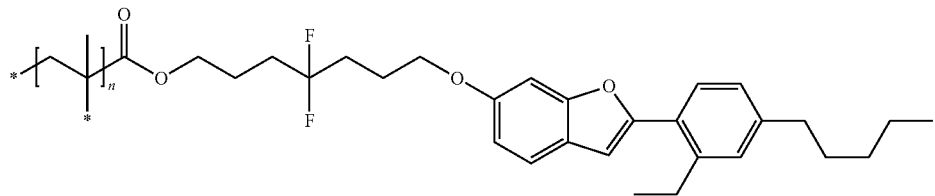
P-151
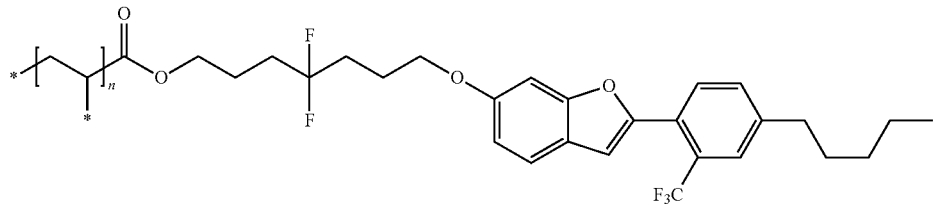
P-152
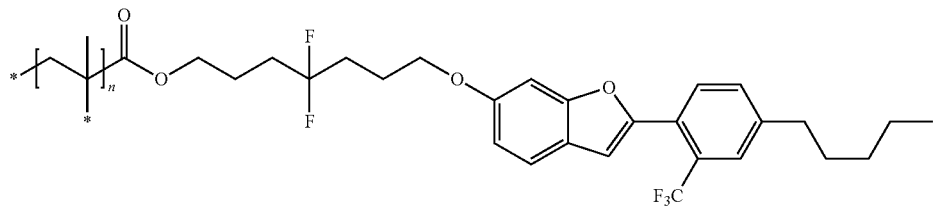
P-153
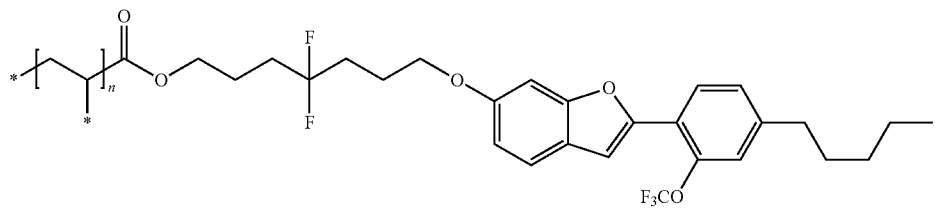
P-154
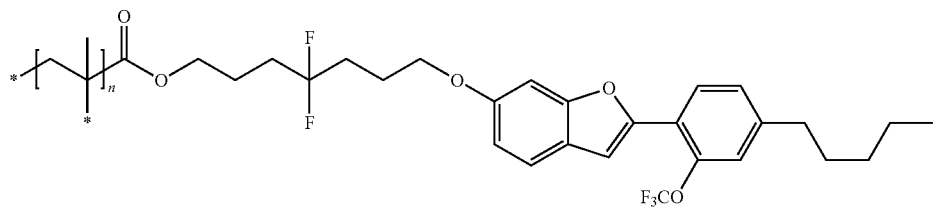
P-155
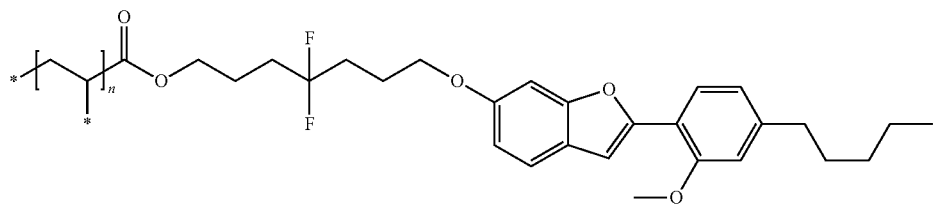
P-156
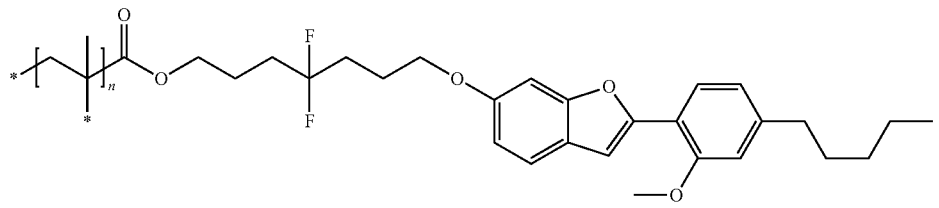
P-157

-continued
P-158
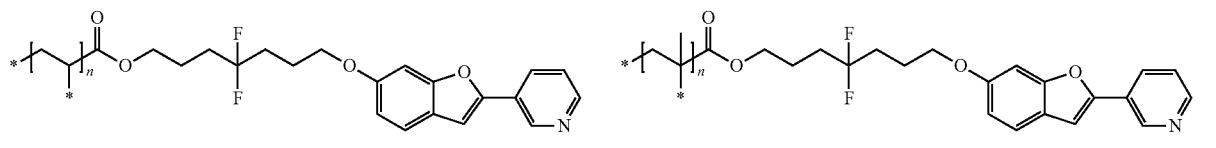
P-159
P-160
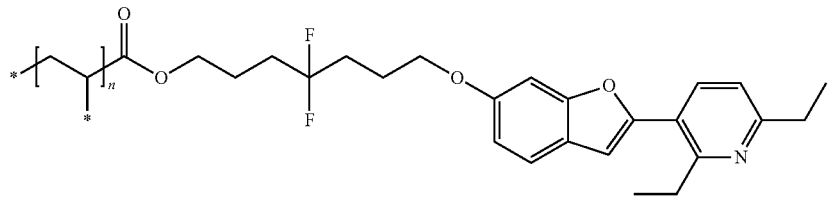
P-161
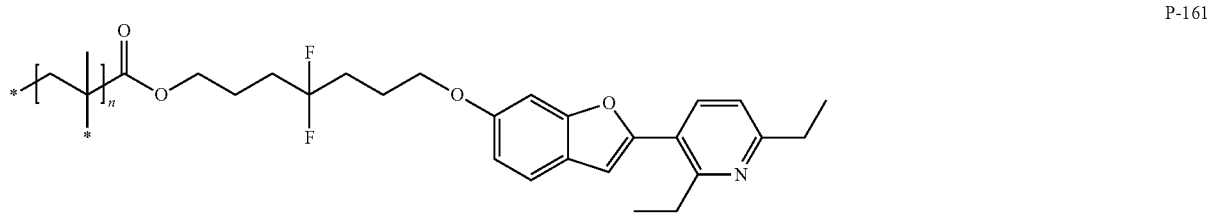
P-162
P-163
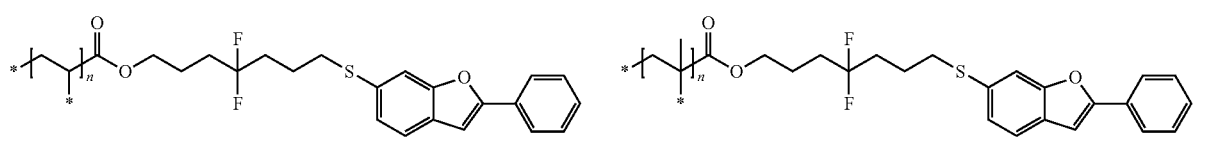
P-164
P-165
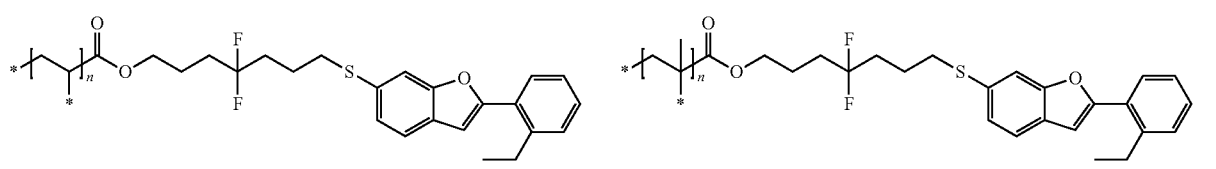
P-166
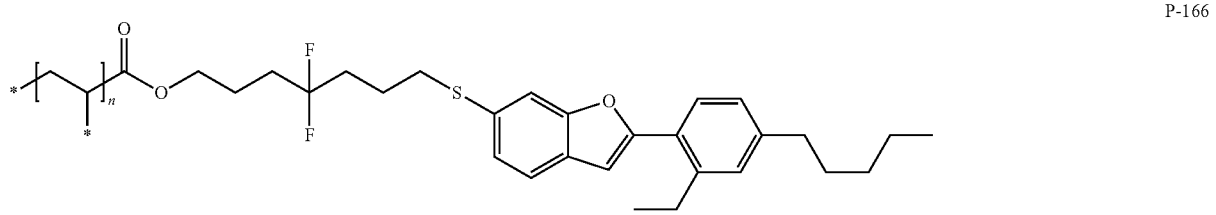
P-167
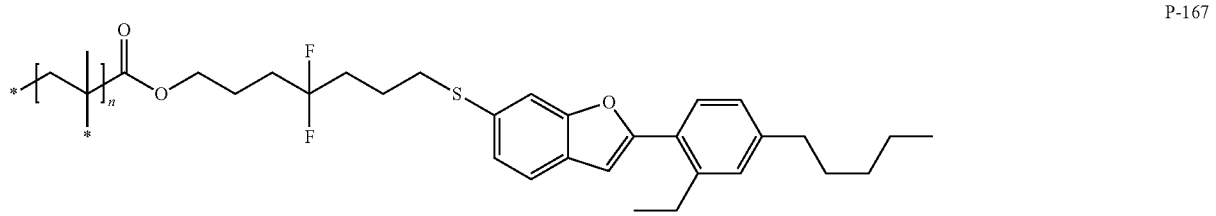
P-168
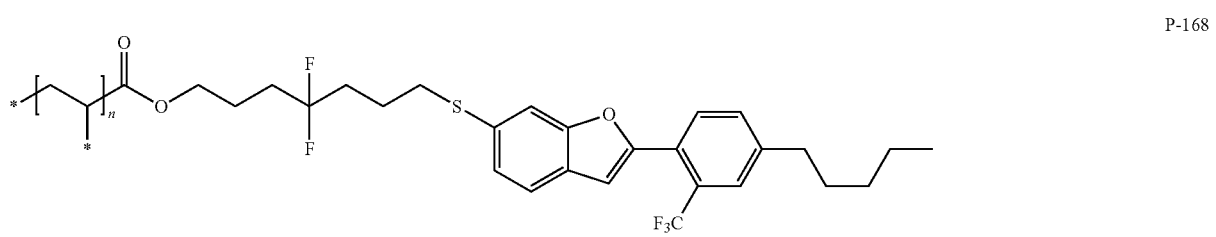

-continued
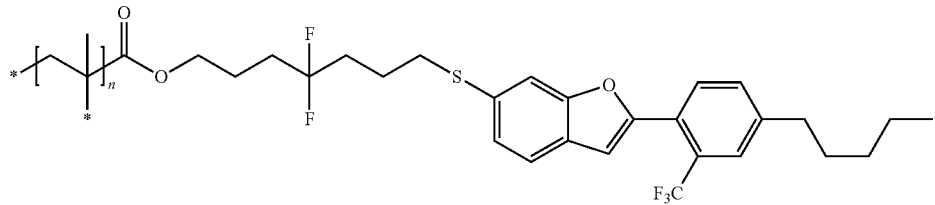
P-169
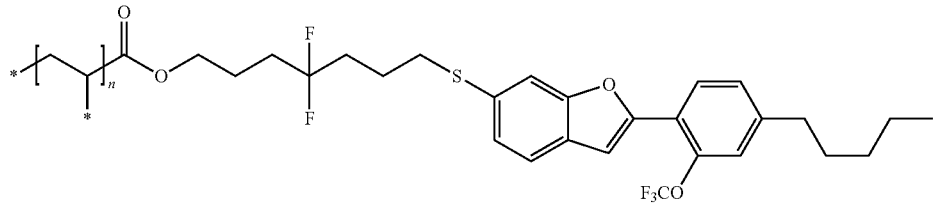
P-170
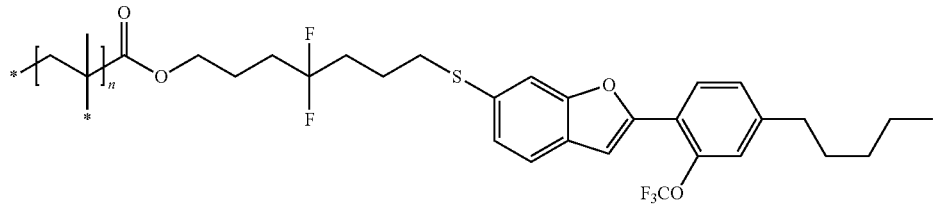
P-171
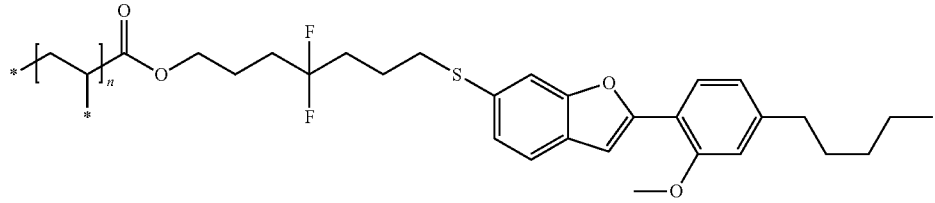
P-172
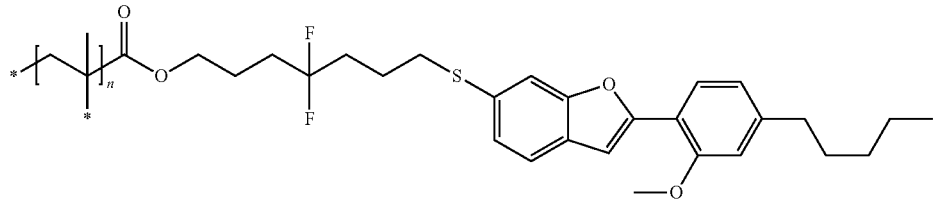
P-173
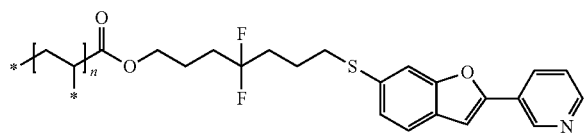
P-174
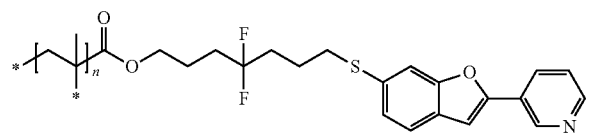
P-175
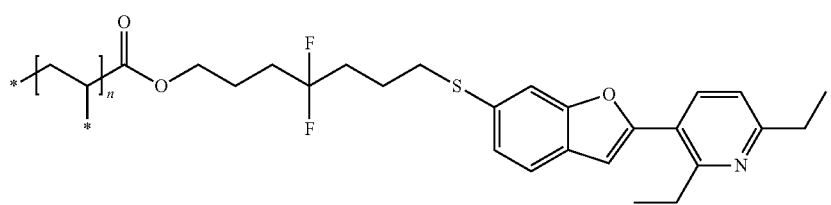
P-176

-continued
P-177
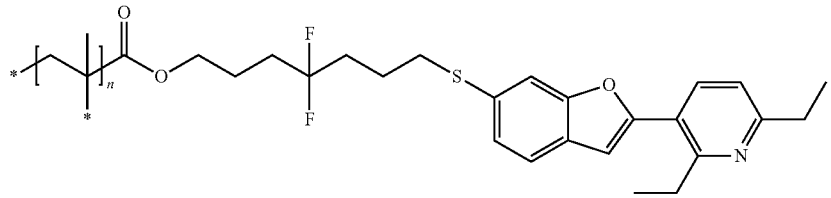
P-178
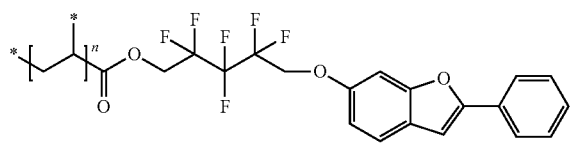
P-179
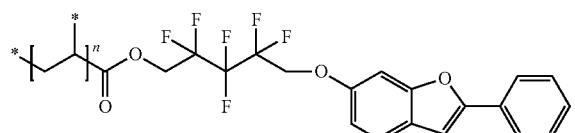
P-180
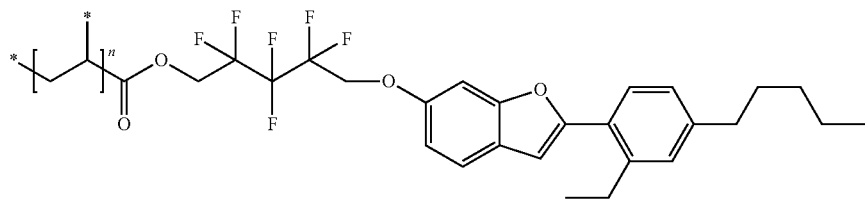
P-181
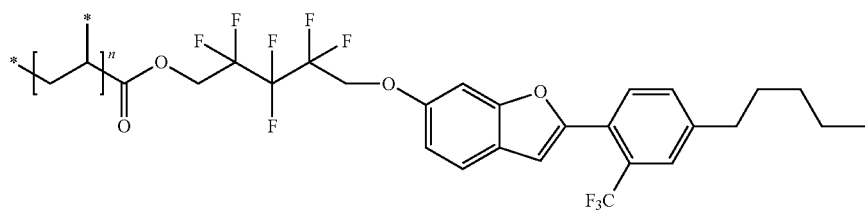
P-182
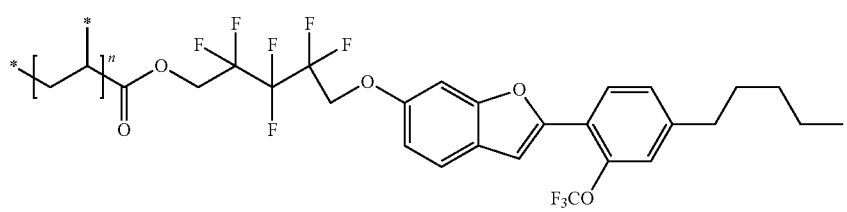
P-183
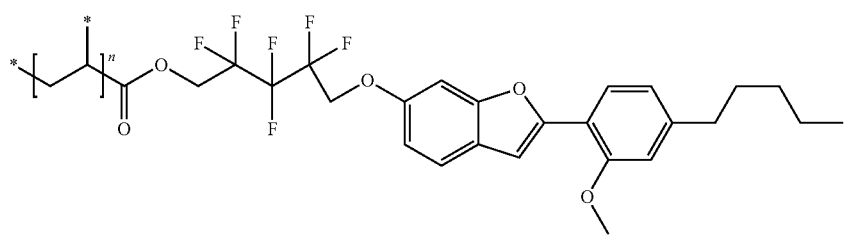
P-184
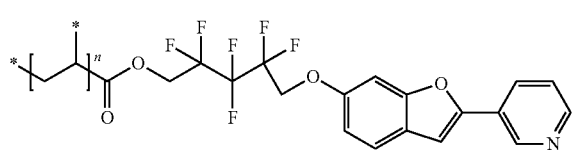
P-185
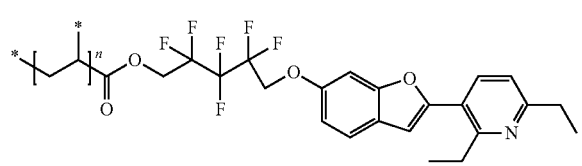

-continued
P-186
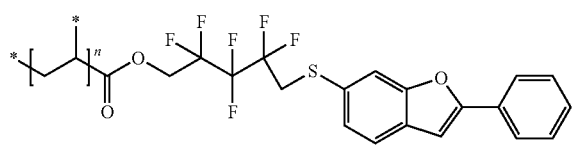
P-187
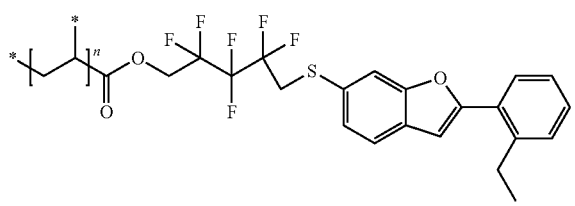
P-188
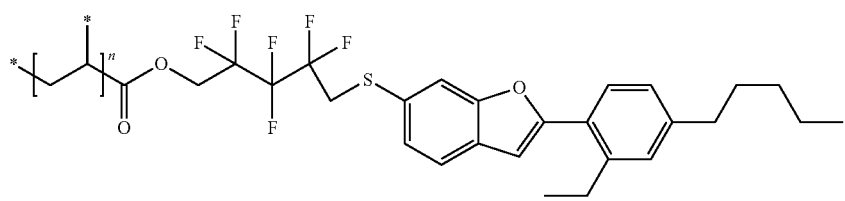
P-189
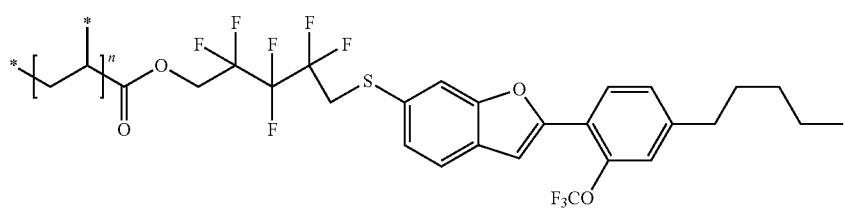
P-190
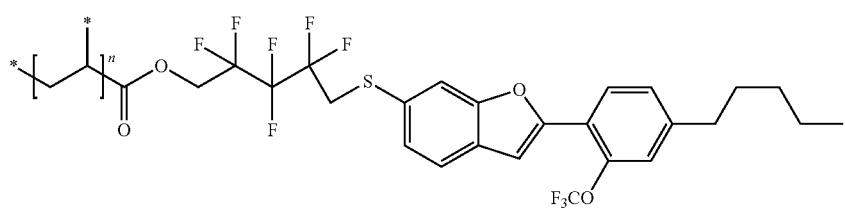
P-191
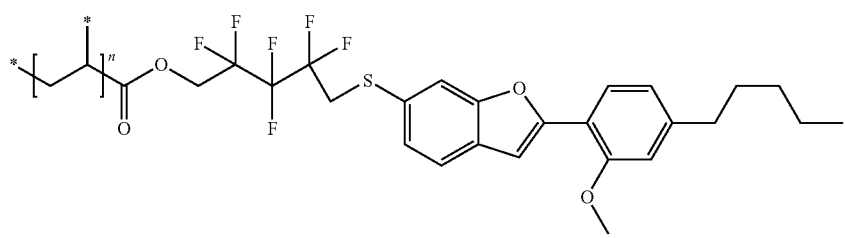
P-192
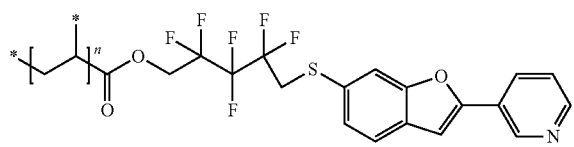
P-193
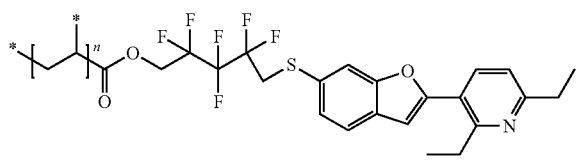
P-194
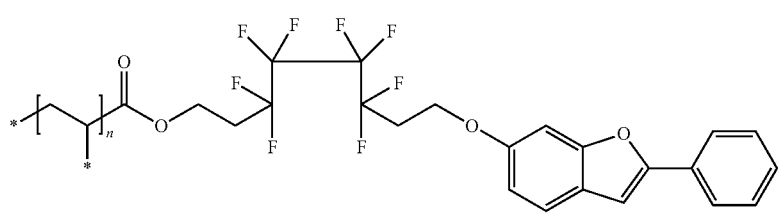

-continued
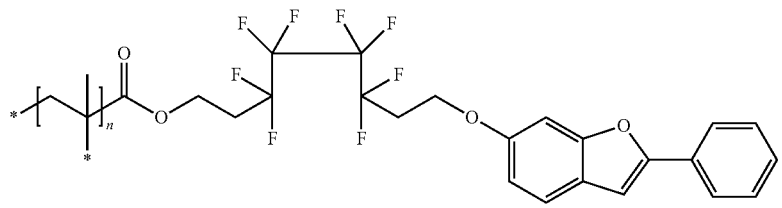
P-195
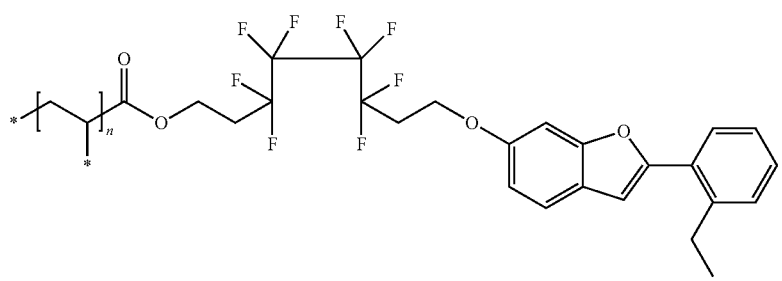
P-196
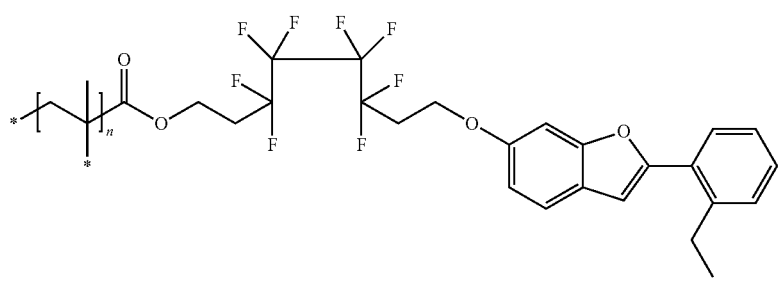
P-197
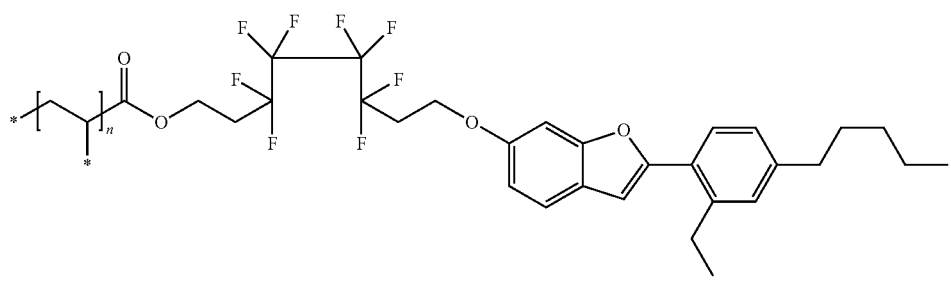
P-198
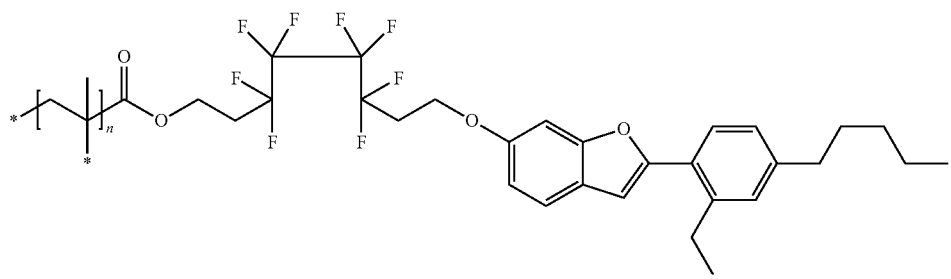
P-199
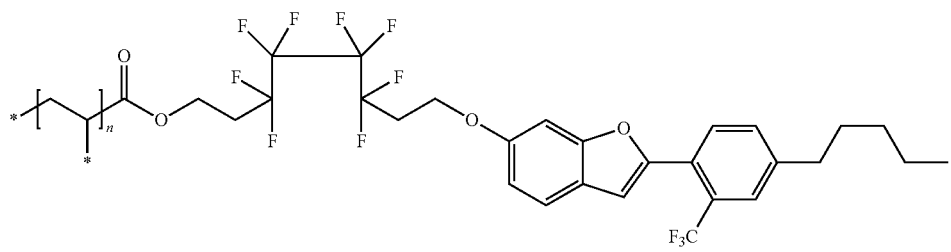
P-200

-continued
P-201
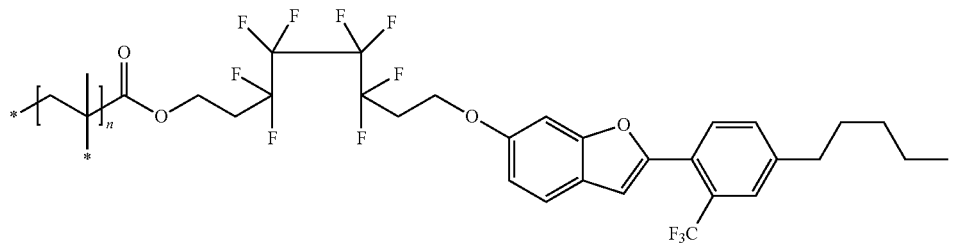
P-202
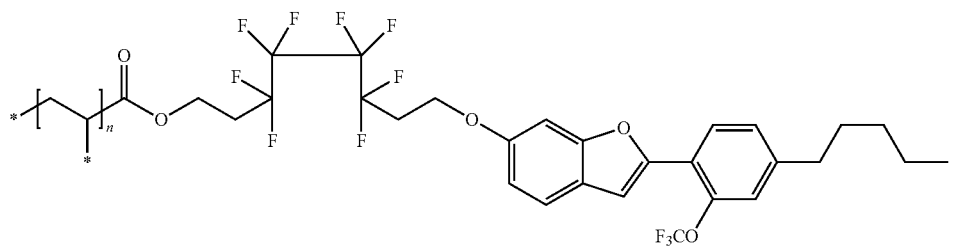
P-203
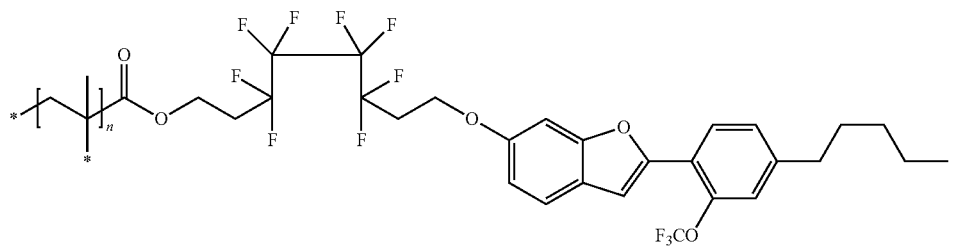
P-204
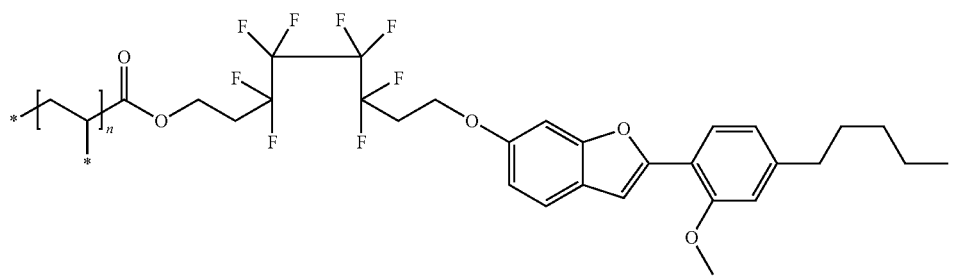
P-205
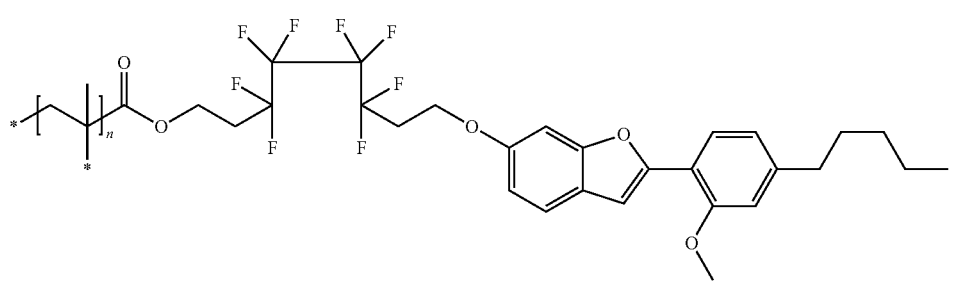
P-206
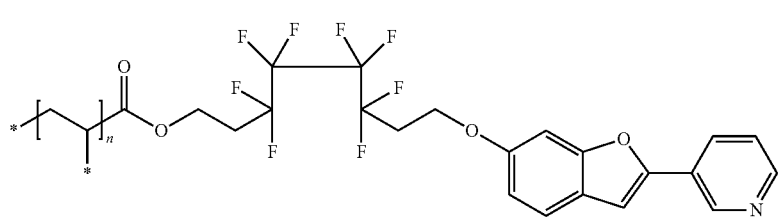

-continued
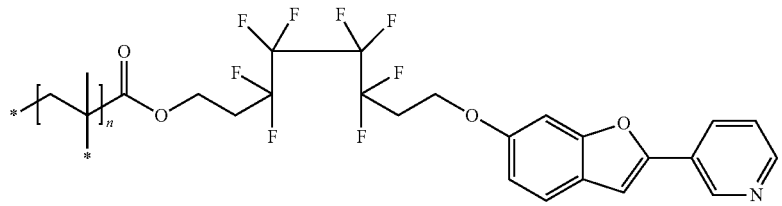
P-207
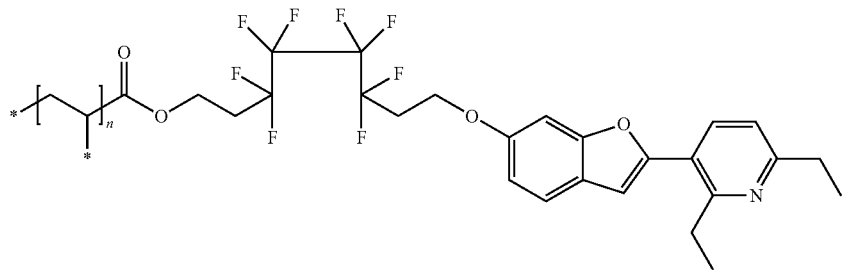
P-208
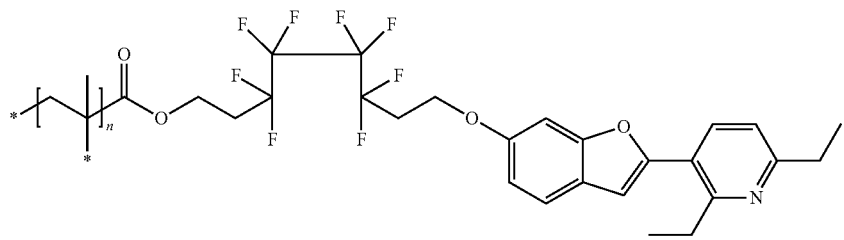
P-209
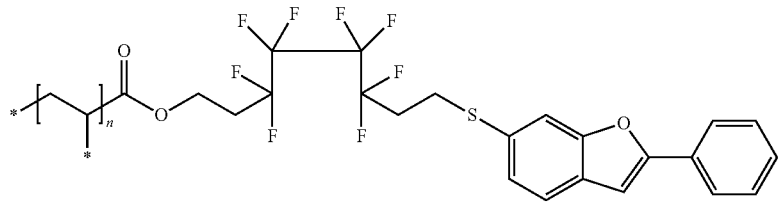
P-210
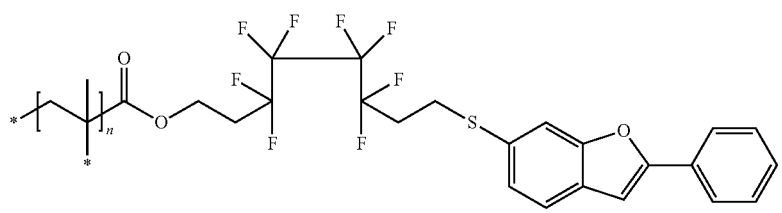
P-211
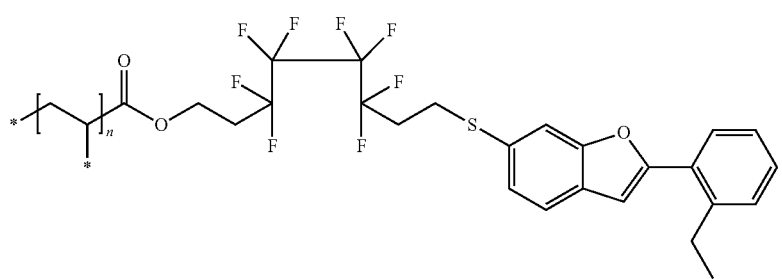
P-212

-continued
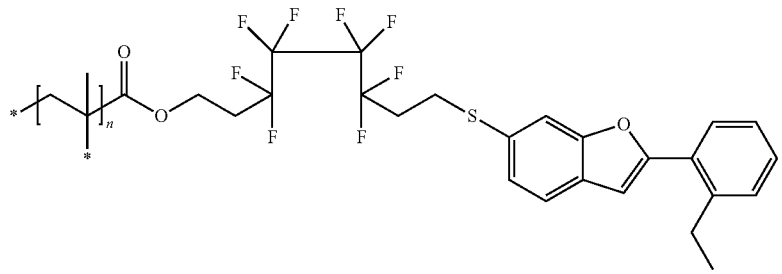
P-213
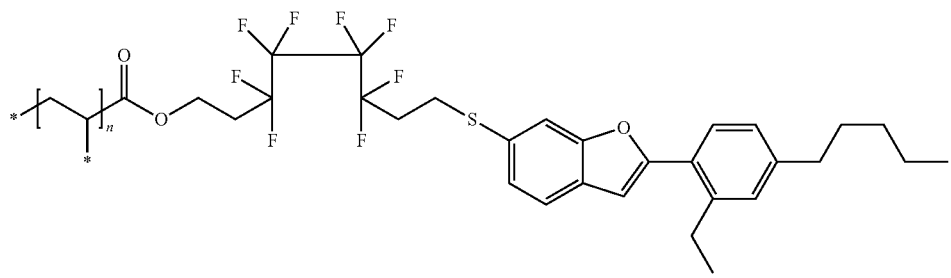
P-214
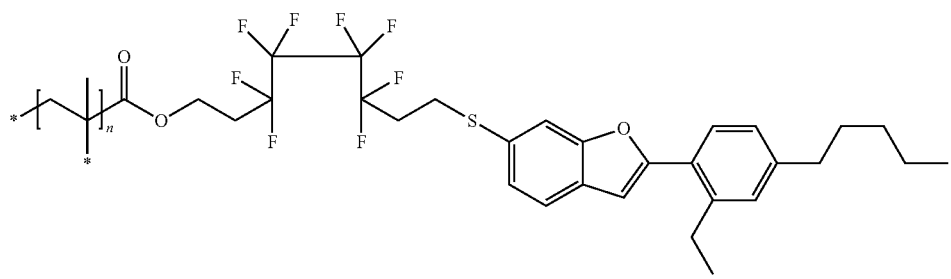
P-215
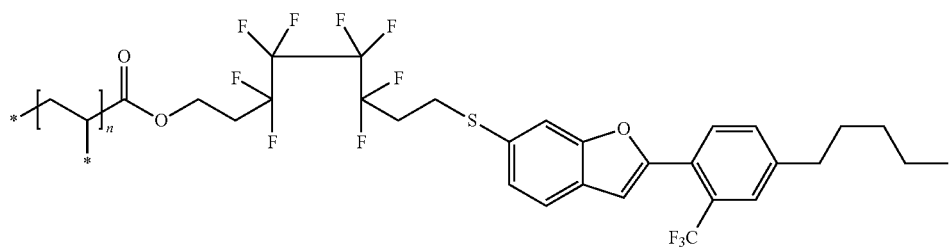
P-216
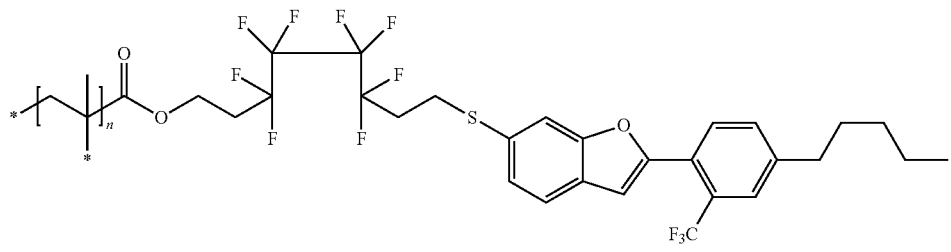
P-217
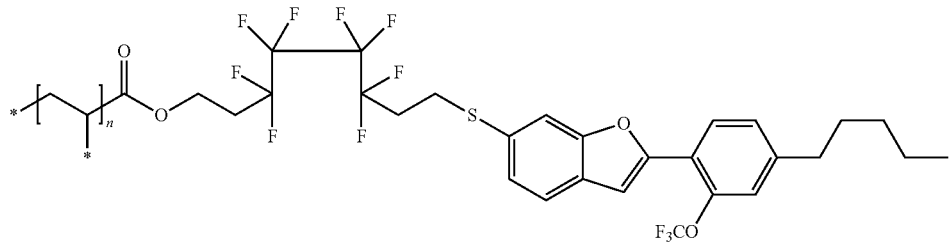
P-218

P-219
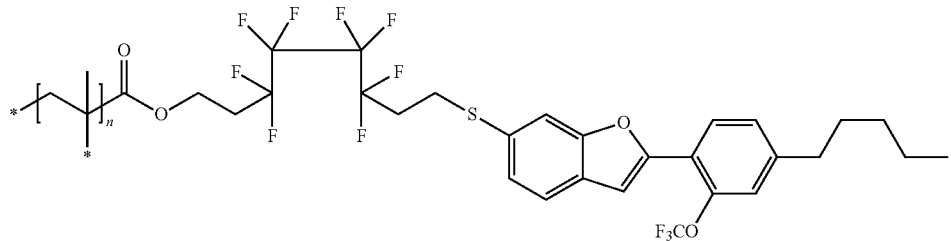
P-220
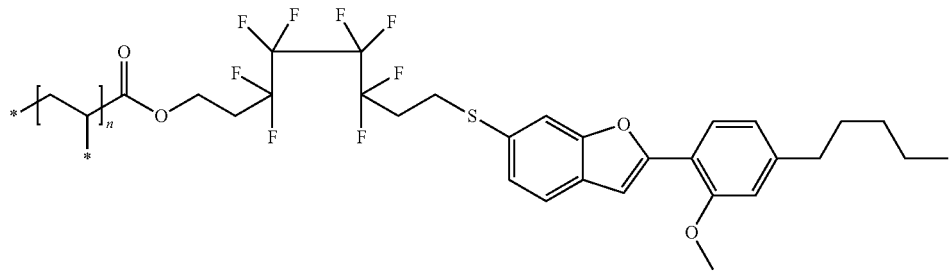
P-221
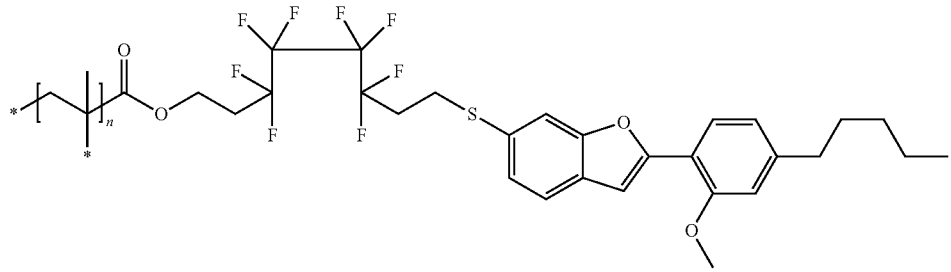
P-222
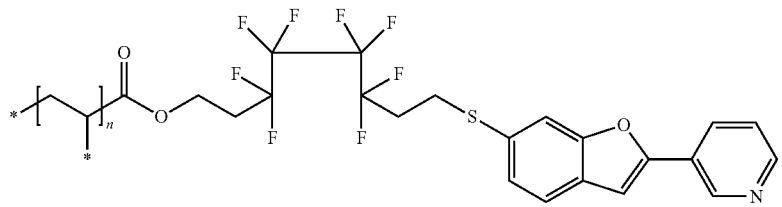
P-223
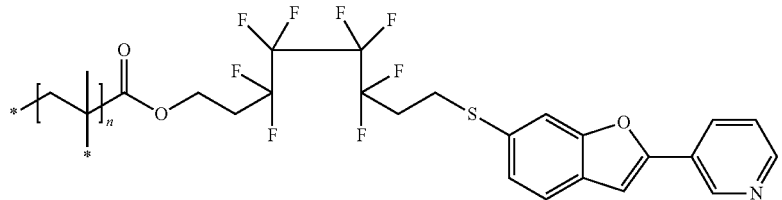
P-224
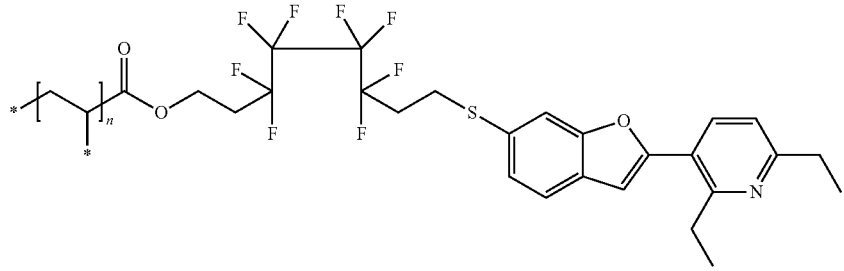

P-225
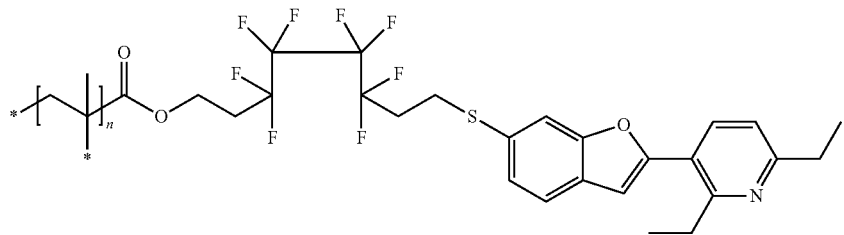
P-226
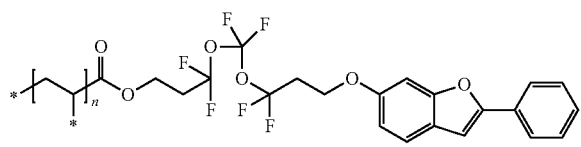
P-227
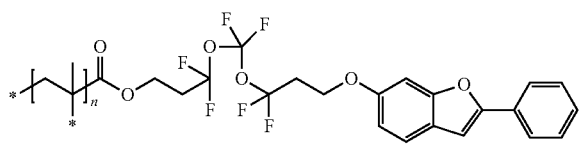
P-228
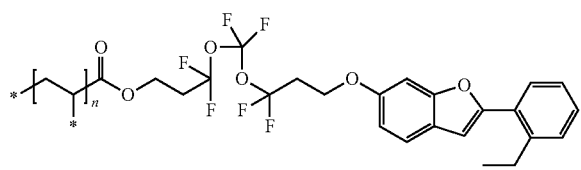
P-229
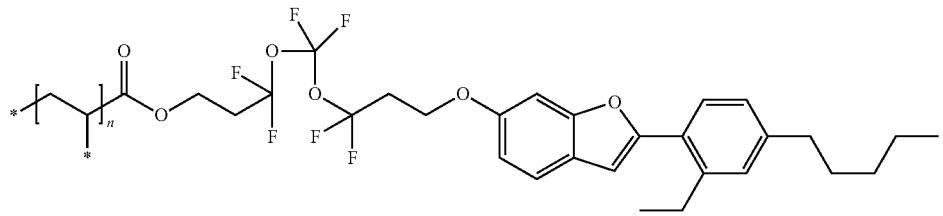
P-230
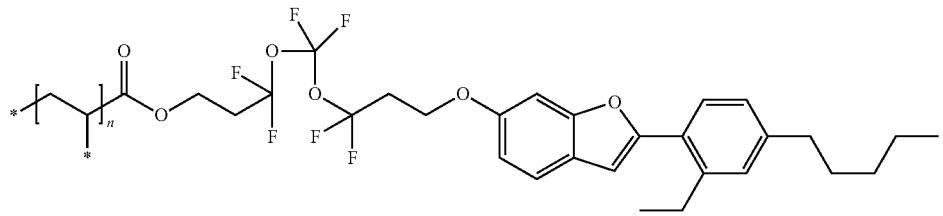
P-231
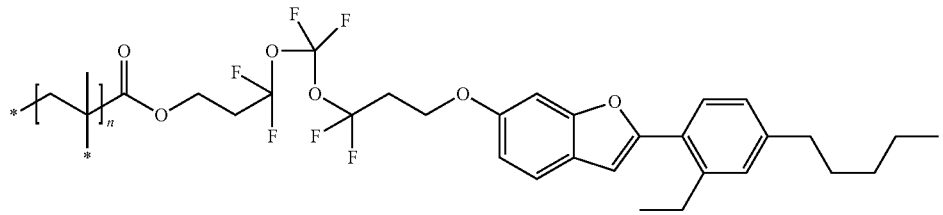
P-232
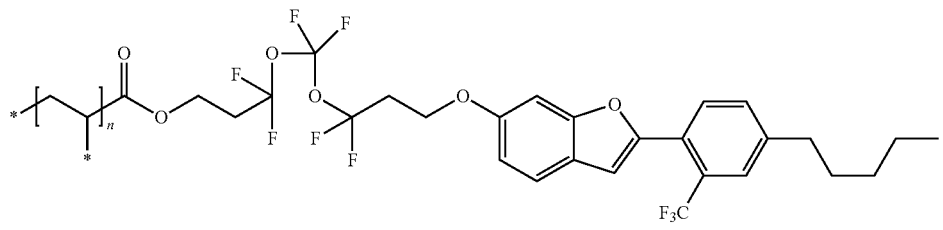
P-233
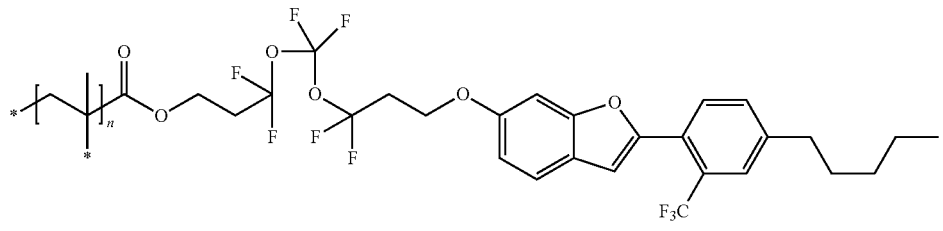

-continued
P-234
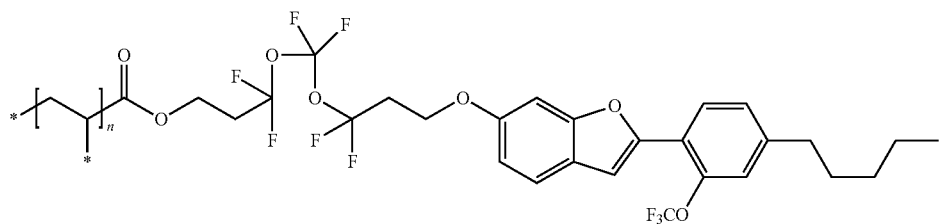
P-235
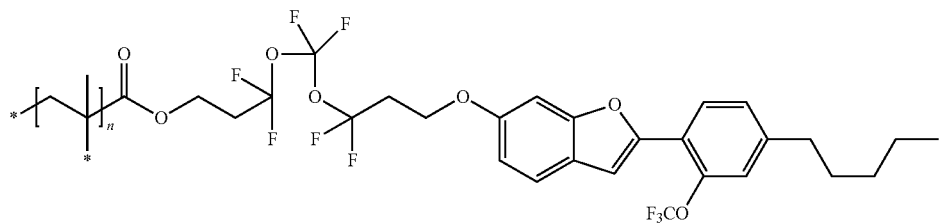
P-236
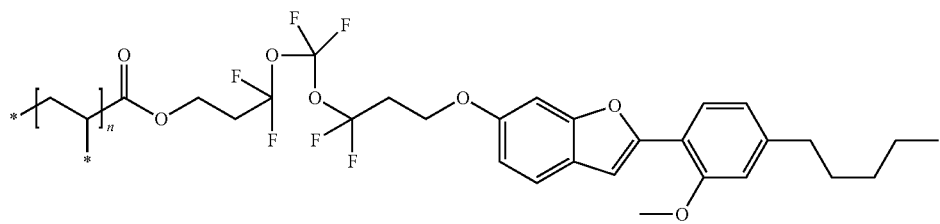
P-237
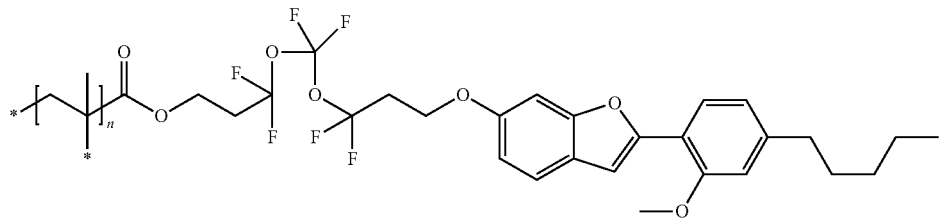
P-238 P-239
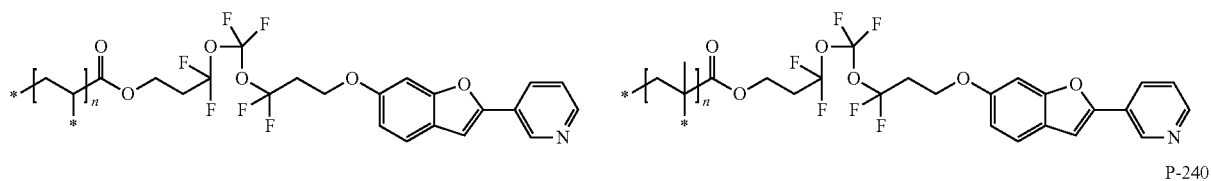
P-240
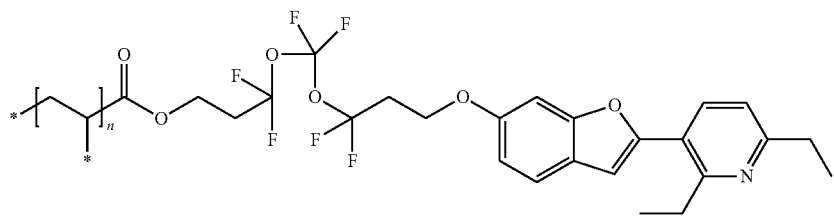
P-241
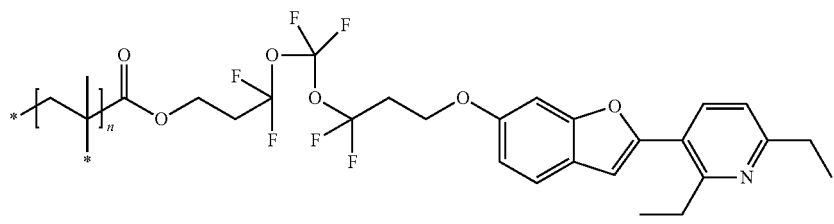

-continued
P-242
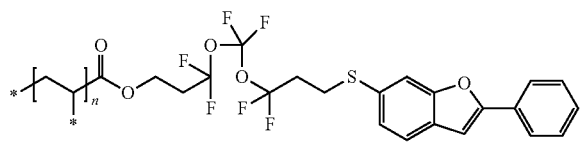
P-243
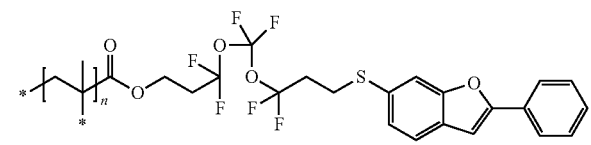
P-244
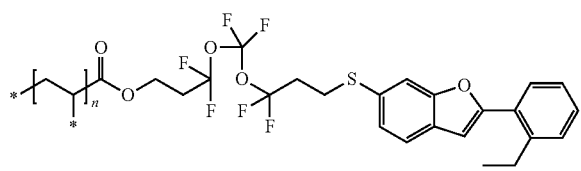
P-245
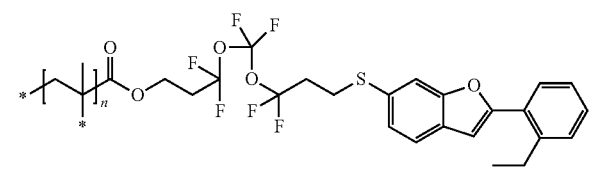
P-246
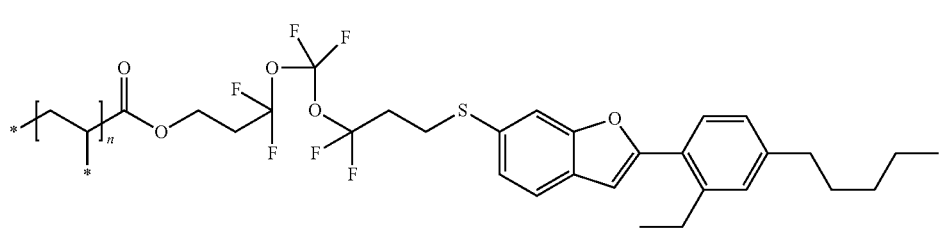
P-247
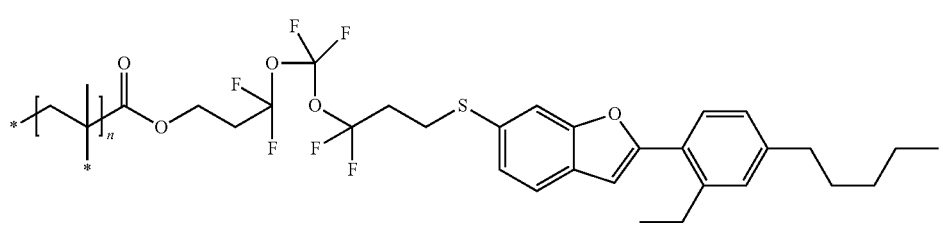
P-248
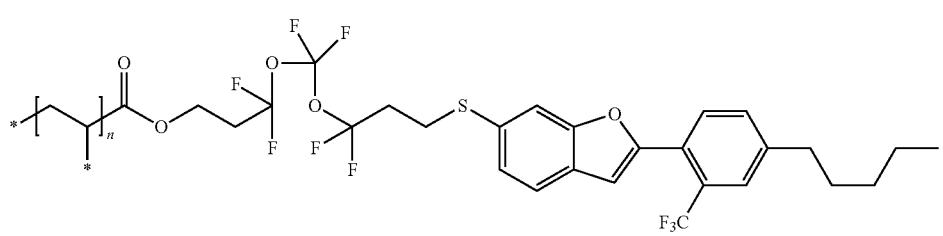
P-249
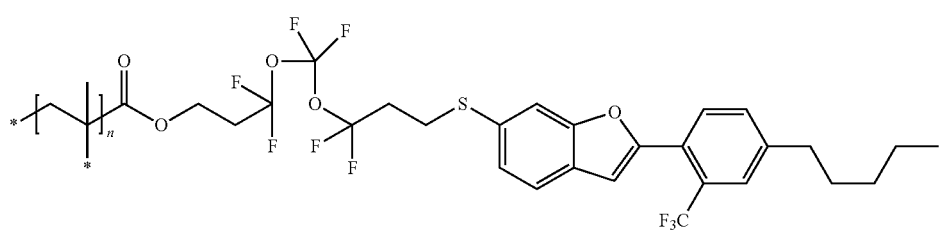
P-250
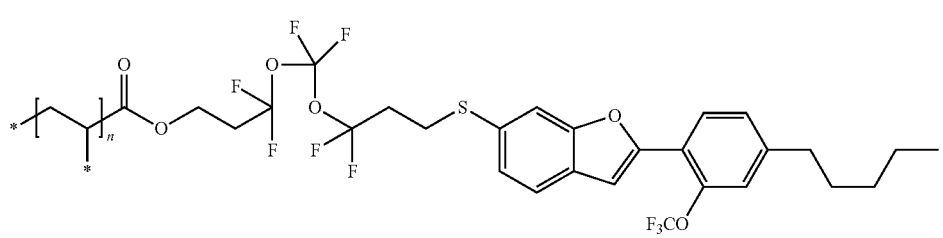

-continued
P-251
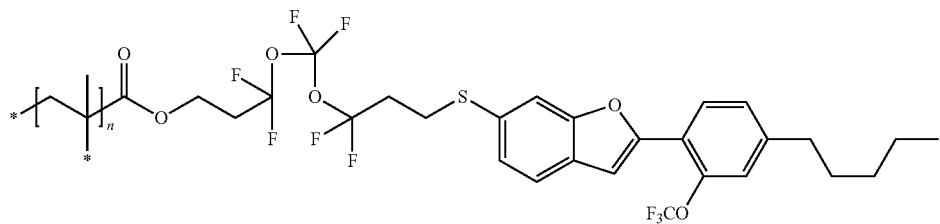
P-252
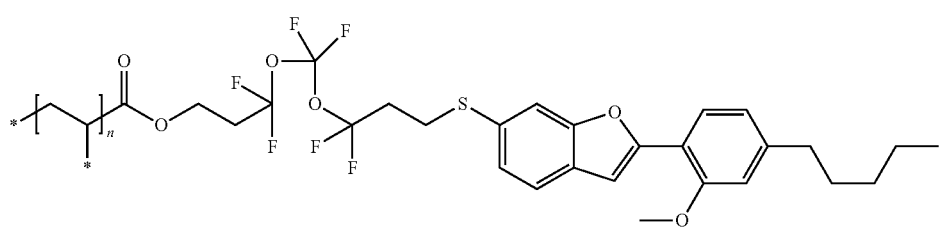
P-253
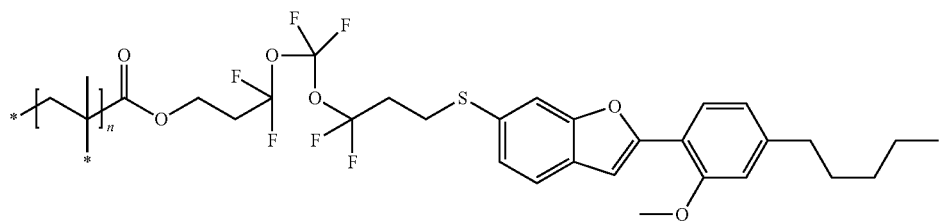
P-254 P-255
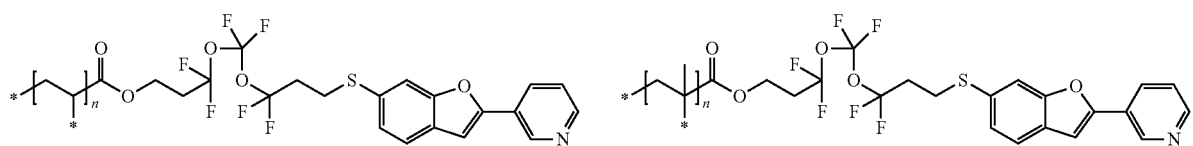
P-256
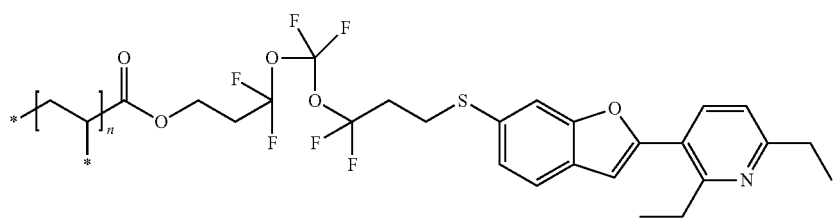
P-257
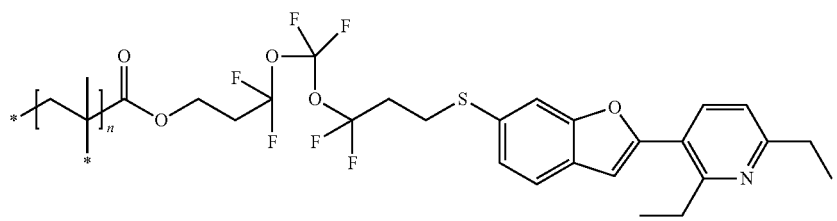
P-258
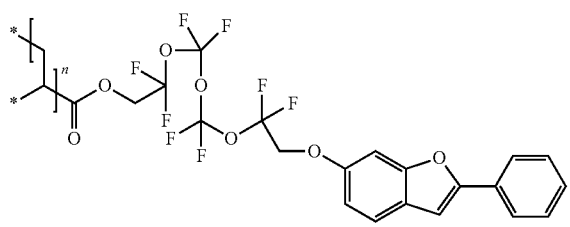
P-259
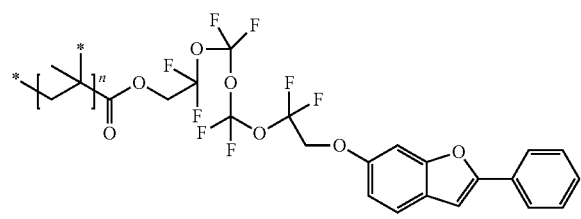

-continued
P-260
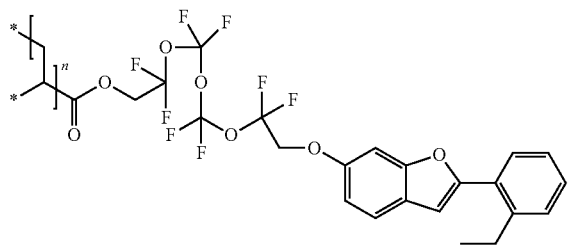
P-261
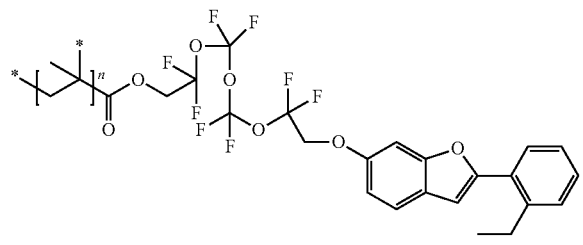
P-262
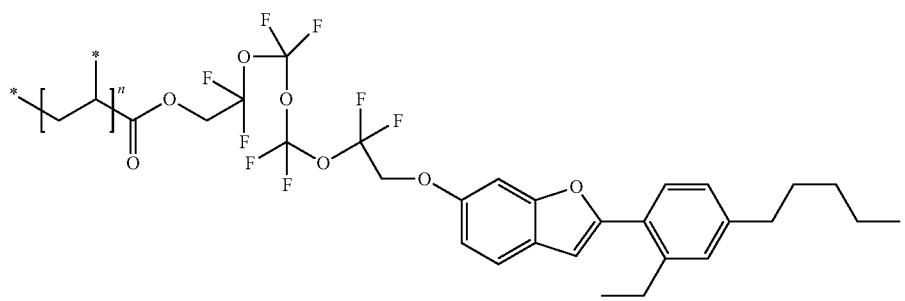
P-263
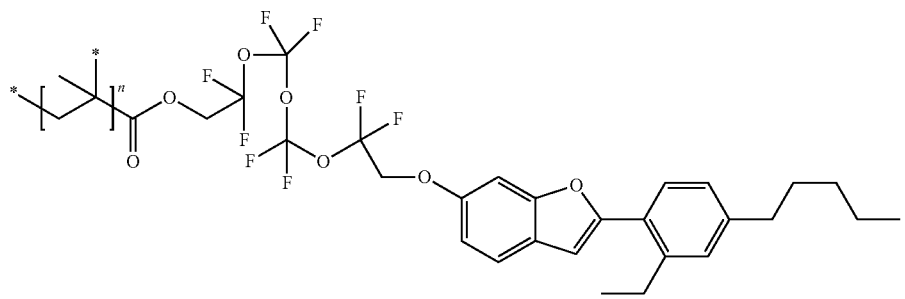
P-264
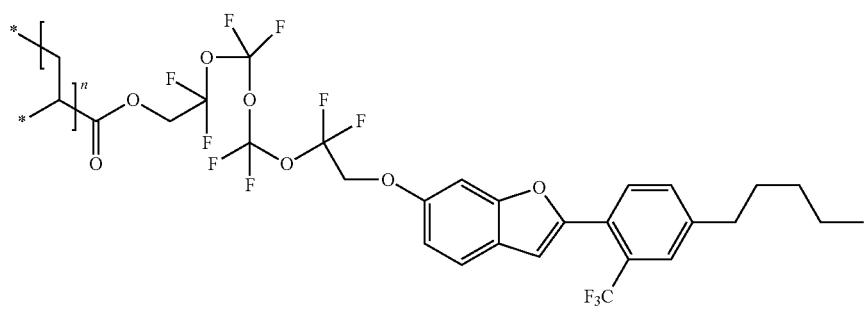
P-265
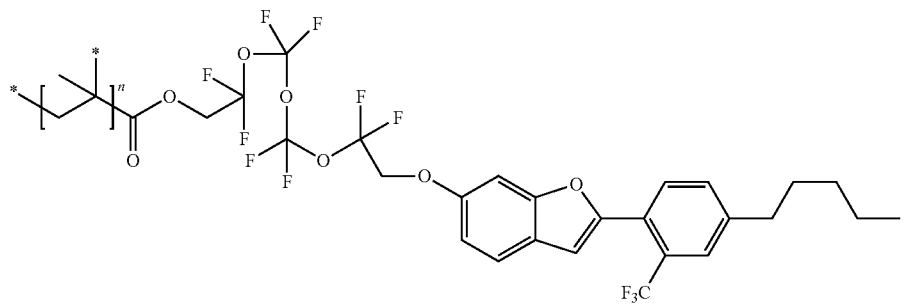

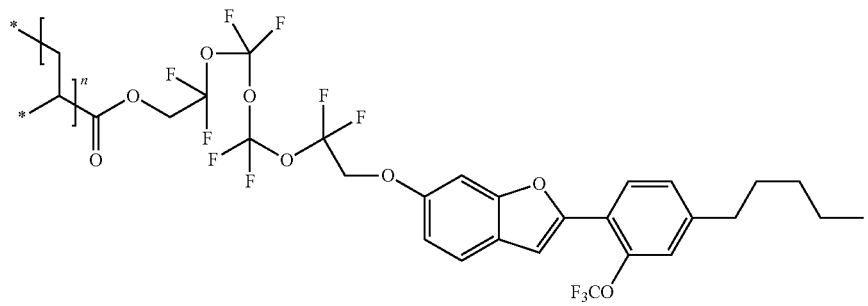
P-266
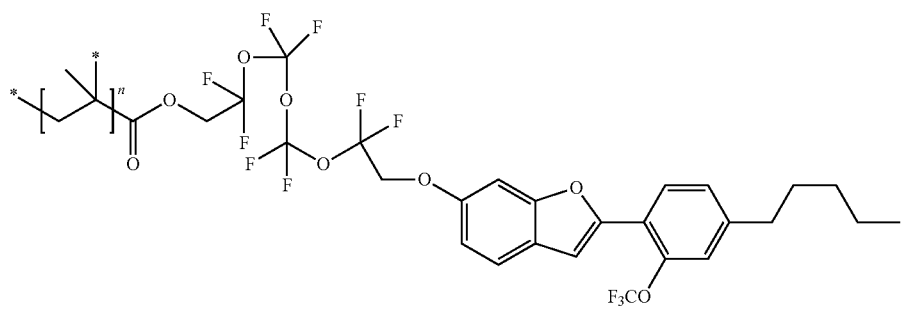
P-267
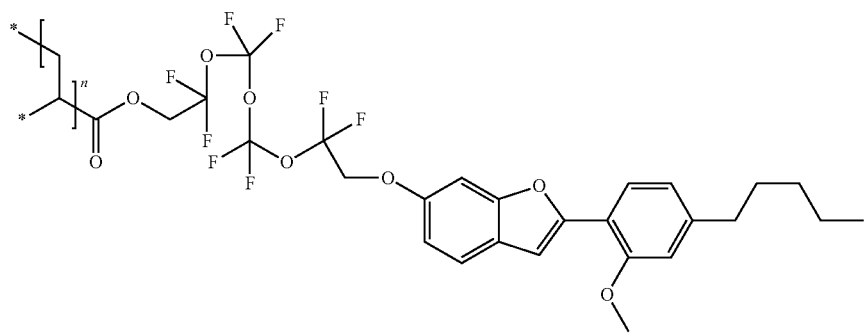
P-268
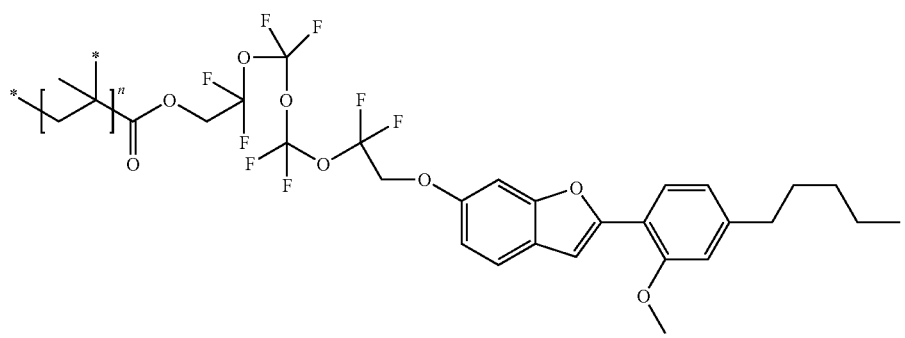
P-269
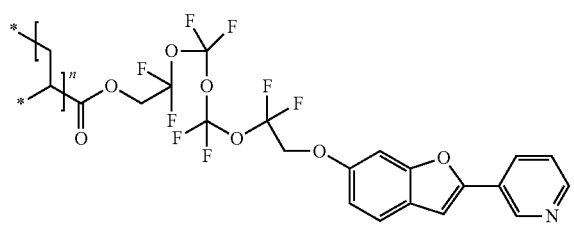
P-270
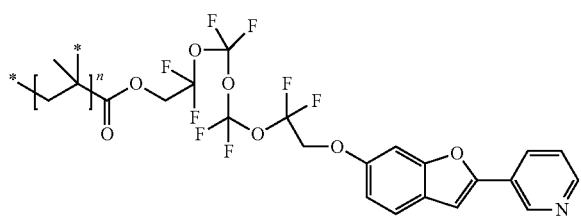
P-271

-continued
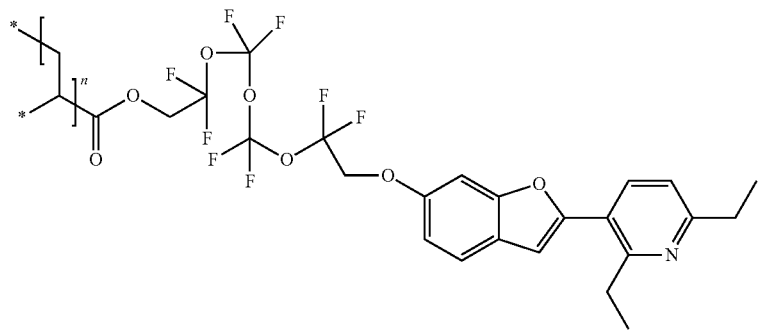
P-272
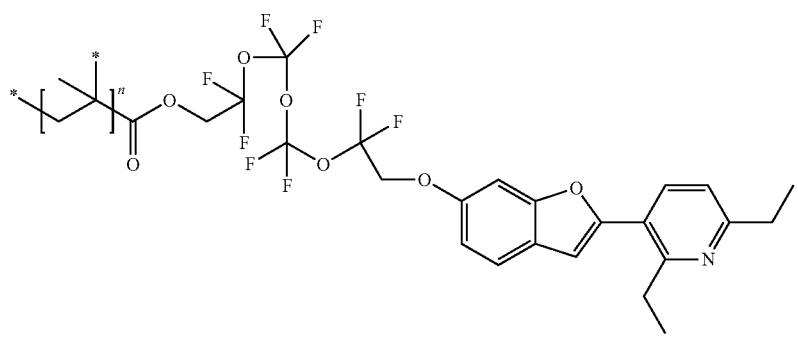
P-273
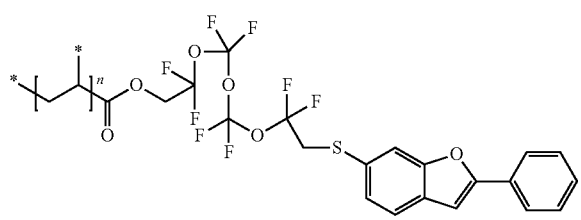
P-274
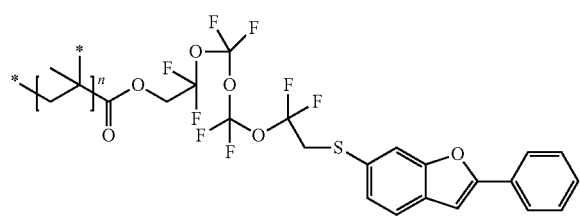
P-275
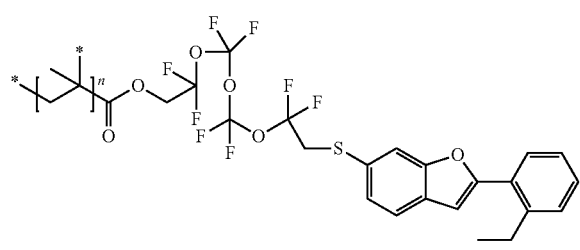
P-277
P-276
P-278

-continued
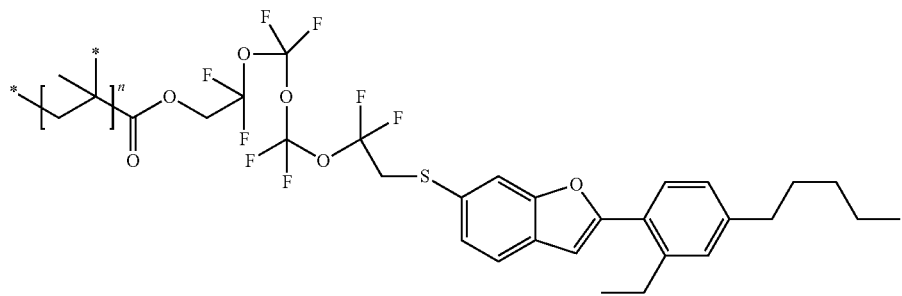
P-279
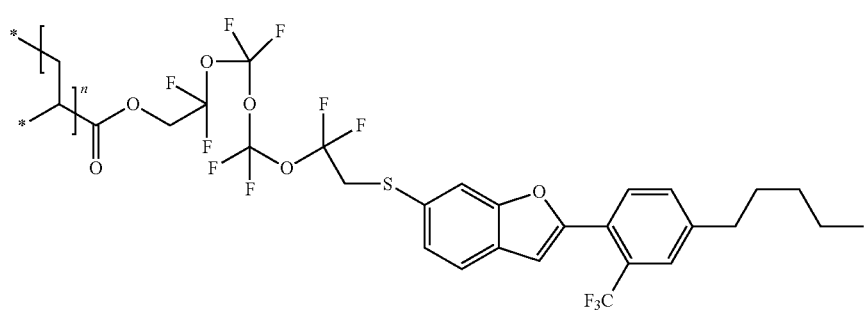
P-280
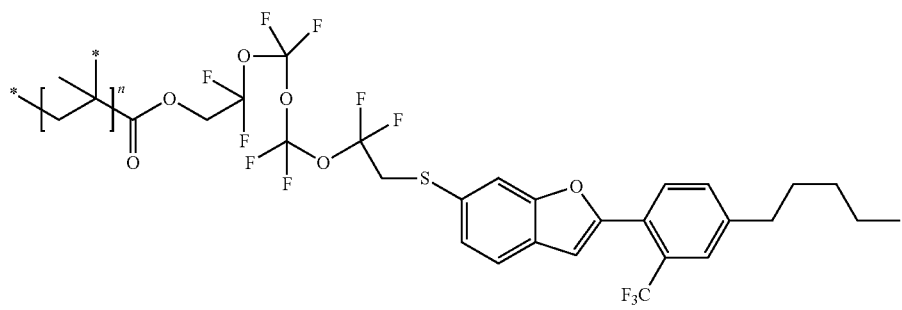
P-281
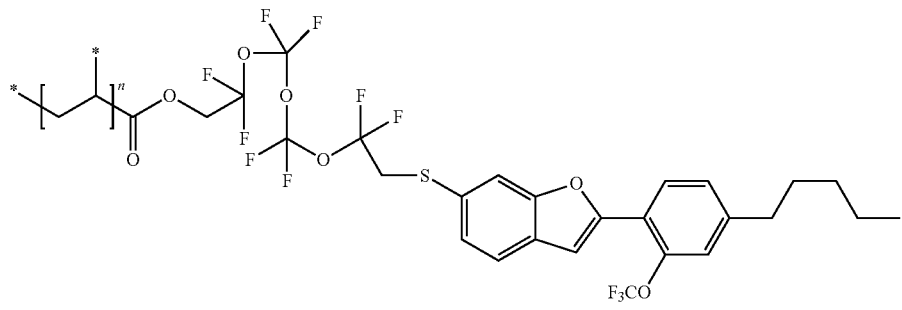
P-282
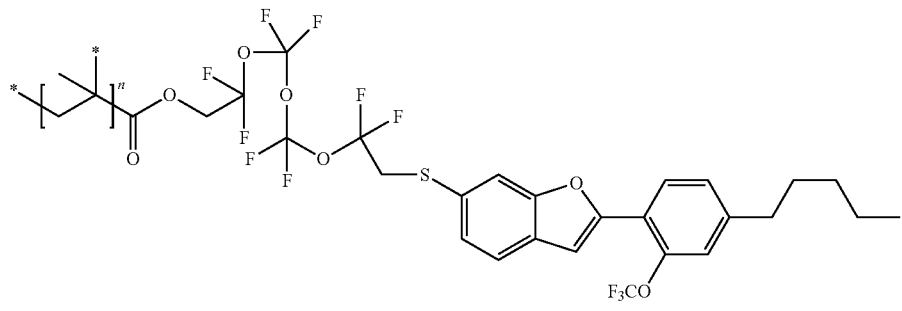
P-283

-continued
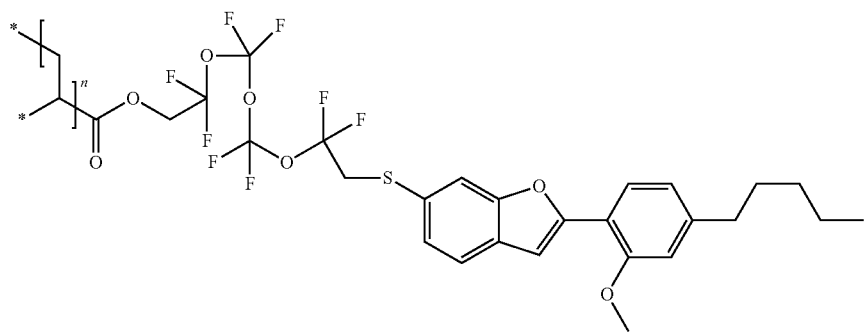
P-284
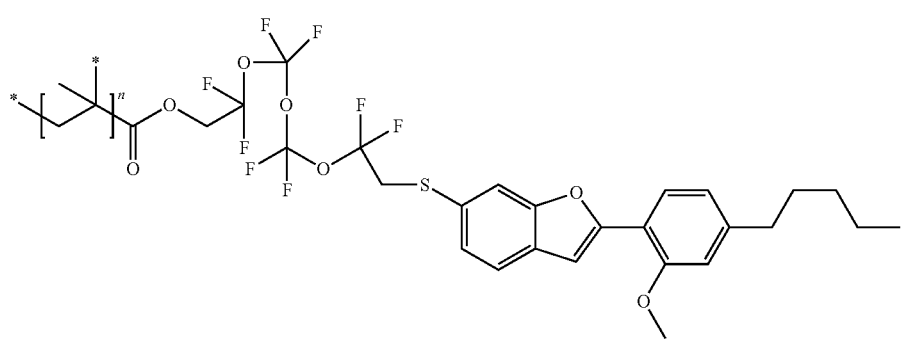
P-285
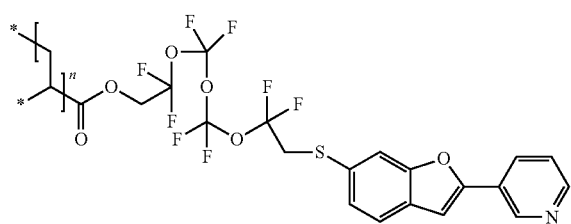
P-286
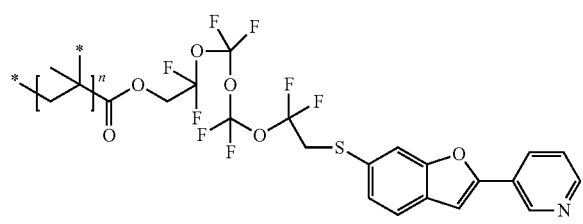
P-287
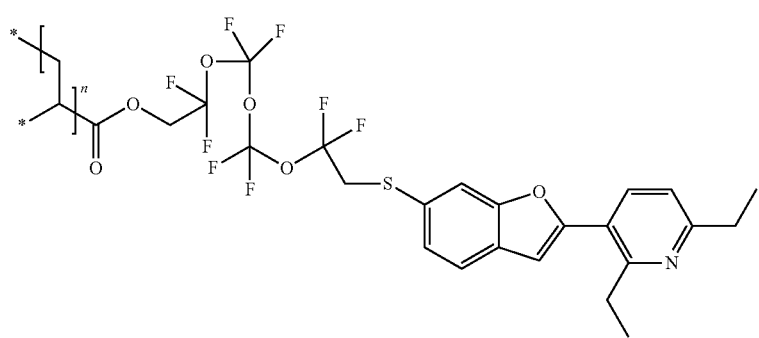
P-288
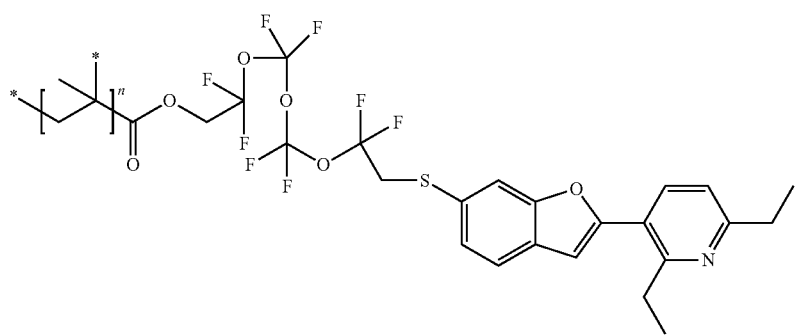
P-289

-continued
P-290
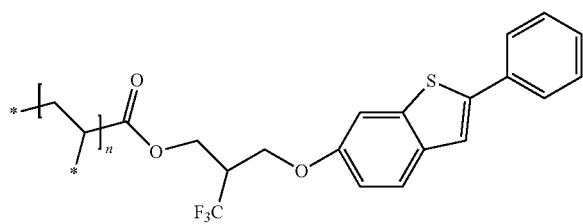
P-291
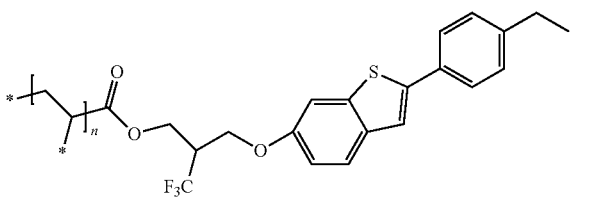
P-292
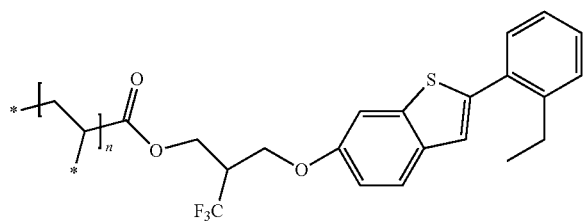
P-293
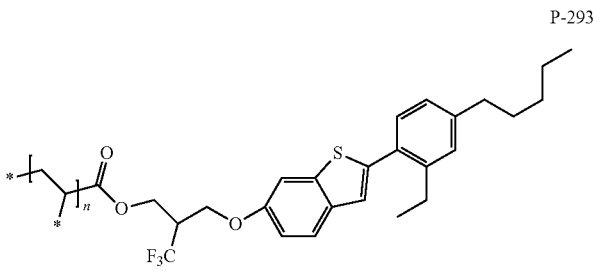
P-294
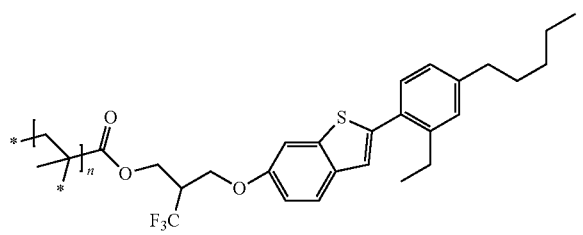
P-295
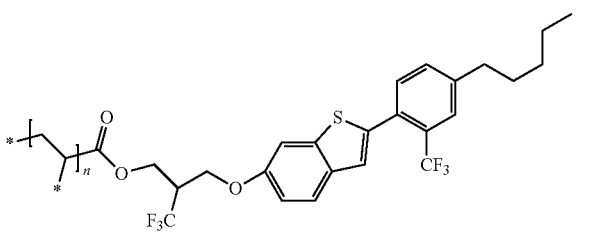
P-296
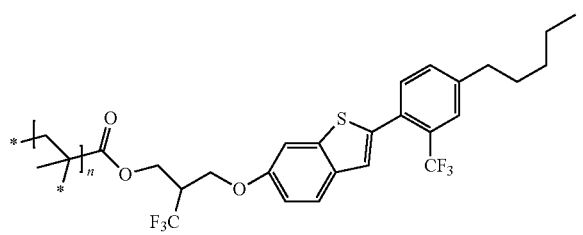
P-297
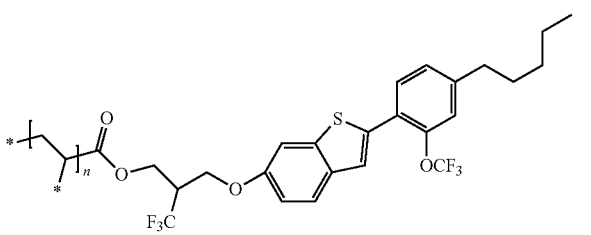
P-298
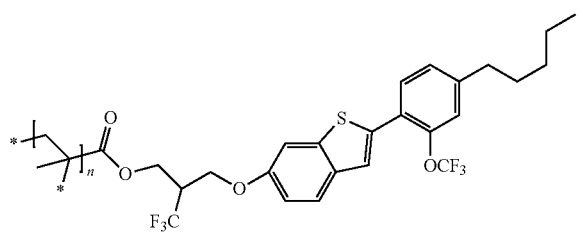
P-299
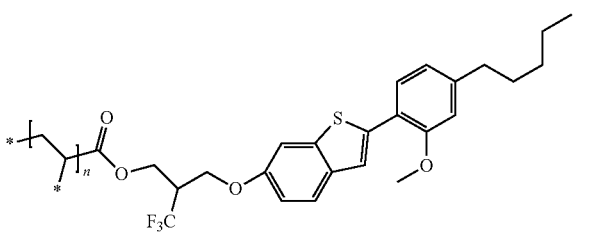
P-300
P-301

-continued
P-302
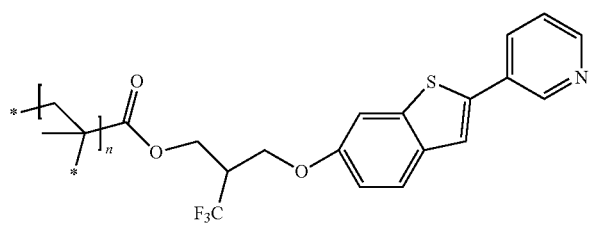
P-303
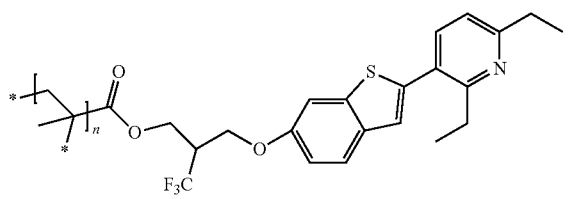
P-304
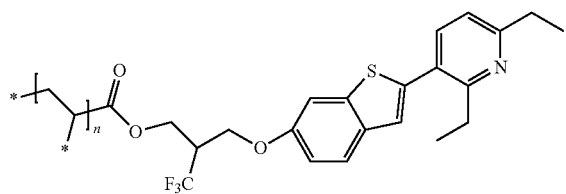
P-305
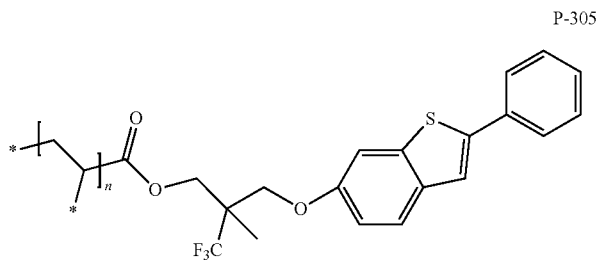
P-306
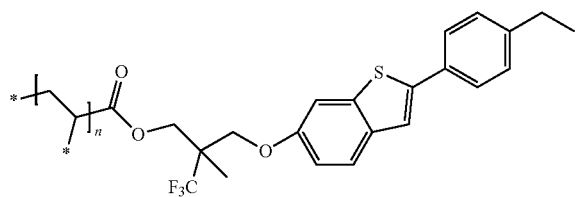
P-307
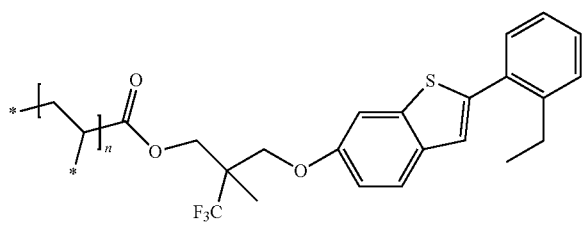
P-308
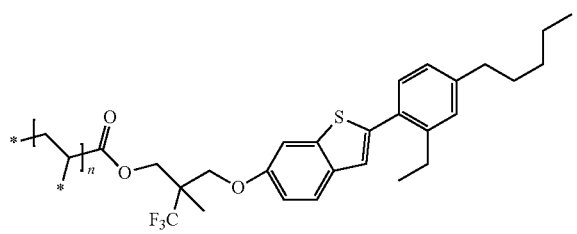
P-309
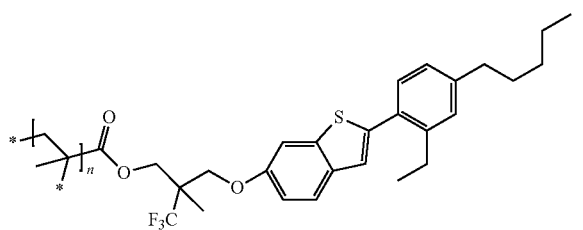
P-310
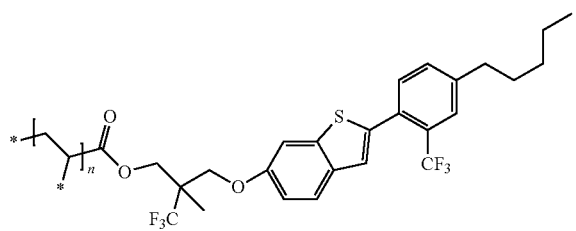
P-311
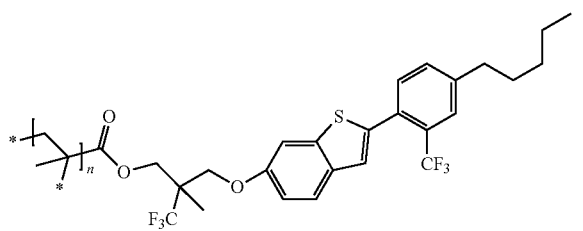
P-312
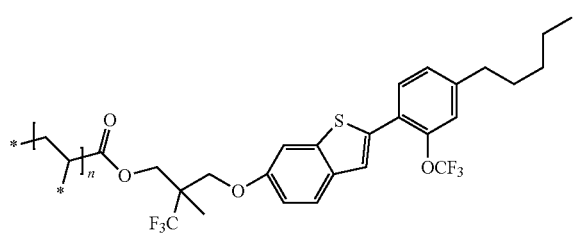
P-313
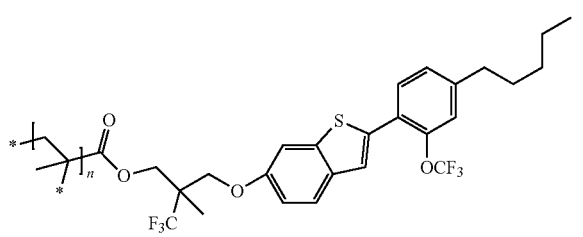

-continued
P-314
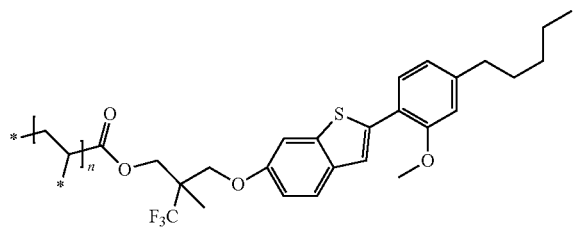
P-315
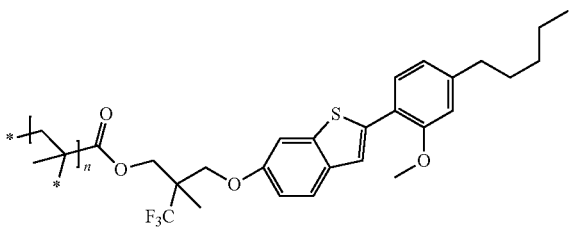
P-316
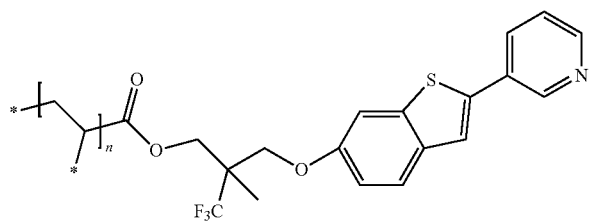
P-317
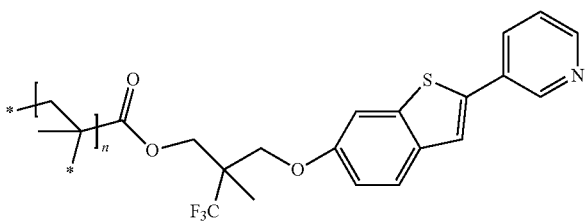
P-318
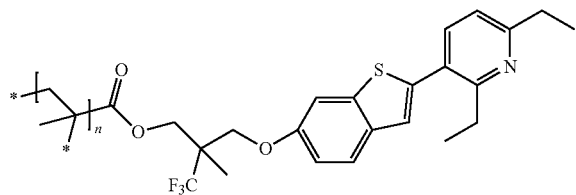
P-319
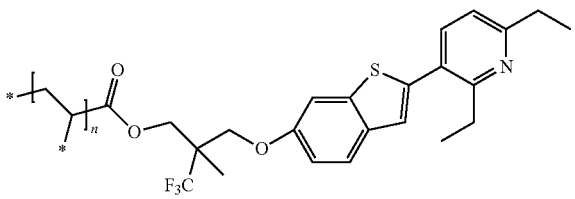
P-320
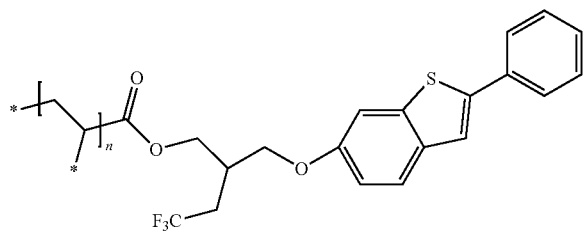
P-321
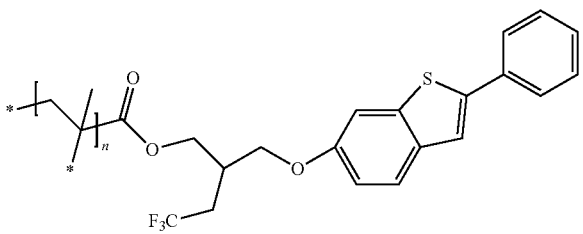
P-322
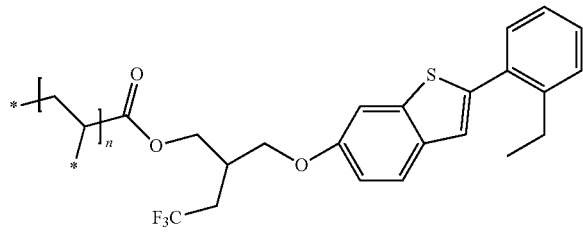
P-323
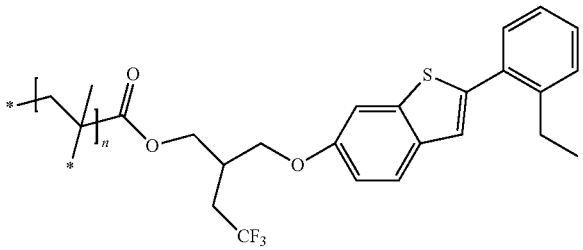
P-324
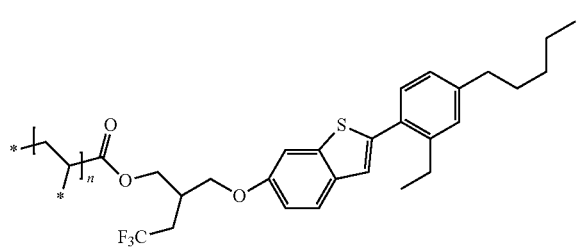
P-325
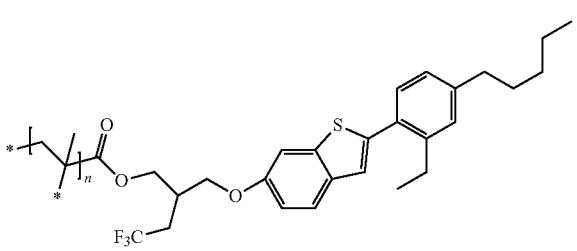

-continued
P-326
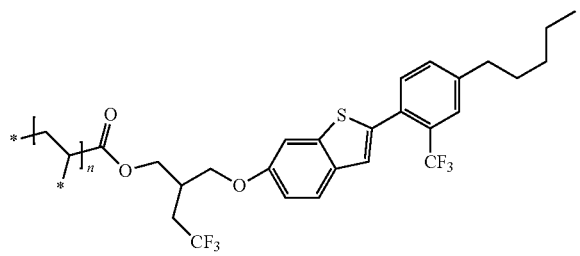
P-327
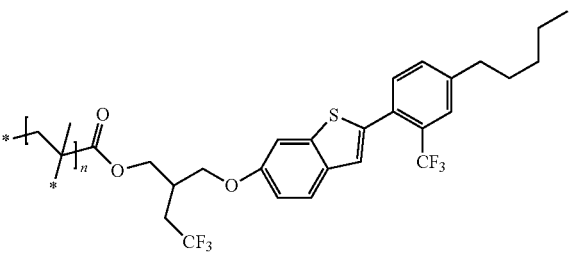
P-328
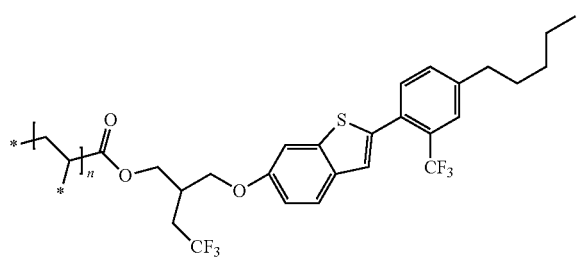
P-329
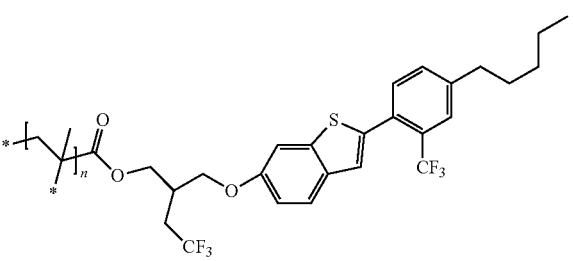
P-330
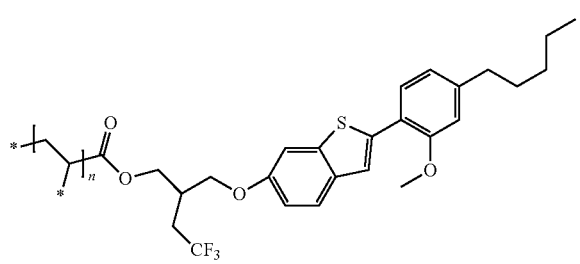
P-331
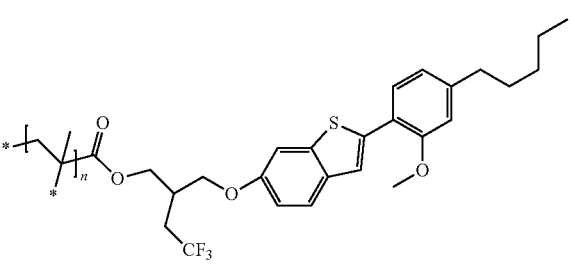
P-332
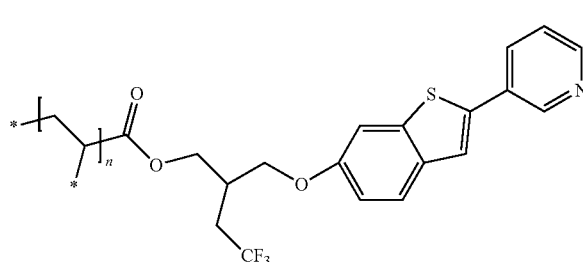
P-333
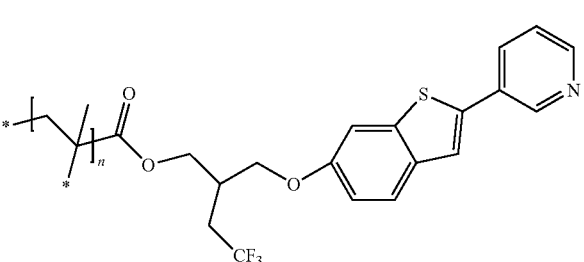
P-334
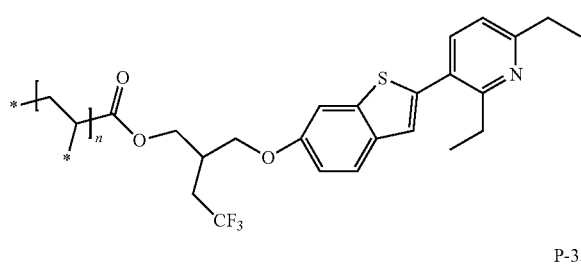
P-335
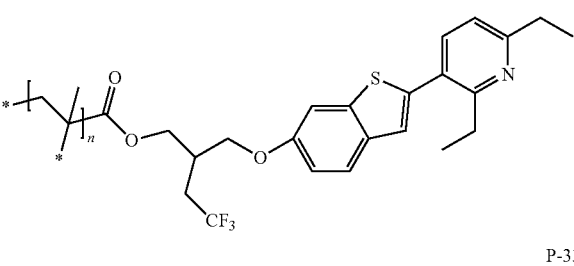
P-336
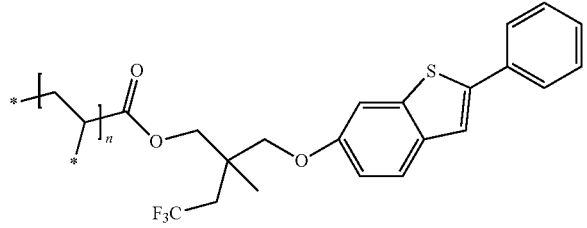
P-337
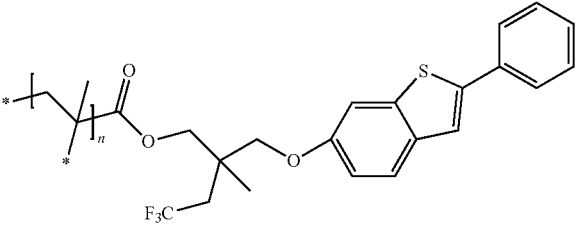

-continued
P-338
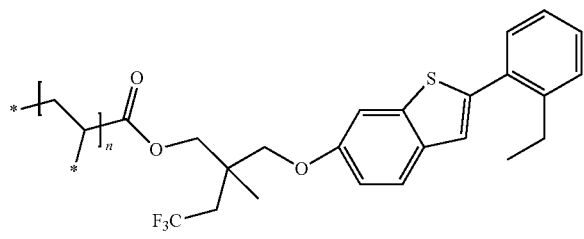
P-339
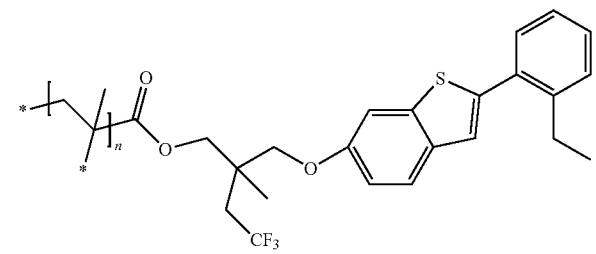
P-340
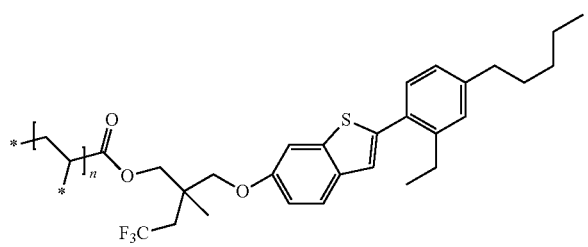
P-341
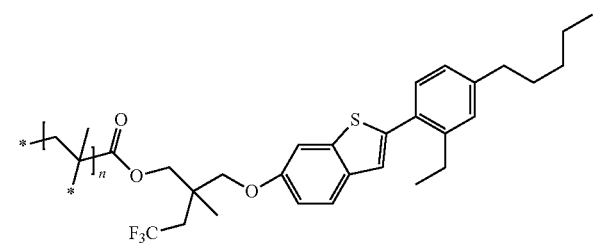
P-342
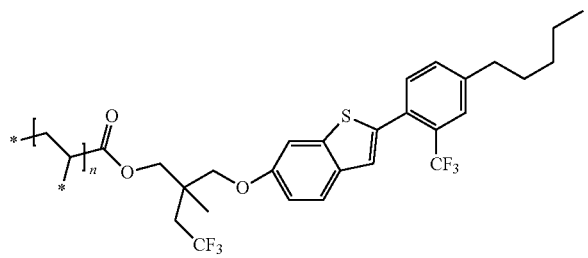
P-343
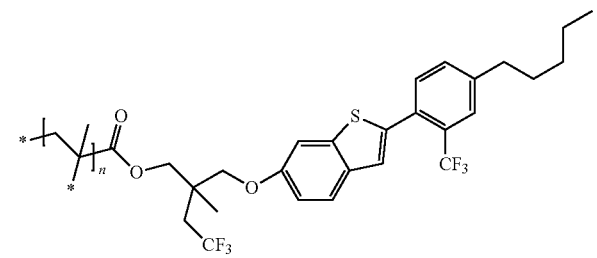
P-344
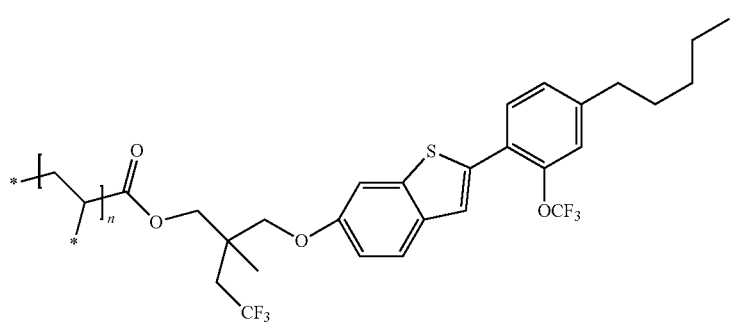
P-345
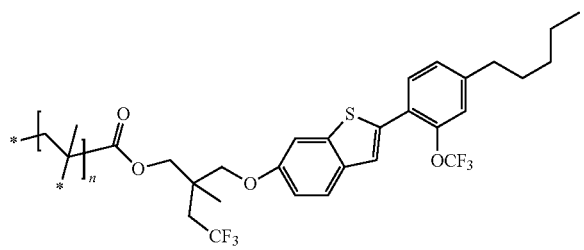
P-346
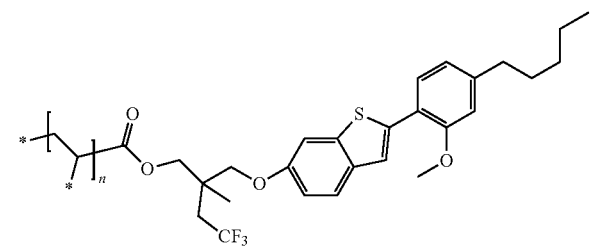

-continued
P-347
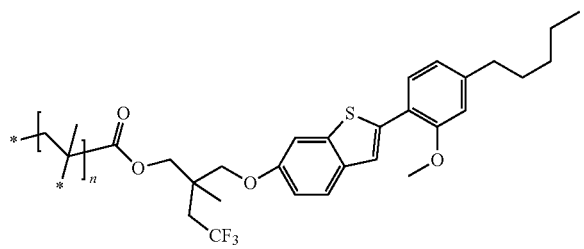
P-348
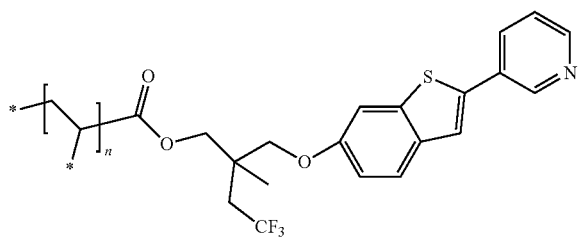
P-349
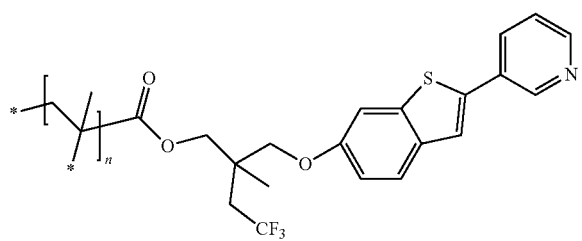
P-350
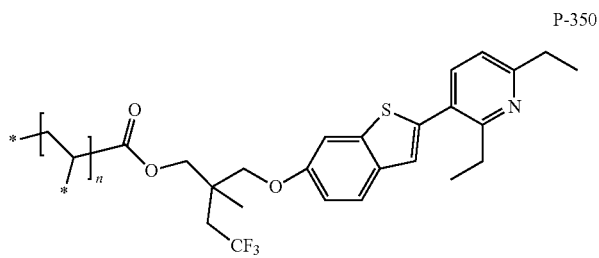
P-351
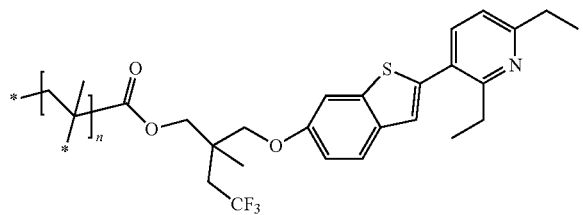
P-352
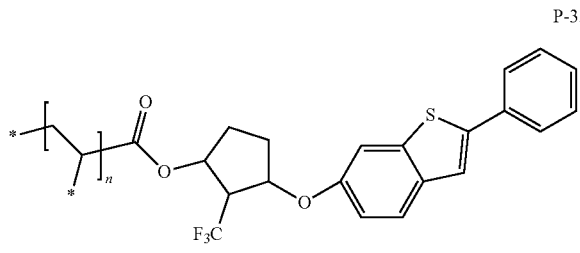
P-353
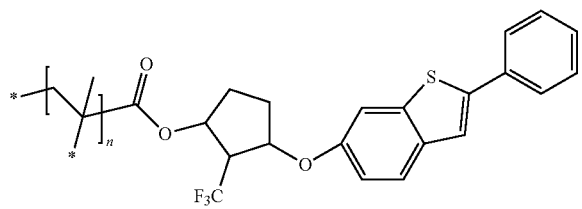
P-354
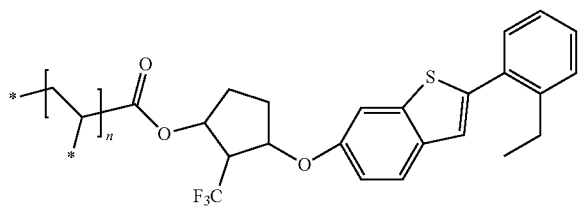
P-355
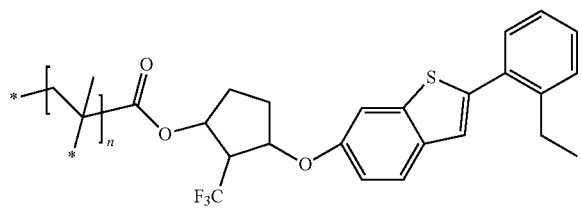
P-356
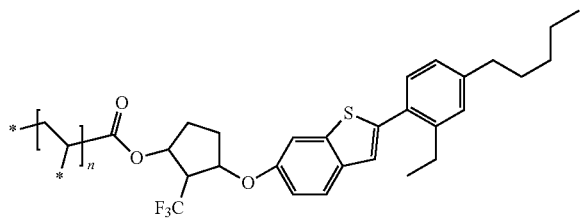
P-357
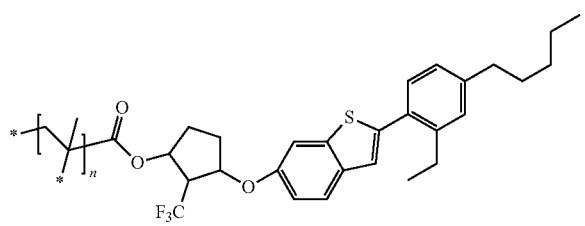
P-358
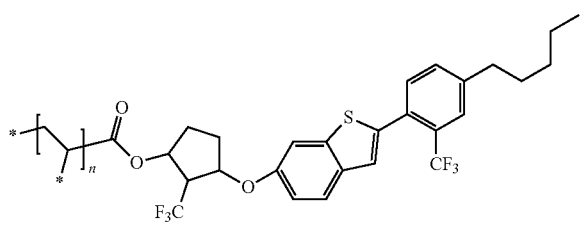

-continued
P-359
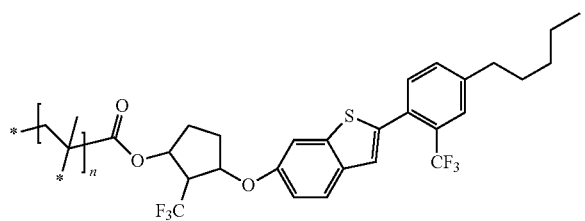
P-360
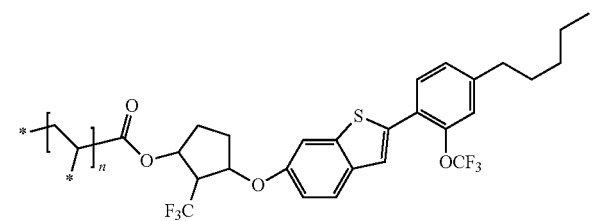
P-361
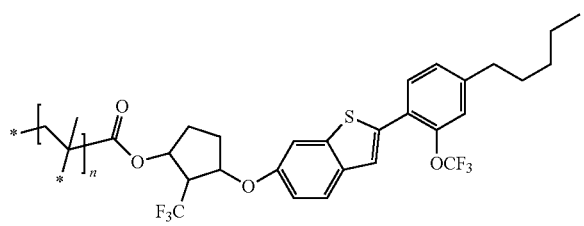
P-362
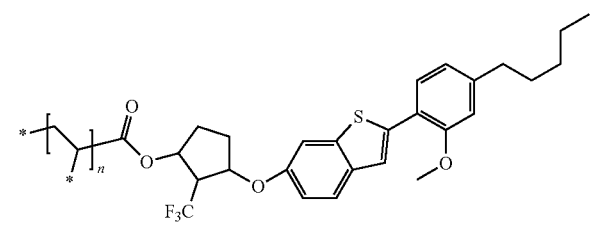
P-363
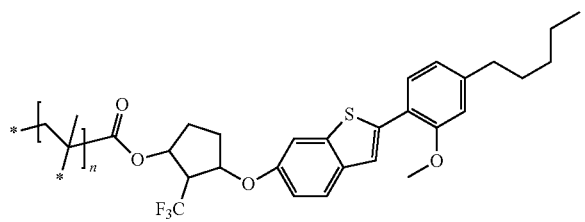
P-364
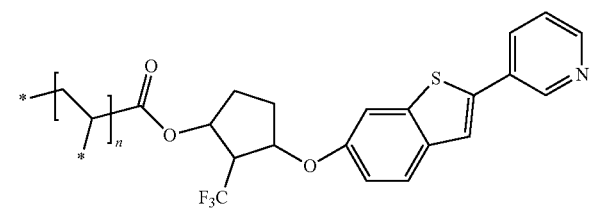
P-365
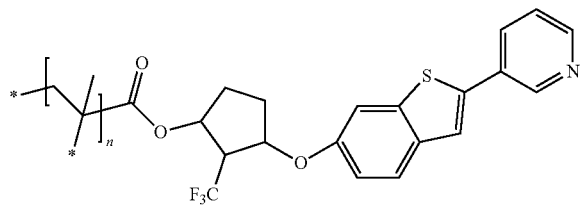
P-366
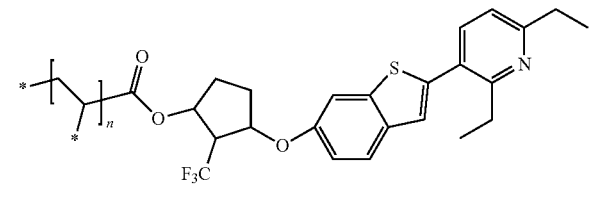
P-367
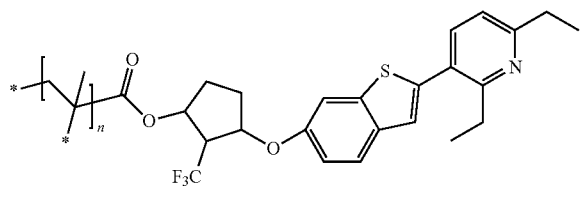
P-368
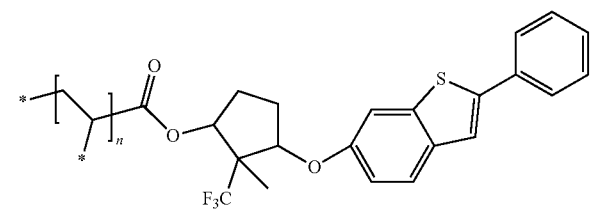
P-369
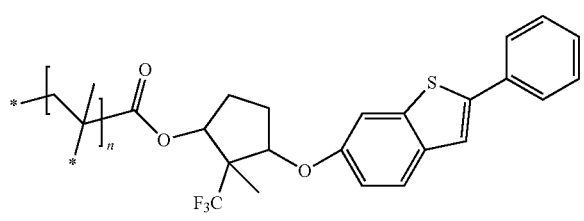
P-370
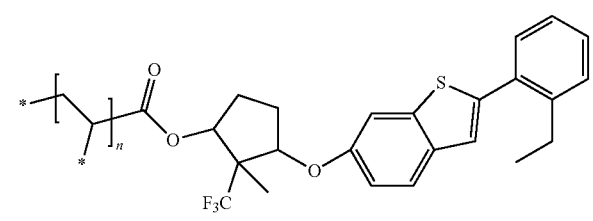

-continued
P-371
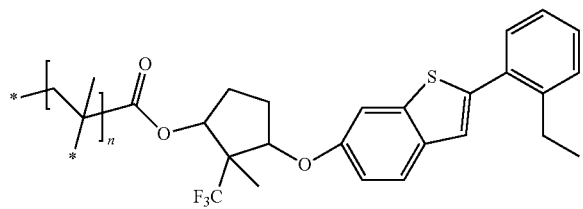
P-372
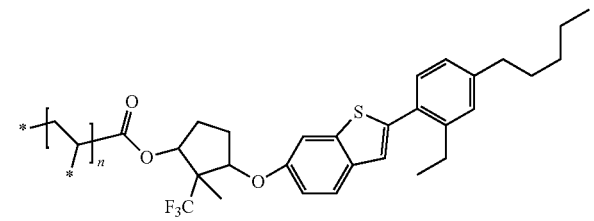
P-373
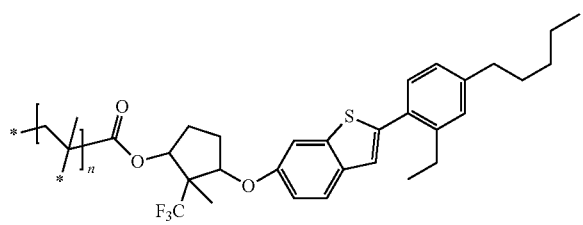
P-374
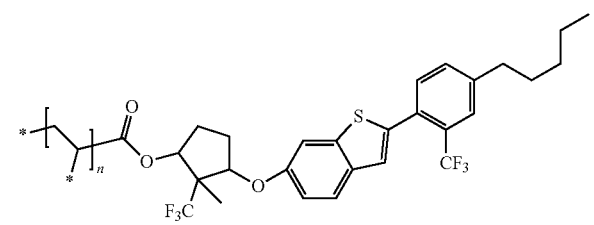
P-375
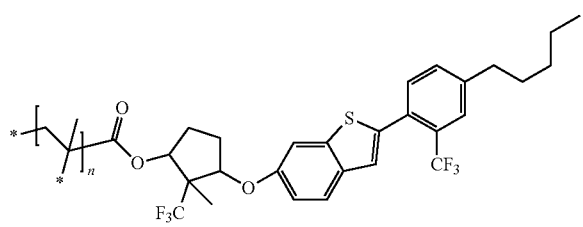
P-376
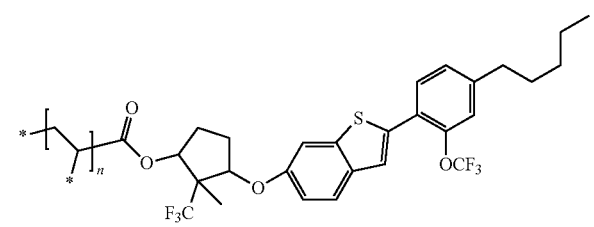
P-377
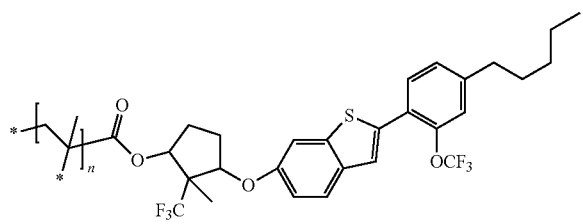
P-378
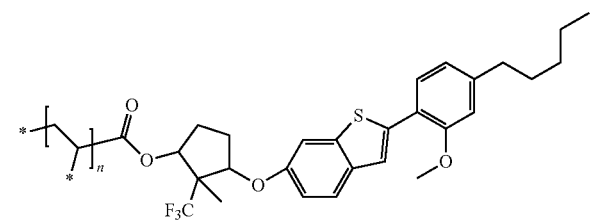
P-379
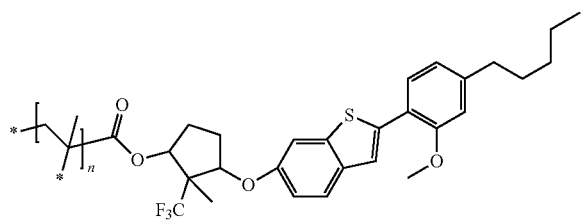
P-380
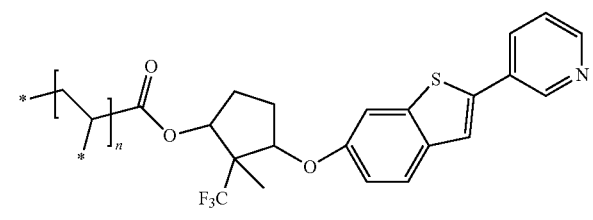
P-381
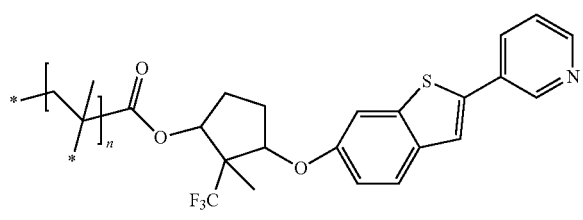
P-382
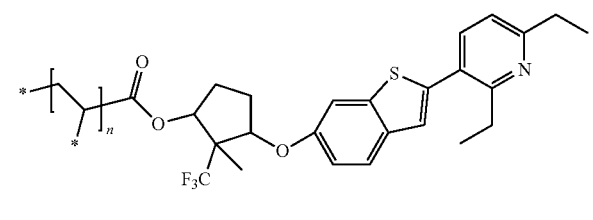

P-383
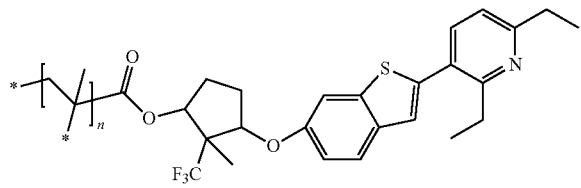
P-384
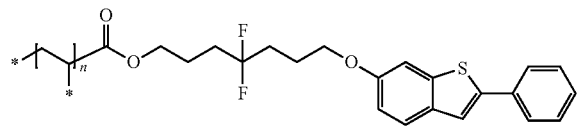
P-385
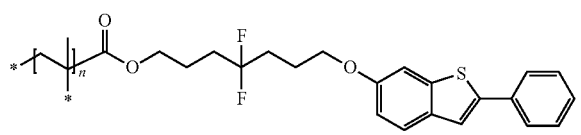
P-386
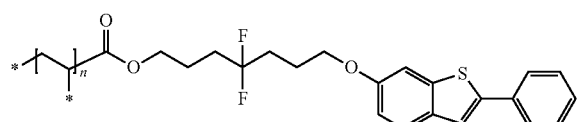
P-387
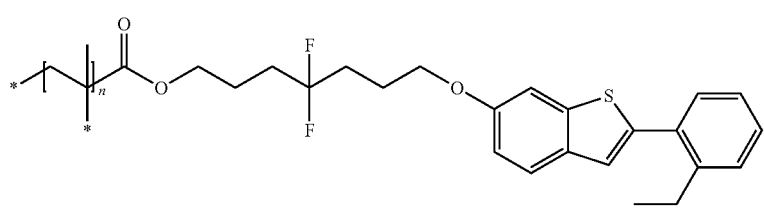
P-388
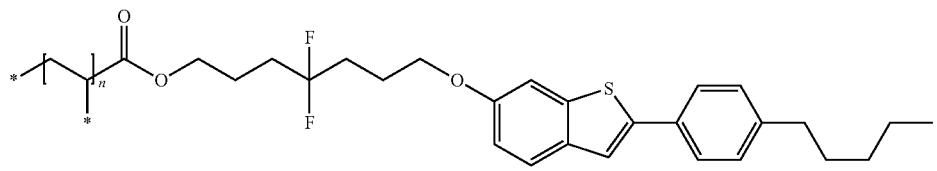
P-389
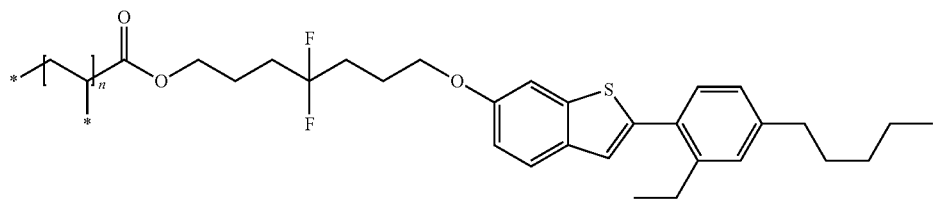
P-390
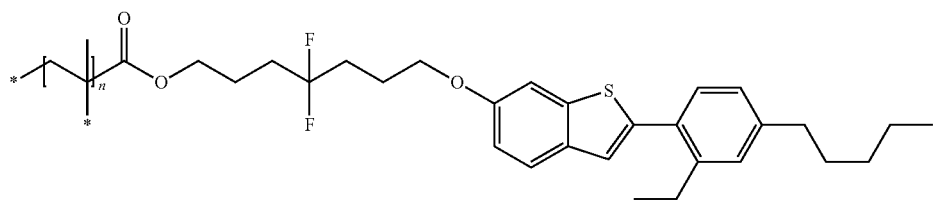
P-391
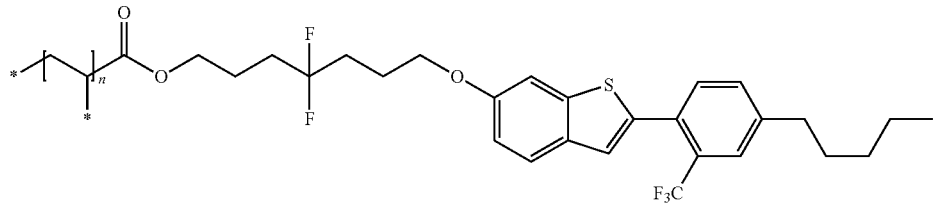
P-392
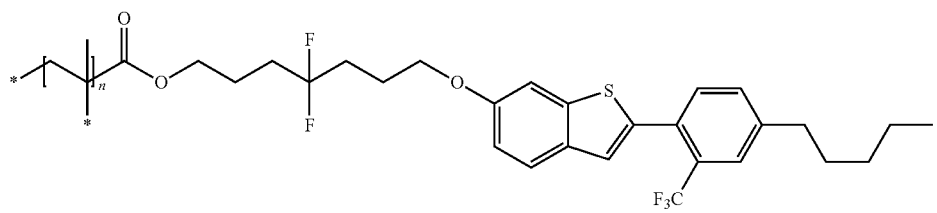

-continued
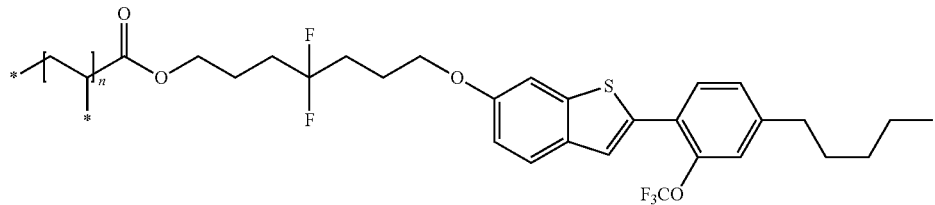
P-393
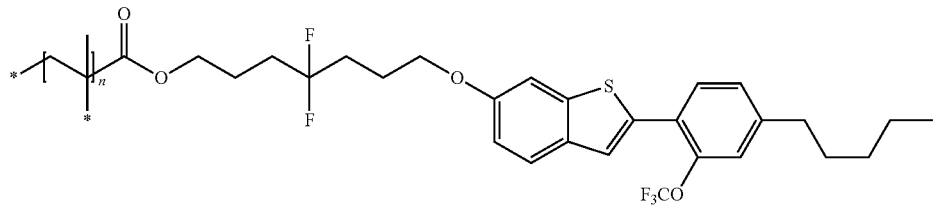
P-394
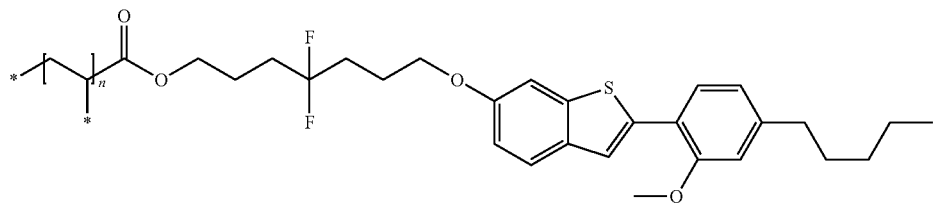
P-395
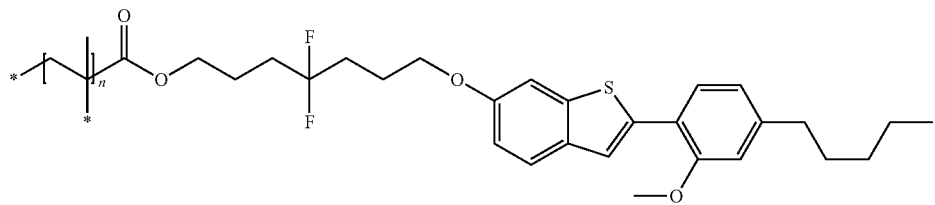
P-396
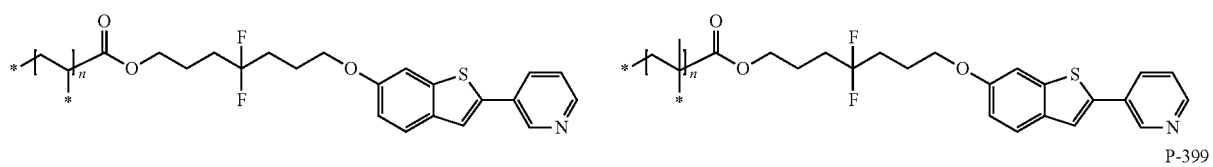
P-397        P-398
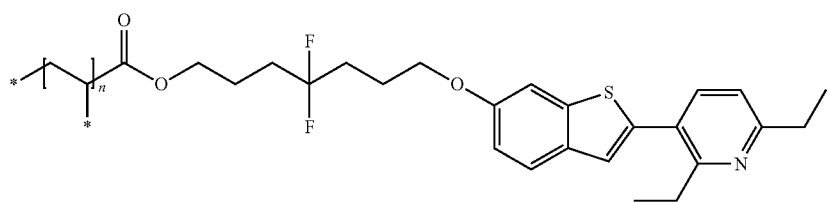
P-399
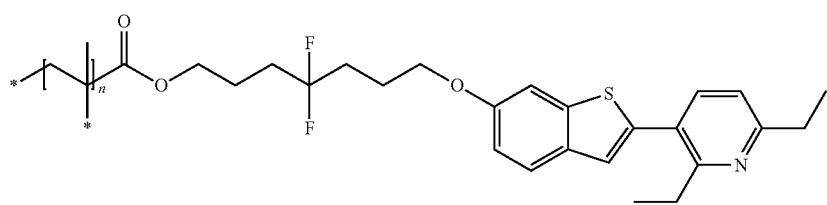
P-400

-continued
P-401
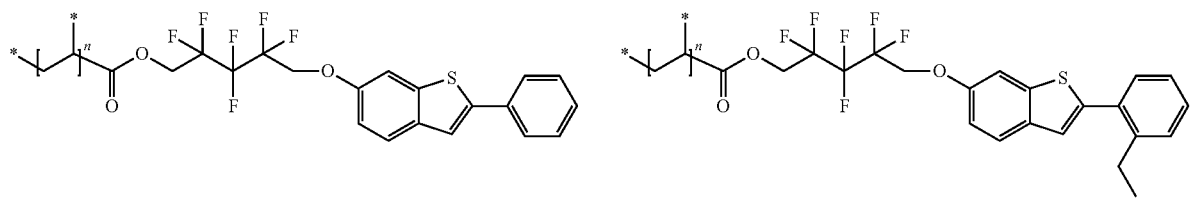
P-402
P-403
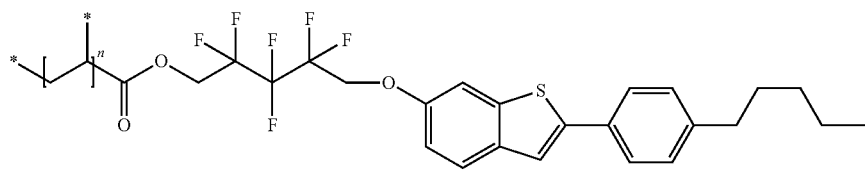
P-404
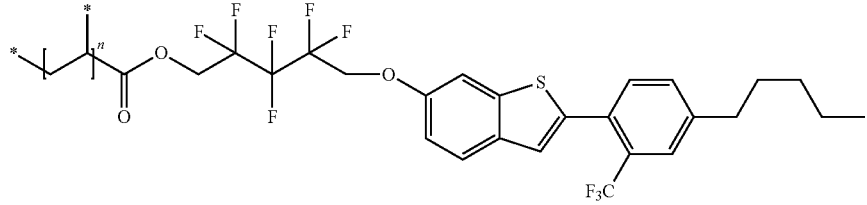
P-405
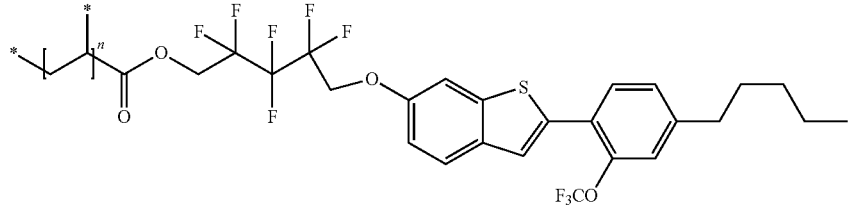
P-406
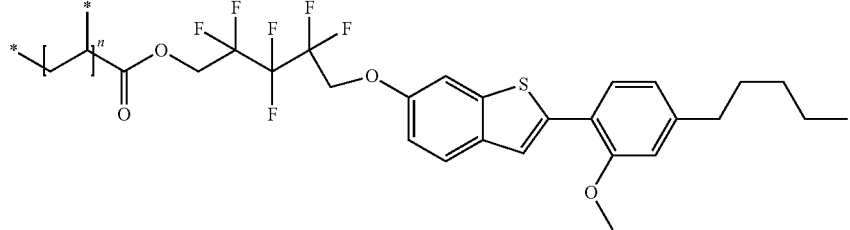
P-407
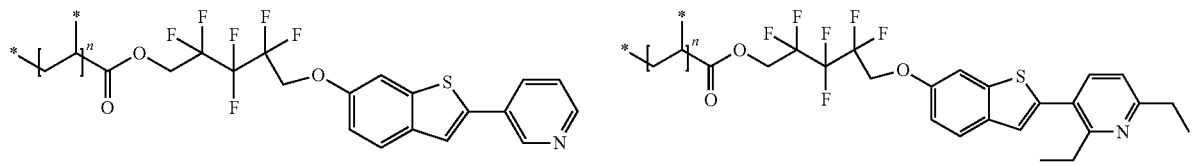
P-408
P-409
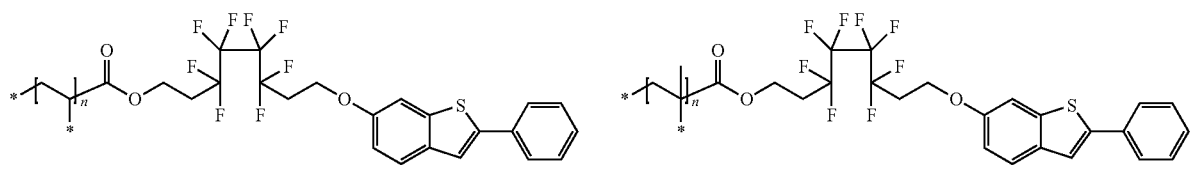
P-410

-continued
P-411
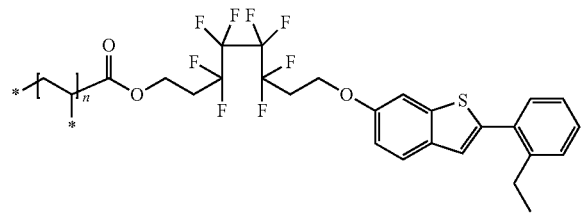
P-412
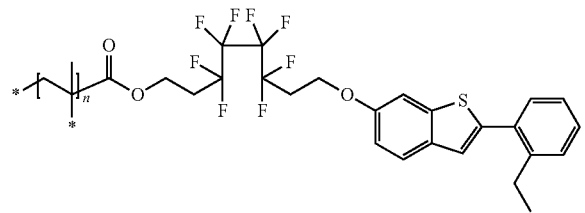
P-413
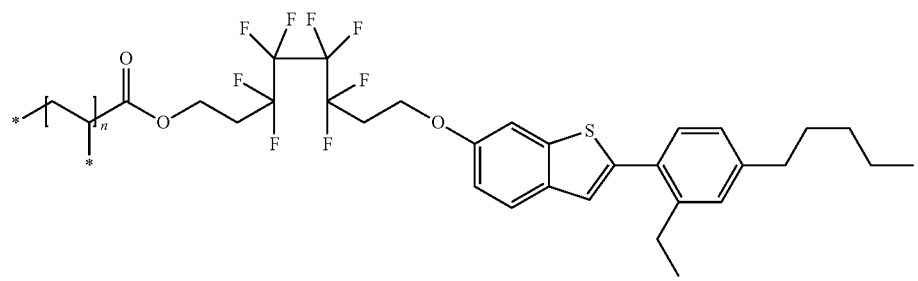
P-414
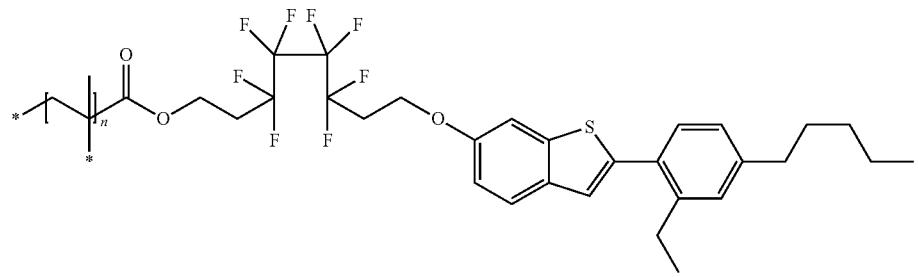
P-415
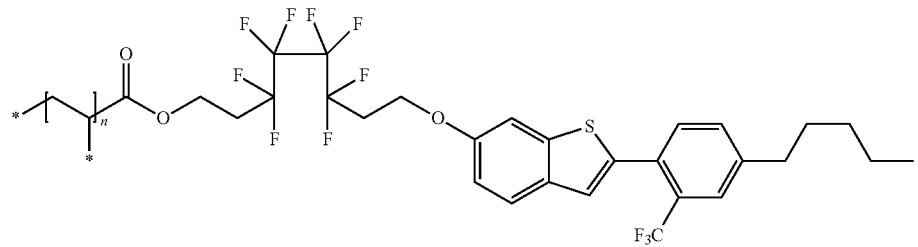
P-416
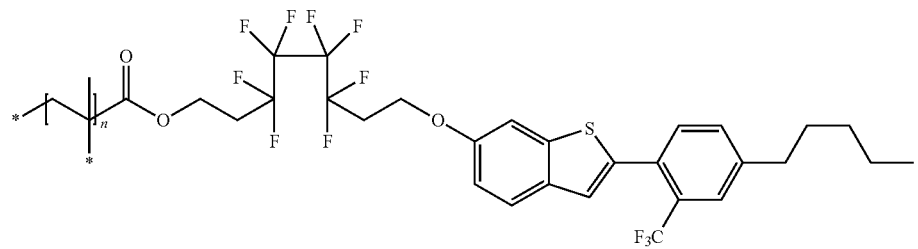
P-417
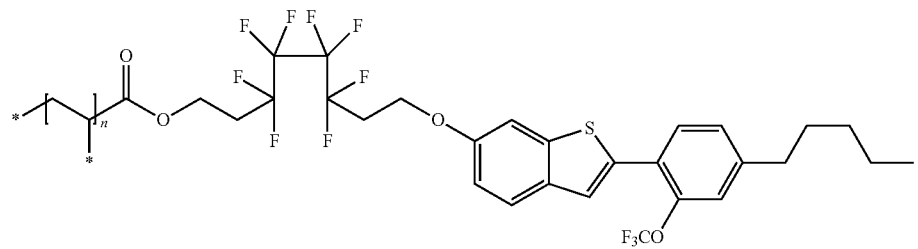

-continued
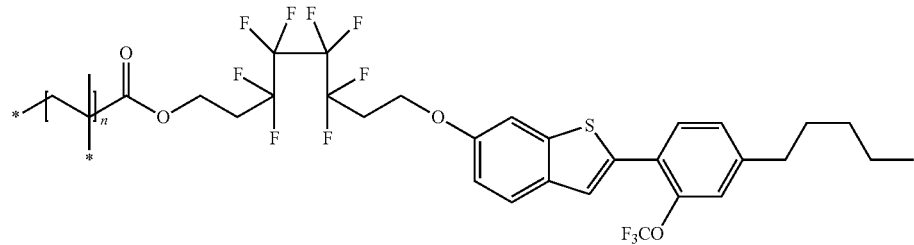
P-418
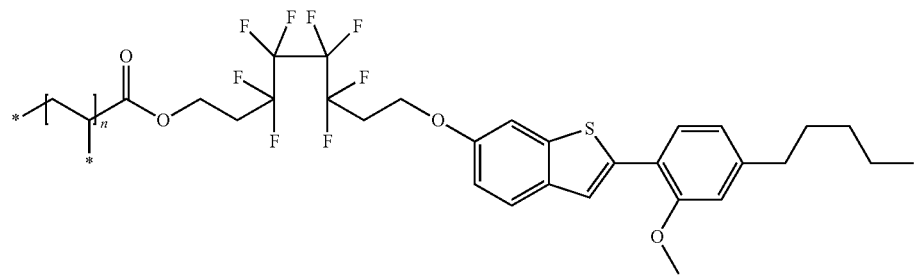
P-419
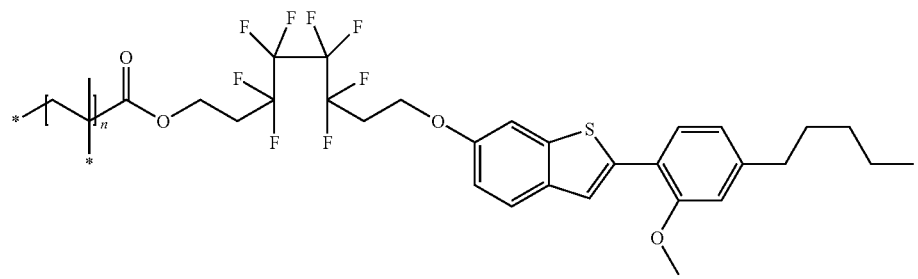
P-420
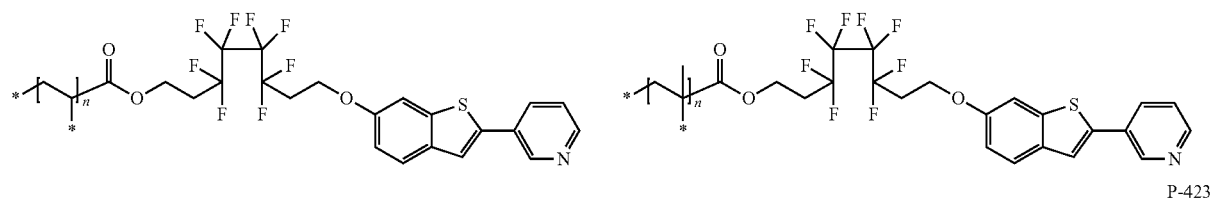
P-421    P-422
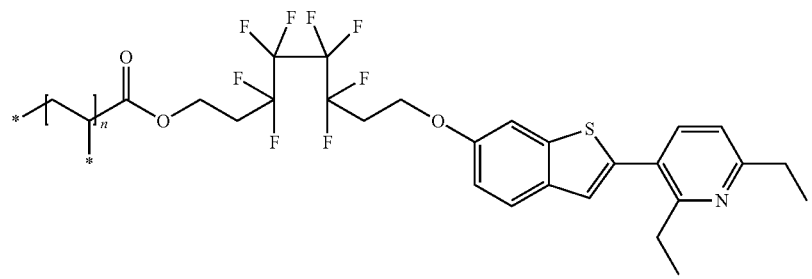
P-423
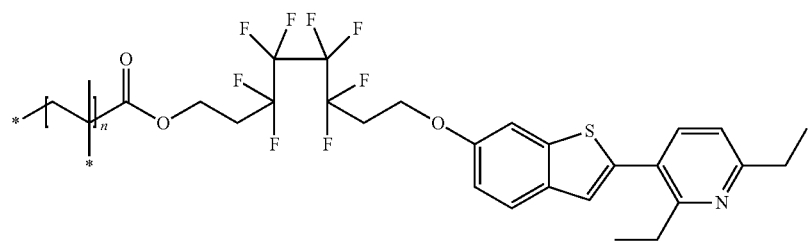
P-424

-continued
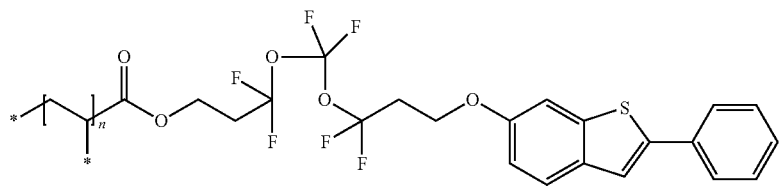
P-425
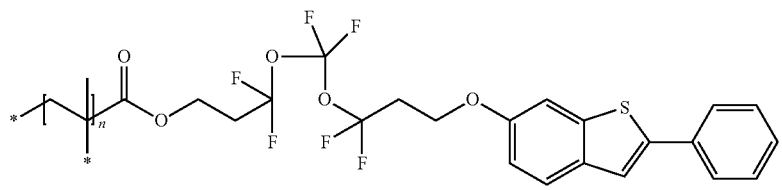
P-426
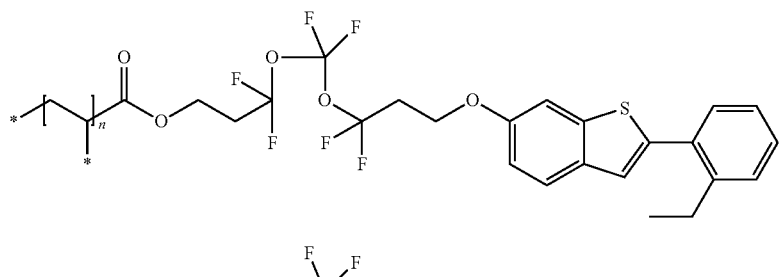
P-427
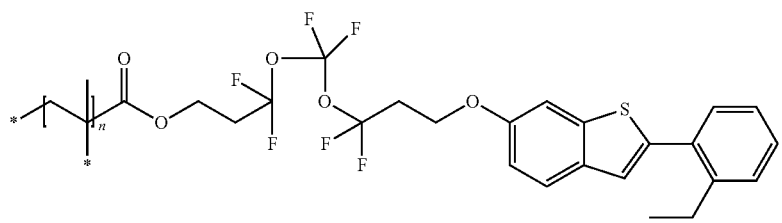
P-428
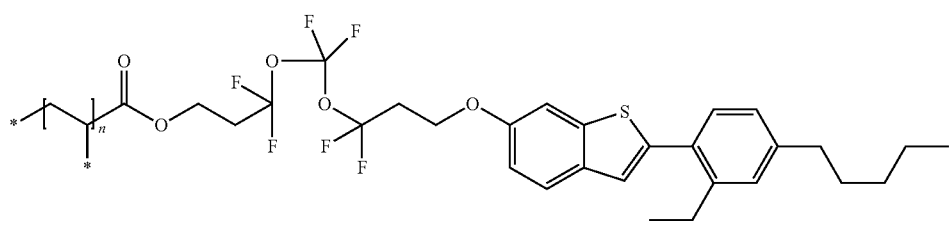
P-429
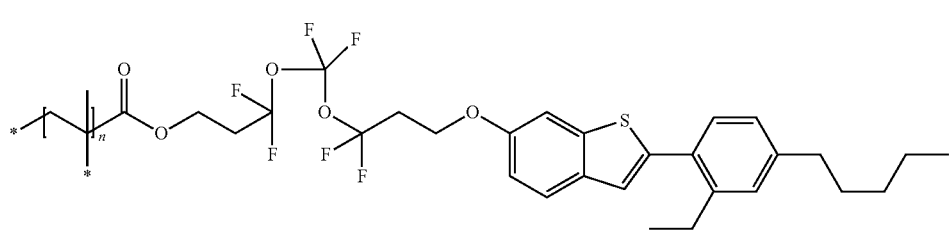
P-430
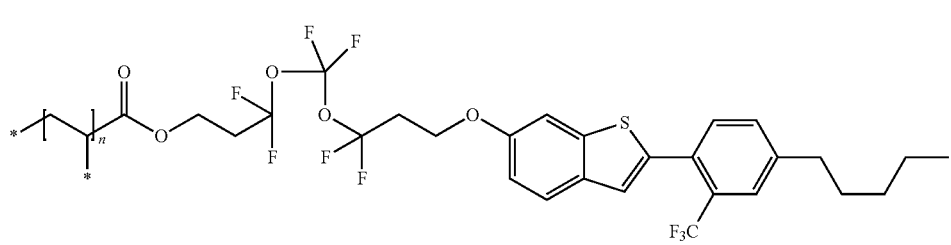
P-431

-continued
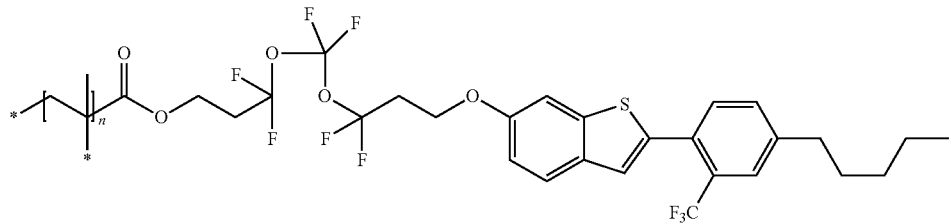
P-432
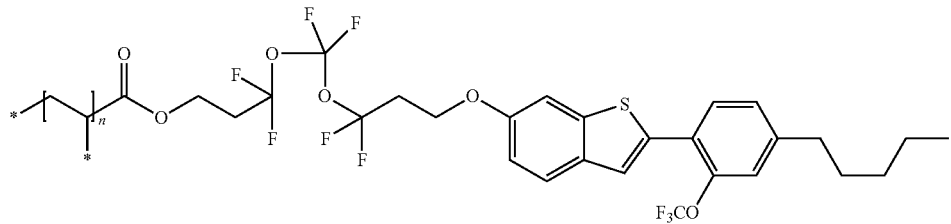
P-433
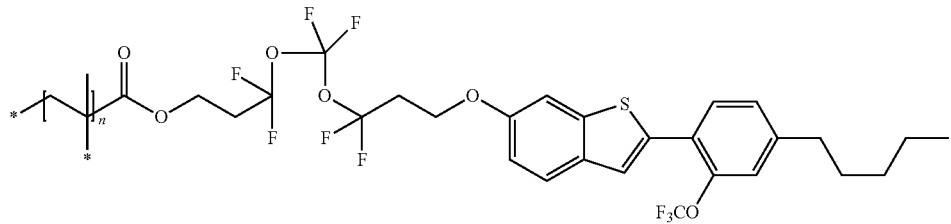
P-434
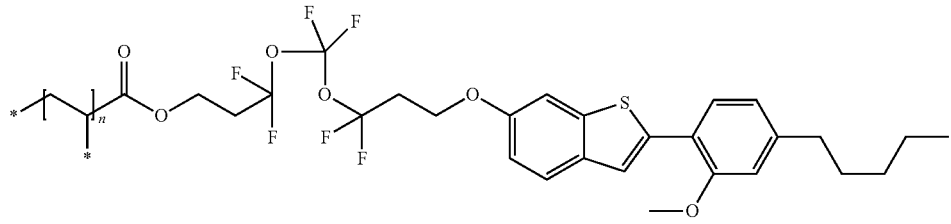
P-435
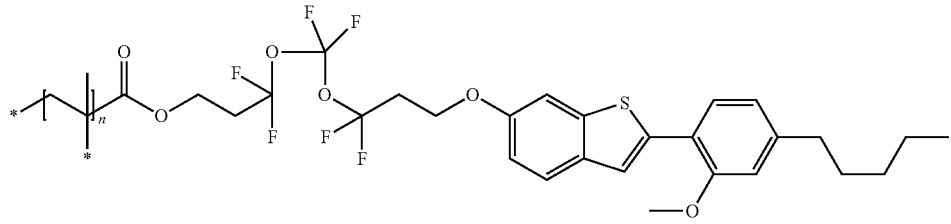
P-436
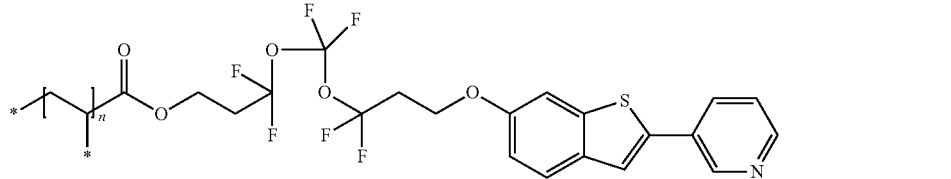
P-437
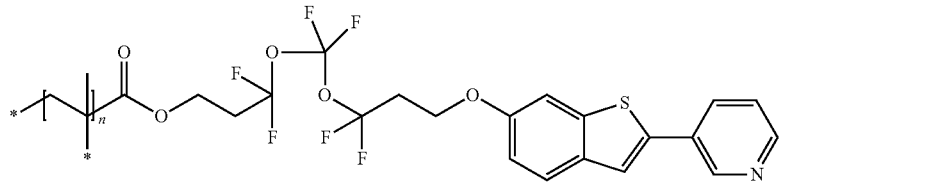
P-438

-continued
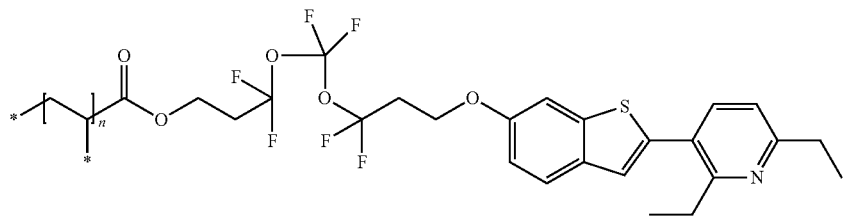
P-439
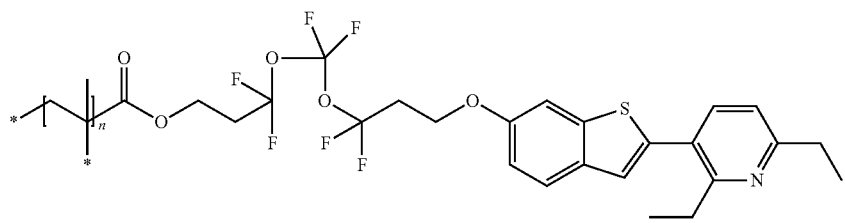
P-440
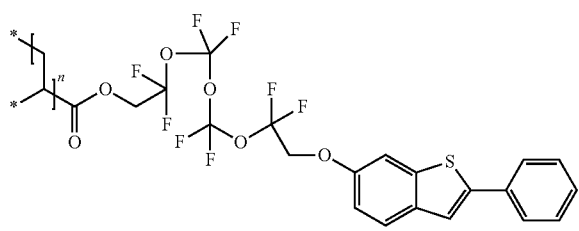
P-441
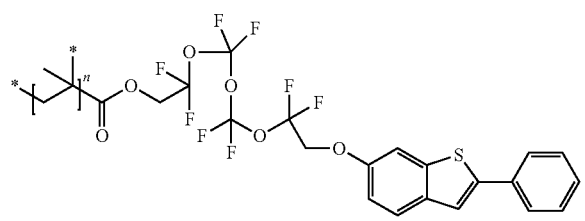
P-442
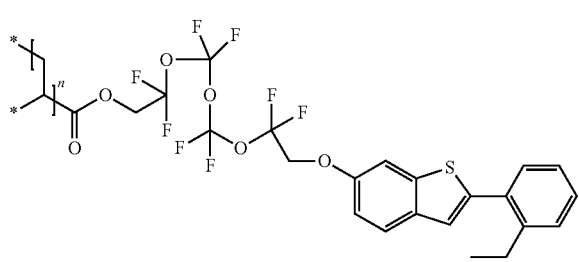
P-443
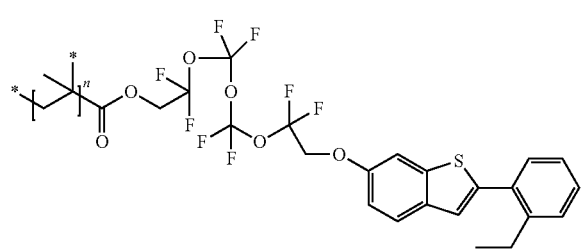
P-444
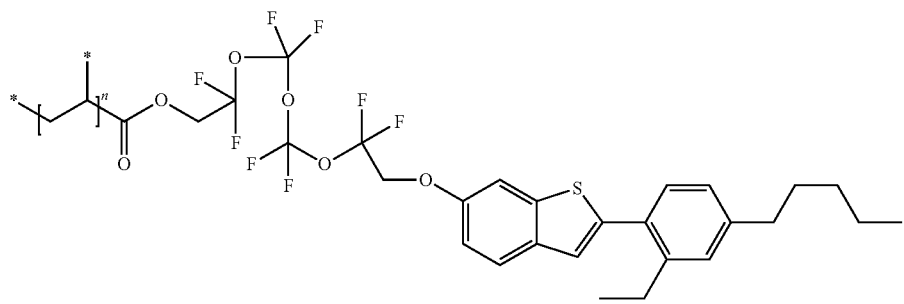
P-445
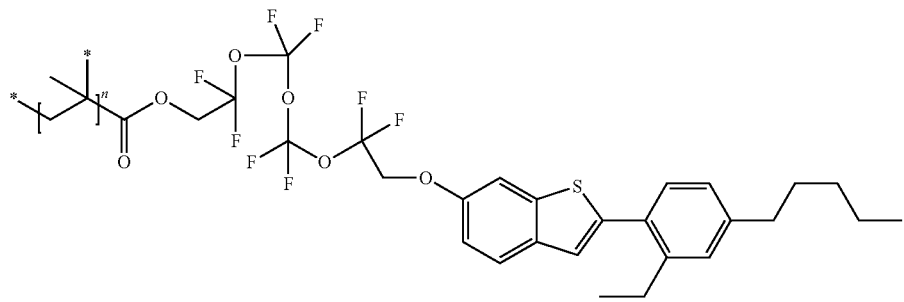
P-446

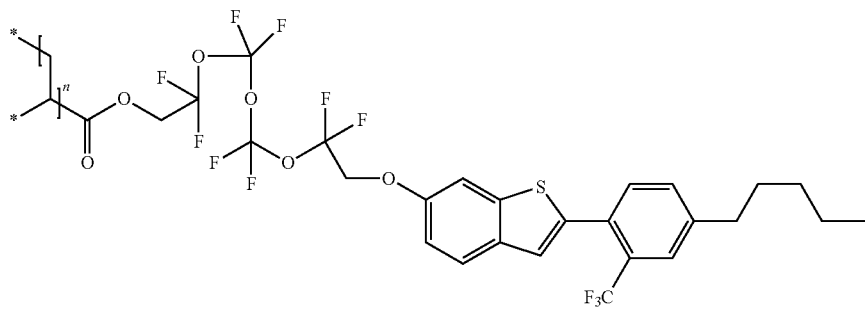
P-447
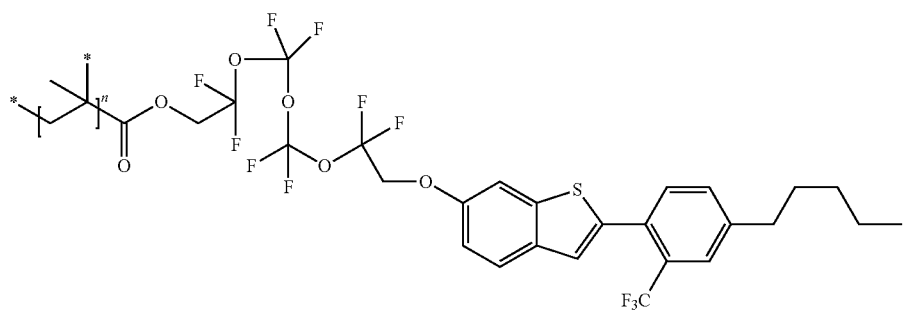
P-448
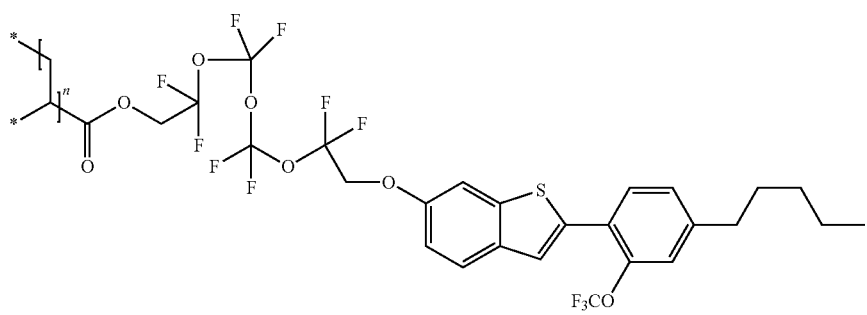
P-449
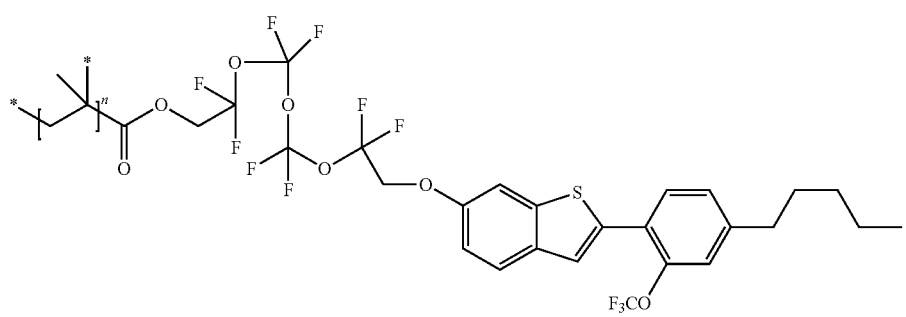
P-450
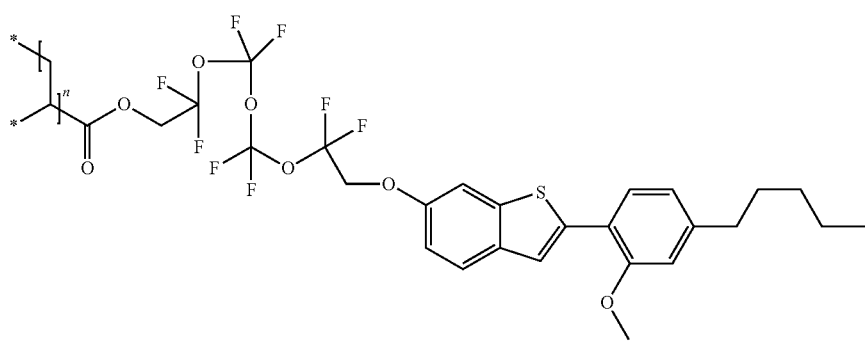
P-451

-continued
P-452
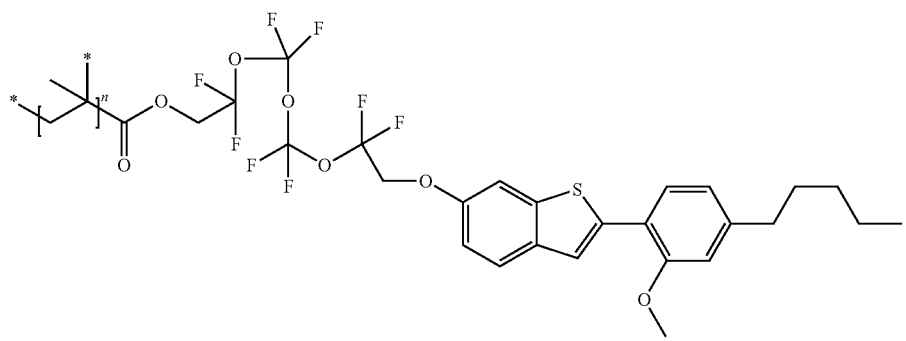
P-453
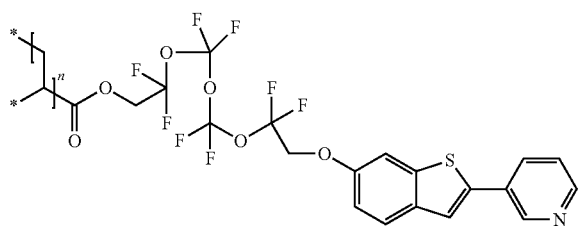
P-454
P-455
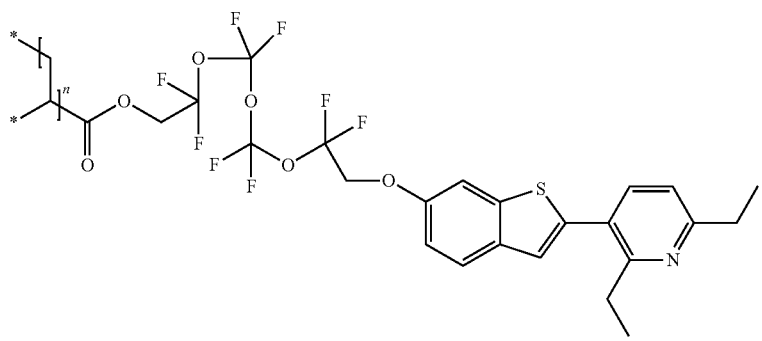
P-456
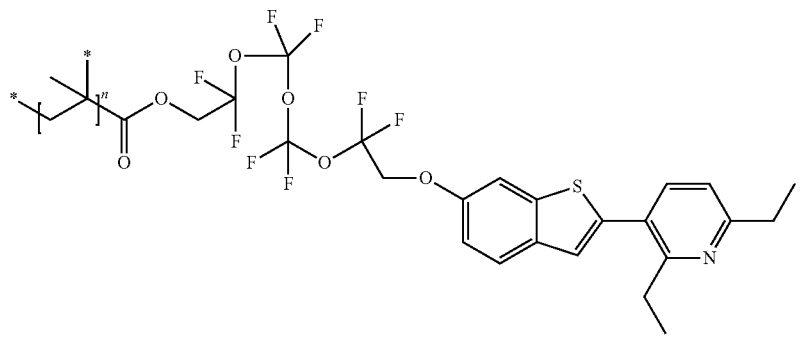
P-457 P-458
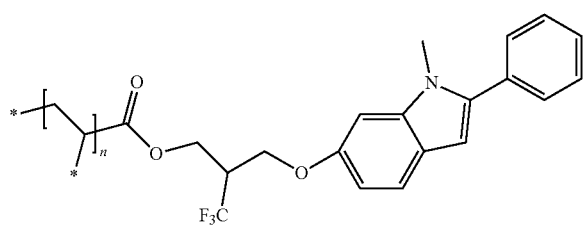

-continued
P-459
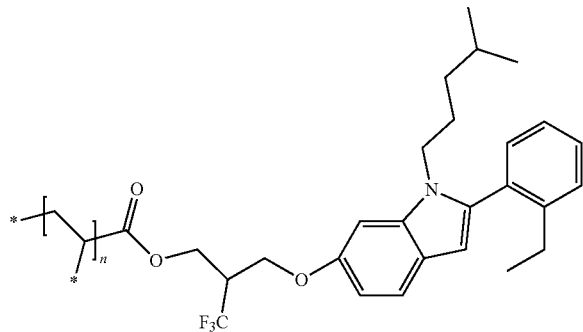
P-460
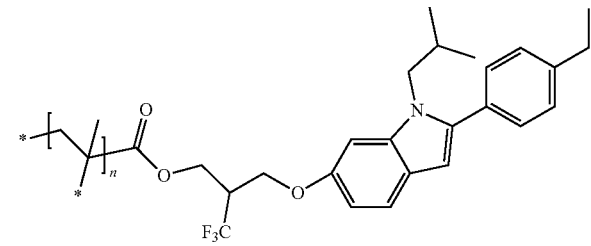
P-461
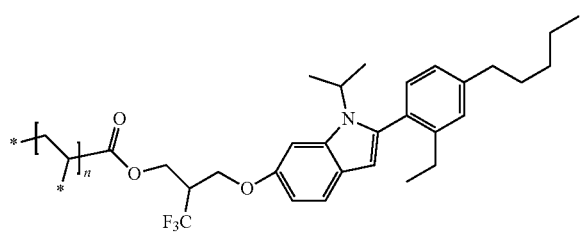
P-462
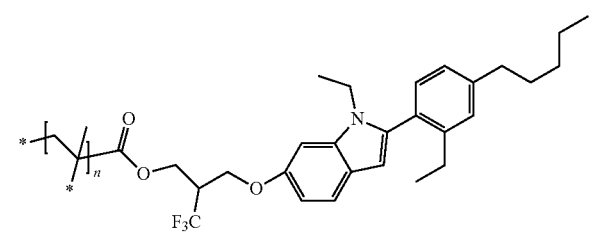
P-463
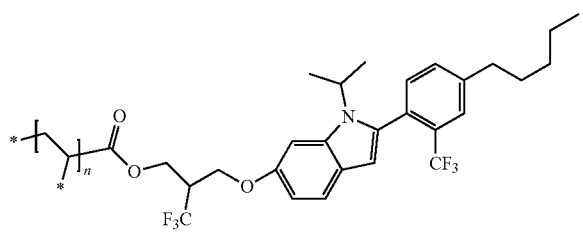
P-464
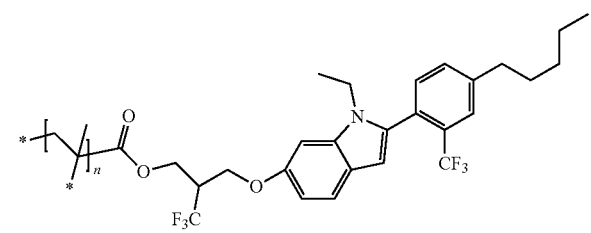
P-465
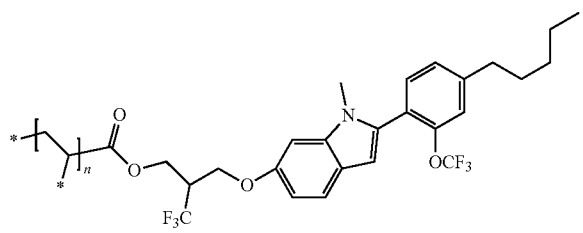
P-466
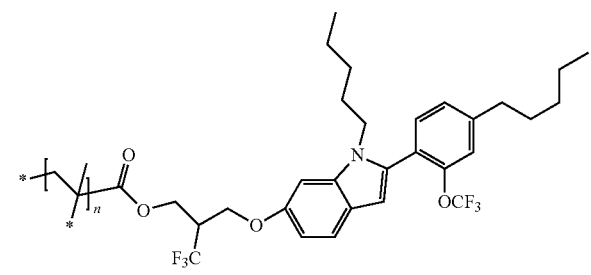
P-467
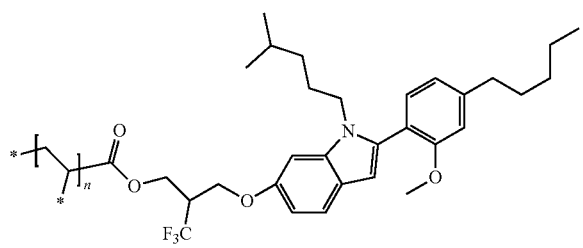
P-468
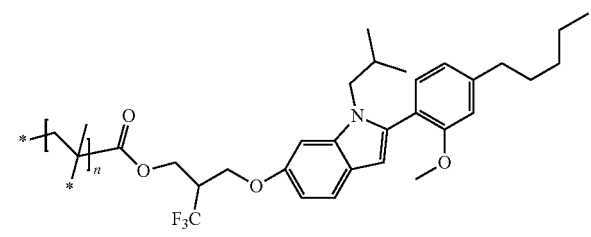

-continued
P-469
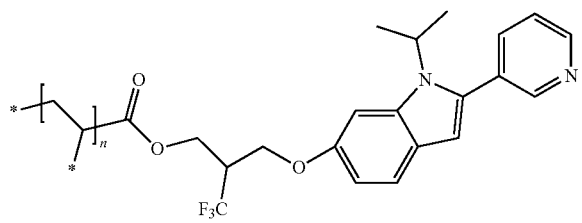
P-470
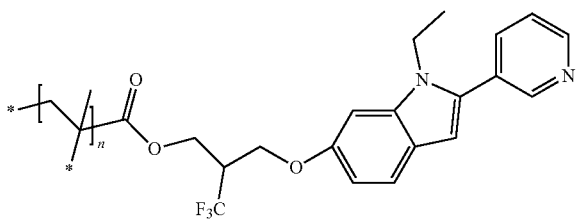
P-471
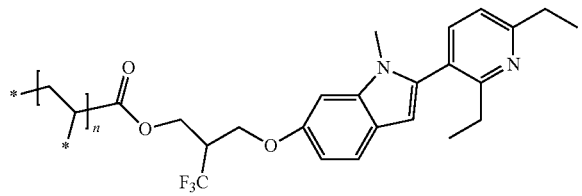
P-472
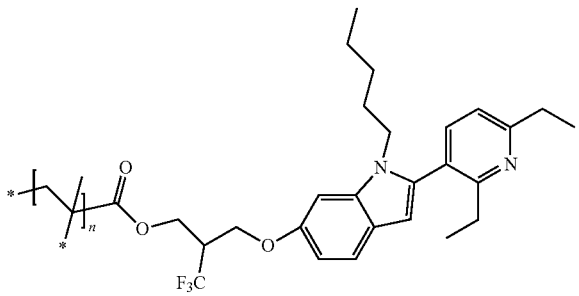
P-473
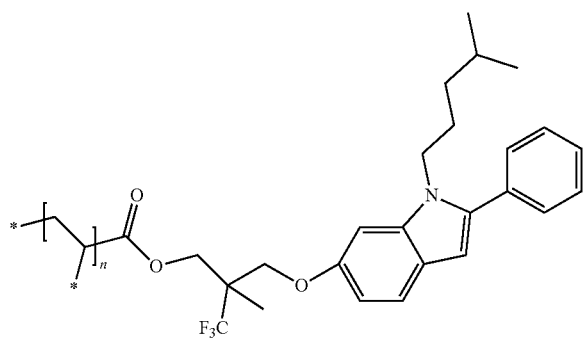
P-474
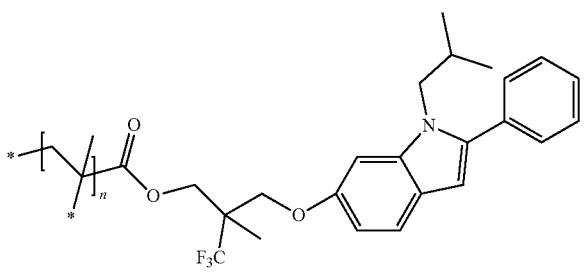
P-475
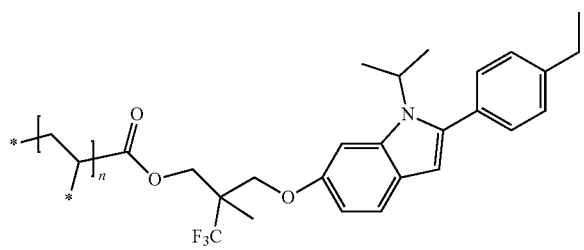
P-476
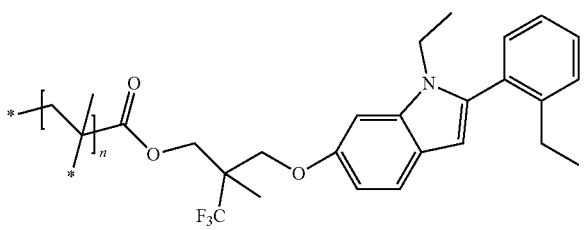
P-477
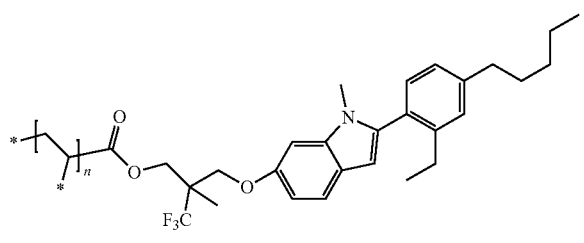
P-478
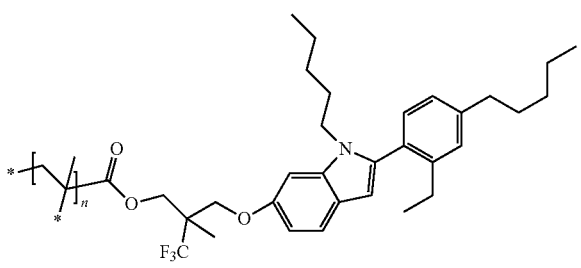

-continued
P-479
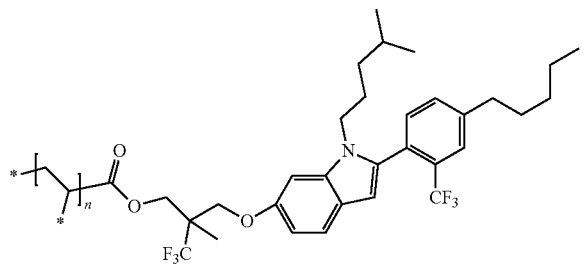
P-480
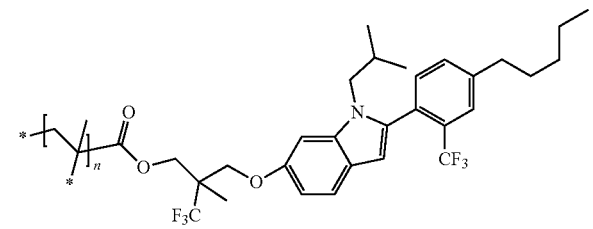
P-481
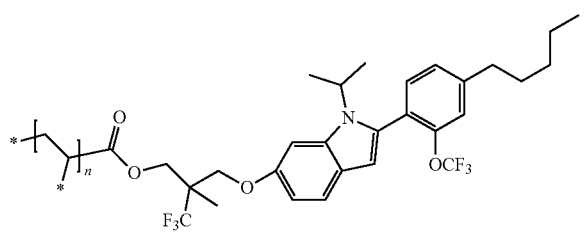
P-482
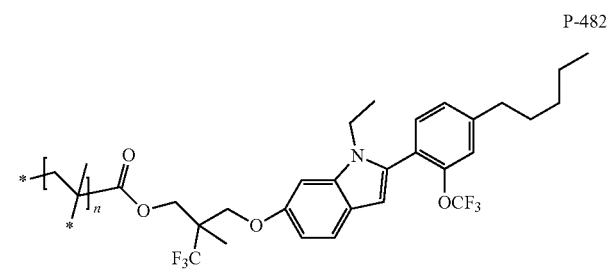
P-483
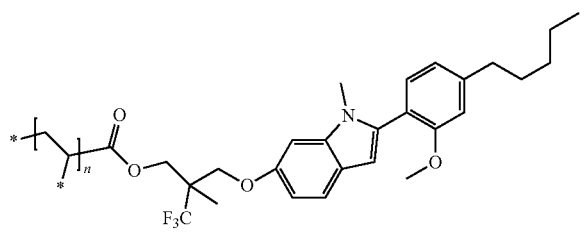
P-484
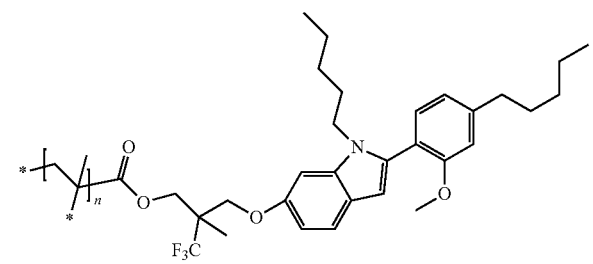
P-485
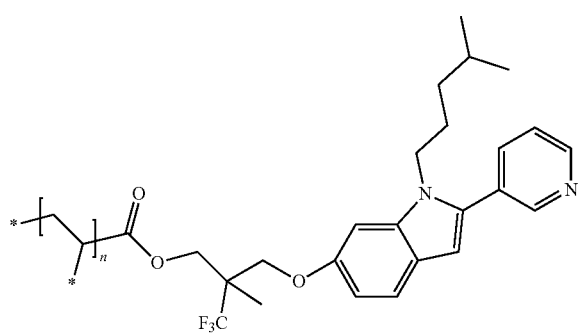
P-486
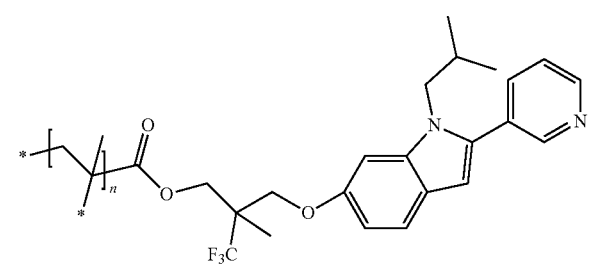
P-487
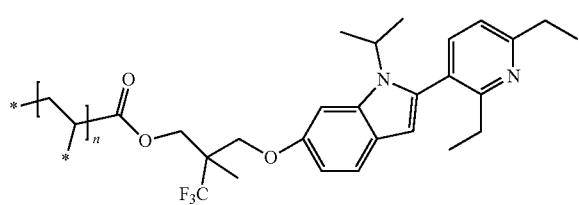
P-488
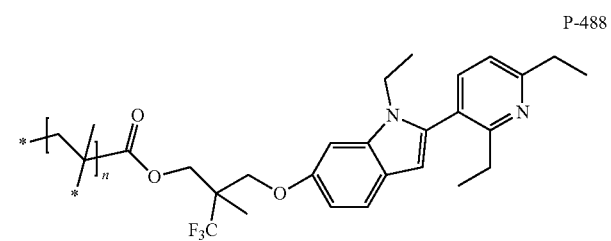

-continued
P-489
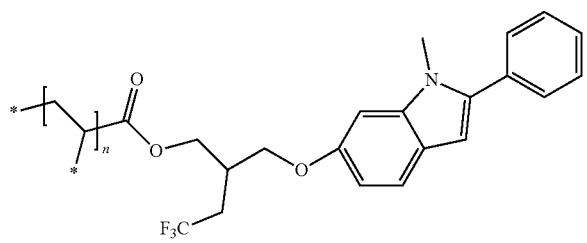
P-490
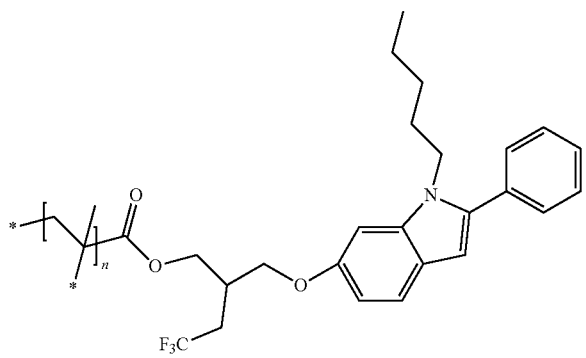
P-491
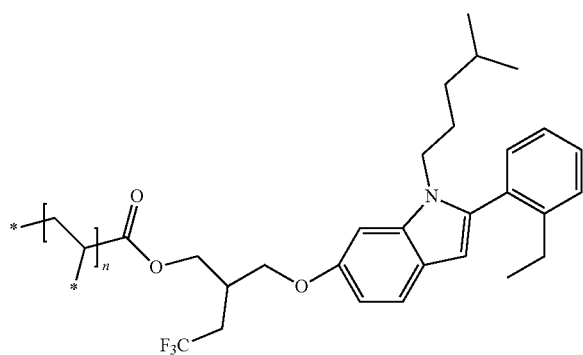
P-492
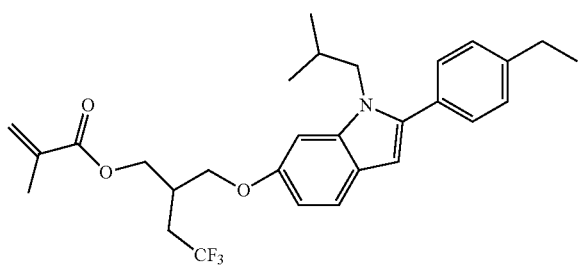
P-493
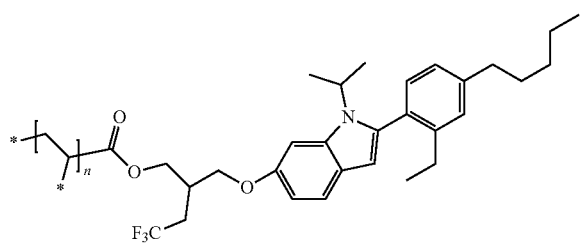
P-494
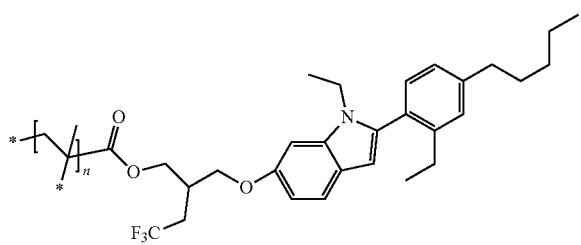
P-495
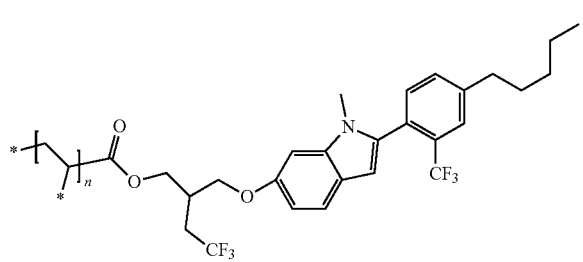
P-496
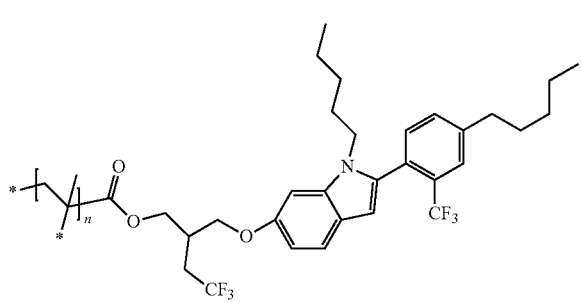
P-497
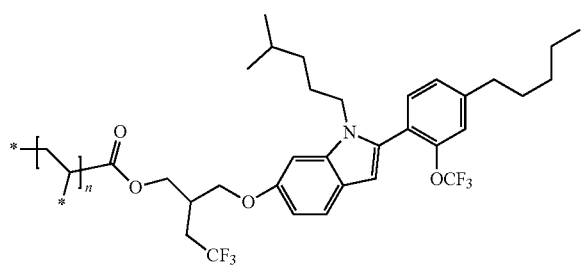
P-498
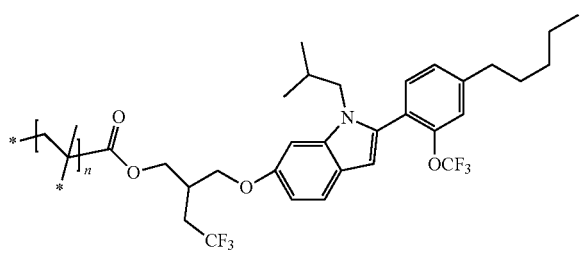

-continued
P-499
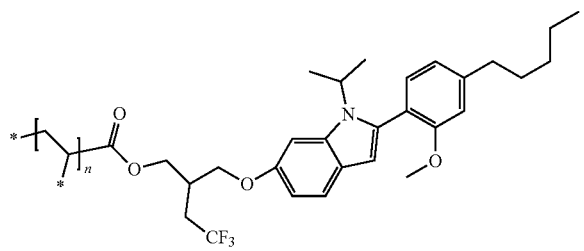
P-500
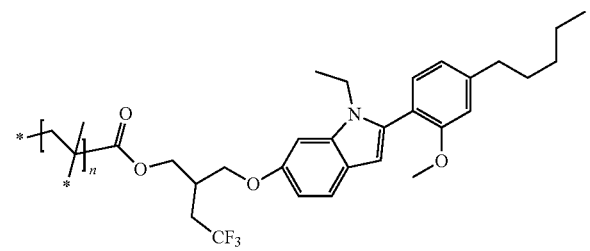
P-501
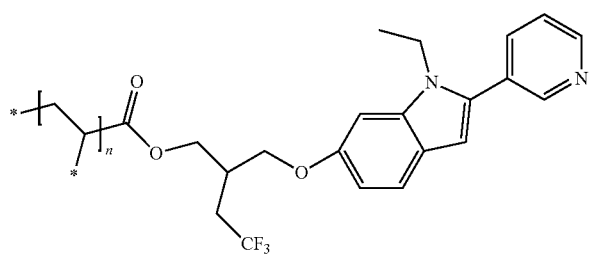
P-502
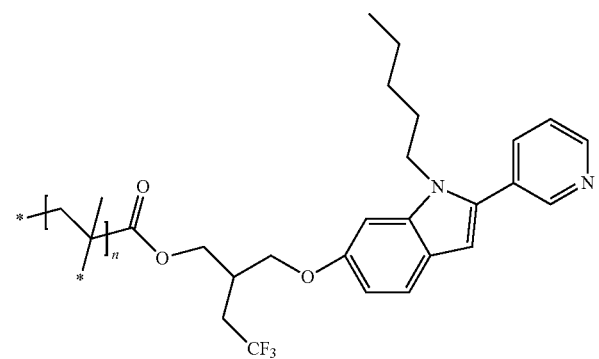
P-503
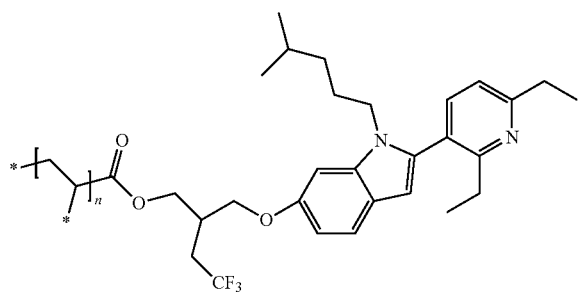
P-504
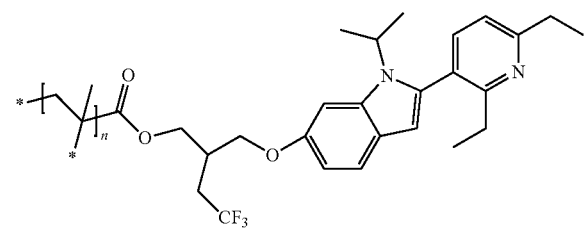
P-505
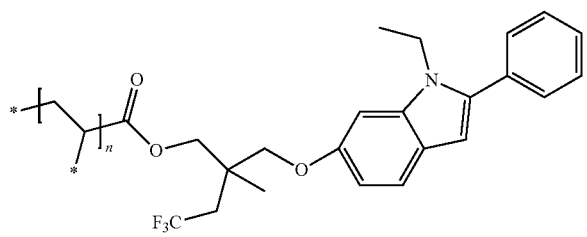
P-506
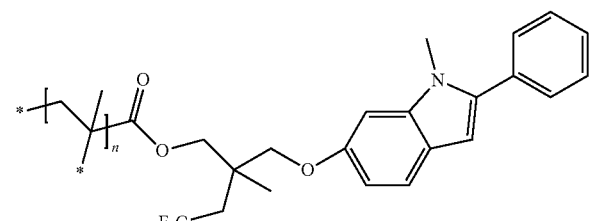
P-507
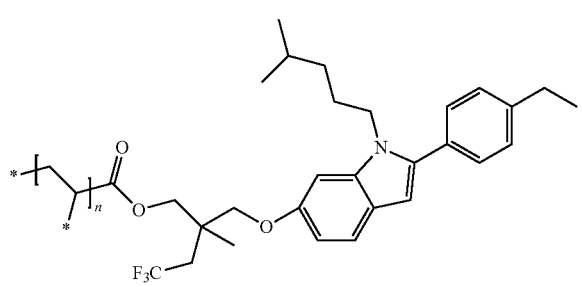
P-508
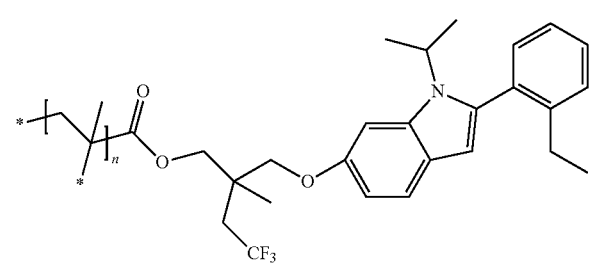

-continued
P-509
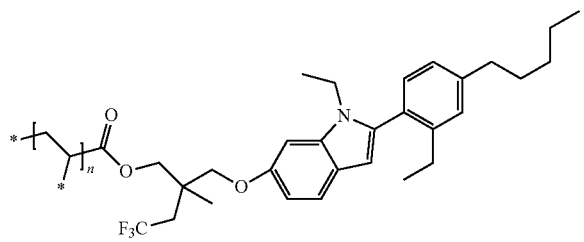
P-510
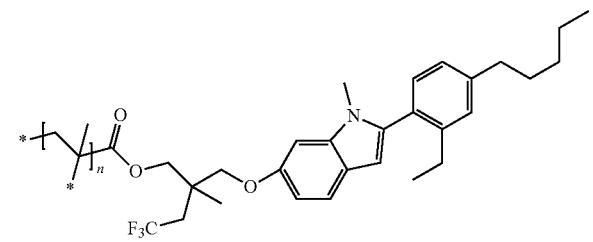
P-511
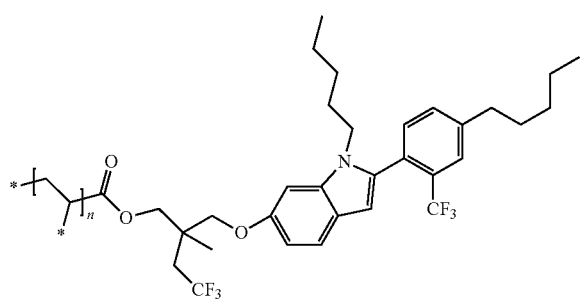
P-512
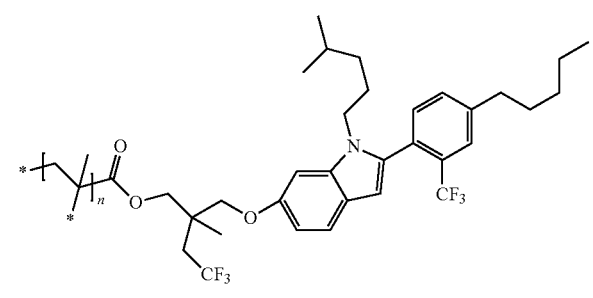
P-513
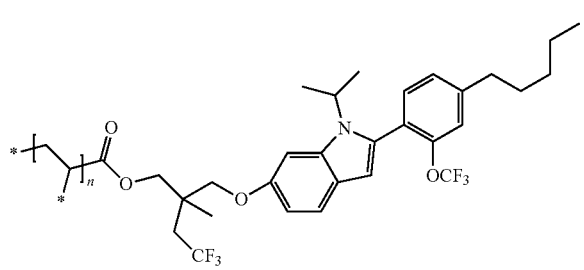
P-514
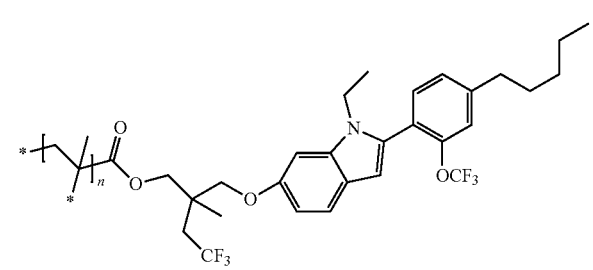
P-515
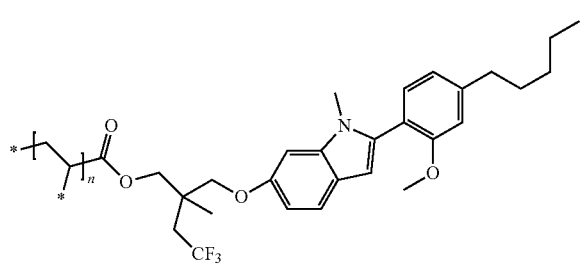
P-516
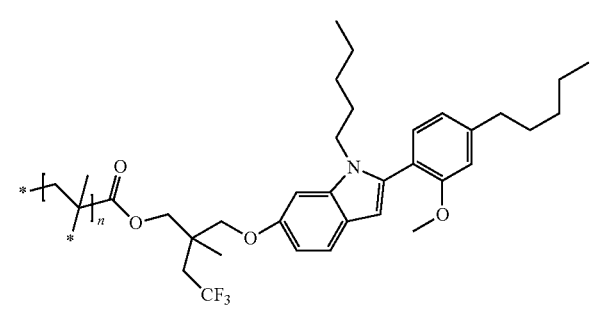
P-517
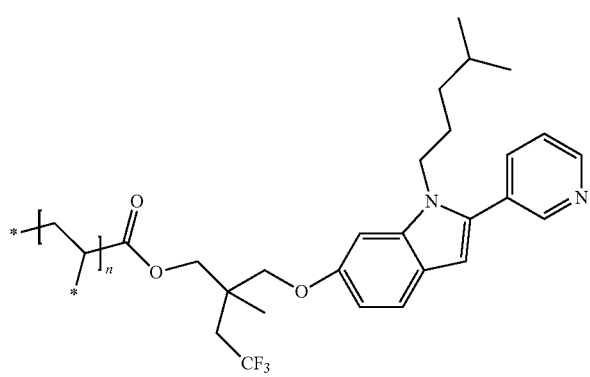
P-518
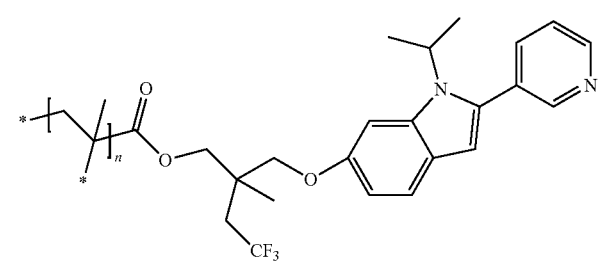

-continued
P-519
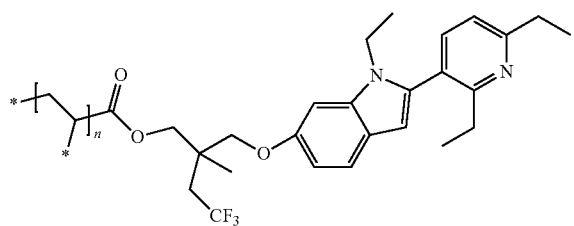
P-520
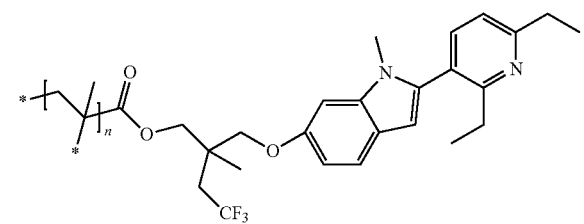
P-521
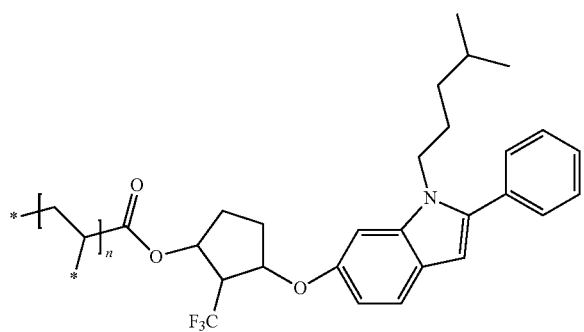
P-522
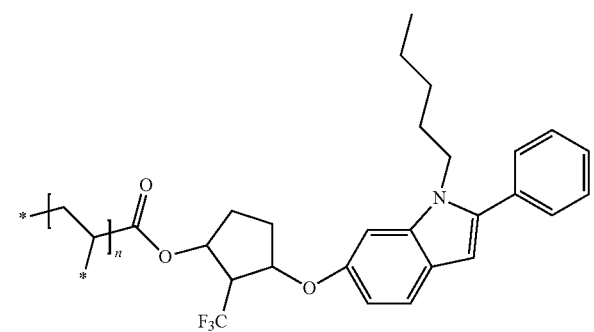
P-523
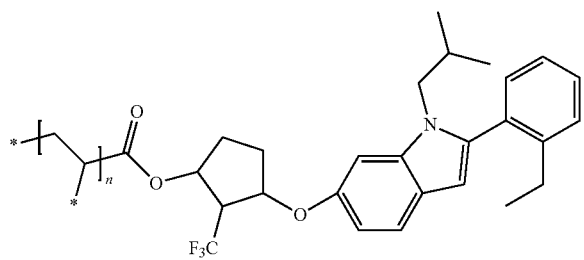
P-524
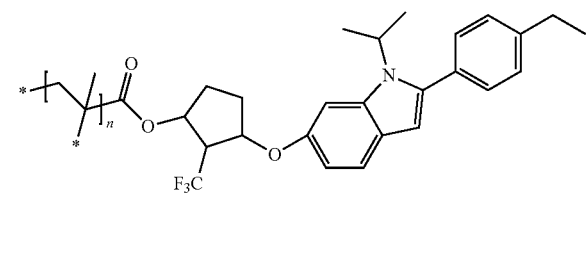
P-525
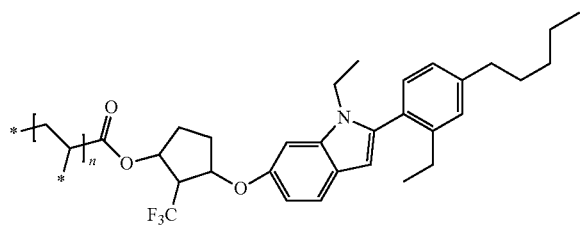
P-526
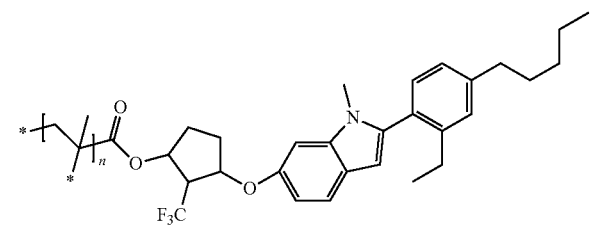
P-527
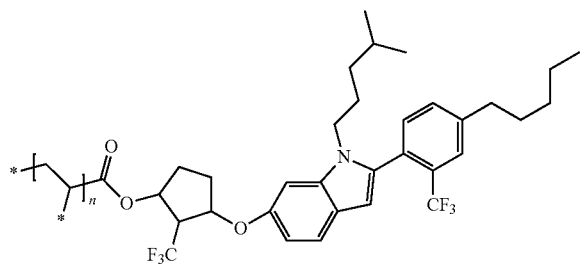
P-528
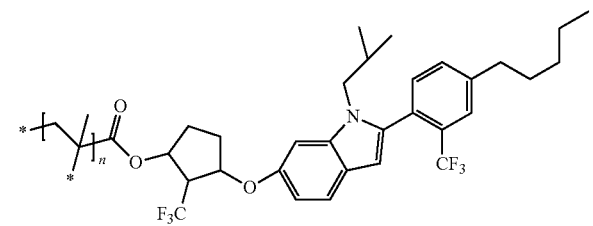

-continued
P-529
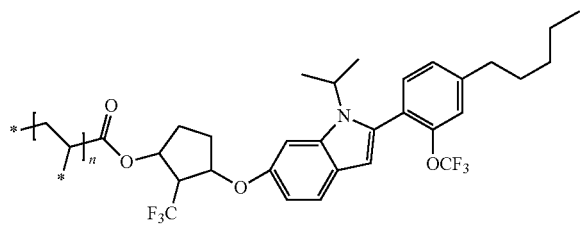
P-530
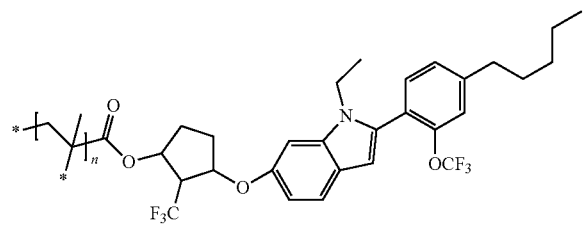
P-531
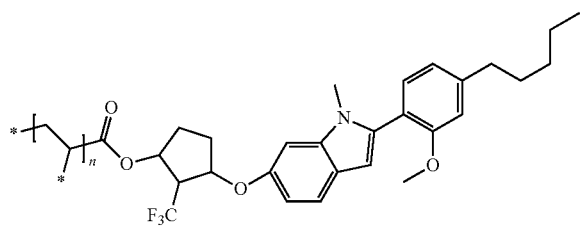
P-532
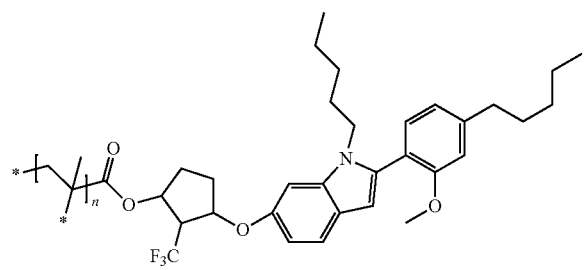
P-533
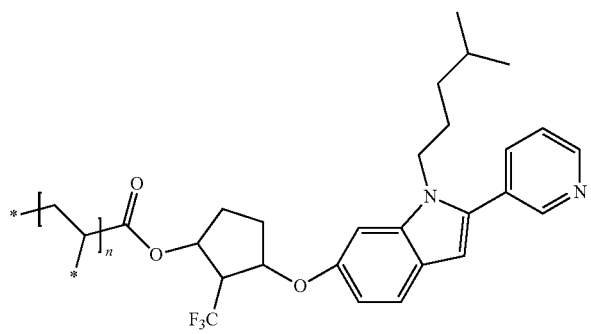
P-534
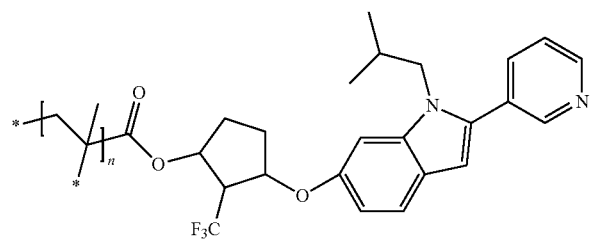
P-535
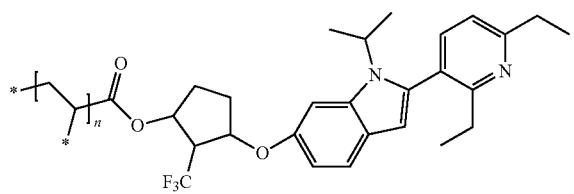
P-536
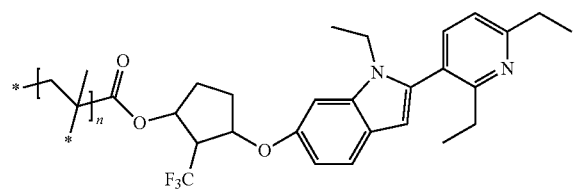
P-537
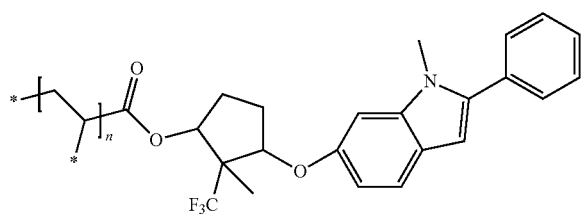
P-538
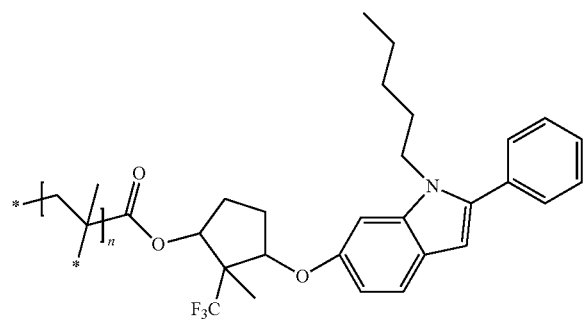

-continued
P-539
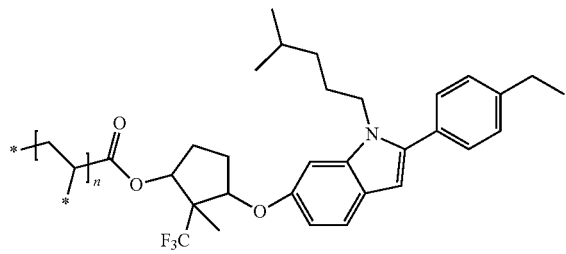
P-540
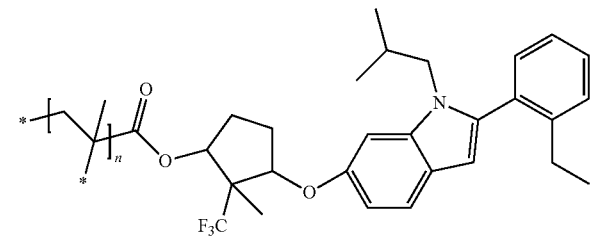
P-541
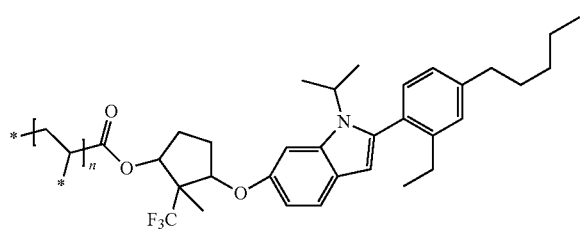
P-542
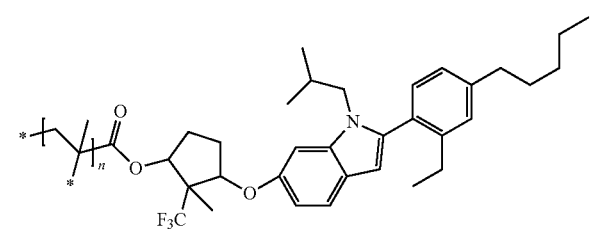
P-543
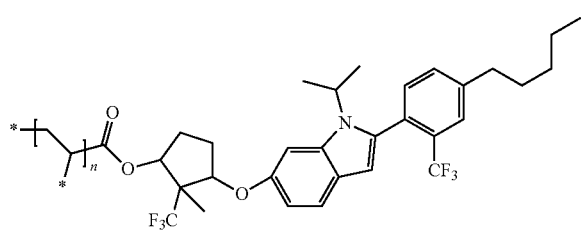
P-544
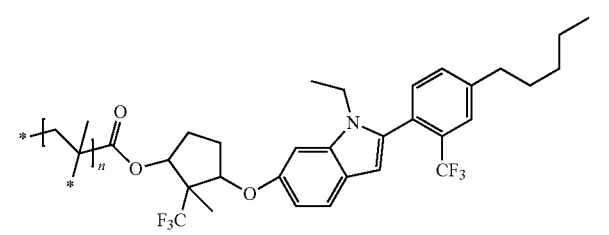
P-545
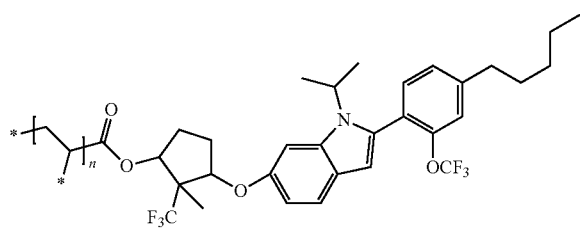
P-546
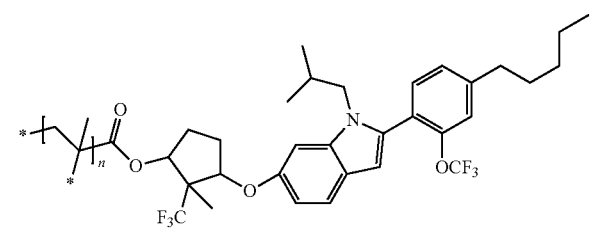
P-547
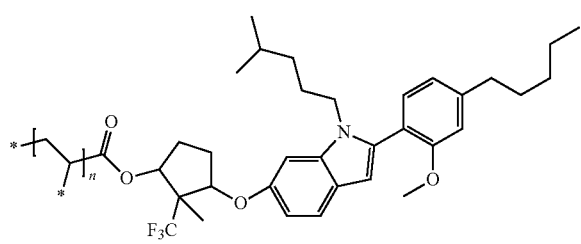
P-548
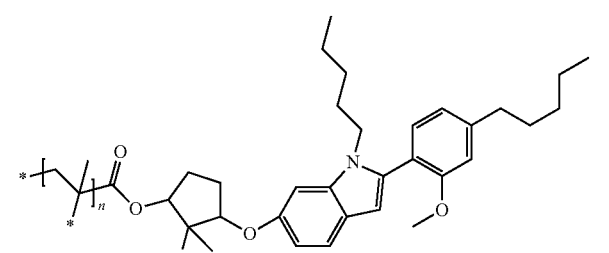
P-549
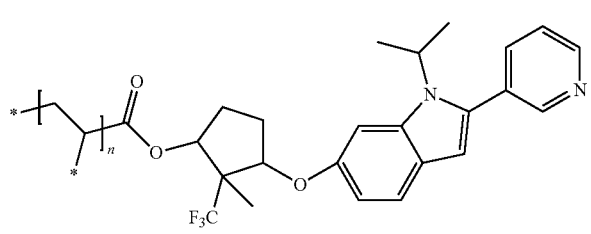
P-550
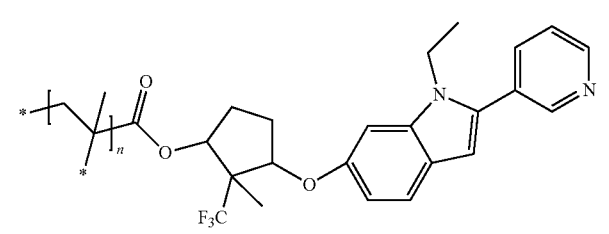

-continued
P-551
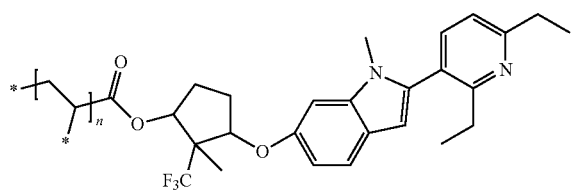
P-552
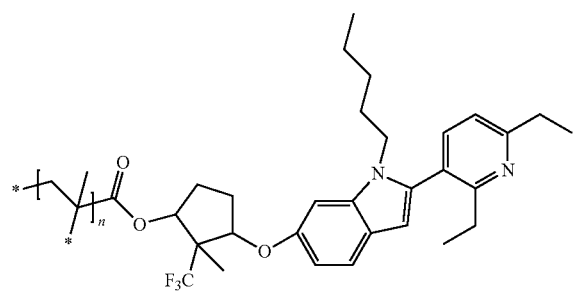
P-553
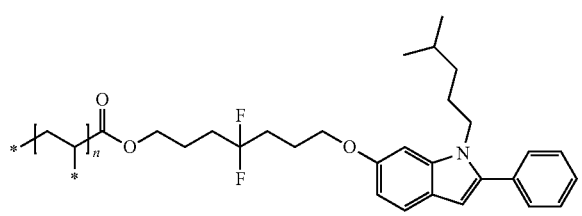
P-554
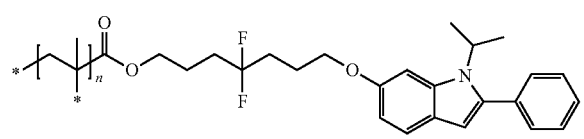
P-555
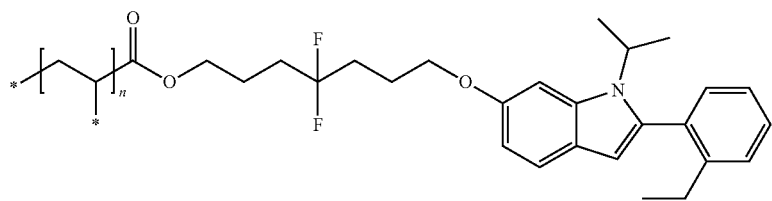
P-556
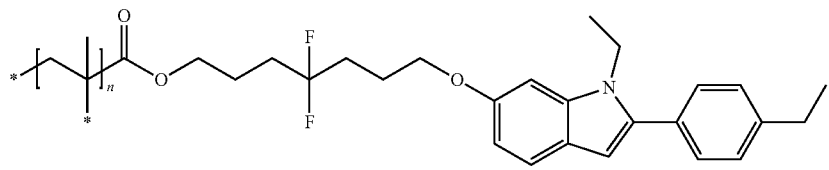
P-557
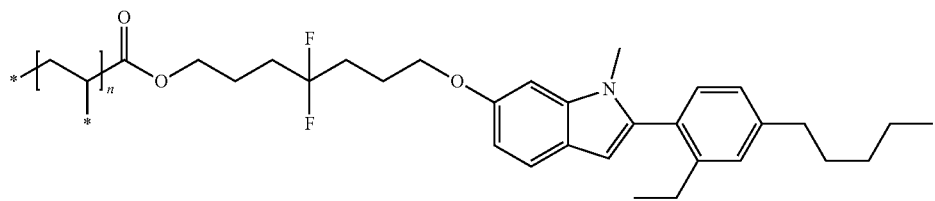
P-558
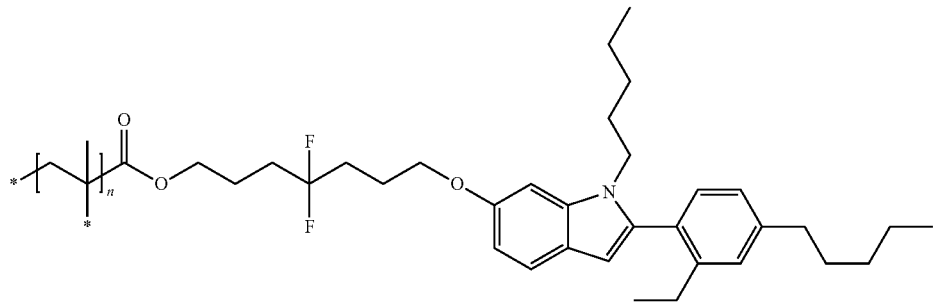

-continued
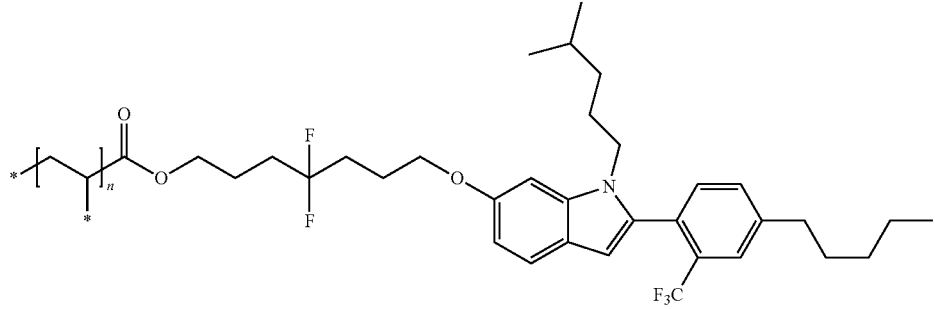
P-559
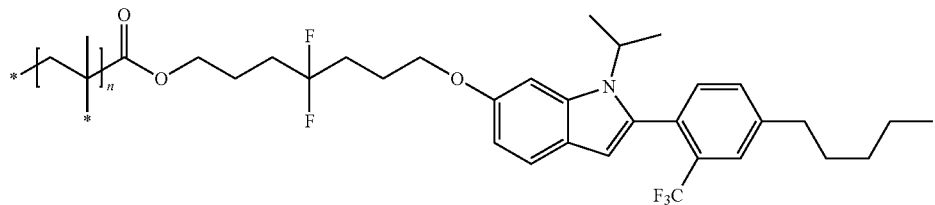
P-560
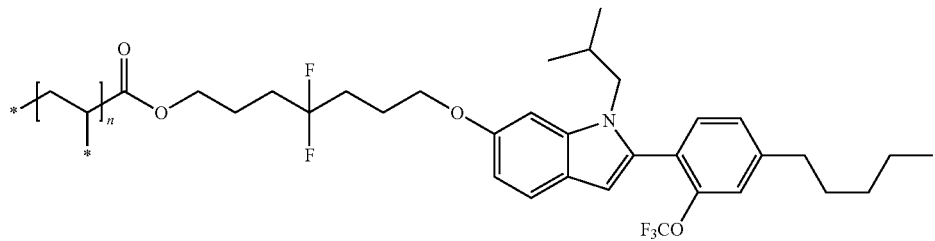
P-561
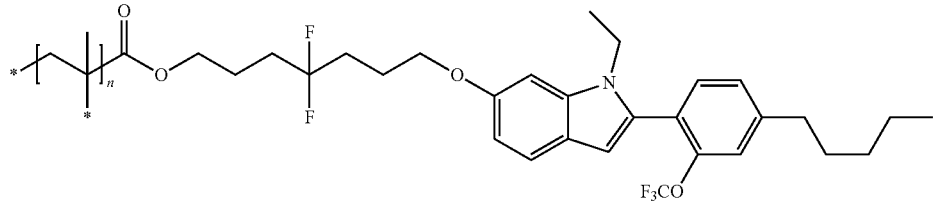
P-562
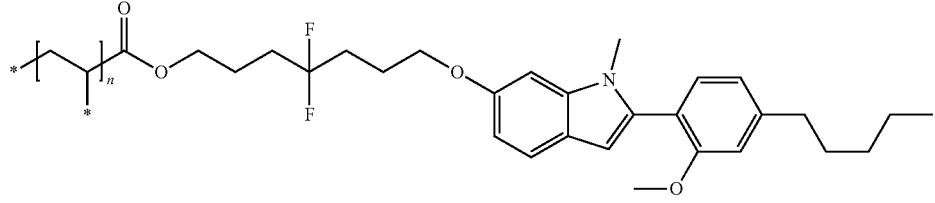
P-563
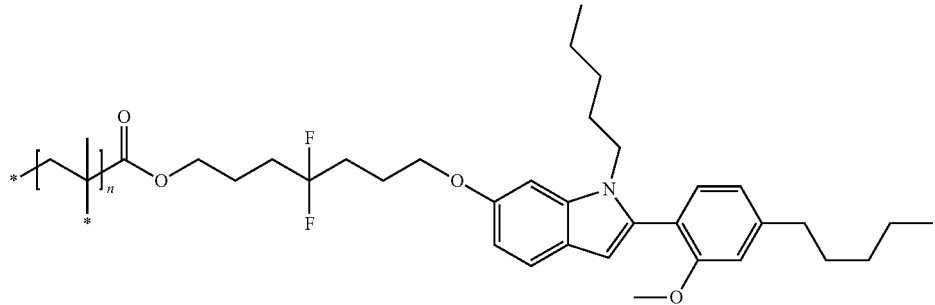
P-564

-continued
P-565
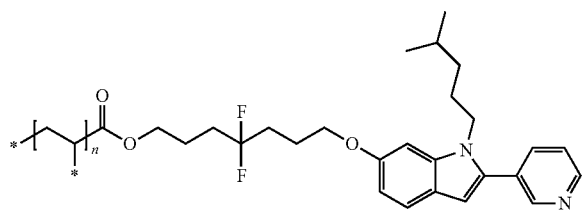
P-566
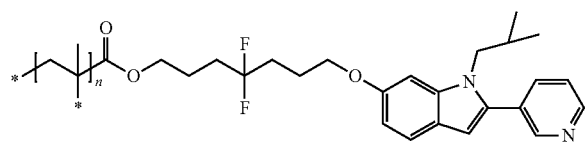
P-567
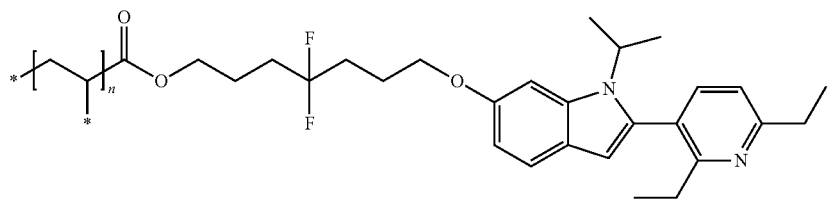
P-568
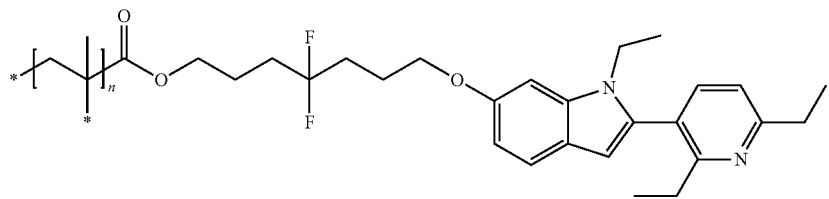
P-569
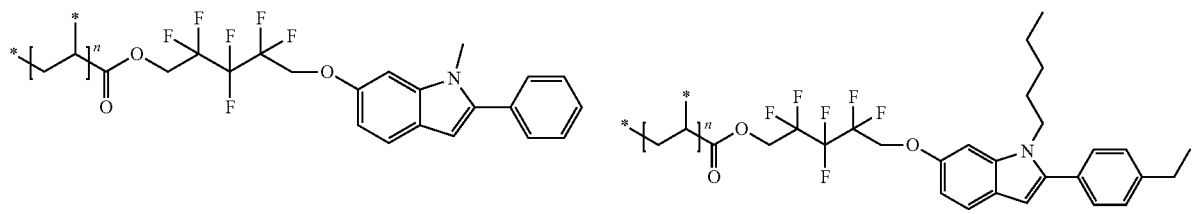
P-570
P-571
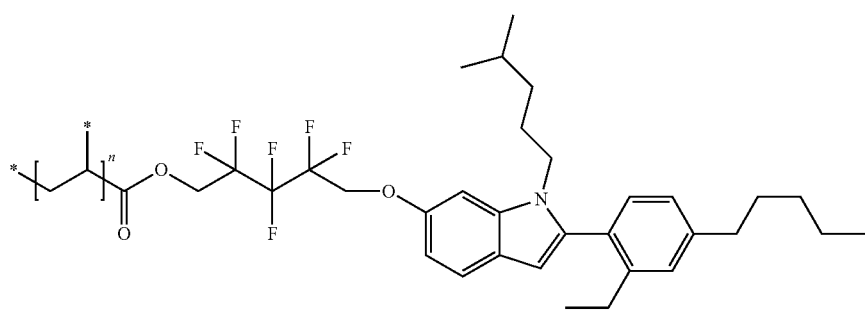
P-572
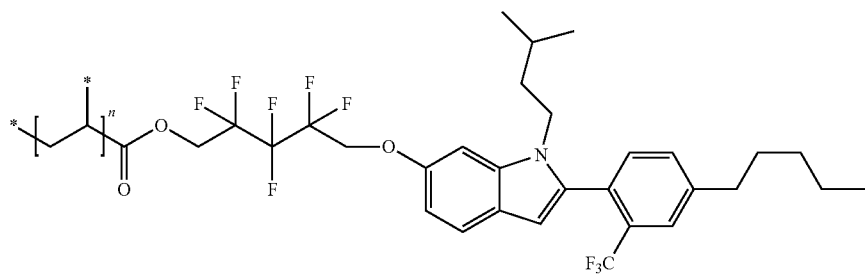

-continued
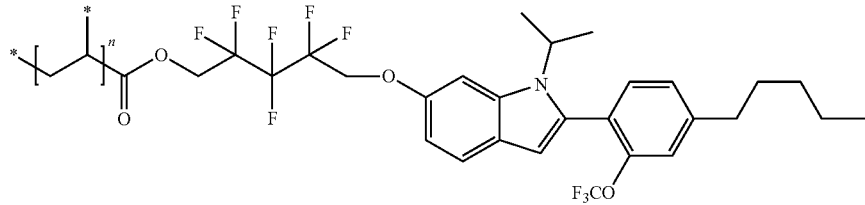
P-573
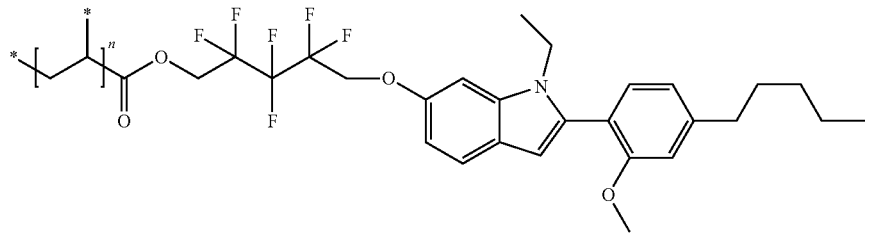
P-574
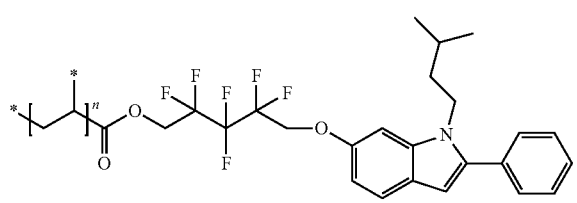
P-575
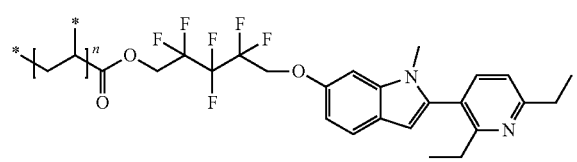
P-576
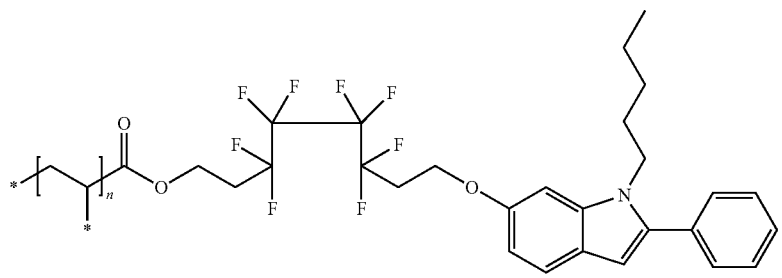
P-577
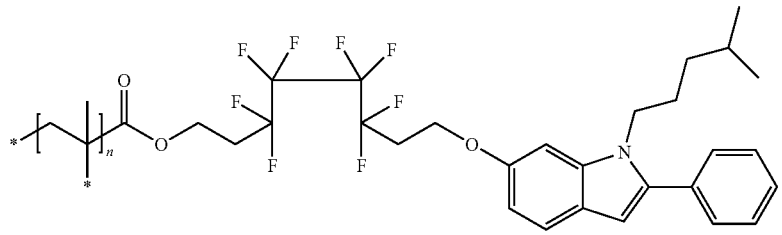
P-578
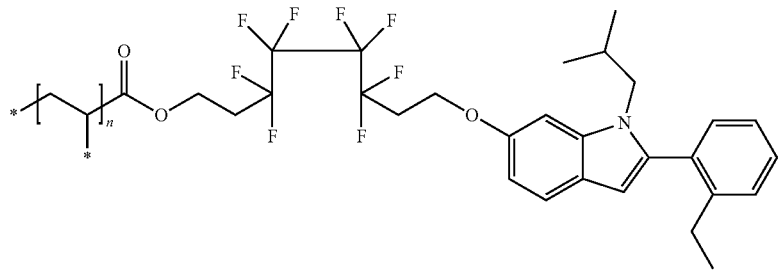
P-579

-continued
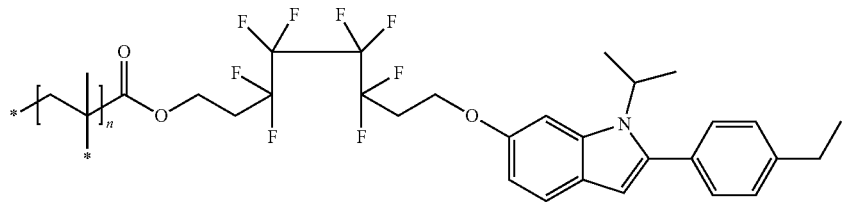
P-580
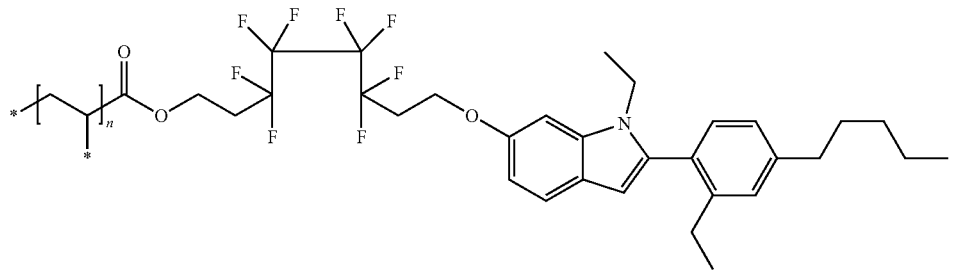
P-581
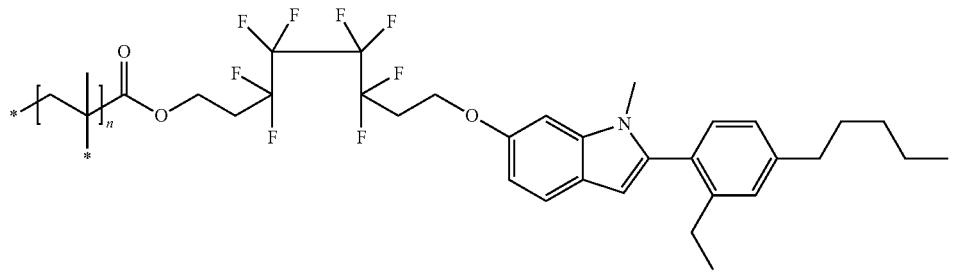
P-582
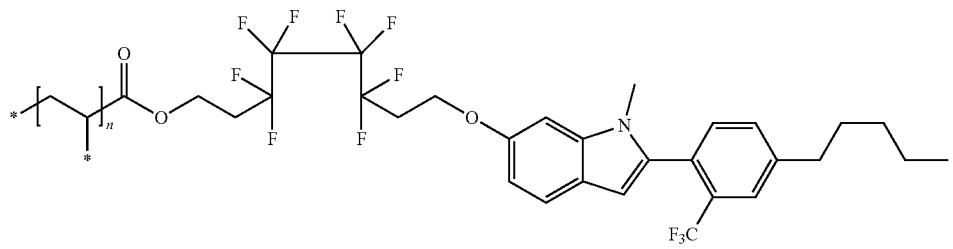
P-583
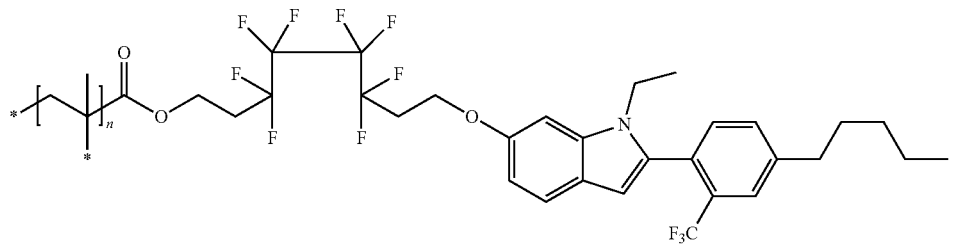
P-584
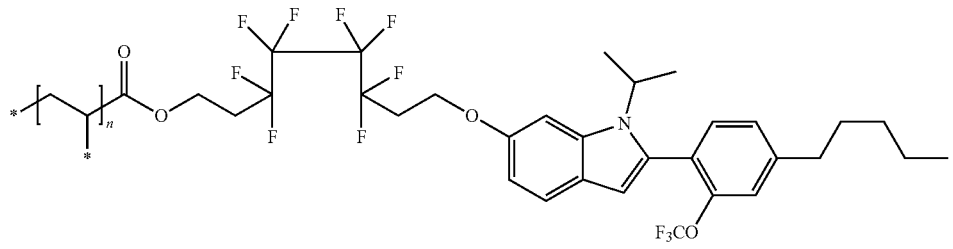
P-585

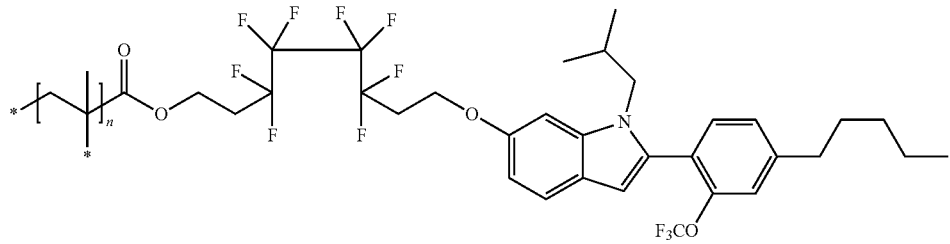
P-586
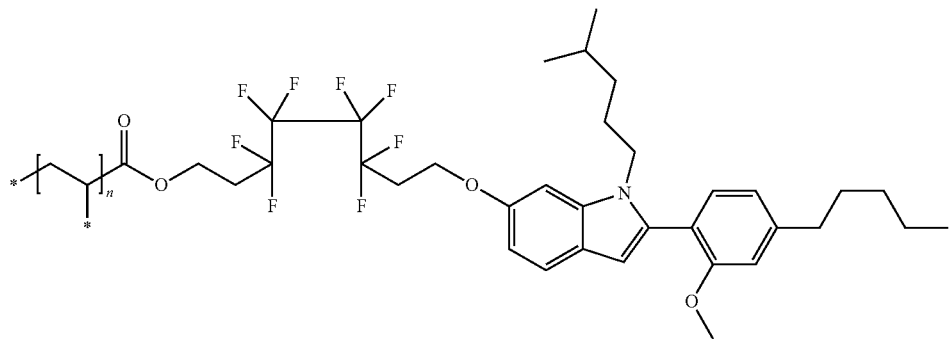
P-587
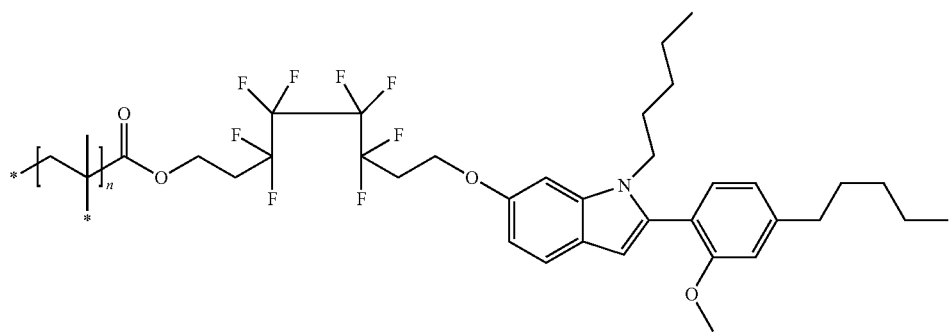
P-588
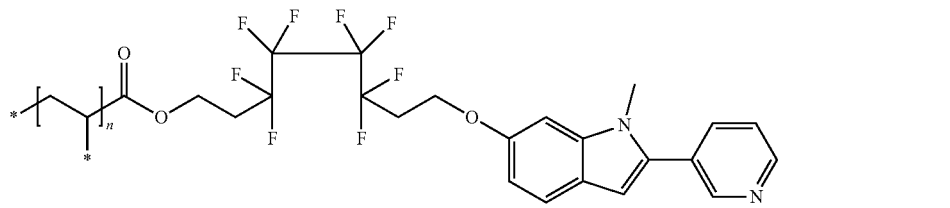
P-589
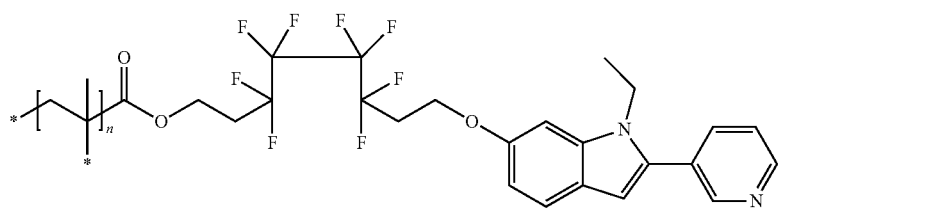
P-590
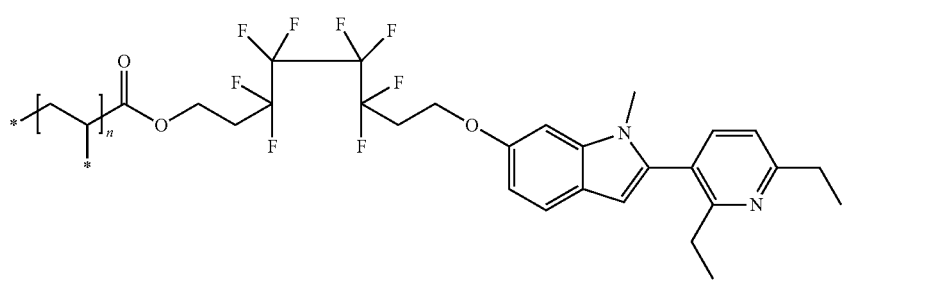
P-591

P-592
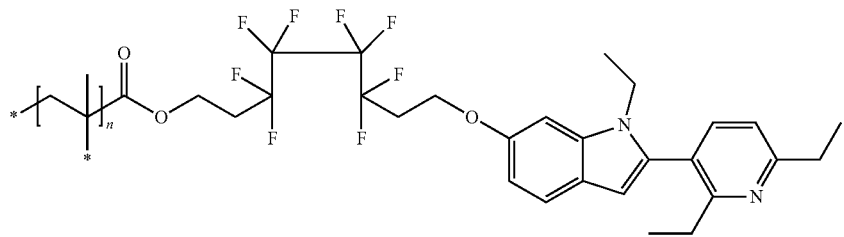
P-593
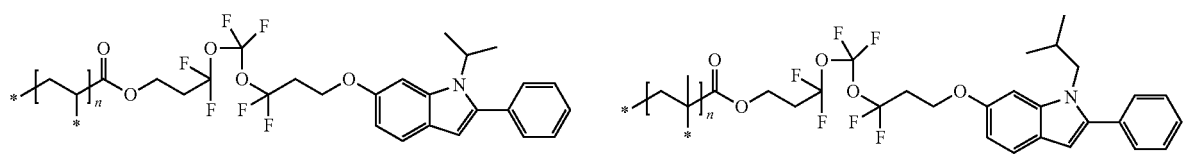
P-594
P-595
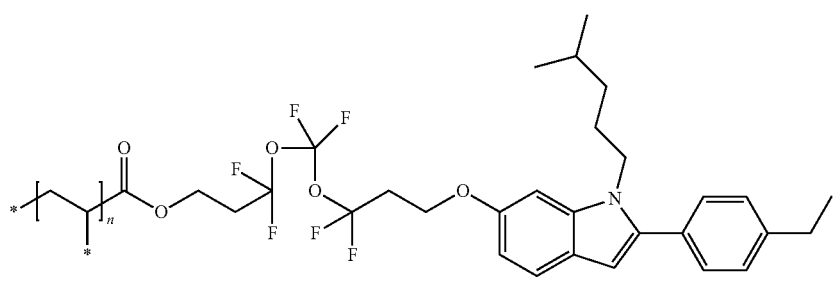
P-596
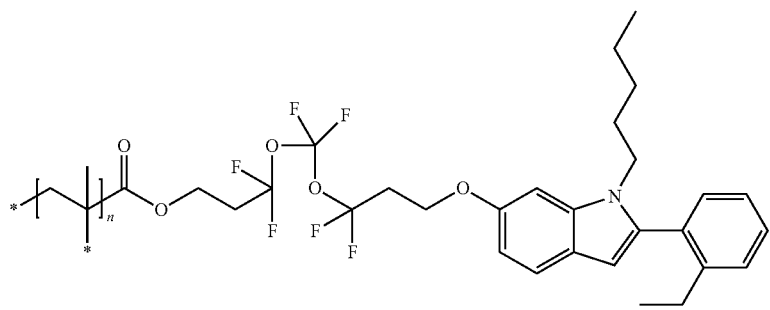
P-597
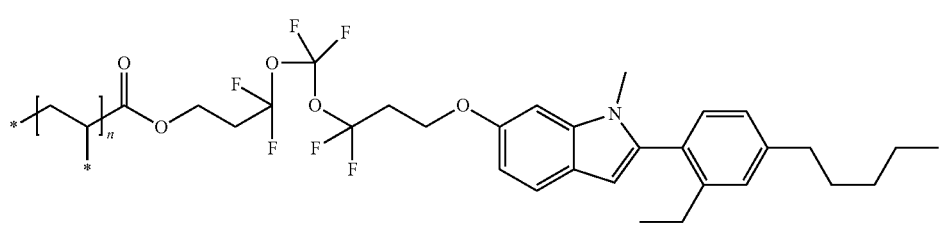
P-598
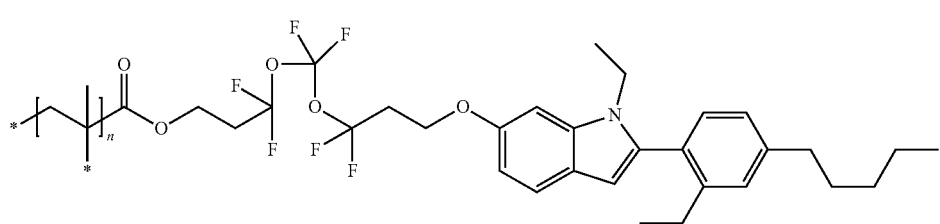

P-599
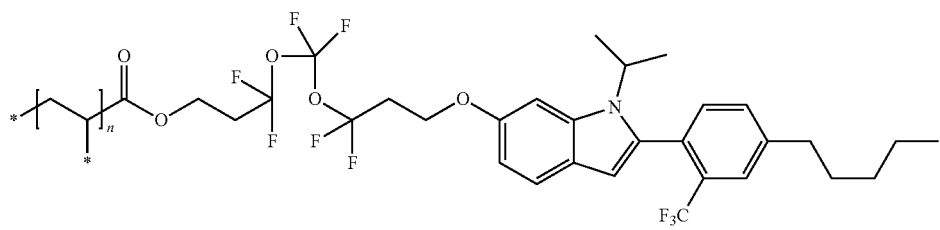
P-600
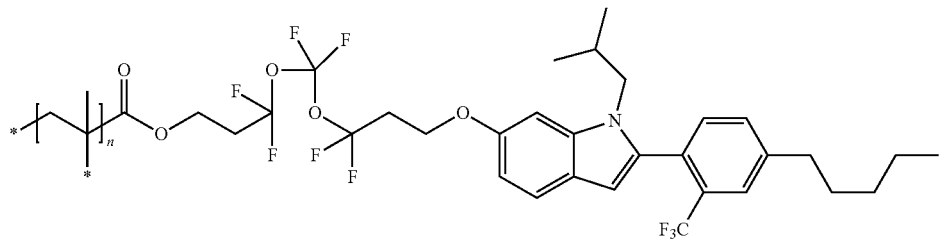
P-601
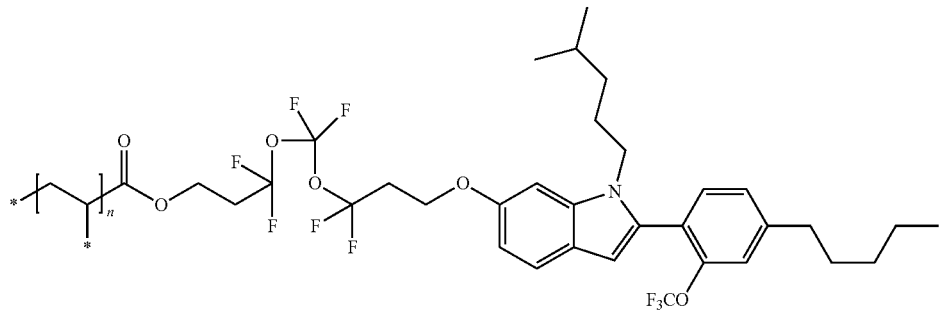
P-602
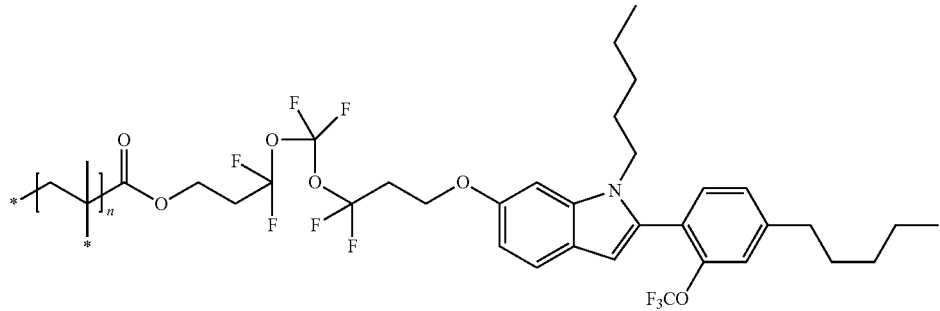
P-603
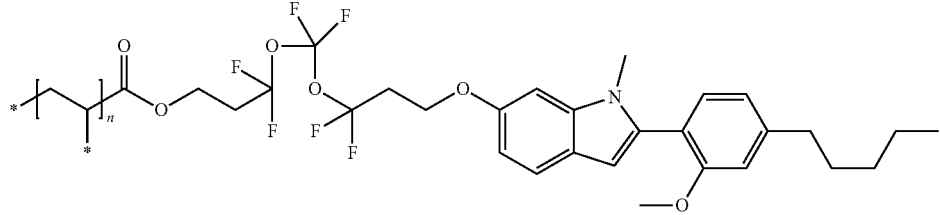
P-604
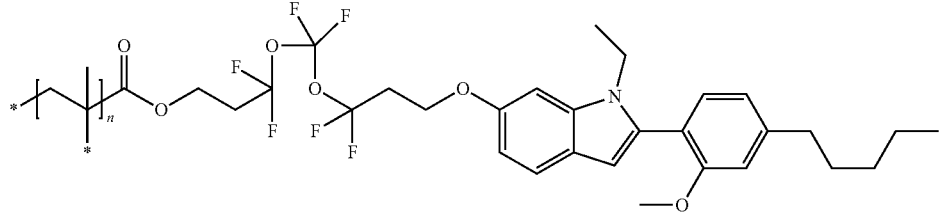

-continued
P-605
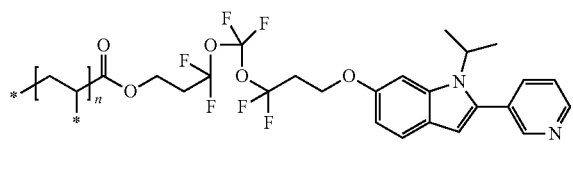
P-606
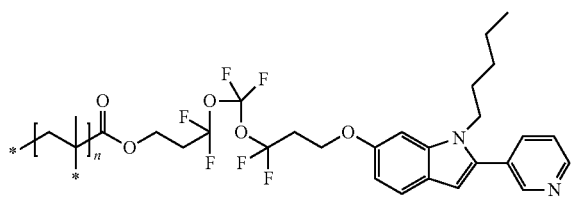
P-607
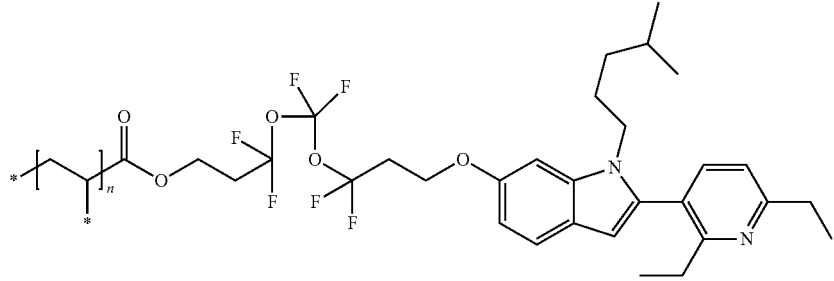
P-608
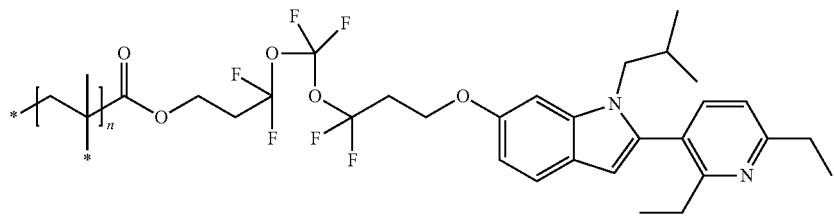
P-609
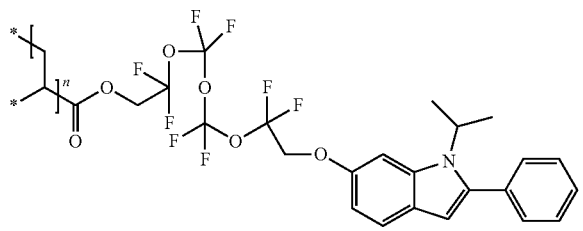
P-610
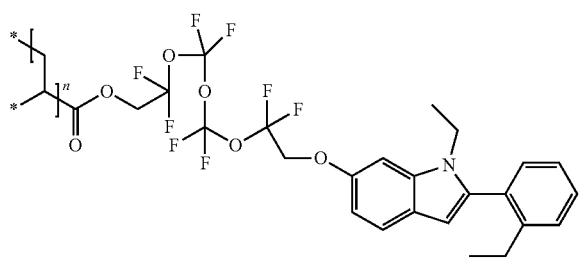
P-611
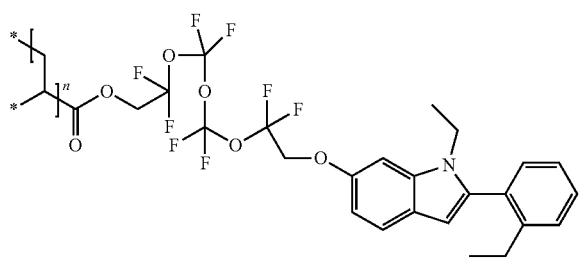
P-612
P-613
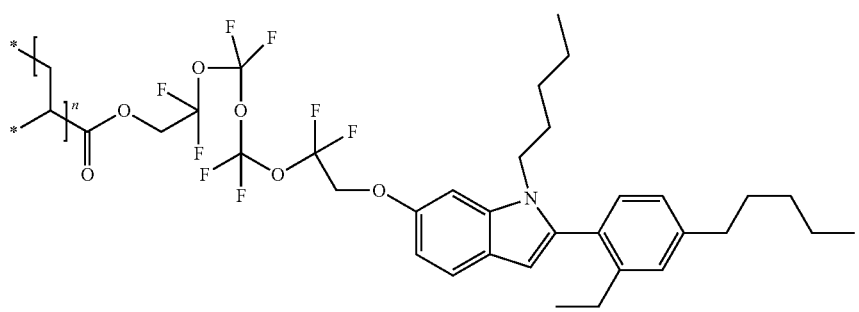

-continued
P-614
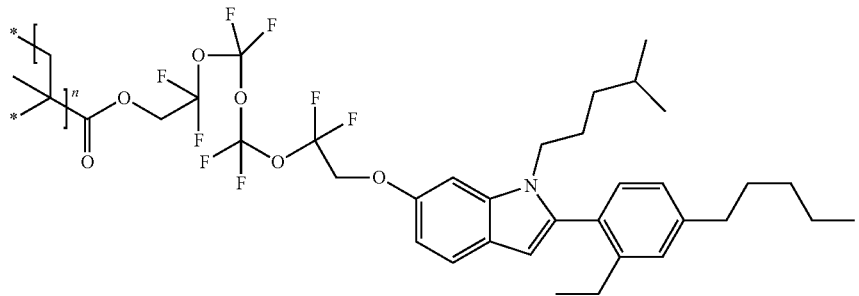
P-615
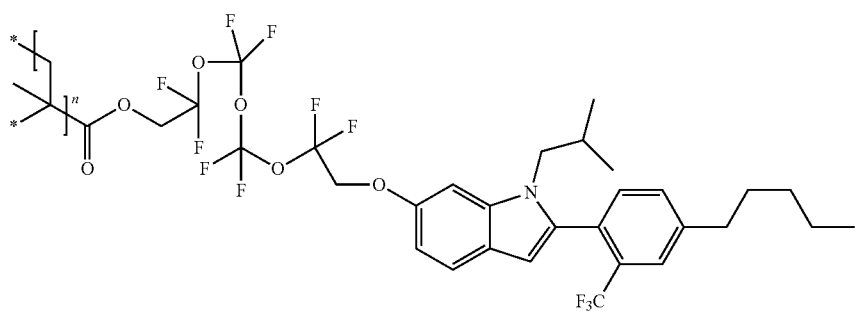
P-616
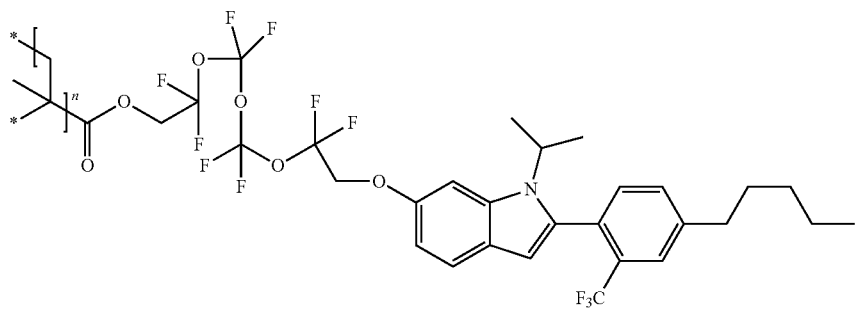
P-617
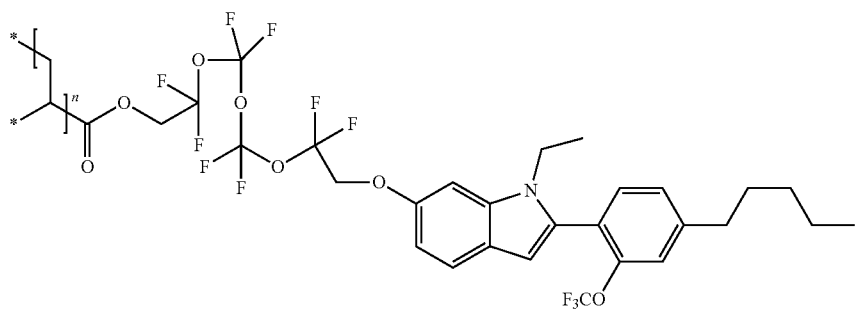
P-618
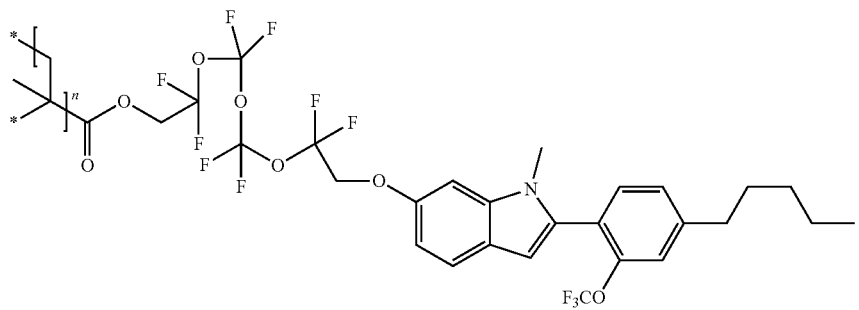

-continued
P-619
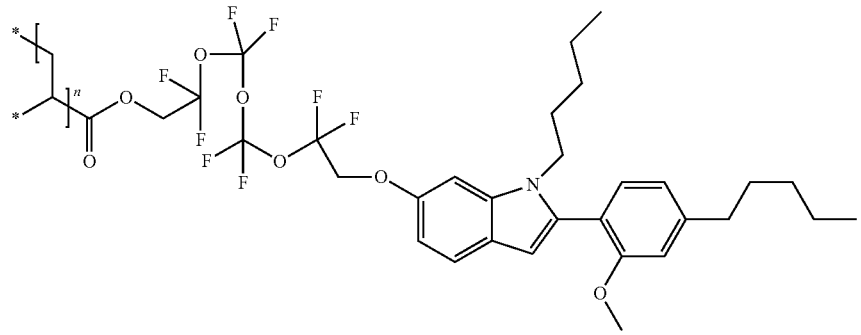
P-620
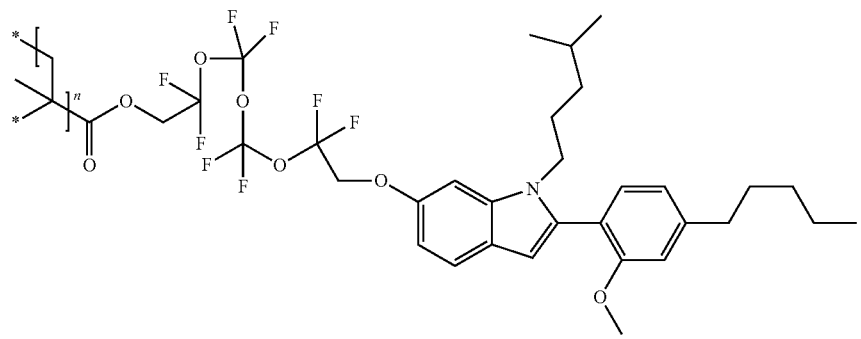
P-621
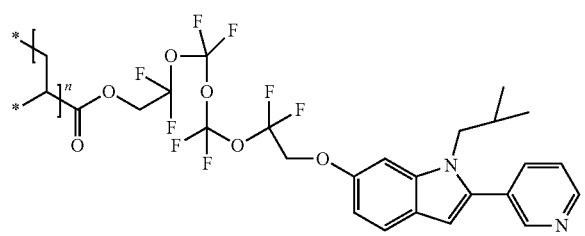
P-622
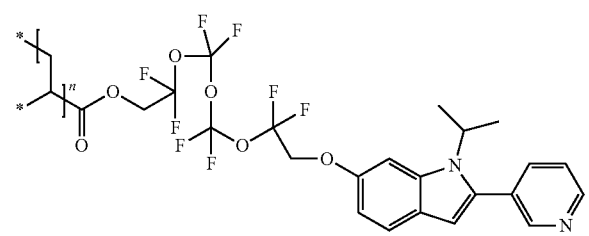
P-623
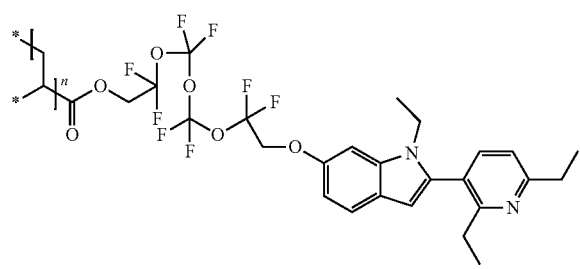
P-624
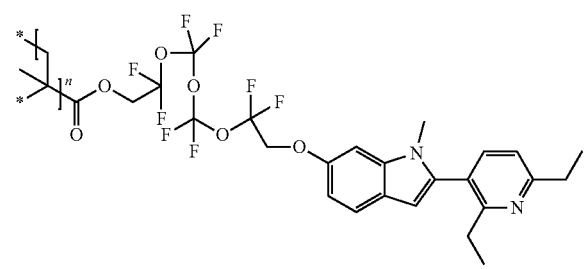
P-625
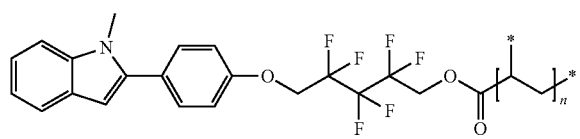
P-626
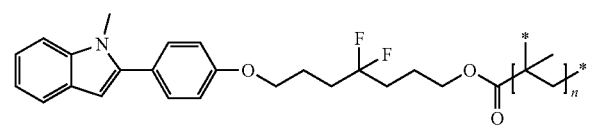

P-627

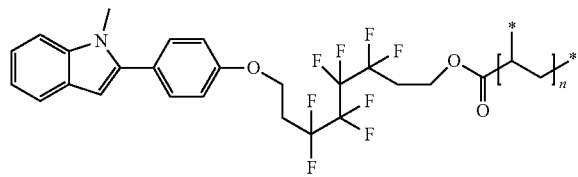

P-628

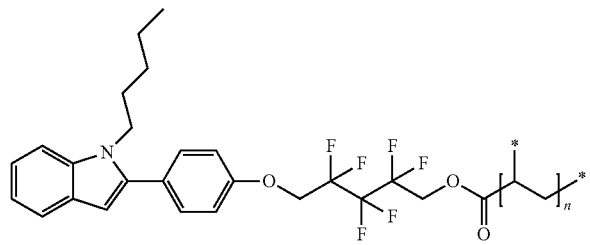

The letter n gives the degree of polymerization as explained before. Preferably a co-polymer according to the invention as described before or preferably described before comprises the one or more constitutional units $M^0$ in a molar ratio m1 and the one or more constitutional units $M^2$ in a molar ratio m2, wherein the ratio m1:m2 is at least 0.01 and at most 100.

The oligomers or polymers according to the invention as described before or preferably described may be cross-linked.

The oligomers and polymers of the present invention may be made by any suitable method. It is, however, preferred that the present oligomers and polymers are made by radical polymerization, wherein the polymerization reaction is started by means of a suitable radical polymerization initiator. For the purposes of the present invention the type of radical polymerization initiator is not particularly limited and may be any suitable radical generating compound. Such compounds are well known to the skilled person. Suitable polymerization initiators may be selected from thermal initiators or photoinitiators, i.e. compounds that generate radicals by exposure to heat or irradiation with light of a suitable wavelength. Examples of suitable thermal polymerization initiators may be selected from the groups of compounds comprising one or more peroxide groups, i.e. compounds comprising a group —O—O—, and/or compounds comprising one or more azo groups, i.e. compounds comprising a group —N=N—.

Suitable polymerization initiators comprising one or more peroxide groups may, for example, be selected from the groups consisting of t-butyl(peroxy-2-ethyl-hexanoate), di-(tert-butylcyclohexyl)peroxydicarbonate and benzoylperoxide.

Suitable polymerization initiators comprising one or more azo groups may, for example, be selected from the group consisting of 1,1'-azobis(cyclohexancarbonitrile) and 2,2'azobis(cyclohexanecarbonitrile) (AIBN).

A suitable example of a photoinitiator is dimethylaminobenzoate/camphorquinone.

If a photoinitiator is used as polymerization initiator, it is preferred that the wavelength required to decompose said photoinitiator is different from the wavelength needed to irradiate the compound of the present application so as to change its optical properties.

Preferably, the radical initiators are used in an amount of at least 0.0001 eq and of at most 0.1 eq of the main monomer. Such radical initiators could be thermal initiators, e.g. azobisisobutyronitrile (AIBN) or photochemical initiators like dimethylaminobenzoate/camphorquinone.

The present invention is also directed to a composition comprising at least one compound of formula (I), (I'), (I") or (I''') as described or preferably described before and/or an oligomer or polymer as described before or preferably described before.

A composition comprising at least one compound of formula (I), (I'), (I") or (I''') as described or preferably described before and an oligomer or polymer as described before is primarily used for the synthesis of block co-polymers with the condition that the oligomer or polymer has at least one reactive group left which may react with the monomers.

Depending upon the intended use such composition may comprise further different components. Such further components may, for example, be selected from the group consisting of UV absorbers, antioxidants and cross-linkers.

The compositions may include or comprise, essentially consist of or consist of the said requisite or optional constituents. All compounds or components which can be used in the compositions are either known and commercially available or can by synthesized by known processes.

The UV absorber that may be used in the present composition is not particularly limited and can easily be selected from those generally known to the skilled person. Generally suitable UV absorbers are characterized by being unsaturated compounds, preferably compounds comprising one or more selected from group consisting of olefinic groups, aryl groups and heteroaryl groups; these groups may be present in any combination.

Suitable UV-absorbers for use in the present composition may, for example, be selected from those comprising a group selected from benzotriazole, benzophenone and triazine. Suitable UV-absorbers are, for example, disclosed in U.S. Pat. Nos. 5,290,892; 5,331,073 and 5,693,095.

Suitable cross-linkers may be used to impart elastomeric properties to the present composition and the articles produced therewith. Typically any suitable di- or tri-functional monomer may be used as crosslinker. Such monomers are generally well known to the skilled person including at least one compound of formula (I''') as described before or preferably described before.

Preferred cross-linker may be selected from the following group of compounds

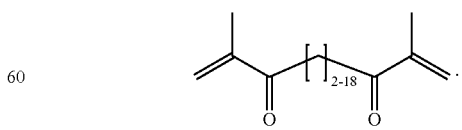

Ethylene glycol dimethacrylate (EGDMA) is particularly preferred.

Suitable antioxidants are phenyl acrylate derivatives bearing a hindered phenol moiety. A preferred antioxidant is

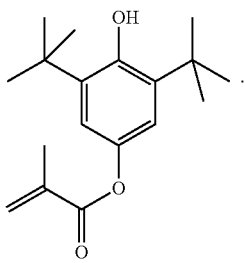 [SMILES: C=C(C)C(=O)Oc1cc(C(C)(C)C)c(O)c(C(C)(C)C)c1]

The compounds of formula (I) according to the invention and their oligomers or polymers as described before or preferably described before are particularly well suited for use in optically active devices.

Hence the present invention is also directed to articles e.g. blanks which may be transformed into optically active devices comprising at least one compound of formula (I) as described before or preferably described before or at least one oligomer or polymer as described before or preferably described before.

Preferred articles are blanks which may be transformed into optically active devices or the optically active devices as such. Preferred optically active devices are ophthalmic devices. Examples of such ophthalmic devices include lenses, keratoprostheses, and cornea inlays or rings. More preferably, said article is a blank which may be transformed into an eye-implant or the eye-implant as such. More preferably, said eye-implant is a lens. Most preferably, such article is a blank which may be transformed into an intraocular lens or the intraocular lens as such, which may, for example, be a posterior chamber intraocular lens or an anterior chamber intraocular lens.

A blank of this invention may be produced as a step in the manufacturing process used to create an intraocular lens. For example, without limitation, a manufacturing process may include the steps of polymer synthesis, polymer sheet casting, blank cutting, optic lathe cutting, optic milling, haptic milling or attachment, polishing, solvent extraction, sterilization and packaging.

The present articles according to the invention as described before or preferably described before may be formed by a process comprising the steps of
  providing a composition comprising at least one compound of formula (I) as defined herein and/or an oligomer or polymer as defined herein; and
  subsequently forming the article of said composition.

Intraocular lenses in accordance with the present invention are believed to show particularly advantageous properties in that they are flexible enough so as to be rolled or folded and consequently requiring a much smaller incision for them to be inserted into the eye. It is believed that this will allow for improved healing of the eye, particularly in respect to the time for the eye to heal.

The type of intraocular lens is not limited in any way. It may, for example, comprise one or more optic and one or more haptic components, wherein the one or more optic components serve as lens and the one or more haptic components are attached to the one or more optic components and hold the one or more optic components in place in the eye. The present intraocular lens may be of a one-piece design or of multi-piece design, depending on whether the one or more optic components and the one or more haptic components are formed from a single piece of material (one-piece design) or are made separately and then combined (multi-piece design). The present intraocular lens is also designed in such a way that it allows to be, for example, rolled up or folded small enough so that it fits through an incision in the eye, said incision being as small as possible, for example, at most 3 mm in length.

Additionally, intraocular lenses in accordance with the present invention allow for the non-invasive adjustment of the optical properties, particularly the refractive power, after implantation of the lens into the eye, thus reducing the need for post-surgery vision aids or reducing or totally avoiding follow-up surgery.

In order to change the optical properties and particularly the refractive power of the intraocular lens it is exposed to irradiation having a wavelength of at least 200 nm and of at most 1500 nm. Hence, the present invention is also directed to a process of changing the optical properties of an article as defined or preferably defined herein, said process comprising the steps of
  providing an article as defined herein; and
  subsequently exposing said article to irradiation having a wavelength of at least 200 nm and at most 1500 nm.

Preferably, said irradiation has a wavelength of at least 250 nm or 300 nm, more preferably of at least 350 nm, even more preferably of at least 400 nm, still even more preferably of at least 450 nm, and most preferably of at least 500 nm. Preferably, said irradiation has a wavelength of at most 1400 nm or 1300 nm or 1200 nm or 1100 nm or 1000 nm, more preferably of at most 950 nm or 900 nm, even more preferably of at most 850 nm, still even more preferably of at most 800 nm and most preferably of at most 750 nm.

EXAMPLES

The following examples are intended to show the advantages of the present compounds in a non-limiting way.

Unless indicated otherwise, all syntheses can be or are carried out under an inert atmosphere using dried (i.e. water-free) solvents. Solvents and reagents are purchased or can be purchased from commercial suppliers.

DCM is used to denote dichloromethane. DMF is used to denote dimethylformamide. EE is used to denote ethyl acetate. THF is used to denote tetrahydrofuran.

Co-polymer-properties can be investigated on blanks, prepared by bulk polymerization of the monomers. Co-monomers, cross-linkers and initiators therefore can be purchased from commercial sources. All chemicals are of highest purity available and can be used as received.

Synthesis of Precursor Materials:

General Remarks & General Synthetic Procedures (GSP)-Trifluormethylation or Trifluorethylation of Carbon Nucleophiles The introduction of a trifluormethyl- or trifluoroethyl group to the corresponding carbon nucleophile is performed with 3,3-dimethyl-1-(trifluoromethyl)-1,2-benziodoxole, 5-(trifluoromethyl)dibenzothiophenium triflate as well as phenyl(2,2,2-trifluoroethyl)iodonium bis((trifluoromethyl)sulfonyl)amid. The experimental procedures for this reactions can be found under the following DOI numbers: 10.1021/jo981065b, 10.1002/chem.200501052, 10.1021/ja00059a009.

Characterization of Precursor Materials:

Diethyl 2-methylmalonat

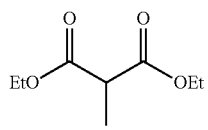

$^1$H NMR (500 MHz, CDCl$_3$) δ 4.23-4.16 (m, 4H), 3.41 (q, 1H, J=7.3 Hz), 1.41 (d, 3H, J=7.3 Hz), 1.27 (t, 6H, J=7.1 Hz).

2,2,3,3,4,4-hexafluoro-5-hydroxypentyl acrylate

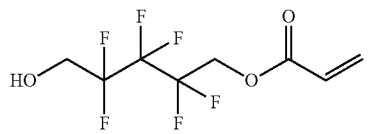 [SMILES: C=CC(=O)OCC(F)(F)C(F)(F)C(F)(F)CO]

This compound is synthesized based on the procedure described in US 2012/308802, preparation example 1, [0071].

$^1$H NMR (500 MHz, CDCl$_3$) δ 6.52 (dd, 1H, J$_1$=17.3 Hz, J$_2$=1.1 Hz), 6.18 (dd, 1H, J$_1$=17.3 Hz, J$_2$=10.5 Hz), 5.97 (dd, 1H, J$_1$=10.5 Hz, J$_2$=1.1 Hz), 4.66 (t, 2H, J=14.1 Hz), 4.12-4.05 (m, 2H), 1.97 (t, 1H, J=7.5 Hz).

Example 1

General Remarks & General Synthetic Procedures (GSP 1) for the Reduction of Aliphatic Diesters or Diketones to the Corresponding Diols

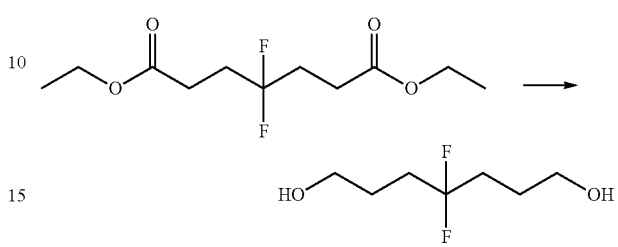

Solid, fine powdered lithiumaluminium hydride (2.0-5.0 equiv.) is suspended in dry THF at room temperature. The corresponding diacid- or diester derivative is dissolved in dry THF and the solution is slowly added dropwise to the lithiumaluminium slurry while cooling with an ice bath. After complete addition, the reaction solution is warmed to room temperature and the consumption of the starting material is checked by TLC. The suspension is carefully quenched with 2M H$_2$SO$_4$, additional water is added. For a better workup, the suspension should have a pH of ~7. The phases are separated and extracted with Et$_2$O. The organic phase is washed with H$_2$O, dried over MgSO$_4$ and evaporated under reduced pressure. The crude product is directly used without further purification or purified via column chromatography using cyclohexane/tert.-butyl methyl ether.

$^1$H NMR (500 MHz, CDCl$_3$) δ 3.70 (t, 4H, J=6.3 Hz), 2.00-1.90 (m, 4H), 1.79-1.74 (m, 4H), 1.38 (br s, 2H).

Analogously, other diol derivatives are prepared in the same manner:

| No. | Starting Material | Product | Yield |
|---|---|---|---|
| 1a | ![EtO-C(O)-CH(CF$_3$)-C(O)-OEt] CAS: 5828-96-6 | HO-CH$_2$-CH(CF$_3$)-CH$_2$-OH | 70 |
| 1b | ![EtO-C(O)-C(CH$_3$)(CF$_3$)-C(O)-OEt] CAS: 129922-42-5 | HO-CH$_2$-C(CH$_3$)(CF$_3$)-CH$_2$-OH | 49 |
| 1c | ![EtO-C(O)-CH(CH$_2$CF$_3$)-C(O)-OEt] CAS: 99783-25-2 | HO-CH$_2$-CH(CH$_2$CF$_3$)-CH$_2$-OH | 41 |

| No. | Starting Material | Product | Yield |
|---|---|---|---|
| 1d | EtO-C(=O)-C(CH3)(CH2CF3)-C(=O)-OEt  CAS: 106241-21-8 | HO-CH2-C(CH3)(CH2CF3)-CH2-OH | 35 |
| 1e | 2-CF3-cyclopentane-1,3-dione  CAS: 89049-67-2 | 2-CF3-cyclopentane-1,3-diol | 88 |
| 1f | 2-methyl-2-CF3-cyclopentane-1,3-dione  CAS: 129922-40-3 | 2-methyl-2-CF3-cyclopentane-1,3-diol | 86 |
| 1g | diethyl 4,4-difluoropimelate  CAS 22515-16-8 | 4,4-difluoroheptane-1,7-diol | 53 |

Example 2

General Remarks & General Synthetic Procedures (GSP 2) for the Synthesis of S-(4-formyl-3-hydroxyphenyl) dimethylcarbamothioate Derivatives Step 1:

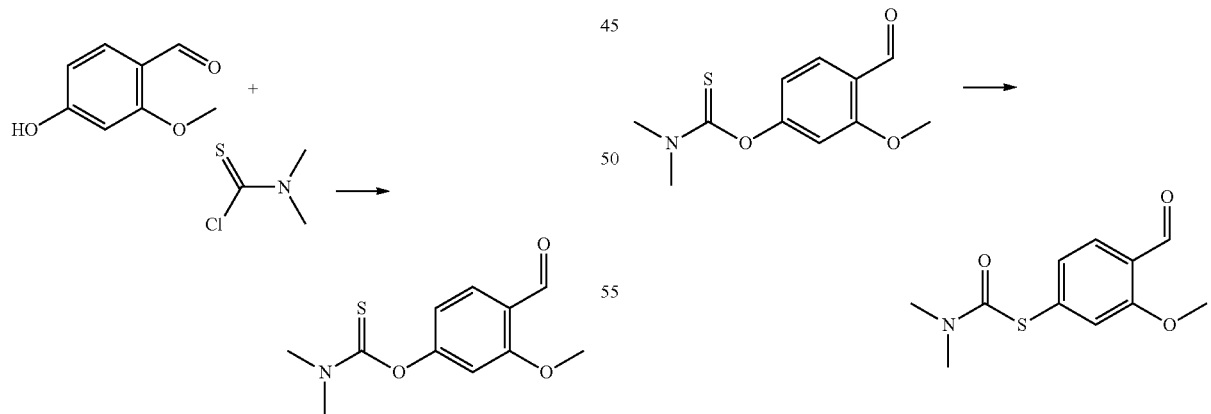

Hydroxy-2-methoxybenzaldehyde (5.00 g; 32.2 mmol) is combined with dimethylthiocarbamoyl chloride (5.34 g, 41.9 mmol) in dimethylformamide (12.52 ml, 161.0 mmol) in an ice bath. 1,8 Diazabicyclo[5.4.0]undec-7-ene (5.05 ml; 33.8 mmol) is added slowly. The reaction is stirred overnight with concomitant warming to RT. The reaction is quenched by pouring on water. The precipitated solid is collected via filtration, washed (3×) with water, and then dried to obtain the crude product. Further purification via recrystallisation with water and enough EtOH to solve product in the heat yields Dimethyl-thiocarbamic acid 4-formyl-3-methoxyphenyl ester (5.26 g, 22.0 mmol, 68% of theory).

Step 2:

Dried Dimethyl-thiocarbamic acid 4-formyl-3-methoxyphenyl ester (5.26 g, 22.0 mmol) is placed in a round bottom flask that is fitted with a reflux condenser. The apparatus is maintained under an argon atmosphere and the reaction is heated in an oil bath to 185° C. The reaction is allowed to progress until TLC analysis indicated that the starting material has been consumed (approx. 4 h). The flask is cooled and the brown solid is dissolved in DCM, adsorbed on silica gel and directly purified with column chromatography (hexane/ethyl acetate; 7:3) to afford dimethyl-thiocarbamic acid 4-formyl-3-methoxy-phenyl ester (4.07 g, 17.0 mmol, 77% of theory).

Step 3:

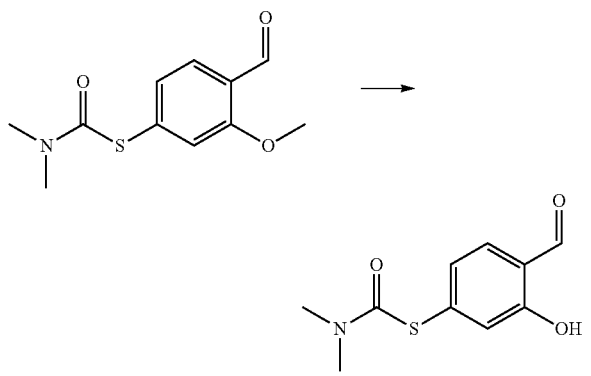

Boron tribromide (1.94 ml, 20.4 mmol) is added slowly to a cooled solution of dimethyl-thiocarbamic acid 4-formyl-3-methoxy-phenyl ester (4.07 g, 17.0 mmol) dissolved in Dichloromethane (anhydrous) (27.15 ml, 425.2 mmol). The solution is kept under Ar atmosphere and left to stir while gradually warming to room temperature until consumption of the starting material is observed by TLC. The reaction is then quenched by poring into a stirred 1M HCl/ice mixture for 10 min. The solution is extracted with ether (2×) and the organic layer is washed with brine, dried with MgSO₄ and evaporated. The remaining solid is recrystallized from heptane with addition of toulene until clear solution is obtained. The precipitate is filtered to yield dimethyl-thiocarbamic acid 4-formyl-3-hydroxy-phenyl ester (3.41 g, 15.1 mmol, 89% of theory).

Example 3

General Remarks & General Synthetic Procedures (GSP 3) for the Bromination of Methyl Phenylacetate Derivatives

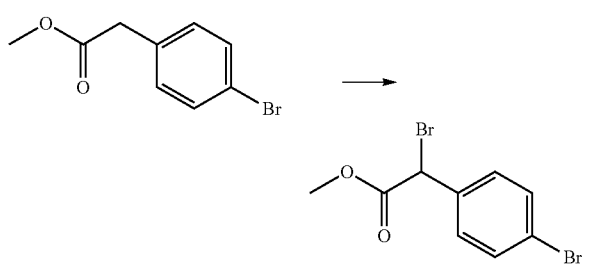

To a stirred solution of the methyl 2-bromophenylacetate (0.86 ml; 5.31 mmol) in dichloromethane (10.2 ml, 159 mmol) are added N-bromosuccinimide (1.04 g, 5.84 mmol) and azobisisobutyronitrile (43.6 mg, 0.27 mmol) at room temperature and the mixture is stirred at 100° C. for 16 h under argon atmosphere. The reaction mixture is cooled down to room temperature. The mixture is diluted with diethyl ether and filtered. The filtrate is evaporated to dryness. The oily residue containing solid succinimid is diluted with heptane and filtered again. The solvent is removed to afford methyl 2-bromo-2-(4-bromophenyl)acetate (1.38 g, 4.56 mmol, 86% of theory).

Analogously, other phenol derivatives are prepared in the same manner:

| No. | Reactant 1 | Product | Yield [%] |
|---|---|---|---|
| 3a | ![structure] CAS: 59793-28-1 | ![structure] | 71 |
| 3b | ![structure] CAS: 1227090-87-0 | ![structure] | 46 |
| 3c | ![structure] CAS: 1805558-53-5 | ![structure] | 52 |
| 3d | ![structure] CAS: 1261878-59-4 | ![structure] | 68 |
| 3e | ![structure] CAS: 39998-25-9 | ![structure] | 43 |

Example 4

General Remarks & General Synthetic Procedures (GSP 4) for the Synthesis of 2-phenyl-benzofurans from Hydroxy-benzaldehyde Derivatives or dimethyl-thiocarbamic Acid 4-formyl-3-hydroxy-phenyl ester derivatives with methyl 2-bromo-2-(4-bromophenyl)acetate

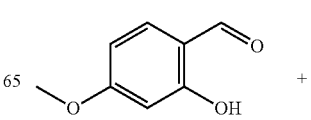 +

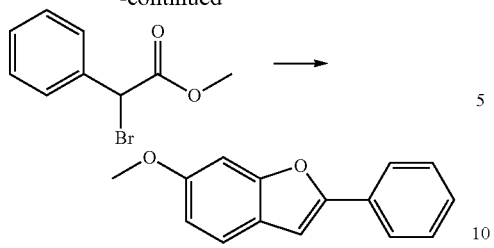

2-Hydroxy-4-methoxybenzaldehyde (1.52 g, 9.99 mmol) and α-bromophenylacetatic acid methyl ester (1.72 ml, 10.99 mmol) are dissolved in dimethylformamide (50.5 ml, 649 mmol). To the solution is added potassium carbonate (6.90 g, 49.9 mmol). The mixture is stirred at 100° C. for 2 h. The mixture is cooled to 25° C. and portioned to EtOAc and HCl (1 N, aq.). The organic layer is separated, washed with brine and dried over MgSO$_4$. Evaporation of solvent gives brownish oily residue. The residue is dissolved in ethanol (40.9 ml, 699 mmol). To the solution is added potassium hydroxide (5.04 g, 89.9 mmol). The mixture is refluxed for 2 h. The mixture is cooled to ambient temperature and acidified with HCl (conc.). The precipitating solid is filtered off and recrystallized from toluene to give 6-methoxy-2-phenyl-benzofuran (1.07 g, 4.78 mmol, 48% of theory).

$^1$H NMR (500 MHz, DMSO-d$_6$) δ 7.86 (d, J=8.4 Hz, 2H), 7.53 (d, J=8.5 Hz, 1H), 7.49 (t, J=7.8 Hz, 2H), 7.38 (t, J=7.4 Hz, 1H), 7.26 (d, J=1.9 Hz, 1H), 6.91 (dd, J=8.5 Hz, 2.2 Hz, 1H), 3.84 (s, 3H).

Analogously, other phenol derivatives are prepared in the same manner: R1 means reactant 1, R2 means reactant 2, [P] means product

| No. | | | Yield [%] |
|---|---|---|---|
| 4a | R1 | 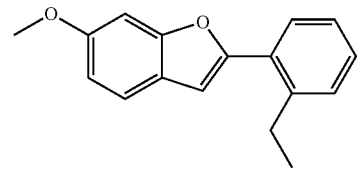 CAS: 673-22-3 | |
| | R2 | 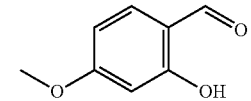 | |
| | [P] | 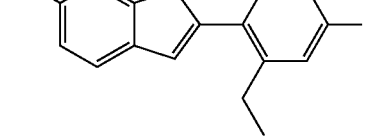 | 39 |
| 4b | R1 | 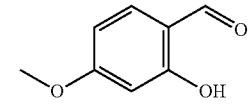 | |
| | R2 | 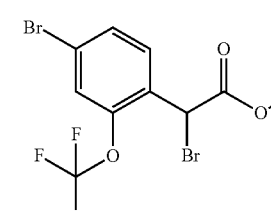 | |
| 4c | R1 | 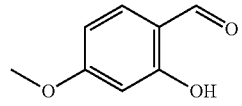 | 57 |
| | R2 | 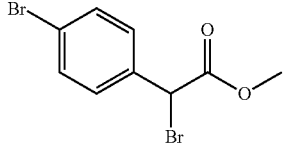 | |
| 4d | R1 | 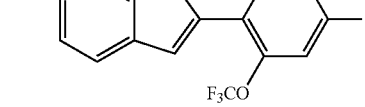 | 47 |
| | R2 | 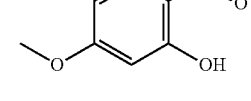 | |
| | [P] | 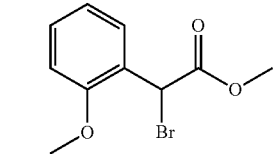 | 69 |
| 4e | R1 | 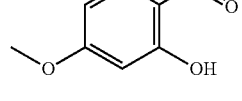 | |
| | R2 | 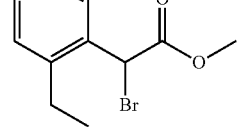 CAS: 99552-78-0 | |

333
-continued
| No. | | Yield [%] |
|---|---|---|
| | [P] 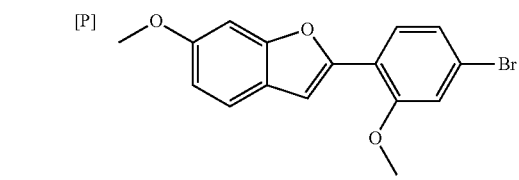 | 62 |
| 4f | R1 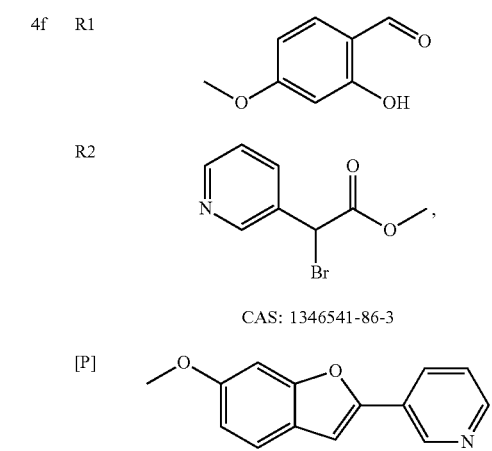 CAS: 1346541-86-3 | |
| | [P] 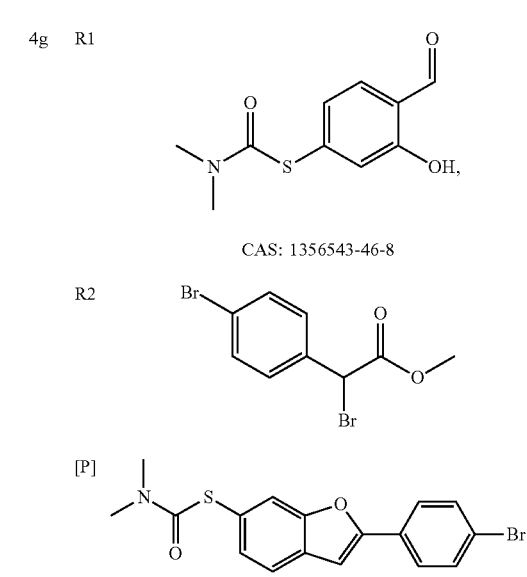 CAS: 1356543-46-8 | 67 |
| 4g | R1 | |
| | R2 | |
| | [P] 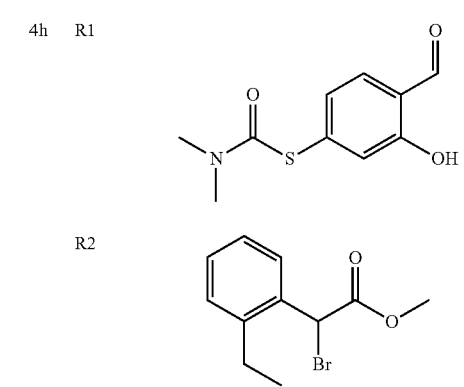 | 57 |
| 4h | R1 | |
| | R2 | |
334
-continued
| No. | | Yield [%] |
|---|---|---|
| | [P] 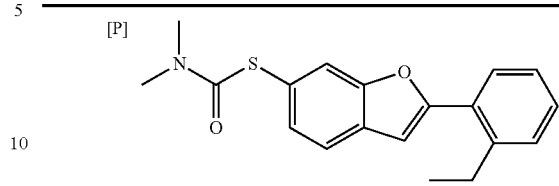 | 49 |
| 4i | R1 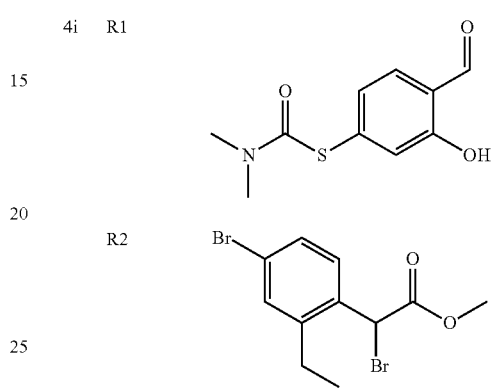 | |
| | R2 | |
| | [P] 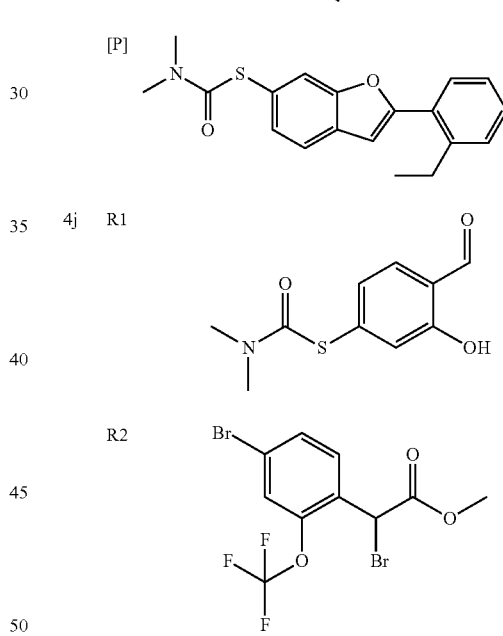 | 44 |
| 4j | R1 | |
| | R2 | |
| | [P] 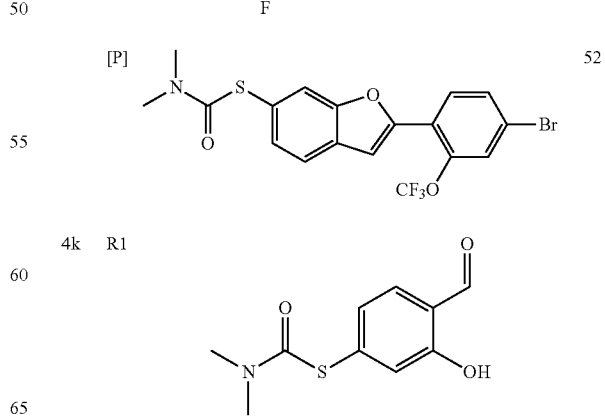 | 52 |
| 4k | R1 | |

| No. | | Yield [%] |
|---|---|---|
| R2 | ![structure: methyl 2-bromo-2-(pyridin-3-yl)acetate] | |
| [P] | ![structure: S-(2-(pyridin-3-yl)benzofuran-6-yl) dimethylcarbamothioate] | 32 |

Example 5

General Remarks & General Synthetic Procedures (GSP 5) for the Suzuki Reaction of Halogen-Substituted 2-phenyl-benzofurans with boronic acids

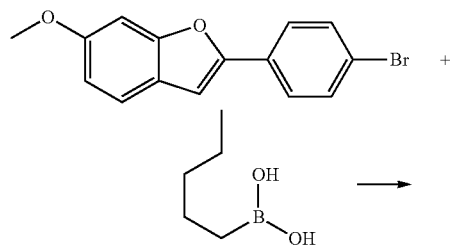

2-(4-Bromo-phenyl)-6-methoxy-benzofuran (550 mg, 1.81 mmol), pentylboronic acid (463 mg, 3.99 mmol) and tripotassium phosphate monohydrate (1.75 g, 7.62 mmol) are dissolved in toluene (19.2 ml, 181 mmol). Then 2-Dicyclohexylphosphino-2',6'-dimethoxybiphenyl [SPhos](149 mg, 359 µmol) and palladium(II) acetate (40.7 mg, 180 µmol) are added and the reaction reaction mixture is heated to 120° C. for 1 d. The cooled reaction mixture is diluted with ethyl acetate and HCl solution (2 M). The solution is transferred to a separatory funnel. The organic phase is extracted with HCl solution (2 M) and water and brine. The organic phase is dried over MgSO₄, filtered and concentrated under reduced pressure. The residue is purified by silica gel column chromatography (heptane/ethyl acetate [5/1]) to yield 6-Methoxy-2-(4-pentyl-phenyl)-benzofuran (350 mg, 1.2 mmol, 66% of theory).

1H NMR (500 MHz, Chloroform-d) b 7.65 (d, J=8.2 Hz, 2H), 7.35 (d, J=8.5 Hz, 1H), 7.17 (d, J=8.1 Hz, 2H), 6.99 (d, J=2.1 Hz, 1H), 6.82 (s, 1H), 6.79 (dd, J=8.5 Hz, 2.3 Hz, 1H), 3.80 (s, 3H), 2.59-2.54 (m, 2H), 1.58 (p, J=7.5 Hz, 2H), 1.32-1.24 (m, 4H), 0.83 (t, J=6.9 Hz, 3H).

Analogously, other phenol derivatives are prepared in the same manner: R1 means reactant 1, R2 means reactant 2, [P] means product

| No. | | | Yield [%] |
|---|---|---|---|
| 5a | R1 | ![structure: 2-(4-bromo-2-ethylphenyl)-6-methoxybenzofuran] | |
| | R2 | ![pentylboronic acid] CAS: 4737-50-2 | |
| | [P] | ![structure: 6-methoxy-2-(2-ethyl-4-pentylphenyl)benzofuran] | 75 |
| 5b | R1 | ![structure: 2-(4-bromo-2-(trifluoromethoxy)phenyl)-6-methoxybenzofuran] | |

| No. | | Yield [%] |
|---|---|---|
| R2 | pentylboronic acid | |
| [P] | 2-(6-methoxybenzofuran-2-yl)-5-pentyl-(2-trifluoromethoxy)benzene | 80 |
| 5c R1 | 2-(6-methoxybenzofuran-2-yl)-5-bromo-(2-methoxy)benzene | |
| R2 | pentylboronic acid | |
| [P] | 2-(6-methoxybenzofuran-2-yl)-5-pentyl-(2-methoxy)benzene | 72 |
| 5d R1 | S-(2-(4-bromo-2-ethylphenyl)benzofuran-6-yl) dimethylcarbamothioate | |
| R2 | pentylboronic acid | |
| [P] | S-(2-(2-ethyl-4-pentylphenyl)benzofuran-6-yl) dimethylcarbamothioate | 73 |
| 5e R1 | S-(2-(4-bromo-2-trifluoromethoxyphenyl)benzofuran-6-yl) dimethylcarbamothioate | |
| R2 | pentylboronic acid | |

| No. | | Yield [%] |
|---|---|---|
| [P] | ![structure with F3CO group] | 92 |
| 5f R1 | ![structure with Br and OMe] | |
| R2 | ![pentylboronic acid] | |
| [P] | ![structure with OMe] | 60 |

Example 6

General Remarks & General Synthetic Procedures (GSP 6) for the Deprotection to Synthesize the Phenol or Thiol Derivatives

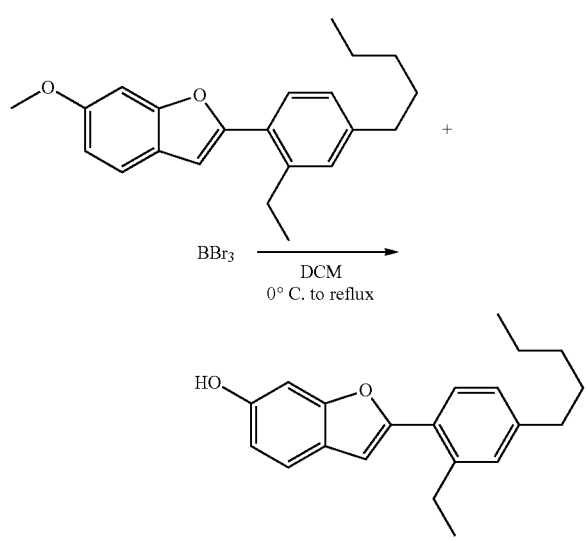

To a solution of 2-(2-ethyl-4-pentylphenyl)-6-methoxy-benzofuran in DCM is added BBr$_3$ (2.0 equiv.) at 0° C. The resulting mixture is heated up to reflux overnight. After cooling down the reaction mixture to room temperature, it is poured on an ice/water mixture, filtrated and the resulting solid is dried in vacuo. The phenol derivative is obtained in 77% of theory.

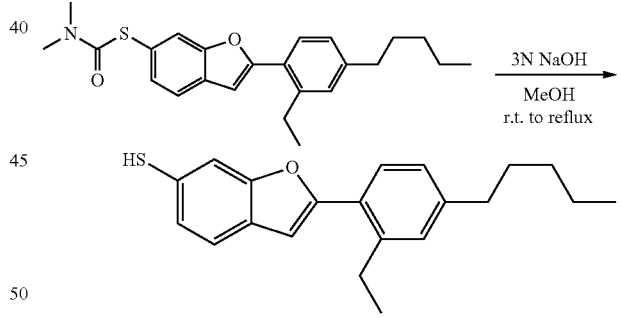

Dimethyl-thiocarbamic acid 3-(4-chloro-2-trifluoromethyl-phenyl)-coumarin-7-yl ester (900.00 mg, 2.1 mmol) is dissolved in methanol (2.09 ml, 51.6 mmol). Sodium hydroxide solution (3N, aq.) (0.42 ml, 1.3 mmol) is added, and the reaction mixture is heated to reflux overnight. The reaction mixture is cooled to 25° C. and acidified by the addition of HCl (10%, aq.). The milky solution is then extracted with EtOAc (×2) and the combined organic layers are washed with brine then dried with MgSO$_4$, filtered and concentrated. The obtained light brown oil is purified using silica gel chromatography (chloroform/methanol; 30/1) to afford 2-(2-ethyl-4-pentylphenyl)benzofuran-6-thiol (400.00 mg, 1.1 mmol, 53% of theory).

Analogously, other phenol and thiol derivatives are prepared in the same manner:

| No. | Reactant 1 | Product | Yield [%] |
|---|---|---|---|
| 6a | | | 62 |
| 6b | | | 70 |
| 6c | | | 53 |
| 6d | | | 74 |
| 6e | | | 84 |
| 6f | | | 79 |
| 6g | | | 92 |
Example 7
General Remarks & General Synthetic Procedures (GSP 7) for the Reaction of the Corresponding Fluorinated Diols or Monoalcohol with 2 phenylbenzofuran-6-ol (Mitsunobu Alkylation Type Reaction)
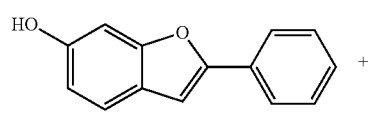
+
-continued
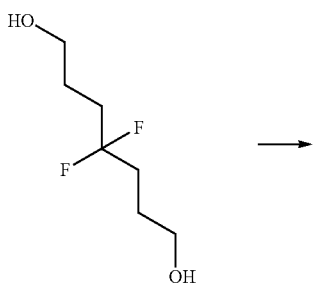

-continued

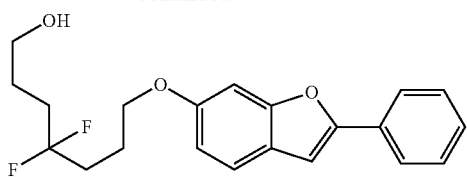

To an ice-cooled solution of 2-phenylbenzofuran-6-ol, aliphatic fluorinated diol or monoalcohol (1.0 equiv.) and triphenylphosphine in THF (1.43 equiv.), diisopropyl azodicarboxylate (1.43 equiv.) is added dropwise. After stirring at room temperature overnight, the reaction mixture is evaporated. The crude product is purified by column chromatography (cyclohexane/EE).

Analogously, other phenol derivatives are prepared in the same manner: R1 means reactant 1, R2 means reactant 2, [P] means product

| No. | | |
|---|---|---|
| 7a | R1 | 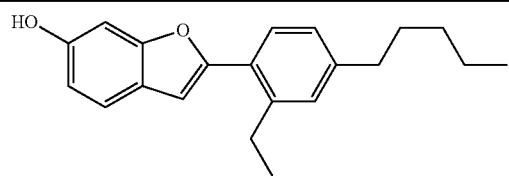 |
| | R2 | 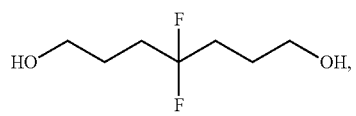<br>CAS: 83192-87-4 |
| | [P] | 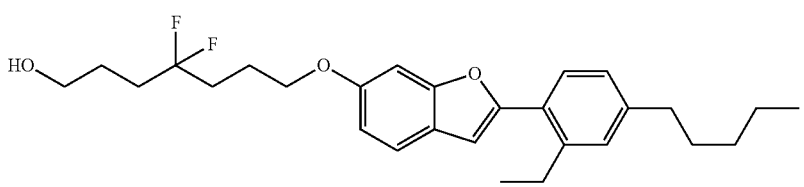 |
| 7b | R1 | 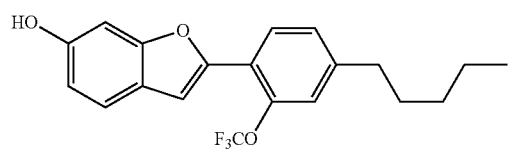 |
| | R2 | 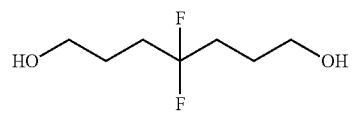 |
| | [P] | 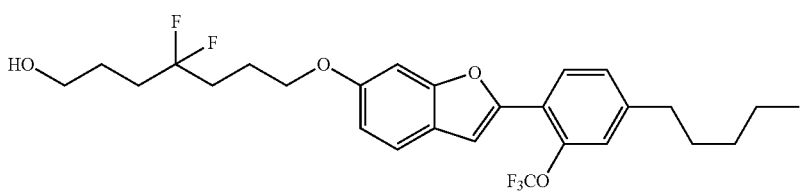 |
| 7c | R1 | 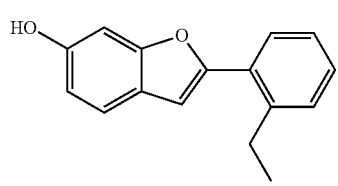 |
| | R2 | 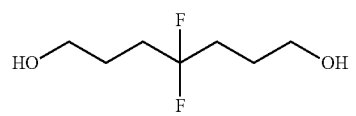 |

-continued
| No. | | |
|---|---|---|
| | [P] | 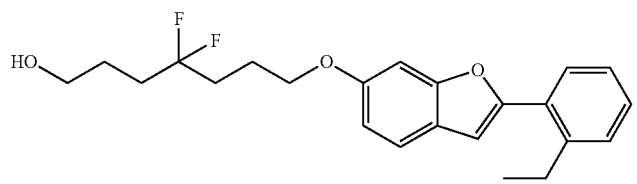 |
| 7d | R1 | 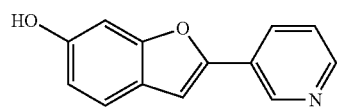 [SMILES: Oc1ccc2cc(-c3cccnc3)oc2c1] |
| | R2 | 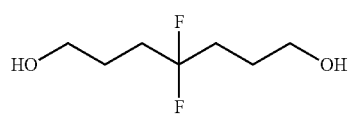 [SMILES: OCCCC(F)(F)CCCO] |
| | [P] | 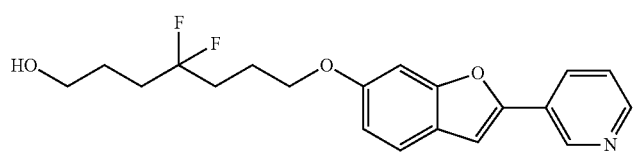 |
| 7e | R1 | 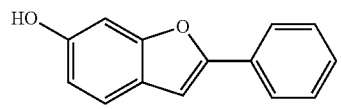 |
| | R2 | 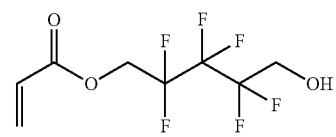 [SMILES: C=CC(=O)OCC(F)(F)C(F)(F)C(F)(F)CO] |
| | [P] | 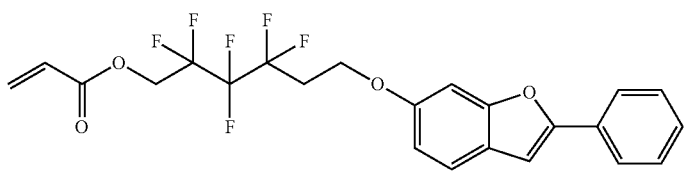 [SMILES: C=CC(=O)OCC(F)(F)C(F)(F)C(F)(F)CCOc1ccc2cc(-c3ccccc3)oc2c1] |
| 7f | R1 | 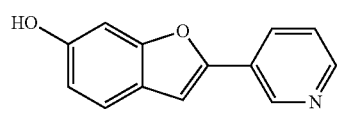 |
| | R2 | 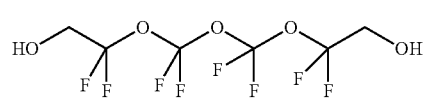 [SMILES: OCC(F)(F)OC(F)(F)OC(F)(F)OC(F)(F)CO] |
| | [P] | 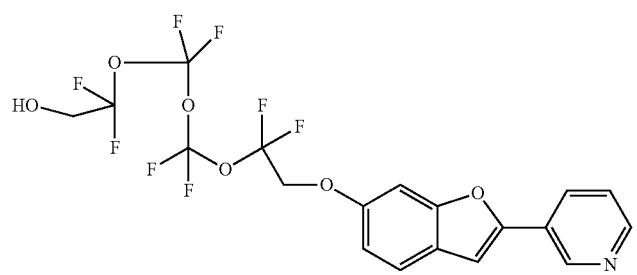 [SMILES: OCC(F)(F)OC(F)(F)OC(F)(F)OC(F)(F)COc1ccc2cc(-c3cccnc3)oc2c1] |

-continued

| No. | | |
|---|---|---|
| 7g | R1 | 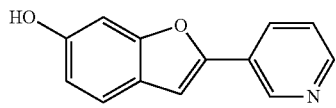 |
| | R2 | 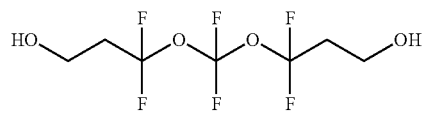 |
| | [P] | 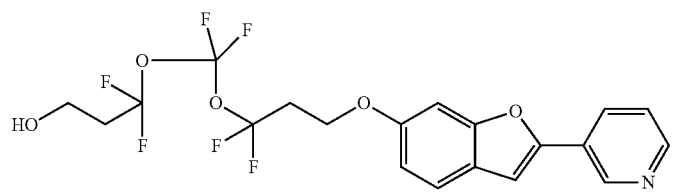 [SMILES: OCCC(F)(F)OC(F)(F)OC(F)(F)CCOc1ccc2cc(-c3cccnc3)oc2c1] |
| 7h | R1 | 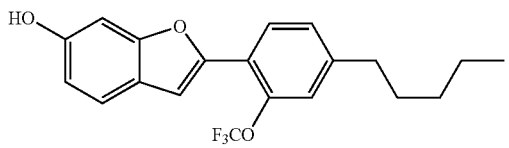 |
| | R2 | 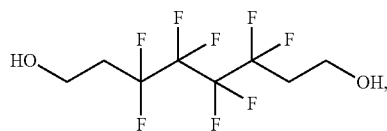 [SMILES: OCCC(F)(F)C(F)(F)C(F)(F)C(F)(F)CCO]<br>CAS: 83192-87-4 |
| | [P] | 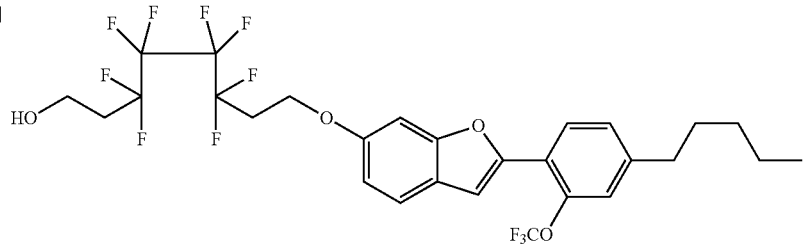 |

Example 8

General Remarks & General Synthetic Procedures (GSP 8) for the Reaction of bromo-Functionalized Hydrophic Linkers with 2-(2-ethyl-4-pentylphenyl)-benzofuran-6-thiol For the reaction of thiols with the fluorinated aliphatic linker, the bromo-functionalized derivatives of the corresponding diols are prepared in advance through reaction of the corresponding diol with HBr in refluxing toluene.

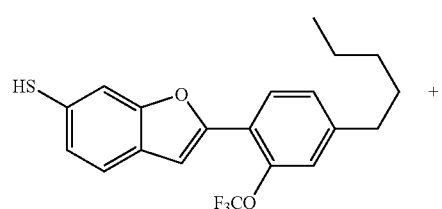

+

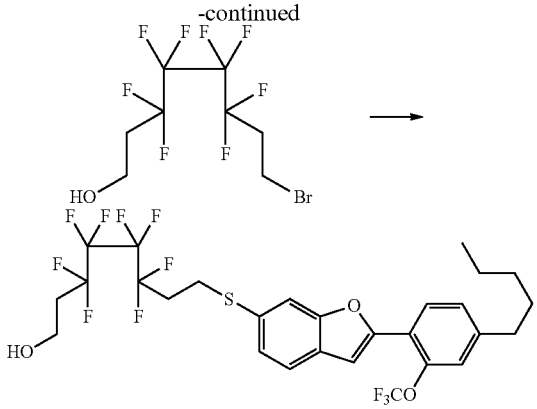

2-(4-Pentyl-2-(trifluoromethoxy)phenyl)benzofuran-6-thiol and 8-bromo-3,3,4,4,5,5,6,6-octafluorooctan-1-ol (1.05 equiv.) are dissolved in anhydrous DMF. Then, $K_2CO_3$ (4.0 equiv.) is added and the suspension is heated up to reflux until completion of the reaction. The reaction mixture is filtrated and the separated solid is thoroughly washed with additional acetone. The filtrate is concentrated in vacuo and the crude product is purified via column chromatography using cyclohexane/EE as an eluent. 3,3,4,4,5,5,6,6-octafluoro-8-((2-(4-pentyl-2-(trifluoromethoxy)phenyl)benzofuran-6-yl)thio)octan-1-ol can be isolated in 76% yield (of theory) as a pale beige solid.

Analogously, other phenol derivatives are prepared in the same manner: R1 means reactant 1, R2 means reactant 2, [P] means product

| No. | | |
|---|---|---|
| 8a | R1 | 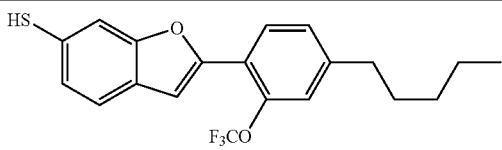 |
| | R2 | 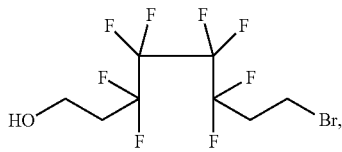 [SMILES: OCCC(F)(F)C(F)(F)C(F)(F)C(F)(F)CCBr]<br>CAS: 83192-87-4 |
| | [P] | 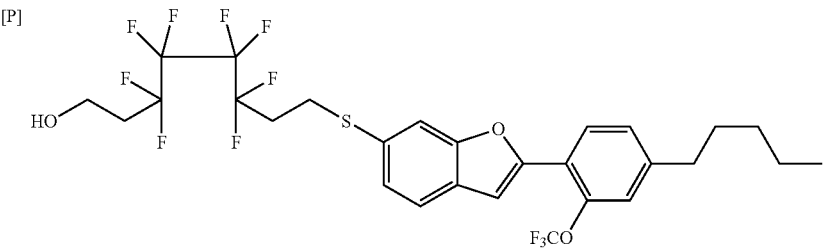 |

Preparation of Compounds According to the Invention

Example 9

General Remarks & General Synthetic Procedures (GSP 9) for the Esterification with Acryloyl Chloride or Methacryloyl Chloride to the Corresponding Monomer

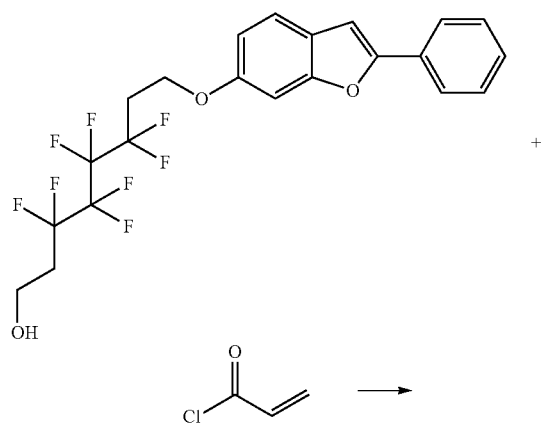

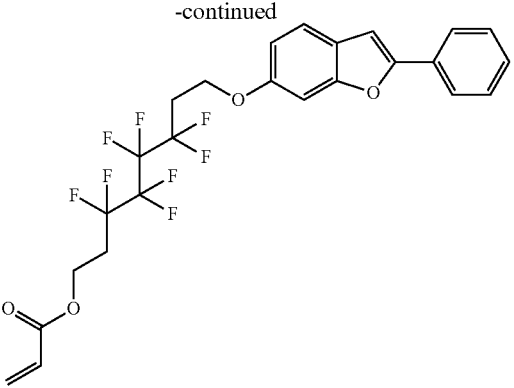

The corresponding aliphatic alcohol is dissolved in dry THF and the solution is cooled with an ice-bath. Triethylamine (4.00 equivs.) is added and the solution is stirred for a few minutes. Then acryloyl chloride or methacryloyl chloride (1.05-2.00 equivs.) is added at ice-bath temperature, while precipitating a colourless solid. The solution is stirred for several hours and is monitored via TLC. Upon completion of the reaction, the suspension is filtrated and washed with THF. The filtrate is evaporated under reduced pressure and purified via column chromatography using cyclohexane/ethyl acetate.

Analogously, other phenol derivatives are prepared in the same manner: R means reactant, [P] means product
| No. | | |
|---|---|---|
| 9a | R | 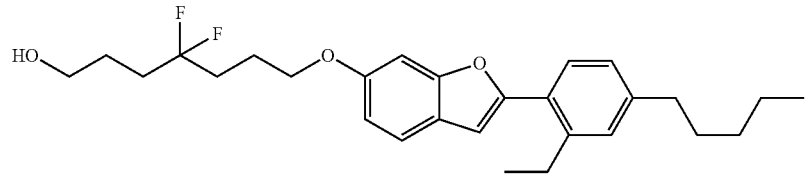 |
| | [P] | 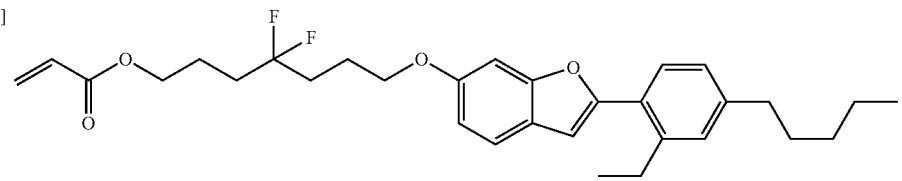 |
| 9b | R | 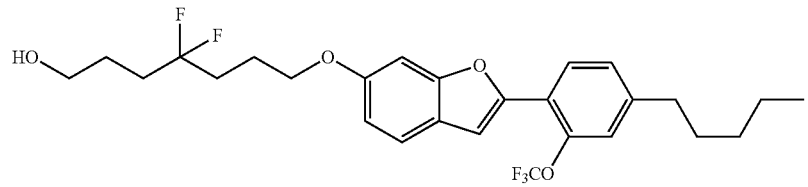 |
| | [P] | 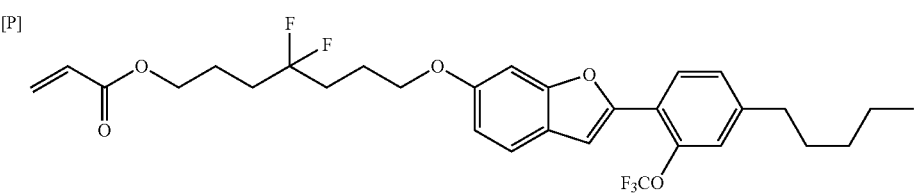 |
| 9c | R | 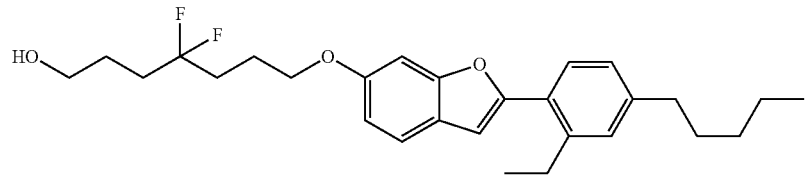 |
| | [P] | 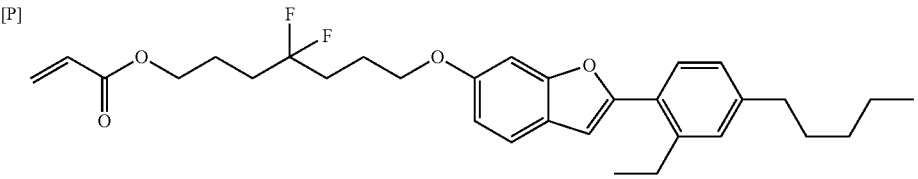 |
| 9d | R | 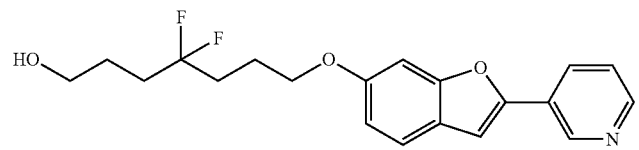 |
| | [P] | 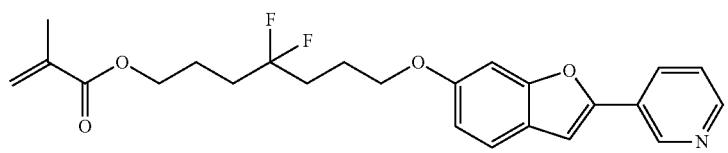 |

-continued
| No. | | |
|---|---|---|
| 9e | R | 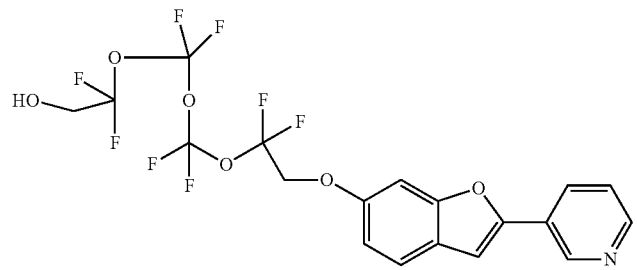 [SMILES: OCC(F)(F)OC(F)(F)OC(F)(F)OC(F)(F)COc1ccc2cc(-c3cccnc3)oc2c1] |
| | [P] | 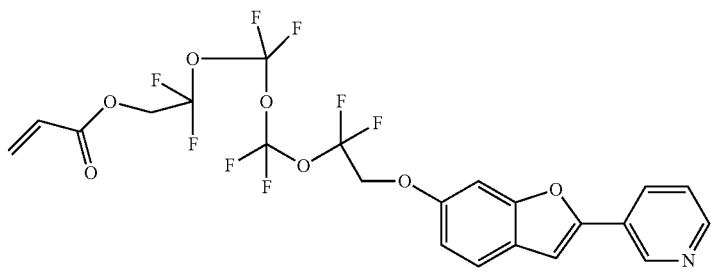 [SMILES: C=CC(=O)OCC(F)(F)OC(F)(F)OC(F)(F)OC(F)(F)COc1ccc2cc(-c3cccnc3)oc2c1] |
| 9f | R | 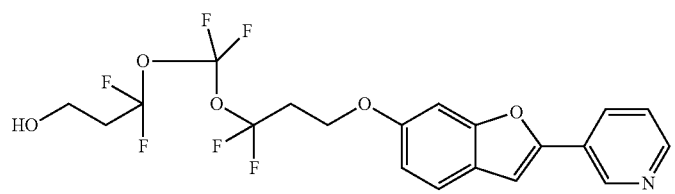 [SMILES: OCCC(F)(F)OC(F)(F)OC(F)(F)CCOc1ccc2cc(-c3cccnc3)oc2c1] |
| | [P] | 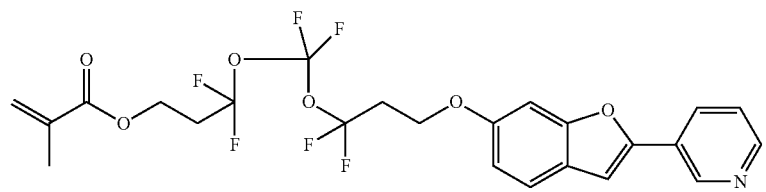 [SMILES: C=C(C)C(=O)OCCC(F)(F)OC(F)(F)OC(F)(F)CCOc1ccc2cc(-c3cccnc3)oc2c1] |
| 9g | R | 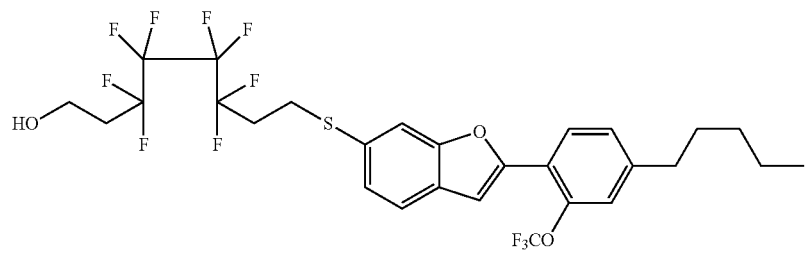 |
| | [P] | 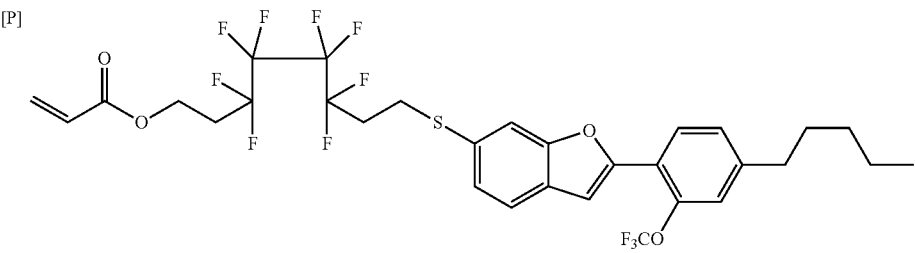 |

Example 10

General Remarks & General Synthetic Procedures (GSP 10) for the for the Solvent Polymerization of the Monomers The corresponding monomer is dissolved in dry N,N-dimethylformamide in a Schlenck-tube with a stirring bar. The solution is degassed performing three times freeze-evacuate-thaw cycles. After that, azoisobutyronitrile (AIBN, 0.05 equiv.) is added in one portion to the degassed solution, which is heated up to 65° C. in an oil bath for a minimum of three days. The solution is cooled to room temperature and is then poured dropwise into cold methanol (100 ml methanol/100 mg monomer) while stirring. The precipitated polymer is collected on a frit or the solution is centrifuged several times to obtain the final polymer material.

Examples of polymers within this invention are given in the following table:

| Monomer |
| --- |
| 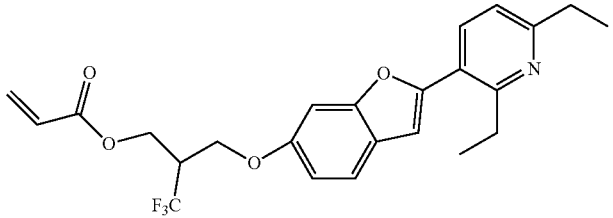 [SMILES: C=CC(=O)OCC(COc1ccc2cc(-c3ccc(CC)nc3CC)oc2c1)C(F)(F)F] (M-01) |
| 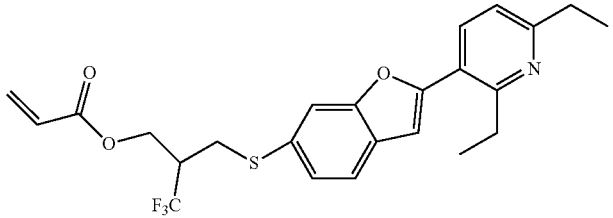 [SMILES: C=CC(=O)OCC(CSc1ccc2cc(-c3ccc(CC)nc3CC)oc2c1)C(F)(F)F] (M-02) |
| 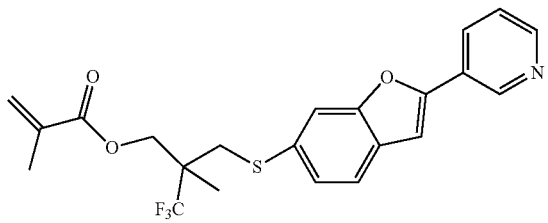 [SMILES: C=C(C)C(=O)OCC(C)(CSc1ccc2cc(-c3cccnc3)oc2c1)C(F)(F)F] (M-03) |
| 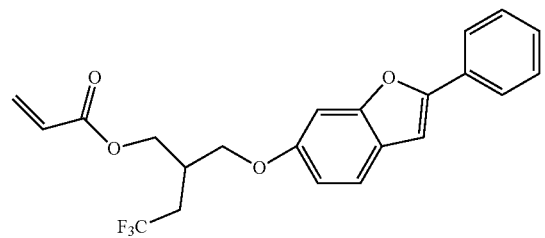 [SMILES: C=CC(=O)OCC(COc1ccc2cc(-c3ccccc3)oc2c1)CC(F)(F)F] (M-04) |

-continued
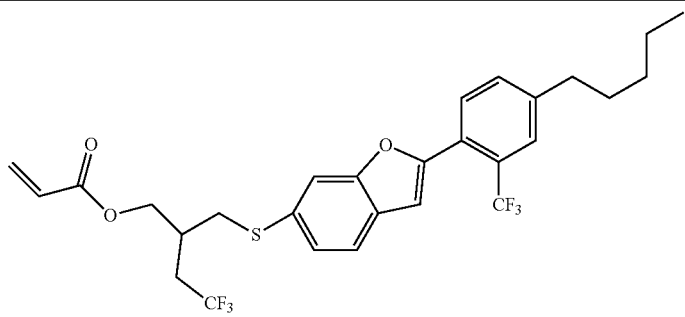
(M-05)
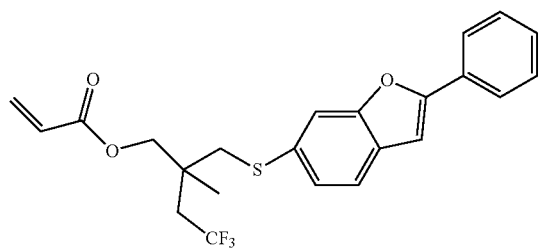 [SMILES: C=CC(=O)OCC(C)(CSc1ccc2cc(-c3ccccc3)oc2c1)CC(F)(F)F]
(M-06)
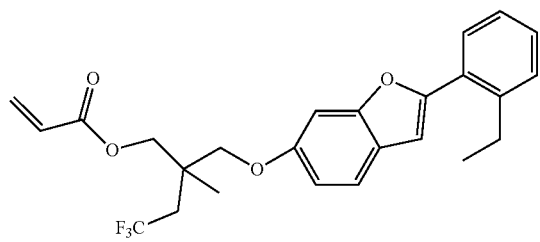 [SMILES: C=CC(=O)OCC(C)(COc1ccc2cc(-c3ccccc3CC)oc2c1)CC(F)(F)F]
(M-07)
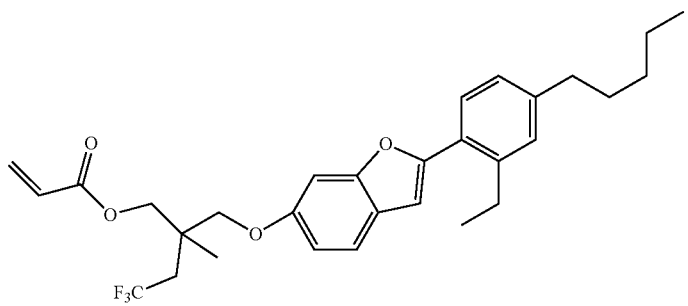 [SMILES: C=CC(=O)OCC(C)(COc1ccc2cc(-c3ccc(CCCCC)cc3CC)oc2c1)CC(F)(F)F]
(M-08)
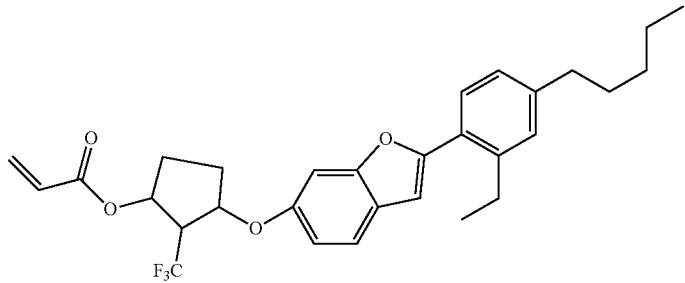 [SMILES: C=CC(=O)OC1CCC(Oc2ccc3cc(-c4ccc(CCCCC)cc4CC)oc3c2)C1C(F)(F)F]
(M-09)

-continued
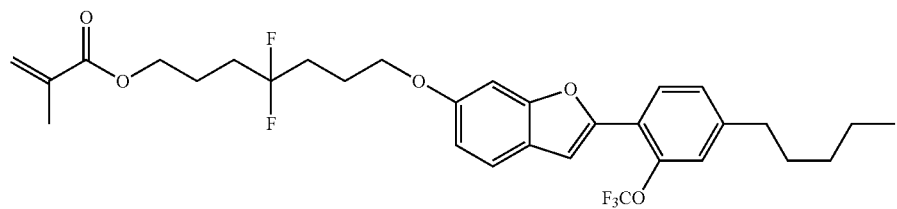
(M-010)
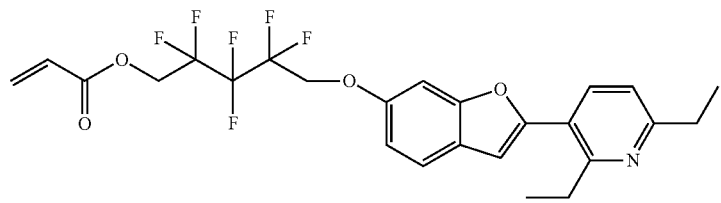 [SMILES: C=CC(=O)OCC(F)(F)C(F)(F)C(F)(F)COc1ccc2cc(-c3ccc(CC)nc3CC)oc2c1]
(M-011)
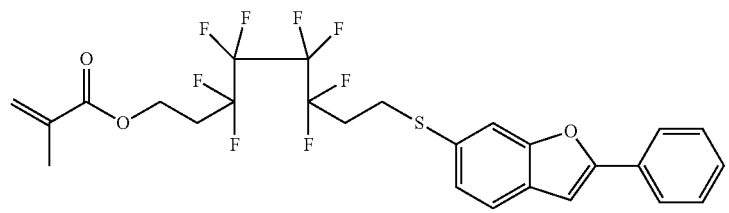 [SMILES: C=C(C)C(=O)OCCC(F)(F)C(F)(F)C(F)(F)C(F)(F)CCSc1ccc2cc(-c3ccccc3)oc2c1]
(M-012)
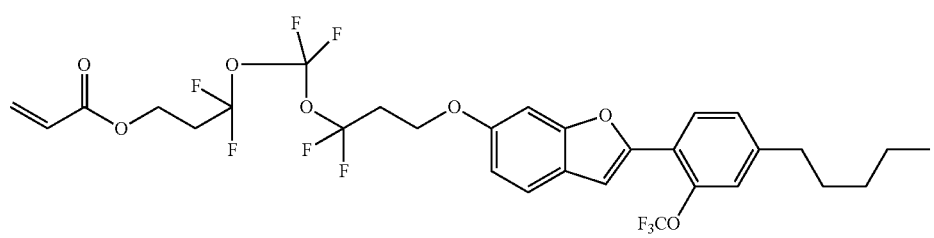 [SMILES: C=CC(=O)OCCC(F)(F)OC(F)(F)OC(F)(F)CCOc1ccc2cc(-c3ccc(CCCCC)cc3OC(F)(F)F)oc2c1]
(M-013)
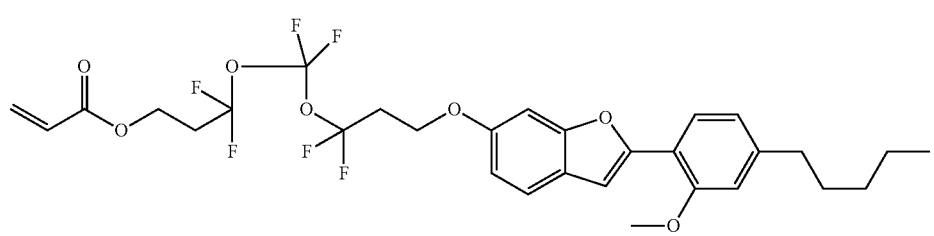 [SMILES: C=CC(=O)OCCC(F)(F)OC(F)(F)OC(F)(F)CCOc1ccc2cc(-c3ccc(CCCCC)cc3OC)oc2c1]
(M-014)
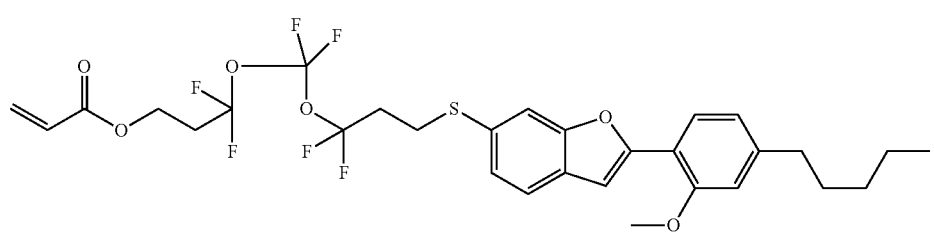 [SMILES: C=CC(=O)OCCC(F)(F)OC(F)(F)OC(F)(F)CCSc1ccc2cc(-c3ccc(CCCCC)cc3OC)oc2c1]
(M-015)

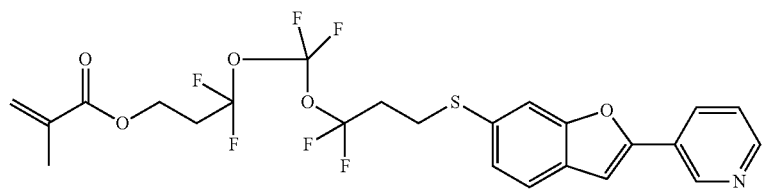
(M-016)
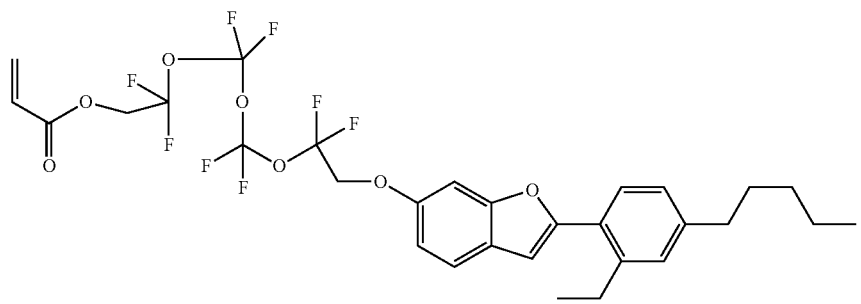 [SMILES: C=CC(=O)OCC(F)(F)OC(F)(F)OC(F)(F)OC(F)(F)COc1ccc2cc(-c3ccc(CCCCC)cc3CC)oc2c1]
(M-017)
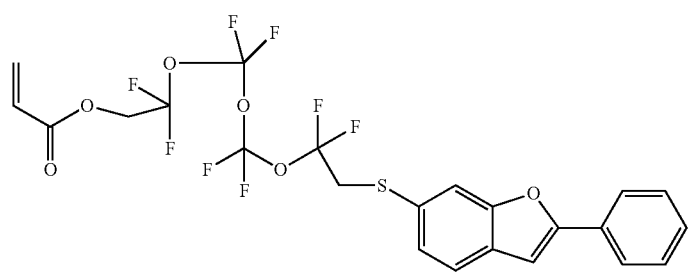 [SMILES: C=CC(=O)OCC(F)(F)OC(F)(F)OC(F)(F)OC(F)(F)CSc1ccc2cc(-c3ccccc3)oc2c1]
(M-018)
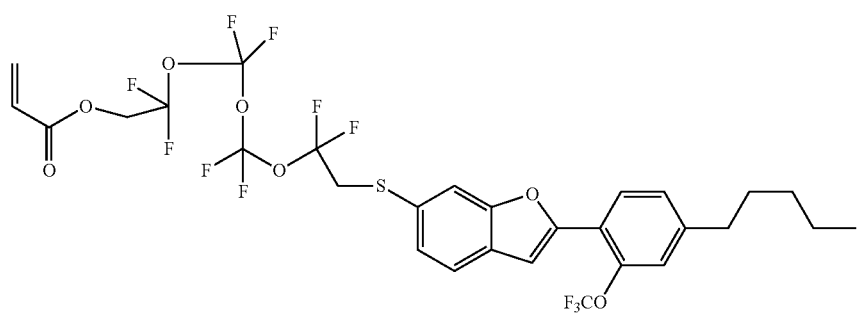 [SMILES: C=CC(=O)OCC(F)(F)OC(F)(F)OC(F)(F)OC(F)(F)CSc1ccc2cc(-c3ccc(CCCCC)cc3OC(F)(F)F)oc2c1]
(M-019)
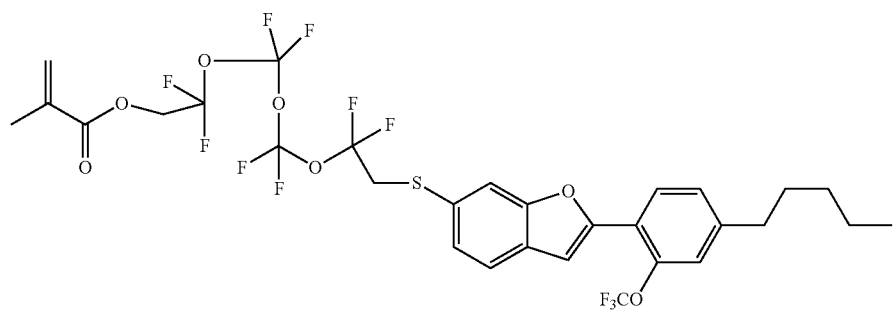 [SMILES: C=C(C)C(=O)OCC(F)(F)OC(F)(F)OC(F)(F)OC(F)(F)CSc1ccc2cc(-c3ccc(CCCCC)cc3OC(F)(F)F)oc2c1]
(M-020)

-continued
| Polymer |
|---|
| 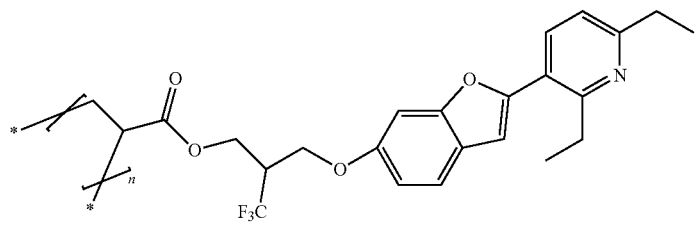<br>(P-025) |
| 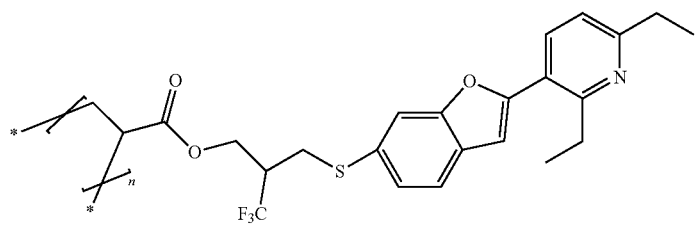<br>(P-027) |
| 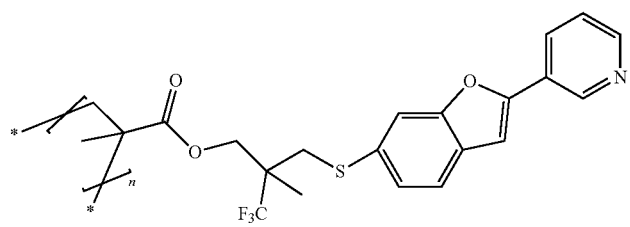<br>(P-052) |
| 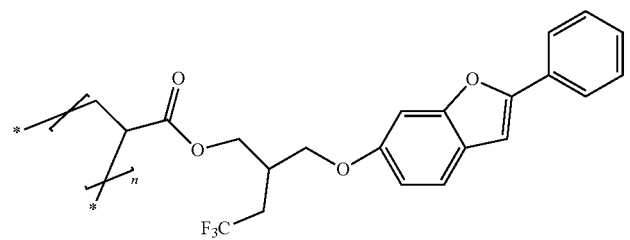<br>(P-057) |
| 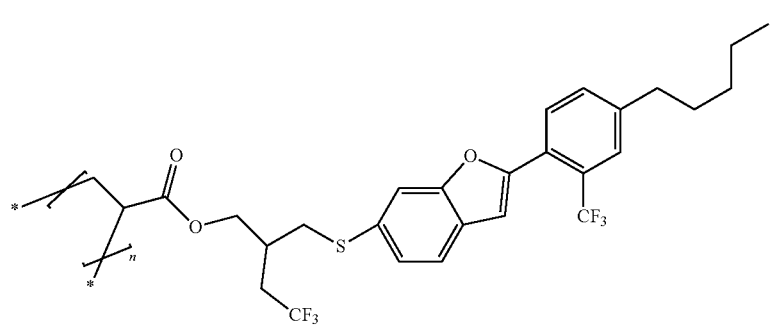<br>(P-067) |

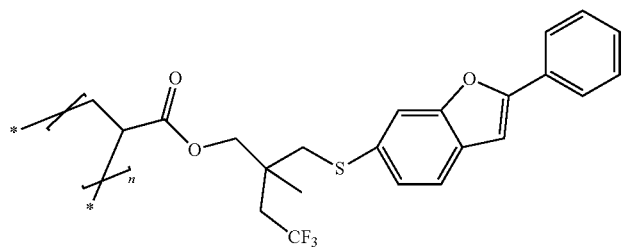
(P-087)
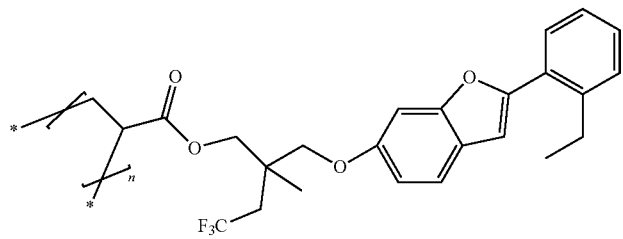
(P-089)
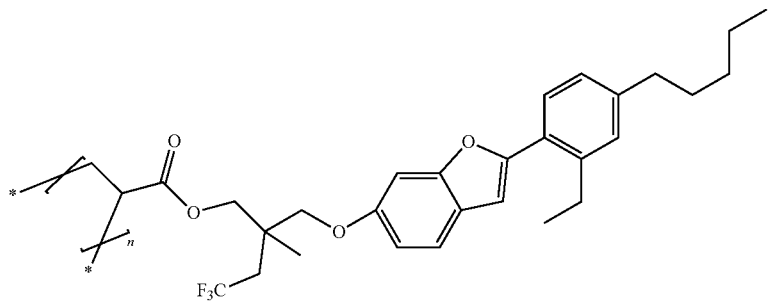
(P-091)
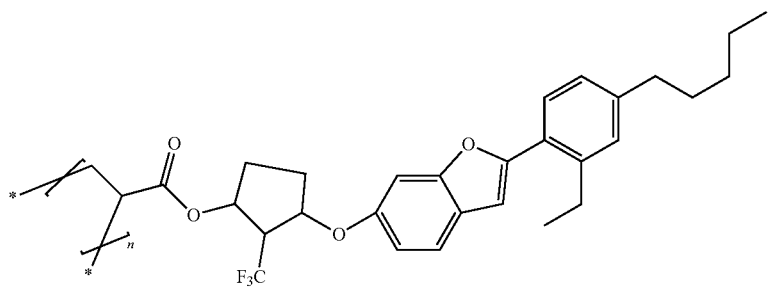
(P-117)
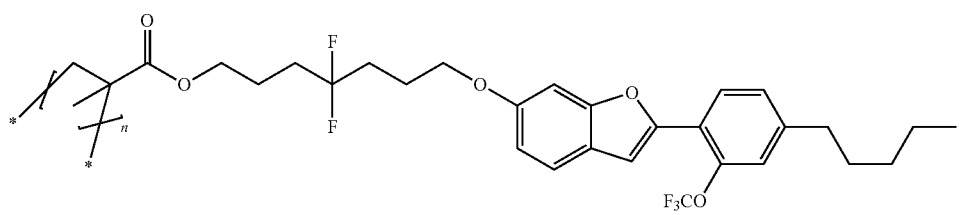
(P-155)

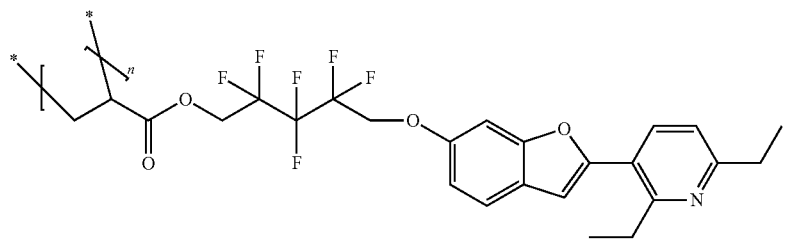
(P-185)
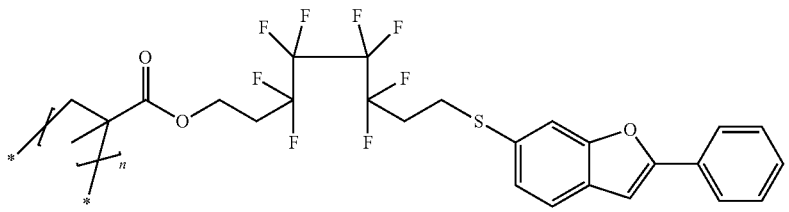
(P-211)
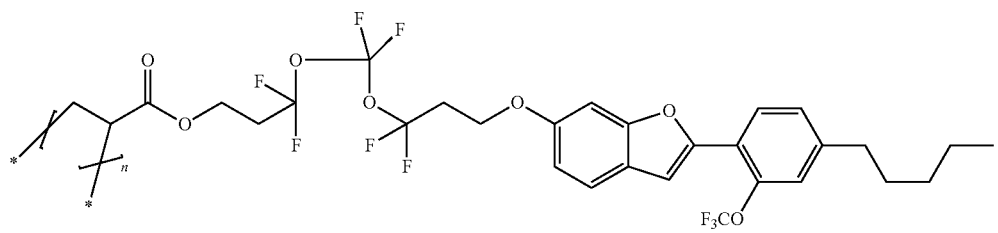
(P-234)
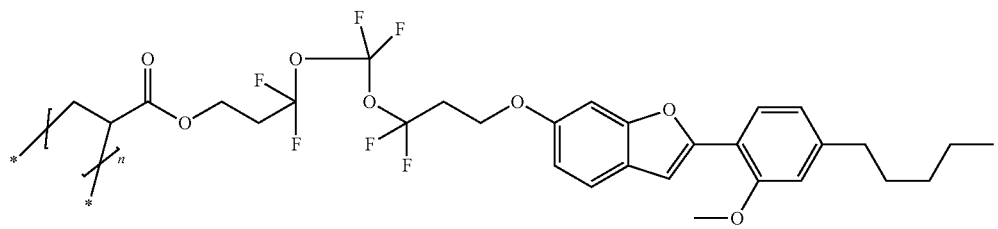
(P-236)
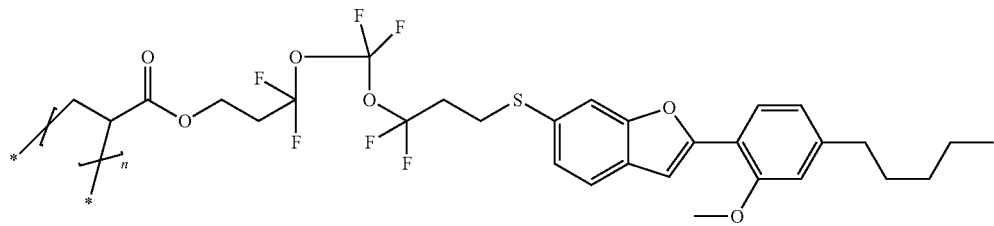
(P-252)
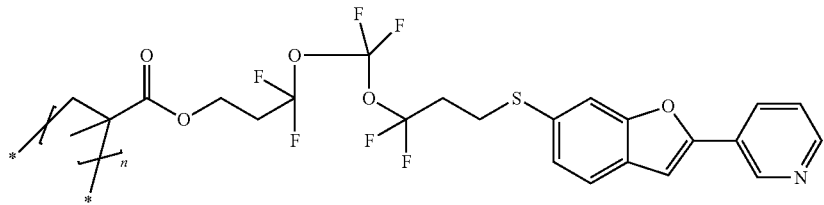
(P-255)

-continued
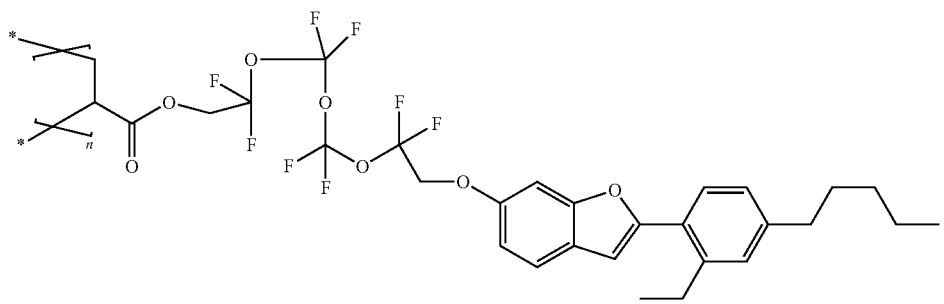
(P-262)
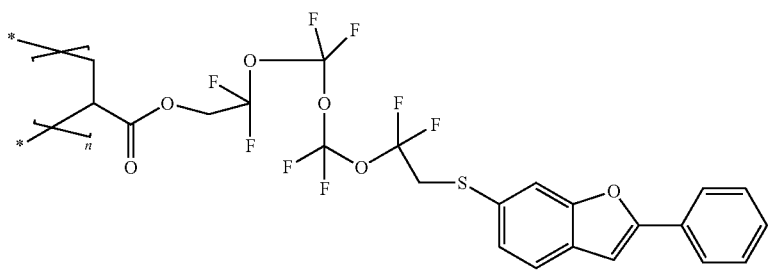
(P-274)
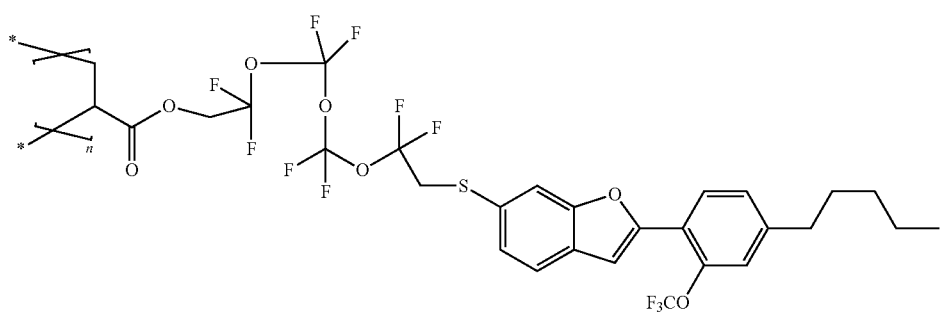
(P-282)
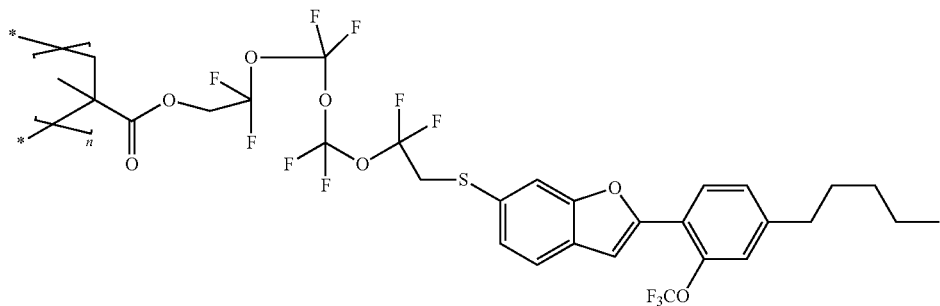
(P-283)

Synthesis of Precursor Materials

Example 11

General Remarks & General Synthetic Procedures (GSP 11) for the Synthesis of 6-Methoxy-2-phenyl-benzothiophene

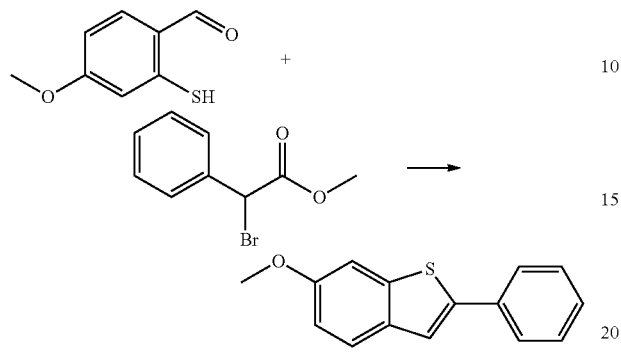

2-Mercapto-4-methoxy-benzaldehyde (944 mg, 5.61 mmol) and α-Bromophenylacetatic acid methyl ester (969 μl, 6.17 mmol) are dissolved in dimethylformamide (28.4 ml, 364 mmol). To the solution is added potassium carbonate (3.88 g, 28.1 mmol). The mixture is stirred at 100° C. for 2 h. The mixture is cooled to 25° C. and portioned to EtOAc and HCl (1 N, aq). The organic layer is separated, washed with brine and dried over MgSO$_4$. Evaporation of solvent gives a colorless solid. The residue is recrystallized from ethanol to yield 6-methoxy-2-phenyl-benzo[b]thiophene (780 mg, 3.25 mmol, 58% of theory).

1H NMR (500 MHz, DMSO-d6) δ 7.77 (s, 1H), 7.76-7.72 (m, 3H), 7.57 (d, J=2.4 Hz, 1H), 7.47 (t, J=7.7 Hz, 2H), 7.36 (t, J=7.3 Hz, 1H), 7.02 (dd, J=8.7 Hz, 2.4 Hz, 1H), 3.85 (s, 3H).

Analogously Prepared benzo[b]thiophenes

| No. | Reactant 1 | Reactant 2 | Product | Yield [%] |
|---|---|---|---|---|
| 11a | (CAS: 294674-98-9) | | | 39 |
| 11b | | | | 40 |
| 11c | | | | 53 |
| 11d | | | | 63 |
| 11e | | (CAS: 1346541-86-3) | | 59 |

Example 12

General Remarks & General Synthetic Procedures (GSP 12) for the Suzuki Reaction of the Corresponding halogenated 2-phenyl-benzothiophenes with boronic acids

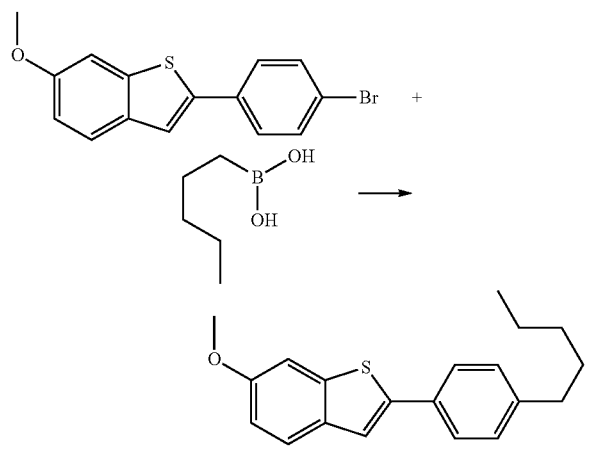

2-(4-Bromo-phenyl)-6-methoxy-benzo[b]thiophene (480 mg, 1.51 mmol), pentylboronic acid (209 mg, 1.80 mmol) and tripotassium phosphate monohydrate (1.45 g, 6.31 mmol) are dissolved in toluene (15 ml, 150 mmol). Then 2-Dicyclohexylphosphino-2',6'-dimethoxybiphenyl [SPhos] (124 mg, 0.301 mmol) and palladium(II) acetate (8.4 mg, 0.040 mmol) are added and the reaction reaction mixture is heated to 90° C. upon completion of the reaction. The cooled reaction mixture is diluted with ethyl acetate and HCl solution (2 M). The solution is transferred to a separatory funnel. The organic phase is extracted with HCl solution (2 M) and water and brine. The organic phase is dried over $MgSO_4$, filtered and concentrated under reduced pressure. The residue is purified by silica gel column chromatography (heptane/ethyl acetate [5/1]) to yield 6-methoxy-2-(4-pentylphenyl)benzo[b]thiophene (390 mg, 1.26 mmol, 84% of theory).

1H NMR (500 MHz, $CDCl_3$) δ 7.63 (d, 1H, J=8.7 Hz), 7.59 (d, 2H, J=8.2 Hz), 7.41 (s, 1H), 7.30 (d, 1H, J=2.4 Hz), 7.25 (d, 2H, J=8.1 Hz), 6.98 (dd, 1H, J=8.7 Hz, 2.4 Hz), 3.89 (s, 3H), 2.61-2.58 (m, 2H), 1.56 (p, 2H, J=7.5 Hz), 1.30-1.22 (m, 4H), 0.83 (t 3H, J=6.9 Hz, 3H).

Analogously, other Suzuki derivatives are prepared in the same manner: R1 means reactant 1, R2 means reactant 2, [P] means product

| No. | | | Yield [%] |
|---|---|---|---|
| 12a | R1 | | |
| | R2 | CAS: 4737-50-2 | |
| | [P] | | 58 |
| 12b | R1 | | |
| | R2 | | |
| | [P] | | 74 |

| No. | | Yield [%] |
|---|---|---|
| 12c R1 | 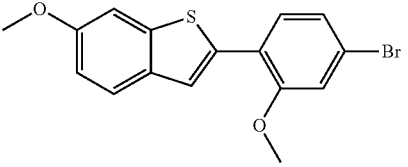 | |
| R2 | 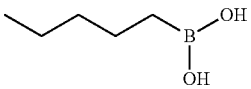 | |
| [P] | 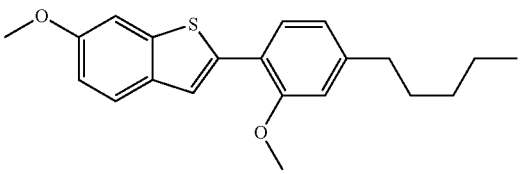 | 68 |
| 12d R1 | 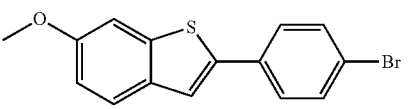 | |
| R2 | 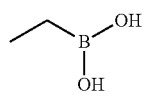 | |
| [P] | 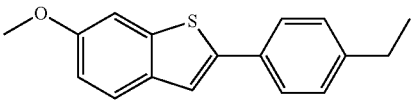 [SMILES: CCc1ccc(-c2cc3ccc(OC)cc3s2)cc1] | 73 |

Selected NMR data for

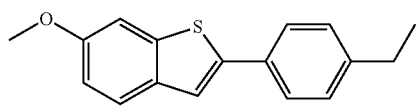 [SMILES: CCc1ccc(-c2cc3ccc(OC)cc3s2)cc1]

1H NMR (500 MHz, CDCl₃) δ 7.63 (d, 1H, J=8.7 Hz), 7.60 (d, 2H, J=8.2 Hz), 7.41 (s, 1H), 7.31 (d, 1H, J=2.4 Hz), 7.24 (d, 2H, J=8.1 Hz), 6.97 (dd, 1H, J=8.7 Hz, 2.4 Hz), 3.8 (s, 3H), 2.69 (q, 2H, J=7.6 Hz), 1.27 (t, 3H, J=7.6 Hz).

Example 13

General Remarks & General Synthetic Procedures (GSP 13) for the Deprotection of the Benzothiophene Ethers to the Phenol Derivatives

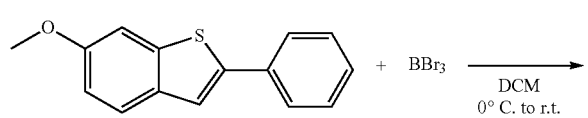

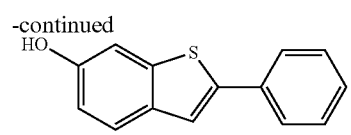

6-Methoxy-2-phenyl-benzo[b]thiophene (780.00 mg, 3.25 mmol) is dissolved in Dichloromethane (anhydrous) (20.73 ml, 324.57 mmol) and cooled to 5° C. Boron tribromide (369.60 µl, 3.89 mmol) is added dropwise to this solution over the course of 10 min, and stirring is continued for 2 h. The reaction mixture is subsequently slowly poured into water, and the organic phase is diluted with ethyl acetate, washed three times with water, dried over MgSO₄, evaporated in a rotary evaporator. Recrystallization from toluene/heptane (1/10) yielded 2-Phenyl-benzo[b]thiophen-6-ol (657.00 mg, 2.90 mmol, 90% of theory).

1H NMR (500 MHz, DMSO-d6) δ 9.65 (s, 1H), 7.70-7.69 (m, 3H), 7.64 (d, 1H, J=8.6 Hz), 7.44 (t, 2H, J=7.7 Hz), 7.33 (t, 1H, J=7.4 Hz), 7.27 (d, 1H, J=1.7 Hz), 6.88 (dd, 1H, J=8.5 Hz, 2.3 Hz).

Analogously, other derivatives are prepared in the same manner: R means reactant, [P] means product

| No. | | Yield [%] |
|---|---|---|
| 13a R | [structure: 6-methoxybenzothiophene-2-yl linked to 2-ethyl-4-pentylphenyl] | |
| [P] | [structure: 6-hydroxybenzothiophene-2-yl linked to 2-ethyl-4-pentylphenyl] | 70 |
| 13b R | [structure: 6-methoxybenzothiophene-2-yl linked to 2-(trifluoromethoxy)-4-pentylphenyl] | |
| [P] | [structure: 6-hydroxybenzothiophene-2-yl linked to 2-(trifluoromethoxy)-4-pentylphenyl] | 82 |
| 13c R | [structure: 6-methoxybenzothiophene-2-yl linked to 2-ethylphenyl] | |
| [P] | [structure: 6-hydroxybenzothiophene-2-yl linked to 2-ethylphenyl] | 94 |
| 13d R | [structure: 6-methoxybenzothiophene-2-yl linked to pyridin-3-yl] | |
| [P] | [structure: 6-hydroxybenzothiophene-2-yl linked to pyridin-3-yl] | 88 |
| 13e R | [structure: 6-methoxybenzothiophene-2-yl linked to 4-ethylphenyl] | |
| [P] | [structure: 6-hydroxybenzothiophene-2-yl linked to 4-ethylphenyl] | 98 |

Selected NMR data for

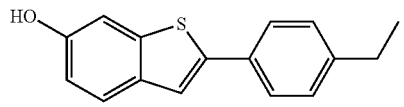 [SMILES: CCc1ccc(-c2cc3ccc(O)cc3s2)cc1]

1H NMR (500 MHz, DMSO-d6) δ 9.61 (s, 1H), 7.65 (d, 1H, J=8.4 Hz), 7.59 (d, 2H, J=8.3 Hz), 7.35 (s, 1H), 7.29 (d, 1H, J=2.1 Hz), 7.21 (d, 2H, J=8.3 Hz), 7.01 (dd, 1H, J=8.3 Hz, 2.1 Hz), 2.73 (q, 2H, J=7.4 Hz), 1.29 (t, 3H, J=7.4 Hz).

Example 14

General Remarks & General Synthetic Procedures (GSP 14) for the Reaction of the Corresponding Fluorinated Diol with 2-Phenyl-benzo[b]thiophen-6-ol (Mitsunobu Alkylation Type Reaction)

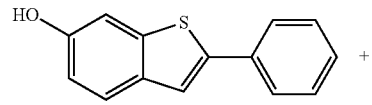

+

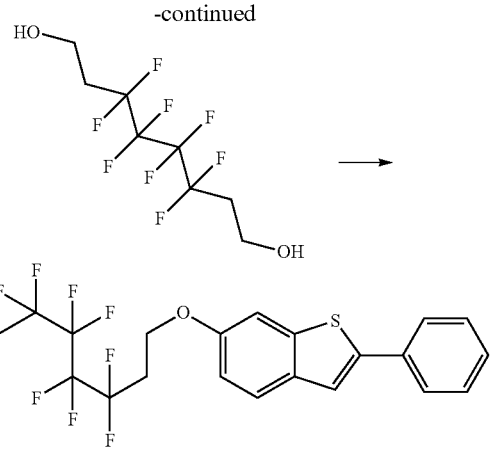

To an ice-cooled solution of 2-phenyl-benzo[b]thiophen-6-ol, aliphatic fluorinated diol or monoalcohol (1.0 equiv.) and triphenylphosphine in THF (1.43 equiv.), diisopropyl azodicarboxylate (1.43 equiv.) is added dropwise. After stirring at room temperature overnight, the reaction mixture is evaporated. The crude product is purified by column chromatography (cyclohexane/EE).

Analogously, other derivatives are prepared in the same manner: R1 means reactant 1, R2 means reactant 2, [P] means product

| No. | | |
|---|---|---|
| 14a | R1 | 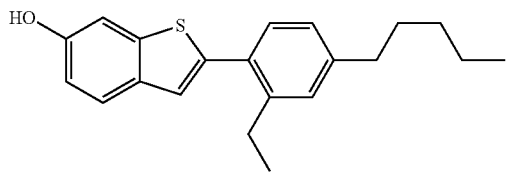 |
| | R2 | 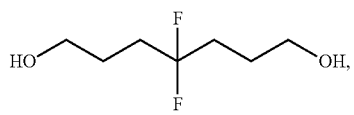  CAS: 83192-87-4 |
| | [P] | 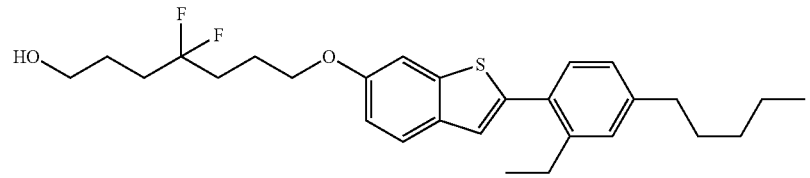 |
| 14b | R1 | 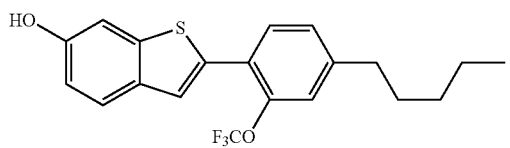 |
| | R2 | 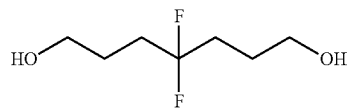 [SMILES: OCCCC(F)(F)CCCO] |

| No. | | |
|---|---|---|
| | [P] | 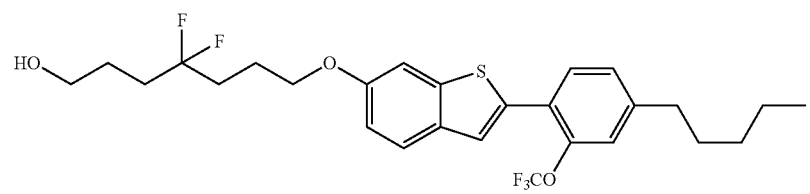 [SMILES: CCCCCc1ccc(-c2cc3ccc(OCCCC(F)(F)CCCO)cc3s2)c(OC(F)(F)F)c1] |
| 14c | R1 | 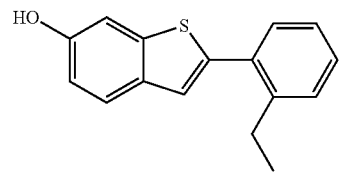 |
| | R2 | 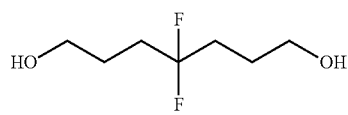 |
| | [P] | 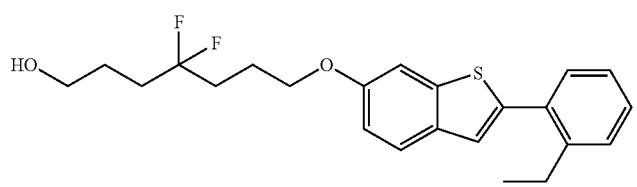 |
| 14d | R1 | 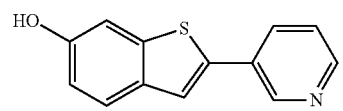 [SMILES: Oc1ccc2cc(-c3cccnc3)sc2c1] |
| | R2 | 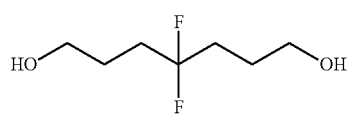 |
| | [P] | 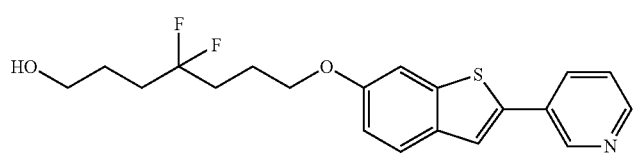 [SMILES: OCCCC(F)(F)CCCOc1ccc2cc(-c3cccnc3)sc2c1] |
| 14e | R1 | 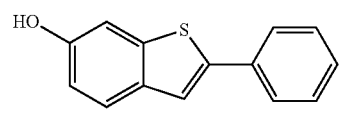 |
| | R2 | 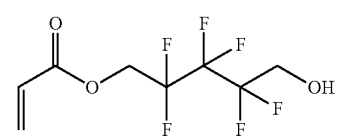 [SMILES: C=CC(=O)OCC(F)(F)C(F)(F)C(F)(F)CO] |
| | [P] | 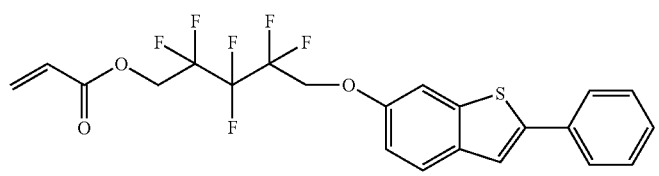 [SMILES: C=CC(=O)OCC(F)(F)C(F)(F)C(F)(F)COc1ccc2cc(-c3ccccc3)sc2c1] |

-continued
| No. | | |
|---|---|---|
| 14f | R1 | 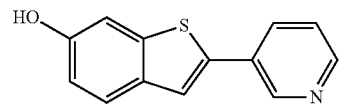 [SMILES: Oc1ccc2cc(-c3cccnc3)sc2c1] |
| | R2 | 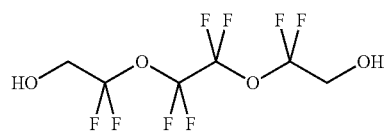 |
| | [P] | 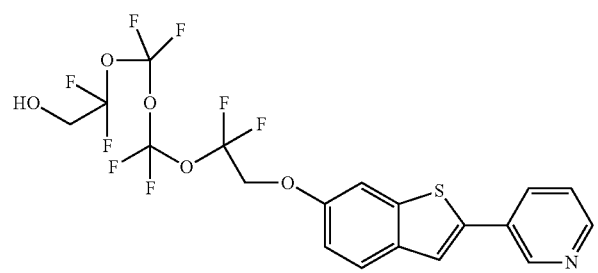 [SMILES: OCC(F)(F)OC(F)(F)OC(F)(F)OC(F)(F)COc1ccc2cc(-c3cccnc3)sc2c1] |
| 14g | R1 | 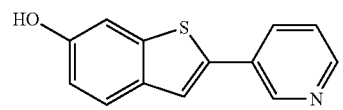 [SMILES: Oc1ccc2cc(-c3cccnc3)sc2c1] |
| | R2 | 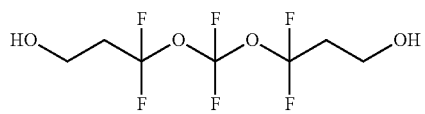 [SMILES: OCCC(F)(F)OC(F)(F)OC(F)(F)CCO] |
| | [P] | 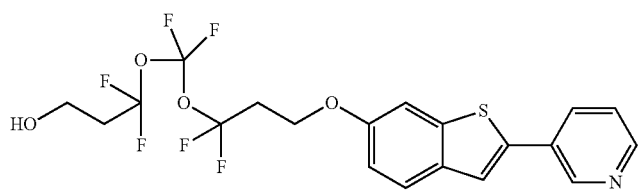 [SMILES: OCCC(F)(F)OC(F)(F)OC(F)(F)CCOc1ccc2cc(-c3cccnc3)sc2c1] |
| 14h | R1 | 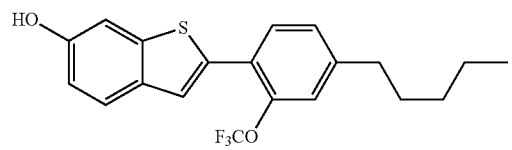 [SMILES: CCCCCc1ccc(-c2cc3ccc(O)cc3s2)c(OC(F)(F)F)c1] |
| | R2 | 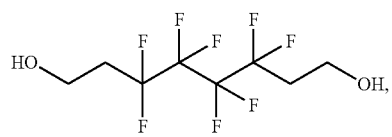  CAS: 83192-87-4 |
| | [P] | 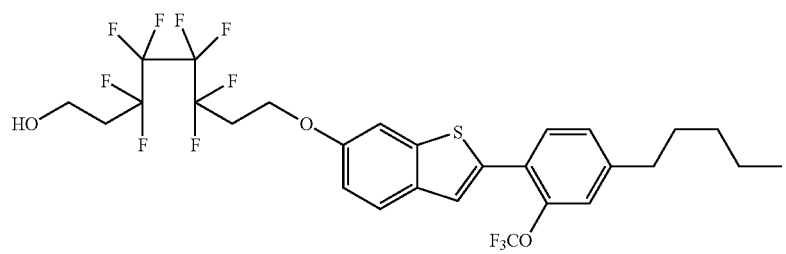 [SMILES: CCCCCc1ccc(-c2cc3ccc(OCCC(F)(F)C(F)(F)C(F)(F)C(F)(F)CCO)cc3s2)c(OC(F)(F)F)c1] |

Preparation of Compounds According to the Invention:

Example 15

General Remarks & General Synthetic Procedures (GSP 15) for the Esterification with Acryloyl Chloride or Methacryloyl Chloride to the Corresponding Monomer

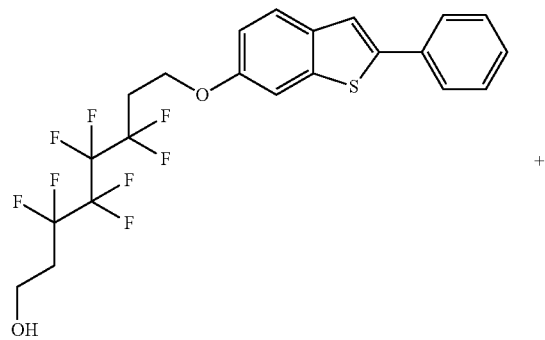

+

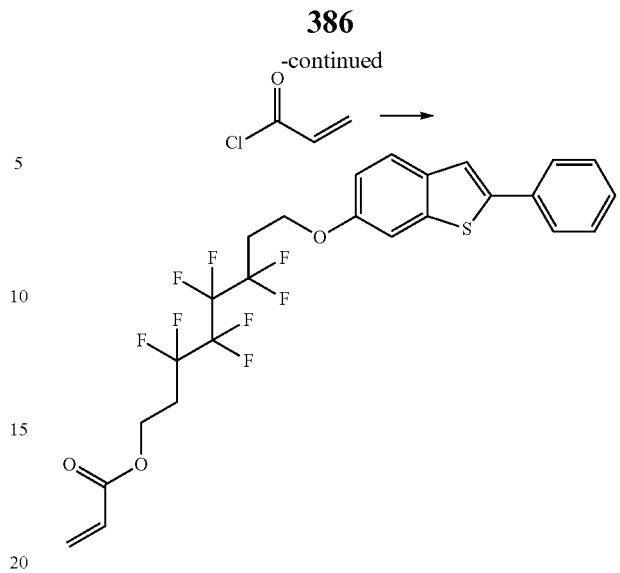

The corresponding aliphatic alcohol is dissolved in dry THF and the solution is cooled with an ice-bath. Triethylamine (4.00 equivs.) is added and the solution is stirred for a few minutes. Then acryloyl chloride or methacryloyl chloride (1.05-2.00 equivs.) is added at ice-bath temperature, while precipitating a colourless solid. The solution is stirred for several hours and is monitored via TLC. Upon completion of the reaction, the suspension is filtrated and washed with THF. The filtrate is evaporated under reduced pressure and purified via column chromatography using cyclohexane/ethyl acetate.

Analogously, other acrylate or methacrylate derivatives are prepared in the same manner: R means reactant, [P] means product

| No. | |
|---|---|
| 15a R | 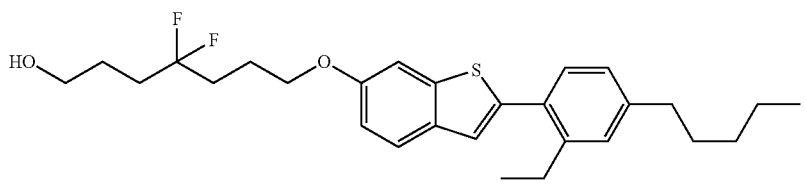 |
| [P] | 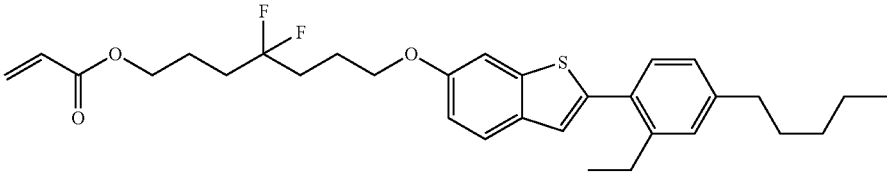 [SMILES: C=CC(=O)OCCCC(F)(F)CCCOc1ccc2cc(-c3ccc(CCCCC)cc3CC)sc2c1] |
| 15b R | |

| No. | |
|---|---|
| [P] | 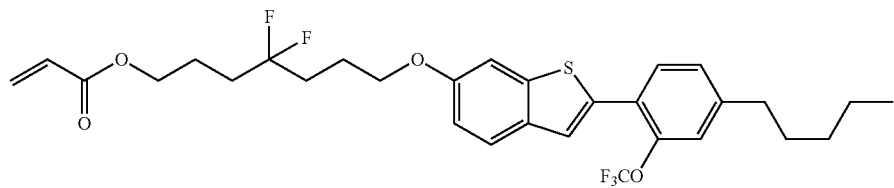 [SMILES: C=CC(=O)OCCCC(F)(F)CCCOc1ccc2cc(-c3ccc(CCCCC)cc3OC(F)(F)F)sc2c1] |
| 15c R | 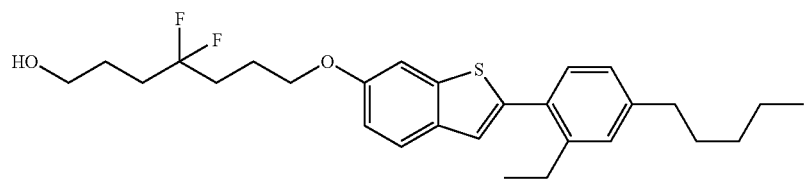 |
| [P] | 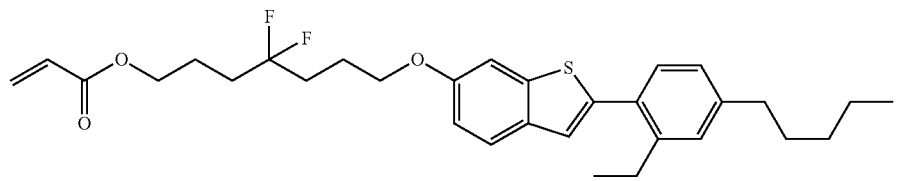 [SMILES: C=CC(=O)OCCCC(F)(F)CCCOc1ccc2cc(-c3ccc(CCCCC)cc3CC)sc2c1] |
| 15d R | 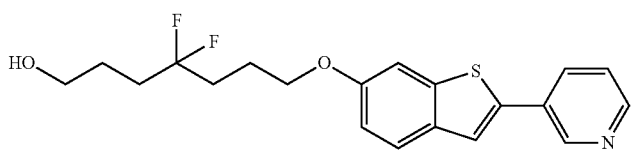 [SMILES: OCCCC(F)(F)CCCOc1ccc2cc(-c3cccnc3)sc2c1] |
| [P] | 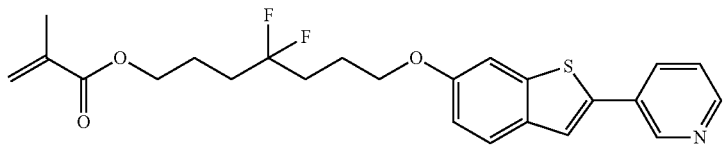 |
| 15e R | 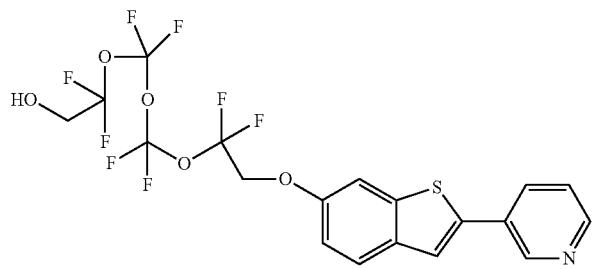 [SMILES: OCC(F)(F)OC(F)(F)OC(F)(F)OC(F)(F)COc1ccc2cc(-c3cccnc3)sc2c1] |
| [P] | 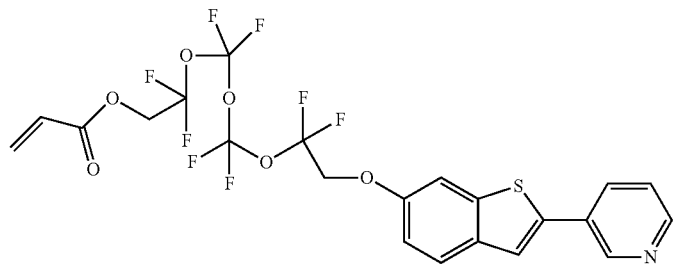 [SMILES: C=CC(=O)OCC(F)(F)OC(F)(F)OC(F)(F)OC(F)(F)COc1ccc2cc(-c3cccnc3)sc2c1] |

-continued

| No. | |
|---|---|
| 15f R | 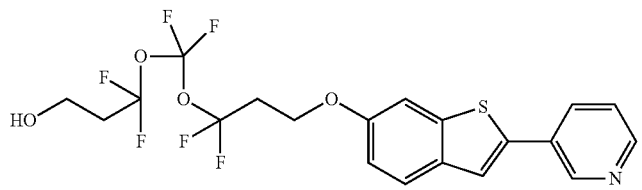 [SMILES: OCCC(F)(F)OC(F)(F)OC(F)(F)CCOc1ccc2cc(-c3cccnc3)sc2c1] |
| [P] | 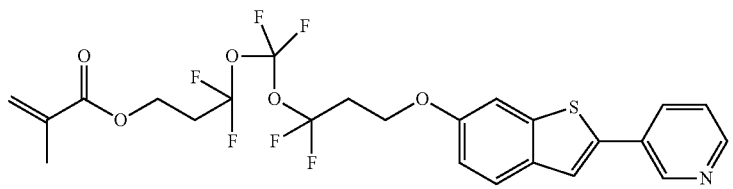 [SMILES: C=C(C)C(=O)OCCC(F)(F)OC(F)(F)OC(F)(F)CCOc1ccc2cc(-c3cccnc3)sc2c1] |
| 15g R | 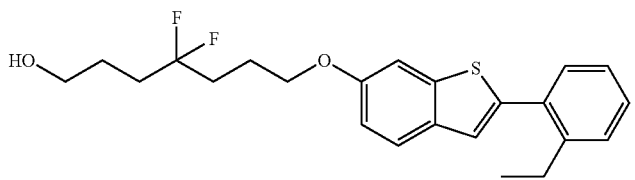 [SMILES: CCc1ccccc1-c1cc2ccc(OCCCC(F)(F)CCCO)cc2s1] |
| [P] | 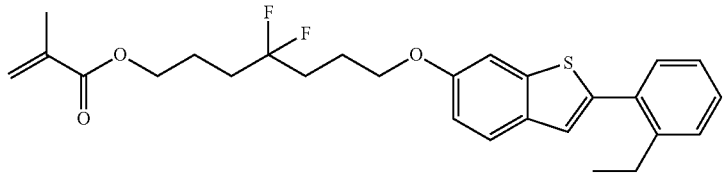 [SMILES: C=C(C)C(=O)OCCCC(F)(F)CCCOc1ccc2cc(-c3ccccc3CC)sc2c1] |

Example 16

General Remarks & General Synthetic Procedures (GSP 16) for the Solvent Polymerization of the Monomers The corresponding monomer is dissolved in dry N,N-dimethylformamide in a Schlenck-tube with a stirring bar. The solution is degassed performing three times freeze-evacuate-thaw cycles. After that, azoisobutyronitrile (AIBN, 0.05 equiv.) is added in one portion to the degassed solution, which is heated up to 65° C. in an oil bath for a minimum of three days. The solution is cooled to room temperature and is then poured dropwise into cold methanol (100 ml methanol/100 mg monomer) while stirring. The precipitated polymer is collected on a frit or the solution is centrifuged several times to obtain the final polymer material.

Examples of polymers within this invention are given in the following table:

| Monomer | Polymer |
|---|---|
| 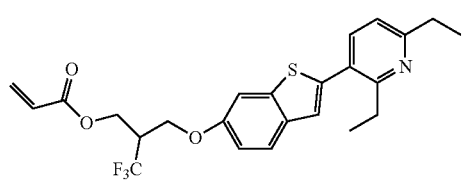<br>(M-S1) | 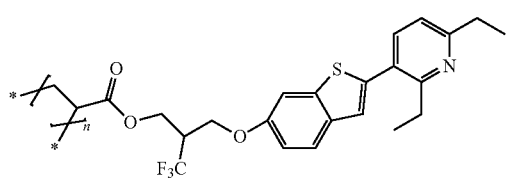<br>(P-304) |

-continued
| Monomer | Polymer |
|---|---|
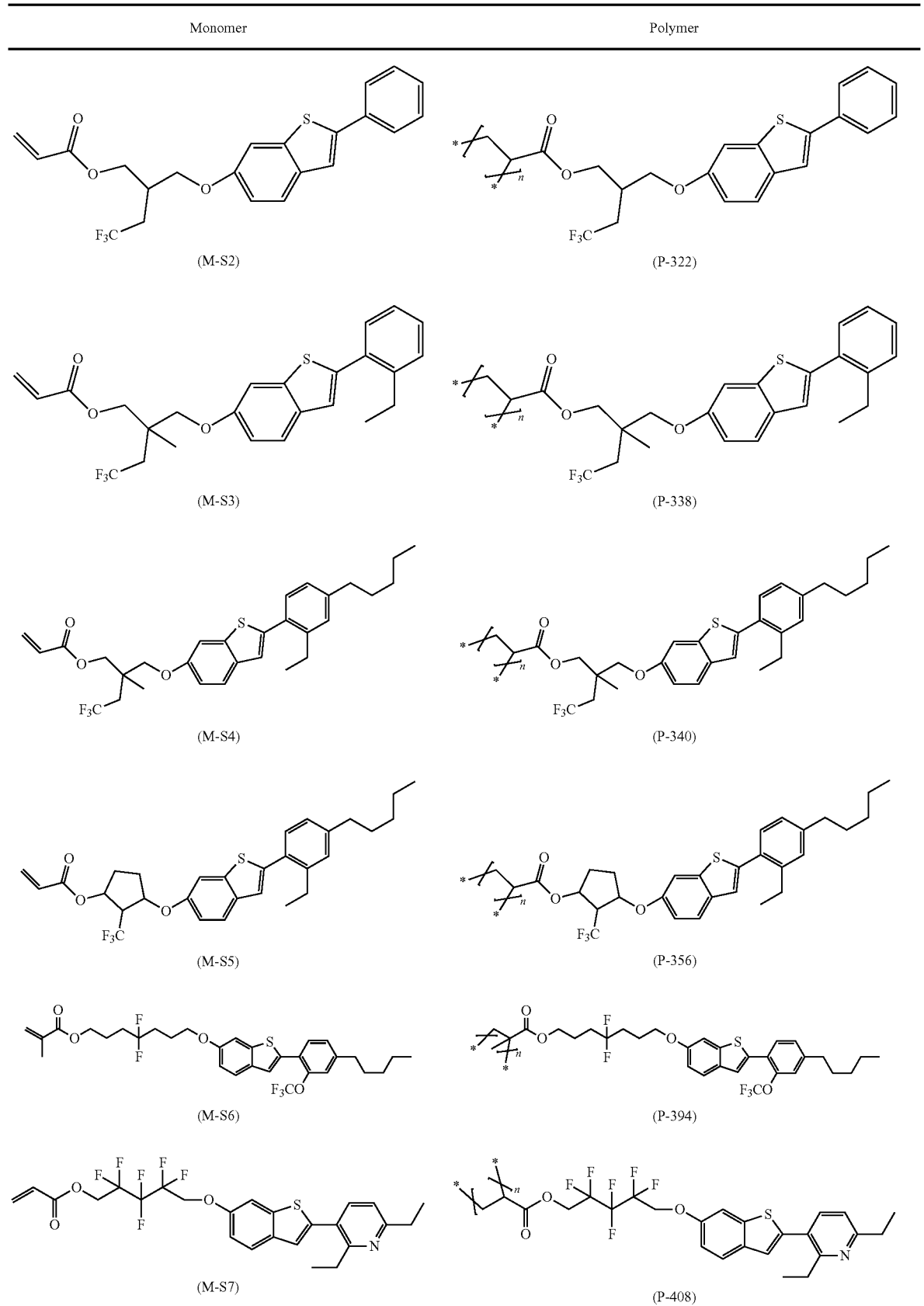

| Monomer | Polymer |
|---|---|
| (M-S8) | (P-433) |
| (M-S9) | (P-435) |
| (M-S10) | (P-445) |

Synthesis of Precursor Materials

Example 17

General Remarks & General Synthetic Procedures (GSP 17) for the Synthesis of 5-methoxy-2-(phenylethynyl)aniline

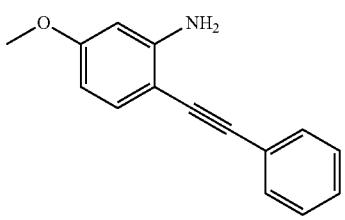 [SMILES: COc1ccc(C#Cc2ccccc2)c(N)c1]

Bis(triphenylphosphine)palladium(II) dichloride (32.1 mg, 45.8 μmol), copper(I) iodide (17.8 mg, 91.5 μmol), 2-iodo-5-methoxyaniline (1.2 g, 4.6 mmol), phenylacetylene (572.5 ml, 5.5 mmol), and diethylamine (10 ml) are refluxed until consumption of the starting materials monitored by TLC. The residue is chromatographed on silica gel (heptane/ EE, 10/1) to afford 5-Methoxy-2-(phenylethynyl)aniline (818 mg, 3.7 mmol, 80% of theory).

1H NMR (500 MHz, Chloroform-d) δ 7.54 (d, J=6.7 Hz, 2H), 7.36 (q, J=8.9 Hz, 7.7 Hz, 2H), 7.32 (q, J=8.9 Hz, 8.5 Hz, 2H), 6.34 (dd, J=8.5 Hz, 2.4 Hz, 1H), 6.30 (d, J=2.3 Hz, 1H), 3.82 (s, 3H).

Example 18

General Remarks & General Synthetic Procedures (GSP 18) for the Synthesis of 6-methoxy-2-phenylindole

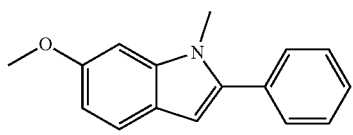 [SMILES: COc1ccc2cc(-c3ccccc3)n(C)c2c1]

To a refluxing solution of 5-Methoxy-2-(phenylethynyl) aniline (826 mg, 3.7 mmol) in toluene (40 ml) is added zinc bromide (420.8 mg, 1.8 mmol) in one portion. After refluxing for 3 d, the reaction mixture is washed with water and extracted with dichloromethane. The combined extracts are dried over MgSO₄, filtered, and the solvent is removed under reduced pressure. The solid is passed through a pad of silica gel (heptane/dichloromethane; 5/1) to afford 6-methoxy-2-phenylindole (585 mg, 2.6 mmol, 71% of theory) and is used in the next step without further analyses.

Example 19

General Remarks & General Synthetic Procedures (GSP 19) for the Synthesis of 6-methoxy-1-methyl-2-phenylindole To a solution of 6-methoxy-2-phenylindole (488 mg, 2.2 mmol) in dimethylformamide (25 ml) is added methyl iodide (304 μl, 4.8 mmol) followed by sodium hydride (182 mg, 4.6 mmol). The mixture is stirred at room temperature for 16 h. Then the mixture is poured onto an ice/NaOH (2M) mixture and the resulting emulsion is extracted with dichloromethane. After drying over MgSO₄, the solution is evaporated to dryness. The residue is purified by column chromatography over silica gel eluting with dichloromethane to yield 198 mg (826 µmol, 38% of theory) of the title compound.

1H NMR (500 MHz, Chloroform-d) b 7.54 (d, J=8.2 Hz, 1H), 7.52 (d, J=7.0 Hz, 2H), 7.48 (t, J=7.6 Hz, 2H), 7.41 (d, J=7.3 Hz, 1H), 6.86 (s, 1H), 6.85 (dd, J=8.4 Hz, 1.4 Hz, 1H), 6.52 (s, 1H), 3.94 (s, 3H), 3.73 (s, 3H).

Analogously, other derivatives are prepared in the same manner: R1 means reactant 1, R2 means reactant 2, [P] means product

Example 20

General Remarks & General Synthetic Procedures (GSP 20) for the Synthesis of 6-hydroxy-1-methyl-2-phenylindole

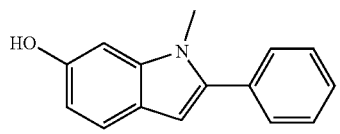 [SMILES: Cn1c(-c2ccccc2)cc2ccc(O)cc21]

6-Methoxy-1-methyl-2-phenylindole (184 mg, 775 µmol) is dissolved in dichloromethane (10 ml) and cooled to 5° C. Boron tribromide (96.6 µl, 1.0 mmol) are added dropwise to this solution, and stirring is continued overnight. Water is subsequently slowly added to the mixture, and the organic phase is diluted with ethyl acetate, washed three times with water, dried over MgSO₄, evaporated under reduced pressure and filtered through a pad of silica gel with dichloromethane to yield 6-hydroxy-1-methyl-2-phenylindole (117 mg, 524 µmol, 68% of theory).

1H NMR (500 MHz, Chloroform-d) δ 7.54-7.46 (m, 5H), 7.41 (t, 1H, J=6.4 Hz), 6.84 (d, 1H, J=2.2 Hz), 6.72 (dd, 1H, J=8.4 Hz, 2.3 Hz), 6.51 (s, 1H), 4.62 (s, 1H), 3.70 (s, 3H).

Analogously, other derivatives are prepared in the same manner:

| No. | Reactant 1 | Product | Yield [%] |
|---|---|---|---|
| 20a | | | 92 |
| 20b | | | 56 |
| 20c | | | 60 |
| 20d | | | 95 |
| 20e | | | 89 |

Example 21

General Remarks & General Synthetic Procedures (GSP 21) for the Reaction of the Corresponding Fluorinated Diol or Monoalcohol with 6-Hydroxy-1-methyl-2-phenylindole (Mitsunobu Alkylation Type Reaction)

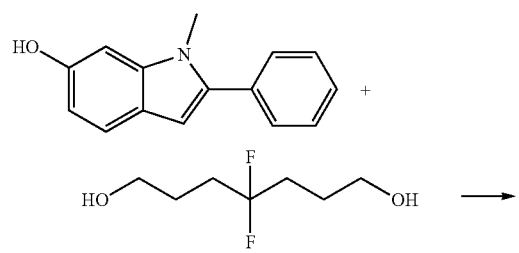

-continued

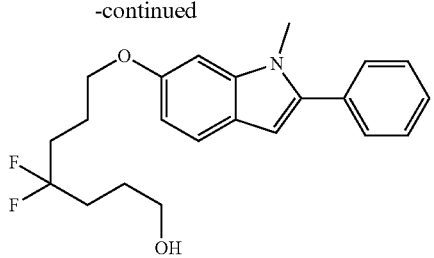

To an ice-cooled solution of 6-hydroxy-1-methyl-2-phenylindole, aliphatic fluorinated diol or monoalcohol (1.0 equiv.) and triphenylphosphine in THF (1.43 equiv.), diisopropyl azodicarboxylate (1.43 equiv.) is added dropwise. After stirring at room temperature overnight, the reaction mixture is evaporated. The crude product is purified by column chromatography (cyclohexane/EE).

Analogously, other derivatives are prepared in the same manner: R1 means reactant 1, R2 means reactant 2, [P] means product

| No. | | |
|---|---|---|
| 21a | R1 | 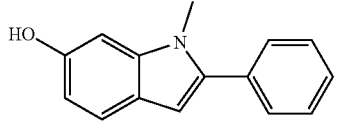 [SMILES: Cn1c(-c2ccccc2)cc2ccc(O)cc21] |
| | R2 | 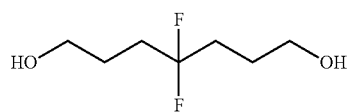 [SMILES: OCCCC(F)(F)CCCO] |
| | [P] | 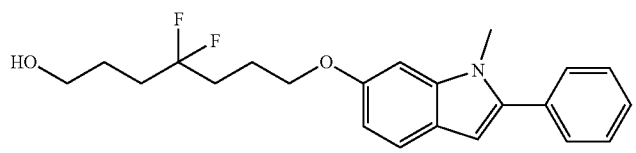 [SMILES: Cn1c(-c2ccccc2)cc2ccc(OCCCC(F)(F)CCCO)cc21] |
| 21b | R1 | 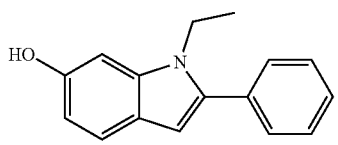 [SMILES: CCn1c(-c2ccccc2)cc2ccc(O)cc21] |
| | R2 | 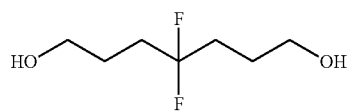 [SMILES: OCCCC(F)(F)CCCO] |
| | [P] | 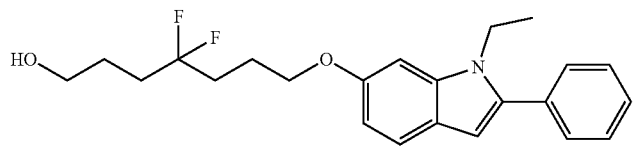 [SMILES: CCn1c(-c2ccccc2)cc2ccc(OCCCC(F)(F)CCCO)cc21] |
| 21c | R1 | 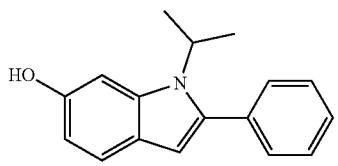 [SMILES: CC(C)n1c(-c2ccccc2)cc2ccc(O)cc21] |
| | R2 | 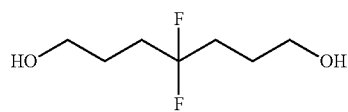 [SMILES: OCCCC(F)(F)CCCO] |
| | [P] | 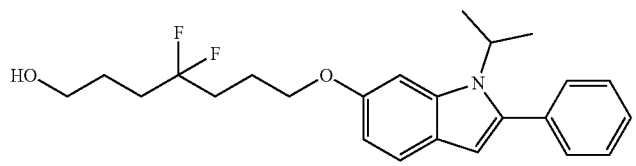 [SMILES: CC(C)n1c(-c2ccccc2)cc2ccc(OCCCC(F)(F)CCCO)cc21] |
| 21d | R1 | 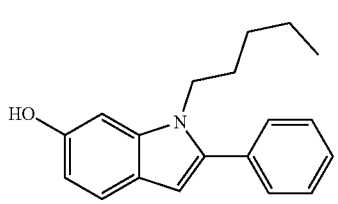 [SMILES: CCCCCn1c(-c2ccccc2)cc2ccc(O)cc21] |
| | R2 | 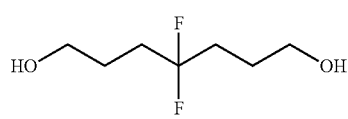 [SMILES: OCCCC(F)(F)CCCO] |

| No. | |
|---|---|
| [P] | 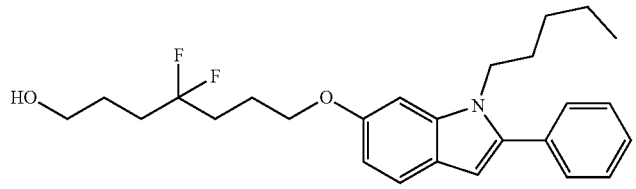 [SMILES: CCCCCn1c(-c2ccccc2)cc2ccc(OCCCC(F)(F)CCCO)cc21] |
| 21e R1 | 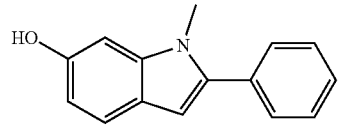 [SMILES: Cn1c(-c2ccccc2)cc2ccc(O)cc21] |
| R2 | 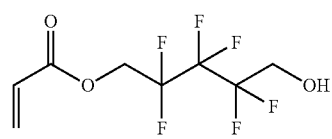 |
| [P] | 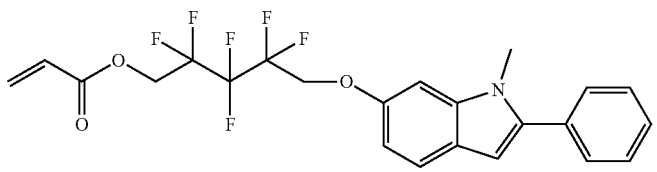 |
| 21f R1 | 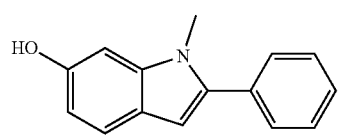 [SMILES: Cn1c(-c2ccccc2)cc2ccc(O)cc21] |
| R2 | 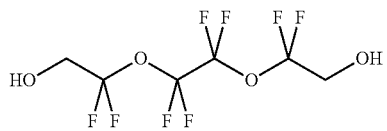 |
| [P] | 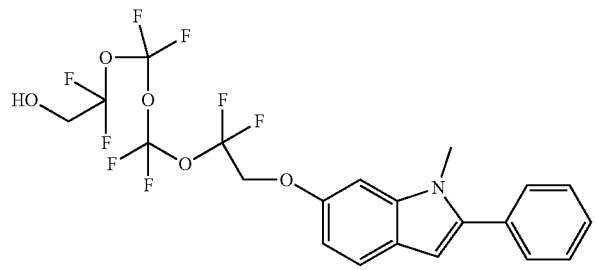 [SMILES: Cn1c(-c2ccccc2)cc2ccc(OCC(F)(F)OC(F)(F)OC(F)(F)OC(F)(F)CO)cc21] |
| 21g R1 | 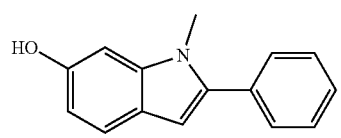 [SMILES: Cn1c(-c2ccccc2)cc2ccc(O)cc21] |
| R2 | 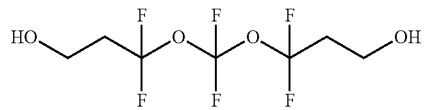 |

-continued
| No. | | |
|---|---|---|
| | [P] | 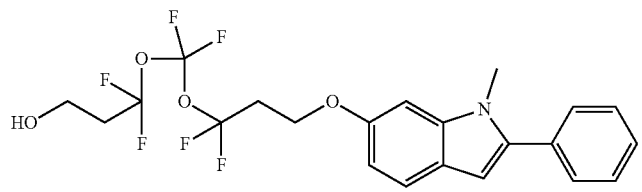 [SMILES: Cn1c(-c2ccccc2)cc2ccc(OCCC(F)(F)OC(F)(F)OC(F)(F)CCO)cc21] |
| 21h | R1 | 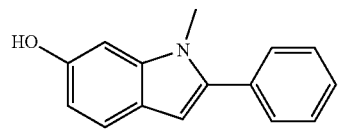 [SMILES: Cn1c(-c2ccccc2)cc2ccc(O)cc21] |
| | R2 | 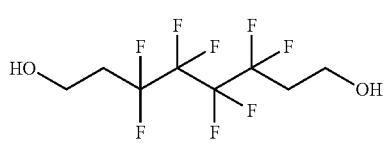 [SMILES: OCCC(F)(F)C(F)(F)C(F)(F)C(F)(F)CCO] |
| | [P] | 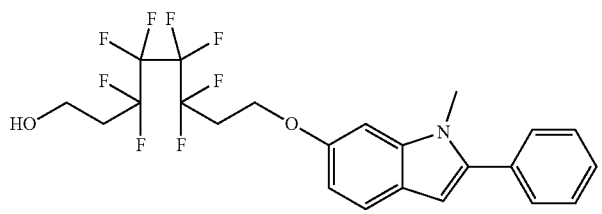 [SMILES: Cn1c(-c2ccccc2)cc2ccc(OCCC(F)(F)C(F)(F)C(F)(F)C(F)(F)CCO)cc21] |
| 21i | R1 | 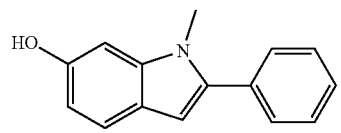 [SMILES: Cn1c(-c2ccccc2)cc2ccc(O)cc21] |
| | R2 | 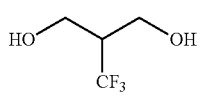 |
| | [P] | 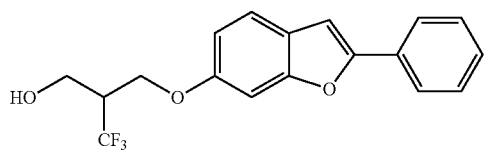 [SMILES: OCC(COc1ccc2cc(-c3ccccc3)oc2c1)C(F)(F)F] |
| 21j | R1 | 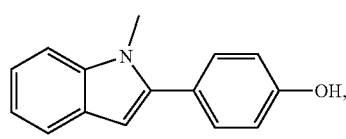  CAS 1013932-64-3 |
| | R2 | 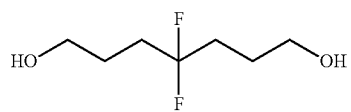 [SMILES: OCCCC(F)(F)CCCO] |
| | [P] | 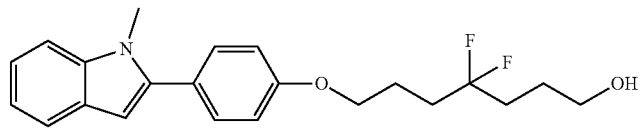 |

| No. | |
|---|---|
| 21k | R1 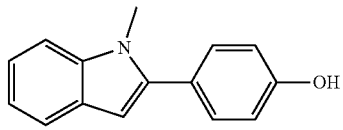 |
| | R2 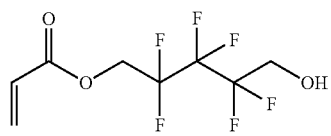 |
| | [P] 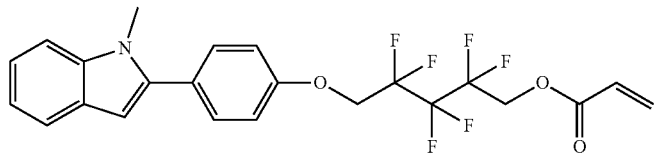 |
| 21l | R1 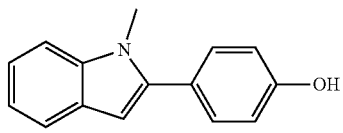 |
| | R2 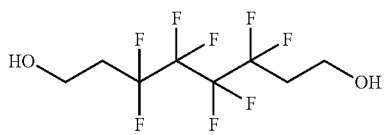 |
| | [P] 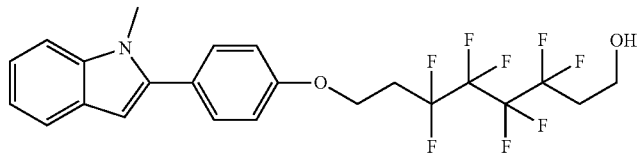 |

Preparation of Compounds According to the Invention

Example 22

General Remarks & General Synthetic Procedures (GSP 22) for the Esterification with Acryloyl Chloride or Methacryloyl Chloride to the Corresponding Monomer

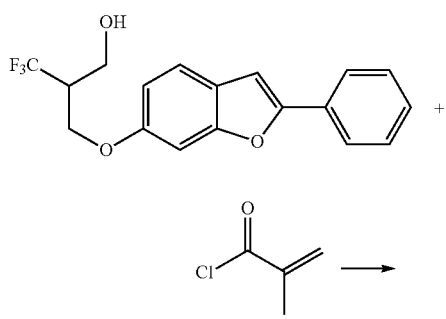

+

-continued

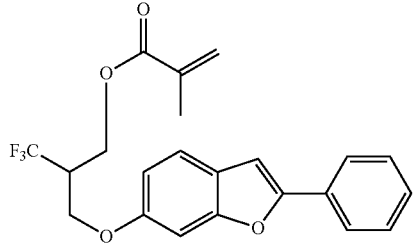

The corresponding aliphatic alcohol is dissolved in dry THF and the solution is cooled with an ice-bath. Triethylamine (4.00 equivs.) is added and the solution is stirred for a few minutes. Then acryloyl chloride or methacryloyl chloride (1.05-2.00 equivs.) is added at ice-bath temperature, while precipitating a colourless solid. The solution is stirred for several hours and is monitored via TLC. Upon completion of the reaction, the suspension is filtrated and washed with THF. The filtrate is evaporated under reduced pressure and purified via column chromatography using cyclohexane/ethyl acetate.

Analogously, other acrylate or methacrylate derivatives are prepared in the same manner: R means reactant, [P] means product

| No. | |
|---|---|
| 22a R | 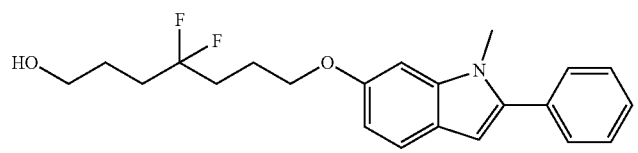 [SMILES: Cn1c(-c2ccccc2)cc2ccc(OCCCC(F)(F)CCCO)cc21] |
| [P] | 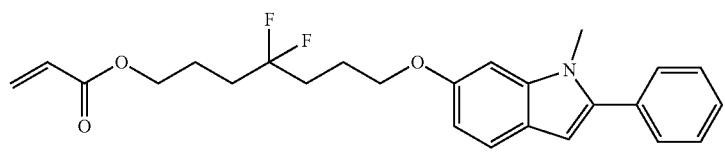 [SMILES: C=CC(=O)OCCCC(F)(F)CCCOc1ccc2cc(-c3ccccc3)n(C)c2c1] |
| 22b R | 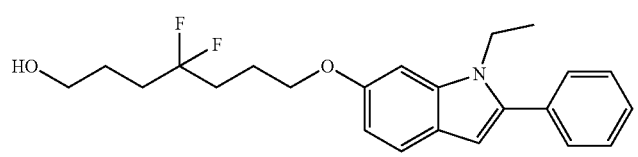 [SMILES: CCn1c(-c2ccccc2)cc2ccc(OCCCC(F)(F)CCCO)cc21] |
| [P] | 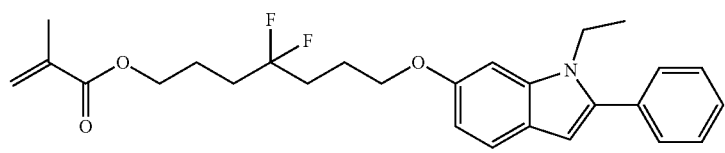 [SMILES: C=C(C)C(=O)OCCCC(F)(F)CCCOc1ccc2cc(-c3ccccc3)n(CC)c2c1] |
| 22c R | 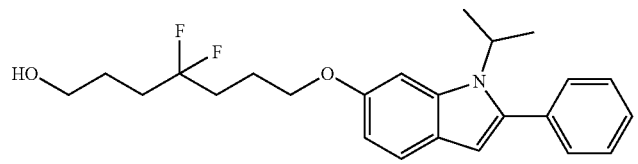 [SMILES: CC(C)n1c(-c2ccccc2)cc2ccc(OCCCC(F)(F)CCCO)cc21] |
| [P] | 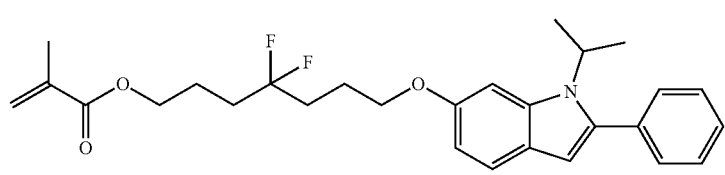 [SMILES: C=C(C)C(=O)OCCCC(F)(F)CCCOc1ccc2cc(-c3ccccc3)n(C(C)C)c2c1] |
| 22d R | 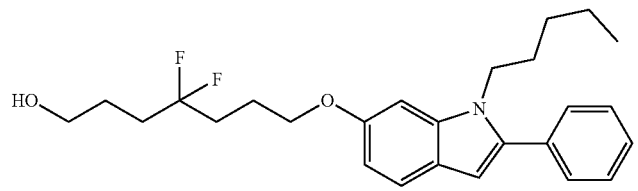 [SMILES: CCCCCn1c(-c2ccccc2)cc2ccc(OCCCC(F)(F)CCCO)cc21] |
| [P] | 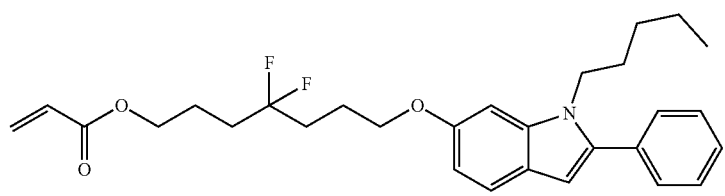 [SMILES: C=CC(=O)OCCCC(F)(F)CCCOc1ccc2cc(-c3ccccc3)n(CCCCC)c2c1] |

-continued
| No. | |
|---|---|
| 22e R | 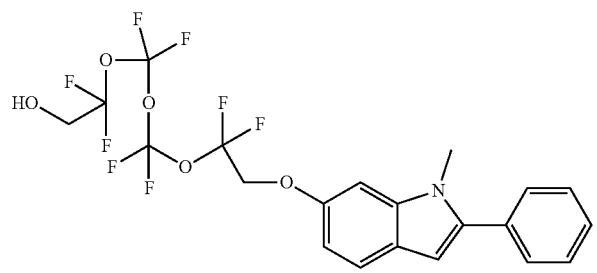 [SMILES: Cn1c(-c2ccccc2)cc2ccc(OCC(F)(F)OC(F)(F)OC(F)(F)OC(F)(F)CO)cc21] |
| [P] | 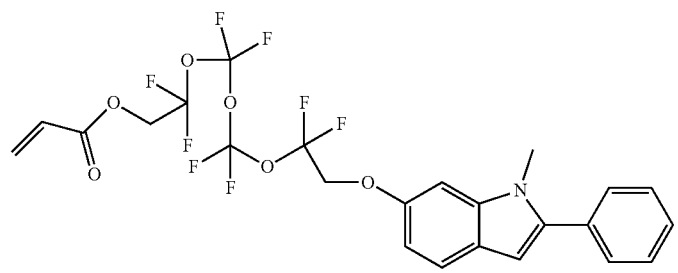 [SMILES: C=CC(=O)OCC(F)(F)OC(F)(F)OC(F)(F)OC(F)(F)COc1ccc2cc(-c3ccccc3)n(C)c2c1] |
| 22f R | 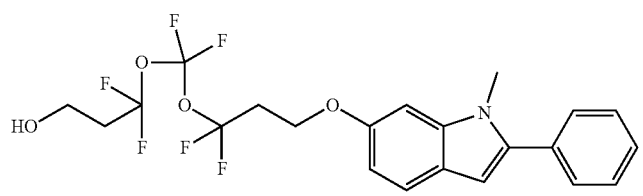 [SMILES: Cn1c(-c2ccccc2)cc2ccc(OCCC(F)(F)OC(F)(F)OC(F)(F)CCO)cc21] |
| [P] | 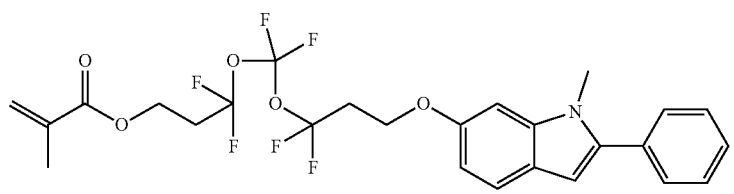 [SMILES: C=C(C)C(=O)OCCC(F)(F)OC(F)(F)OC(F)(F)CCOc1ccc2cc(-c3ccccc3)n(C)c2c1] |
| 22g R | 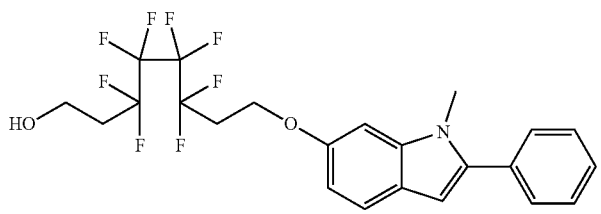 [SMILES: Cn1c(-c2ccccc2)cc2ccc(OCCC(F)(F)C(F)(F)C(F)(F)C(F)(F)CCO)cc21] |
| [P] | 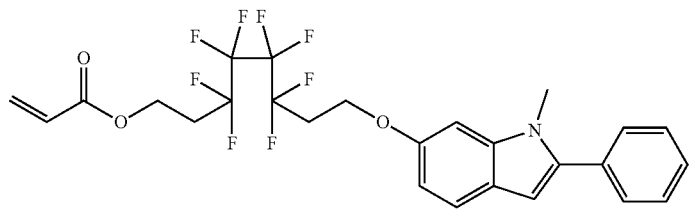 [SMILES: C=CC(=O)OCCC(F)(F)C(F)(F)C(F)(F)C(F)(F)CCOc1ccc2cc(-c3ccccc3)n(C)c2c1] |
| 22h R | 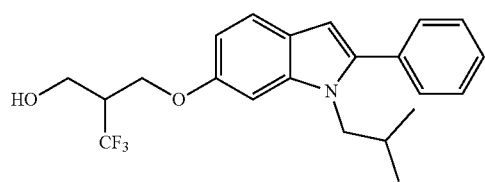 [SMILES: CC(C)Cn1c(-c2ccccc2)cc2ccc(OCC(CO)C(F)(F)F)cc21] |

| No. | |
|---|---|
| [P] | 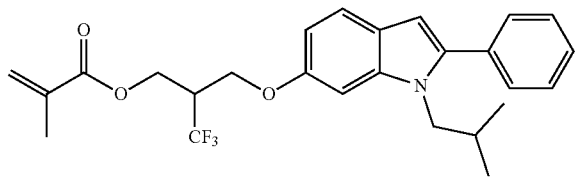 [SMILES: C=C(C)C(=O)OCC(COc1ccc2cc(-c3ccccc3)n(CC(C)C)c2c1)C(F)(F)F] |
| 22i R | 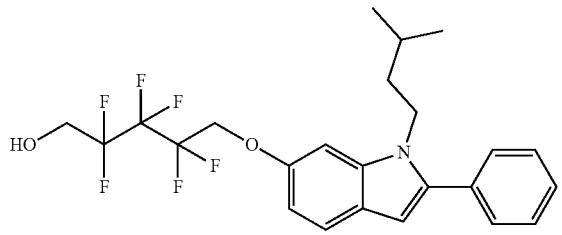 [SMILES: CC(C)CCn1c(-c2ccccc2)cc2ccc(OCC(F)(F)C(F)(F)C(F)(F)CO)cc21] |
| [P] | 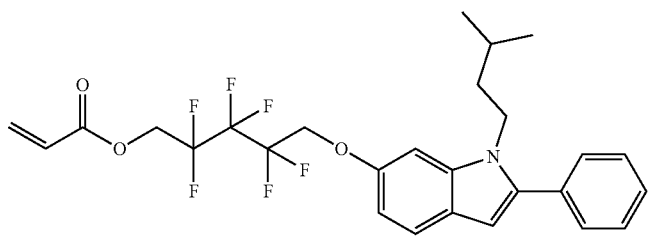 [SMILES: C=CC(=O)OCC(F)(F)C(F)(F)C(F)(F)COc1ccc2cc(-c3ccccc3)n(CCC(C)C)c2c1] |
| 22j R | 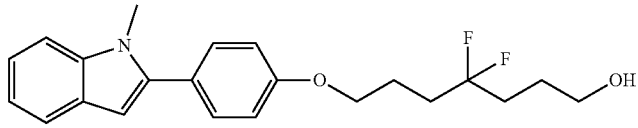 [SMILES: Cn1c(-c2ccc(OCCCC(F)(F)CCCO)cc2)cc2ccccc21] |
| [P] | 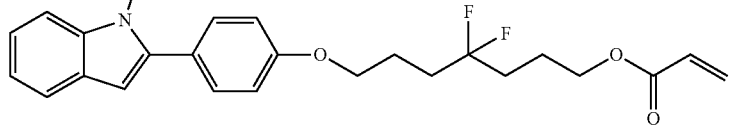 |
| 22k R | 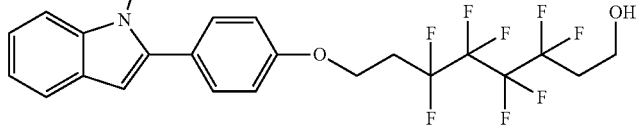 |
| [P] | 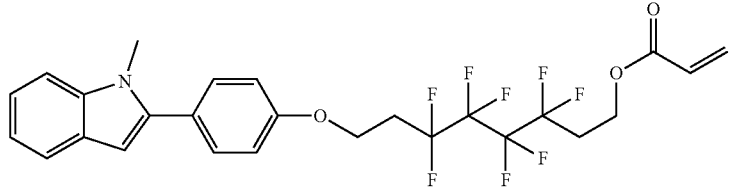 [SMILES: C=CC(=O)OCCC(F)(F)C(F)(F)C(F)(F)C(F)(F)CCOc1ccc(-c2cc3ccccc3n2C)cc1] |

Example 23

General Remarks & General Synthetic Procedures (GSP 23) for the Solvent Polymerization of the Monomers The corresponding monomer is dissolved in dry N,N-dimethylformamide in a Schlenck-tube with a stirring bar. The solution is degassed performing three times freeze-evacuate-thaw cycles. After that, azoisobutyronitrile (AIBN, 0.05 equiv.) is added in one portion to the degassed solution, which is heated up to 65° C. in an oil bath for a minimum of three days. The solution is cooled to room temperature and is then poured dropwise into cold methanol (100 ml methanol/100 mg monomer) while stirring. The precipitated polymer is collected on a frit or the solution is centrifuged several times to obtain the final polymer material.

Examples of polymers within this invention are given in the following table:

| Monomer | Polymer |
|---|---|
| 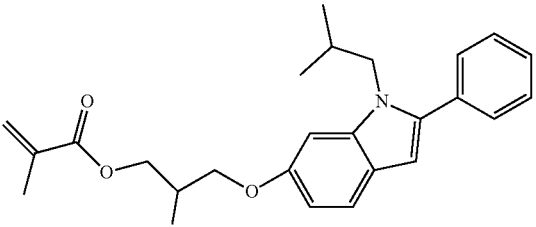 (M-N1) | 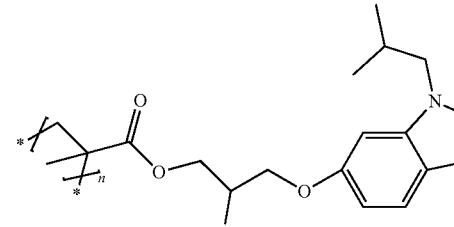 (P-458) |
| 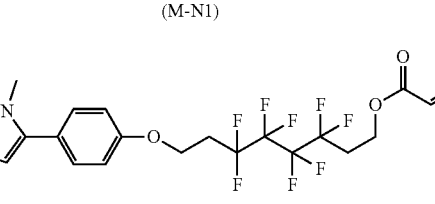 (M-N2) | 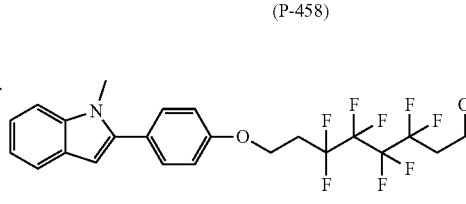 (P-627) |
| 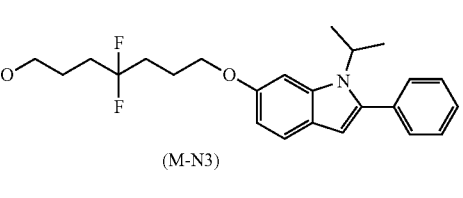 (M-N3) | 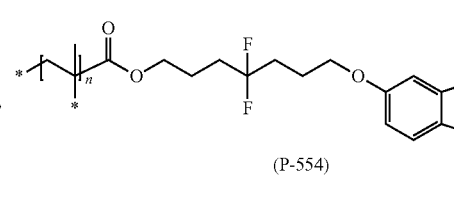 (P-554) |
| 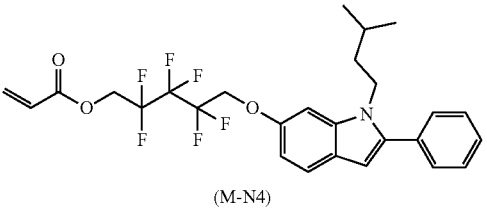 (M-N4) | 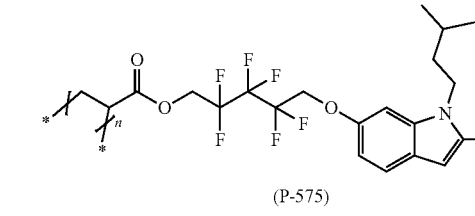 (P-575) |

Examples of Application

Example 24—General Bulk Polymerization Procedure to Produce Blank

A composition of 1H-indol derivative M-N3 and methyl methacrylate, initiator azobisisobutyronitrile (0.04 eq) and crosslinker ethylene glycol dimethacrylate (0.1-0.4 eq) in different ratios is degassed by three freeze-pump-thaw cycles.

Two glass plates are coated with a polyethylene sheet and a 0.5 mm thick cell is created between the polyethylene sheets using a silicone rubber gasket. The coated faces of the glass sheets are clipped together using spring clips with a syringe needle being placed between the gasket and the polyethylene sheets. The cavity is then filled with the above formulation through the needle using a gastight syringe. Once the cavity is filled the syringe needle is removed, a final clip is used to seal the mould and the assembly is placed in an oven at 60° C. for 24 hours before the oven is ramped to a temperature of 90° C. for a period of 3 hours. The moulds are allowed to cool to room temperature before the film is removed from the mould.

Examples Directed to the Properties of the Compounds

Example 25—Photoinduced Refractive Index Change and Glass Transition Temperature The phase transition temperatures are determined with a TA Instruments Q2000 differential scanning calorimeter during heating in the second heating run with 20 K/min from −100° C. to 200° C. in a hermetic aluminum pans.

Irradiations of the blanks are performed with a Coherent Avia 355-7000 UV-Laser.

Common photoactive polymers that undergo refractive index change upon irradiation with UV-light exhibit glass transition temperatures as low as 34° C.

Polymer films for refractive index measurements are prepared by spin coating or drop casting from 1-8 wt % solutions of the polymers in chloroform onto silicon wafers or quartz plates. For production of bulk polymer blanks, the monomers are melted under vacuum. Appropriate amounts of a radical initiator and cross-linker are mixed in and quickly filled into a heated polymerization chamber. Cross-linked polymer plates are obtained.

Refractive index change is induced by irradiation at 340-365 nm. The refractive indices (n) of the polymer films and blanks at 590 nm are measured on Schmidt+Haensch AR12 before and after irradiation. The following table shows the refractive indices before and after irradiation as well as the change in refractive index (max. Δn).

Expected values for the cited polymers are given in the following table:

| Polymer No | $T_g$ [° C.] | n | Δn |
|---|---|---|---|
| P-554 | 9.8 | 1.569 | 0.004 |
| P-185 | 16.9 | 1.542 | 0.049 |
| P-340 | 12.8 | 1.580 | 0.029 |

The invention claimed is:
1. A compound of formula (I)

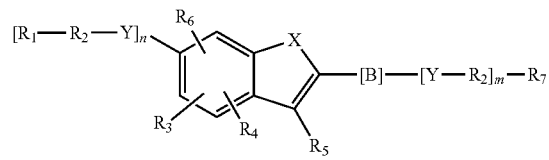

wherein
X is O, S or $NR_0$,
Y is independently of each other O, S or a bond,
n is 0 or 1,
m is 0 or 1,
n+m is 1 or 2,
—[B]— is selected from formula (1) to formula (4),

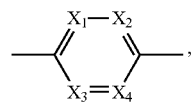

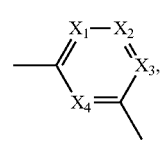

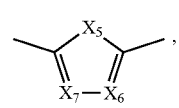

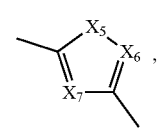

$X_1$, $X_2$, $X_3$, $X_4$ are each independently of each other CR' or N,
$X_5$ is each independently O, S, C=O or $NR_0$,
$X_6$, $X_7$ are each independently CR' or N,
R is at each occurrence independently H, F, a linear or branched alkyl group having 1 to 8 C atoms, or a linear or branched partially or fully fluorinated alkyl group having 1 to 4 C atoms,
R' is at each occurrence H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, or a linear or branched, non-halogenated, partially or completely halogenated thioalkyl group having 1 to 20 C atoms,
$R_0$ is at each occurrence independently a linear or branched alkyl group having 1 to 10 C atoms or a cycloalkyl group having 3 to 6 C atoms,
$R_1$ is a polymerizable group selected from:
an alkenyl group of formula (5),

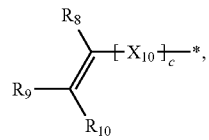

wherein
$X_{10}$ is O, S, C(=O), or C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms, and
c is 0 or 1;
trialkoxysilyl groups or dialkoxyalkylsilyl groups where the alkyl and/or alkoxy groups are each independently linear or branched having 1 to 6 C atoms; and
silyl groups of formula (6), (7) or (8),

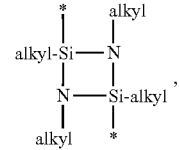

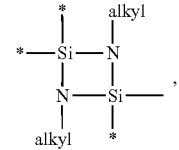

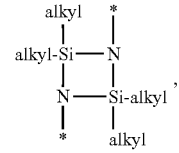

where alkyl means at each occurrence independently of each other a linear or branched alkyl group having 1 to 6 C atoms and the asterisk "*" denotes at each occurrence independently of each other a linkage to the linker [—$R_2$—Y]$_n$ and/or [Y—$R_2$]$_m$,
—$R_2$— is $(C(R)_2)_o$— or —$(C(R)_2)_p$—$X_8$—$(C(R)_2)_q$—$(X_9)_s$—$(C(R)_2)_r$—$(X_{10})_t$—$(C(R)_2)_u$—, wherein at least one R is F or a linear or branched partially or fully fluorinated alkyl group having 1 to 4 C atoms, or a cycloalkylene group having 5 or 6 C atoms which is substituted with at least one R which is F or a linear or branched partially or fully fluorinated alkyl group having 1 to 4 C atoms, o is 1 to 20, $X_8, X_9, X_{10}$ are at each occurrence independently O, S, or $NR_0$, s, t are at each occurrence independently 0 or 1, p, q are at each occurrence independently 1 to 10, r, u are at each occurrence independently 0 to 10, wherein the overall number of atoms for $-(C(R)_2)_p-X_8-(C(R)_2)_q-(X_9)_s-(C(R)_2)_r-(X_{10})_t-(C(R)_2)_u-$, is up to 20 atoms, $R_3, R_4, R_5, R_6$ are at each occurrence independently R', $R_7$ is R' in case m is 0, and $R_7$ is $R_1$ in case m is 1.

2. The compound according to claim 1, wherein —[B]— is of formula (1) or formula (2).

3. The compound according to claim 1, wherein $X_1$, $X_3$, and $X_4$ in formulae (1) or (2) are CR' and R' has at each occurrence independently a meaning as indicated in claim 1.

4. The compound according to claim 1, wherein $X_2$ is CR' and R' has a meaning as indicated in claim 1.

5. The compound according to claim 1, wherein at least one R' within $X_1, X_2, X_3, X_4, X_6$, or $X_7$ in formulae (1) to (4) is not H.

6. The compound according to claim 1, wherein n is 1 and m is 0, and said compound is of formula (I')

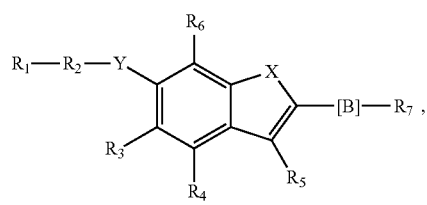

wherein $R_1$, —$R_2$—, Y, $R_3$, $R_4$, $R_5$, $R_6$, X, —[B]—, and $R_7$ have the meanings indicated in claim 1.

7. The compound according to claim 1, wherein n is 0 and m is 1, and said compound is of formula (I")

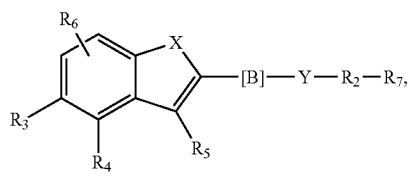

wherein $R_1$, —$R_2$—, Y, $R_3$, $R_4$, $R_5$, $R_6$, X, —[B]— and $R_7$ have the meanings indicated in claim 1.

8. The compound according to claim 1, wherein n is 1 and m is 1, and said compound is of formula (I''')

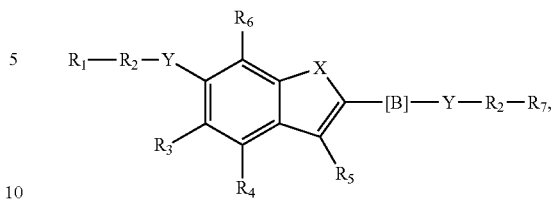

wherein $R_1$, —$R_2$—, Y, $R_3$, $R_4$, $R_5$, $R_6$, X, —[B]— and $R_7$ have the meanings indicated in claim 1.

9. The compound according to claim 1, wherein —$R_2$— is at each occurrence independently —$(C(R)_2)_o$— or —$(C(R)_2)_p-X_8-(C(R)_2)_q-(X_9)_s-(C(R)_2)_r-(X_{10})_t-(C(R)_2)_u$—, and wherein at least one R is F or a linear or branched partially or fully fluorinated alkyl group having 1 to 4 C atoms and all other R, o, $X_8, X_9, X_{10}$, s, t, p, q, r, and u have the meanings indicated in claim 1.

10. The compound according to claim 1, wherein $R_1$ is at each occurrence independently an acryl or methacryl radical.

11. An oligomer or polymer comprising a polymerized compound of formula (I) according to claim 1.

12. A composition comprising at least one compound of formula (I) according to claim 1.

13. An article comprising at least one oligomer or polymer according to claim 11.

14. A process of forming an article of claim 13, said process comprising:
providing a composition comprising said at least one compound of formula (I); and
subsequently forming the article from said composition.

15. A process of changing the optical properties of an article according to claim 13, said process comprising the steps of
providing an article according to claim 13, and
subsequently exposing said article to irradiation having a wavelength of at least 200 nm and at most 1500 nm.

16. The article according to claim 13, wherein said article is an eye implant.

17. A composition comprising at least one oligomer or polymer according to claim 11.

18. The article according to claim 13, wherein said article is an intraocular lens.

19. The article according to claim 13, wherein said article is an ophthalmic device.

20. The article according to claim 19, wherein said ophthalmic device is a lens, a keratoprosthesis, a cornea inlay, or a cornea ring.

21. A process of forming an article, said process comprising:
introducing a compound according to claim 1 into a mold and polymerizing said compound to form a blank,
transforming the blank into the article, wherein said article is an ophthalmic device.

22. A process of forming an article, said process comprising:
polymerizing a compound according to claim 1 to form an oligomer or polymer composition,
introducing the oligomer or polymer composition into a mold to form a blank, shaping the blank by cutting, optic lathe cutting, optic milling, and/or haptic milling to form the article.

23. A copolymer comprising a polymerized compound of formula (I) according to claim 1 wherein the polymerizable group $R_1$ forms part of a co-polymer backbone.

24. The copolymer according to claim 23, wherein said copolymer comprises one or more constitutional units $M^0$ of formulae (5-p-1), (5-p-2), or (5-p-3):

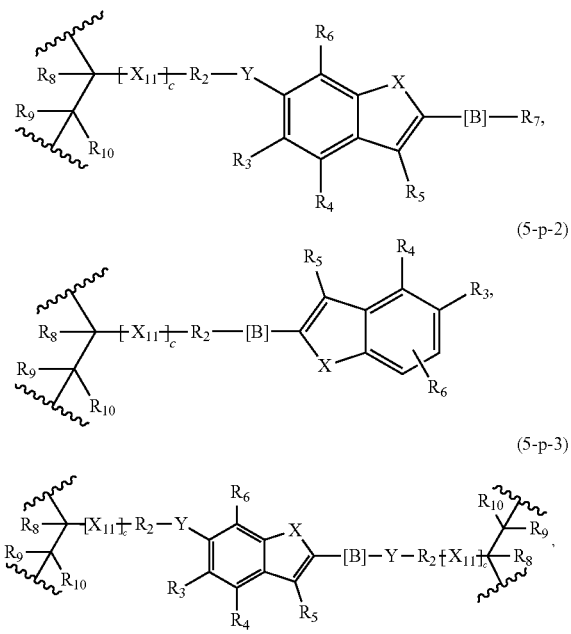

wherein $-R_2-$, Y, $R_3$, $R_4$, $R_5$, $R_6$, X, $-[B]-$, $R_7$, $X_{11}$, $R_8$, $R_9$, $R_{10}$ and c meanings as defined in claim 1.

25. The copolymer according to claim 24, wherein said copolymer further comprises one or more constitutional units $M^2$ which are chemically different from the units $M^0$.

26. The copolymer according to claim 25, wherein said one or more constitutional units $M^2$ which are derived by polymerization of one or more monomers selected from styrene, ethoxyethyl methacrylate, methyl methacrylate, n-alkyl methacrylates wherein the n-alkyl groups contain 2-20 C-atoms, n-alkyl methacrylates wherein the n-alkyl groups contain 2-20 C-atoms, ethoxyethoxy ethylacrylate, 2-hydroxyethyl methacrylate, tetrahydrofuryl methacrylate, glycidylmethacrylate, 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate, bisphenol A diacrylate-1 EO/Phenol, 2-[3'-2'H-benzotriazol-2'-yl)-4'-hydroxyphenyl]ethyl methacrylate, trialkoxyalkenylsilane, dialkoxyalkylalkenylsilane, and silanes of formula (9) and (10),

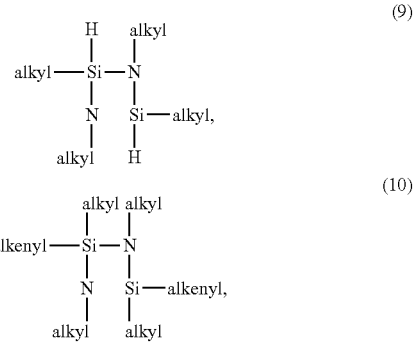

where the alkyl and/or alkoxy groups are at each occurrence independently of each other linear or branched having 1 to 6 C atoms and the alkenyl group is at each occurrence independently linear having 2 to 4 C atoms.

27. An article comprising at least one copolymer according to claim 24.

28. An article comprising at least one copolymer according to claim 25.

29. An article comprising at least one copolymer according to claim 26.

30. The article according to claim 27, wherein said copolymer is cross-linked.

31. The article according to claim 28, wherein said copolymer is cross-linked.

32. The article according to claim 29, wherein said copolymer is cross-linked.

33. The copolymer according to claim 25, wherein said copolymer comprises the one or more constitutional units $M^0$ in a molar ratio m1 and the one or more constitutional units $M^2$ in a molar ratio m2, wherein the ratio m1:m2 is at least 0.01 and at most 100.

34. An article comprising at least one copolymer according to claim 33.

35. An article according to claim 19, wherein the ophthalmic device comprises one or more optic components and one or more haptic components, wherein the one or more optic components serve as a lens and the one or more haptic components are attached to the one or more optic components and hold the one or more optic components in place in the eye.

36. An article according to claim 18, wherein the article has a one-piece design.

37. An article according to claim 18, wherein the article has a multi-piece design.

38. An article produced by the process according to claim 15.

* * * * *